US011299490B2

(12) United States Patent
Andrez et al.

(10) Patent No.: US 11,299,490 B2
(45) Date of Patent: Apr. 12, 2022

(54) BENZENESULFONAMIDE COMPOUNDS AND THEIR USE AS THERAPEUTIC AGENTS

(71) Applicant: Xenon Pharmaceuticals Inc., Burnaby (CA)

(72) Inventors: Jean-Christophe Andrez, Vancouver (CA); Kristen Nicole Burford, Burnaby (CA); Sultan Chowdhury, Surrey (CA); Charles Jay Cohen, Vancouver (CA); Christoph Martin Dehnhardt, Burnaby (CA); Robert Joseph Devita, Westfield, NJ (US); James Roy Empfield, Natick, MA (US); Thilo Focken, Burnaby (CA); Michael Edward Grimwood, North Vancouver (CA); Syed Abid Hasan, Vancouver (CA); James Philip Johnson, Jr., Vancouver (CA); Alla Yurevna Zenova, Vancouver (CA)

(73) Assignee: Xenon Pharmaceuticals Inc., Burnaby (CA)

(*) Notice: Subject to any disclaimer, the term of this patent is extended or adjusted under 35 U.S.C. 154(b) by 0 days.

(21) Appl. No.: 16/940,696

(22) Filed: Jul. 28, 2020

(65) Prior Publication Data

US 2020/0354354 A1 Nov. 12, 2020

Related U.S. Application Data

(63) Continuation of application No. 16/821,294, filed on Mar. 17, 2020, now Pat. No. 10,815,229, which is a continuation of application No. 16/289,212, filed on Feb. 28, 2019, now Pat. No. 10,662,184, which is a continuation of application No. 15/600,490, filed on May 19, 2017, now Pat. No. 10,246,453.

(60) Provisional application No. 62/432,152, filed on Dec. 9, 2016, provisional application No. 62/339,773, filed on May 20, 2016.

(51) Int. Cl.
| C07D 451/06 | (2006.01) |
| C07D 403/12 | (2006.01) |
| C07D 213/76 | (2006.01) |
| C07D 237/20 | (2006.01) |
| C07D 239/69 | (2006.01) |
| C07D 413/12 | (2006.01) |
| C07D 417/12 | (2006.01) |
| C07D 261/16 | (2006.01) |
| C07D 493/10 | (2006.01) |
| C07D 277/52 | (2006.01) |
| C07D 285/08 | (2006.01) |
| C07D 401/12 | (2006.01) |
| C07D 417/14 | (2006.01) |

(52) U.S. Cl.
CPC ....... *C07D 451/06* (2013.01); *C07D 213/76* (2013.01); *C07D 237/20* (2013.01); *C07D 239/69* (2013.01); *C07D 261/16* (2013.01); *C07D 277/52* (2013.01); *C07D 285/08* (2013.01); *C07D 401/12* (2013.01); *C07D 403/12* (2013.01); *C07D 413/12* (2013.01); *C07D 417/12* (2013.01); *C07D 417/14* (2013.01); *C07D 493/10* (2013.01)

(58) Field of Classification Search
CPC .................................................. C07D 451/06
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 5,877,193 A | 3/1999 | Cesura et al. | |
| 5,958,910 A | 9/1999 | Cesura et al. | |
| 8,222,281 B2 | 7/2012 | Toda et al. | |
| 9,481,677 B2 | 11/2016 | Liu et al. | |
| 9,630,929 B2* | 4/2017 | Sun | C07D 239/42 |
| 10,246,453 B2* | 4/2019 | Andrez | C07D 261/16 |
| 10,662,184 B2* | 5/2020 | Andrez | C07D 277/52 |
| 10,745,392 B2* | 8/2020 | Burford | C07D 277/52 |
| 10,815,229 B1 | 10/2020 | Burford et al. | |
| 2009/0023740 A1 | 1/2009 | Fulp et al. | |
| 2010/0267782 A1 | 10/2010 | Beaudoin et al. | |
| 2014/0045862 A1 | 2/2014 | Shinozuka et al. | |
| 2014/0256736 A1 | 9/2014 | Liu et al. | |
| 2014/0315878 A1 | 10/2014 | Storer et al. | |
| 2014/0315933 A1 | 10/2014 | Owen et al. | |
| 2017/0334902 A1 | 11/2017 | Andrez et al. | |
| 2018/0162868 A1 | 6/2018 | Andrez et al. | |

(Continued)

FOREIGN PATENT DOCUMENTS

| EP | 2 813 491 | 12/2014 |
| JP | 2014-532640 | 12/2014 |
| JP | 2014-534213 | 12/2014 |

(Continued)

OTHER PUBLICATIONS

U.S. Appl. No. 16/440,459, filed Jun. 13, 2019, Burford et al.
U.S. Appl. No. 16/556,055, filed Aug. 29, 2019, Andrez et al.
U.S. Appl. No. 16/805,895, filed Mar. 2, 2020, Andrez et al.
Andrez et al., entitled "Benzenesulfonamide Compounds and Their Use as Therapeutic Agents," Office Action dated Dec. 14, 2017, for U.S. Appl. No. 15/600,490, 16 pages.

(Continued)

*Primary Examiner* — Golam M Shameem
(74) *Attorney, Agent, or Firm* — Fish & Richardson P.C.

(57) ABSTRACT

This invention is directed to benzenesulfonamide compounds, as stereoisomers, enantiomers, tautomers thereof or mixtures thereof; or pharmaceutically acceptable salts, solvates or prodrugs thereof, for the treatment of diseases or conditions associated with voltage-gated sodium channels, such as epilepsy.

24 Claims, No Drawings

(56) References Cited

U.S. PATENT DOCUMENTS

| | | | |
|---|---|---|---|
| 2019/0194184 A1 | 6/2019 | Andrez et al. | |
| 2020/0071313 A1 | 3/2020 | Andrez et al. | |

FOREIGN PATENT DOCUMENTS

| | | |
|---|---|---|
| JP | 2015-518863 | 7/2015 |
| WO | WO 1998/50016 | 11/1998 |
| WO | WO 2000/42003 | 7/2000 |
| WO | WO 2001/05393 | 1/2001 |
| WO | WO 2001/40222 | 6/2001 |
| WO | WO 2003/076406 | 9/2003 |
| WO | WO 2004/002481 | 1/2004 |
| WO | WO 2005/021536 | 3/2004 |
| WO | WO 2004/092123 | 10/2004 |
| WO | WO 2005/000309 | 1/2005 |
| WO | WO 2005/005421 | 1/2005 |
| WO | WO 2005/013914 | 2/2005 |
| WO | WO 2006/038594 | 4/2006 |
| WO | WO 2006/129199 | 12/2006 |
| WO | WO 2007/039171 | 4/2007 |
| WO | WO 2007/075895 | 7/2007 |
| WO | WO 2008/019967 | 2/2008 |
| WO | WO 2008/051494 | 5/2008 |
| WO | WO 2009/012242 | 1/2009 |
| WO | WO 2009/013171 | 1/2009 |
| WO | WO 2009/157418 | 12/2009 |
| WO | WO 2010/002956 | 1/2010 |
| WO | WO 2010/029300 | 3/2010 |
| WO | WO 2010/079443 | 7/2010 |
| WO | WO 2012/004743 | 1/2012 |
| WO | WO 2012/022265 | 2/2012 |
| WO | WO 2013/025883 | 2/2013 |
| WO | WO 2013/063459 | 5/2013 |
| WO | WO 2013/064983 | 5/2013 |
| WO | WO 2013/118854 | 8/2013 |
| WO | WO 2013/122897 | 8/2013 |
| WO | WO 2014/061970 | 4/2014 |
| WO | WO 2014/066490 | 5/2014 |
| WO | WO 2014/066491 | 5/2014 |
| WO | WO 2014/170793 | 10/2014 |
| WO | WO 2014/198849 | 12/2014 |
| WO | WO 2014/201206 | 12/2014 |
| WO | WO 2015/035278 | 3/2015 |
| WO | WO 2015/038533 | 3/2015 |
| WO | WO 2015/077905 | 6/2015 |
| WO | WO 2015/078374 | 6/2015 |
| WO | WO 2015/080988 | 6/2015 |
| WO | WO 2015/099841 | 7/2015 |
| WO | WO 2016/007534 | 1/2016 |
| WO | WO 2006/066109 | 6/2016 |
| WO | WO 2016/177340 | 11/2016 |
| WO | WO 2017/106409 | 6/2017 |
| WO | WO 2017/201468 | 11/2017 |
| WO | WO 2018/093694 | 5/2018 |
| WO | WO 2018/106284 | 6/2018 |

OTHER PUBLICATIONS

Barton et al., "Pharmacological characterization of the 6 Hz psychomotor seizure model of partial epilepsy," Epilepsy Research 47: 217-227, 2001.

Bean et al., "Lidocaine Block of Cardiac Sodium Channels," J Gen. Physiol. 81: 613-642, May 1983.

Boerma et al., "Remarkable Phenytoin Sensitivity in 4 Children with SCN8A-related Epilepsy: A Molecular Neuropharmacological Approach," Neurotherapeutics 13: 192-197, 2016.

Bordwell et al., "The Reduction of Sulfones to Sulfides," JACS 73: 2251-2253, May 1951.

Burgess et al., "Mutation of a new sodium channel gene, Scn8a, in the mouse mutant 'motor endplate disease'," Nature Genetics 10: 461-465, Aug. 1995.

Carroll et al., "Mutation screening of SCN2A in schizophrenia and identification of a novel loss-of-function mutation," Psychiatr. Genet. 26: 60-65, 2016.

Catterall, "Sodium Channels, Inherited Epilepsy, and Antiepileptic Drugs," Annu. Rev. Pharmacol. Toxicol. 54: 317-338, 2014.

Cestele et al., "Molecular mechamsms of neurotoxin action on voltage-gated sodium channels," Biochimie 82: 883-892, 2000.

Cheah et al., "Correlations in timing of sodium channel expression, epilepsy, and sudden death in Dravet syndrome," Channels 7(6): 468-472, Nov./Dec. 2013.

Cojocariu et al., "SintezaunorN4-(2-hidroxi-4-clorbenzoil)-sulfamide cu activitate antimicotica potentiala," Revista de Chimie 30(12): C-1261, 1979, 3 pages.

De Kovel, et al., "Characterization of a de nova SCN8A mutation in a patient with epileptic encephalopathy," Epilepsy Research 108: 1511-1518, 2014.

Dravet et al., Handbook of Clinical Neurology, vol. 111 (3rd series)—Pediatric Neurology Part 1, Elsevier B.V., Amsterdam, Netherlands, 2013, Chapter 65, "Dravet syndrome (severe myoclonic epilepsy in infancy)," pp. 627-633.

Dutton et al., "Preferential inactivation of Scn1a in parvalbumin interneurons increases seizure susceptibility," Neurobiology of Disease 49: 211-220, 2013.

Estacion et al., "A novel de novo mutation of SCN8A (Nav1.6) with enhanced channel activation in a child with epileptic encephalopathy," Neurobiology of Disease 69: 117-123, 2014.

Focken et al., "Discovery of Aryl Sulfonamides as Isoform-Selective Inhibitors ofNav1.7 with Efficacy in Rodent Pain Models," ACS Med.Chem. Lett. 7: 277-282, 2016.

Fukasawa et al., "A case of recurrent encephalopathy with SCN2A missense mutation," Brain & Development 37: 631-634, 2015.

Gardner et al., "A Facile Reduction of Sulfones to Sulfides," Can. J Chem. 51: 1419-1421, 1973.

Hadzi et al., "The Role of Hydrogen Bonding in Drug-Receptor Interactions," Journal of Molecular Structure 237: 139-150, 1990.

Hawkins et al., "Hlf is a genetic modifier of epilepsy caused by voltage-gated sodium channel mutations," Epilepsy Research 119: 20-23, 2016.

Hawkins et al., "Neuronal voltage-gated ion channels are genetic modifiers of generalized epilepsy with febrile seizures plus," Neurobiology of Disease 41: 655-660, 2011.

Helbig, "Genetic Causes of Generalized Epilepsies," Semin. Neural. 35: 288-292, 2015.

Hille, "Local Anesthetics: Hydrophilic and Hydrophobic Pathways for the Drug-Receptor Reaction," The Journal of General Physiology 69: 497-515, 1977.

Hitchcock et al., "Perspective: Structure—Brain Exposure Relationships," Journal of Medicinal Chemistry 49(26): 7559-7583, Dec. 28, 2006.

Hossfeld, "Paper Partition Chromatography of Simple Phenols," J Am. Chem. Soc. 73: 852-854, 1951.

Howell et al., "SCN2A encephalopathy: A major cause of epilepsy of infancy with migrating focal seizures," Neurology 85: 958-966, 2015.

Hu et al., "Distinct contributions of NAv1.6 and Nav1.2 in action potential initiation and backpropagation," Nature Neuroscience 12(8): 996-1002, Aug. 2009, 9 pages.

International Preliminary Report on Patentability, dated Jun. 20, 2019, for PCTAN PCT/US2017/033666, 21 pages.

International Preliminary Report on Patentability, dated Nov. 20, 2018, for International Application No. PCT/US2017/033634, 7 pages.

International Search Report and Written Opinion, dated Jul. 4, 2017, for PCTAN PCT/US2017/033634, 13 pages.

International Search Report and Written Opinion, dated Sep. 11, 2019, for International Application No. PCT/US2019/03701 1, 13 pages.

International Search Report and Written Opinion, dated Sep. 25, 2017, for PCTAN PCT/US2017/033666, 30 pages.

James et al., "A modular, gold-catalysed approach to the synthesis of lead-like piperazine scaffolds," Org. Lett. 15(23): 6094-6097, 2013.

(56) References Cited

OTHER PUBLICATIONS

Kearney et al., "A Gain-of-Function Mutation in the Sodium Channel Gene Scn2a Results in Seizures and Behavioral Abnormalities," Neuroscience 102(2): 307-317, 2001.
Kong et al., "SCN8A mutations in Chinese children with early onset epilepsy and intellectual disability," Epilepsia 56(3): 431-438, 2015.
Kuzma et al., "Progress in the Development of Ultra-Long-Acting Local Anesthetics," Regional Anesthesia 22(6): 543-551, 1997.
Larsen et al., "The phenotypic spectrum of SCN8A encephalopathy," Neurology 84: 480-489, 2015.
Leuwer et al., "An improved model for the binding of lidocaine and structurally related local anaesthetics to fast-inactivated voltage-operated sodium channels, showing evidence of cooperativity," British Journal of Pharmacology 141: 47-54, 2004.
Liu et al., "Mutations in Cardiac Sodium Channels: Clinical Implications," Am. J Pharmacogenomics 3(3): 173-179, 2003.
Loscher et al., "Which animal models should be used in the search for new antiepileptic drugs? A proposal based on experimental and clinical considerations," Epilepsy Res. 2: 145-181, 1988.
Luci et al., "Synthesis and Structure—Activity Relationship Studies of 4-((2-Hydroxy-3-methoxybenzyl)amino)benzenesulfonamide Derivatives as Potent and Selective Inhibitors of 12-Lipoxygenase," J Med. Chem. 57: 495-506, 2014.
Makinson et al., "An Senia epilepsy mutation in Scn8a alters seizure susceptibility and behavior," Experimental Neurology, 275: 46-58, 2016.
Makinson et al., "Role of the hippocampus in Nav1.6 (Scn8a) mediated seizure resistance," Neurobiology of Disease 68: 16-25, 2014.
Martin et al., "Altered Function of the SCN1A Voltage-gated Sodium Channel Leads toy-Aminobutyric Acid-ergic (GABAergic) Intereuron Abnormalities," The Journal of Biological Chemistry 285(13): 9823-9834, Mar. 26, 2010.
Martin et al., "The voltage-gated sodium channel Scn8a is a genetic modifier of severe myoclonic epilepsy of infancy," Human Molecular Genetics 16(23): 2892-2899, 2007.
Massey et al., "Mechanisms of sudden unexpected death in epilepsy: the pathway to prevention," Nature Reviews Neurology 10: 271-282, May 2014.
Matsukawa et al., "Studies on Chemotherapeutics. XII. Syntheses of p-Hydroxybenezenesulfonamide Derivatives," Yakugaku Zasshi 70(10): 557-561, 1950.
McKusik et al., Epileptic Encephalopathy, Early Infantile 6; EIEE6, Online Mendelian Inheritance in Man: John Hopkins University, 2012, 12 pages, URL=http:omin.org/entry/607208, download date Sep. 6, 2017.
Miller et al., "Mapping genetic modifiers of survival in a mouse model of Dravet syndrome," Genes, Brain and Behavior 13: 163-172, 2014.
Mistry et al., "Strain- and age-dependent hippocampal neuron sodium currents correlate with epilepsy severity in Dravet syndrome mice," Neurobiology of Disease 65: 1-11, 2014.
Norinder et al., "QSAR investigation of NaV1.7 active compounds using the SVM/Signature approach and the Bioclipse Modeling platform," Bioorganic & Medicinal Chemistry Letters 23: 261-263, 2013.
Ogiwara et al., "Nav1.1 Localizes to Axons of Parvalbumin-Positive Inhibitory Interneurons: A Circuit Basis for Epileptic Seizures in Mice Carrying an Senia Gene Mutation," The Journal of Neuroscience 27(22): 5903-5914, May 30, 2007.
Ohba et al., "Early onset epileptic encephalopathy caused by de novo Scn8A mutations," Epilepsia 55(7): 994-1000, 2014.
Patani et al., "Bioisosterism: A Rational Approach in Drug Design," Chem. Rev. 96: 3147-3176, 1996.
Payne et al., "Identification of KD5170: A novel mercaptoketone-based histone deacetylase inhibitor," Bioorganic & Medicinal Chemistiy Letters 18: 6093-6096, 2008.

Piredda et al., "Effect of Stimulus Intensity on the Profile of Anticonvulsant Activity of Phenytoin, Ethosuximide and Valproate," The Journal of Pharmacology and Experimental Therapeutics 232(3): 741-745, 1985.
Prasanthy et al., "Synthesis and Biological Evaluation of 1-Substituted Imidazole Derivatives," Int. J Pharma 1(2): 92-99, 2011.
Raymond et al., "Expression of Alternatively Spliced Sodium Channel a-Subunit Genes," Journal of Biological Chemistiy 279(44): 46234-46241, Oct. 29, 2004.
Rogers et al., "Characterization of Endogenous Sodium Channels in the ND7-23 Neuroblastoma Cell Line: Implications for Use as a Heterologous Ion Channel Expression System Suitable for Automated Patch Clamp Screening," Assay and Drug Development Technologies 14(2): 109-130, Mar. 2016.
Royeck et al., "Role of Axonal Nav1.6 Sodium Channels in Action Potential Initiation of CA1 Pyramidal Neurons," J Neurophysiol. 100: 2361-2380, 2008.
Saitoh et al., "Missense mutations in sodium channel SCN1A and SCN2A predispose children to encephalopathy with severe febrile seizures," Epilepsy Research 117: 1-6, 2015.
Samanta et al., "De novo R853Q mutation of SCN2A gene and West syndrome," Acta Neural. Belz. 115:773-776, 2015.
Schwarz et al., "Mutations in the sodium channel gene SCN2A cause neonatal epilepsy with late-onset episodic ataxia," J Neurol. 263: 334-343, 2016.
Stumpf et al., "Development of an Expedient Process for the Multi-Kilogram Synthesis ofChkl Inhibitor GDC-0425," Onz. Process Res. Dev. 19: 661-672, 2015.
Suzuki et al., "Morphogenetic Effect of Kainate on Adult Hippocampal Neurons Associated with a Prolonged Expression of Brain-derived Neurotrophic Factor," Neuroscience 64(3): 665-674, 1995.
Toman et al., "Properties of Maximal Seizures, and Their Alteration by Anticonvulsant Drugs and Other Agents," J Neurophysiol. 9: 231-239, 1946.
Trudeau et al., "Heterozygosity for a protein truncation mutation of sodium channel SCN8A in a patient with cerebellar atrophy, ataxia, and mental retardation," J Med. Genet. 43: 527-530, 2006.
Tuncer et al., "A clinical variant in SCN1A inherited from a mosaic father cosegregates with a novel variant to cause Dravet syndrome in a consanguineous family," Epilepsy Research 113: 5-10, 2015.
Vaher et al., "De Novo SCN8A Mutation Identified by Whole-Exome Sequencing in a Boy With Neonatal Epileptic Encephalopathy, Multiple Congenital Anomalies, and Movement Disorders," Journal of Child Neurology 29(12): NP202-NP206, 2014.
Veeramah et al., "De Novo Pathogenic SCN8A Mutation Identified by Whole-Genome Sequencing of a Family Quartet Affected by Infantile Epileptic Encephalopathy and SUDEP," The American Journal of Human Genetics 90: 502-510, Mar. 9, 2012.
Vega et al., "Reduced expression of Nav1.6 sodium channels and compensation ofNav1.2 channels in mice heterozygous for a null mutation in Scn8a," Neuroscience Letters 442: 69-73, 2008.
Wagnon et al., "Convulsive seizures and SUDEP in a mouse model of SCN8A epileptic encephalopathy," Human Molecular Genetics 24(2): 506-515, 2015.
Ward, "Chiral Separations," Anal. Chem. 74: 2863-2872, 2002.
White et al., "The early identification of anticonvulsant activity: role of the maximal electroshock and subcutaneous pentylenetetrazol seizure models," Ital. J Neural. Sci 16: 73-77, 1995.
Wilmshurst et al., Summary of recommendations for the management of infantile seizures: TaskForce Report forthe ILAE Commission of Pediatrics, Epilepsia 56(8): 1185-1197, 2015.
Wu et al., "Development of New Benzenesulfonamides as Potent and Selective Nav1.7 Inhibitors for the Treatment of Pain," J Med. Chem. 60: 2513-2525, 2017.
Yu et al., "Reduced sodium current in GABAergic interneurons in a mouse model of severe myoclonic epilepsy in infancy," Nature Neuroscience 9(9): 1142-1149, Sep. 2006.
Zerem et al., "Paternal germline mosaicism of a SCN2A mutation results in Ohtahara syndrome in half siblings," European Journal of Paediatric Neurology 18: 567-571, 2014.

\* cited by examiner

BENZENESULFONAMIDE COMPOUNDS AND THEIR USE AS THERAPEUTIC AGENTS

FIELD OF THE INVENTION

The present invention is directed to benzenesulfonamide compounds and pharmaceutical compositions comprising the compounds and methods of using the compounds and the pharmaceutical compositions in treating sodium channel-mediated diseases or conditions, such as epilepsy and/or epileptic seizure disorder, as well as other diseases and conditions associated with the mediation of sodium channels.

BACKGROUND OF THE INVENTION

Voltage gated sodium channels ($Na_V$'s) are critical determinants of cellular excitability in muscle and nerve (Hille, B, Ion Channels of Excitable Membranes (2001), Sunderland, Mass., Sinauer Associates, Inc.). Four isoforms in particular, $Na_V1.1$, $Na_V1.2$, $Na_V1.3$, and $Na_V1.6$, account for the majority of sodium current in the neurons of the central nervous system. $Na_V1.3$ is primarily expressed embryonically. Beyond the neonatal stage, $Na_V1.1$, $Na_V1.2$, and $Na_V1.6$ are the critical isoforms that regulate neuronal signaling in the brain (Catterall, W. A., *Annual Review of Pharmacology and Toxicology* (2014), Vol. 54, pp. 317-338).

$Na_V1.5$ is expressed mainly in cardiac myocytes (Raymond, C. K. et al., *J. Biol. Chem.* (2004), Vol. 279, No. 44, pp. 46234-41), including atria, ventricles, the sino-atrial node, atrio-ventricular node and cardiac Purkinje fibers. Mutations in human $Na_V1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H., et al., *Am. J. Pharmacogenomics* (2003), Vol. 3, No. 3, pp. 173-9). Sodium channel blocker therapy has been used extensively in treating cardiac arrhythmias.

Epilepsy is a condition characterized by excessive synchronous excitability in the brain that arises when the delicate balance of excitatory and inhibitory signals in the brain fall out of equilibrium. This can happen either due to an excess of excitation, or a deficiency of inhibition. Mutations in the genes encoding $Na_V$ channels have been linked to both types of disequilibrium.

$Na_V1.1$ has been identified as the primary $Na_V$ isoform of inhibitory interneurons (Yu, F. H. et al., *Nat. Neurosci.* (2006), Vol. 9, pp. 1142-1149). These interneurons synapse on many other neurons, including excitatory glutamatergic neurons. Action potentials in the interneurons induce the release of the neurotransmitter GABA onto other neurons, hyperpolarizing them and thus dampening excitation. This results in a negative feedback that enables controlled signaling and prevents local signals from expanding into waves of excitation that spread across large brain regions. Because of this critical role in inhibitory interneurons, mutations that impair $Na_V1.1$ channel function can lead to a failure of those neurons to activate and release GABA (Ogiwara, I. et al., *J. Neurosci.* (2007), Vol. 27, pp. 5903-5914; Martin, M. S. et al., *J. Biol. Chem.* (2010), Vol. 285, pp. 9823-9834; Cheah, C. S. et al., *Channels (Austin)* (2013), Vol. 7, pp. 468-472; and Dutton, S. B., et al., (2013), Vol. 49, pp. 211-220). The result is a loss in the inhibitory tone of the brain and a failure to contain the excitability of the glutamatergic neurons. This failure of the inhibitory interneurons can result in aberrant wide-scale synchronous firing of neurons across regions of the brain (epilepsy).

Mutations in the gene encoding $Na_V1.1$ (SCN1A) fall into two broad classes, those that cause generalized epilepsy with febrile seizures plus (GEFS+) and those that cause severe myoclonic epilepsy of infancy (SMEI), also known as Dravet Syndrome or early infantile epileptic encephalopathy 6 (EIEE6) (McKusik, V. K. et al., *A Epileptic Encephalopathy, Early Infantile 6, EIEE6* (2012), Online Mendelian Inheritance in Man: John Hopkins University). SMEI mutations are heterozygous autosomal dominant mutations and are often caused by a gene deletion or truncation that leads to a channel with little or no function. The mutations arise de novo, or in a few cases have been shown to arise in asymptomatic mosaic parents (Tuncer, F. N. et al., *Epilepsy Research* (2015), Vol. 113, pp. 5-10). Patients are born phenotypically normal and meet developmental milestones until the onset of seizures, typically between the age of 6 months and 1 year. This time of onset is believed to be a consequence of the normal decrease in the expression of the embryonic isoform $Na_V1.3$ and the coincident rise of $Na_V1.1$. When the $Na_V1.1$ channels fail to reach normal levels, the phenotype is revealed (Cheah, C. S. et al., *Channels (Austin)* (2013), Vol. 7, pp. 468-472). The initial seizure is often triggered by a febrile episode and can manifest as status epilepticus. Seizures continue and increase in frequency and severity for the first several years of life and can reach frequencies of over 100 episodes per day. Seizures may be triggered by fever or may arise spontaneously without apparent cause. After seizure onset patients begin to miss developmental milestones and significant cognitive and behavioral deficits accrue (Dravet, C. and Oguni, H., *Handbook of Clinical Neurology* (2013), Vol. 111, pp. 627-633). 80 to 85% of phenotypically diagnosed Dravet syndrome patients are believed to have a responsible mutation in SCN1A, while the other 15-20% of patients have other mutations or are of unknown etiology. There is a high rate of sudden unexplained death in epilepsy (SUDEP) in SMEI patients, with an estimated 37% of patients dying by SUDEP, but the mechanism for this catastrophic outcome remains unclear (Massey, C. A., et al., *Nature Reviews Neurology* (2014), Vol. 10, pp. 271-282). Clinically useful anti-epileptic drugs that target voltage-gated sodium channels non-selectively, like carbamazepine and phenytoin, are contra-indicated for SMEI patients as they can exacerbate seizures in these patients (Wilmshurst, J. M. et al., *Epilepsia* (2015), Vol. 56, pp. 1185-1197). This is presumed to be because patients cannot tolerate further reductions in $Na_V1.1$ function.

GEFS+ is often caused by missense SCN1A mutations that induce relatively mild channel dysfunction, consistent with the relatively milder seizure phenotype. A large and growing number of mutations have been identified, and both the severity and the penetrance of the phenotype varies considerably. Many GEFS+ patients outgrow the seizure phenotype, however not all do, and GEFS+ patients with childhood epilepsy are considerably more prone to have epilepsy as adults than are the general population. Mutations that cause deficits in other genes involved with GABA-ergic signaling, like SCN1B that encodes the sodium channel auxiliary subunit and GABRG2 that encodes a subunit of $GABA_A$ receptors can also give rise to GEFS+ (Helbig, I., *Seminars in Neurology* (2015) Vol. 35, pp. 288-292).

Transgenic mice have been developed that harbor the same mutations identified in SMEI and GEFS+ patients. In both cases the mice replicate the human phenotype well, though the penetrance of the phenotype can be significantly impacted by the genetic background. Some mouse strains tolerate the mutations relatively well, while in other strains the same mutations can cause drastic seizure phenotypes. These differences are presumed to be due to differing levels of expression of other genes that modulate the excitation phenotype (Miller, A. R. et al., *Genes, Brain, and Behavior* (2014), Vol. 13, pp. 163-172; Mistry, A. M. et al., *Neurobiology of Disease* (2014), Vol. 65, pp. 1-11; and Hawkins, N. A. et al., *Epilepsy Research* (2016), Vol. 119, pp. 20-23).

In the brain, $Na_V1.2$ and $Na_V1.6$ are primarily expressed in excitatory glutamatergic neurons. Both channels are especially dense in the action initial segment (AIS), a region of the neuron adjacent to the neuronal soma that acts to integrate inputs and initiates action potential propagation to the soma and the distal dendrites (Royeck, M. et al., *J. Neurophysiol.* (2008), Vol. 100, pp. 2361-2380; Vega, A. V. et al., *Neurosci. Lett.* (2008), Vol. 442, pp. 69-73; and Hu, W. et al., *Nat. Neurosci.* (2009), Vol. 12, pp. 996-1002). $Na_V1.6$ tends to be especially densely localized the early AIS (distal from the soma) where it is thought to act to trigger action potential initiation. $Na_V1.2$ is more highly localized to the segment of the AIS most proximal to the soma. Mutations in both SCN2A ($Na_V1.2$) and SCN8A ($Na_V1.6$) have been linked to epilepsy and cognitive delay. The effects of the mutations are diverse both at the level of the impact on channel function, and on the patient phenotype. Both $Na_V1.2$ and $Na_V1.6$ are also expressed in peripheral neurons. $Na_V1.6$ is especially dense at the nodes of Ranvier of myelinated neurons, where it is critical for maintaining salutatory conduction and high speed neuronal signaling.

Only a handful of $Na_V1.2$ mutations have been described, but they are primarily linked with central nervous system pathologies, especially epilepsy (Kearney, J. A. et al., *Neuroscience* (2001), Vol. 102, pp. 307-317; Zerem, A. et al., *European Journal of Paediatric Neurology: EJPN: Official Journal of the European Paediatric Neurology Society* (2014), Vol. 18, pp. 567-571; Fukasawa, T. et al., *Brain & Development* (2015), Vol. 37, pp. 631-634; Howell, K. B. et al., *Neurology* (2015), Vol. 85, pp. 958-966; Saitoh, M. et al., *Epilepsy Research* (2015), Vol. 117, pp. 1-6; Samanta, D. et al., *Acta Neurologica Belgica* (2015), Vol. 115, pp. 773-776; Carroll, L. S. et al., *Psychiatric Genetics* (2016), Vol. 26, pp. 60-65; and Schwarz, N. et al., Journal of Neurology (2016), Vol. 263, pp. 334-343). The epilepsy mutations are presumed to be primarily gain of function mutations, meaning that they lead to an increase in the amount of sodium current and thereby increasing excitability. Establishing the impact on channel function in vivo beyond reasonable doubt is challenging and some of these mutations may yet lead to loss of function phenotypes.

Mutations in SCN8A have likewise been reported to show a range of gain and loss of function effects on the $Na_V1.6$ channel though, for $Na_V1.6$, most mutations examined have been associated with gain of function phenotypes. Mutations in $Na_V1.6$ have been linked with epilepsy and autism spectrum disorders (Trudeau, M. M. et al., *Journal of Medical Genetics* (2006), Vol. 43, pp. 527-530; Veeramah, K. R. et al., *Am. J. Hum. Genet.* (2012), Vol. 90, pp. 502-510; Vaher, U. et al., *Journal of Child Neurology* (2013); de Kovel, C. G. et al., *Epilepsy Research* (2014); Estacion, M. et al., *Neurobiology of Disease* (2014), Vol. 69, pp. 117-123; Ohba, C. et al., *Epilepsia* (2014), Vol. 55, pp. 994-1000; Wagnon, J. L. et al., *Human Molecular Genetics* (2014); Kong, W. et al., *Epilepsia* (2015), Vol. 56, pp. 431-438; and Larsen, J. et al., *Neurology* (2015), Vol. 84, pp. 480-489). The best described SCN8A mutant patients have a syndrome known as early infantile epileptic encephalopathy, 13 (EIEE13). Over 100 EIEE13 patients have been identified. Patients typically present with intractable seizures between birth and 18 months of age. Patients have developmental and cognitive delay, and motor impairment often associated with chronic muscular hypotonia. The most severely impacted patients never gain sufficient motor control to walk. Many are not verbal. Less severe phenotypes learn to walk and talk but are motor-impaired and miss cognitive and social milestones. Most of the identified mutations are missense mutations, and it is assumed that the specific functional impact of the mutation contributes to the variability in the phenotype, though genetic background is also likely involved (Larsen, J. et al., *Neurology* (2015), Vol. 84, pp. 480-489). In contrast to SMEI patients, anecdotal evidence suggests that antiepileptic drugs that target voltage-gated sodium channels non-selectively can ameliorate symptoms in EIEE13 patients, though no controlled clinical trials have been completed (Boerma, R. S. et al., *Neurotherapeutics: The Journal of the American Society for Experimental Neuro Therapeutics* (2016), Vol. 13, pp. 192-197). While phenytoin does seem to provide efficacy for EIEE13 patients, it does so at a cost. Efficacy is only achieved at very high doses where the significant adverse effects are tolerated only because the patients are in such dire need. Adverse effects commonly associated with phenytoin therapy include hepatic necrosis, hypertrichosis, nervousness, tremor of hands, numbness, dizziness, drowsiness, tremor, depression, confusion, fatigue, constipation, vertigo, ataxia, mental status changes, myasthenia, mood changes, restlessness, irritability, and excitement. It seems likely that a drug that selectively targets $Na_V1.6$ would retain efficacy while reducing its adverse event burden.

Loss of function mutations in SCN8A in mice lead to a phenotype known as motor endplate disease (med) and multiple mutations and phenotypes were linked to the med gene region prior to the identification of the SCN8A gene (Burgess, D. L. et al., *Nat. Genet.* (1995), Vol. 10, pp. 461-465). Mice with $SCN8A^{med}$ mutations have varying degrees of muscle hypotonia, consistent with the degree of dysfunction of the $Na_V1.6$ function. Mice with the $SCN8A^{med/jo}$ have $Na_V1.6$ channels that have a loss of function, but not null, phenotype. $SCN8A^{med}$ and $SCN8A^{med/jo}$ mice are resistant to seizures induced by chemical insult (flurothyl, kainic acid, and picrotoxin) (Martin, M. S. et al., *Human Molecular Genetics* (2007), Vol. 16, pp. 2892-2899; Hawkins, N. A. et al., *Neurobiology of Disease* (2011), Vol. 41, pp. 655-660; and Makinson, C. D. et al., *Neurobiology of Disease* (2014), Vol. 68, pp. 16-25). Curiously, when $SCN8A^{med/jo}$ mice are crossed with $SCN1A^{null}$ mutant mice to produce a mouse that is heterozygous for both the $SCN1A^{null}$ allele and the $SCN8A^{med/jo}$ allele the double mutant mice have a much improved seizure and cognitive phenotype than those with only an $SCN1A^{null}$ mutation (Martin, M. S. et al., *Human Molecular Genetics* (2007), Vol. 16, pp. 2892-2899). Such mice have a spontaneous seizure and death rate similar to wild type mice and their seizure threshold after chemical insult is also increased. A similar result occurs upon crossing mice with missense mutations of SCN1A (a model for GEFS+) and mice with SCN8A loss of function mutations. Having a single allele of $SCN8A^{med/jo}$ protected the GEFS+ model mice from seizures and premature death (Hawkins, N. A. et al., *Neurobiology of Disease* (2011), Vol. 41, pp. 655-660). The ability of SCN8A knock down to improve seizure resistance is not limited to knockouts where the gene is globally absent throughout animal development. Knock down of SCN8A in adult mice either globally or specifically in the hippocampus via a CRE-LOX inducible knockout approach also improved resistance to electrically and chemically induced seizures Makinson, C. D. et al., *Neurobiology of Disease* (2014), Vol. 68, pp. 16-25). These data suggest that the suppression of inhibitory signaling caused by decreased $Na_V1.1$ current can be offset, at least in part, by suppressing excitatory signaling via decreased in $Na_V1.6$ current.

Voltage-gated sodium channel antagonism is the most common mechanism of widely prescribed antiepileptic drugs (AED's) (Ochoa, J. R. et al., *Sodium Channel Blockers. In: Antiepileptic Drugs* (2016), Vol. (Benbadis, S., ed) Medscape News & Perspectives). Carbamazepine, Eslicarbazepine, Oxcarbazepine, Lacosamide, Lamotrigine, Phenytoin, Rufinamide and Zonisamide are all believed to act primarily by blocking that function of $Na_V$ channels. Despite the presumed mechanism of action, these drugs are relatively promiscuous. They block all $Na_V$ channel isoforms indiscriminately, thus block of $Na_V1.1$ would be expected to proconvulsant. Block of $Na_V1.6$, and perhaps $Na_V1.2$, would be anticonvulsant. In addition to sodium channels, these compounds also block other targets, including voltage-gated calcium channels. Selective $Na_V$ antagonists that spare $Na_V1.1$ and other off-target receptors are expected to have both improved efficacy and therapeutic index relative to the currently available $Na_V$ blocking drugs.

There is therefore an unmet medical need to treat epilepsy and other $Na_V1.6$ associated pathological states effectively and without adverse side effects due to the blocking of other sodium channels, such as $Na_V1.1$ and/or $Na_V1.5$. The present invention provides methods to meet these critical needs.

SUMMARY OF THE INVENTION

The present invention is directed to benzenesulfonamide compounds and pharmaceutical compositions comprising the compounds and methods of using the compounds and the pharmaceutical compositions of the invention for the treatment of diseases or conditions associated with the activity of voltage-gated sodium channels, particularly, $Na_V1.6$ activity, such as epilepsy and/or epileptic seizure disorder.

Accordingly, in one aspect, this invention is directed to benzenesulfonamide compounds of formula (I):

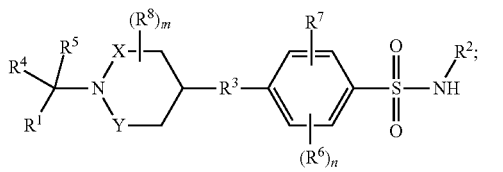

wherein:
n is 1, 2, 3;
m is 1, 2, 3 or 4;
X is a direct bond or —C($R^9$)$R^{10}$—;
Y is a direct bond or —C($R^{11}$)$R^{12}$—;
$R^1$ is hydrogen, alkyl, —$R^{17}$—$OR^{14}$, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;
$R^2$ is an optionally substituted 5-membered N-heteroaryl or an optionally substituted 6-membered N-heteroaryl;
$R^3$ is —O— or —N($R^{13}$)—;
$R^4$ and $R^5$ are each independently hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl or optionally substituted heteroarylalkyl;
or $R^4$ and $R^1$, together with the carbon to which they are attached, form an optionally substituted cycloalkyl, an optionally substituted heterocyclyl or an optionally substituted aryl, and $R^5$, if present, is hydrogen, alkyl, haloalkyl, optionally substituted cycloalkyl, optionally substituted cycloalkylalkyl, optionally substituted aryl, optionally substituted heterocyclyl, optionally substituted heterocyclylalkyl, optionally substituted heteroaryl or optionally substituted heteroarylalkyl;
each $R^6$ is independently hydrogen, alkyl, alkenyl, halo, haloalkyl, cyano, —$OR^{14}$ or optionally substituted cycloalkyl;
$R^7$ is alkyl, halo, haloalkyl, cyano or —$OR^{14}$;
each $R^8$ is independently hydrogen, alkyl, halo, haloalkyl or —$OR^{14}$;
or two $R^8$'s, together with the carbon to which they are both attached, may form an optionally substituted cycloalkyl;
$R^9$, $R^{10}$, $R^{11}$ and $R^{12}$ are each independently hydrogen, alkyl, haloalkyl or —$OR^{14}$;
or $R^9$ and $R^{11}$ form an optionally substituted alkylene chain and $R^{10}$ and $R^{12}$ are as defined above; and
$R^{13}$ is hydrogen, alkyl or haloalkyl;
each $R^{14}$ are each independently hydrogen, alky, haloalkyl, optionally substituted aryl or optionally substituted aralkyl; and
$R^{17}$ is a direct bond or an optionally substituted alkylene chain;
as an individual stereoisomer, enantiomer or tautomer thereof or a mixture thereof;
or a pharmaceutically acceptable salt, solvate or prodrug thereof;
provided that when $R^3$ is —O—, $R^2$ is not optionally substituted thiadiazolyl.

The compounds of the invention, which are compounds of formula (I), as described above, as individual stereoisomers, enantiomers or tautomers thereof or mixtures thereof; or as pharmaceutically acceptable salts, solvates or prodrugs thereof, are useful in treating diseases or conditions associated with voltage-gated sodium channels, preferably $Na_V1.6$. Preferably, the compounds of the invention are $Na_V1.6$ inhibitors. More preferably, the compounds of the invention show selectivity of inhibiting $Na_V1.6$ as compared with inhibiting $Na_V1.5$ and/or $Na_V1.1$. Without wishing to be bound by theory, such selectivity is thought to advantageously reduce any side effects which may be associated with the inhibition of $Na_V1.5$ and/or $Na_V1.1$.

In another aspect, the invention provides pharmaceutical compositions comprising a pharmaceutically acceptable excipient and a compound of formula (I), as described above, as a stereoisomer, enantiomer or tautomer thereof or mixtures thereof; or a pharmaceutically acceptable salt, solvate or prodrug thereof.

In another aspect, the invention provides methods for the treatment of epilepsy and/or epileptic seizure disorder in a mammal, preferably a human, wherein the methods comprise administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the present invention provides a method for treating or lessening the severity of a disease, condition, or disorder in a mammal where activation or hyperactivity of $Na_V1.6$ is implicated in the disease, condition or disorder, wherein the method comprises administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or ameliorating, but not preventing, epilepsy and/or epileptic seizure disorder in a mammal, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed herein.

In another aspect, this invention is directed to methods of selectively inhibiting a first voltage-gated sodium channel in a mammal over a second voltage-gated sodium channel, wherein the method comprises administering to the mammal a inhibitory amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a inhibitory amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, this invention is directed to the use of the compounds of the invention, as set forth above, as a stereoisomer, enantiomer or tautomer thereof or mixtures thereof, or a pharmaceutically acceptable salt, solvate or prodrug thereof, or the use of a pharmaceutical composition comprising a pharmaceutically acceptable excipient and a compound of the invention, as set forth above, as a stereoisomer, enantiomer or tautomer thereof or mixtures thereof, or a pharmaceutically acceptable salt, solvate or prodrug thereof, in the preparation of a medicament for the treatment of a disease or condition associated with the activity of a voltage-gated sodium channel, preferably $Na_V1.6$, in a mammal and preferably wherein the disease or condition is epilepsy and/or epileptic seizure disorder.

DETAILED DESCRIPTION OF THE INVENTION

Definitions

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: halo, cyano, nitro, aryl, cycloalkyl, heterocyclyl, heteroaryl, oxo, trimethylsilanyl, —$OR^{20}$, —OC(O)—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)_pR^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: halo, cyano, nitro, aryl, cycloalkyl, heterocyclyl, heteroaryl, oxo, trimethylsilanyl, —$OR^{20}$, —OC(O)—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)_pR^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. When specifically stated in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, $-OR^{20}$, $-OC(O)-R^{20}$, $-N(R^{20})_2$, $-C(O)R^{20}$, $-C(O)OR^{20}$, $-C(O)N(R^{20})_2$, $-N(R^{20})C(O)OR^{22}$, $-N(R^2)C(O)R^{22}$, $-N(R^{20})S(O)_pR^{22}$ (where p is 1 to 2), $-S(O)_pOR^{22}$ (where p is 1 to 2), $-S(O)_tR^{22}$ (where t is 0 to 2), and $-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl. Preferably, the optional substituents on an optionally substituted aryl group for $R^1$ herein are selected from alkyl, optionally substituted cycloalkyl, halo, haloalkyl, optionally substituted aryl, $-R^{21}-OR^{20}$, $-R^{21}-C(O)OR^{20}$ and $-R^{21}-N(R^{20})_2$ (where $R^{20}$ and $R^{21}$ are as defined above). Preferably, the optional substituents on an optionally substituted aryl group for $R^5$ herein are halo.

"Aralkyl" refers to a radical of the formula $-R_b-R_c$ where $R_b$ is an alkylene chain as defined above and $R_c$ is one or more aryl radicals as defined above, for example, benzyl, diphenylmethyl and the like. The alkylene chain part of the aralkyl radical may be optionally substituted as described above for an alkylene chain. The aryl part of the aralkyl radical may be optionally substituted as described above for an aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl. Preferably, the optional substituents on the optionally substituted cycloalkyl group when $R^4$ and $R^1$, together with the carbon to which they are attached, form an optionally substituted cycloalkyl herein are aryl.

"Cycloalkylalkyl" refers to a radical of the formula $-R_bR_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused, bridged and spiro ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heterocyclyl" refers to a heterocyclyl radical as defined above containing at least one nitrogen. The point of attachment of the N-heterocyclyl to the rest of the molecule can be through a nitrogen atom or a carbon atom in the N-heterocyclyl. When specifically stated in the specification, an N-heterocyclyl radical may be optionally substituted as described above for an optionally substituted heterocyclyl radical.

"Heterocyclylalkyl" refers to a radical of the formula $-R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkylene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, phthalazinyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^{21}-C(O)N(R^{20})_2$, $-R^{21}-N(R^{20})C(O)OR^{22}$, $-R^{21}-N(R^{20})C(O)R^{22}$, $-R^{21}-N(R^{20})S(O)_pR^{22}$ (where p is 1 to 2), $-R^{21}-N=C(OR^{20})R^{20}$, $-R^{21}-S(O)_pOR^{22}$ (where p is 1 to 2), $-R^{21}-S(O)_tR^{22}$ (where t is 0 to 2), and $-R^{21}-S(O)_pN(R^{20})_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. The point of attachment of the N-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical. Preferably, the optional substituents on an optionally substituted N-heteroaryl group for $R^1$ herein are alkyl, optionally substituted cycloalkyl, halo, haloalkyl, optionally substituted aryl, optionally substituted heterocyclyl and $-R^{21}-OR^{20}$ (where $R^{20}$ and $R^{21}$ are as defined above for heteroaryl groups). Preferably the optional substituents on an optionally substituted N-heteroaryl group for $R^2$ herein are halo.

"O-heteroaryl" refers to a heteroaryl radical as defined above wherein the only heteroatoms present are oxygen. The point of attachment of the O-heteroaryl to the rest of the molecule is through a carbon atom in the O-heteroaryl radical. When specifically stated in the specification, an O-heteroaryl radical may be optionally substituted as described above for an optionally substituted heteroaryl radical. Preferably, the optional substituents on an optionally substituted O-heteroaryl group for $R^1$ herein are alkyl and haloalkyl.

"S-heteroaryl" refers to a heteroaryl radical as defined above wherein the only heteroatoms present are sulfur. The point of attachment of the S-heteroaryl to the rest of the molecule is through a carbon atom in the S-heteroaryl radical. When specifically stated in the specification, an S-heteroaryl radical may be optionally substituted as described above for an optionally substituted heteroaryl radical. Preferably, the optional substituents on an optionally substituted S-heteroaryl group for $R^1$ herein are alkyl.

"Heteroarylalkyl" refers to a radical of the formula $-R_bR_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," *A.C.S. Symposium Series*, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of formula (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances. In one embodiment of the invention, the compounds of formula (I) are enriched with deuterium. Such deuterated compounds can be achieved by methods known to one skilled in the art, such as exchanging protons with deuterium or by synthesizing the molecule with enriched starting materials.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples and Preparations as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethane-sulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a sodium channel-mediated disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, e.g., relieving epilepsy without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry:*

Reactions, Mechanisms, and Structure, 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

The chemical naming protocol and structure diagrams used herein are a modified form of the I.U.P.A.C. nomenclature system, using ChemBioDraw Ultra Version 14.0 software program, wherein the compounds of the invention are named herein as derivatives of a central core structure, e.g., the benzenesulfonamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

"Enantiomers" refer to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions).

The designations, "R" and "S", for the absolute configuration of an enantiomer of the invention may appear as a prefix or as a suffix in the name of the compound; they may or may not be separated from the enantiomer name by a hyphen; they may or may not be hyphenated; and they may or may not be surrounded by parentheses.

Following the standard chemical literature description practice and as used in this specification, a solid full bond, as illustrated above in Structure (A) and a dashed full bond, as illustrated by the exemplary structure (A) below, means that the substituents are in a trans-configuration with respect to the plane of the ring:

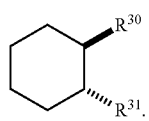

(A)

In the same manner, the bonds in the following exemplary structures (Aa) and (Ab) are in a cis-configuration with respect to the plane of the ring:

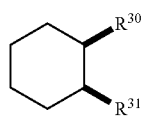

(Aa)

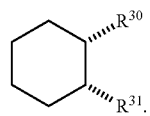

(Ab)

Following the standard chemical literature description practice and as used in this specification, a full wedge bond, as illustrated below in structure (B), means that the substituent bonded to the ring by this bond, in this case the $R^{30}$ substituent, is above the ring plane as illustrated on the page in a two dimensional representation, and a dashed wedge bond, as illustrated below in Structure (B), means that the substituent bonded to the ring by this bond, in this case the $R^{31}$ substituent, is below the ring plane as shown on the page in a two dimensional representation;

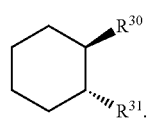

(B)

Following the standard chemical literature description practice and as used in this specification, a wavy bond, as illustrated below in structure (C), indicates that the substituent, in this case the $R^{30}$ substituent, is either below the plane of the ring or above the plane of the ring:

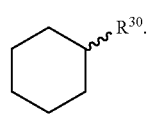

(C)

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, in the following structure (D), the bond attaching the $R^{30}$ substituent can be on any of the carbons, including the carbon to which the $R^{31}$ is attached, provided that the valency allows for such an attachment:

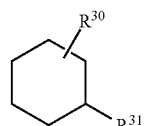

(D)

"Resolution" or "resolving" when used in reference to a racemic compound or a racemic mixture of a compound of the invention refers to the separation of the racemic compound or a racemic mixture into its two enantiomeric forms (i.e., (+) and (−); (R) and (S) forms).

"Enantiomeric excess" or "ee" as used herein refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purposes of this invention, the (S)-enantiomer of a compound prepared by the methods disclosed herein is considered to be "substantially free" of the corresponding (R)-enantiomer when the (S)-enantiomer is present in enantiomeric excess of greater than 80%, preferably greater than 90%, more preferably greater than 95% and most preferably greater than 99%.

The chemical naming protocol and structure diagrams used herein are a modified form of the I.U.P.A.C. nomenclature system, using ChemBioDraw Ultra Version 14.0 software program, wherein the compounds of the invention are named herein as derivatives of a central core structure, e.g., the benzenesulfonamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Accordingly, the (R) enantiomer of a compound of formula (I) as described above in the Summary of the Invention wherein n is 1, m is 1, X is a direct bond, Y is —C($R^{11}$)$R^{12}$—, $R^1$ is phenyl, $R^2$ is thiazol-2-yl, $R^3$ is —N($R^{13}$)—, $R^4$ and $R^5$ are each hydrogen, $R^6$ is hydrogen, $R^7$ is chloro, $R^{11}$ is hydrogen, $R^{12}$ is hydrogen and $R^{13}$ is hydrogen, i.e., the compound of the following formula:

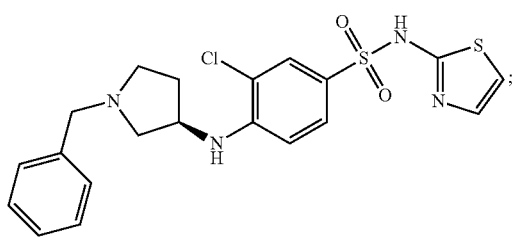 [SMILES: O=S(=O)(Nc1nccs1)c1ccc(N[C@@H]2CCN(Cc3ccccc3)C2)c(Cl)c1]

is named herein as (R)-4-(1-benzylpyrrolidin-3-ylamino)-3-chloro-N-(thiazol-2-yl)benzenesulfonamide.

EMBODIMENTS OF THE INVENTION

One aspect of the invention are compounds of formula (I) as set forth above in the Summary of the Invention, as an individual stereoisomer, enantiomer or tautomer thereof or a mixture thereof; or a pharmaceutically acceptable salt, solvate or prodrug thereof.

In one embodiment, a compound of formula (I) is a compound of formula (I) wherein $R^3$ is —O—, wherein the compound has the following formula (Ia):

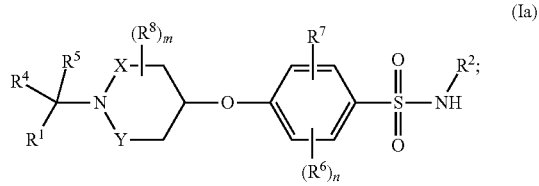

(Ia)

wherein m, n, X, Y, $R^1$, $R^2$, $R^4$, $R^5$, $R^6$, $R^7$ and $R^8$ are each as defined above in the Summary of the Invention for compounds of formula (I);
as an individual stereoisomer, enantiomer or tautomer thereof or a mixture thereof;
or a pharmaceutically acceptable salt, solvate or prodrug thereof.

In another embodiment, a compound of formula (I) is a compound of formula (Ia) as defined above wherein:
n is 1 or 2;
m is 1 or 2;
X is a direct bond or —C($R^9$)$R^{10}$—;
Y is a direct bond or —C($R^{11}$)$R^{12}$—;
$R^1$ is hydrogen, alkyl, —$R^{17}$—$OR^{14}$, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;
$R^2$ is an optionally substituted 5-membered N-heteroaryl or an optionally substituted 6-membered N-heteroaryl;
$R^4$ and $R^5$ are each independently hydrogen, alkyl or haloalkyl;
or $R^4$ and $R^1$, together with the carbon to which they are attached, form an optionally substituted cycloalkyl or an optionally substituted aryl, and $R^5$, if present, if present, is hydrogen, alkyl, haloalkyl or optionally substituted aryl;
each $R^6$ is independently hydrogen, alkyl, alkenyl, halo, haloalkyl, cyano, —$OR^{14}$ or optionally substituted cycloalkyl;
$R^7$ is alkyl, halo, haloalkyl, cyano or —$OR^{14}$;
each $R^8$ is independently hydrogen, alkyl, halo, haloalkyl or —$OR^{14}$; or two $R^8$'s, together with the carbon to which they are both attached, may form an optionally substituted cycloalkyl;
$R^9$, $R^{10}$, $R^{11}$ and $R^{12}$ are each independently hydrogen, alkyl, haloalkyl, alkyl or —$OR^{14}$;
or $R^9$ and $R^{11}$ form an optionally substituted alkylene chain and $R^{10}$ and $R^{12}$ are as defined above; and
$R^{13}$ is hydrogen, alkyl or haloalkyl;
each $R^{14}$ are each independently hydrogen, alky, haloalkyl, optionally substituted aryl or optionally substituted aralkyl; and
$R^{17}$ is a direct bond or an optionally substituted alkylene chain;
as an individual stereoisomer, enantiomer or tautomer thereof or a mixture thereof;
or a pharmaceutically acceptable salt, solvate or prodrug thereof.

In another embodiment, a compound of formula (I) is a compound of formula (Ia) wherein X and Y are both a direct bond, i.e., a compound of formula (Ia1):

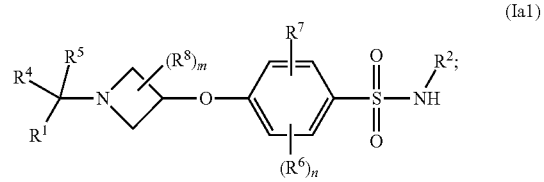

(Ia1)

wherein:
n is 1 or 2;
m is 1 or 2;

R¹ is hydrogen, alkyl, —R¹⁷—OR¹⁴, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;

R² is an optionally substituted 5-membered N-heteroaryl or an optionally substituted 6-membered N-heteroaryl;

R⁴ and R⁵ are each independently hydrogen, alkyl or haloalkyl;

or R⁴ and R¹, together with the carbon to which they are attached, form an optionally substituted cycloalkyl or an optionally substituted aryl, and R⁵, if present, if present, is hydrogen, alkyl, haloalkyl or optionally substituted aryl;

each R⁶ is independently hydrogen, alkyl, alkenyl, halo, haloalkyl, cyano, —OR¹⁴ or optionally substituted cycloalkyl;

R⁷ is alkyl, halo, haloalkyl, cyano or —OR¹⁴;

each R⁸ is independently hydrogen, alkyl, halo, haloalkyl or —OR¹⁴;

or two R⁸'s, together with the carbon to which they are both attached, may form an optionally substituted cycloalkyl;

each R¹⁴ are each independently hydrogen, alky, haloalkyl, optionally substituted aryl or optionally substituted aralkyl; and R¹⁷ is a direct bond or an optionally substituted alkylene chain;

as an individual stereoisomer, enantiomer or tautomer thereof or a mixture thereof;

or a pharmaceutically acceptable salt, solvate or prodrug thereof.

One embodiment of the compounds of formula (Ia1) are compounds of formula (Ia1) wherein R² is an optionally substituted 5-membered N-heteroaryl.

Of this embodiment, a preferred embodiment are compounds of formula (Ia1) wherein R² is optionally substituted isoxazolyl, optionally substituted thiazolyl or optionally substituted thiadiazolyl.

Of this embodiment, a preferred compound is 4-((1-benzylazetidin-3-yl)oxy)-3-chloro-N-(thiazol-2-yl)benzenesulfonamide.

Another preferred embodiment of the compounds of formula (Ia1) are compounds of formula (Ia1) wherein R² is an optionally substituted 6-membered N-heteroaryl.

Of this embodiment, a preferred embodiment are compounds of formula (Ia1) wherein R² is optionally substituted pyridinyl.

In another embodiment, the compound of formula (I) is a compound of formula (Ia) wherein X is —C(R⁹)R¹⁰— and Y is a direct bond, i.e., a compound of formula (Ia2):

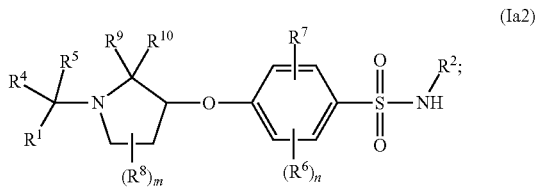

(Ia2)

wherein:
n is 1 or 2;
m is 1 or 2;
R¹ is hydrogen, alkyl, —R¹⁷—OR¹⁴, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;

R² is an optionally substituted 5-membered N-heteroaryl or an optionally substituted 6-membered N-heteroaryl;

R⁴ and R⁵ are each independently hydrogen, alkyl or haloalkyl;

or R⁴ and R¹, together with the carbon to which they are attached, form an optionally substituted cycloalkyl or an optionally substituted aryl, and R⁵, if present, if present, is hydrogen, alkyl, haloalkyl or optionally substituted aryl;

each R⁶ is independently hydrogen, alkyl, alkenyl, halo, haloalkyl, cyano, —OR¹⁴ or optionally substituted cycloalkyl;

R⁷ is alkyl, halo, haloalkyl, cyano or —OR¹⁴;

each R⁸ is independently hydrogen, alkyl, halo, haloalkyl or —OR¹⁴;

or two R⁸'s, together with the carbon to which they are both attached, may form an optionally substituted cycloalkyl;

R⁹ and R¹⁰ are each independently hydrogen, alkyl, haloalkyl, alkyl or —OR¹⁴;

each R¹⁴ are each independently hydrogen, alky, haloalkyl, optionally substituted aryl or optionally substituted aralkyl; and R¹⁷ is a direct bond or an optionally substituted alkylene chain;

as an individual stereoisomer, enantiomer or tautomer thereof or a mixture thereof; or a pharmaceutically acceptable salt, solvate or prodrug thereof.

One embodiment of the compounds of formula (Ia2) are compounds of formula (Ia2) wherein R² is an optionally substituted 5-membered N-heteroaryl.

Of this embodiment, a preferred embodiment are compounds of formula (Ia2) wherein R² is optionally substituted isoxazolyl, optionally substituted thiazolyl or optionally substituted thiadiazolyl.

Of the compounds of formula (Ia2), preferred compounds are selected from:
(S)-4-((1-benzyl-3-methylpyrrolidin-3-yl)oxy)-2,6-difluoro-3-methyl-N-(thiazol-4-yl)benzenesulfonamide;
(S)-4-((1-benzylpyrrolidin-3-yl)oxy)-3-ethyl-2,6-difluoro-N-(thiazol-4-yl)benzenesulfonamide;
(S)-4-((1-benzylpyrrolidin-3-yl)oxy)-3-bromo-2,6-difluoro-N-(thiazol-4-yl)benzenesulfonamide;
(S)-4-((1-benzyl-3-methylpyrrolidin-3-yl)oxy)-2,6-difluoro-3-methyl-N-(thiazol-2-yl)benzenesulfonamide;
(S)-4-((1-benzylpyrrolidin-3-yl)oxy)-2,6-difluoro-N-(thiazol-4-yl)-3-vinylbenzenesulfonamide;
rac-4-((1-benzyl-3-methylpyrrolidin-3-yl)oxy)-5-chloro-2-fluoro-N-(thiazol-4-yl)benzenesulfonamide;
(S)-4-((1-benzyl-3-methylpyrrolidin-3-yl)oxy)-5-chloro-2-fluoro-N-(thiazol-4-yl)benzenesulfonamide;
(R)-4-((1-benzyl-3-methylpyrrolidin-3-yl)oxy)-5-chloro-2-fluoro-N-(thiazol-4-yl)benzenesulfonamide;
(S)-4-((1-benzylpyrrolidin-3-yl)oxy)-2-fluoro-5-methyl-N-(thiazol-4-yl)benzenesulfonamide;
(S)-4-((1-benzyl-3-methylpyrrolidin-3-yl)oxy)-2-fluoro-5-methyl-N-(thiazol-4-yl)benzenesulfonamide;
(S)-4-((1-benzylpyrrolidin-3-yl)oxy)-2,6-difluoro-3-methyl-N-(thiazol-4-yl)benzenesulfonamide; and
(S)-4-((1-benzylpyrrolidin-3-yl)oxy)-3-chloro-2,6-difluoro-N-(thiazol-4-yl)benzenesulfonamide.

Another preferred embodiment of the compounds of formula (Ia2) are compounds of formula (Ia2) wherein R² is an optionally substituted 6-membered N-heteroaryl.

Of this embodiment, a preferred embodiment are compounds of formula (Ia2) wherein $R^2$ is optionally substituted pyridinyl.

In another embodiment, the compound of formula (I) is a compound of formula (Ia) wherein X is —C($R^9$)$R^{10}$— and Y is —C($R^{11}$)$R^{12}$—, i.e., a compound of formula (Ia3):

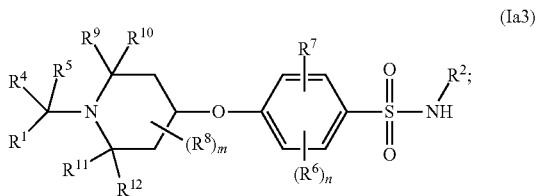

(Ia3)

n is 1 or 2;
m is 1 or 2;
X is a direct bond or —C($R^9$)$R^{10}$—;
Y is a direct bond or —C($R^{11}$)$R^{12}$—;
$R^1$ is hydrogen, alkyl, —$R^{17}$—O$R^{14}$, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;
$R^2$ is an optionally substituted 5-membered N-heteroaryl or an optionally substituted 6-membered N-heteroaryl;
$R^4$ and $R^5$ are each independently hydrogen, alkyl or haloalkyl;
or $R^4$ and $R^1$, together with the carbon to which they are attached, form an optionally substituted cycloalkyl or an optionally substituted aryl, and $R^5$, if present, if present, is hydrogen, alkyl, haloalkyl or optionally substituted aryl;
each $R^6$ is independently hydrogen, alkyl, alkenyl, halo, haloalkyl, cyano, —O$R^{14}$ or optionally substituted cycloalkyl;
$R^7$ is alkyl, halo, haloalkyl, cyano or —O$R^{14}$;
each $R^8$ is independently hydrogen, alkyl, halo, haloalkyl or —O$R^{14}$;
or two $R^8$'s, together with the carbon to which they are both attached, may form an optionally substituted cycloalkyl;
$R^9$, $R^{10}$, $R^{11}$ and $R^{12}$ are each independently hydrogen, alkyl, haloalkyl, alkyl or —O$R^{14}$;
or $R^9$ and $R^{11}$ form an optionally substituted alkylene chain and $R^{10}$ and $R^{12}$ are as defined above; and
each $R^{14}$ are each independently hydrogen, alky, haloalkyl, optionally substituted aryl or optionally substituted aralkyl; and
$R^{17}$ is a direct bond or an optionally substituted alkylene chain;
as an individual stereoisomer, enantiomer or tautomer thereof or a mixture thereof;
or a pharmaceutically acceptable salt, solvate or prodrug thereof.

Of this embodiment, a preferred embodiment are compounds of formula (Ia3) wherein $R^2$ is an optionally substituted 5-membered N-heteroaryl.

Of this embodiment, a more preferred embodiment are compounds of formula (Ia3) wherein $R^2$ is optionally substituted isoxazolyl, optionally substituted thiazolyl or optionally substituted thiadiazolyl.

Of this preferred embodiment, a preferred embodiment are compounds of formula (Ia3) wherein $R^1$ is optionally substituted aryl or optionally substituted aralkyl; and $R^9$, $R^{10}$, $R^{11}$ and $R^{12}$ are each independently hydrogen or alkyl.

Of the compounds of formula (Ia3), preferred compounds are selected from:
5-chloro-2-fluoro-4-(1-(1-phenylethyl)piperidin-4-yloxy)-N-(thiazol-2-yl)benzenesulfonamide;
3-chloro-4-(1-(1-phenylethyl)piperidin-4-yloxy)-N-(thiazol-2-yl)benzenesulfonamide;
3-chloro-4-(1-(3-fluorobenzyl)piperidin-4-yloxy)-N-(thiazol-2-yl)benzenesulfonamide;
3-chloro-4-(1-(3-(difluoromethyl)benzyl)piperidin-4-yloxy)-N-(thiazol-2-yl)benzenesulfonamide;
3-chloro-4-(1-(3-(difluoromethoxy)benzyl)piperidin-4-yloxy)-N-(thiazol-2-yl)benzenesulfonamide;
3-chloro-4-(1-((6-methylpyridin-2-yl)methyl)piperidin-4-yloxy)-N-(thiazol-2-yl)benzenesulfonamide;
3-chloro-4-(1-(3-methoxybenzyl)piperidin-4-yloxy)-N-(thiazol-2-yl)benzenesulfonamide;
3-chloro-4-(1-(3-chlorobenzyl)piperidin-4-yloxy)-N-(thiazol-2-yl)benzenesulfonamide;
3-chloro-4-(1-(2-fluorobenzyl)-3-methylpiperidin-4-yloxy)-N-(thiazol-2-yl)benzenesulfonamide;
3-chloro-4-(3-methyl-1-(3-methylbenzyl)piperidin-4-yloxy)-N-(thiazol-2-yl)benzenesulfonamide;
4-(1-benzyl-3-methylpiperidin-4-yloxy)-3-chloro-N-(thiazol-2-yl)benzenesulfonamide;
3-chloro-4-(1-(2-fluorobenzyl)-3-methylpiperidin-4-yloxy)-N-(thiazol-2-yl)benzenesulfonamide;
3-chloro-4-(3-methyl-1-(3-methylbenzyl)piperidin-4-yloxy)-N-(thiazol-2-yl)benzenesulfonamide;
4-(1-benzyl-3-methylpiperidin-4-yloxy)-3-chloro-N-(thiazol-2-yl)benzenesulfonamide;
3-chloro-4-(1-(naphthalen-2-ylmethyl)piperidin-4-yloxy)-N-(thiazol-2-yl)benzenesulfonamide;
3-chloro-4-(1-(2-fluorobenzyl)piperidin-4-yloxy)-N-(thiazol-2-yl)benzenesulfonamide;
3-chloro-4-(1-(2-methylbenzyl)piperidin-4-yloxy)-N-(thiazol-2-yl)benzenesulfonamide;
3-chloro-4-(1-(3-methylbenzyl)piperidin-4-yloxy)-N-(thiazol-2-yl)benzenesulfonamide;
3-chloro-4-(1-(pyridin-2-ylmethyl)piperidin-4-yloxy)-N-(thiazol-2-yl)benzenesulfonamide;
3-chloro-4-(1-(pyridin-3-ylmethyl)piperidin-4-yloxy)-N-(thiazol-2-yl)benzenesulfonamide;
3-chloro-4-(1-(pyridin-4-ylmethyl)piperidin-4-yloxy)-N-(thiazol-2-yl)benzenesulfonamide;
3-chloro-4-(1-(4-methoxybenzyl)piperidin-4-yloxy)-N-(thiazol-2-yl)benzenesulfonamide;
3-chloro-4-(1-(3,4-dimethylbenzyl)piperidin-4-yloxy)-N-(thiazol-2-yl)benzenesulfonamide;
3-chloro-4-(1-(3,5-dimethylbenzyl)piperidin-4-yloxy)-N-(thiazol-2-yl)benzenesulfonamide;
3-chloro-4-(1-(4-methylbenzyl)piperidin-4-yloxy)-N-(thiazol-2-yl)benzenesulfonamide;
4-(1-benzylpiperidin-4-yloxy)-5-chloro-2-fluoro-N-(thiazol-2-yl)benzenesulfonamide;
3-chloro-N-(thiazol-2-yl)-4-(1-(4-(trifluoromethyl)benzyl)piperidin-4-yloxy)benzenesulfonamide;
3-chloro-4-(1-(4-fluorobenzyl)piperidin-4-yloxy)-N-(thiazol-2-yl)benzenesulfonamide;
4-(1-benzylpiperidin-4-yloxy)-3-chloro-N-(thiazol-2-yl)benzenesulfonamide;
3-chloro-4-((1-(cyclohexylmethyl)piperidin-4-yl)oxy)-N-(thiazol-2-yl)benzenesulfonamide;
3-chloro-4-((1-cyclohexylpiperidin-4-yl)oxy)-N-(thiazol-2-yl)benzenesulfonamide;

3-chloro-N-(thiazol-2-yl)-4-((1-(2-(trifluoromethyl)benzyl)
piperidin-4-yl)oxy)benzenesulfonamide;
3-chloro-4-((1-(2-chlorobenzyl)piperidin-4-yl)oxy)-N-(thiazol-2-yl)benzenesulfonamide;
3-chloro-4-((1-((4-methylpyridin-2-yl)methyl)piperidin-4-yl)oxy)-N-(thiazol-2-yl)benzenesulfonamide;
4-((1-benzyl-4-methylpiperidin-4-yl)oxy)-3-chloro-N-(thiazol-2-yl)benzenesulfonamide;
3-chloro-4-((1-(3-chlorobenzyl)-4-methylpiperidin-4-yl)oxy)-N-(thiazol-2-yl)benzenesulfonamide;
3-chloro-4-((1-(3-difluoromethyl)benzyl)-4-methylpiperidin-4-yl)oxy)-N-(thiazol-2-yl)benzenesulfonamide;
3-chloro-4-((1-(2,3-dihydro-1H-inden-1-yl)piperidin-4-yl)oxy)-N-(thiazol-2-yl)benzenesulfonamide;
(R)-3-chloro-4-((1-(1-phenylethyl)piperidin-4-yl)oxy)-N-(thiazol-2-yl)benzenesulfonamide;
(R)-5-chloro-2-fluoro-4-((1-(1-phenylethyl)piperidin-4-yl)oxy)-N-(thiazol-2-yl)benzenesulfonamide;
(R)-3-chloro-4-((1-(1-phenylethyl)piperidin-4-yl)oxy)-N-(thiazol-4-yl)benzenesulfonamide;
(S)-3-chloro-4-((1-(1-phenylethyl)piperidin-4-yl)oxy)-N-(thiazol-2-yl)benzenesulfonamide;
3-chloro-4-((1-(2-phenylpropan-2-yl)piperidin-4-yl)oxy)-N-(thiazol-2-yl)benzenesulfonamide;
5-chloro-2-fluoro-4-((1-(2-phenylpropan-2-yl)piperidin-4-yl)oxy)-N-(thiazol-2-yl)benzenesulfonamide;
(R)-2,3-difluoro-4-((1-(1-phenylethyl)piperidin-4-yl)oxy)-N-(thiazol-4-yl)benzenesulfonamide;
(R)-3-chloro-2-fluoro-4-((1-(1-phenylethyl)piperidin-4-yl)oxy)-N-(thiazol-4-yl)benzenesulfonamide;
4-((1-benzylpiperidin-4-yl)oxy)-2-fluoro-3-methyl-N-(thiazol-4-yl)benzenesulfonamide;
4-((1-benzylpiperidin-4-yl)oxy)-5-chloro-2-fluoro-N-(thiazol-4-yl)benzenesulfonamide;
3-chloro-4-((1-(1-phenylcyclopropyl)piperidin-4-yl)oxy)-N-(thiazol-4-yl)benzenesulfonamide;
5-chloro-4-(((3R,4S)-1-(3-(difluoromethyl)benzyl)-3-fluoropiperidin-4-yl)oxy)-2-fluoro-N-(thiazol-4-yl)benzenesulfonamide;
(R)-5-chloro-2-fluoro-4-((1-(1-phenylethyl)piperidin-4-yl)oxy)-N-(thiazol-4-yl)benzenesulfonamide;
(R)-3-chloro-4-((1-(1-(5-chloro-2-fluorophenyl)ethyl)piperidin-4-yl)oxy)-N-(thiazol-4-yl)benzenesulfonamide;
(R)-2,6-difluoro-4-((1-(1-phenylethyl)piperidin-4-yl)oxy)-N-(thiazol-4-yl)benzenesulfonamide;
(R)-3-chloro-N-(isoxazol-3-yl)-4-((1-(1-phenylethyl)piperidin-4-yl)oxy)benzenesulfonamide;
3-chloro-4-((1-phenethylpiperidin-4-yl)oxy)-N-(thiazol-2-yl)benzenesulfonamide;
(R)-3-chloro-4-((1-(1-(2-fluoro-5-(trifluoromethyl)phenyl)ethyl)piperidin-4-yl)oxy)-N-(thiazol-4-yl)benzenesulfonamide;
4-((1-benzylpiperidin-4-yl)oxy)-2,6-difluoro-3-methyl-N-(thiazol-2-yl)benzenesulfonamide;
4-((1-benzylpiperidin-4-yl)oxy)-2,6-difluoro-N-(thiazol-4-yl)benzenesulfonamide;
4-((cis-1-benzyl-2-methylpiperidin-4-yl)oxy)-3-chloro-N-(thiazol-2-yl)benzenesulfonamide; and
4-((trans-1-benzyl-2-methylpiperidin-4-yl)oxy)-3-chloro-N-(thiazol-2-yl)benzenesulfonamide.
(R)-3-chloro-4-((1-(1-(5-cyclopropyl-2-fluorophenyl)ethyl)piperidin-4-yl)oxy)-N-(thiazol-4-yl)benzenesulfonamide;
(R)-3-chloro-4-((1-(1-(5-(difluoromethyl)-2-fluorophenyl)ethyl)piperidin-4-yl)oxy)-N-(thiazol-4-yl)benzenesulfonamide;
(R)-3-chloro-2,6-difluoro-4-((1-(1-phenylethyl)piperidin-4-yl)oxy)-N-(thiazol-4-yl)benzenesulfonamide;
3-chloro-4-((1-(3-(difluoromethyl)benzyl)piperidin-4-yl)oxy)-N-(thiazol-4-yl)benzenesulfonamide;
(R)-5-chloro-2-fluoro-4-((1-(1-(2-fluoro-5-(trifluoromethyl)phenyl)ethyl)piperidin-4-yl)oxy)-N-(thiazol-4-yl)benzenesulfonamide;
4-((1-benzylpiperidin-4-yl)oxy)-2-fluoro-5-methyl-N-(thiazol-4-yl)benzenesulfonamide;
(R)-2,6-difluoro-3-methyl-4-((1-(1-phenylethyl)piperidin-4-yl)oxy)-N-(thiazol-4-yl)benzenesulfonamide;
4-((1-benzylpiperidin-4-yl)oxy)-3-chloro-2,6-difluoro-N-(thiazol-4-yl)benzenesulfonamide; and
4-((1-benzylpiperidin-4-yl)oxy)-2,6-difluoro-3-methyl-N-(thiazol-4-yl)benzenesulfonamide.

Another preferred embodiment of the compounds of formula (Ia3) are the compounds of formula (Ia3) wherein:
$R^1$ is optionally substituted aryl or optionally substituted aralkyl;
$R^9$ and $R^{11}$ form an optionally substituted alkylene chain; and
$R^{11}$ and $R^{12}$ are each independently hydrogen or alkyl.

Of this embodiment, preferred compounds of formula (Ia3) are selected from:
4-((1R,3s,5S)-8-benzyl-8-azabicyclo[3.2.1]octan-3-yloxy)-3-chloro-N-(thiazol-2-yl)benzenesulfonamide;
4-((1R,3r,5S)-8-benzyl-8-azabicyclo[3.2.1]octan-3-yloxy)-3-chloro-N-(thiazol-2-yl)benzenesulfonamide;
4-(((1R,3s,5S)-8-benzyl-8-azabicyclo[3.2.1]octan-3-yl)oxy)-5-chloro-2-fluoro-N-(thiazol-2-yl)benzenesulfonamide;
5-chloro-4-(((1R,3s,5S)-8-(3-chlorobenzyl)-8-azabicyclo[3.2.1]octan-3-yl)oxy)-2-fluoro-N-(thiazol-2-yl)benzenesulfonamide;
3-chloro-4-(((1R,3s,5S)-8-(5-chloro-2-fluorobenzyl)-8-azabicyclo[3.2.1]octan-3-yl)oxy)-N-(thiazol-4-yl)benzenesulfonamide;
4-(((1R,3s,5S)-8-benzyl-8-azabicyclo[3.2.1]octan-3-yl)oxy)-3-chloro-N-(thiazol-4-yl)benzenesulfonamide;
3-chloro-4-(((1R,3s,5S)-8-(3-chloro-4-fluorobenzyl)-8-azabicyclo[3.2.1]octan-3-yl)oxy)-N-(thiazol-4-yl)benzenesulfonamide; and
3-chloro-4-(((1R,3s,5S)-8-(3-(difluoromethyl)benzyl)-8-azabicyclo[3.2.1]octan-3-yl)oxy)-N-(thiazol-4-yl)benzenesulfonamide.

Another preferred embodiment of the compounds of formula (Ia3) are compounds of formula (Ia3) wherein $R^2$ is an optionally substituted 6-membered N-heteroaryl.

Of this embodiment, a preferred embodiment are compounds of formula (Ia3) wherein $R^2$ is optionally substituted pyridinyl or optionally substituted pyrimidinyl.

Of this embodiment, preferred compounds of formula (Ia3) are selected from:
(R)-3-chloro-4-((1-(1-phenylethyl)piperidin-4-yl)oxy)-N-(pyrimidin-4-yl)benzenesulfonamide;
(R)-3-chloro-N-(5-fluoropyrimidin-2-yl)-4-((1-(1-phenylethyl)piperidin-4-yl)oxy)benzenesulfonamide;
(S)-3-chloro-4-((1-(1-phenylethyl)piperidin-4-yl)oxy)-N-(pyrimidin-4-yl)benzenesulfonamide;
4-((1-benzylpiperidin-4-yl)oxy)-3-chloro-N-(6-fluoropyridin-2-yl)benzenesulfonamide; and
4-((1-benzylpiperidin-4-yl)oxy)-3-chloro-2-fluoro-N-(6-fluoropyridin-2-yl)benzenesulfonamide.

In another embodiment, a compound of formula (I) is a compound of formula (I) wherein $R^3$ is —N($R^{13}$)—, wherein the compound has the following formula (Ib):

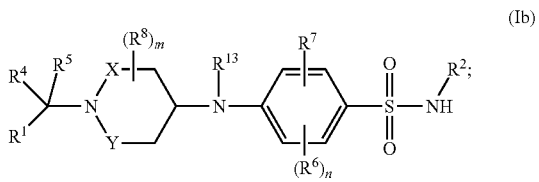
(Ib)

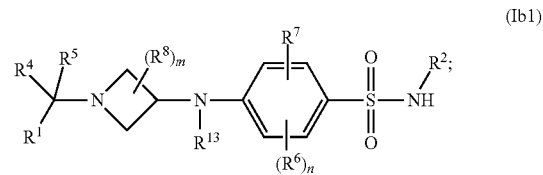
(Ib1)

wherein m, n, X, Y, $R^1$, $R^2$, $R^4$, $R^5$, $R^6$, $R^7$, R and $R^{13}$ are each as defined above in the Summary of the Invention for compounds of formula (I);

as an individual stereoisomer, enantiomer or tautomer thereof or a mixture thereof;

or a pharmaceutically acceptable salt, solvate or prodrug thereof.

In another embodiment, the compound of formula (I) is a compound of formula (Ib) as defined above wherein:

n is 1 or 2;

m is 1 or 2;

X is a direct bond or —$C(R^9)R^{10}$—;

Y is a direct bond or —$C(R^{11})R^{12}$—;

$R^1$ is hydrogen, alkyl, —$R^{17}$—$OR^{14}$, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;

$R^2$ is an optionally substituted 5-membered N-heteroaryl or an optionally substituted 6-membered N-heteroaryl;

$R^4$ and $R^5$ are each independently hydrogen, alkyl or haloalkyl;

or $R^4$ and $R^1$, together with the carbon to which they are attached, form an optionally substituted cycloalkyl or an optionally substituted aryl, and $R^5$, if present, if present, is hydrogen, alkyl, haloalkyl or optionally substituted aryl;

each $R^6$ is independently hydrogen, alkyl, alkenyl, halo, haloalkyl, cyano, —$OR^{14}$ or optionally substituted cycloalkyl;

$R^7$ is alkyl, halo, haloalkyl, cyano or —$OR^{14}$;

each $R^8$ is independently hydrogen, alkyl, halo, haloalkyl or —$OR^{14}$;

or two $R^8$'s, together with the carbon to which they are both attached, may form an optionally substituted cycloalkyl;

$R^9$, $R^{10}$, $R^{11}$ and $R^{12}$ are each independently hydrogen, alkyl, haloalkyl, alkyl or —$OR^{14}$;

or $R^9$ and $R^{11}$ form an optionally substituted alkylene chain and $R^{10}$ and $R^{12}$ are as defined above; and $R^{13}$ is hydrogen, alkyl or haloalkyl;

each $R^{14}$ are each independently hydrogen, alky, haloalkyl, optionally substituted aryl or optionally substituted aralkyl; and $R^{17}$ is a direct bond or an optionally substituted alkylene chain;

as an individual stereoisomer, enantiomer or tautomer thereof or a mixture thereof;

or a pharmaceutically acceptable salt, solvate or prodrug thereof.

In another embodiment, the compound of formula (I) is a compound of formula (Ib) wherein X and Y are both a direct bond, i.e., a compound of formula (Ib1):

n is 1 or 2;

m is 1 or 2;

$R^1$ is hydrogen, alkyl, —$R^{17}$—$OR^{14}$, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;

$R^2$ is an optionally substituted 5-membered N-heteroaryl or an optionally substituted 6-membered N-heteroaryl;

$R^4$ and $R^5$ are each independently hydrogen, alkyl or haloalkyl;

or $R^4$ and $R^1$, together with the carbon to which they are attached, form an optionally substituted cycloalkyl or an optionally substituted aryl, and $R^5$, if present, if present, is hydrogen, alkyl, haloalkyl or optionally substituted aryl;

each $R^6$ is independently hydrogen, alkyl, alkenyl, halo, haloalkyl, cyano, —$OR^{14}$ or optionally substituted cycloalkyl;

$R^7$ is alkyl, halo, haloalkyl, cyano or —$OR^{14}$;

each $R^8$ is independently hydrogen, alkyl, halo, haloalkyl or —$OR^{14}$;

or two $R^8$'s, together with the carbon to which they are both attached, may form an optionally substituted cycloalkyl;

$R^{13}$ is hydrogen, alkyl or haloalkyl;

each $R^{14}$ are each independently hydrogen, alky, haloalkyl, optionally substituted aryl or optionally substituted aralkyl; and $R^{17}$ is a direct bond or an optionally substituted alkylene chain;

as an individual stereoisomer, enantiomer or tautomer thereof or a mixture thereof;

or a pharmaceutically acceptable salt, solvate or prodrug thereof.

One embodiment of the compounds of formula (Ib1) are compounds of formula (Ib1) wherein $R^2$ is an optionally substituted 5-membered N-heteroaryl.

Of this embodiment, a preferred embodiment are compounds of formula (Ib1) wherein $R^2$ is optionally substituted isoxazolyl, optionally substituted thiazolyl or optionally substituted thiadiazolyl.

Of this embodiment, preferred compounds of formula (Ib1) are selected from:

4-((1-benzyl-3-methylazetidin-3-yl)amino)-2,6-difluoro-3-methyl-N-(thiazol-4-yl)benzenesulfonamide 2,2,2-trifluoroacetate;

4-((1-benzyl-3-methylazetidin-3-yl)amino)-2,6-difluoro-3-methyl-N-(thiazol-4-yl)benzenesulfonamide;

4-((1-benzyl-3-methylazetidin-3-yl)amino)-3-chloro-N-(thiazol-4-yl)benzenesulfonamide;

4-((1-benzyl-3-methylazetidin-3-yl)amino)-3-chloro-N-(thiazol-2-yl)benzenesulfonamide; and 4-((1-benzylazetidin-3-yl)amino)-3-chloro-N-(thiazol-2-yl)benzenesulfonamide.

Another preferred embodiment of the compounds of formula (Ib1) are compounds of formula (Ib1) wherein $R^2$ is an optionally substituted 6-membered N-heteroaryl.

Of this embodiment, a preferred embodiment are compounds of formula (Ib1) wherein $R^2$ is optionally substituted pyridinyl.

In another embodiment, the compound of formula (I) is a compound of formula (Ib) wherein X is $—C(R^9)R^{10}—$ and Y is a direct bond, i.e., a compound of formula (Ib2):

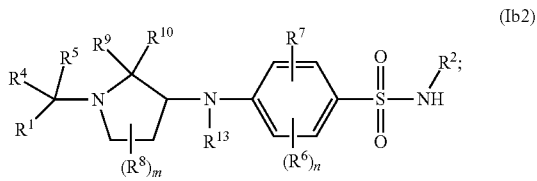

(Ib2)

n is 1 or 2;

m is 1 or 2;

$R^1$ is hydrogen, alkyl, $—R^{17}—OR^{14}$, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;

$R^2$ is an optionally substituted 5-membered N-heteroaryl or an optionally substituted 6-membered N-heteroaryl;

$R^4$ and $R^5$ are each independently hydrogen, alkyl or haloalkyl;

or $R^4$ and $R^1$, together with the carbon to which they are attached, form an optionally substituted cycloalkyl or an optionally substituted aryl, and $R^5$, if present, if present, is hydrogen, alkyl, haloalkyl or optionally substituted aryl;

each $R^6$ is independently hydrogen, alkyl, alkenyl, halo, haloalkyl, cyano, $—OR^{14}$ or optionally substituted cycloalkyl;

$R^7$ is alkyl, halo, haloalkyl, cyano or $—OR^{14}$;

each $R^8$ is independently hydrogen, alkyl, halo, haloalkyl or $—OR^{14}$;

or two $R^8$'s, together with the carbon to which they are both attached, may form an optionally substituted cycloalkyl;

$R^9$ and $R^{10}$ are each independently hydrogen, alkyl, haloalkyl, alkyl or $—OR^{14}$;

$R^{13}$ is hydrogen, alkyl or haloalkyl;

each $R^{14}$ are each independently hydrogen, alky, haloalkyl, optionally substituted aryl or optionally substituted aralkyl; and $R^{17}$ is a direct bond or an optionally substituted alkylene chain;

as an individual stereoisomer, enantiomer or tautomer thereof or a mixture thereof;

or a pharmaceutically acceptable salt, solvate or prodrug thereof.

One embodiment of the compounds of formula (Ia2) are compounds of formula (Ib2) wherein $R^2$ is an optionally substituted 5-membered N-heteroaryl.

Of this embodiment, a preferred embodiment are compounds of formula (Ia2) wherein $R^2$ is optionally substituted isoxazolyl, optionally substituted thiazolyl or optionally substituted thiadiazolyl.

Of this embodiment, a preferred embodiment are compounds of formula (Ia2) wherein $R^2$ is optionally substituted thiadiazolyl.

Of this embodiment, preferred compounds of formula (Ib2) are selected from:
(S)-3-chloro-4-((1-(3,5-difluorobenzyl)pyrrolidin-3-yl)(methyl)amino)-N-(1,2,4-thiadiazol-5-yl)benzenesulfonamide;
(S)-3-chloro-4-((1-(2,5-difluorobenzyl)pyrrolidin-3-yl)(methyl)amino)-N-(1,2,4-thiadiazol-5-yl)benzenesulfonamide;
(S)-4-((1-benzylpyrrolidin-3-yl)(methyl)amino)-2,6-difluoro-3-methyl-N-(1,2,4-thiadiazol-5-yl)benzenesulfonamide;
(S)-3-chloro-4-((1-(2,6-difluorobenzyl)pyrrolidin-3-yl)(methyl)amino)-N-(1,2,4-thiadiazol-5-yl)benzenesulfonamide;
(S)-3-chloro-4-((1-(2-chlorobenzyl)pyrrolidin-3-yl)(methyl)amino)-N-(1,2,4-thiadiazol-5-yl)benzenesulfonamide;
(S)-2,6-difluoro-3-methyl-4-(methyl(1-((6-methylpyridin-2-yl)methyl)pyrrolidin-3-yl)amino)-N-(1,2,4-thiadiazol-5-yl)benzenesulfonamide;
(S)-3-chloro-2,6-difluoro-4-(methyl(1-((6-methylpyridin-2-yl)methyl)pyrrolidin-3-yl)amino)-N-(1,2,4-thiadiazol-5-yl)benzenesulfonamide;
(S)-4-((1-benzylpyrrolidin-3-yl)(methyl)amino)-2,6-difluoro-3-methyl-N-(1,2,4-thiadiazol-5-yl)benzenesulfonamide;
(S)-3-chloro-4-(ethyl(1-(3-methylbenzyl)pyrrolidin-3-yl)amino)-N-(1,2,4-thiadiazol-5-yl)benzenesulfonamide;
(S)-4-((1-benzylpyrrolidin-3-yl)(ethyl)amino)-3-chloro-N-(1,2,4-thiadiazol-5-yl)benzenesulfonamide;
(S)-3-chloro-4-(methyl(1-(3-methylbenzyl)pyrrolidin-3-yl)amino)-N-(1,2,4-thiadiazol-5-yl)benzenesulfonamide;
(S)-4-((1-benzylpyrrolidin-3-yl)(methyl)amino)-3-chloro-N-(1,2,4-thiadiazol-5-yl)benzenesulfonamide;
(R)-4-((1-benzylpyrrolidin-3-yl)(methyl)amino)-3-chloro-N-(1,2,4-thiadiazol-5-yl)benzenesulfonamide;
(S)-4-(1-benzylpyrrolidin-3-ylamino)-3-chloro-N-(1,2,4-thiadiazol-5-yl)benzenesulfonamide;
(R)-4-(1-benzylpyrrolidin-3-ylamino)-3-chloro-N-(1,2,4-thiadiazol-5-yl)benzenesulfonamide;
4-(1-benzylpyrrolidin-3-ylamino)-3-chloro-N-(1,2,4-thiadiazol-5-yl)benzenesulfonamide;
(S)-3-chloro-4-((1-(3-chlorobenzyl)pyrrolidin-3-yl)(methyl)amino)-N-(1,2,4-thiadiazol-5-yl)benzenesulfonamide;
(S)-3-chloro-4-((1-(3-(difluoromethyl)benzyl)pyrrolidin-3-yl)(methyl)amino)-N-(1,2,4-thiadiazol-5-yl)benzenesulfonamide;
(S)-3-chloro-4-((1-(3-chloro-2-fluorobenzyl)pyrrolidin-3-yl)(methyl)amino)-N-(1,2,4-thiadiazol-5-yl)benzenesulfonamide;
(S)-3-chloro-4-((1-(5-chloro-2-fluorobenzyl)pyrrolidin-3-yl)(methyl)amino)-N-(1,2,4-thiadiazol-5-yl)benzenesulfonamide;
(S)-3-chloro-4-((1-(2-fluoro-3-methylbenzyl)pyrrolidin-3-yl)(methyl)amino)-N-(1,2,4-thiadiazol-5-yl)benzenesulfonamide; and
(S)-3-chloro-4-((1-(2-fluoro-5-methylbenzyl)pyrrolidin-3-yl)(methyl)amino)-N-(1,2,4-thiadiazol-5-yl)benzenesulfonamide.

Of the preferred embodiment of compounds of formula (Ib2) wherein $R^2$ is optionally substituted isoxazolyl, optionally substituted thiazolyl or optionally substituted thiadiazolyl, a preferred embodiment are compounds of formula (Ib2) wherein $R^1$ is optionally substituted aryl or optionally substituted aralkyl; and $R^2$ is optionally substituted thiazolyl or isoxazolyl.

Of this preferred embodiment, preferred compounds of formula (Ib2) are selected from:

(S)-4-((1-benzylpyrrolidin-3-yl)(methyl)amino)-5-bromo-2-fluoro-N-(thiazol-4-yl)benzenesulfonamide;
(S)-4-((1-benzylpyrrolidin-3-yl)amino)-2-fluoro-5-methyl-N-(thiazol-4-yl)benzenesulfonamide;
(S)-5-chloro-2-fluoro-4-((1-(3-(2-hydroxypropan-2-yl)benzyl)pyrrolidin-3-yl)(methyl)amino)-N-(thiazol-4-yl)benzenesulfonamide;
(S)-5-chloro-4-((1-(5-chloro-2-fluorobenzyl)pyrrolidin-3-yl)(methyl)amino)-2-fluoro-N-(thiazol-4-yl)benzenesulfonamide;
(S)-5-chloro-2-fluoro-4-((1-(2-fluoro-4-methylbenzyl)pyrrolidin-3-yl)(methyl)amino)-N-(thiazol-4-yl)benzenesulfonamide;
(S)-5-chloro-2-fluoro-4-(methyl(1-(3-phenylpropyl)pyrrolidin-3-yl)amino)-N-(thiazol-4-yl)benzenesulfonamide;
(S)-4-((1-(2-(difluoromethyl)benzyl)pyrrolidin-3-yl)(methyl)amino)-2-fluoro-5-methyl-N-(thiazol-4-yl)benzenesulfonamide;
(S)-2-fluoro-4-((1-(2-hydroxybenzyl)pyrrolidin-3-yl)(methyl)amino)-5-methyl-N-(thiazol-4-yl)benzenesulfonamide;
(S)-2-fluoro-4-((1-(3-hydroxybenzyl)pyrrolidin-3-yl)(methyl)amino)-5-methyl-N-(thiazol-4-yl)benzenesulfonamide;
(R)-4-((1-benzylpyrrolidin-3-yl)amino)-2-fluoro-5-methyl-N-(thiazol-4-yl)benzenesulfonamide;
(S)-5-chloro-4-((1-(3-(difluoromethoxy)benzyl)pyrrolidin-3-yl)(methyl)amino)-2-fluoro-N-(thiazol-4-yl)benzenesulfonamide;
(S)-4-((1-benzylpyrrolidin-3-yl)(methyl)amino)-5-cyclopropyl-2-fluoro-N-(thiazol-4-yl)benzenesulfonamide;
(S)-5-chloro-4-((1-(2,5-dichlorobenzyl)pyrrolidin-3-yl)(methyl)amino)-2-fluoro-N-(thiazol-4-yl)benzenesulfonamide;
5-chloro-2-fluoro-4-(methyl((S)-1-((R)-1-phenylpropyl)pyrrolidin-3-yl)amino)-N-(thiazol-4-yl)benzenesulfonamide;
(S)-5-chloro-2-fluoro-4-(methyl(1-(4-propylbenzyl)pyrrolidin-3-yl)amino)-N-(thiazol-4-yl)benzenesulfonamide;
(S)-5-chloro-2-fluoro-4-((1-(2-fluoro-5-methylbenzyl)pyrrolidin-3-yl)(methyl)amino)-N-(thiazol-4-yl)benzenesulfonamide;
(S)-4-((1-benzylpyrrolidin-3-yl)(methyl)amino)-3-chloro-2-fluoro-N-(thiazol-4-yl)benzenesulfonamide;
(R)-4-((1-benzylpyrrolidin-3-yl)(methyl)amino)-5-chloro-2-fluoro-N-(thiazol-4-yl)benzenesulfonamide;
(S)-4-((1-(3-(difluoromethyl)benzyl)pyrrolidin-3-yl)(methyl)amino)-2,6-difluoro-N-(thiazol-4-yl)benzenesulfonamide;
(S)-5-chloro-2-fluoro-4-(methyl(1-(2-phenylpropan-2-yl)pyrrolidin-3-yl)amino)-N-(thiazol-4-yl)benzenesulfonamide;
3-chloro-4-(methyl((S)-1-((R)-1-phenylethyl)pyrrolidin-3-yl)amino)-N-(thiazol-4-yl)benzenesulfonamide;
(S)-2-fluoro-5-methyl-4-(methyl(1-phenethylpyrrolidin-3-yl)amino)-N-(thiazol-4-yl)benzenesulfonamide;
(S)-4-((1-benzylpyrrolidin-3-yl)(methyl)amino)-2-fluoro-N-(isothiazol-3-yl)-5-methylbenzenesulfonamide;
(S)-4-((1-benzylpyrrolidin-3-yl)(methyl)amino)-2,6-difluoro-N-(isothiazol-3-yl)-3-methylbenzenesulfonamide;
(S)-2-fluoro-4-((1-(2-fluorobenzyl)pyrrolidin-3-yl)(methyl)amino)-5-methyl-N-(thiazol-4-yl)benzenesulfonamide;
(S)-4-((1-benzylpyrrolidin-3-yl)(ethyl)amino)-2-fluoro-5-methyl-N-(thiazol-4-yl)benzenesulfonamide;
(S)-4-((1-benzylpyrrolidin-3-yl)(methyl)amino)-3-methyl-N-(thiazol-4-yl)benzenesulfonamide;
methyl (S)-3-((3-((2-chloro-5-fluoro-4-(N-(thiazol-4-yl)sulfamoyl)phenyl)(methyl)amino)pyrrolidin-1-yl)methyl)benzoate;
(S)-5-chloro-4-((1-(2-chlorobenzyl)pyrrolidin-3-yl)(methyl)amino)-2-fluoro-N-(thiazol-4-yl)benzenesulfonamide;
(S)-5-chloro-4-((1-(4-(dimethylamino)benzyl)pyrrolidin-3-yl)(methyl)amino)-2-fluoro-N-(thiazol-4-yl)benzenesulfonamide;
(S)-4-((1-benzylpyrrolidin-3-yl)(ethyl)amino)-5-chloro-2-fluoro-N-(thiazol-4-yl)benzenesulfonamide;
(S)-4-((1-benzyl-3-methylpyrrolidin-3-yl)amino)-3-chloro-N-(thiazol-4-yl)benzenesulfonamide;
(S)-3-chloro-4-((1-(5-chloro-2-fluorobenzyl)pyrrolidin-3-yl)(methyl)amino)-N-(thiazol-4-yl)benzenesulfonamide;
(S)-4-((1-benzylpyrrolidin-3-yl)(methyl)amino)-5-bromo-2-fluoro-N-(thiazol-4-yl)benzenesulfonamide;
(S)-2-fluoro-4-((1-(3-fluorobenzyl)pyrrolidin-3-yl)(methyl)amino)-5-methyl-N-(thiazol-4-yl)benzenesulfonamide;
(S)-4-((1-(2,5-difluorobenzyl)pyrrolidin-3-yl)(methyl)amino)-2,6-difluoro-3-methyl-N-(thiazol-4-yl)benzenesulfonamide;
(S)-4-((1-benzylpyrrolidin-3-yl)(methyl)amino)-5-ethyl-2-fluoro-N-(thiazol-4-yl)benzenesulfonamide;
(S)-5-chloro-2-fluoro-4-((1-(3-isopropoxybenzyl)pyrrolidin-3-yl)(methyl)amino)-N-(thiazol-4-yl)benzenesulfonamide;
(S)-5-chloro-2-fluoro-4-(methyl(1-(4-methylbenzyl)pyrrolidin-3-yl)amino)-N-(thiazol-4-yl)benzenesulfonamide;
(S)-5-chloro-4-((1-(2,6-dimethylbenzyl)pyrrolidin-3-yl)(methyl)amino)-2-fluoro-N-(thiazol-4-yl)benzenesulfonamide;
(S)-5-chloro-2-fluoro-4-((1-(3-fluoro-2-methylbenzyl)pyrrolidin-3-yl)(methyl)amino)-N-(thiazol-4-yl)benzenesulfonamide;
(S)-5-chloro-2-fluoro-4-(methyl(1-phenethylpyrrolidin-3-yl)amino)-N-(thiazol-4-yl)benzenesulfonamide;
(S)-5-chloro-4-((1-(3-chloro-2-fluorobenzyl)pyrrolidin-3-yl)(methyl)amino)-2-fluoro-N-(thiazol-4-yl)benzenesulfonamide;
(S)-5-chloro-2-fluoro-4-((1-(2-methoxybenzyl)pyrrolidin-3-yl)(methyl)amino)-N-(thiazol-4-yl)benzenesulfonamide;
(S)-5-chloro-2-fluoro-4-((1-(4-fluorobenzyl)pyrrolidin-3-yl)(methyl)amino)-N-(thiazol-4-yl)benzenesulfonamide;
4-(((2R,3R)-1-benzyl-2-methylpyrrolidin-3-yl)(methyl)amino)-5-chloro-2-fluoro-N-(thiazol-4-yl)benzenesulfonamide;
(S)-4-((1-benzylpyrrolidin-3-yl)amino)-5-chloro-2-fluoro-N-(thiazol-4-yl)benzenesulfonamide;
3-chloro-4-(methyl((S)-1-((S)-1-phenylethyl)pyrrolidin-3-yl)amino)-N-(thiazol-4-yl)benzenesulfonamide;
(S)-4-((1-(2,3-difluorobenzyl)pyrrolidin-3-yl)(methyl)amino)-2-fluoro-5-methyl-N-(thiazol-4-yl)benzenesulfonamide;
(S)-4-((1-(2,3-difluorobenzyl)pyrrolidin-3-yl)(methyl)amino)-2,6-difluoro-3-methyl-N-(thiazol-4-yl)benzenesulfonamide;
(S)-2,6-difluoro-4-((1-(2-fluorobenzyl)pyrrolidin-3-yl)(methyl)amino)-3-methyl-N-(thiazol-4-yl)benzenesulfonamide;
(S)-4-((1-(3-(difluoromethyl)benzyl)pyrrolidin-3-yl)(methyl)amino)-2-fluoro-3-methyl-N-(thiazol-4-yl)benzenesulfonamide;

(S)-4-((1-(2,5-difluorobenzyl)pyrrolidin-3-yl)(methyl) amino)-2-fluoro-3-methyl-N-(thiazol-4-yl)benzenesulfonamide;

(S)-4-((1-benzylpyrrolidin-3-yl)(methyl)amino)-2,6-difluoro-N-(thiazol-4-yl)benzenesulfonamide;

(S)-5-chloro-4-((1-(2,5-difluorobenzyl)pyrrolidin-3-yl) (methyl)amino)-2-fluoro-N-(thiazol-4-yl)benzenesulfonamide;

(S)-5-chloro-4-((1-(3-chlorobenzyl)pyrrolidin-3-yl) (methyl)amino)-2-fluoro-N-(thiazol-4-yl)benzenesulfonamide;

(S)-3-chloro-4-((1-(2-fluoro-5-methylbenzyl)-3-methylpyrrolidin-3-yl)amino)-N-(thiazol-4-yl)benzenesulfonamide;

(S)-4-((1-benzylpyrrolidin-3-yl)(methyl)amino)-2,5-difluoro-N-(thiazol-4-yl)benzenesulfonamide;

(S)-2-fluoro-4-((1-(2-methoxybenzyl)pyrrolidin-3-yl) (methyl)amino)-5-methyl-N-(thiazol-4-yl)benzenesulfonamide;

4-(((3S,5S)-1-benzyl-5-methylpyrrolidin-3-yl)(methyl) amino)-5-chloro-2-fluoro-N-(thiazol-4-yl)benzenesulfonamide;

5-chloro-4-(((S)-1-((S)-1-(2-chlorophenyl)propyl)pyrrolidin-3-yl)(methyl)amino)-2-fluoro-N-(thiazol-4-yl)benzenesulfonamide;

(S)-5-chloro-4-((1-(2-(difluoromethoxy)benzyl)pyrrolidin-3-yl)(methyl)amino)-2-fluoro-N-(thiazol-4-yl)benzenesulfonamide;

(S)-5-chloro-2-fluoro-4-((1-(4-fluoro-3-methylbenzyl)pyrrolidin-3-yl)(methyl)amino)-N-(thiazol-4-yl)benzenesulfonamide;

5-chloro-2-fluoro-4-(methyl((S)-1-((S)-1-phenylpropyl) pyrrolidin-3-yl)amino)-N-(thiazol-4-yl)benzenesulfonamide;

4-((1-benzyl-3-methylpyrrolidin-3-yl)(methyl)amino)-3-chloro-N-(thiazol-2-yl)benzenesulfonamide;

(S)-5-chloro-4-((1-(4-chlorobenzyl)pyrrolidin-3-yl) (methyl)amino)-2-fluoro-N-(thiazol-4-yl)benzenesulfonamide;

(R)-4-((1-benzylpyrrolidin-3-yl)amino)-5-chloro-2-fluoro-N-(thiazol-4-yl)benzenesulfonamide;

(S)-4-((1-benzylpyrrolidin-3-yl)(methyl)amino)-2-fluoro-N-(isothiazol-4-yl)-5-methylbenzenesulfonamide;

(S)-2,6-difluoro-4-((1-(3-fluorobenzyl)pyrrolidin-3-yl) (methyl)amino)-3-methyl-N-(thiazol-4-yl)benzenesulfonamide;

(R)-4-((1-benzylpyrrolidin-3-yl)(methyl)amino)-2-fluoro-5-methyl-N-(thiazol-4-yl)benzenesulfonamide;

(S)-4-((1-benzylpyrrolidin-3-yl)(methyl)amino)-5-(difluoromethyl)-2-fluoro-N-(thiazol-4-yl)benzenesulfonamide;

(S)-5-chloro-2-fluoro-4-(methyl(1-(2-methylbenzyl)pyrrolidin-3-yl)amino)-N-(thiazol-4-yl)benzenesulfonamide;

(S)-5-chloro-2-fluoro-4-((1-(2-hydroxybenzyl)pyrrolidin-3-yl)(methyl)amino)-N-(thiazol-4-yl)benzenesulfonamide;

(S)-5-chloro-2-fluoro-4-((1-(3-fluorobenzyl)pyrrolidin-3-yl)(methyl)amino)-N-(thiazol-4-yl)benzenesulfonamide;

(S)-5-chloro-4-((1-(2,3-difluorobenzyl)pyrrolidin-3-yl) (methyl)amino)-2-fluoro-N-(thiazol-4-yl)benzenesulfonamide;

(S)-5-chloro-2-fluoro-4-(methyl(1-(3-(trifluoromethyl)benzyl)pyrrolidin-3-yl)amino)-N-(thiazol-4-yl)benzenesulfonamide;

(S)-5-chloro-2-fluoro-4-((1-(2-fluoro-3-methylbenzyl)pyrrolidin-3-yl)(methyl)amino)-N-(thiazol-4-yl)benzenesulfonamide;

(S)-5-chloro-2-fluoro-4-((1-(2-fluoro-5-methoxybenzyl) pyrrolidin-3-yl)(methyl)amino)-N-(thiazol-4-yl)benzenesulfonamide;

(S)-5-chloro-4-((1-(3-(difluoromethyl)benzyl)pyrrolidin-3-yl)(methyl)amino)-2-fluoro-N-(thiazol-4-yl)benzenesulfonamide;

(R)-4-((1-benzyl-3-methylpyrrolidin-3-yl)amino)-3-chloro-N-(thiazol-4-yl)benzenesulfonamide;

(S)-2-fluoro-5-methyl-4-(methyl(1-(2-methylbenzyl)pyrrolidin-3-yl)amino)-N-(thiazol-4-yl)benzenesulfonamide;

(S)-2-fluoro-4-((1-(4-hydroxybenzyl)pyrrolidin-3-yl) (methyl)amino)-5-methyl-N-(thiazol-4-yl)benzenesulfonamide;

(S)-4-((1-benzylpyrrolidin-3-yl)(methyl)amino)-N-(thiazol-4-yl)-3-(trifluoromethyl)benzenesulfonamide;

(S)-2-fluoro-4-((1-(2-fluoro-3-methylbenzyl)pyrrolidin-3-yl)(methyl)amino)-5-methyl-N-(thiazol-4-yl)benzenesulfonamide;

(S)-4-((1-(2,5-difluorobenzyl)pyrrolidin-3-yl)(methyl) amino)-3-methyl-N-(thiazol-4-yl)benzenesulfonamide;

(S)-4-((1-benzylpyrrolidin-3-yl)(methyl)amino)-2-fluoro-3-methyl-N-(thiazol-4-yl)benzenesulfonamide;

(S)-4-((1-(4-bromobenzyl)pyrrolidin-3-yl)(methyl)amino)-5-chloro-2-fluoro-N-(thiazol-4-yl)benzenesulfonamide;

(S)-5-chloro-2-fluoro-4-((1-(2-fluorobenzyl)pyrrolidin-3-yl)(methyl)amino)-N-(thiazol-4-yl)benzenesulfonamide;

(S)-5-chloro-2-fluoro-4-((1-(3-methoxybenzyl)pyrrolidin-3-yl)(methyl)amino)-N-(thiazol-4-yl)benzenesulfonamide;

(S)-5-chloro-4-((1-(2-chloro-6-fluorobenzyl)pyrrolidin-3-yl)(methyl)amino)-2-fluoro-N-(thiazol-4-yl)benzenesulfonamide;

(S)-3-chloro-4-((1-(3-(difluoromethyl)benzyl)pyrrolidin-3-yl)(methyl)amino)-N-(thiazol-4-yl)benzenesulfonamide;

(S)-4-((5-benzyl-5-azaspiro[2.4]heptan-7-yl)amino)-5-chloro-2-fluoro-N-(thiazol-4-yl)benzenesulfonamide;

(S)-4-((5-benzyl-5-azaspiro[2.4]heptan-7-yl)(methyl) amino)-5-chloro-2-fluoro-N-(thiazol-4-yl)benzenesulfonamide;

(S)-4-((1-benzylpyrrolidin-3-yl)(methyl)amino)-2,6-difluoro-3-methyl-N-(thiazol-4-yl)benzenesulfonamide;

(S)-4-((1-benzylpyrrolidin-3-yl)(methyl)amino)-3-chloro-2,6-difluoro-N-(thiazol-4-yl)benzenesulfonamide;

(S)-4-((1-benzylpyrrolidin-3-yl)(methyl)amino)-2-fluoro-5-methyl-N-(thiazol-4-yl)benzenesulfonamide;

(R)-4-(1-benzylpyrrolidin-3-ylamino)-3-chloro-N-(thiazol-2-yl)benzenesulfonamide;

(S)-4-((1-benzylpyrrolidin-3-yl)(methyl)amino)-3-chloro-N-(thiazol-2-yl)benzenesulfonamide;

(S)-5-chloro-2-fluoro-4-(1-(3-methylbenzyl)pyrrolidin-3-ylamino)-N-(thiazol-2-yl)benzenesulfonamide;

(S)-4-(1-benzylpyrrolidin-3-ylamino)-5-chloro-2-fluoro-N-(thiazol-2-yl)benzenesulfonamide;

(R)-5-chloro-2-fluoro-4-(1-(3-methylbenzyl)pyrrolidin-3-ylamino)-N-(thiazol-2-yl)benzenesulfonamide;

(R)-4-(1-benzylpyrrolidin-3-ylamino)-5-chloro-2-fluoro-N-(thiazol-2-yl)benzenesulfonamide;

(S)-3-chloro-4-((1-(3-chlorobenzyl)pyrrolidin-3-yl) (methyl)amino)-N-(thiazol-2-yl)benzenesulfonamide;

(S)-3-chloro-4-((1-(3-(difluoromethyl)benzyl)pyrrolidin-3-yl)(methyl)amino)-N-(thiazol-2-yl)benzenesulfonamide;

(S)-4-((1-benzylpyrrolidin-3-yl)(methyl)amino)-5-chloro-2-fluoro-N-(thiazol-4-yl)benzenesulfonamide;

(S)-4-((1-benzylpyrrolidin-3-yl)(methyl)amino)-5-chloro-2-fluoro-N-(thiazol-2-yl)benzenesulfonamide bis(trifluoroacetic acid) salt;

(S)-4-((1-benzylpyrrolidin-3-yl)(methyl)amino)-3-chloro-N-(thiazol-4-yl)benzenesulfonamide;

3-chloro-4-(methyl((S)-1-((S)-1-phenylethyl)pyrrolidin-3-yl)amino)-N-(thiazol-2-yl)benzenesulfonamide;

3-chloro-4-(methyl((S)-1-((R)-1-phenylethyl)pyrrolidin-3-yl)amino)-N-(thiazol-2-yl)benzenesulfonamide;
4-((1-benzyl-3-methylpyrrolidin-3-yl)amino)-3-chloro-N-(thiazol-2-yl)benzenesulfonamide;
(S)-3-chloro-4-(methyl(1-(2-phenylpropan-2-yl)pyrrolidin-3-yl)amino)-N-(thiazol-4-yl)benzenesulfonamide;
(R)-3-chloro-4-((1-(3-chlorobenzyl)pyrrolidin-3-yl)amino)-N-(thiazol-2-yl) benzenesulfonamide;
(R)-3-chloro-4-((1-(3-methylbenzyl)pyrrolidin-3-yl)amino)-N-(thiazol-2-yl) benzenesulfonamide;
(R)-3-chloro-4-((1-(2-fluorobenzyl)pyrrolidin-3-yl)amino)-N-(thiazol-2-yl) benzenesulfonamide;
4-((trans-1-benzyl-4-methylpyrrolidin-3-yl)amino)-3-chloro-N-(thiazol-2-yl)benzenesulfonamide;
4-((cis-1-benzyl-4-methylpyrrolidin-3-yl)amino)-3-chloro-N-(thiazol-2-yl)benzenesulfonamide; and
(S)-4-((1-benzylpyrrolidin-3-yl)(methyl)amino)-2-fluoro-N-(isoxazol-3-yl)-5-methylbenzenesulfonamide.

Of the preferred embodiment of compounds of formula (Ib2) wherein $R^2$ is optionally substituted isoxazolyl, optionally substituted thiazolyl or optionally substituted thiadiazolyl, another preferred embodiment are compounds of formula (Ib2) wherein:
$R^1$ is an optionally substituted N-heterocyclyl, an optionally substituted N-heteroaryl, an optionally substituted O-heteroaryl or an optionally substituted S-heteroaryl; and
$R^2$ is optionally substituted thiazolyl.

Of this preferred embodiment, preferred compounds of formula (Ib2) are selected from:
(S)-4-((1-((1,4-dimethyl-1H-imidazol-2-yl)methyl)pyrrolidin-3-yl)(methyl)amino)-2-fluoro-5-methyl-N-(thiazol-4-yl)benzenesulfonamide;
(S)-2-fluoro-5-methyl-4-(methyl(1-((4-methylthiazol-2-yl)methyl)pyrrolidin-3-yl)amino)-N-(thiazol-4-yl)benzenesulfonamide;
(S)-2-fluoro-5-methyl-4-(methyl(1-(pyridin-2-ylmethyl)pyrrolidin-3-yl)amino)-N-(thiazol-4-yl)benzenesulfonamide;
(S)-2-fluoro-5-methyl-4-(methyl(1-((1-(2,2,2-trifluoroethyl)-1H-pyrazol-5-yl)methyl)pyrrolidin-3-yl)amino)-N-(thiazol-4-yl)benzenesulfonamide;
(S)-2-fluoro-5-methyl-4-(methyl(1-((2-methylthiazol-4-yl)methyl)pyrrolidin-3-yl)amino)-N-(thiazol-4-yl)benzenesulfonamide;
(S)-2-fluoro-5-methyl-4-(methyl(1-((1-methyl-1H-pyrazol-3-yl)methyl)pyrrolidin-3-yl)amino)-N-(thiazol-4-yl)benzenesulfonamide;
(S)-2-fluoro-4-((1-((3-fluoro-6-methylpyridin-2-yl)methyl)pyrrolidin-3-yl)(methyl)amino)-5-methyl-N-(thiazol-4-yl)benzenesulfonamide;
(S)-4-((1-((1-benzyl-1H-pyrazol-4-yl)methyl)pyrrolidin-3-yl)(methyl)amino)-5-chloro-2-fluoro-N-(thiazol-4-yl)benzenesulfonamide;
(S)-5-chloro-2-fluoro-4-(methyl(1-((5-(trifluoromethyl)furan-2-yl)methyl)pyrrolidin-3-yl)amino)-N-(thiazol-4-yl)benzenesulfonamide;
(S)-2-fluoro-5-methyl-4-(methyl(1-((2-methyloxazol-4-yl)methyl)pyrrolidin-3-yl)amino)-N-(thiazol-4-yl)benzenesulfonamide;
(S)-2-fluoro-5-methyl-4-(methyl(1-((5-methylfuran-2-yl)methyl)pyrrolidin-3-yl)amino)-N-(thiazol-4-yl)benzenesulfonamide;
(S)-2-fluoro-4-((1-((2-isopropyloxazol-4-yl)methyl)pyrrolidin-3-yl)(methyl)amino)-5-methyl-N-(thiazol-4-yl)benzenesulfonamide;
(S)-5-chloro-2-fluoro-4-((1-((6-methoxypyridin-2-yl)methyl)pyrrolidin-3-yl)(methyl)amino)-N-(thiazol-4-yl)benzenesulfonamide;
(S)-5-chloro-2-fluoro-4-((1-((3-fluoro-6-methylpyridin-2-yl)methyl)pyrrolidin-3-yl)(methyl)amino)-N-(thiazol-4-yl)benzenesulfonamide;
(S)-5-chloro-2-fluoro-4-(methyl(1-(quinolin-8-ylmethyl)pyrrolidin-3-yl)amino)-N-(thiazol-4-yl)benzenesulfonamide;
(S)-4-((1-((4-cyclopropylthiazol-2-yl)methyl)pyrrolidin-3-yl)(methyl)amino)-2-fluoro-5-methyl-N-(thiazol-4-yl)benzenesulfonamide;
(S)-4-((1-((6-(azetidin-1-yl)pyridin-2-yl)methyl)pyrrolidin-3-yl)(methyl)amino)-5-chloro-2-fluoro-N-(thiazol-4-yl)benzenesulfonamide;
(S)-2-fluoro-5-methyl-4-(methyl(1-((2-phenylthiazol-4-yl)methyl)pyrrolidin-3-yl)amino)-N-(thiazol-4-yl)benzenesulfonamide;
(S)-2-fluoro-5-methyl-4-(methyl(1-(thiazol-2-ylmethyl)pyrrolidin-3-yl)amino)-N-(thiazol-4-yl)benzenesulfonamide;
(S)-2-fluoro-5-methyl-4-(methyl(1-((2-(trifluoromethyl)thiazol-4-yl)methyl)pyrrolidin-3-yl)amino)-N-(thiazol-4-yl)benzenesulfonamide;
(S)-4-((1-((2-cyclopropylthiazol-4-yl)methyl)pyrrolidin-3-yl)(methyl)amino)-2-fluoro-5-methyl-N-(thiazol-4-yl)benzenesulfonamide;
(S)-2-fluoro-5-methyl-4-(methyl(1-((4-methyloxazol-2-yl)methyl)pyrrolidin-3-yl)amino)-N-(thiazol-4-yl)benzenesulfonamide;
(S)-2-fluoro-4-((1-((3-isopropoxypyridin-2-yl)methyl)pyrrolidin-3-yl)(methyl)amino)-5-methyl-N-(thiazol-4-yl)benzenesulfonamide;
(S)-2-fluoro-4-((1-((3-fluoro-6-methylpyridin-2-yl)methyl)pyrrolidin-3-yl)(methyl)amino)-3-methyl-N-(thiazol-4-yl)benzenesulfonamide;
(S)-5-chloro-2-fluoro-4-((1-((3-methoxypyridin-2-yl)methyl)pyrrolidin-3-yl)(methyl)amino)-N-(thiazol-4-yl)benzenesulfonamide;
(S)-4-((1-((6-bromopyridin-2-yl)methyl)pyrrolidin-3-yl)(methyl)amino)-5-chloro-2-fluoro-N-(thiazol-4-yl)benzenesulfonamide;
(S)-4-((1-((1H-pyrrol-2-yl)methyl)pyrrolidin-3-yl)(methyl)amino)-5-chloro-2-fluoro-N-(thiazol-4-yl)benzenesulfonamide;
(S)-5-chloro-2-fluoro-4-(methyl(1-((5-methylfuran-2-yl)methyl)pyrrolidin-3-yl)amino)-N-(thiazol-4-yl)benzenesulfonamide;
(S)-2-fluoro-5-methyl-4-(methyl(1-(thiazol-4-ylmethyl)pyrrolidin-3-yl)amino)-N-(thiazol-4-yl)benzenesulfonamide;
(S)-4-((1-((1,5-dimethyl-1H-pyrazol-3-yl)methyl)pyrrolidin-3-yl)(methyl)amino)-2-fluoro-5-methyl-N-(thiazol-4-yl)benzenesulfonamide;
(S)-3-chloro-2,6-difluoro-4-(methyl(1-((6-methylpyridin-2-yl)methyl)pyrrolidin-3-yl)amino)-N-(thiazol-4-yl)benzenesulfonamide;
(S)-5-chloro-2-fluoro-4-(methyl(1-((1-methyl-1H-pyrrol-2-yl)methyl)pyrrolidin-3-yl)amino)-N-(thiazol-4-yl)benzenesulfonamide;
(S)-4-((1-((1H-indol-3-yl)methyl)pyrrolidin-3-yl)(methyl)amino)-5-chloro-2-fluoro-N-(thiazol-4-yl)benzenesulfonamide;
(S)-2-fluoro-5-methyl-4-(methyl(1-((5-(trifluoromethyl)furan-2-yl)methyl)pyrrolidin-3-yl)amino)-N-(thiazol-4-yl)benzenesulfonamide;
(S)-2-fluoro-5-methyl-4-(methyl(1-(oxazol-4-ylmethyl)pyrrolidin-3-yl)amino)-N-(thiazol-4-yl)benzenesulfonamide;

(S)-2-fluoro-5-methyl-4-(methyl(1-((1-(2,2,2-trifluoro-ethyl)-1H-pyrazol-3-yl)methyl)pyrrolidin-3-yl)amino)-N-(thiazol-4-yl)benzenesulfonamide;

(S)-2-fluoro-4-((1-((3-methoxypyridin-2-yl)methyl)pyrrolidin-3-yl)(methyl)amino)-5-methyl-N-(thiazol-4-yl)benzenesulfonamide;

(S)-5-chloro-2-fluoro-4-(methyl(1-((1-methyl-1H-pyrazol-3-yl)methyl)pyrrolidin-3-yl)amino)-N-(thiazol-4-yl)benzenesulfonamide;

(S)-5-chloro-2-fluoro-4-((1-(imidazo[1,5-a]pyridin-3-ylmethyl)pyrrolidin-3-yl)(methyl)amino)-N-(thiazol-4-yl)benzenesulfonamide;

(S)-5-chloro-2-fluoro-4-(methyl(1-((2-(trifluoromethyl)pyridin-4-yl)methyl)pyrrolidin-3-yl)amino)-N-(thiazol-4-yl)benzenesulfonamide;

(S)-5-chloro-4-((1-((6-(difluoromethyl)pyridin-2-yl)methyl)pyrrolidin-3-yl)(methyl)amino)-2-fluoro-N-(thiazol-4-yl)benzenesulfonamide;

(S)-5-chloro-2-fluoro-4-((1-(isoquinolin-8-ylmethyl)pyrrolidin-3-yl)(methyl)amino)-N-(thiazol-4-yl)benzenesulfonamide;

(S)-5-chloro-2-fluoro-4-(methyl(1-((6-(trifluoromethyl)pyridin-2-yl)methyl)pyrrolidin-3-yl)amino)-N-(thiazol-4-yl)benzenesulfonamide;

(S)-2-fluoro-4-((1-((2-isopropylthiazol-4-yl)methyl)pyrrolidin-3-yl)(methyl)amino)-5-methyl-N-(thiazol-4-yl)benzenesulfonamide;

(S)-4-((1-(benzo[d]thiazol-2-ylmethyl)pyrrolidin-3-yl)(methyl)amino)-2-fluoro-5-methyl-N-(thiazol-4-yl)benzenesulfonamide;

(S)-2-fluoro-5-methyl-4-(methyl(1-((5-methylisothiazol-3-yl)methyl)pyrrolidin-3-yl)amino)-N-(thiazol-4-yl)benzenesulfonamide;

(S)-2-fluoro-5-methyl-4-(methyl(1-(pyrazolo[1,5-a]pyridin-2-ylmethyl)pyrrolidin-3-yl)amino)-N-(thiazol-4-yl)benzenesulfonamide;

(S)-4-((1-((1H-indol-5-yl)methyl)pyrrolidin-3-yl)(methyl)amino)-5-chloro-2-fluoro-N-(thiazol-4-yl)benzenesulfonamide;

(S)-5-chloro-2-fluoro-4-(methyl(1-(thiophen-2-ylmethyl)pyrrolidin-3-yl)amino)-N-(thiazol-4-yl)benzenesulfonamide;

(S)-5-chloro-2-fluoro-4-(methyl(1-((4-methylpyridin-2-yl)methyl)pyrrolidin-3-yl)amino)-N-(thiazol-4-yl)benzenesulfonamide;

(S)-5-chloro-2-fluoro-4-(methyl(1-((6-methylpyridin-2-yl)methyl)pyrrolidin-3-yl)amino)-N-(thiazol-4-yl)benzenesulfonamide;

(S)-2-fluoro-4-((1-((4-isopropylthiazol-2-yl)methyl)pyrrolidin-3-yl)(methyl)amino)-5-methyl-N-(thiazol-4-yl)benzenesulfonamide;

(S)-4-((1-((5-chlorothiazol-2-yl)methyl)pyrrolidin-3-yl)(methyl)amino)-2-fluoro-5-methyl-N-(thiazol-4-yl)benzenesulfonamide;

(S)-4-((1-((1-(difluoromethyl)-1H-pyrazol-3-yl)methyl)pyrrolidin-3-yl)(methyl)amino)-2-fluoro-5-methyl-N-(thiazol-4-yl)benzenesulfonamide;

(S)-2,6-difluoro-3-methyl-4-(methyl(1-((6-(trifluoromethyl)pyridin-2-yl)methyl)pyrrolidin-3-yl)amino)-N-(thiazol-4-yl)benzenesulfonamide;

(S)-5-chloro-4-((1-((6-(difluoromethyl)-3-fluoropyridin-2-yl)methyl)pyrrolidin-3-yl)(methyl)amino)-2-fluoro-N-(thiazol-4-yl)benzenesulfonamide;

(S)-5-chloro-2-fluoro-4-(methyl(1-((5-methylthiophen-2-yl)methyl)pyrrolidin-3-yl)amino)-N-(thiazol-4-yl)benzenesulfonamide;

(S)-4-((1-((1-(2,2-difluoroethyl)-1H-pyrazol-3-yl)methyl)pyrrolidin-3-yl)(methyl)amino)-2-fluoro-5-methyl-N-(thiazol-4-yl)benzenesulfonamide;

(S)-2-fluoro-5-methyl-4-(methyl(1-((2-methyl-5-(trifluoromethyl)oxazol-4-yl)methyl)pyrrolidin-3-yl)amino)-N-(thiazol-4-yl)benzenesulfonamide;

(S)-4-((1-((2,5-dimethyloxazol-4-yl)methyl)pyrrolidin-3-yl)(methyl)amino)-2-fluoro-5-methyl-N-(thiazol-4-yl)benzenesulfonamide;

(S)-2-fluoro-5-methyl-4-(methyl(1-((4,5,6,7-tetrahydropyrazolo[1,5-a]pyridin-2-yl)methyl)pyrrolidin-3-yl)amino)-N-(thiazol-4-yl)benzenesulfonamide;

(S)-2-fluoro-5-methyl-4-(methyl(1-((4-(trifluoromethyl)thiazol-2-yl)methyl)pyrrolidin-3-yl)amino)-N-(thiazol-4-yl)benzenesulfonamide; and (S)-2,6-difluoro-3-methyl-4-(methyl(1-((6-methylpyridin-2-yl)methyl)pyrrolidin-3-yl)amino)-N-(thiazol-4-yl)benzenesulfonamide.

Of the preferred embodiment of compounds of formula (Ib2) wherein $R^2$ is optionally substituted isoxazolyl, optionally substituted thiazolyl or optionally substituted thiadiazolyl, another preferred embodiment are compounds of formula (Ib2) wherein:

$R^1$ is hydrogen, alkyl, —$R^1$—$OR^{14}$ or an optionally substituted cycloalkyl; and $R^4$ and $R^5$ are each independently hydrogen, alkyl or haloalkyl;

or $R^4$ and $R^1$, together with the carbon to which they are attached, form an optionally substituted cycloalkyl or an optionally substituted aryl, and $R^5$, if present, if present, is hydrogen, alkyl, haloalkyl or optionally substituted aryl.

Of this preferred embodiment, preferred compounds of formula (Ib2) are selected from:

2-fluoro-5-methyl-4-(methyl((S)-1-((1s,3R)-3-phenylcyclobutyl)pyrrolidin-3-yl)amino)-N-(thiazol-4-yl)benzenesulfonamide;

(S)-5-chloro-4-((1-(2,3-dihydro-1H-inden-2-yl)pyrrolidin-3-yl)(methyl)amino)-2-fluoro-N-(thiazol-4-yl)benzenesulfonamide;

(S)-5-chloro-2-fluoro-4-(methyl(1-(1-phenycyclopropyl)pyrrolidin-3-yl)amino)-N-(thiazol-4-yl)benzenesulfonamide;

(S)-4-((1-(2,3-dihydro-1H-inden-2-yl)pyrrolidin-3-yl)(methyl)amino)-2-fluoro-5-methyl-N-(thiazol-4-yl)benzenesulfonamide;

(S)-5-chloro-4-((1-(3,3-dimethylbutyl)pyrrolidin-3-yl)(methyl)amino)-2-fluoro-N-(thiazol-4-yl)benzenesulfonamide;

4-(((S)-1-((S)-2,3-dihydro-1H-inden-1-yl)pyrrolidin-3-yl)(methyl)amino)-2-fluoro-5-methyl-N-(thiazol-4-yl)benzenesulfonamide;

(S)-5-chloro-2-fluoro-4-((1-(1-(2-fluorophenyl)cyclobutyl)pyrrolidin-3-yl)(methyl)amino)-N-(thiazol-4-yl)benzenesulfonamide;

(S)-4-((1-(2-(benzyloxy)ethyl)pyrrolidin-3-yl)(methyl)amino)-5-chloro-2-fluoro-N-(thiazol-4-yl)benzenesulfonamide;

5-chloro-4-(((S)-1-((R)-2,3-dihydro-1H-inden-1-yl)pyrrolidin-3-yl)(methyl)amino)-2-fluoro-N-(thiazol-4-yl)benzenesulfonamide;

2-fluoro-5-methyl-4-(methyl((S)-1-((1r,3S)-3-phenylcyclobutyl)pyrrolidin-3-yl)amino)-N-(thiazol-4-yl)benzenesulfonamide;

(S)-4-((1-(cyclohexylmethyl)pyrrolidin-3-yl)(methyl)amino)-2-fluoro-5-methyl-N-(thiazol-4-yl)benzenesulfonamide;

3-chloro-4-(((S)-1-((S)-2,3-dihydro-1H-inden-1-yl)pyrrolidin-3-yl)(methyl)amino)-2-fluoro-N-(thiazol-4-yl)benzenesulfonamide;

5-chloro-4-(((S)-1-((S)-2,3-dihydro-1H-inden-1-yl)pyrrolidin-3-yl)(methyl)amino)-2-fluoro-N-(thiazol-4-yl)benzenesulfonamide;

(S)-2-fluoro-5-methyl-4-(methyl(1-neopentylpyrrolidin-3-yl)amino)-N-(thiazol-4-yl)benzenesulfonamide; and (S)-4-((1-(3,3-dimethybutyl)pyrrolidin-3-yl)(methyl)amino)-2-fluoro-5-methyl-N-(thiazol-4-yl)benzenesulfonamide.

Another preferred embodiment of the compounds of formula (Ib2) are compounds of formula (Ib2) wherein $R^2$ is an optionally substituted 6-membered N-heteroaryl.

Of this embodiment, a preferred embodiment are compounds of formula (Ib2) wherein $R^2$ is optionally substituted pyridinyl.

Of this preferred embodiment, preferred compounds of formula (Ib2) are selected from:

(S)-4-((1-benzylpyrrolidin-3-yl)(methyl)amino)-2,6-difluoro-N-(5-fluoropyridin-2-yl)-3-methylbenzenesulfonamide;

(S)-5-chloro-2-fluoro-N-(6-fluoropyridin-2-yl)-4-(methyl(1-(2-phenylpropan-2-yl)pyrrolidin-3-yl)amino)benzenesulfonamide;

(S)-4-((1-benzylpyrrolidin-3-yl)(methyl)amino)-2,6-difluoro-N-(6-fluoropyridin-2-yl)-3-methylbenzenesulfonamide;

(S)-4-((1-benzylpyrrolidin-3-yl)(methyl)amino)-2-fluoro-N-(5-fluoropyridin-2-yl)-5-methylbenzenesulfonamide;

(S)-4-((1-benzylpyrrolidin-3-yl)(methyl)amino)-2-fluoro-N-(6-fluoropyridin-2-yl)-5-methylbenzenesulfonamide;

(S)-4-((1-benzylpyrrolidin-3-yl)(methyl)amino)-5-chloro-2-fluoro-N-(6-fluoropyridin-2-yl)benzenesulfonamide bis (trifluoroacetic acid) salt;

3-chloro-2-fluoro-N-(6-fluoropyridin-2-yl)-4-(((S)-1-((S)-1-phenylethyl)pyrrolidin-3-yl)amino)benzenesulfonamide; and 5-chloro-2-fluoro-N-(6-fluoropyridin-2-yl)-4-(methyl((S)-1-((R)-1-phenylethyl)pyrrolidin-3-yl)amino)benzenesulfonamide.

In another embodiment, the compound of formula (I) is a compound of formula (Ib) wherein X is —$C(R^9)R^{10}$— and Y is —$C(R^{11})R^{12}$—, i.e., a compound of formula (Ib3):

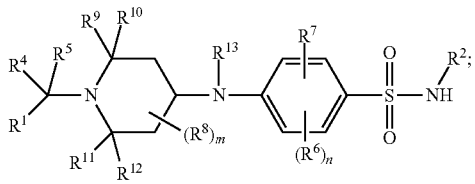

(Ib3)

n is 1 or 2;
m is 1 or 2;
X is a direct bond or —$C(R^9)R^{10}$—;
Y is a direct bond or —$C(R^{11})R^{12}$—;
$R^1$ is hydrogen, alkyl, —$R^{17}$—$OR^{14}$, an optionally substituted cycloalkyl, an optionally substituted aryl, an optionally substituted aralkyl, an optionally substituted N-heterocyclyl, an optionally substituted N-heteroaryl, an optionally substituted O-heteroaryl or an optionally substituted S-heteroaryl;
$R^2$ is an optionally substituted 5-membered N-heteroaryl or an optionally substituted 6-membered N-heteroaryl;

$R^4$ and $R^5$ are each independently hydrogen, alkyl or haloalkyl;
or $R^4$ and $R^1$, together with the carbon to which they are attached, form an optionally substituted cycloalkyl or an optionally substituted aryl, and $R^5$, if present, if present, is hydrogen, alkyl, haloalkyl or optionally substituted aryl;
each $R^6$ is independently hydrogen, alkyl, alkenyl, halo, haloalkyl, cyano, —$OR^{14}$ or optionally substituted cycloalkyl;
$R^7$ is alkyl, halo, haloalkyl, cyano or —$OR^{14}$;
each $R^8$ is independently hydrogen, alkyl, halo, haloalkyl or —$OR^{14}$;
or two $R^8$'s, together with the carbon to which they are both attached, may form an optionally substituted cycloalkyl;
$R^9$, $R^{10}$, $R^{11}$ and $R^{12}$ are each independently hydrogen, alkyl, haloalkyl, alkyl or —$OR^{14}$;
or $R^9$ and $R^{11}$ form an optionally substituted alkylene chain and $R^{10}$ and $R^{12}$ are as defined above; and
$R^{13}$ is hydrogen, alkyl or haloalkyl;
each $R^{14}$ are each independently hydrogen, alky, haloalkyl, optionally substituted aryl or optionally substituted aralkyl; and
$R^{17}$ is a direct bond or an optionally substituted alkylene chain;
as an individual stereoisomer, enantiomer or tautomer thereof or a mixture thereof;
or a pharmaceutically acceptable salt, solvate or prodrug thereof.

Of this embodiment, a preferred embodiment are compounds of formula (Ib3) wherein $R^2$ is an optionally substituted 5-membered N-heteroaryl.

Of this embodiment, a more preferred embodiment are compounds of formula (Ib3) wherein $R^2$ is optionally substituted isoxazolyl, optionally substituted thiazolyl or optionally substituted thiadiazolyl.

Of this preferred embodiment, preferred compounds of formula (Ib3) are selected from:

(R)-5-chloro-2-fluoro-4-(methyl(1-(1-phenylethyl)piperidin-4-yl)amino)-N-(thiazol-4-yl)benzenesulfonamide;

(R)-2-fluoro-5-methyl-4-(methyl(1-(1-phenylethyl)piperidin-4-yl)amino)-N-(thiazol-4-yl)benzenesulfonamide;

4-((1-benzylpiperidin-4-yl)(methyl)amino)-5-chloro-2-fluoro-N-(thiazol-2-yl)benzenesulfonamide; and 4-(1-benzylpiperidin-4-ylamino)-3-chloro-N-(1,2,4-thiadiazol-5-yl)benzenesulfonamide.

Another preferred embodiment of the compounds of formula (Ia3) are compounds of formula (Ib3) wherein $R^2$ is an optionally substituted 6-membered N-heteroaryl.

Of this embodiment, a preferred embodiment are compounds of formula (Ib3) wherein $R^2$ is optionally substituted pyridinyl.

Another embodiment of the invention are compounds of formula (I) wherein $R^7$ is in the ortho position relative to $R^3$.

Another embodiment of the invention are compounds of formula (I) wherein $R^7$ is in the ortho position relative to $R^3$ and is halo.

Another embodiment of the invention is where $R^7$ is chloro or fluoro.

Another embodiment of the invention are compounds of formula (I) wherein $R^2$ is an optionally substituted monocyclic N-heteroaryl. Another embodiment of the invention are compounds of formula (I) wherein $R^2$ is an optionally substituted 5-membered N-heteroaryl. Another embodiment of the invention are compounds of formula (I) wherein $R^2$ is an optionally substituted 5-membered N-heteroaryl selected from isoxazolyl, thiazolyl or thiadiazolyl. Another embodiment of the invention are compounds of formula (I) wherein $R^2$ is an optionally substituted 6-membered N-heteroaryl. Another embodiment of the invention are compounds of formula (I) wherein $R^2$ is an optionally substituted 6-membered N-heteroaryl selected from pyridinyl, pyrimidinyl, pyridazinyl or pyrazinyl. Another embodiment of the invention are compounds of formula (I) wherein $R^2$ is an optionally substituted pyridinyl.

Another embodiment of the invention is a method of using the compounds of formula (I) as standards or controls in in vitro or in vivo assays in determining the efficacy of test compounds in modulating voltage-dependent sodium channels.

It is understood that any embodiment of the compounds of the invention, as set forth above, and any specific substituent set forth herein for a particular n, m, X, Y, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{17}$ group in the compounds of the invention, as set forth above, may be independently combined with other embodiments and/or substituents of compounds of the invention to form embodiments of the inventions not specifically set forth above. In addition, in the event that a list of substituents is disclosed for any particular n, m, X, Y, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{17}$ group in a particular embodiment and/or claim, it is understood that one or more substituents may be deleted from the list and that the remaining list of substituents will be considered to be an embodiment of the invention.

It is also understood that the proviso set forth above in the Summary of the Invention for the compounds of formula (I) applies to all of the relevant embodiments of the compounds of formula (I) as described above.

Another aspect of the invention is a pharmaceutical composition comprising a pharmaceutically acceptable excipient and a compound of the invention, as described above, as a stereoisomer, enantiomer or tautomer thereof or a mixture thereof; or a pharmaceutically acceptable salt, solvate or prodrug thereof.

Another aspect of the invention is a method of treating a disease or a condition associated with $Na_V1.6$ activity in a mammal wherein the disease or condition is epilepsy and/or epileptic seizure disorder and wherein the method comprises administering to the mammal in need thereof a therapeutically effective amount of a compound of the invention, as described above, as a stereoisomer, enantiomer or tautomer thereof or a mixture thereof; or a pharmaceutically acceptable salt, solvate or prodrug thereof.

In one embodiment of this aspect, the epilepsy or epileptic seizure disorder is selected from photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia.

In one embodiment of this embodiment, the epilepsy or epileptic seizure disorder is selected from Dravet syndrome, infantile spasms/West's syndrome, temporal lobe epilepsy, Lennox-Gastaut syndrome (LGS), generalized epilepsy with febrile seizures+ and early infantile epileptic encephalopathy.

Another aspect of the invention is a method of decreasing ion flux through $Na_V1.6$ in a mammalian cell, wherein the method comprises contacting the cell with a compound of the invention, as described above, as a stereoisomer, enantiomer or tautomer thereof or a mixture thereof; or a pharmaceutically acceptable salt, solvate or prodrug thereof.

Another aspect of the invention is a method of selectively inhibiting a first voltage-gated sodium channel over a second voltage-gated sodium channel in a mammal, wherein the method comprises administering to the mammal a modulating amount of a compound of the invention, as described above, as a stereoisomer, enantiomer or tautomer thereof or a mixture thereof; or a pharmaceutically acceptable salt, solvate or prodrug thereof.

In one embodiment of this aspect, the first voltage-gated sodium channel is $Na_V1.6$.

In another embodiment of this aspect, the first voltage-gated sodium channel is $Na_V1.6$ and the second voltage-gated sodium channel is $Na_V1.5$.

In another embodiment of this aspect, the first voltage-gated sodium channel is $Na_V1.6$ and the second voltage-gated sodium channel is $Na_V1.1$.

Specific embodiments of the compounds of the invention are described in more detail below in the Preparation of the Compounds of the Invention.

Utility and Testing of the Compounds of the Invention

The compounds of the invention modulate, preferably inhibit, ion flux through a voltage-dependent sodium channel, preferably $Na_V1.6$, in a mammal, especially in a human. Any such modulation, whether it be partial or complete inhibition or prevention of ion flux, is sometimes referred to herein as "blocking" and corresponding compounds as "blockers" or "inhibitors". In general, the compounds of the invention modulate the activity of a voltage-gated sodium channel downwards by inhibiting the voltage-dependent activity of the sodium channel, and/or reduce or prevent sodium ion flux across a cell membrane by preventing sodium channel activity such as ion flux.

The compounds of the invention inhibit the ion flux through a voltage-dependent sodium channel, preferably $Na_V1.6$. The compounds of the invention are state or frequency dependent modifiers of the sodium channel, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestèle, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention are voltage-gated sodium channel inhibitors, preferably $Na_V1.6$ inhibitors, and are therefore useful for treating diseases and conditions, preferably epilepsy and/or epileptic seizure disorder, in mammals, preferably humans, and other organisms, including all those human diseases and conditions which are the result of aberrant voltage-dependent sodium channel biological activity, preferably aberrant Na$_v$1.6 activity, or which may be ameliorated by modulation of voltage-dependent sodium channel biological activity. In particular, the compounds of the invention, i.e., the compounds of formula (I), as set forth above in the Summary of the Invention, as individual stereoisomers, enantiomers or tautomers thereof or mixtures thereof; or as pharmaceutically acceptable salts, solvates or prodrugs thereof, are useful for treating diseases and conditions in mammals, preferably humans, which are the result of aberrant voltage-dependent Na$_v$1.6 biological activity or which may be ameliorated by the modulation, preferably the inhibition, of Na$_v$1.6 biological activity. Preferably the compounds of the invention selectively inhibit Na$_v$1.6 over Na$_v$1.5 and/or Na$_v$1.1.

As defined herein, a disease, disorder or condition associated with Na$_v$1.6 activity includes, but is not limited to, epilepsy and/or epileptic seizure disorder. Such epilepsy and/or epileptic seizure disorders include, but are not limited to, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia.

The present invention therefore relates to compounds, pharmaceutical compositions and methods of using the compounds and pharmaceutical compositions for the treatment of diseases or conditions associated by the activity of Na$_v$1.6 in a mammal, preferably a human, by administering to the mammal, preferably the human, in need of such treatment an effective amount of a compound of the invention or an pharmaceutical composition comprising a compound of the invention.

The general value of the compounds of the invention in inhibiting the Na$_v$1.6 ion flux can be determined using the assays described below in the Biological Assays section. Alternatively, the general value of the compounds in treating conditions and diseases in humans may be established in industry standard animal models for demonstrating the efficacy of compounds in treating epilepsy and/or epileptic seizure disorder. Animal models of human epileptic conditions have been developed that result in reproducible sensory deficits over a sustained period of time that can be evaluated by sensory testing.

For example, many rodent models have been developed to assess the propensity for seizures or epileptiform activity (Klein, B. R. et al., (2016), "Models Currently in Active Use. In: Epilepsy Therapy Screening Program", Vol. 2016, National Institute of Neurological Disorders and Stroke). These include acute chemical or electrical insults that induce seizures, as well as chronic chemical or genetic insults that create seizure prone animals. These models can be used to determine the relative ability of a compound to promote or prevent seizure activity. The maximal electroshock seizure (MES) assay and the 6 hertz psychomotor seizure test (6 Hz) are two examples of acute insult seizure assays used to evaluate anticonvulsive interventions (Suzuki, F. et al., *Neuroscience* (1995), Vo. 64, pp. 665-674; Barton, M. E. et al., *Epilepsy Research* (2001), Vol. 47, pp. 217-227). Both assays involve an electrical insult applied with electrodes placed on the corneas or ears in order to provoke an acute seizure. Acute seizures may also be induced chemically, for instance by administration of the proconvulsant ether compound flurothyl (Makinson, C. D. et al., *Exp. Neurol.* (2016), Vol. 275, Pt 1, pp. 46-58).

Genetic epilepsies have been linked to many distinct genes, including multiple voltage gated sodium channel genes. Genetically modified mice can be created that harbor mutations identified in human patients. In some cases these genetic modifications result in animals that behave much like the human patients in whom the genetic variations were initially identified. Mutant mice can be used to test anticonvulsant interventions. Such experiments can involve prevention of spontaneous seizures, or may make use of similar seizure provoking stimuli as those employed in wild type mice. Animal models of early infantile epileptic encephalopathy 6 (EIEE6), also known as severe myoclonic epilepsy of infancy or Dravet syndrome, have been created by mutating the SCN1A gene that encodes the Na$_v$1.1 voltage gated sodium channel (Yu, F. H. et al., *Nat. Neurosci.* (2006), Vol. 9, pp. 1142-1149). Models of EIEE13 have likewise been created by mutating the SCN6A gene that encodes the Na$_v$1.6 voltage gated sodium channel (Wagnon, J. L. et al., Human Molecular Genetics (2014)). Both of these mouse strains provide the opportunity to evaluate potential therapeutic interventions that might prove useful in clinical patient populations (Martin, M. S. et al., *J. Biol. Chem.* (2010), Vol. 285, pp. 9823-9834; and Martin, M. S. et al., *Human Molecular Genetics* (2007), Vol. 16, pp. 2892-2899).

The present invention readily affords many different means for identification of Na$_v$1.6 inhibitory agents that are useful as therapeutic agents. Identification of Na$_v$1.6 inhibitors can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., *J. General Physiology* (1983), 83:613-642, and Leuwer, M., et al., *Br. J. Pharmacol* (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they are useful in treating the disease or condition associated with the activity of the sodium channel of interest, preferably $Na_V1.6$, with minimal adverse events. The assays described below in the Biological Assays Section are useful in assessing the biological activity of the instant compounds.

Typically, the efficacy of a compound of the invention is expressed by its $IC_{50}$ value ("Inhibitory Concentration—50%"), which is the measure of the amount of compound required to achieve 50% inhibition of the activity of the target sodium channel over a specific time period. For example, representative compounds of the present invention have demonstrated $IC_{50}$'s ranging from less than 100 nanomolar to less than 10 micromolar in the patch voltage clamp $Na_V1.6$ electrophysiology assay described herein.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_V1.6$ activity in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_V1.6$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention, as set forth above in the Summary of the Invention, as stereoisomers, enantiomers, tautomers thereof or mixtures thereof, or pharmaceutically acceptable salts, solvates or prodrugs thereof, and/or the pharmaceutical compositions described herein which comprise a pharmaceutically acceptable excipient and one or more compounds of the invention, as set forth above in the Summary of the Invention, as a stereoisomer, enantiomer or tautomer thereof or mixtures thereof, or a pharmaceutically acceptable salt, solvate or prodrug thereof, can be used in the preparation of a medicament for the treatment of diseases or conditions associated with voltage-gated sodium channel activity, preferably $Na_v1.6$ activity, in a mammal.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier, excipient or diluent and in an amount effective to modulate, preferably inhibit, ion flux through a voltage-dependent sodium channel to treat sodium channel mediated diseases, such as epilepsy and/or epileptic seizure disorder, when administered to an animal, preferably a mammal, most preferably a human patient.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in *Remington's Pharmaceutical Sciences* (Mack Pub. Co., N.J. current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer.

In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts (see, e.g., Berkow et al., eds., *The Merck Manual*, $19^{th}$ edition, Merck and Co., Rahway, N.J., 2011; Brunton et al. eds., *Goodman and Cilman's The Pharmacological Basis of Therapeutics*, $12^{th}$ edition, McGraw-Hill 2011; Avery's Drug Treatment: Principles and Practice of Clinical Pharmacology and Therapeutics, 3rd edition, ADIS Press, LTD., Williams and Wilkins, Baltimore, Md. (1987), Ebadi, *Pharmacology*, Little, Brown and Co., Boston, (1985); Osolci al., eds., *Remington's Pharmaceutical Sciences*, current edition, Mack Publishing Co., Easton, Pa.; Katzung, *Basic and Clinical Pharmacology*, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats and hamsters), Lagamorpha (including rabbits) and Carnivora (including cats and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al., *Regional Anesthesia* 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the compound for safe and effective intra-ocular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the invention may be usefully combined with one or more other compounds of the invention or one or more other therapeutic agent or as any combination thereof, in the treatment of diseases and conditions associated with voltage-gated sodium channel activity. For example, a compound of the invention may be administered simultaneously, sequentially or separately in combination with other therapeutic agents, including, but not limited to:

opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g., acetaminophen, salicylates (e.g., aspirin);

nonsteroidal anti-inflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g., carbamazepine, oxcarbazepine, lamotrigine, valproate, topiramate, gabapentin and pregabalin;

antidepressants such as tricyclic antidepressants, e.g., amitriptyline, clomipramine, despramine, imipramine and nortriptyline;

COX-2 selective inhibitors, e.g., celecoxib, rofecoxib, parecoxib, valdecoxib, deracoxib, etoricoxib, and lumiracoxib;

alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;

barbiturate sedatives, e.g., amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g., (αR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g., maprotiline, lofepramine, mirtazepine, oxaprotiline, fezolamine, tomoxetine, mianserin, buprorion, buprorion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT$_3$ antagonists such as ondansetron;

metabotropic glutamate receptor (mGluR) antagonists;

local anaesthetic such as mexiletine and lidocaine;

corticosteroid such as dexamethasone;

antiarrhythimics, e.g., mexiletine and phenytoin;

muscarinic antagonists, e.g., tolterodine, propiverine, tropsium chloride, darifenacin, solifenacin, temiverine and ipratropium;

cannabinoids;

vanilloid receptor agonists (e.g., resinferatoxin) or antagonists (e.g., capsazepine);

sedatives, e.g., glutethimide, meprobamate, methaqualone, and dichloralphenazone;

anxiolytics such as benzodiazepines,
antidepressants such as mirtazapine,
topical agents (e.g., lidocaine, capsacin and resiniferotoxin);
muscle relaxants such as benzodiazepines, baclofen, carisoprodol, chlorzoxazone, cyclobenzaprine, methocarbamol and orphrenadine;
anti-histamines or H1 antagonists;
NMDA receptor antagonists;
5-HT receptor agonists/antagonists;
PDEV inhibitors;
Tramadol®;
cholinergic (nicotinic) analgesics;
alpha-2-delta ligands;
prostaglandin E2 subtype antagonists;
leukotriene B4 antagonists;
5-lipoxygenase inhibitors; and
5-$HT_3$ antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

Kits-of-Parts

The present invention also provides kits that contain a pharmaceutical composition which includes one or more compounds of the invention. The kit also includes instructions for the use of the pharmaceutical composition for inhibiting the activity of voltage-gated sodium channels, preferably $Na_v1.6$, for the treatment of epilepsy, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds of the Invention

The following Reaction Schemes illustrate methods to make compounds of this invention, i.e., compounds of formula (I), as individual stereoisomers, enantiomers or tautomers thereof or mixtures thereof; or as pharmaceutically acceptable salts, solvates or prodrugs thereof It is also understood that one skilled in the art would be able to make the compounds of the invention by similar methods or by methods known to one skilled in the art. It is also understood that one skilled in the art would be able to make in a similar manner as described below other compounds of the invention not specifically illustrated below by using the appropriate starting components and modifying the parameters of the synthesis as needed. It is also understood that simple functional group transformations (see, e.g., Larock, R. C. *Comprehensive Organic Transformations, 2$^{nd}$ edition* (Wiley, 1999) can be effected by methods known to one skilled in the art. In general, starting components may be obtained from sources such as Sigma Aldrich, Combi-Blocks, Oakwood Chemicals, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure*, 6th edition (Wiley, 2007)) or prepared as described herein.

It is also understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy (i.e., "oxygen-protecting groups") include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino (i.e., "nitrogen-protecting groups") include t-butoxycarbonyl, benzyloxycarbonyl, and the like. Suitable protecting groups for mercapto (i.e., "sulfur-protecting groups") include —C(O)—R" (where R" is alkyl, aryl or aralkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Greene's Protective Groups in Organic Synthesis* (2006), 4$^{th}$ Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The compounds of formula (I) may contain at least one asymmetric carbon atom and thus can exist as racemates, enantiomers and/or diastereoisomers. Specific enantiomers or diastereoisomers may be prepared by utilizing the appropriate chiral starting material. Alternatively, diastereoisomeric mixtures or racemic mixtures of compounds of formula (I) may be resolved into their respective enantiomers or diastereoisomers. Methods for resolution of diastereoisomeric mixtures or racemic mixtures of the compounds of formula (I), as described herein, or intermediates prepared herein, are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g., preferential crystallization, preferential crystallization in the presence of additives), asymmetric transformation of racemates, chemical separation (e.g., formation and separation of diastereomers such as diastereomeric salt mixtures or the use of other resolving agents; separation via complexes and inclusion compounds), kinetic resolution (e.g., with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, *Analytical Chemistry*, 2002, 2863-2872).

Preparation of Compounds of Formula (I)

In general, compounds of formula (I), as described above in the Summary of the Invention, can be synthesized following the general procedure described below in Reaction Scheme 1 where X, Y, n, m, $R^1$, $R^2$, $R^3$, $R^4$, $R^5$, $R^6$, $R^7$ and $R^8$ are as described above in the Summary of the Invention for compounds of formula (I):

REACTION SCHEME 1

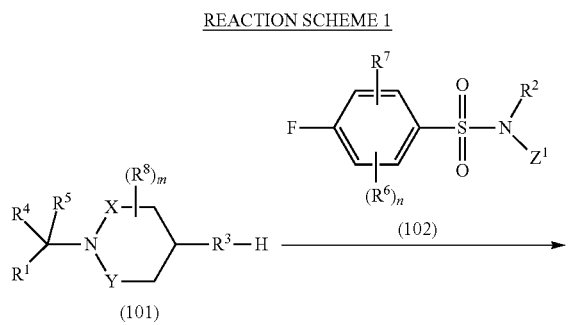

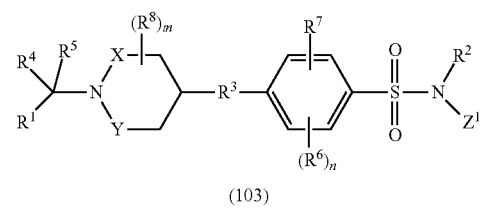

Compounds of formulae (101), (102) and (103) are commercially available or can be prepared according to methods known to one skilled in the art or by methods disclosed herein. In general, the compounds of formula (I) are prepared as described above in Reaction Scheme 1 as follows:

The compound of formula (101) is reacted with sulfonamide (102) (wherein Z is optionally a hydrogen or a nitrogen-protecting group, for example, but not limited to, tert-butyloxycarbonyl, 2,4-dimethoxybenzyl, 4-methoxybenzyl, or 2-(trimethylsilyl)ethoxymethyl) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (103). The compound of formula (103) is then treated with an acid, such as, but not limited to, trifluoroacetic acid, in a polar aprotic solvent, such as, but not limited to, dichloromethane, at a temperature of between about 0° C. and ambient temperature to generate a compound of formula (I), which can be isolated from the reaction mixture by standard techniques. One skilled in the art would also readily recognize that, under certain conditions, the preparation of a compound of formula (103) may result in a compound of formula (I), which can be isolated from the reaction mixture by standard techniques.

Alternatively, compounds of formula (I) where $R^4$ is hydrogen, as described above in the Summary of the Invention, can be synthesized following the general procedure described below in Reaction Scheme 2 where X, Y, n, m, $R^1$, $R^2$, $R^3$, $R^5$, $R^6$, $R^7$ and $R^8$ are as described above in the Summary of the Invention for compounds of formula (I):

REACTION SCHEME 2

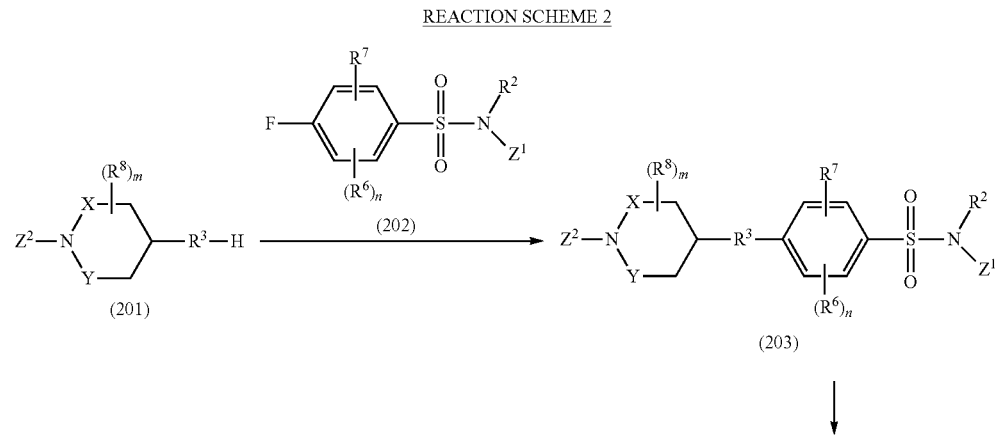

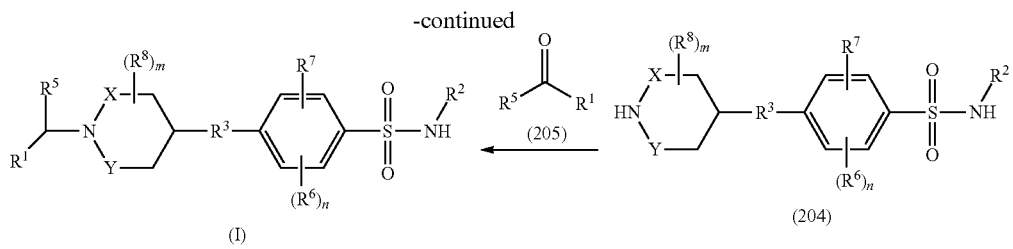

Compounds of formulae (201), (202), (203), and (204) are commercially available or can be prepared according to methods known to one skilled in the art or by methods disclosed herein. In general, the compounds of formula (1) are prepared as described above in Reaction Scheme 2 as follows:

The compound of formula (201) (wherein $Z^2$ is a nitrogen-protecting group, for example, but not limited to, tert-butyloxycarbonyl or benzyl) is reacted with sulfonamide (202) (wherein $Z^1$ is optionally a hydrogen or a nitrogen protecting group, for example, but not limited to, tert-butyloxycarbonyl, 2,4-dimethoxybenzyl, 4-methoxybenzyl, or 2-(trimethylsilyl)ethoxymethyl) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (203). The compound of formula (203) is then treated with an acid, such as, but not limited to, trifluoroacetic acid, in a polar aprotic solvent, such as, but not limited to, dichloromethane, at a temperature of between about 0° C. and ambient temperature to generate a compound of formula (204). The compound of formula (204) is then reacted with, for example, but not limited to, an aldehyde or ketone of formula (205) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to generate a compound of formula (1), which can be isolated from the reaction mixture by standard techniques.

Compounds of formula (I) where $R^3$ is —$N(R^{13})$— and $R^4$ is hydrogen, i.e., compounds of formula (Ib) where $R^4$ is hydrogen, as described above in the Embodiments of the Invention, can be synthesized following the general procedure described below in Reaction Scheme 3 where X, Y, n, m, $R^1$, $R^2$, $R^5$, $R^6$, $R^7$, $R^8$ and $R^{13}$ are as described above in the Embodiments of the Invention for compounds of formula (Ib):

REACTION SCHEME 3

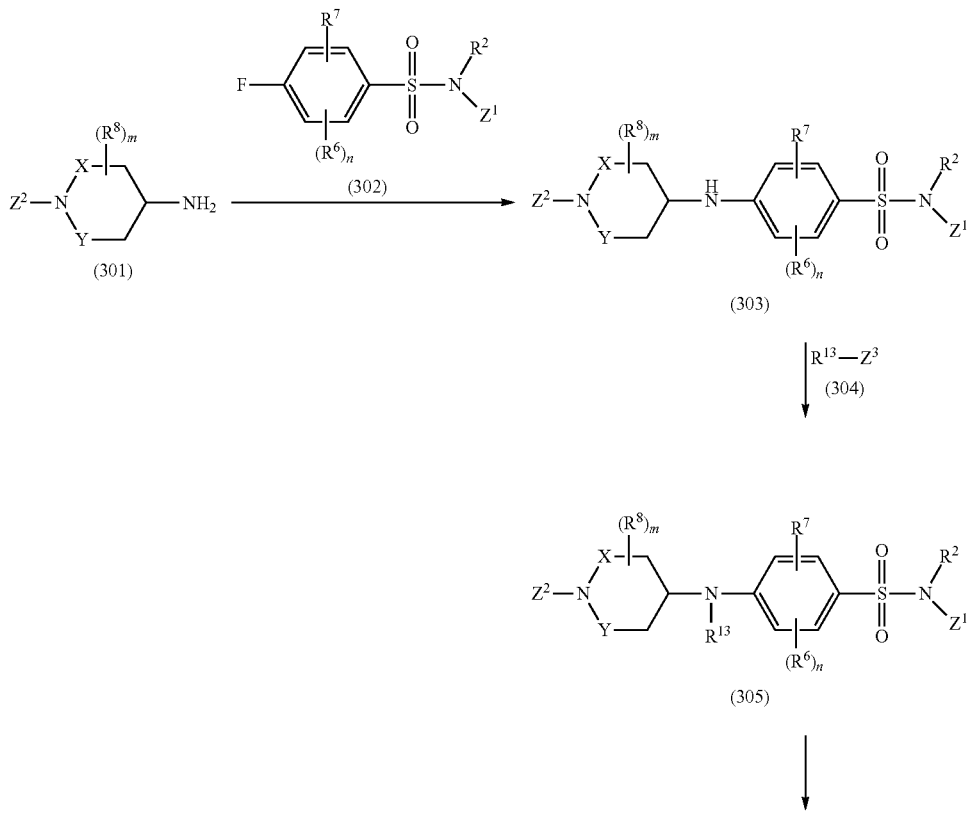

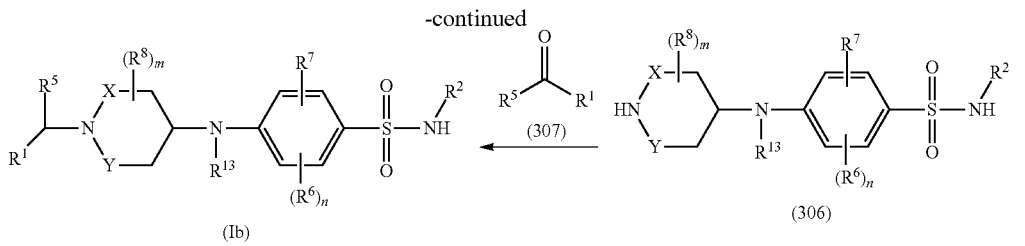

Compounds of formulae (301), (302), (303), (304), (305), (306) and (307) are commercially available or can be prepared according to methods known to one skilled in the art or by methods disclosed herein. In general, the compounds of formula (Ib) are prepared as described above in Reaction Scheme 3 as follows:

The compound of formula (301) (wherein $Z^2$ is a nitrogen-protecting group, for example, but not limited to, tert-butyloxycarbonyl or benzyl) is reacted with sulfonamide (302) (wherein $Z^1$ is optionally a hydrogen or a nitrogen-protecting group, for example, but not limited to, tert-butyloxycarbonyl, 2,4-dimethoxybenzyl, 4-methoxybenzyl, or 2-(trimethylsilyl)ethoxymethyl) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (303). The compound of formula (303) can then be alkylated with alkylating agents $R^{13}$—$Z^3$ (304) (wherein $Z^3$ is a leaving group such as, but not limited to, bromide, iodide, sulfate), such as, but not limited to, methyl iodide, in presence of a base, such as, but not limited to, lithium bis(trimethylsilyl)amide in a polar aprotic solvent such as, but not limited to, tetrahydrofuran, at temperature of between about −78° C. and ambient temperature, to provide a compound of formula (305). The compound of formula (305) is then treated with an acid, such as, but not limited to, trifluoroacetic acid, in a polar aprotic solvent, such as, but not limited to, dichloromethane, at a temperature of between about 0° C. and ambient temperature to generate a compound of formula (306). The compound of formula (306) is then reacted with, for example, but not limited to, an aldehyde or ketone of formula (307) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to generate a compound of formula (I), which can be isolated from the reaction mixture by standard techniques.

Alternatively, compounds of formula (I) where $R^3$ is —N($R^{13}$)— and $R^4$ is hydrogen, i.e., compounds of formula (Ib) where $R^4$ is hydrogen, as described above in the Embodiments of the Invention, can be synthesized following the general procedure described below in Reaction Scheme 4 where X, Y, n, m, $R^1$, $R^2$, $R^5$, $R^6$, $R^7$, $R^8$ and $R^{13}$ are as described above in the Embodiments of the Invention for compounds of formula (Ib):

REACTION SCHEME 4

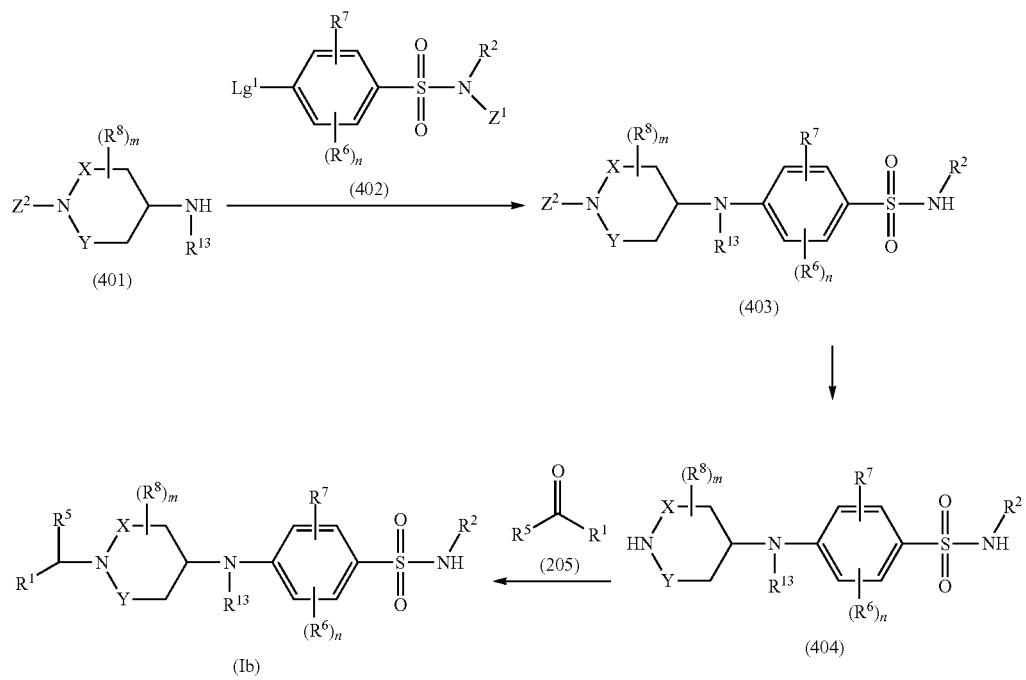

Compounds of formulae (401), (402), (403), and (404) are commercially available or can be prepared according to methods known to one skilled in the art or by methods disclosed herein. In general, the compounds of formula (Ib) are prepared as described above in Reaction Scheme 4 as follows:

The compound of formula (401) (wherein $Z^2$ is a protecting group, for example, but not limited to, tert-butyloxycarbonyl or benzyl) is reacted with sulfonamide (402) (wherein $Lg^1$ is a leaving group, for example bromo, iodo or trifluorosulfonate and $Z^1$ is hydrogen or a protecting group, for example, but not limited to, tert-butyloxycarbonyl, 2,4-dimethoxybenzyl, 4-methoxybenzyl, or 2-(trimethylsilyl)ethoxymethyl) under standard Buchwald-Hartwig cross coupling conditions, such as, but not limited to, the use of a solvent, such as, but not limited to, toluene, in the presence of a base, such as, but not limited to, cesium carbonate, and in the presence of a palladium catalyst composed of for example, but not limited to, 4,5-bis(diphenylphosphino)-9,9-dimethylxanthene and bis(dibenzylideneacetone)palladium(0), at a temperature of between about ambient temperature and 120° C., for about 1 to 20 hours to afford a compound of formula (403). The compound of formula (403) is then treated with an acid, such as, but not limited to, trifluoroacetic acid, in a polar aprotic solvent, such as, but not limited to, dichloromethane, at a temperature of between about 0° C. and ambient temperature to generate a compound of formula (404). The compound of formula (404) is then reacted with, for example, but not limited to, an aldehyde or ketone of formula (405) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to generate a compound of formula (I), which can be isolated from the reaction mixture by standard techniques.

Alternatively, compounds of formula (I) where $R^3$ is $-N(R^{13})-$ and $R^4$ is hydrogen, i.e., compounds of formula (Ib) where $R^4$ is hydrogen, as described above in the Embodiments of the Invention, can be synthesized following the general procedure described below in Reaction Scheme 5 where X, Y, n, m, $R^1$, $R^2$, $R^3$, $R^5$, $R^6$, $R^7$, $R^8$ and $R^{13}$ are as described above in the Embodiments of the Invention for compounds of formula (Ib):

REACTION SCHEME 5

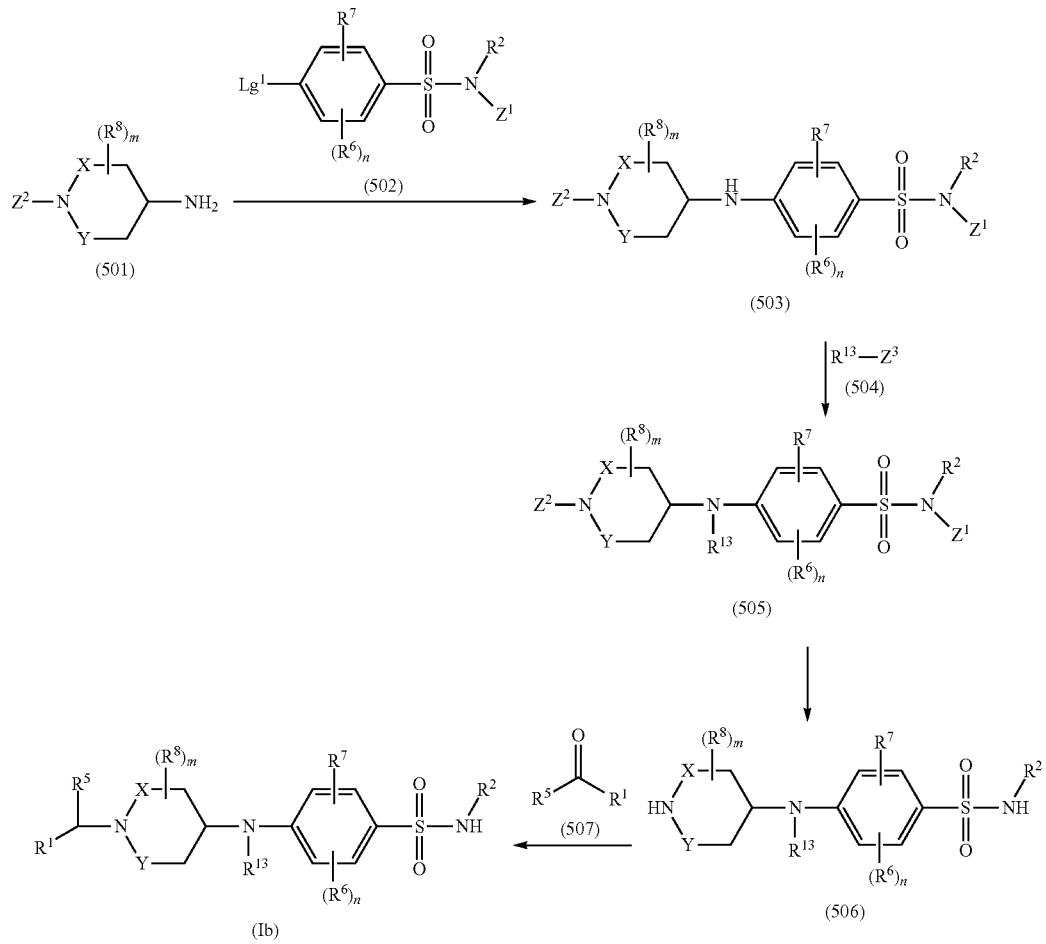

Compounds of formulae (501), (502), (503), (504), (505), (506) and (507) are commercially available or can be prepared according to methods known to one skilled in the art or by methods disclosed herein. In general, the compounds of formula (Ib) are prepared as described above in Reaction Scheme 5 as follows:

The compound of formula (501) (wherein $Z^2$ is a nitrogen-protecting group, for example, but not limited to, tert-butyloxycarbonyl or benzyl) is reacted with sulfonamide (502) (wherein $Lg^1$ is a leaving group, for example bromo, iodo or trifluorosulfonate and $Z^1$ is hydrogen or a protecting group, for example, but not limited to, tert-butyloxycarbonyl, 2,4-dimethoxybenzyl, 4-methoxybenzyl, or 2-(trimethylsilyl)ethoxymethyl) under standard Buchwald-Hartwig cross coupling conditions, such as, but not limited to, the use of a solvent, such as, but not limited to, toluene, in the presence of a base, such as, but not limited to, cesium carbonate, and in the presence of a palladium catalyst composed of for example, but not limited to, 4,5-bis(diphenylphosphino)-9,9-dimethylxanthene and bis(dibenzylideneacetone)palladium(0), at a temperature of between about ambient temperature and 120° C., for about 1 to 20 hours to afford a compound of formula (503). The compound of formula (503) can then be alkylated with alkylating agents $R^{13}$—$Z^3$ (504) (wherein $Z^3$ is a leaving group such as, but not limited to, bromide, iodide, sulfate), such as, but not limited to, methyl iodide, in presence of a base, such as, but not limited to, lithium bis(trimethylsilyl)amide in a polar aprotic solvent such as, but not limited to, tetrahydrofuran, at temperature of between about −78° C. and ambient temperature, to provide a compound of formula (505). The compound of formula (505) is then treated with an acid, such as, but not limited to, trifluoroacetic acid, in a polar aprotic solvent, such as, but not limited to, dichloromethane, at a temperature of between about 0° C. and ambient temperature to generate a compound of formula (506). The compound of formula (506) is then reacted with, for example, but not limited to, an aldehyde or ketone of formula (507) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to generate a compound of formula (I), which can be isolated from the reaction mixture by standard techniques.

Alternatively, compounds of formula (1) where $R^3$ is —N($R^{13}$)—, i.e., compounds of formula (Ib), as described above in the Embodiments of the Invention, can be synthesized following the general procedure described below in Reaction Scheme 6 where X, Y, n, m, $R^1$, $R^2$, $R^3$, $R^4$, $R^5$, $R^6$, $R^7$, $R^8$ and $R^{13}$ are as described above in the Embodiments of the Invention for compounds of formula (Ib):

REACTION SCHEME 6

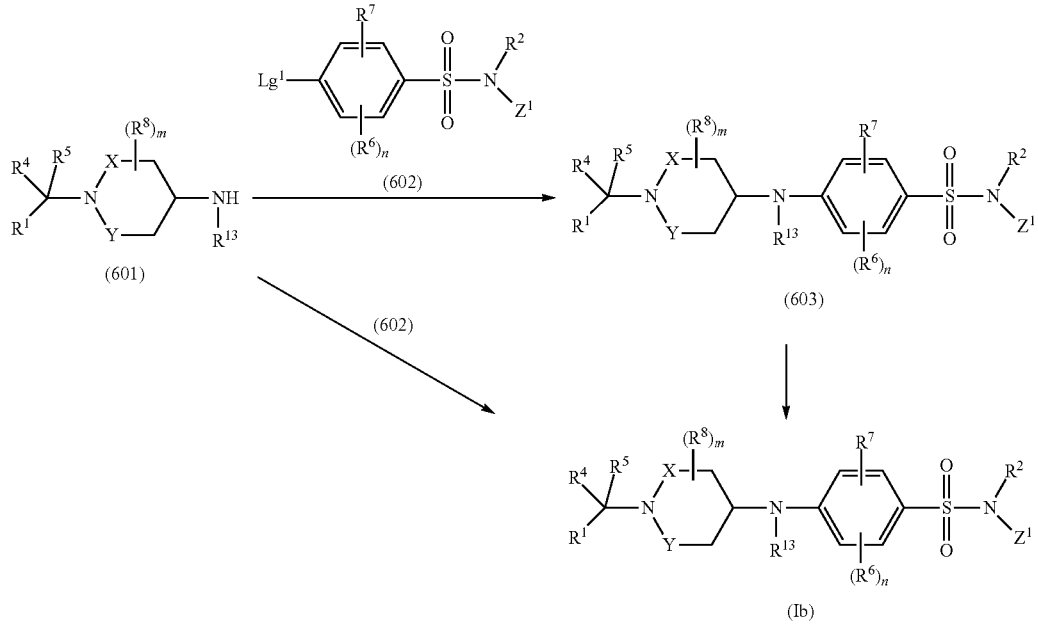

Compounds of formulae (601), (602) and (603) are commercially available or can be prepared according to methods known to one skilled in the art or by methods disclosed herein. In general, the compounds of formula (Ib) are prepared as described above in Reaction Scheme 5 as follows:

The compound of formula (601) is reacted with sulfonamide (602) (wherein $Lg^1$ is a leaving group, for example, but not limited to, bromo, iodo or trifluorosulfonate and $Z^1$ is hydrogen or a protecting group, for example, but not limited to, tert-butyloxycarbonyl, 2,4-dimethoxybenzyl, 4-methoxybenzyl, or 2-(trimethylsilyl)ethoxymethyl) under standard Buchwald reaction conditions, such as, but not limited to, the use of a solvent, such as, but not limited to, toluene, in the presence of a base, such as, but not limited to, cesium carbonate, and in the presence of a palladium catalyst composed of for example, but not limited to, 4,5-bis(diphenylphosphino)-9,9-dimethylxanthene and bis(dibenzylideneacetone)palladium(0), at a temperature of between about ambient temperature and 120° C., for about 1 to 20 hours to generate a compound of formula (Ib), which can be isolated from the reaction mixture by standard techniques.

Under certain conditions, the above transformations will afford a compound of formula (603) instead of a compound of formula (Ib). In those instances, $Z^1$ can be removed from the compound of formula (603) by methods known in the art, such as, but not limited to, the use of an acid, such as, but not limited to, trifluoroacetic acid, in a polar aprotic solvent, such as, but not limited to, dichloromethane, at a temperature of between about 0° C. and ambient temperature to generate a compound of formula (Ib).

A compound of formula (Ib) wherein $R^{13}$ is hydrogen can be converted into a compound of formula (Ib) wherein $R^{13}$ is alkyl, such as, but not limited to, methyl, by reaction with an aldehyde, such as, but not limited to, paraformaldehyde, in an acidic solvent, such as, but not limited to, formic acid or trifluoroacetic acid, in the presence of a reducing agent, such as, but not limited to, sodium triacetoxyborohydride or formic acid. The compound of formula (Ib) can then be isolated from the reaction mixture by standard techniques.

Alternatively, compounds of formula (I) where $R^3$ is —N($R^{13}$)—, $R^4$ is hydrogen and $R^7$ is alkyl or cycloalkyl, i.e., compounds of formula (Ib) where $R^4$ is hydrogen and $R^7$ is alkyl or cycloalkyl, as described above in the Embodiments of the Invention, can be synthesized following the general procedure described below in Reaction Scheme 7 where X, Y, n, m, $R^1$, $R^2$, $R^3$, $R^5$, $R^6$, $R^8$ and $R^{13}$ are as described above in the Embodiments of the Invention for compounds of formula (Ib) and where $R^7$ is alkyl or cycloalkyl:

REACTION SCHEME 7

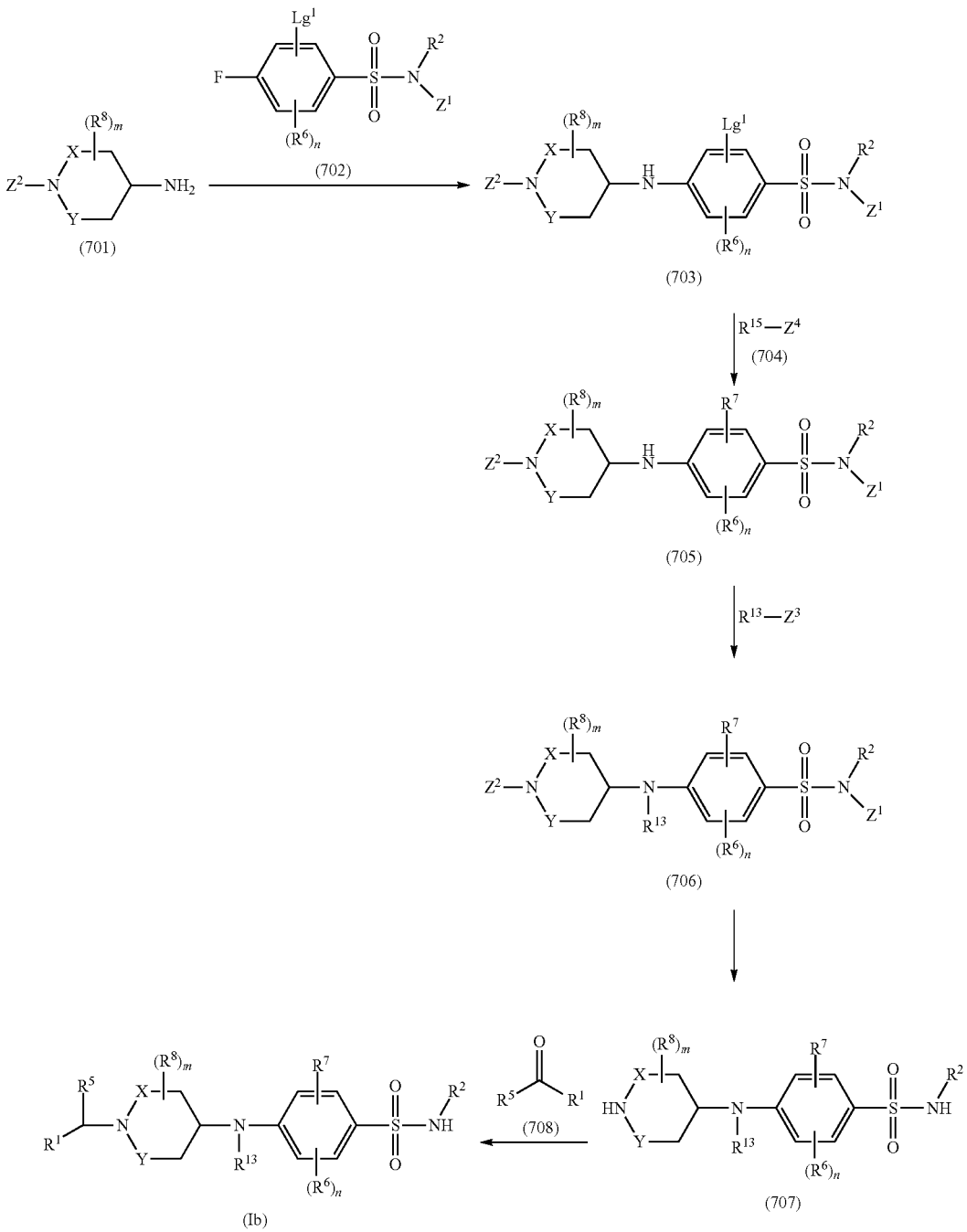

Compounds of formulae (701), (702), (703), (704), (705), (706), (707) and (708) are commercially available or can be prepared according to methods known to one skilled in the art or by methods disclosed herein. In general, the compounds of formula (Ib) are prepared as described above in Reaction Scheme 7 as follows:

The compound of formula (701) (wherein $Z^2$ is a nitrogen-protecting group, for example, but not limited to, tert-butyloxycarbonyl or benzyl) is reacted with sulfonamide (702) (wherein $Z^1$ is optionally a hydrogen or a nitrogen-protecting group, for example, but not limited to, tert-butyloxycarbonyl, 2,4-dimethoxybenzyl, 4-methoxybenzyl, or 2-(trimethylsilyl)ethoxymethyl and wherein $Lg^1$ is a leaving group, for example, but not limited to, chloro, bromo or iodo) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (703). The compound of formula (703) can then be reacted with boronic acid derivatives of formula (704) (wherein $Z^4$ is for example, but not limited to, $B(OH)_2$ or 4,4,5,5-tetramethyl-1,3,2$\lambda_2$-dioxaborolane and $R^{15}$ is, for example, but not limited to, methyl, ethyl or cyclopropyl) under standard Suzuki-Miyaura reaction conditions, such as, but not limited to, the use of a solvent, such as, but not limited to, 1,4-dioxane, in the presence of a base, such as, but not limited to, potassium phosphate tribasic, and in the presence of a palladium catalyst composed of for example, but not limited to, palladium acetate and tricyclohexylphosphine tetrafluoroborate, at a temperature of between about ambient temperature and 120° C., for about 1 to 20 hours to generate a compound of formula (705). The compound of formula (705) can then be alkylated with alkylating agents $R^{13}$—$Z^3$ (wherein $Z^3$ is a leaving group such as, but not limited to, bromide, iodide, sulfate) such as, but not limited to, methyl iodide, in presence of a base, such as, but not limited to, lithium bis(trimethylsilyl)amide or sodium hydride, in a polar aprotic solvent such as, but not limited to, tetrahydrofuran or N,N-dimethylformamide, at temperature of between about −78° C. and ambient temperature, to provide a compound of formula (706). The compound of formula (706) is then treated with an acid, such as, but not limited to, trifluoroacetic acid, in a polar aprotic solvent, such as, but not limited to, dichloromethane, at a temperature of between about 0° C. and ambient temperature to generate a compound of formula (707). The compound of formula (707) is then reacted with, for example, but not limited to, an aldehyde or ketone of formula (708) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to generate a compound of formula (Ib), which can be isolated from the reaction mixture by standard techniques.

Alternatively, compounds of formula (I) where $R^3$ is —N($R^{13}$)—, $R^4$ is hydrogen and $R^7$ is alkyl or cycloalkyl, i.e., compounds of formula (Ib) where $R^4$ is hydrogen and $R^7$ is alkyl or cycloalkyl, as described above in the Embodiments of the Invention, can be synthesized following the general procedure described below in Reaction Scheme 8 where X, Y, n, m, $R^1$, $R^2$, $R^3$, $R^5$, $R^6$, $R^8$ and $R^{13}$ are as described above in the Embodiments of the Invention for compounds of formula (Ib) and where $R^7$ is alkyl or cycloalkyl:

REACTION SCHEME 8

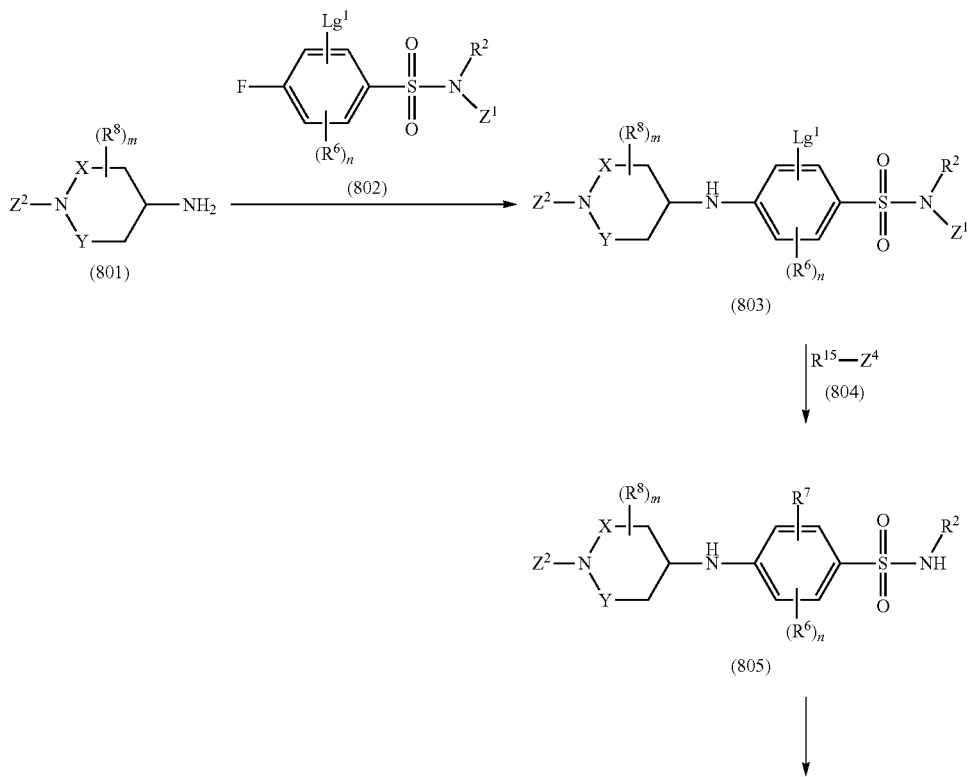

-continued

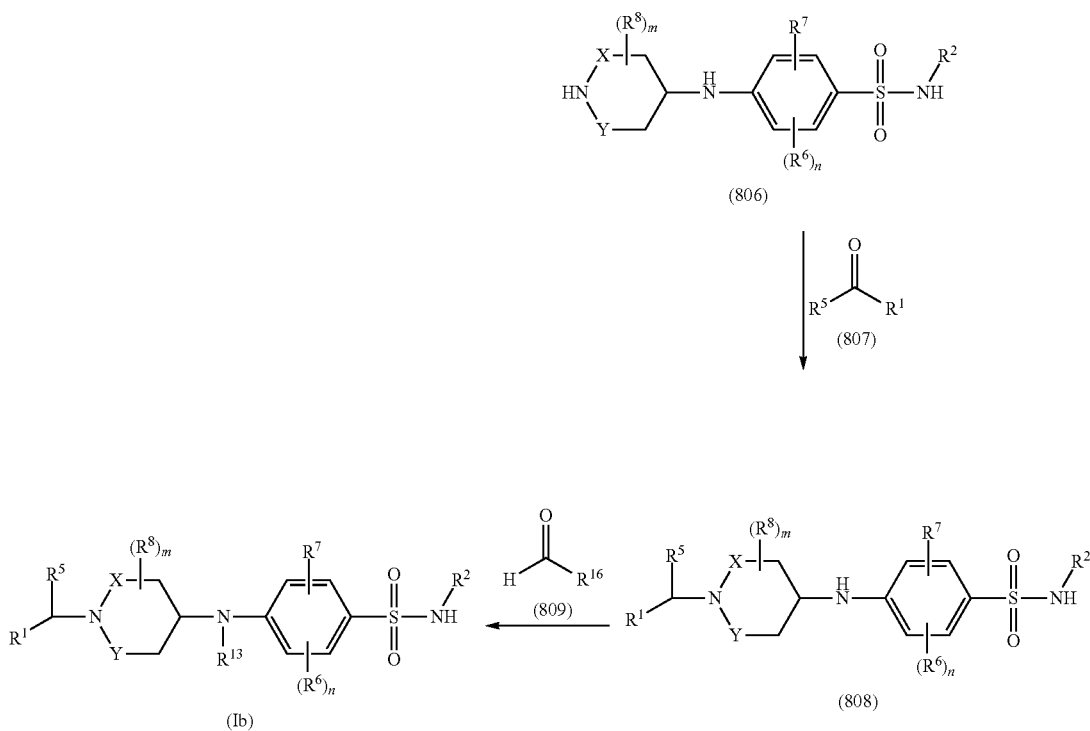

Compounds of formulae (801), (802), (803), (804), (805), (806), (807), (808) and (809) are commercially available or can be prepared according to methods known to one skilled in the art or by methods disclosed herein. In general, the compounds of formula (Ib) are prepared as described above in Reaction Scheme 8 as follows:

The compound of formula (801) (wherein $Z^2$ is a nitrogen-protecting group, for example, but not limited to, tert-butyloxycarbonyl, is reacted with sulfonamide (802) (wherein $Z^1$ is optionally a hydrogen or a nitrogen-protecting group, for example, but not limited to, tert-butyloxycarbonyl, 2,4-dimethoxybenzyl, 4-methoxybenzyl, or 2-(trimethylsilyl)ethoxymethyl and wherein $Lg^1$ is a leaving group, for example, but not limited to, chloro, bromo or iodo) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (803). The compound of formula (803) can then be reacted with boronic acid derivatives of formula (804) (wherein $Z^4$ is for example, but not limited to, B(OH)$_2$ or 4,4,5,5-tetramethyl-1,3,2λ$_2$-dioxaborolane and $R^{15}$ is for example, but not limited to, methyl, ethyl or cyclopropyl) under standard Suzuki-Miyaura reaction conditions, such as, but not limited to, the use of a solvent, such as, but not limited to, 1,4-dioxane, in the presence of a base, such as, but not limited to, potassium phosphate tribasic, and in the presence of a palladium catalyst composed of for example, but not limited to, palladium acetate and tricyclohexylphosphine tetrafluoroborate, at a temperature of between about ambient temperature and 120° C., for about 1 to 20 hours to generate a compound of formula (805). The compound of formula (805) is then treated with an acid, such as, but not limited to, trifluoroacetic acid, in a polar aprotic solvent, such as, but not limited to, dichloromethane, at a temperature of between about 0° C. and ambient temperature to generate a compound of formula (806). The compound of formula (806) is then reacted with, for example, but not limited to, an aldehyde or ketone of formula (807) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to provide a compound of formula (808). The compound of formula (808) can then be alkylated at the aniline nitrogen by reaction with an aldehyde of formula (809) (wherein $R^{16}$ is for example, but not limited to, hydrogen or methyl) in presence of a reducing agent, such as, but not limited to, sodium triacetoxyborohydride, in a polar solvent or solvent mixture, such as, but not limited to, trifluoroacetic acid, at a temperature of between about 0° C. and ambient temperature to generate a compound of formula (Ib), which can be isolated from the reaction mixture by standard techniques.

Alternatively, compounds of formula (I) where $R^7$ is alkyl or cycloalkyl, as described above in the Summary of the Invention, can be synthesized following the general procedure described below in Reaction Scheme 9 where X, Y, n, m, $R^1$, $R^2$, $R^3$, $R^4$, $R^5$, $R^6$ and $R^8$ are as described above in the Summary of the Invention for compounds of formula (I) and $R^7$ is alkyl or cycloalkyl:

REACTION SCHEME 9

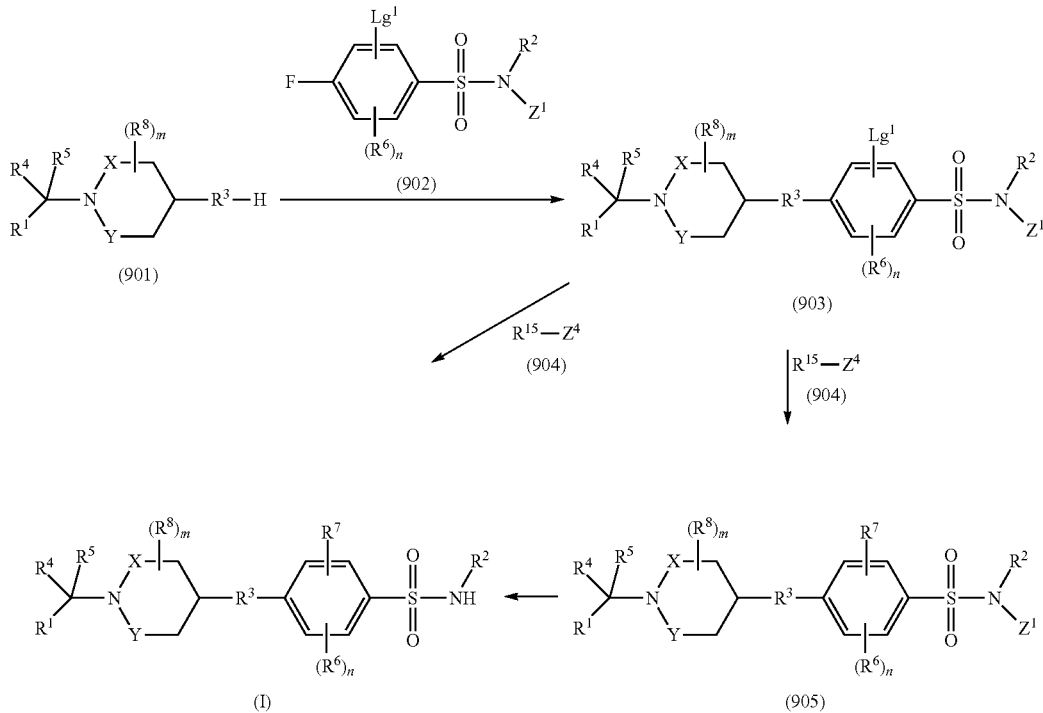

Compounds of formulae (901), (902), (903), (904) and (905) are commercially available or can be prepared according to methods known to one skilled in the art or by methods disclosed herein. In general, the compounds of formula (1) are prepared as described above in Reaction Scheme 9 as follows:

The compound of formula (901) is reacted with sulfonamide (902) (wherein Z is optionally a hydrogen or a nitrogen-protecting group, for example, but not limited to, tert-butyloxycarbonyl, 2,4-dimethoxybenzyl, 4-methoxybenzyl, or 2-(trimethylsilyl)ethoxymethyl and wherein $Lg^1$ is a leaving group, for example, but not limited to, chloro, bromo or iodo) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (903). The compound of formula (903) can then be reacted with boronic acid derivatives of formula (904) (wherein $Z^4$ is for example, but not limited to, $B(OH)_2$ or 4,4,5,5-tetramethyl-1,3,2$\lambda_2$-dioxaborolane and $R^{15}$ is for example, but not limited to, methyl, ethyl or cyclopropyl) under standard Suzuki-Miyaura reaction conditions, such as, but not limited to, the use of a solvent, such as, but not limited to, 1,4-dioxane, in the presence of a base, such as, but not limited to, potassium phosphate tribasic, and in the presence of a palladium catalyst composed of for example, but not limited to, palladium acetate and tricyclohexylphosphine tetrafluoroborate, at a temperature of between about ambient temperature and 120° C., for about 1 to 20 hours to generate a compound of formula (I), which can be isolated from the reaction mixture by standard techniques.

Alternatively, the compound of formula (903) can be reacted with organotin reagents of formula (904) (wherein $Z^4$ is, for example, but not limited to, trimethylstannyl and $R^{15}$ is for example, but not limited to, methyl, under standard Stille-coupling conditions, such as, but not limited to, the use of a solvent, such as, but not limited to, N,N-dimethylformamide, in the presence of an additive, such as, but not limited to, lithium chloride, and in the presence of a palladium catalyst, such as, but not limited to, bis(triphenylphosphine)palladium dichloride, at a temperature of between ambient temperature and 120° C., for about 1 to 20 hours to generate a compound of formula (I), which can be isolated from the reaction mixture by standard techniques.

Under certain conditions, the above transformations will afford a compound of formula (905) instead of a compound of formula (I). In these instances, $Z^1$ can be removed from the compound of formula (905) by methods known in the art, such as, but not limited to, the use of an acid, such as, but not limited to, trifluoroacetic acid, in a polar aprotic solvent, such as, but not limited to, dichloromethane, at a temperature of between about 0° C. and ambient temperature to generate a compound of formula (I).

Alternatively, compounds of formula (I) wherein $R^4$ is hydrogen, as described above in the Summary of the Invention, can be synthesized following the general procedure described below in Reaction Scheme 10 where X, Y, n, m, $R^1$, $R^2$, $R^3$, $R^5$, $R^6$, $R^7$ and $R^8$ are as described above in the Summary of the Invention for compounds of formula (I):

REACTION SCHEME 10

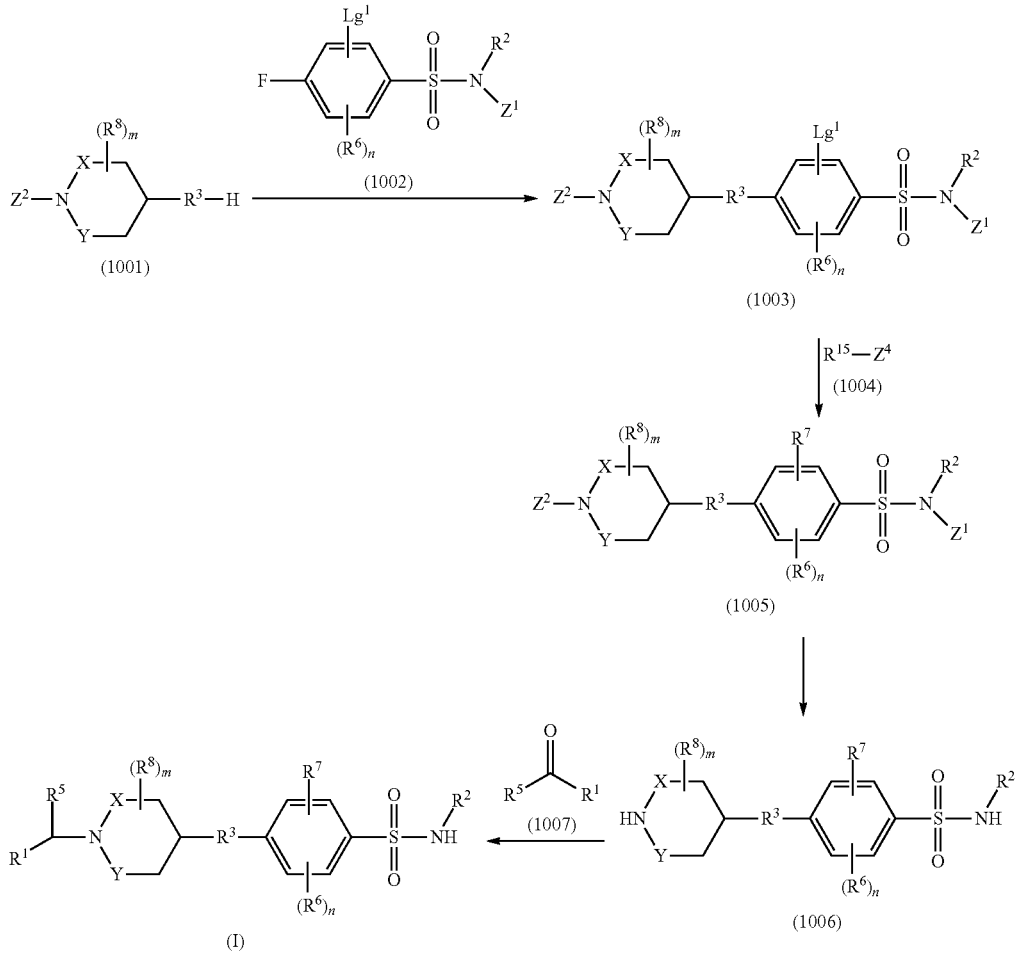

Compounds of formulae (1001), (1002), (1003), (1004), (1005), (1006), and (1007) are commercially available or can be prepared according to methods known to one skilled in the art or by methods disclosed herein. In general, the compounds of formula (I) are prepared as described above in Reaction Scheme 10 as follows:

The compound of formula (1001) (wherein $Z^2$ is a nitrogen-protecting group, for example, but not limited to, tert-butyloxycarbonyl, is reacted with sulfonamide (1002) (wherein $Z^1$ is optionally a hydrogen or a nitrogen-protecting group, for example, but not limited to, tert-butyloxycarbonyl, 2,4-dimethoxybenzyl, 4-methoxybenzyl, or 2-(trimethylsilyl)ethoxymethyl and wherein $Lg^1$ is a leaving group, for example, but not limited to, chloro, bromo or iodo) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (1003). The compound of formula (1003) can then be reacted with boronic acid derivatives of formula (1004) (wherein $Z^4$ is for example, but not limited to, $B(OH)_2$ or 4,4,5,5-tetramethyl-1,3,2$\lambda_2$-dioxaborolane and $R^{15}$ is, for example, but not limited to, methyl, ethyl or cyclopropyl) under standard Suzuki-Miyaura reaction conditions, such as, but not limited to, the use of a solvent, such as, but not limited to, 1,4-dioxane, in the presence of a base, such as, but not limited to, potassium phosphate tribasic, and in the presence of a palladium catalyst composed of for example, but not limited to, palladium acetate and tricyclohexylphosphine tetrafluoroborate, at a temperature of between about ambient temperature and 120° C., for about 1 to 20 hours to generate a compound of formula (1005). The compound of formula (1005) is then treated with an acid, such as, but not limited to, trifluoroacetic acid, in a polar aprotic solvent, such as, but not limited to, dichloromethane, at a temperature of between about 0° C. and ambient temperature to generate a compound of formula (1006). The compound of formula (1006) is then reacted with, for example, but not limited to, an aldehyde or ketone of formula (1007) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to generate a compound of formula (Ib), which can be isolated from the reaction mixture by standard techniques.

Alternatively, compounds of formula (Ib) where $R^4$ is hydrogen, as described above in the Embodiments of the Invention, can be synthesized following the general procedure described below in Reaction Scheme 11 where X, Y, n, m, $R^1$, $R^2$, $R^3$, $R^5$, $R^6$, $R^7$ and $R^8$ are as described above in the Embodiments of the Invention for compounds of formula (Ib):

ing group, for example, but not limited to, tert-butyloxycarbonyl, 2,4-dimethoxybenzyl, 4-methoxybenzyl, or 2-(trimethylsilyl)ethoxymethyl and wherein $Lg^1$ is a leaving group,

REACTION SCHEME 11

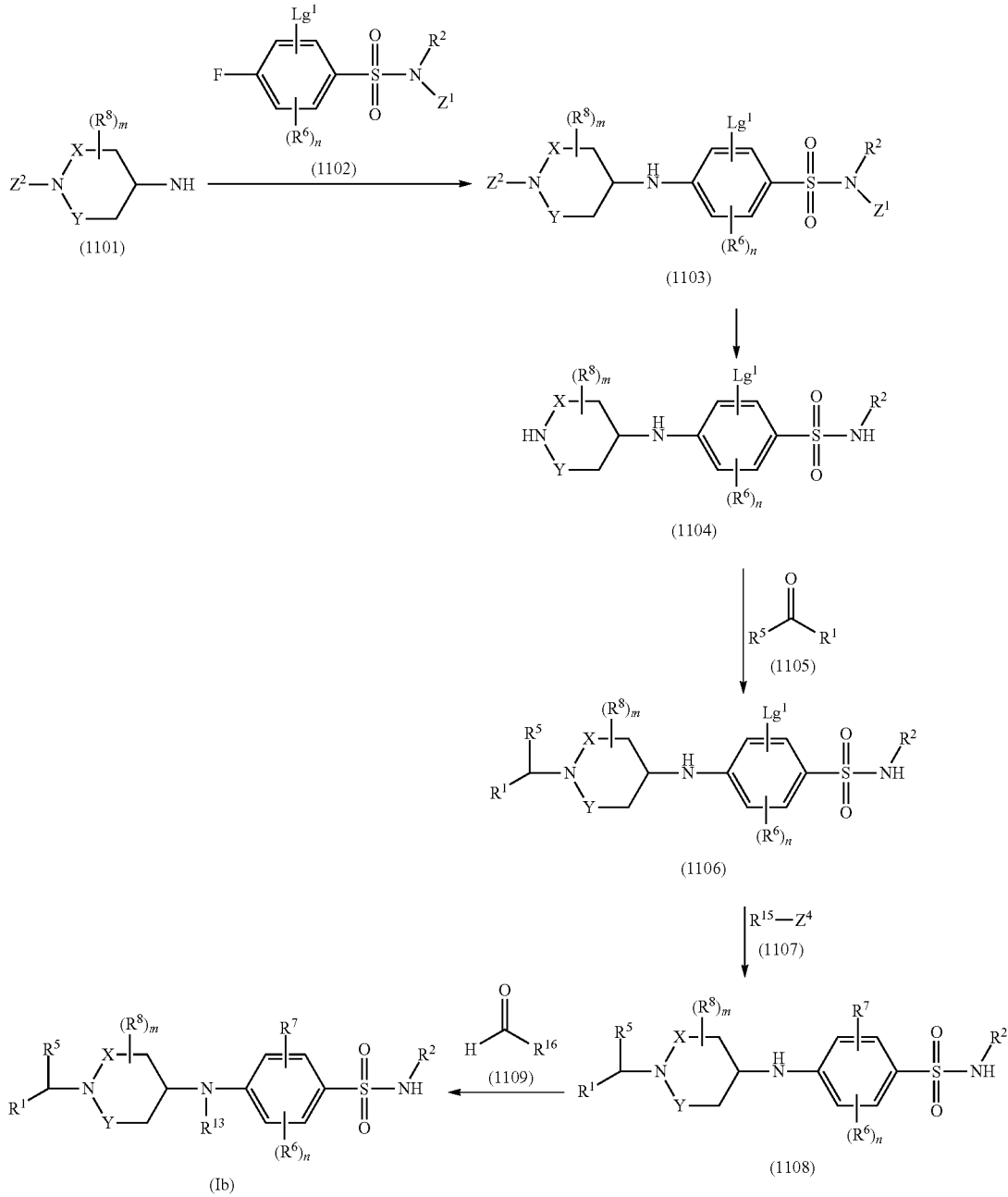

Compounds of formulae (1101), (1102), (1103), (1104), (1105), (1106), (1107), (1108), and (1109) are commercially available or can be prepared according to methods known to one skilled in the art or by methods disclosed herein. In general, the compounds of formula (Ib) are prepared as described above in Reaction Scheme 11 as follows:

The compound of formula (1101) (wherein $Z^2$ is a nitrogen-protecting group, for example, but not limited to, tert-butyloxycarbonyl, is reacted with sulfonamide (1102) (wherein $Z^1$ is optionally a hydrogen or a nitrogen-protectfor example, but not limited to, chloro, bromo or iodo) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (1103). The compound of formula (1103) is then treated with an acid, such as, but not limited to, trifluoroacetic acid, in a polar aprotic solvent, such as, but not limited to, dichloromethane, at a temperature of between about 0° C. and ambient temperature to generate a compound of formula (1104). The compound of formula (1104) is then reacted with, for example, but not limited to, an aldehyde or ketone of formula (1105) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to generate a compound of formula (1106). The compound of formula (1106) can then be reacted with boronic acid derivatives of formula (1107) (wherein $Z^4$ is for example, but not limited to, $B(OH)_2$ or 4,4,5,5-tetramethyl-1,3,2$\lambda_2$-dioxaborolane and $R^{15}$ is for example, but not limited to, methyl, ethyl or cyclopropyl) under standard Suzuki-Miyaura reaction conditions, such as, but not limited to, the use of a solvent, such as, but not limited to, 1,4-dioxane, in the presence of a base, such as, but not limited to, potassium phosphate tribasic, and in the presence of a palladium catalyst composed of for example, but not limited to, palladium acetate and tricyclohexylphosphine tetrafluoroborate, at a temperature of between about ambient temperature and 120° C., for about 1 to 20 hours to generate a compound of formula (1108). The compound of formula (1108) is then reacted with, for example, but not limited to, an aldehyde or ketone of formula (1109) (wherein $R^{16}$ is for example, but not limited to, hydrogen or methyl) in presence of a reducing agent, such as, but not limited to, sodium triacetoxyborohydride, in a polar aprotic solvent mixture, such as, but not limited to, N,N-dimethylformamide and 1,2-dichloroethane, at a temperature of between about 0° C. and ambient temperature to generate a compound of formula (Ib), which can be isolated from the reaction mixture by standard techniques.

Alternatively, compounds of formula (Ib) where $R^4$ is hydrogen and $R^{13}$ is hydrogen or alkyl, as described above in the Embodiments of the Invention, can be synthesized following the general procedure described below in Reaction Scheme 12 where X, Y, n, m, $R^1$, $R^2$, $R^3$, $R^5$, $R^6$, $R^7$ and $R^8$ are as described above in the Embodiments of the Invention for compounds of formula (Ib) and where $R^{13}$ is hydrogen or alkyl:

REACTION SCHEME 12

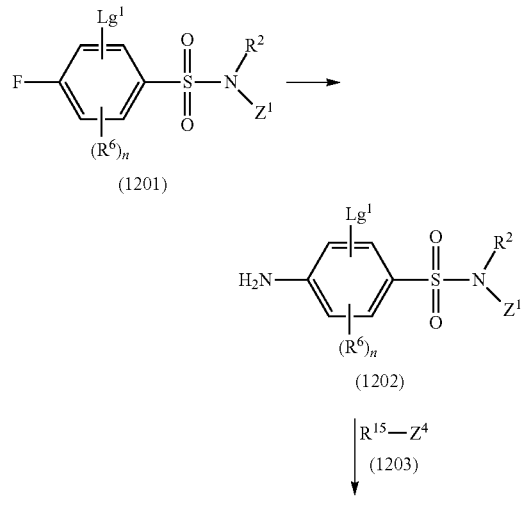
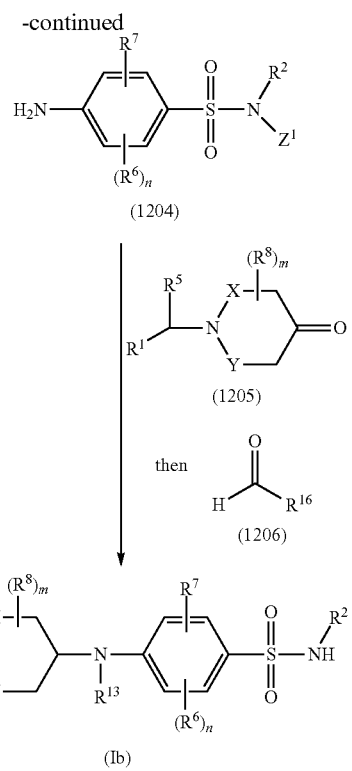

Compounds of formulae (1201), (1202), (1203), (1204), (1205), and (1206) are commercially available or can be prepared according to methods known to one skilled in the art or by methods disclosed herein. In general, the compounds of formula (Ib) are prepared as described above in Reaction Scheme 12 as follows:

The compound of formula (1201) (wherein $Z^1$ is optionally a hydrogen or a nitrogen-protecting group, for example, but not limited to, tert-butyloxycarbonyl, 2,4-dimethoxybenzyl, 4-methoxybenzyl, or 2-(trimethylsilyl)ethoxymethyl and wherein $Lg^1$ is a leaving group, for example, but not limited to, chloro, bromo or iodo) is reacted with a nitrogen nucleophile, such as, but not limited to, sodium azide, under standard reaction conditions, such as, but not limited to, the use of a polar aprotic solvent, such as, but not limited to, dimethyl sulfoxide or N,N-dimethylformamide, at a temperature of between about 0° C. and 80° C., for about 1 to 48 hours. The compound which can isolated from the reaction mixture by standard techniques is then treated with a reducing agent, such as, but not limited to, zinc dust, in a polar aprotic solvent, such as, but not limited to, tetrahydrofuran, in the presence of a weak acid, such as, but not limited to, aqueous ammonium chloride, to afford a compound of formula (1202).

Alternatively, $Lg^1$ in compound of formula (1202) can be converted into $R^7$ by reaction with boronic acid derivatives of formula (1203) (wherein $Z^4$ is for example, but not limited to, $B(OH)_2$ or 4,4,5,5-tetramethyl-1,3,2$\lambda_2$-dioxaborolane and $R^{15}$ is for example, but not limited to, methyl, ethyl or cyclopropyl) under standard Suzuki-Miyaura reaction conditions, such as, but not limited to, the use of a solvent, such as, but not limited to, 1,4-dioxane, in the presence of a base, such as, but not limited to, potassium phosphate tribasic, and in the presence of a palladium catalyst composed of for example, but not limited to, palladium acetate and tricyclohexylphosphine tetrafluoroborate, at a temperature of between about ambient temperature and 120° C., for about 1 to 20 hours to generate a compound of formula (1204).

Compounds of formula (1202) or compounds of formula (1204) are then reacted with, for example, but not limited to, a ketone of formula (1205) in the presence of a reducing agent, such as, but not limited to, sodium triacetoxyborohydride, in an acidic solvent, such as, but not limited to, trifluoroacetic acid, at a temperature of between about 0° C. and ambient temperature, followed by reaction with an aldehyde of formula (1206) (wherein $R^{16}$ is for example, but not limited to, hydrogen or methyl) in the presence of a reducing agent, such as, but not limited to, sodium triacetoxyborohydride, in an acidic solvent, such as, but not limited to, trifluoroacetic acid, at a temperature of between about 0° C. and ambient temperature, to generate a compound of formula (Ib), which can be isolated from the reaction mixture by standard techniques.

Alternatively, compounds of formula (Ib), as described above in the Embodiments of the Invention, can be synthesized following the general procedure described below in Reaction Scheme 13 where X, Y, n, m, $R^1$, $R^2$, $R^3$, $R^4$, $R^5$, $R^6$, $R^7$ and $R^8$ are as described above in the Embodiments of the Invention for compounds of formula (Ib) and $R^{13}$ is hydrogen or alkyl:

bromo or iodo) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (1303). The compound of formula (1303) can then be reacted with boronic acid derivatives of formula (1304) (wherein $Z^4$ is for example, but not limited to, $B(OH)_2$ or 4,4,5,5-tetramethyl-1,3,2$\lambda_2$-dioxaborolane and $R^{15}$ is for example, but not limited to, methyl, ethyl or cyclopropyl) under standard Suzuki-Miyaura reaction conditions, such as, but not limited to, the use of a solvent, such as, but not limited to, 1,4-dioxane, in the presence of a base, such as, but not limited to, potassium phosphate tribasic, and in the presence of a palladium catalyst composed of for example, but not limited to, palladium acetate and tricyclohexylphosphine tetrafluoroborate, at a temperature of between about ambient temperature and 120° C., for about 1 to 20 hours to generate a compound of formula (1305). The compound of formula (1305) can then be alkylated at the aniline nitrogen by reaction with an aldehyde of formula (1306) (wherein $R^{16}$ is for example, but not limited to, hydrogen or methyl) in presence of a reducing agent, such as, but not limited to, sodium triacetoxyboro-

REACTION SCHEME 13

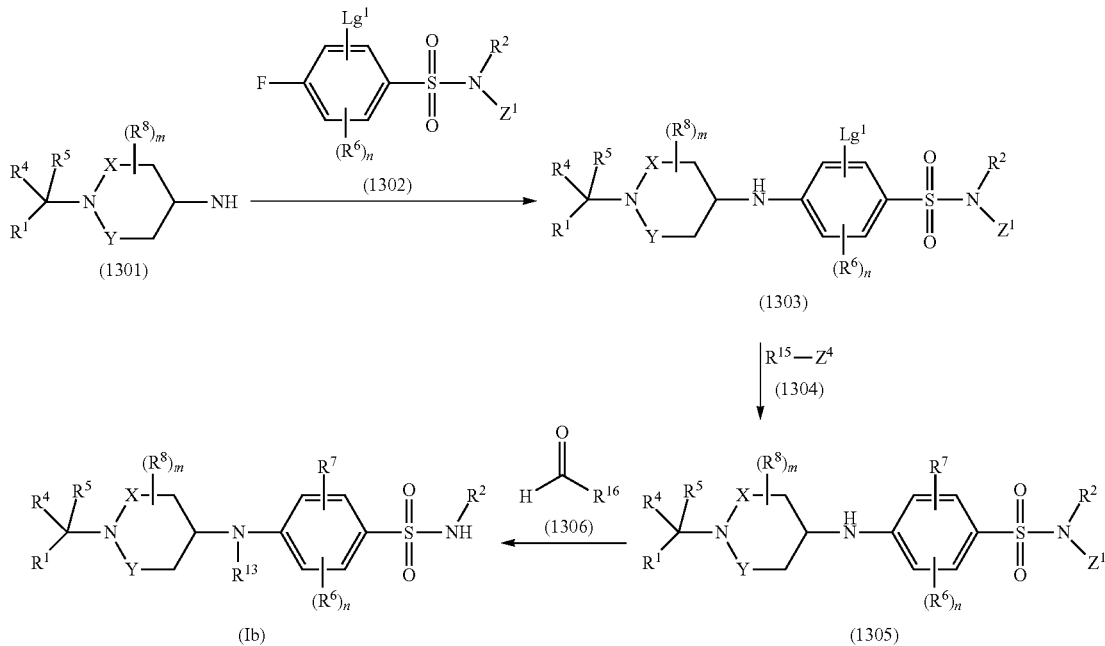

Compounds of formulae (1301), (1302), (1303), (1304), (1305), and (1306) are commercially available or can be prepared according to methods known to one skilled in the art or by methods disclosed herein. In general, the compounds of formula (I) are prepared as described above in Reaction Scheme 13 as follows:

The compound of formula (1301) is reacted with sulfonamide (1302) (wherein $Z^1$ is optionally a hydrogen or a nitrogen-protecting group, for example, but not limited to, tert-butyloxycarbonyl, 2,4-dimethoxybenzyl, 4-methoxybenzyl, or 2-(trimethylsilyl)ethoxymethyl and wherein $Lg^1$ is a leaving group, for example, but not limited to, chloro, hydride, in a polar solvent or solvent mixture, such as, but not limited to, trifluoroacetic acid, at a temperature of between about 0° C. and ambient temperature to generate a compound of formula (Ib), which can be isolated from the reaction mixture by standard techniques.

Alternatively, compounds of formula (1305) can be alkylated at the aniline nitrogen by reaction with alkylating agents such as, but not limited to, methyl iodide, in presence of a base, such as, but not limited to, sodium hydride, in a polar aprotic solvent such as, but not limited to, N,N-dimethylformamide, at temperature of between about −5° C. and ambient temperature. The alkylated compound is then treated with an acid, such as, but not limited to, trifluoroacetic acid, in a polar aprotic solvent, such as, but not limited to, dichloromethane, at a temperature of between about 0° C. and ambient temperature, to generate a compound of formula (Ib), which can be isolated from the reaction mixture by standard techniques.

Alternatively, compounds of formula (Ib), as described above in the Embodiments of the Invention, can be synthesized following the general procedure described below in Reaction Scheme 14 where X, Y, n, m, $R^1$, $R^2$, $R^4$, $R^3$, $R^5$, $R^6$, $R^7$, $R^8$ and $R^{13}$ are as described above in the Embodiments of the Invention for compounds of formula (Ib):

but not limited to, 4,5-bis(diphenylphosphino)-9,9-dimethylxanthene and bis(dibenzylideneacetone)palladium(0) or chloro(2-dicyclohexylphosphino-2',6'-diisopropoxy-1,1'-biphenyl)[2-(2'-amino-1,1'-biphenyl)]palladium(II), at a temperature of between about ambient temperature and 120° C., for about 1 to 20 hours to generate a compound of formula (1403). The compound of formula (1403) can then be alkylated with alkylating agents $R^{13}$—$Z^3$ (1404) (wherein $Z^3$ is a leaving group such as, but not limited to, bromide, iodide, sulfate), such as, but not limited to, methyl iodide, in presence of a base, such as, but not limited to, sodium hydride, in a polar aprotic solvent such as, but not limited to,

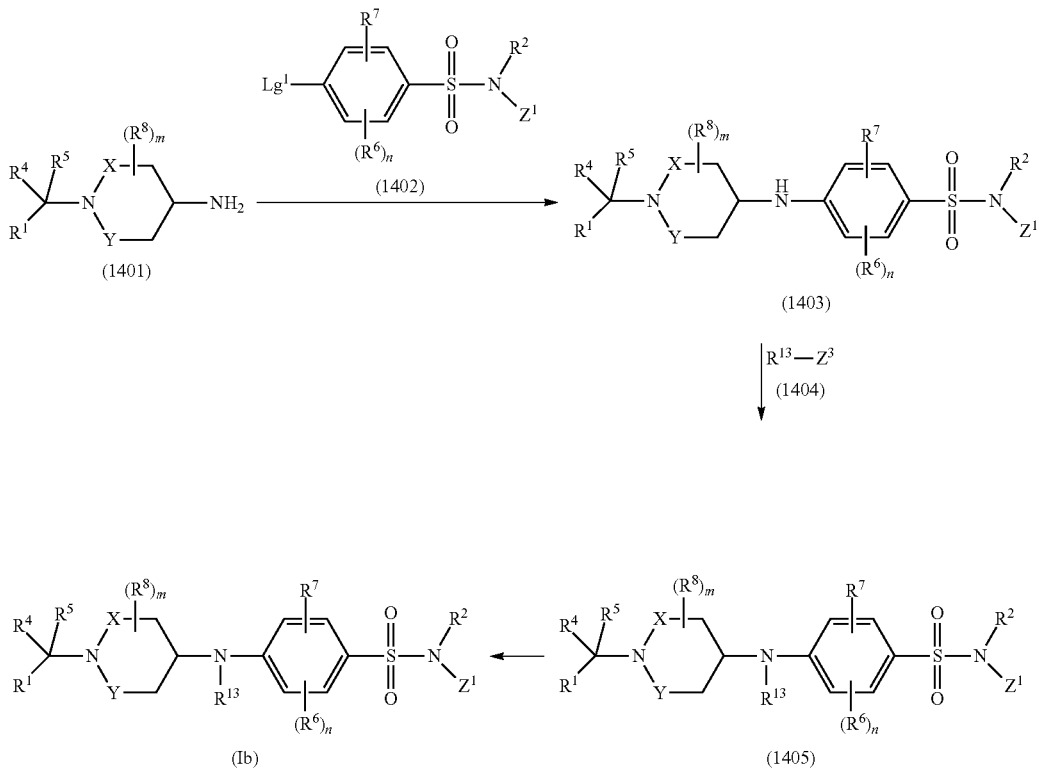

REACTION SCHEME 14

Compounds of formulae (1401), (1402), (1403), (1404) and (1405) are commercially available or can be prepared according to methods known to one skilled in the art or by methods disclosed herein. In general, the compounds of formula (Ib) are prepared as described above in Reaction Scheme 14 as follows:

The compound of formula (1401) is reacted with sulfonamide (1402) (wherein $Lg^1$ is a leaving group, for example, but not limited to, bromo, iodo or trifluorosulfonate and $Z^1$ is hydrogen or a protecting group, for example, but not limited to, tert-butyloxycarbonyl, 2,4-dimethoxybenzyl, 4-methoxybenzyl, or 2-(trimethylsilyl)ethoxymethyl) under standard Buchwald reaction conditions, such as, but not limited to, the use of a solvent, such as, but not limited to, toluene or 2-methyl-2-butanol, in the presence of a base, such as, but not limited to, cesium carbonate, and in the presence of a palladium catalyst composed of for example, N,N-dimethyl formamide, at a temperature of between about 0° C. and ambient temperature, to provide a compound of formula (1405). The compound of formula (1405) is then treated with an acid, such as, but not limited to, trifluoroacetic acid, in a polar aprotic solvent, such as, but not limited to, dichloromethane, at a temperature of between about 0° C. and ambient temperature to generate a compound of formula (Ib), which can be isolated from the reaction mixture by standard techniques.

Compounds of formula (Ib1), which are compounds of formula (Ib) where $R^4$ is hydrogen and at least one $R^6$ is haloalkyl, as described above in the Embodiments of the Invention, can be synthesized following the general procedure described below in Reaction Scheme 15 where X, Y, m, $R^1$, $R^2$, $R^3$, $R^5$, $R^6$, $R^7$ and $R^8$ are as described above in the Summary of the Invention for compounds of formula (Ib), n is 1 or 2 and $R^{6a}$ is haloalkyl:

REACTION SCHEME 15

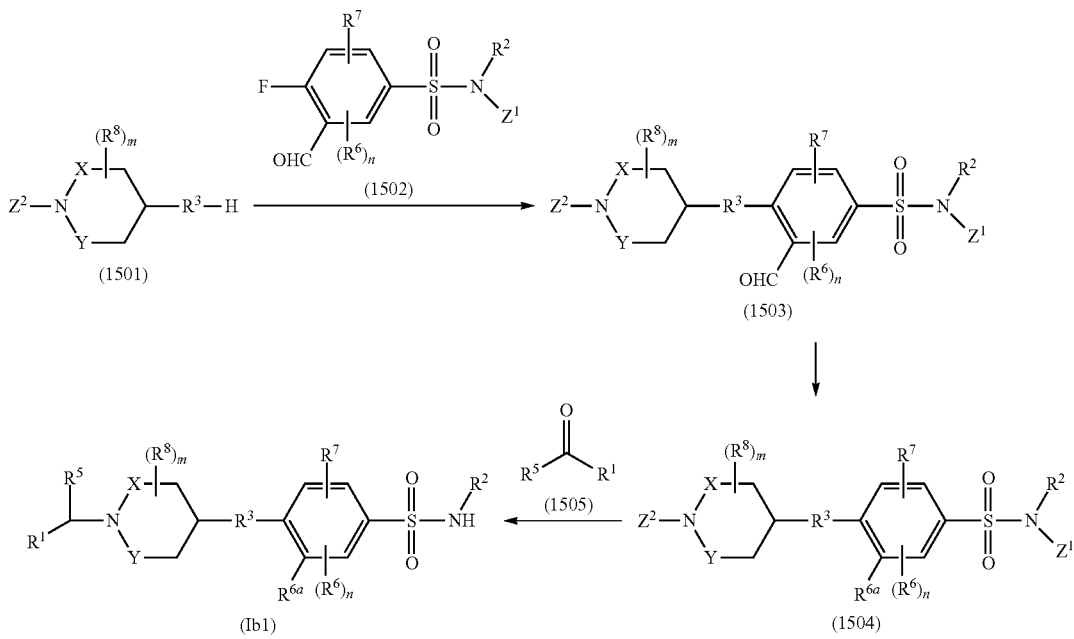

Compounds of formulae (1501), (1502), (1503), (1504), and (1505) are commercially available or can be prepared according to methods known to one skilled in the art or by methods disclosed herein. In general, the compounds of formula (1) are prepared as described above in Reaction Scheme 15 as follows:

The compound of formula (1501) (wherein $Z^2$ is a nitrogen-protecting group, for example, but not limited to, tert-butyloxycarbonyl or benzyl) is reacted with sulfonamide (1502) (wherein $Z^1$ is optionally a hydrogen or a nitrogen protecting group, for example, but not limited to, tert-butyloxycarbonyl, 2,4-dimethoxybenzyl, 4-methoxybenzyl, or 2-(trimethylsilyl)ethoxymethyl) under standard reaction conditions, such as, but not limited to, the use of a polar aprotic solvent, such as, but not limited to, dimethyl sulfoxide or N,N-dimethylformamide, in the presence of a base, such as, but not limited to, potassium carbonate or sodium hydride, at a temperature of between about 0° C. and 80° C., for about 1 to 48 hours to afford a compound of formula (1503). The compound of formula (1503) is then treated with a halogenating reagent, such as, but not limited to, diethylaminosulfur trifluoride, in a polar aprotic solvent such as, but not limited to, dichloromethane, at a temperature of between about 0° C. and ambient temperature to generate a compound of formula (1504) wherein $R^6$ is haloalkyl. The compound of formula (1504) is then treated with an acid, such as, but not limited to, trifluoroacetic acid, in a polar aprotic solvent, such as, but not limited to, dichloromethane, at a temperature of between ambient temperature and 120° C., followed by reaction with, for example, but not limited to, an aldehyde or ketone of formula (1505) in presence of a reducing agent, such as, but not limited to, sodium triacetoxyborohydride, in a polar aprotic solvent mixture, such as, but not limited to, N,N-dimethylformamide and dichloromethane, at a temperature of between about 0° C. and ambient temperature to generate a compound of formula (1), which can be isolated from the reaction mixture by standard techniques.

Alternatively, compounds of formula (I), as described above in the Summary of the Invention, can be synthesized by one skilled in the art by simple functional group transformations. As such, but not limited to, a compound of formula (I) where $R^6$ is alkenyl can be converted into a compound of formula (I) where $R^6$ is alkyl by treatment with hydrogen in the presence of, but not limited to, palladium on carbon, in solvents such as, but not limited to, methanol and ethyl acetate. Alternatively, but not limited to, a compound of formula (I) where $R^1$ is (methoxycarbonyl)phenyl can be converted into a compound of formula (I), whereas $R^1$ is (2-hydroxypropan-2-yl)phenyl by reaction with an organometallic reagent, such as, but not limited to, methylmagnesium bromide, in a polar aprotic solvent such as, but not limited to, tetrahydrofuran.

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

The following Examples, which are directed to the synthesis of the compounds of the invention; and the following Biological Examples are provided as a guide to assist in the practice of the invention, and are not intended as a limitation on the scope of the invention.

In the Examples below, unless otherwise indicated all temperatures are set forth in degrees Celsius. Commercially available reagents were purchased from suppliers such as Aldrich Chemical Company, Combi-Blocks, TCI or Oakwood Chemicals and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Yields were not optimized. Melting points were determined on a Büchi hot-stage apparatus and are uncorrected. $^1$H NMR, $^1$F and $^{13}$C NMR data were obtained in deuterated CDCl$_3$, DMSO-d$_6$, CD$_3$OD, CD$_3$CN, or acetone-d$_6$ solvent solutions with chemical shifts (δ) reported in parts-per-million (ppm) relative to trimethylsilane (TMS) or the residual non-deuterated solvent peaks as the reference standard. Data are reported as follows, if applicable: chemical shift, multiplicity, coupling constant in Hz, and number of protons, fluorine or carbon atoms. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, are reported in Hz (Hertz).

Example 1

Synthesis of 3-chloro-4-((3,3-dimethylpiperidin-4-yl)oxy)-N-(1,2,4-thiadiazol-5-yl)benzenesulfonamide 2,2,2-trifluoroacetate

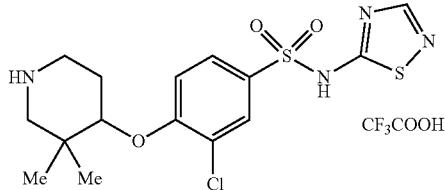 [SMILES: CC1(C)CNCCC1Oc1ccc(S(=O)(=O)Nc2ncns2)cc1Cl ; "CF3COOH"]

Step 1. Preparation of 3-chloro-N-(2,4-dimethoxybenzyl)-4-fluoro-N-(1,2,4-thiadiazol-5-yl)benzenesulfonamide

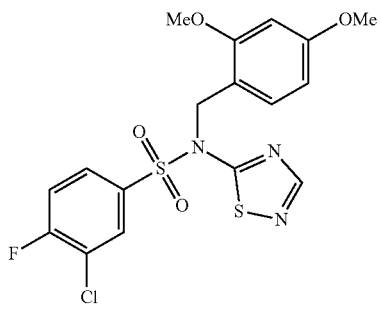 [SMILES: COc1ccc(CN(c2ncns2)S(=O)(=O)c2ccc(F)c(Cl)c2)c(OC)c1]

To a mixture of N-(2,4-dimethoxybenzyl)-1,2,4-thiadiazol-5-amine (prepared according to PCT Published Patent Application No. WO 2010/079443, 15.1 g, 60.2 mmol) in anhydrous tetrahydrofuran (200 mL) was added a 1 M solution of lithium bis(trimethylsilyl)amide in tetrahydrofuran (72.1 mL, 72.1 mmol) at 0° C. and the reaction mixture was stirred for 1 h at ambient temperature. The reaction mixture was cooled to −78° C. and a solution of 3-chloro-4-fluorobenzenesulfonyl chloride (13.8 g, 60.2 mmol) in anhydrous tetrahydrofuran (40 mL)) was added to it. The reaction mixture was allowed to warm to ambient temperature, stirred for 2 h, and diluted with ethyl acetate (280 mL). The mixture was washed with saturated ammonium chloride solution (2×150 mL), brine (150 mL), dried over anhydrous sodium sulfate, and filtered. Concentration of the filtrate in vacuo and trituration of the residue in methanol (110 mL) provided the title compound as a colorless solid (14.8 g, 55% yield): $^1$H NMR (300 MHz, CDCl$_3$) δ 8.22 (s, 1H), 7.71-7.65 (m, 2H), 7.20-7.13 (m, 1H), 7.09 (d, J=8.4 Hz, 1H), 6.36 (dd, J=8.4, 2.4 Hz, 1H), 6.30 (d, J=2.4 Hz, 1H), 5.31 (s, 2H), 3.79 (s, 3H), 3.68 (s, 3H); MS (ES+) m/z 444.0 (M+1), 446.0 (M+1).

Step 2: Preparation of tert-butyl 4-hydroxy-3,3-dimethylpiperidine-1-carboxylate

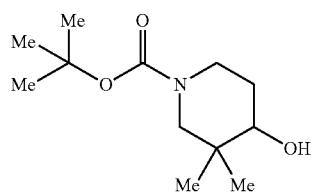 [SMILES: CC(C)(C)OC(=O)N1CCC(O)C(C)(C)C1]

To a solution of tert-butyl 3,3-dimethyl-4-oxopiperidine-1-carboxylate (4.61 g, 20.3 mmol) in anhydrous methanol (75 mL) was added sodium borohydride (0.77 g, 20.3 mmol) at 0° C. The reaction mixture was allowed to warm to ambient temperature and stirred for 48 hours. The mixture was diluted with ethyl acetate (300 mL), washed with 0.5 M hydrochloric acid (4×80 mL), brine (3×60 mL), dried over anhydrous sodium sulfate, and filtered. Concentration of the filtrate in vacuo provided the title compound as a colorless solid (4.59 g, 99% yield): $^1$H NMR (300 MHz, CDCl$_3$) δ 3.90-3.78 (m, 1H), 3.57-3.48 (m, 1H), 3.41 (dd, J=9.2, 4.2 Hz, 1H), 3.08-2.99 (m, 1H), 2.73 (d, J=13.4 Hz, 1H), 1.85-1.71 (m, 2H), 1.62-1.55 (m, 1H), 1.42 (s, 9H), 0.95 (s, 3H), 0.88 (s, 3H); MS (ES+) m/z 230.2 (M+1).

Step 3. Preparation of tert-butyl 4-(2-chloro-4-(N-(2,4-dimethoxybenzyl)-N-(1,2,4-thiadiazol-5-yl)sulfamoyl)phenoxy)-3,3-dimethylpiperidine-1-carboxylate

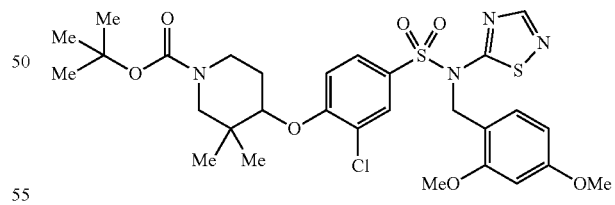

To a solution of tert-butyl 4-hydroxy-3,3-dimethylpiperidine-1-carboxylate (1.37 g, 5.97 mmol) in anhydrous tetrahydrofuran (180 mL) was added a 1.0 M solution of lithium bis(trimethylsilyl)amide in tetrahydrofuran (6.0 mL, 6.0 mmol) at −78° C. The reaction mixture was allowed to warm to ambient temperature, stirred for 1 h, and cooled to −78° C. To it was then added a mixture of 3-chloro-N-(2,4-dimethoxybenzyl)-4-fluoro-N-(1,2,4-thiadiazol-5-yl)benzenesulfonamide (2.65 g, 5.97 mmol) in anhydrous tetrahydrofuran (10 mL). The reaction mixture was allowed to warm to ambient temperature, stirred for 4 h, and diluted with ethyl acetate (200 mL). The mixture was washed with saturated ammonium chloride (2×200 mL), dried over anhydrous sodium sulfate, and filtered. Concentration of the filtrate in vacuo provided a residue which was purified by column chromatography eluting with 30% of ethyl acetate in hexanes. The title compound was obtained as a clear oil (2.36 g, 61% yield): $^1$H NMR (300 MHz, CDCl$_3$) δ 8.18 (s, 1H), 7.67 (d, J=2.4 Hz, 1H), 7.62 (dd, J=8.8, 2.3 Hz, 1H), 7.05 (d, J=8.2 Hz, 1H), 6.83 (d, J=8.8 Hz, 1H), 6.37-6.28 (m, 2H), 5.25 (s, 2H), 4.12 (dd, J=7.1, 4.4 Hz, 1H), 3.76 (s, 3H), 3.72 (s, 3H), 3.63-3.36 (m, 4H), 3.15 (d, J=13.5 Hz, 1H), 1.94-1.86 (m, 1H), 1.48 (s, 9H), 1.06 (s, 3H), 1.03 (s, 3H).

Step 4. Preparation of 3-chloro-4-((3,3-dimethylpiperidin-4-yl)oxy)-N-(1,2,4-thiadiazol-5-yl)benzenesulfonamide 2,2,2-trifluoroacetate

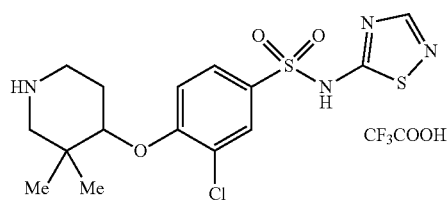 [SMILES: CC1(C)CNCCC1Oc1ccc(S(=O)(=O)Nc2ncns2)cc1Cl ; "CF3COOH"]

To a solution of tert-butyl 4-(2-chloro-4-(N-(2,4-dimethoxybenzyl)-N-(1,2,4-thiadiazol-5-yl)sulfamoyl)phenoxy)-3,3-dimethylpiperidine-1-carboxylate (2.36 g, 3.61 mmol) in dichloromethane (15 mL) was added trifluoroacetic acid (5 mL) and the resulting mixture was stirred for 2 h. The reaction mixture was concentrated in vacuo, triturated in methanol (60 mL), and filtered. Concentration of the filtrate in vacuo provided the title compound as a colorless foam (1.87 g, quantitative yield): $^1$H NMR (300 MHz, DMSO-d$_6$) δ 8.79 (br s, 1H), 8.64 (br s, 1H), 8.43 (s, 1H), 7.76 (d, J=2.3 Hz, 1H), 7.70 (dd, J=8.7, 2.3 Hz, 1H), 7.38 (d, J=8.7 Hz, 1H), 4.53 (dd, J=7.7, 3.0 Hz, 1H), 3.12-2.98 (m, 3H), 2.96-2.85 (m, 1H), 2.09-1.97 (m, 1H), 1.85-1.70 (m, 1H), 1.07 (s, 3H), 1.02 (s, 3H), NH not observed; MS (ES+) m/z 403.0 (M+1), 405.0 (M+1).

Example 2

Synthesis of 4-((1-benzyl-3,3-dimethylpiperidin-4-yl)oxy)-3-chloro-N-(1,2,4-thiadiazol-5-yl)benzenesulfonamide 2,2,2-trifluoroacetate

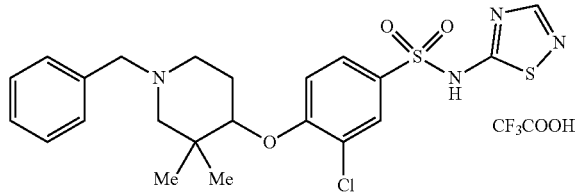 [SMILES: CC1(C)CN(Cc2ccccc2)CCC1Oc1ccc(S(=O)(=O)Nc2ncns2)cc1Cl ; "CF3COOH"]

To a mixture of 3-chloro-4-((3,3-dimethylpiperidin-4-yl)oxy)-N-(1,2,4-thiadiazol-5-yl)benzenesulfonamide 2,2,2-trifluoroacetate (0.20 g, 0.39 mmol) and benzaldehyde (0.08 g, 0.78 mmol) in anhydrous 1,2-dichloroethane (8 mL) was added sodium triacetoxyborohydride (0.17 g, 0.78 mmol) and the resulting mixture was stirred for 18 h. The mixture was diluted with ethyl acetate (50 mL), washed with saturated ammonium chloride (2×30 mL), and the organic phase was concentrated in vacuo. The residue was purified by preparative reverse-phase HPLC eluting with a gradient of 10 to 60% of acetonitrile in water containing 0.1% of trifluoroacetic acid to provide the title compound as a colorless solid (0.075 g, 32% yield): $^1$H NMR (300 MHz, DMSO-d$_6$) δ 9.71 (br s, 1H), 8.43 (s, 1H), 7.75-7.70 (m, 1H), 7.68 (dd, J=8.7, 2.3 Hz, 1H), 7.56-7.32 (m, 6H), 4.55-4.41 (m, 1H), 4.39-4.23 (m, 2H), 3.52-2.73 (m, 4H), 2.22-2.07 (m, 1H), 2.00-1.76 (m, 1H), 1.15 (s, 3H), 0.92 (s, 3H), NH not observed; MS (ES+) m/z 493.0 (M+1), 495.0 (M+1).

Example 3

Synthesis of 3-chloro-4-((1-(3,5-dimethylbenzyl)-3,3-dimethylpiperidin-4-yl)oxy)-N-(1,2,4-thiadiazol-5-yl)benzenesulfonamide 2,2,2-trifluoroacetate

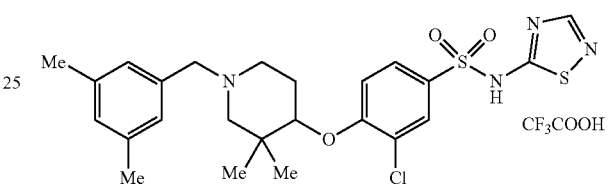

Following the procedure as described for EXAMPLE 2 and making non-critical variations as required to replace benzaldehyde with 3,5-dimethylbenzaldehyde, the title compound was obtained as a colorless solid (0.17 g, 67% yield): $^1$H NMR (300 MHz, DMSO-d$_6$) δ 9.51 (br s, 1H), 8.43 (s, 1H), 7.74 (d, J=2.1 Hz, 1H), 7.68 (dd, J=8.7, 2.1 Hz, 1H), 7.42-7.33 (m, 1H), 7.16-7.03 (m, 3H), 4.58-4.40 (m, 1H), 4.29-4.13 (m, 2H), 3.45-3.02 (m, 3H), 2.99-2.78 (m, 1H), 2.26 (s, 6H), 2.19-2.05 (m, 1H), 2.01-1.75 (m, 1H), 1.16 (d, J=13.1 Hz, 3H), 0.93 (s, 3H) (Note: NH not observed); MS (ES+) m/z 521.0 (M+1), 523.0 (M+1).

Example 4

Synthesis of 3-chloro-4-((1-(3,5-dichlorobenzyl)-3,3-dimethylpiperidin-4-yl)oxy)-N-(1,2,4-thiadiazol-5-yl)benzenesulfonamide 2,2,2-trifluoroacetate

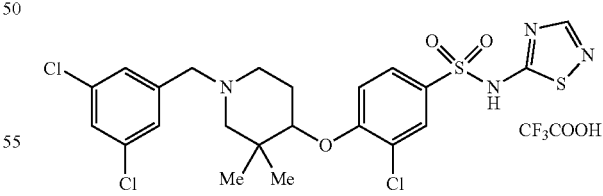

Following the procedure as described for EXAMPLE 2 and making non-critical variations as required to replace benzaldehyde with 3,5-chlorobenzaldehyde, the title compound was obtained as a colorless solid (0.135 g, 51% yield): $^1$H NMR (300 MHz, DMSO-d$_6$) δ 9.92 (br s, 1H), 8.44 (s, 1H), 7.76-7.62 (m, 5H), 7.37 (d, J=8.9 Hz, 1H), 5.56 (br s, 1H), 4.54-4.43 (m, 1H), 4.30 (s, 2H), 3.46-2.74 (m, 4H), 2.21-2.06 (m, 1H), 1.99-1.81 (m, 1H), 1.04 (br s, 6H); MS (ES+) m/z 561.0 (M+1), 563.0, 564.9 (M+1).

Example 5

Synthesis of 3-chloro-4-((1-(3-(difluoromethoxy)benzyl)piperidin-4-yl)oxy)-N-(thiazol-2-yl)benzenesulfonamide

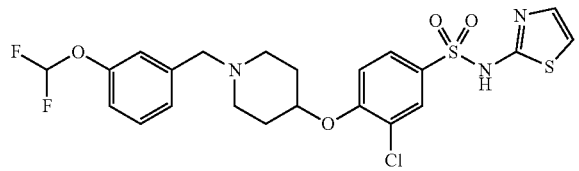 [SMILES: O=S(=O)(Nc1nccs1)c1ccc(OC2CCN(Cc3cccc(OC(F)F)c3)CC2)c(Cl)c1]

Step 1. Preparation of 3-chloro-N-(2,4-dimethoxybenzyl)-4-fluoro-N-(thiazol-2-yl)benzenesulfonamide

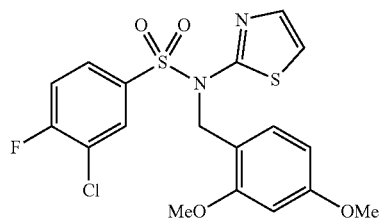 [SMILES: COc1ccc(CN(c2nccs2)S(=O)(=O)c2ccc(F)c(Cl)c2)c(OC)c1]

To a mixture of N-(2,4-dimethoxybenzyl)thiazol-2-amine (prepared according to WO 2013063459, 35.0 g, 140 mmol) in anhydrous tetrahydrofuran (350 mL) was added a 1 M solution of lithium bis(trimethylsilyl)amide in tetrahydrofuran (182 mL, 182 mmol) at −78° C. The reaction mixture was warmed to 0° C. and stirred for 30 minutes. The reaction mixture was cooled to −78° C. and a solution of 3-chloro-4-fluorobenzenesulfonyl chloride (41.6 g, 182 mmol) in anhydrous tetrahydrofuran (100 mL)) was added to it. The reaction mixture was allowed to warm to ambient temperature, stirred for 2 h, quenched by addition of water (200 mL), and extracted with ethyl acetate (3×200 mL). The combined organic phase was washed with brine (50 mL), dried over anhydrous sodium sulfate, filtered, and the filtrate was concentrated in vacuo. Purification of the residue by column chromatography eluting with a gradient of 2 to 20% of ethyl acetate in petroleum ether followed trituration in methanol (2×150 mL) provided the title compound as a colorless solid (32.0 g, 50% yield): $^1$H NMR (300 MHz, CDCl$_3$) δ 7.86 (dd, J=8.0, 2.4 Hz, 1H), 7.78-7.71 (m, 1H), 7.47 (d, J=4.0 Hz, 1H), 7.23 (t, J=8.0 Hz, 1H), 7.16 (d, J=12.0 Hz, 1H), 7.08 (d, J=4.0 Hz, 1H), 6.41-6.35 (m, 2H), 5.07 (s, 2H), 3.79 (s, 3H), 3.71 (s, 3H); MS (ES+) m/z 464.9 (M+23), 467.0 (M+23).

Step 2. Preparation of tert-butyl 4-(2-chloro-4-(N-(2,4-dimethoxybenzyl)-N-(thiazol-2-yl)sulfamoyl)phenoxy)piperidine-1-carboxylate

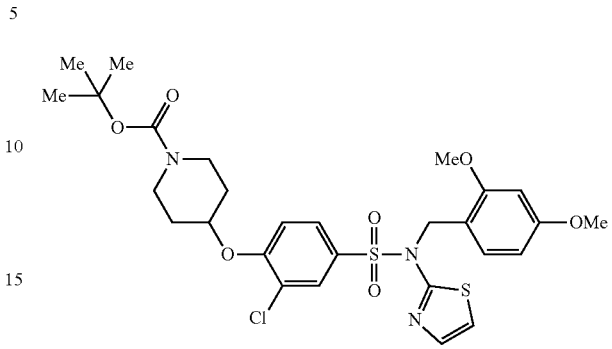

To a solution of tert-butyl 4-hydroxypiperidine-1-carboxylate (4.43 g, 22.0 mmol) in anhydrous tetrahydrofuran (75 mL) was added a 1.0 M solution of lithium bis(trimethylsilyl)amide in tetrahydrofuran (25.0 mL, 25.0 mmol) at −78° C. The resulting mixture was warmed to ambient temperature and stirred for 1 hour. The reaction mixture was cooled to −78° C. and 3-chloro-N-(2,4-dimethoxybenzyl)-4-fluoro-N-(thiazol-2-yl)benzenesulfonamide (8.86 g, 20.0 mmol) was added. The resulting mixture was warmed to ambient temperature and stirred for 18 hours. The reaction mixture was cooled to 0° C. and a dispersion of 60% sodium hydride in mineral oil (0.80 g, 20.0 mmol) was added to it. The resulting mixture was heated at 45° C. for 2 hours and then cooled to ambient temperature. The reaction mixture was quenched with the slow addition of water (100 mL) and diluted with ethyl acetate (250 mL). The mixture was washed with saturated ammonium chloride (2×150 mL), brine (100 mL), dried over anhydrous sodium sulfate, and filtered. Concentration of the filtrate in vacuo and purification of the residue by column chromatography, eluting with a gradient of 10 to 60% of ethyl acetate in hexanes, provided the title compound was obtained as foam (10.68 g, 86% yield): $^1$H NMR (300 MHz, CDCl$_3$) δ 7.80 (d, J=2.3 Hz, 1H), 7.67 (dd, J=8.7, 2.3 Hz, 1H), 7.43 (d, J=3.6 Hz, 1H), 7.18-7.15 (m, 1H), 7.03 (d, J=3.6 Hz, 1H), 6.94 (d, J=8.8 Hz, 1H), 6.39-6.35 (m, 2H), 5.07 (s, 2H), 4.69-4.63 (m, 1H), 3.77 (s, 3H), 3.73 (s, 3H), 3.67-3.49 (m, 4H), 1.95-1.82 (m, 4H), 1.49 (s, 9H); MS (ES+) m/z 624.3 (M+1), 626.3 (M+1).

Step 3. Preparation of 3-chloro-4-(piperidin-4-yloxy)-N-(thiazol-2-yl)benzenesulfonamide 2,2,2-trifluoroacetate

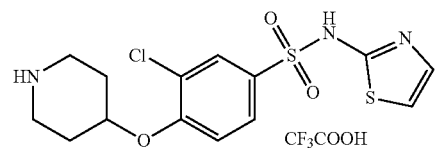 [SMILES: O=S(=O)(Nc1nccs1)c1ccc(OC2CCNCC2)c(Cl)c1 ; "CF3COOH"]

To a solution of tert-butyl 4-(2-chloro-4-(N-(2,4-dimethoxybenzyl)-N-(thiazol-2-yl)sulfamoyl)phenoxy)piperidine-1-carboxylate (10.68 g, 17.11 mmol) in dichloromethane (80 mL) was added trifluoroacetic acid (25 mL) and the resulting mixture was stirred at ambient temperature for 1.5 h. The mixture was concentrated in vacuo, and the residue was triturated in methanol (60 mL). Filtration of the mixture and concentration of the filtrate in vacuo provided the title compound as a brown foam (8.35 g, quantitative yield): $^1$H NMR (300 MHz, DMSO-$d_6$) δ 12.79 (br s, 1H), 8.71 (br s, 2H), 7.74 (d, J=2.1 Hz, 1H), 7.68 (dd, J=8.7, 2.3 Hz, 1H), 7.36 (d, J=8.7 Hz, 1H), 7.24 (d, J=4.6 Hz, 1H), 6.82 (d, J=4.6 Hz, 1H), 4.88-4.78 (m, 1H), 3.23-3.00 (m, 4H), 2.13-2.00 (m, 2H), 1.91-1.75 (m, 2H); MS (ES+) m/z 374.1 (M+1), 376.1 (M+1).

Step 4. Preparation of 3-chloro-4-((1-(3-(difluoromethoxy)benzyl)piperidin-4-yl)oxy)-N-(thiazol-2-yl)benzenesulfonamide

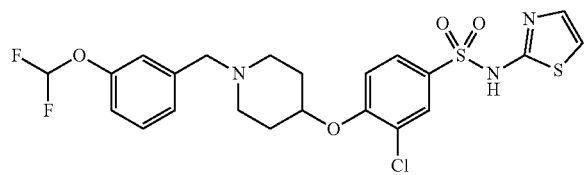 [SMILES: O=S(=O)(Nc1nccs1)c1ccc(OC2CCN(Cc3cccc(OC(F)F)c3)CC2)c(Cl)c1]

To a mixture of 3-(difluoromethoxy)benzaldehyde (0.18 g, 1.04 mmol) and 3-chloro-4-(piperidin-4-yloxy)-N-(thiazol-2-yl)benzenesulfonamide 2,2,2-trifluoroacetate (0.25 g, 0.52 mmol) in anhydrous N,N-dimethylformamide (3 mL) and anhydrous 1,2-dichloroethane (5 mL) was added sodium triacetoxyborohydride (0.42 g, 1.04 mmol) and the resulting mixture was stirred at ambient temperature for 18 h. The reaction mixture was diluted with ethyl acetate (50 mL), washed with saturated ammonium chloride (40 mL), saturated sodium bicarbonate (40 mL), dried over anhydrous sodium sulfate, and filtered. Concentration of the filtrate in vacuo gave a residue which was purified by flash chromatography eluting with a gradient of 0 to 20% of methanol (containing 0.2% of ammonium hydroxide) in dichloromethane to provide the title compound as a colorless solid (0.20 g, 73% yield): $^1$H NMR (300 MHz, DMSO-$d_6$) δ 7.71 (d, J=2.2 Hz, 1H), 7.64 (dd, J=8.7, 2.3 Hz, 1H), 7.37-7.26 (m, 2H), 7.22 (d, J=4.6 Hz, 1H), 7.20 (t, J=74.2 Hz, 1H), 7.15 (d, J=7.5 Hz, 1H), 7.11-7.07 (m, 1H), 7.05-6.99 (m, 1H), 6.78 (d, J=4.5 Hz, 1H), 4.64-4.55 (m, 1H), 3.50 (s, 2H), 2.66-2.54 (m, 2H), 2.36-2.25 (m, 2H), 1.96-1.84 (m, 2H), 1.74-1.60 (m, 2H), NH not observed; MS (ES+) m/z 530.1 (M+1), 532.1 (M+1).

Example 6

Synthesis of 3-chloro-4-((1-(cyclohexylmethyl)piperidin-4-yl)oxy)-N-(thiazol-2-yl)benzenesulfonamide 2,2,2-trifluoroacetate

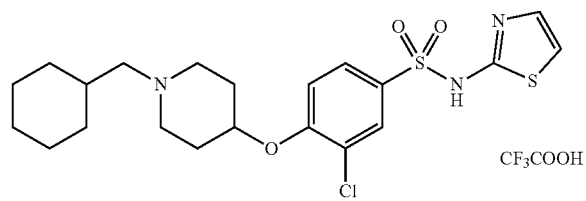 [SMILES: O=S(=O)(Nc1nccs1)c1ccc(OC2CCN(CC3CCCCC3)CC2)c(Cl)c1 ; "CF3COOH"]

Following the procedure as described for EXAMPLE 5, Step 4 and making non-critical variations as required to replace 3-(difluoromethoxy)benzaldehyde with cyclohexanecarbaldehyde, the title compound was obtained as a colorless solid (0.16 g, 27% yield): $^1$H NMR (300 MHz, DMSO-$d_6$) δ 12.77 (br s, 1H), 9.16 (br s, 1H), 7.76-7.72 (m, 1H), 7.69 (d, J=8.6, 2.3 Hz, 1H), 7.42-7.31 (m, 1H), 7.25 (d, J=4.6 Hz, 1H), 6.82 (d, J=4.5 Hz, 1H), 4.97-4.88 (m, 0.5H), 4.77-4.64 (m, 0.5H), 3.58-3.32 (m, 2H), 3.11-2.87 (m, 4H), 2.30-1.99 (m, 3H), 1.96-1.53 (m, 7H), 1.30-1.04 (m, 3H), 1.00-0.82 (m, 2H); MS (ES+) m/z 470.1 (M+1), 472.1 (M+1).

Example 7

Synthesis of 3-chloro-4-((1-cyclohexylpiperidin-4-yl)oxy)-N-(thiazol-2-yl)benzenesulfonamide 2,2,2-trifluoroacetate

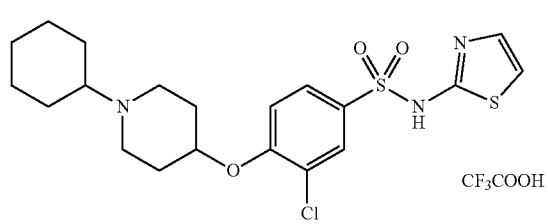 [SMILES: O=S(=O)(Nc1nccs1)c1ccc(OC2CCN(C3CCCCC3)CC2)c(Cl)c1 ; "CF3COOH"]

Following the procedure as described for EXAMPLE 5, Step 4 and making non-critical variations as required to replace 3-(difluoromethoxy)benzaldehyde with cyclohexanone, the title compound was obtained as a colorless solid (0.20 g, 35% yield): $^1$H NMR (300 MHz, DMSO-$d_6$) δ 12.81 (br s, 1H), 9.76 (br s, 0.5H), 9.54 (br s, 0.5H), 7.77-7.72 (m, 1H), 7.69 (dd, J=8.7, 2.1 Hz, 1H), 7.41-7.33 (m, 1H), 7.25 (d, J=4.6 Hz, 1H), 6.82 (d, J=4.7 Hz, 1H), 5.01-4.93 (m, 0.5H), 4.77-4.65 (m, 0.5H), 3.45 (d, J=12.5 Hz, 1H), 3.31 (d, J=12.0 Hz, 1H), 3.24-2.99 (m, 3H), 2.33-1.69 (m, 8H), 1.63-0.97 (m, 6H); MS (ES+) m/z 456.1 (M+1), 458.1 (M+1).

Example 8A and 8B

Synthesis of 4-((cis-1-benzyl-3-methylpiperidin-4-yl)oxy)-3-chloro-N-(thiazol-2-yl)benzenesulfonamide and 4-((trans-1-benzyl-3-methylpiperidin-4-yl)oxy)-3-chloro-N-(thiazol-2-yl)benzenesulfonamide

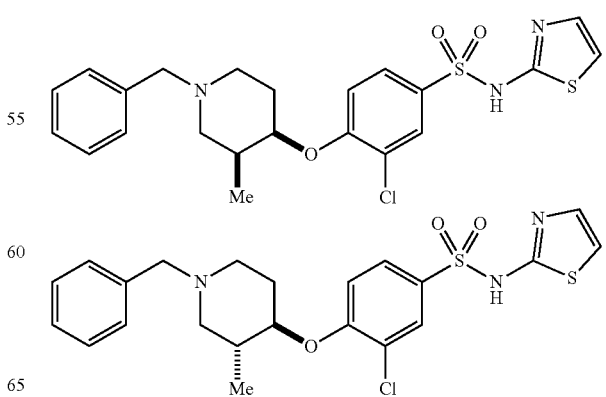

Step 1. Preparation of tert-butyl 4-hydroxy-3-methylpiperidine-1-carboxylate

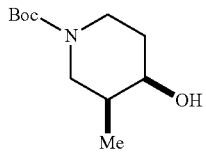

Following the procedure as described for EXAMPLE 1, Step 2 and making non-critical variations as required to replace tert-butyl 3,3-dimethyl-4-oxopiperidine-1-carboxylate with tert-butyl 3-methyl-4-oxopiperidine-1-carboxylate, the title compound was obtained as colorless oil as a 2:1 mixture of diastereomers (2.83 g, 95% yield). Data reported for major isomer: $^1$H NMR (300 MHz, CDCl$_3$) δ 4.09-3.86 (m, 2H), 3.28 (td, J=9.7, 4.2 Hz, 1H), 2.87-2.76 (m, 1H), 2.51-2.39 (m, 1H), 2.00-1.64 (m, 3H), 1.45 (s, 9H), 0.99 (d, J=6.6 Hz, 3H), OH not observed; MS (ES+) m/z 216.3 (M+1).

Step 2. Preparation of tert-butyl 4-(2-chloro-4-(N-(2,4-dimethoxybenzyl)-N-(thiazol-2-yl)sulfamoyl)phenoxy)-3-methylpiperidine-1-carboxylate

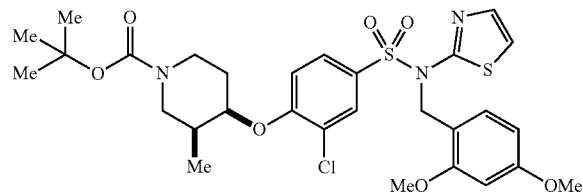 [SMILES: COc1ccc(CN(c2nccs2)S(=O)(=O)c2ccc(O[C@@H]3CCN(C(=O)OC(C)(C)C)C[C@@H]3C)c(Cl)c2)c(OC)c1]

Following the procedure as described for EXAMPLE 5, Step 2 and making non-critical variations as required to replace tert-butyl 4-hydroxy-3,3-dimethylpiperidine-1-carboxylate with tert-butyl 4-hydroxy-3-methylpiperidine-1-carboxylate, the title compound was obtained as a colorless foam as a 2:1 mixture of diastereomers (3.29 g, 80% yield). Data reported for major isomer: $^1$H NMR (300 MHz, CDCl$_3$) δ 7.80 (d, J=2.3 Hz, 1H), 7.67 (dd, J=8.8, 2.3 Hz, 1H), 7.43 (d, J=3.6 Hz, 1H), 7.16 (d, J=9.1 Hz, 1H), 7.04 (s, 1H), 6.93 (d, J=8.9 Hz, 1H), 6.39-6.35 (m, 2H), 5.07 (s, 2H), 4.60-4.54 (m, 1H), 3.82-3.72 (m, 8H), 3.26-3.14 (m, 2H), 2.05-1.92 (m, 2H), 1.79-1.69 (m, 1H), 1.49 (s, 9H), 1.03 (d, J=6.9 Hz, 3H); MS (ES+) m/z 638.2 (M+1), 640.2 (M+1).

Step 3. Preparation of 3-chloro-4-((3-methylpiperidin-4-yl)oxy)-N-(thiazol-2-yl)benzenesulfonamide 2,2,2-trifluoroacetate

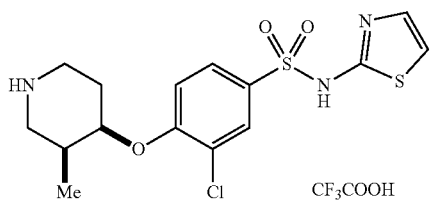 [SMILES: C[C@H]1CNCC[C@H]1Oc1ccc(S(=O)(=O)Nc2nccs2)cc1Cl ; "CF3COOH"]

Following the procedure as described for EXAMPLE 1, Step 4 and making non-critical variations as required to replace tert-butyl 4-(2-chloro-4-(N-(2,4-dimethoxybenzyl)-N-(1,2,4-thiadiazol-5-yl)sulfamoyl)phenoxy)-3,3-dimethylpiperidine-1-carboxylate with tert-butyl 4-(2-chloro-4-(N-(2,4-dimethoxybenzyl)-N-(thiazol-2-yl)sulfamoyl)phenoxy)-3-methylpiperidine-1-carboxylate, the title compound was obtained as a colorless foam (1.58 g, quantitative yield): MS (ES+) m/z 388.1 (M+1), 390.1 (M+1).

Step 4. Preparation of 4-((cis-1-benzyl-3-methylpiperidin-4-yl)oxy)-3-chloro-N-(thiazol-2-yl)benzenesulfonamide and 4-((trans-1-benzyl-3-methylpiperidin-4-yl)oxy)-3-chloro-N-(thiazol-2-yl)benzenesulfonamide

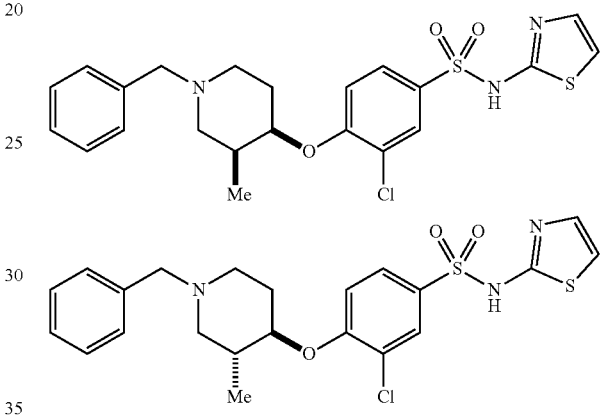

To a mixture of benzaldehyde (0.28 g, 2.60 mmol) and 3-chloro-4-((3-methylpiperidin-4-yl)oxy)-N-(thiazol-2-yl)benzenesulfonamide 2,2,2-trifluoroacetate (0.65 g, 1.30 mmol) in anhydrous N,N-dimethylformamide (5 mL) and anhydrous 1,2-dichloroethane (5 mL) was added sodium triacetoxyborohydride (0.55 g, 2.60 mmol) and the resulting mixture was stirred at ambient temperature for 18 h. The reaction mixture was diluted with ethyl acetate (50 mL), washed with saturated ammonium chloride (40 mL), saturated sodium bicarbonate (40 mL), and concentrated in vacuo. The residue was purified by column chromatography eluting with a gradient of 0 to 20% of methano (containing 0.2% of ammonium hydroxide) in dichloromethane to provide the title compounds as diastereomerically pure, colorless solids. First eluting isomer (0.20 g, 32% yield): $^1$H NMR (300 MHz, CD$_3$OD) δ 7.81 (d, J=2.3 Hz, 1H), 7.73 (dd, J=8.7, 2.3 Hz, 1H), 7.41-7.24 (m, 5H), 7.16 (d, J=8.6 Hz, 1H), 7.06 (d, J=4.6 Hz, 1H), 6.68 (d, J=4.6 Hz, 1H), 4.13-4.03 (m, 1H), 3.65 (d, J=2.0 Hz, 2H), 3.03-2.91 (m, 2H), 2.41-2.29 (m, 1H), 2.18-1.99 (m, 3H), 1.73-1.58 (m, 1H), 0.98 (d, J=6.0 Hz, 3H), NH not observed; MS (ES+) m/z 478.1 (M+1), 480.1 (M+1). Second eluting isomer (0.20 g, 32% yield): $^1$H NMR (300 MHz, CD$_3$OD) δ 7.83 (d, J=2.2 Hz, 1H), 7.75 (dd, J=8.8, 2.3 Hz, 1H), 7.47-7.36 (m, 5H), 7.20 (d, J=8.8 Hz, 1H), 7.08 (d, J=4.5 Hz, 1H), 6.69 (d, J=4.5 Hz, 1H), 4.73-4.67 (m, 1H), 4.01 (s, 2H), 3.06-2.94 (m, 2H), 2.87-2.70 (m, 2H), 2.30-2.17 (m, 1H), 2.15-2.05 (m, 1H), 2.01-1.87 (m, 1H), 1.01 (d, J=6.8 Hz, 3H), NH not observed; MS (ES+) m/z 478.1 (M+1), 480.1 (M+1).

Example 9A and 9B

Synthesis of 3-chloro-4-((cis-3-methyl-1-(3-methyl-benzyl)piperidin-4-yl)oxy)-N-(thiazol-2-yl)benzene-sulfonamide and 3-chloro-4-((trans-3-methyl-1-(3-methylbenzyl)piperidin-4-yl)oxy)-N-(thiazol-2-yl)benzenesulfonamide

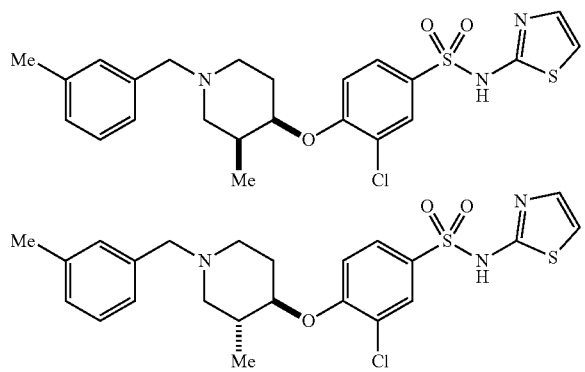

Following the procedure as described for EXAMPLE 8, Step 4 and making non-critical variations as required to replace benzaldehyde with 3,3-dimethylbenzaldehyde, and purification by column chromatography eluting with a gradient of 0 to 20% of methano (containing 0.2% of ammonium hydroxide) in dichloromethane, the title compounds were obtained as diastereomerically pure, colorless solids. First eluting isomer (0.10 g, 16% yield): $^1$H NMR (300 MHz, CD$_3$OD) δ 7.81 (d, J=2.2 Hz, 1H), 7.72 (dd, J=8.6, 2.2 Hz, 1H), 7.24-7.03 (m, 6H), 6.67 (d, J=4.5 Hz, 1H), 4.11-4.00 (m, 1H), 3.57 (d, J=2.3 Hz, 2H), 3.00-2.89 (m, 2H), 2.36-2.25 (m, 4H), 2.17-1.96 (m, 3H), 1.72-1.57 (m, 1H), 0.97 (d, J=6.0 Hz, 3H), NH not observed; MS (ES+) m/z 492.1 (M+1), 494.1 (M+1). Second eluting isomer (0.24 g, 38% yield): $^1$H NMR (300 MHz, CD$_3$OD) δ 7.84 (d, J=2.3 Hz, 1H), 7.76 (dd, J=8.7, 2.3 Hz, 1H), 7.36-7.19 (m, 5H), 7.08 (d, J=4.6 Hz, 1H), 6.70 (d, J=4.6 Hz, 1H), 4.77-4.72 (m, 1H), 4.19 (d, J=1.3 Hz, 2H), 3.25-3.14 (m, 2H), 3.07-2.92 (m, 2H), 2.36 (s, 3H), 2.34-2.25 (m, 1H), 2.22-2.12 (m, 1H), 2.08-1.95 (m, 1H), 1.04 (d, J=6.7 Hz, 3H), NH not observed; MS (ES+) m/z 492.1 (M+1), 494.1 (M+1).

Example 10A and 10B

Synthesis of 3-chloro-4-((cis-1-(2-fluorobenzyl)-3-methylpiperidin-4-yl)oxy)-N-(thiazol-2-yl)benzene-sulfonamide and 3-chloro-4-((trans-1-(2-fluoroben-zyl)-3-methylpiperidin-4-yl)oxy)-N-(thiazol-2-yl)benzenesulfonamide

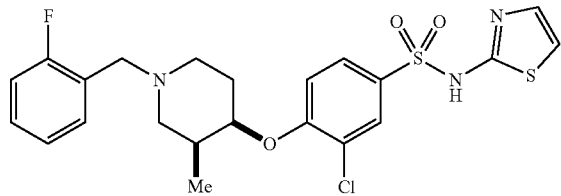

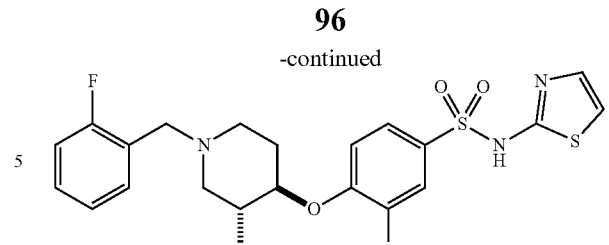

Following the procedure as described for EXAMPLE 8, Step 4 and making non-critical variations as required to replace benzaldehyde with 2-fluorobenzaldehyde, and purification by column chromatography eluting with a gradient of 0 to 20% of methano (containing 0.2% of ammonium hydroxide) in dichloromethane, the title compounds were obtained as diastereomerically pure, colorless solids. First eluting isomer (0.16 g, 25% yield): $^1$H NMR (300 MHz, CD$_3$OD) δ 7.80 (d, J=2.1 Hz, 1H), 7.72 (dd, J=8.7, 2.2 Hz, 1H), 7.44-7.37 (m, 1H), 7.34-7.24 (m, 1H), 7.18-7.02 (m, 4H), 6.68 (d, J=4.5 Hz, 1H), 4.10-3.99 (m, 1H), 3.65 (s, 2H), 2.96-2.88 (m, 2H), 2.35-2.24 (m, 1H), 2.17-1.96 (m, 3H), 1.72-1.56 (m, 1H), 0.97 (d, J=5.8 Hz, 3H), NH not observed; MS (ES+) m/z 496.1 (M+1), 498.1 (M+1). Second eluting isomer (0.16, 25% yield): $^1$H NMR (300 MHz, 1:1 CDCl$_3$:CD$_3$OD) δ 7.84 (s, 1H), 7.72 (d, J=8.6 Hz, 1H), 7.46-7.23 (m, 2H), 7.16-6.91 (m, 4H), 6.54 (d, J=4.3 Hz, 1H), 4.54-4.49 (m, 1H), 3.73 (s, 2H), 2.78-2.65 (m, 2H), 2.59-2.39 (m, 2H), 2.21-2.07 (m, 1H), 2.02-1.79 (m, 2H), 0.97 (d, J=6.1 Hz, 3H), NH not observed; MS (ES+) m/z 496.1 (M+1), 498.1 (M+1).

Example 11

Synthesis of 3-chloro-4-((1-(3-(difluoromethyl)ben-zyl)piperidin-4-yl)oxy)-N-(thiazol-2-yl)benzene-sulfonamide

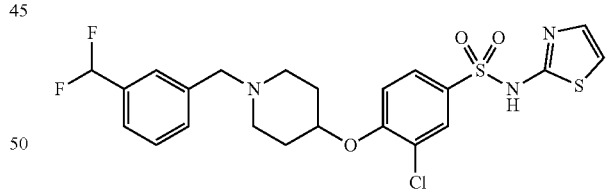

Following the procedure as described for EXAMPLE 5, Step 4 and making non-critical variations as required to replace 3-(difluoromethoxy)benzaldehyde with 3-(difluo-romethyl)benzaldehyde, the title compound was obtained as a colorless solid (0.20 g, 75% yield): $^1$H NMR (300 MHz, DMSO-d$_6$) δ 7.70 (d, J=2.2 Hz, 1H), 7.64 (dd, J=8.7, 2.3 Hz, 1H), 7.50-7.47 (m, 1H), 7.46-7.40 (m, 3H), 7.29 (d, J=8.9 Hz, 1H), 7.22 (d, J=4.6 Hz, 1H), 6.99 (t, J=56.0 Hz, 1H), 6.78 (d, J=4.5 Hz, 1H), 4.65-4.55 (m, 1H), 3.54 (s, 2H), 2.66-2.54 (m, 2H), 2.37-2.25 (m, 2H), 1.97-1.84 (m, 2H), 1.74-1.60 (m, 2H), NH not observed; MS (ES+) m/z 514.1 (M+1), 516.1 (M+1).

Example 12

Synthesis of 3-chloro-N-(thiazol-2-yl)-4-((1-(2-(trifluoromethyl)benzyl)piperidin-4-yl)oxy)benzenesulfonamide

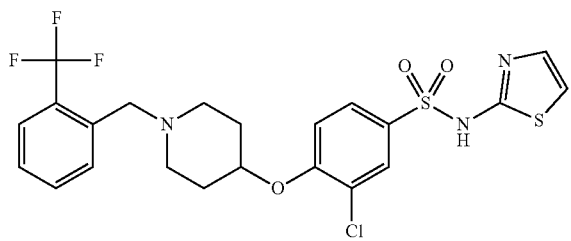 [SMILES: O=S(=O)(Nc1nccs1)c1ccc(OC2CCN(Cc3ccccc3C(F)(F)F)CC2)c(Cl)c1]

Following the procedure as described for EXAMPLE 5, Step 4 and making non-critical variations as required to replace 3-(difluoromethoxy)benzaldehyde with 2-(trifluoromethyl)benzaldehyde, the title compound was obtained as a colorless solid (0.21 g, 64% yield): $^1$H NMR (300 MHz, DMSO-$d_6$) δ 12.65 (br s, 1H), 7.76 (d, J=7.8 Hz, 1H), 7.71 (d, J=2.3 Hz, 1H), 7.68-7.58 (m, 3H), 7.45-7.38 (m, 1H), 7.31 (d, J=8.7 Hz, 1H), 7.23 (d, J=4.8 Hz, 1H), 6.80 (d, J=4.6 Hz, 1H), 4.68-4.57 (m, 1H), 3.59 (s, 2H), 2.66-2.54 (m, 2H), 2.38-2.24 (m, 2H), 1.97-1.83 (m, 2H), 1.74-1.59 (m, 2H); MS (ES+) m/z 532.1 (M+1), 534.1 (M+1).

Example 13

Synthesis of 3-chloro-4-((1-(2-chlorobenzyl)piperidin-4-yl)oxy)-N-(thiazol-2-yl)benzenesulfonamide

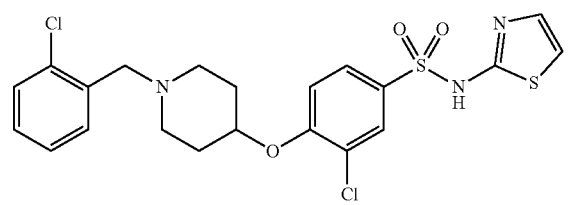 [SMILES: O=S(=O)(Nc1nccs1)c1ccc(OC2CCN(Cc3ccccc3Cl)CC2)c(Cl)c1]

Following the procedure as described for EXAMPLE 5, Step 4 and making non-critical variations as required to replace 3-(difluoromethoxy)benzaldehyde with 2-chlorobenzaldehyde, the title compound was obtained as a colorless solid (0.14 g, 45% yield): $^1$H NMR (300 MHz, DMSO-$d_6$) δ 12.71 (br s, 1H), 7.70 (dd, J=2.3 Hz, 1H), 7.65 (dd, J=8.6, 2.1 Hz, 1H), 7.46 (dd, J=7.4, 1.9 Hz, 1H), 7.39 (dd, J=7.4, 1.7 Hz, 1H), 7.34-7.20 (m, 4H), 6.80 (d, J=4.5 Hz, 1H), 4.67-4.56 (m, 1H), 3.56 (s, 2H), 2.69-2.58 (m, 2H), 2.41-2.29 (m, 2H), 1.97-1.85 (m, 2H), 1.73-1.60 (m, 2H); MS (ES+) m/z 498.1 (M+1), 500.1 (M+1).

Example 14

Synthesis of 3-chloro-4-((1-((4-methylpyridin-2-yl)methyl)piperidin-4-yl)oxy)-N-(thiazol-2-yl)benzenesulfonamide

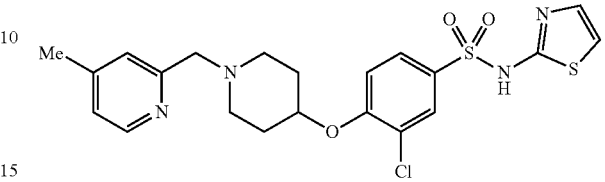

Following the procedure as described for EXAMPLE 5, Step 4 and making non-critical variations as required to replace 3-(difluoromethoxy)benzaldehyde with 4-methylpicolinaldehyde, the title compound was obtained as a colorless solid (0.09 g, 30% yield): $^1$H NMR (300 MHz, DMSO-$d_6$) δ 8.31 (d, J=5.0 Hz, 1H), 7.71 (d, J=2.1 Hz, 1H), 7.64 (dd, J=8.7, 2.3 Hz, 1H), 7.30 (d, J=8.9 Hz, 1H), 7.26-7.23 (m, 1H), 7.21 (d, J=4.3 Hz, 1H), 7.08-7.03 (m, 1H), 6.78 (d, J=4.5 Hz, 1H), 4.66-4.55 (m, 1H), 3.59 (s, 2H), 2.74-2.63 (m, 2H), 2.43-2.32 (m, 2H), 2.27 (s, 3H), 1.98-1.86 (m, 2H), 1.74-1.62 (m, 2H), NH not observed; MS (ES+) m/z 479.1 (M+1), 481.1 (M+1).

Example 15

Synthesis of 4-(((1R,3r,5S)-8-benzyl-8-azabicyclo[3.2.1]octan-3-yl)oxy)-3-chloro-N-(thiazol-2-yl)benzenesulfonamide

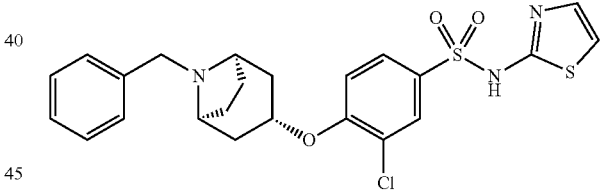

Step 1. Preparation of tert-butyl (1R,3r,5S)-3-(2-chloro-4-(N-(2,4-dimethoxybenzyl)-N-(thiazol-2-yl)sulfamoyl)phenoxy)-8-azabicyclo[3.2.1]octane-8-carboxylate

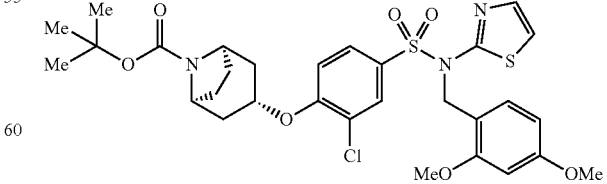

Following the procedure as described for EXAMPLE 5, Step 2 and making non-critical variations as required to replace tert-butyl 4-hydroxypiperidine-1-carboxylate with tert-butyl (1R,3r,5S)-3-hydroxy-8-azabicyclo[3.2.1]octane- 8-carboxylate, the title compound was obtained as a colorless foam (0.30 g, 23% yield): ¹H NMR (300 MHz, CDCl₃) δ 7.82 (d, J=2.3 Hz, 1H), 7.67 (dd, J=8.7, 2.3 Hz, 1H), 7.43 (d, 3.6 Hz, 1H), 7.16 (d, J=9.0 Hz, 1H), 7.03 (d, J=3.6 Hz, 1H), 6.78 (d, J=9.0 Hz, 1H), 6.50-6.46 (m, 1H), 6.39-6.34 (m, 2H), 5.07 (s, 2H), 4.76-4.72 (m, 1H), 4.26-4.13 (m, 2H), 3.77 (s, 3H), 3.74 (s, 3H), 2.23-2.13 (m, 3H), 2.01-1.93 (m, 2H), 1.74-1.69 (m, 2H), 1.49 (s, 9H); MS (ES+) m/z 650.1 (M+1), 652.1 (M+1).

Step 2. Preparation of 4-(((1R,3r,5S)-8-benzyl-8-azabicyclo[3.2.1]octan-3-yl)oxy)-3-chloro-N-(thiazol-2-yl)benzenesulfonamide

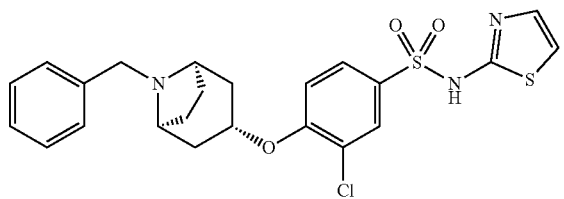 [SMILES: O=S(=O)(Nc1nccs1)c1ccc(O[C@H]2C[C@H]3CC[C@@H](C2)N3Cc2ccccc2)c(Cl)c1]

To a solution of tert-butyl (1R,3r,5S)-3-(2-chloro-4-(N-(2,4-dimethoxybenzyl)-N-(thiazol-2-yl)sulfamoyl)phenoxy)-8-azabicyclo[3.2.1]octane-8-carboxylate (0.30 g, 0.46 mmol) in dichloromethane (10 mL) was added trifluoroacetic acid (2 mL) and the resulting mixture was stirred for 1 h. The reaction mixture was concentrated in vacuo. The residue was triturated in methanol (10 mL), filtered, and the filtrate concentrated in vacuo. To it was then added 1,2-dichloroethane (4 mL), N,N-dimethylformamide (4 mL), benzaldehyde (0.15 g, 1.38 mmol), sodium triacetoxyborohydride (0.29 g, 1.38 mmol), and the resulting reaction mixture was stirred for 18 h. The mixture was diluted with ethyl acetate (50 mL), washed with saturated ammonium chloride (2×30 mL), and the combined organic phase was concentrated in vacuo. Purification of the residue was purified by column chromatography eluting with a gradient of 0 to 20% of methanol (containing 0.2% of ammonium hydroxide) in dichloromethane provided the title compound as a colorless solid (0.03 g, 13% yield): ¹H NMR (300 MHz, DMSO-d₆) δ 11.65 (br s, 1H), 7.73 (d, J=2.3 Hz, 1H), 7.65 (dd, J=8.7, 2.3 Hz, 1H), 7.51-7.45 (m, 2H), 7.38-7.27 (m, 3H), 7.20 (d, J=7.5 Hz, 1H), 7.17 (d, J=8.8 Hz, 1H), 6.77 (d, J=4.5 Hz, 1H), 4.83-4.77 (m, 1H), 3.81 (s, 2H), 3.38 (s, 2H), 2.33-2.22 (m, 2H), 2.15-2.05 (m, 4H), 1.91 (s, 1H), 1.87 (s, 1H); MS (ES+) m/z 490.1 (M+1), 492.1 (M+1).

Example 16

Synthesis of 4-(((1R,3s,5S)-8-benzyl-8-azabicyclo[3.2.1]octan-3-yl)oxy)-3-chloro-N-(thiazol-2-yl)benzenesulfonamide

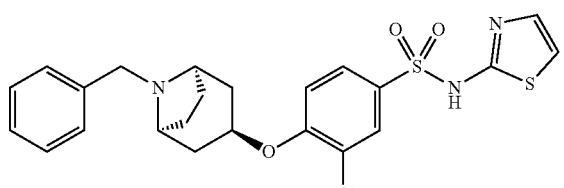

Step 1. Preparation of tert-butyl (1R,3s,5S)-3-(2-chloro-4-(N-(2,4-dimethoxybenzyl)-N-(thiazol-2-yl)sulfamoyl)phenoxy)-8-azabicyclo[3.2.1]octane-8-carboxylate

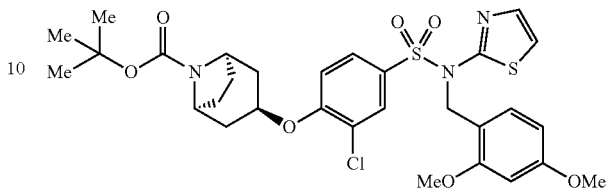

Following the procedure as described for EXAMPLE 5, Step 2 and making non-critical variations as required to replace tert-butyl 4-hydroxypiperidine-1-carboxylate with tert-butyl (1R,3s,5S)-3-hydroxy-8-azabicyclo[3.2.1]octane-8-carboxylate, the title compound was obtained as a colorless foam (0.32 g, 25% yield): ¹H NMR (300 MHz, CDCl₃) δ 7.78 (d, J=2.3 Hz, 1H), 7.70-7.65 (m, 1H), 7.42 (d, J=3.6 Hz, 1H), 7.15 (d, J=9.1 Hz, 1H), 7.03 (d, J=3.6 Hz, 1H), 6.96 (d, J=8.7 Hz, 1H), 6.49-6.46 (m, 1H), 6.38-6.34 (m, 2H), 5.06 (s, 2H), 4.82-4.71 (m, 1H), 4.40-4.28 (m, 3H), 3.77 (s, 3H), 3.72 (m, 2H), 2.17-2.09 (m, 2H), 1.99-1.82 (m, 2H), 1.74-1.66 (m, 3H), 1.50 (s, 9H); MS (ES+) m/z 650.2 (M+1), 652.2 (M+1).

Step 2. Preparation of 4-(((1R,3s,5S)-8-benzyl-8-azabicyclo[3.2.1]octan-3-yl)oxy)-3-chloro-N-(thiazol-2-yl)benzenesulfonamide

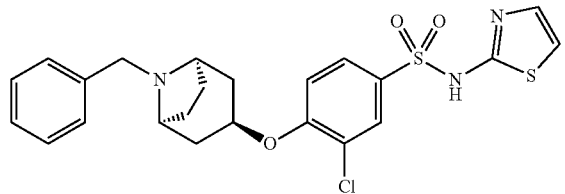 [SMILES: O=S(=O)(Nc1nccs1)c1ccc(O[C@@H]2C[C@H]3CC[C@@H](C2)N3Cc2ccccc2)c(Cl)c1]

Following the procedure as described for EXAMPLE 15, Step 2 and making non-critical variations as required to replace tert-butyl (1R,3r,5S)-3-(2-chloro-4-(N-(2,4-dimethoxybenzyl)-N-(thiazol-2-yl)sulfamoyl)phenoxy)-8-azabicyclo[3.2.1]octane-8-carboxylate with tert-butyl (1R,3s,5S)-3-(2-chloro-4-(N-(2,4-dimethoxybenzyl)-N-(thiazol-2-yl)sulfamoyl)phenoxy)-8-azabicyclo[3.2.1]octane-8-carboxylate, the title compound was obtained as a colorless solid (0.11 g, 49% yield): ¹H NMR (300 MHz, DMSO-d₆) δ 7.68 (d, J=2.2 Hz, 1H), 7.63 (dd, J=8.7 Hz, 1H), 7.39-7.33 (m, 3H), 7.33-7.26 (m, 2H), 7.25-7.17 (m, 2H), 6.75 (d, J=4.3 Hz, 1H), 4.82-4.69 (m, 1H), 3.62 (s, 2H), 3.30-3.23 (m, 2H), 2.04-1.93 (m, 4H), 1.80-1.64 (m, 4H), NH not observed; MS (ES+) m/z 490.1 (M+1), 492.1 (M+1).

Example 17

Synthesis of 4-(((1R,3s,5S)-8-benzyl-8-azabicyclo[3.2.1]octan-3-yl)oxy)-5-chloro-2-fluoro-N-(thiazol-2-yl)benzenesulfonamide

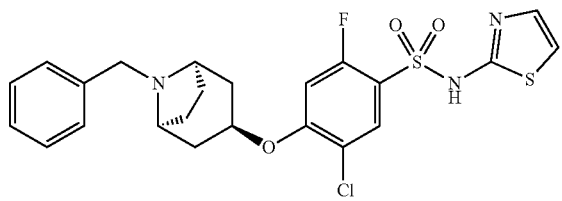 [SMILES: O=S(=O)(Nc1nccs1)c1cc(Cl)c(O[C@@H]2C[C@H]3CC[C@@H](C2)N3Cc2ccccc2)cc1F]

Step 1. Preparation of 5-chloro-N-(2,4-dimethoxybenzyl)-2,4-difluoro-N-(thiazol-2-yl)benzenesulfonamide

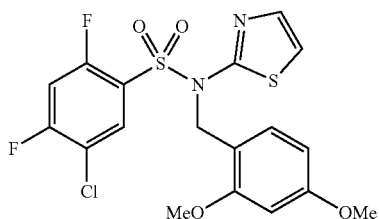 [SMILES: COc1ccc(CN(c2nccs2)S(=O)(=O)c2cc(Cl)c(F)cc2F)c(OC)c1]

A solution of N-(2,4-dimethoxybenzyl)thiazol-2-amine (20.86 g, 83.3 mmol, prepared according to WO2013063459) in anhydrous tetrahydrofuran (350 mL) was treated with a 1 M solution of bis(trimethylsilyl)amide in tetrahydrofuran (100.0 mL, 100.0 mmol) at −78° C. The resulting mixture was warmed to ambient temperature and stirred for 1 h. The reaction mixture was cooled to −78° C., and a solution of 5-chloro-2,4-difluorobenzenesulfonyl chloride (20.58 g, 83.3 mmol) in anhydrous tetrahydrofuran (75 mL) was added to it. The reaction mixture was allowed to warm to ambient temperature, stirred for 2 h, and diluted with ethyl acetate (700 mL). The organic phase was washed with saturated sodium bicarbonate (200 mL), saturated ammonium chloride (2×150 mL), brine (2×150 mL), dried over anhydrous sodium sulfate, and filtered. Concentration of the filtrate under reduced pressure gave a residue which was triturated with methanol (80 mL) to provide the title compound as a colorless solid (12.7 g, 33% yield): $^1$H NMR (300 MHz, CDCl$_3$) δ 7.94 (t, J=7.4 Hz, 1H), 7.44 (d, J=3.6 Hz, 1H) 7.21 (d, J=8.1 Hz, 1H), 7.06-6.99 (m, 2H), 6.41-6.36 (m, 2H), 5.20 (s, 2H), 3.78 (s, 3H), 3.74 (s, 3H); MS (ES+) m/z 461.0 (M+1), 463.0 (M+1).

Step 2. Preparation of tert-butyl (1R,3s,5S)-3-(2-chloro-4-(N-(2,4-dimethoxybenzyl)-N-(thiazol-2-yl)sulfamoyl)-5-fluorophenoxy)-8-azabicyclo[3.2.1]octane-8-carboxylate

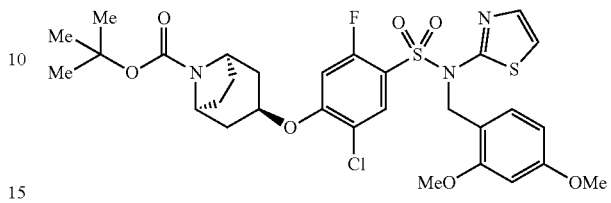

To a mixture of tert-butyl (1R,3s,5S)-3-hydroxy-8-azabicyclo[3.2.1]octane-8-carboxylate (1.18 g, 5.21 mmol) and 5-chloro-N-(2,4-dimethoxybenzyl)-2,4-difluoro-N-(thiazol-2-yl)benzenesulfonamide (2.40 g, 5.21 mmol) in anhydrous dimethyl sulfoxide (35 mL) was added cesium carbonate (2.55 g, 7.82 mmol) and the reaction mixture was stirred at ambient temperature for 18 h. The reaction mixture was diluted with ethyl acetate (150 mL), washed with water (100 mL), saturated ammonium chloride (80 mL), brine (50 mL), and dried over anhydrous sodium sulfate. Filtration and concentration of the filtrate under reduced pressure gave a residue which was purified by column chromatography, eluting with 10 to 50% of ethyl acetate in hexanes, to provide the title compound was obtained as a colorless foam (1.39 g, 40% yield): $^1$H NMR (300 MHz, CDCl$_3$) δ 7.86 (d, J=7.3 Hz, 1H), 7.43-7.41 (m, 1H), 7.21 (d, J=8.8 Hz, 1H), 7.03-7.00 (m, 1H), 6.69 (d, J=11.3 Hz, 1H), 6.37-6.35 (m, 2H), 5.20 (s, 2H), 4.76-4.65 (m, 1H), 4.43-4.29 (m, 2H), 3.82-3.71 (m, 7H), 2.15-2.06 (m, 3H), 1.95-1.81 (m, 2H), 1.73-1.66 (m, 2H), 1.50 (s, 9H); MS (ES+) m/z 668.1 (M+1), 670.0 (M+1).

Step 3. Preparation of 4-(((1R,3s,5S)-8-azabicyclo[3.2.1]octan-3-yl)oxy)-5-chloro-2-fluoro-N-(thiazol-2-yl)benzenesulfonamide 2,2,2-trifluoroacetate To a solution of tert-butyl (1R,3s,5S)-3-(2-chloro-4-(N-(2,4-dimethoxybenzyl)-N-(thiazol-2-yl)sulfamoyl)-5-fluorophenoxy)-8-azabicyclo[3.2.1]octane-8-carboxylate (1.39 g, 2.08 mmol) in dichloromethane (40 mL) was added trifluoroacetic acid (10 mL) and the resulting mixture was stirred at ambient temperature for 1.5 h. The reaction mixture was concentrated in vacuo. The residue was suspended in methanol (25 mL) and the mixture was filtered. The filtrate was concentrated in vacuo to provide the title compound as a tan foam (0.81 g, 73% yield): MS (ES+) m/z 418.0 (M+1), 420.0 (M+1).

Step 4. Preparation of 4-(((1R,3s,5S)-8-benzyl-8-azabicyclo[3.2.1]octan-3-yl)oxy)-5-chloro-2-fluoro-N-(thiazol-2-yl)benzenesulfonamide 2,2,2-trifluoroacetate

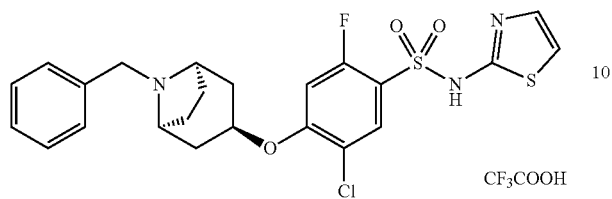

To a mixture of benzaldehyde (0.16 g, 1.53 mmol) and 4-(((1R,3s,5S)-8-azabicyclo[3.2.1]octan-3-yl)oxy)-5-chloro-2-fluoro-N-(thiazol-2-yl)benzenesulfonamide 2,2,2-trifluoroacetate (0.27 g, 0.51 mmol) in anhydrous N,N-dimethylformamide (5 mL) and anhydrous 1,2-dichloroethane (5 mL) was added sodium triacetoxyborohydride (0.22 g, 1.02 mmol) and the reaction mixture was stirred at ambient temperature for 18 h. The reaction mixture was diluted with ethyl acetate (50 mL), washed with saturated ammonium chloride (40 mL), saturated sodium bicarbonate (40 mL), and concentrated in vacuo. The residue was purified by column chromatography eluting with a gradient of 0 to 20% of methanol (containing 0.2% of ammonium hydroxide) in dichloromethane, and then by preparative reverse-phase HPLC, eluting with a gradient of 10 to 60% of acetonitrile in water containing 0.1% of trifluoroacetic acid, to provide the title compound as a colorless solid (0.025 g, 10% yield): $^1$H NMR (300 MHz, CD$_3$OD) δ 7.84 (d, J=7.5 Hz, 1H), 7.56-7.45 (m, 5H), 7.25 (d, J=11.5 Hz, 1H), 7.11 (d, J=4.6 Hz, 1H), 6.74 (d, J=4.5 Hz, 1H), 5.06-4.94 (m, 1H), 4.22 (s, 2H), 4.05-3.97 (m, 2H), 2.52-2.37 (m, 4H), 2.32-2.22 (m, 2H), 2.10-1.94 (m, 2H), NH and COOH not observed; MS (ES+) m/z 508.1 (M+1), 510.2 (M+1).

Example 18

Synthesis of 5-chloro-4-(((1R,3s,5S)-8-(3-chlorobenzyl)-8-azabicyclo[3.2.1]octan-3-yl)oxy)-2-fluoro-N-(thiazol-2-yl)benzenesulfonamide 2,2,2-trifluoroacetate

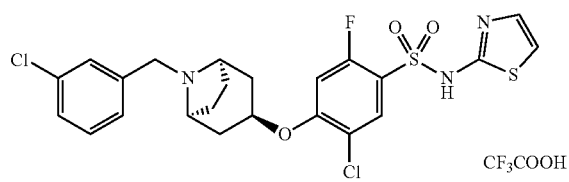 [SMILES: O=S(=O)(Nc1nccs1)c1cc(Cl)c(O[C@@H]2C[C@H]3CC[C@@H](C2)N3Cc2cccc(Cl)c2)cc1F ; "CF3COOH"]

Following the procedure as described for EXAMPLE 17, Step 4 and making non-critical variations as required to replace benzaldehyde with 3-chlorobenzaldehyde, the title compound was obtained as a colorless solid (0.08 g, 28% yield): $^1$H NMR (300 MHz, CD$_3$OD) 7.83 (d, J=7.3 Hz, 1H), 7.63-7.60 (m, 1H), 7.54-7.45 (m, 3H), 7.24 (d, J=11.3 Hz, 1H), 7.11 (d, J=4.8 Hz, 1H), 6.74 (d, J=4.5 Hz, 1H), 5.06-4.93 (m, 1H), 4.23 (s, 2H), 4.05-3.99 (m, 2H), 2.52- 2.38 (m, 4H), 2.32-2.23 (m, 2H), 2.11-1.98 (m, 2H), NH and COOH not observed; MS (ES+) m/z 542.1 (M+1), 544.1 (M+1).

Example 19

Synthesis of 4-((1-benzyl-4-methylpiperidin-4-yl)oxy)-3-chloro-N-(thiazol-2-yl)benzenesulfonamide

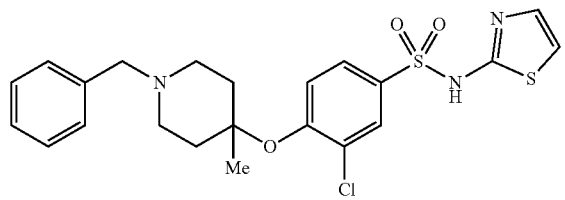 [SMILES: CC1(Oc2ccc(S(=O)(=O)Nc3nccs3)cc2Cl)CCN(Cc2ccccc2)CC1]

Step 1. Preparation of tert-butyl 4-(2-chloro-4-(N-(2,4-dimethoxybenzyl)-N-(thiazol-2-yl)sulfamoyl)phenoxy)-4-methylpiperidine-1-carboxylate

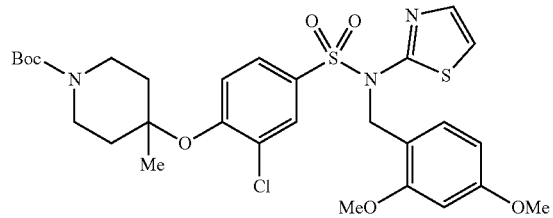 [SMILES: COc1ccc(CN(c2nccs2)S(=O)(=O)c2ccc(OC3(C)CCN(C(=O)OC(C)(C)C)CC3)c(Cl)c2)c(OC)c1]

To a solution of tert-butyl 4-hydroxy-4-methylpiperidine-1-carboxylate (0.75 g, 3.49 mmol) in anhydrous N,N-dimethylformamide (12 mL) was added a dispersion of 60% sodium hydride in mineral oil (0.14 g, 3.49 mmol) and the reaction mixture was stirred at ambient temperature for 45 minutes. To it was then added 3-chloro-N-(2,4-dimethoxybenzyl)-4-fluoro-N-(thiazol-2-yl)benzenesulfonamide (0.77 g, 1.75 mmol) and the reaction mixture was stirred at ambient temperature for 18 h. The reaction mixture was quenched by careful addition of water (50 mL), and extracted with ethyl acetate (100 mL). The organic layer was washed with saturated ammonium chloride (2×50 mL), brine (50 mL), dried over anhydrous sodium sulfate, and filtered. Concentration of the filtrate in vacuo gave a residue which was purified by column chromatography eluting with a gradient of 0 to 100% of ethyl acetate in hexanes to provide the title compound as a colorless foam (0.98 g, 44% yield): $^1$H NMR (300 MHz, CDCl$_3$) δ 7.82-7.79 (m, 1H), 7.66-7.61 (m, 1H), 7.46-7.41 (m, 1H), 7.18-7.14 (m, 1H), 7.11-7.02 (m, 2H), 6.40-6.35 (m, 2H), 5.08 (s, 2H), 3.78-3.72 (m, 6H), 3.31-3.20 (m, 8H), 1.46 (s, 9H), 1.27 (s, 3H); MS (ES+) m/z 638.2 (M+1), 640.1 (M+1).

105

Step 2. Preparation of 3-chloro-4-((4-methylpiperidin-4-yl)oxy)-N-(thiazol-2-yl)benzenesulfonamide 2,2,2-trifluoroacetate

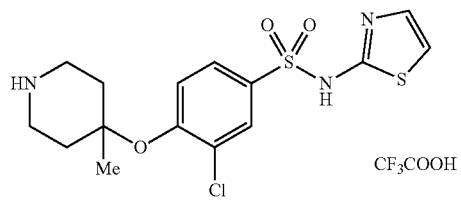 [SMILES: CC1(Oc2ccc(S(=O)(=O)Nc3nccs3)cc2Cl)CCNCC1 ; "CF3COOH"]

Following the procedure as described for EXAMPLE 1, Step 4 and making non-critical variations as required to replace tert-butyl 4-(2-chloro-4-(N-(2,4-dimethoxybenzyl)-N-(1,2,4-thiadiazol-5-yl)sulfamoyl)phenoxy)-3,3-dimethylpiperidine-1-carboxylate with tert-butyl 4-(2-chloro-4-(N-(2,4-dimethoxybenzyl)-N-(thiazol-2-yl)sulfamoyl)phenoxy)-4-methylpiperidine-1-carboxylate, the title compound was obtained an off-white foam (0.77 g, quantitative yield): MS (ES+) m/z 388.1 (M+1), 390.1 (M+1).

Step 3. Preparation of 4-((1-benzyl-4-methylpiperidin-4-yl)oxy)-3-chloro-N-(thiazol-2-yl)benzenesulfonamide

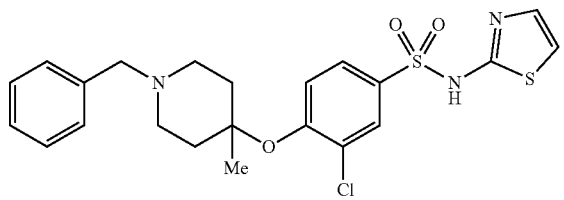 [SMILES: CC1(Oc2ccc(S(=O)(=O)Nc3nccs3)cc2Cl)CCN(Cc2ccccc2)CC1]

Following the procedure as described for EXAMPLE 2 and making non-critical variations as required to 3-chloro-4-((3,3-dimethylpiperidin-4-yl)oxy)-N-(1,2,4-thiadiazol-5-yl)benzenesulfonamide 2,2,2-trifluoroacetate with 3-chloro-4-((4-methylpiperidin-4-yl)oxy)-N-(thiazol-2-yl) benzenesulfonamide 2,2,2-trifluoroacetate, and purification by column chromatography eluting with a gradient of 0 to 20% of methanol (containing 0.2% of ammonium hydroxide) in dichloromethane, the title compound was obtained as a colorless solid (0.065 g, 26% yield): $^1$H NMR (300 MHz, DMSO-$d_6$) δ 7.72 (d, J=2.3 Hz, 1H), 7.60 (dd, J=8.7, 2.3 Hz, 1H), 7.35 (d, J=8.8 Hz, 1H), 7.30-7.19 (m, 6H), 6.78 (d, J=4.6 Hz, 1H), 3.55 (s, 2H), 2.60-2.50 (m, 2H), 2.49-2.38 (m, 2H), 2.08-1.98 (m, 2H), 1.78-1.65 (m, 2H), 1.35 (s, 3H), NH not observed; MS (ES+) m/z 478.1 (M+1), 480.1 (M+H).

106

Example 20

Synthesis of 3-chloro-4-((1-(3-chlorobenzyl)-4-methylpiperidin-4-yl)oxy)-N-(thiazol-2-yl)benzenesulfonamide

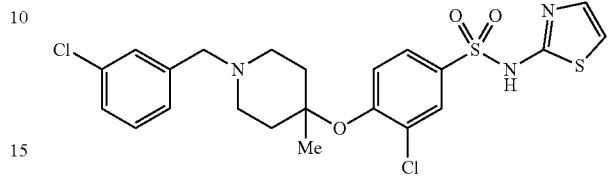

To a mixture of 3-chlorobenzaldehyde (0.15 g, 1.04 mmol) and 3-chloro-4-((4-methylpiperidin-4-yl)oxy)-N-(thiazol-2-yl)benzenesulfonamide 2,2,2-trifluoroacetate (0.20 g, 0.52 mmol) in anhydrous N,N-dimethylformamide (4 mL) and anhydrous 1,2-dichloroethane (4 mL) was added sodium triacetoxyborohydride (0.22 g, 1.04 mmol) and the reaction mixture was stirred at ambient temperature for 18 h. The reaction mixture was diluted with ethyl acetate (50 mL), washed with saturated ammonium chloride (40 mL), and concentrated in vacuo. The residue was purified by column chromatography eluting with a gradient of 0 to 20% of methanol (containing 0.2% of ammonium hydroxide) in dichloromethane to provide the title compound as a colorless solid (0.065 g, 24% yield): $^1$H NMR (300 MHz, DMSO-$d_6$) δ 7.72 (d, J=2.3 Hz, 1H), 7.60 (dd, J=8.6, 2.2 Hz, 1H), 7.37-7.20 (m, 6H), 6.79 (d, J=4.6 Hz, 1H), 3.48 (s, 2H), 2.53-2.31 (m, 4H), 2.07-1.97 (m, 2H), 1.76-1.64 (m, 2H), 1.35 (s, 3H), NH not observed; MS (ES+) m/z 512.0 (M+1), 514.0 (M+1).

Example 21

Synthesis of 3-chloro-4-((1-(3-(difluoromethyl)benzyl)-4-methylpiperidin-4-yl)oxy)-N-(thiazol-2-yl)benzenesulfonamide

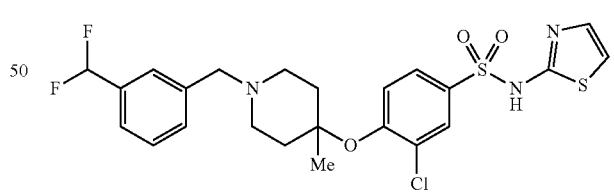

Following the procedure as described for EXAMPLE 21 and making non-critical variations as required to replace 3-chlorobenzaldehyde with 3-(difluoromethyl)benzaldehyde, the title compound was obtained as a colorless solid (0.095 g, 35% yield): $^1$H NMR (300 MHz, DMSO-$d_6$) δ 7.72 (d, J=2.3 Hz, 1H), 7.60 (dd, J=8.6, 2.3 Hz, 1H), 7.49-7.39 (m, 4H), 7.35 (d, J=8.7 Hz, 1H), 7.22 (d, J=4.6 Hz, 1H), 6.98 (t, J=56.3 Hz, 1H), 6.79 (d, J=4.5 Hz, 1H), 3.54 (s, 2H), 2.55-2.33 (m, 4H), 2.08-1.97 (m, 2H), 1.77-1.63 (m, 2H), 1.36 (s, 3H), NH not observed; MS (ES+) m/z 528.1 (M+1), 530.1 (M+1).

Example 22

Synthesis of 3-chloro-4-((1-(4-fluorobenzyl)piperidin-4-yl)oxy)-N-(thiazol-2-yl)benzenesulfonamide 2,2,2-trifluoroacetate

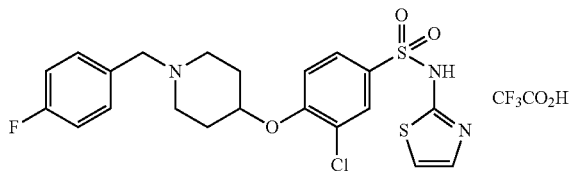 [SMILES: O=S(=O)(Nc1nccs1)c1ccc(OC2CCN(Cc3ccc(F)cc3)CC2)c(Cl)c1 ; "CF3CO2H"]

To a mixture of 3-chloro-4-(piperidin-4-yloxy)-N-(thiazol-2-yl)benzenesulfonamide 2,2,2-trifluoroacetate (0.30 g, 0.62 mmol) and 4-fluorobenzaldehyde (0.13 mL, 1.2 mmol) in N,N-dimethylformamide (1.5 mL) and 1,2-dichloroethane (1.5 mL) was added sodium triacetoxyborohydride (0.26 g, 1.23 mmol) and the mixture was stirred for 17 h. The reaction mixture was diluted with dichloromethane (4 mL) and water (4 mL) and the layers were separated. The aqueous phase was extracted with dichloromethane (2×5 mL) and the combined organic extracts were washed with brine (2×5 mL), dried over anhydrous magnesium sulfate and filtered. Concentration of the filtrate in vacuo and purification of the residue by reverse-phase preparative HPLC using acetonitrile in water containing 0.1% trifluoroacetic acid as eluent afforded the title compound as a colorless solid (0.10 g, 34% yield): $^1$H NMR (300 MHz, CD$_3$OD) δ 87.90-7.85 (m, 1H), 7.82-7.76 (m, 1H), 7.67-7.53 (m, 2H), 7.32-7.21 (m, 3H), 7.12 (d, J=4.8 Hz, 1H), 6.74 (d, J=4.5 Hz, 1H), 4.97 (br s, 1H), 4.39 (s, 2H), 3.66-3.50 (m, 1H), 3.49-3.34 (m, 3H), 2.49-1.88 (m, 4H); NH and COOH not observed $^{19}$F NMR (282 MHz, CD$_3$OD) δ −78.5, −114.1; MS (ES+) m/z 482.0 (M+1), 484.0 (M+1).

Example 23

Synthesis of 3-chloro-N-(thiazol-2-yl)-4-((1-(4-(trifluoromethyl)benzyl)piperidin-4-yl)oxy)benzenesulfonamide 2,2,2-trifluoroacetate

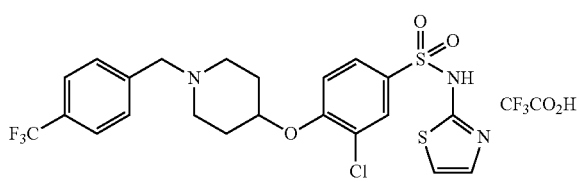 [SMILES: O=S(=O)(Nc1nccs1)c1ccc(OC2CCN(Cc3ccc(C(F)(F)F)cc3)CC2)c(Cl)c1 ; "CF3CO2H"]

Following the procedure as described in Example 22, and making non-critical variations as required to replace 4-fluorobenzaldehyde with 4-(trifluoromethyl)benzaldehyde, the title compound was obtained as a colorless solid (0.078 g, 15% yield): $^1$H NMR (300 MHz, CD$_3$OD) δ 7.85 (d, J=2.1 Hz, 1H), 7.82-7.78 (m, 3H), 7.76-7.72 (m, 2H), 7.26 (d, J=8.7 Hz, 1H), 7.09 (d, J=4.8 Hz, 1H), 6.72 (d, J=4.5 Hz, 1H), 4.95 (br s, 1H), 4.47 (s, 2H), 3.68-3.34 (m, 3H), 2.49-1.91 (m, 5H); NH and COOH not observed; $^{19}$F NMR (282 MHz, CD$_3$OD) δ −61.4, −77.1; MS (ES+) m/z 531.9 (M+1), 533.9 (M+1).

Example 24

Synthesis of 3-chloro-N-(thiazol-2-yl)-4-((1-(4-methylbenzyl)piperidin-4-yl)oxy)benzenesulfonamide 2,2,2-trifluoroacetate

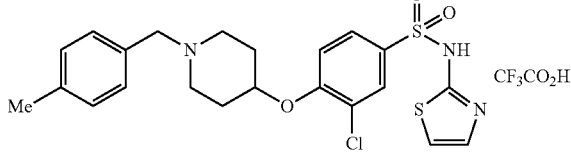

Following the procedure as described in Example 22, and making non-critical variations as required to replace 4-fluorobenzaldehyde with 4-methylbenzaldehyde, the title compound was obtained as a colorless solid (0.29 g, 60% yield): $^1$H NMR (300 MHz, CD$_3$OD) δ 7.84 (d, J=2.1 Hz, 1H), 7.77 (dd, J=8.7, 2.4 Hz, 1H), 7.38 (d, J=8.1 Hz, 2H), 7.29 (d, J=8.1 Hz, 2H), 7.27-7.19 (m, 1H), 7.09 (d, J=4.5 Hz, 1H), 6.71 (d, J=4.5 Hz, 1H), 4.94 (s, 1H), 4.31 (s, 2H), 3.64-3.48 (m, 1H), 3.46-3.34 (m, 2H), 3.21-3.06 (m, 1H), 2.37 (s, 3H), 2.24-1.79 (m, 4H); NH and COOH not observed; MS (ES+) m/z 478.1 (M+1), 480.0 (M+1).

Example 25

Synthesis of 4-((1-benzyl-3-methylazetidin-3-yl)amino)-3-chloro-N-(thiazol-2-yl)benzenesulfonamide 2,2,2-trifluoroacetate

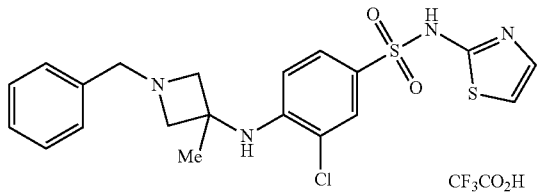 [SMILES: CC1(Nc2ccc(S(=O)(=O)Nc3nccs3)cc2Cl)CN(Cc2ccccc2)C1 ; "CF3CO2H"]

Step 1. Preparation of 4-((1-benzyl-3-methylazetidin-3-yl)amino)-3-chloro-N-(2,4-dimethoxybenzyl)-N-(thiazol-2-yl)benzenesulfonamide

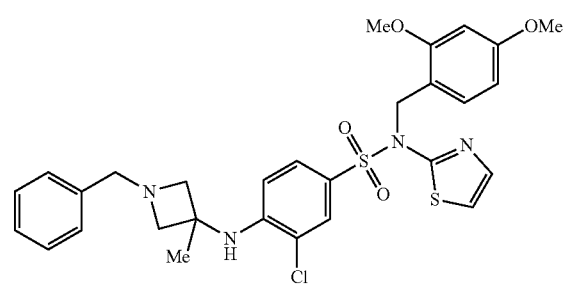 [SMILES: COc1ccc(CN(c2nccs2)S(=O)(=O)c2ccc(NC3(C)CN(Cc4ccccc4)C3)c(Cl)c2)c(OC)c1]

To a solution of 3-amino-3-methyl-N-benzylazetidine (0.25 g, 1.42 mmol) and 3-chloro-N-(2,4-dimethoxybenzyl)-4-fluoro-N-(thiazol-2-yl)benzenesulfonamide (0.63 g, 1.42 mmol) in anhydrous dimethyl sulfoxide (3 mL) was added potassium carbonate (0.39 g, 2.84 mmol) and the reaction mixture was heated to 70-75° C. for 24 h. The reaction mixture was allowed to cool to ambient temperature and diluted with ethyl acetate (150 mL) and water (15 mL). The organic phase was washed with water (15 mL), brine (15 mL), dried over anhydrous sodium sulfate, and filtered. Concentration of the filtrate in vacuo and purification of the residue by column chromatography, eluting with a gradient of 0 to 100% of ethyl acetate in hexanes provided the title compound as a colorless, amorphous solid (0.26 g, 31% yield): MS (ES+) m/z 599.1 (M+1), 601.1 (M+1).

Step 2. Preparation of 4-((1-benzyl-3-methylazetidin-3-yl)amino)-3-chloro-N-(thiazol-2-yl)benzenesulfonamide 2,2,2-trifluoroacetate

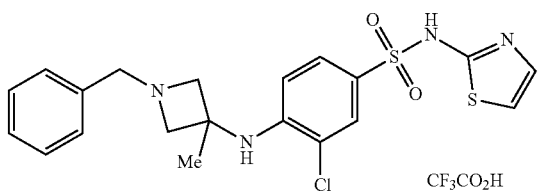 [SMILES: CC1(Nc2ccc(S(=O)(=O)Nc3nccs3)cc2Cl)CN(Cc2ccccc2)C1 ; "CF3CO2H"]

To a mixture of 4-((1-benzyl-3-methylazetidin-3-yl)amino)-3-chloro-N-(2,4-dimethoxybenzyl)-N-(thiazol-2-yl)benzenesulfonamide (0.26 g, 0.44 mmol) in anhydrous dichloromethane (10 mL) was added trifluoroacetic acid (0.5 mL) at 0° C. and the reaction mixture was stirred at 0° C. for 30 minutes. The reaction mixture was concentrated in vacuo and methanol (10 mL) was added to it. The mixture was filtered and the filtrate concentrated in vacuo. Trituration of the residue in diethyl ether (15 mL) provided the title compound as an off-white solid (0.26 g, quantitative yield): $^1$H NMR (300 MHz, CDCl$_3$) δ 7.64 (d, J=2.1 Hz, 1H), 7.53-7.42 (m, 6H), 7.26 (d, J=4.6 Hz, 1H), 6.82 (d, J=4.6 Hz, 1H), 6.75-6.67 (m, 1H), 6.48 (d, J=8.2 Hz, 1H), 4.41 (s, 2H), 4.27 (d, J=10.5 Hz, 2H), 4.19 (d, J=10.6 Hz, 2H), 1.56 (s, 3H), NH and COOH not observed; MS (ES+) m/z 449.0 (M+1), 451.0 (M+1).

Example 26

Synthesis of 4-((1-benzylpyrrolidin-3-yl)amino)-3-chloro-N-(1,2,4-thiadiazol-5-yl)benzenesulfonamide Trifluoroacetate

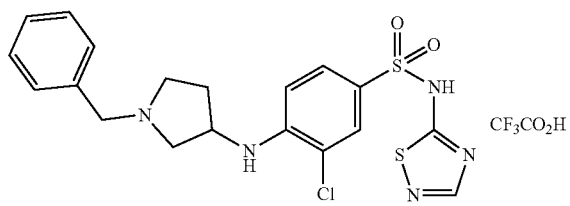 [SMILES: O=S(=O)(Nc1ncns1)c1ccc(NC2CCN(Cc3ccccc3)C2)c(Cl)c1 ; "CF3CO2H"]

Step 1. Preparation of 4-((1-benzylpyrrolidin-3-yl)amino)-3-chloro-N-(2,4-dimethoxybenzyl)-N-(1,2,4-thiadiazol-5-yl)benzenesulfonamide

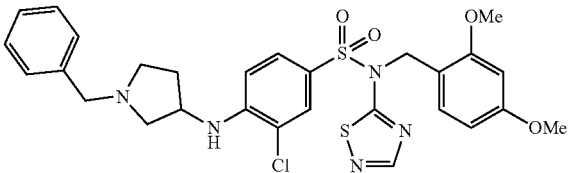 [SMILES: COc1ccc(CN(c2ncns2)S(=O)(=O)c2ccc(NC3CCN(Cc4ccccc4)C3)c(Cl)c2)c(OC)c1]

To a mixture of 3-chloro-N-(2,4-dimethoxybenzyl)-4-fluoro-N-(1,2,4-thiadiazol-5-yl)benzenesulfonamide (0.25 g, 0.56 mmol) and 1-benzylpyrrolidin-3-amine (0.096 mL, 0.56 mmol) in anhydrous dimethyl sulfoxide (5 mL) was added potassium carbonate (0.19 g, 1.35 mmol) and the reaction mixture was stirred at ambient temperature for 18 h. The reaction mixture was diluted with ethyl acetate (5 mL) and water (5 mL) and the aqueous phase was extracted ethyl acetate (3×5 mL). The combined organic phase was washed with brine (1×5 mL), dried over anhydrous sodium sulfate, filtered, and the filtrate was concentrated in vacuo. Purification of the residue by column chromatography eluting with 6 to 50% of ethyl acetate in hexanes afforded the title compound as a yellow oil (0.33 g, 97% yield): $^1$H NMR (300 MHz, CDCl$_3$) δ 8.11 (s, 1H), 7.56-7.46 (m, 2H), 7.36-7.21 (m, 6H), 7.01 (d, J=9.0 Hz, 1H), 6.45 (d, J=9.3 Hz, 1H), 6.34-6.26 (m, 2H), 5.16 (s, 2H), 4.05-3.92 (m, 1H), 3.72 (s, 3H), 3.69 (s, 3H), 3.64 (s, 2H), 2.89-2.71 (m, 2H), 2.51-2.42 (m, 1H), 2.40-2.25 (m, 1H), 1.72-1.56 (m, 2H).

Step 2. Preparation of 4-((1-benzylpyrrolidin-3-yl)amino)-3-chloro-N-(1,2,4-thiadiazol-5-yl)benzenesulfonamide 2,2,2-trifluoroacetate

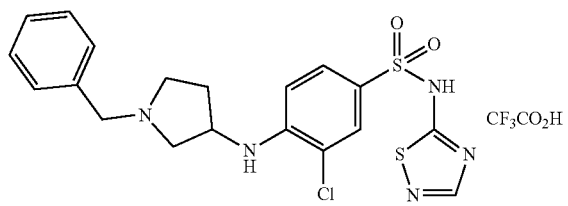 [SMILES: O=S(=O)(Nc1ncns1)c1ccc(NC2CCN(Cc3ccccc3)C2)c(Cl)c1 ; "CF3CO2H"]

To a mixture of 4-((1-benzylpyrrolidin-3-yl)amino)-3-chloro-N-(2,4-dimethoxybenzyl)-N-(1,2,4-thiadiazol-5-yl)benzenesulfonamide (0.33 g, 0.55 mmol) in dichloromethane (8 mL) was added trifluoroacetic acid (1 mL) and the reaction mixture was stirred at ambient temperature for 30 minutes. The reaction mixture was concentrated in vacuo and the residue triturated in methanol (10 mL). The mixture was filtered and the filtrate concentrated in vacuo to yield the title compound as a colorless solid (0.27 g, 85% yield): $^1$H NMR (300 MHz, CDCl$_3$) δ 10.04 (s, 1H), 8.40 (s, 1H), 7.59 (d, J=2.1 Hz, 1H), 7.56 (d, J=2.1 Hz, 1H), 7.53 (d, J=2.4 Hz, 1H), 7.51-7.47 (m, 2H), 7.46-7.41 (m, 3H), 6.84 (d, J=8.4 Hz, 1H), 6.47-6.21 (m, 1H), 6.17-5.89 (m, 1H), 4.38 (s, 2H), 3.59-3.10 (m, 4H), 2.51 (s, 1H), 2.10-1.83 (m, 1H); MS (ES+) m/z 449.9 (M+1), 451.9 (M+1).

Example 27

Synthesis of (S)-3-chloro-4-((1-(3-chlorobenzyl)pyrrolidin-3-yl)(methyl)amino)-N-(thiazol-2-yl)benzenesulfonamide

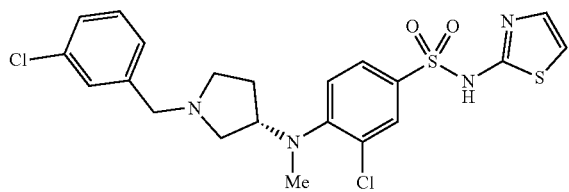 [SMILES: CN(c1ccc(S(=O)(=O)Nc2nccs2)cc1Cl)[C@H]1CCN(Cc2cccc(Cl)c2)C1]

Step 1. Preparation of tert-butyl (S)-3-((2-chloro-4-(N-(2,4-dimethoxybenzyl)-N-(thiazol-2-yl)sulfamoyl)phenyl)amino)pyrrolidine-1-carboxylate

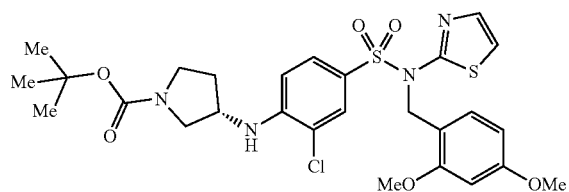 [SMILES: COc1ccc(CN(c2nccs2)S(=O)(=O)c2ccc(N[C@H]3CCN(C(=O)OC(C)(C)C)C3)c(Cl)c2)c(OC)c1]

To a mixture of 3-chloro-N-(2,4-dimethoxybenzyl)-4-fluoro-N-(thiazol-2-yl)benzenesulfonamide (3.39 g, 7.65 mmol) and tert-butyl (S)-3-aminopyrrolidine-1-carboxylate (1.71 g, 9.18 mmol) in anhydrous dimethyl sulfoxide (40 mL) was added and potassium carbonate (2.11 g, 15.3 mmol) and the reaction mixture was stirred at ambient temperature for 3 days. The mixture was diluted with ethyl acetate (200 mL), washed with water (200 mL), saturated ammonium chloride (100 mL), brine (100 mL), dried over anhydrous sodium sulfate, and filtered. Concentration of the filtrate in vacuo gave a residue which was purified by column chromatography eluting with a gradient of 10 to 80% of ethyl acetate in hexanes to provide the title compound as a colorless foam (3.95 g, 85% yield): $^1$H NMR (300 MHz, CDCl$_3$) δ 7.67 (s, 1H), 7.61 (d, J=8.5 Hz, 1H), 7.41 (dd, J=3.6, 1.1 Hz, 1H), 7.17 (d, J=9.0 Hz, 1H), 7.00 (d, J=3.6 Hz, 1H), 6.63 (d, J=8.6 Hz, 1H), 6.41-6.53 (m, 2H), 5.07 (s, 2H), 4.86 (d, J=6.4 Hz, 1H), 4.13-4.06 (m, 1H), 3.79-3.69 (m, 7H), 3.56-3.49 (m, 2H), 3.39-3.22 (m, 1H), 2.33-2.21 (m, 1H), 2.00-1.93 (m, 1H), 1.46 (s, 9H); MS (ES+) m/z 609.2 (M+1), 611.2 (M+1).

Step 2. Preparation of tert-butyl (S)-3-((2-chloro-4-(N-(2,4-dimethoxybenzyl)-N-(thiazol-2-yl)sulfamoyl)phenyl)(methyl)amino)pyrrolidine-1-carboxylate

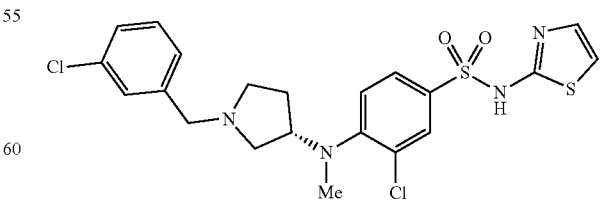

To a solution of tert-butyl (S)-3-((2-chloro-4-(N-(2,4-dimethoxybenzyl)-N-(thiazol-2-yl)sulfamoyl)phenyl)amino)pyrrolidine-1-carboxylate (2.44 g, 4.00 mmol) in anhydrous tetrahydrofuran (35 mL) was added a 1.0 M solution of lithium bis(trimethylsilyl)amide in tetrahydrofuran (4.8 mL, 4.8 mmol) at 0° C. The reaction mixture was stirred for 1.5 h at 0° C., cooled to −78° C., and a 1.0 M solution of methyl iodide in tetrahydrofuran (4.4 mL, 4.4 mmol) was added to it. The reaction mixture was allowed to warm to ambient temperature and stirred for 18 h. The mixture was diluted with ethyl acetate (100 mL), washed with saturated ammonium chloride (2×80 mL), brine (2×50 mL), dried over anhydrous sodium sulfate, and filtered. Concentration of the filtrate in vacuo gave a residue which was purified by column chromatography eluting with a gradient of 0 to 100% of ethyl acetate in hexanes to provide the title compound as a colorless foam (1.75 g, 70% yield): $^1$H NMR (300 MHz, CDCl$_3$) 37.75 (s, 1H), 7.68-7.61 (m, 1H), 7.43 (d, J=3.6 Hz, 1H), 7.17 (dd, J=9.0, 4.4 Hz, 1H), 7.06-7.03 (m, 2H), 6.40-6.33 (m, 2H), 5.08 (s, 2H), 4.12-4.06 (m, 1H), 3.77 (s, 3H), 3.73 (s, 3H), 3.67-3.52 (m, 2H), 3.37-3.26 (m, 2H), 2.79 (s, 3H), 2.04-2.01 (m, 2H), 1.47 (s, 9H); MS (ES+) m/z 623.2 (M+1), 625.2 (M+1).

Step 3. Preparation of (S)-3-chloro-4-(methyl(pyrrolidin-3-yl)amino)-N-(thiazol-2-yl)benzenesulfonamide 2,2,2-trifluoroacetate

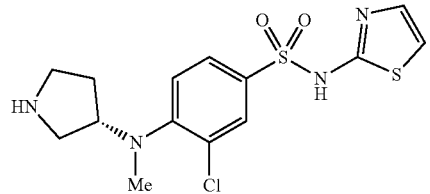

Following the procedure as described for EXAMPLE 1, Step 4 and making non-critical variations as required to replace tert-butyl 4-(2-chloro-4-(N-(2,4-dimethoxybenzyl)-N-(1,2,4-thiadiazol-5-yl)sulfamoyl)phenoxy)-3,3-dimethylpiperidine-1-carboxylate with tert-butyl (S)-3-((2-chloro-4-(N-(2,4-dimethoxybenzyl)-N-(thiazol-2-yl)sulfamoyl)phenyl)(methyl)amino)pyrrolidine-1-carboxylate, the title compound was obtained as a beige foam (1.37 g, quantitative yield): MS (ES+) m/z 373.1 (M+1), 375.1 (M+1).

Step 4. Preparation of (S)-3-chloro-4-((1-(3-chlorobenzyl)pyrrolidin-3-yl)(methyl)amino)-N-(thiazol-2-yl)benzenesulfonamide

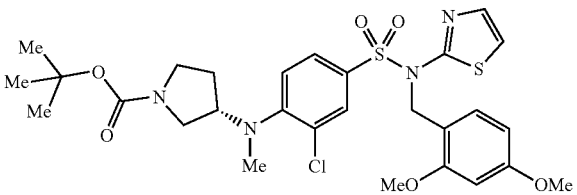 [SMILES: COc1ccc(CN(c2nccs2)S(=O)(=O)c2ccc(N(C)[C@H]3CCN(C(=O)OC(C)(C)C)C3)c(Cl)c2)c(OC)c1]

To a mixture of 3-chlorobenzaldehyde (0.15 g, 1.08 mmol) and (S)-3-chloro-4-(methyl(pyrrolidin-3-yl)amino)-N-(thiazol-2-yl)benzenesulfonamide 2,2,2-trifluoroacetate (0.20 g, 0.54 mmol) in anhydrous N,N-dimethylformamide (4 mL) and anhydrous 1,2-dichloroethane (4 mL) was added sodium triacetoxyborohydride (0.23 g, 1.08 mmol) and the reaction mixture was stirred at ambient temperature for 18 h. The reaction mixture was diluted with ethyl acetate (50 mL), washed with saturated ammonium chloride (40 mL), and concentrated in vacuo. Purification of the residue by column chromatography eluting with a gradient of 0 to 20% of methanol (containing 0.2% of ammonium hydroxide) in dichloromethane provided the title compound as a colorless solid (0.11 g, 41% yield): $^1$H NMR (300 MHz, DMSO-$d_6$) δ 7.64 (d, J=2.2 Hz, 1H), 7.58 (dd, J=8.6, 2.2 Hz, 1H), 7.34-7.15 (m, 6H), 6.77 (d, J=4.6 Hz, 1H), 4.09-3.97 (m, 1H), 3.61 (d, J=13.4 Hz, 1H), 3.5 (d, J=13.4 Hz, 1H), 2.68 (s, 3H), 2.66-2.53 (m, 3H), 2.42-2.31 (m, 1H), 2.02-1.92 (m, 1H), 1.81-1.67 (m, 1H), NH not observed; MS (ES+) m/z 497.0 (M+1), 499.0 (M+1).

Example 28

Synthesis of (S)-3-chloro-4-((1-(3-(difluoromethyl)benzyl)pyrrolidin-3-yl)(methyl)amino)-N-(thiazol-2-yl)benzenesulfonamide

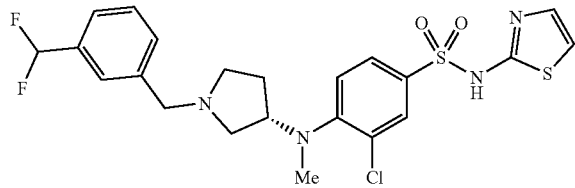 [SMILES: CN(c1ccc(S(=O)(=O)Nc2nccs2)cc1Cl)[C@H]1CCN(Cc2cccc(C(F)F)c2)C1]

Following the procedure as described for EXAMPLE 27, Step 4 and making non-critical variations as required to replace 3-chlorobenzaldehyde with 3-(difluoromethyl)benzaldehyde, the title compound was obtained as a colorless solid (0.195 g, 70% yield): $^1$H NMR (300 MHz, DMSO-$d_6$) δ 7.64 (d, J=2.2 Hz, 1H), 7.58 (dd, J=8.5, 2.2 Hz, 1H), 7.50-7.40 (m, 4H), 7.21 (d, J=4.5 Hz, 1H), 7.18 (d, J=8.5 Hz, 1H), 6.99 (t, J=56.0 Hz, 1H), 6.77 (d, J=4.5 Hz, 1H), 4.10-3.98 (m, 1H), 3.69 (d, J=13.3 Hz, 1H), 3.55 (d, J=13.3 Hz, 1H), 2.68 (s, 3H), 2.67-2.53 (m, 3H), 2.43-2.32 (m, 1H), 2.07-1.93 (m, 1H), 1.81-1.68 (m, 1H), NH not observed; MS (ES+) m/z 513.1 (M+1), 515.1 (M+1).

Example 29

Synthesis of (S)-4-((1-benzylpyrrolidin-3-yl)(methyl)amino)-3-chloro-N-(1,2,4-thiadiazol-5-yl)benzenesulfonamide hydrochloride salt

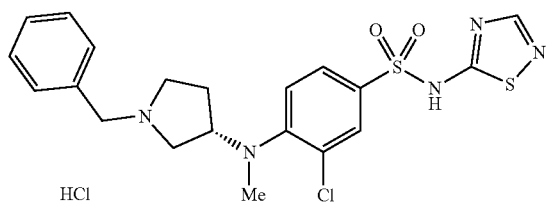 [SMILES: CN(c1ccc(S(=O)(=O)Nc2ncns2)cc1Cl)[C@H]1CCN(Cc2ccccc2)C1 ; Cl]

Step 1. Preparation of tert-butyl (S)-3-((2-chloro-4-(N-(2,4-dimethoxybenzyl)-N-(1,2,4-thiadiazol-5-yl)sulfamoyl)phenyl)amino)pyrrolidine-1-carboxylate

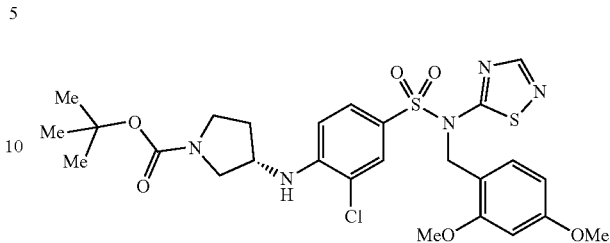

To a mixture of 3-chloro-N-(2,4-dimethoxybenzyl)-4-fluoro-N-(1,2,4-thiadiazol-5-yl)benzenesulfonamide (12.46 g, 28.07 mmol) in anhydrous dimethyl sulfoxide (100 mL) was added tert-butyl (S)-3-aminopyrrolidine-1-carboxylate (15.69 g, 84.21 mmol) and the reaction mixture was heated to 50° C. for 6 h. The reaction mixture was allowed to cool to ambient temperature and stirred for 18 h. The reaction mixture was diluted with ethyl acetate (550 mL), washed with saturated ammonium chloride (2×200 mL), brine (100 mL), dried over anhydrous sodium sulfate, and filtered. Concentration of the filtrate in vacuo and purification of the residue by column chromatography eluting with a gradient of 0 to 100% of ethyl acetate in hexanes provided the title compound as a colorless foam (17.13 g, quantitative yield): $^1$H NMR (300 MHz, CDCl$_3$) δ 8.16 (s, 1H), 7.65-7.61 (m, 2H), 7.06 (d, J=9.0 Hz, 1H), 6.58 (d, J=8.6 Hz, 1H), 6.37-6.33 (m, 2H), 5.21 (s, 2H), 4.93 (d, J=6.6 Hz, 1H), 4.10-4.05 (m, 1H), 3.78-3.72 (m, 7H), 3.56-3.47 (m, 2H), 3.37-3.22 (m, 1H), 2.34-2.18 (m, 1H), 1.99-1.90 (m, 1H), 1.48 (s, 9H); MS (ES+) m/z 610.1 (M+1), 612.1 (M+1).

Step 2. Preparation of tert-butyl (S)-3-((2-chloro-4-(N-(2,4-dimethoxybenzyl)-N-(1,2,4-thiadiazol-5-yl)sulfamoyl)phenyl)(methyl)amino)pyrrolidine-1-carboxylate

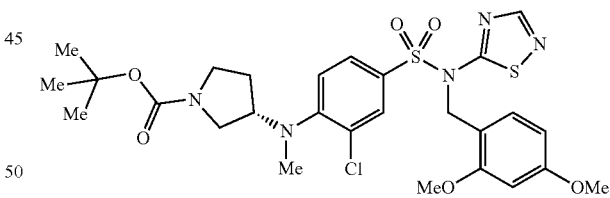

To a solution of tert-butyl (S)-3-((2-chloro-4-(N-(2,4-dimethoxybenzyl)-N-(1,2,4-thiadiazol-5-yl)sulfamoyl)phenyl)amino)pyrrolidine-1-carboxylate (10.26 g, 16.82 mmol) in anhydrous tetrahydrofuran (100 mL) was added a 1 M solution of lithium bis(trimethylsilyl)amide in tetrahydrofuran (20.2 mL, 20.2 mmol) at 0° C. The reaction mixture was stirred at 0° C. for 40 minutes, cooled to −78° C., and methyl iodide (1.15 mL, 18.50 mmol) was added to it. The reaction mixture was stirred at −78° C. for 30 minutes, allowed to warm to ambient temperature, and stirred for 4 h. The reaction mixture was diluted with ethyl acetate (250 mL), washed with saturated ammonium chloride (2×150 mL), brine (100 mL), dried over anhydrous sodium sulfate, and filtered. Concentration of the filtrate in vacuo and purification of the residue by column chromatography eluting with a gradient of 0 to 100% of ethyl acetate in hexanes provided the title compound as a colorless foam (6.50 g, 62% yield): ¹H NMR (300 MHz, CDCl₃) δ 8.19 (s, 1H), 7.64-7.58 (m, 2H), 7.07 (d, J=8.3 Hz, 1H), 6.99 (d, J=8.2 Hz, 1H), 6.35-6.32 (m, 1H), 6.30 (d, J=2.3 Hz, 1H), 5.27 (s, 2H), 4.09-4.03 (m, 1H), 3.77 (s, 3H), 3.72 (s, 3H), 3.64-3.55 (m, 2H), 3.36-3.26 (m, 2H), 2.79 (s, 3H), 2.05-1.98 (m, 2H), 1.48 (s, 9H); MS (ES+) m/z 624.1 (M+1), 626.1 (M+1).

Step 3. Preparation of (S)-3-chloro-4-(methyl(pyrrolidin-3-yl)amino)-N-(1,2,4-thiadiazol-5-yl)benzenesulfonamide 2,2,2-trifluoroacetate

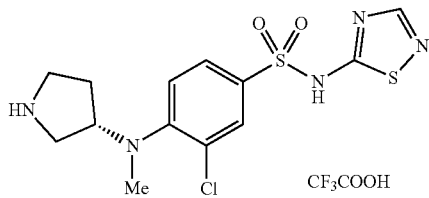 [SMILES: CN(c1ccc(S(=O)(=O)Nc2ncns2)cc1Cl)[C@H]1CCNC1 ; "CF3COOH"]

To a solution of tert-butyl (S)-3-((2-chloro-4-(N-(2,4-dimethoxybenzyl)-N-(1,2,4-thiadiazol-5-yl)sulfamoyl)phenyl)(methyl)amino)pyrrolidine-1-carboxylate (3.0 g, 4.8 mmol) in dichloromethane (60 mL) was added 2,2,2-trifluoroacetic acid (18 mL). The reaction mixture was stirred at ambient temperature for 40 minutes and then concentrated in vacuo. The residue was triturated with methanol (40 mL) containing activated charcoal (1.0 g), and the resulting mixture was filtered. The filtrate was concentrated in vacuo to afford the title compound as a brownish oil (2.1 g, 91% yield): ¹H NMR (300 MHz, DMSO-d₆) δ 9.03-8.83 (m, 2H), 8.46 (s, 1H), 7.75-7.74 (m, 1H), 7.72-7.68 (m, 1H), 7.37 (d, J=8.5 Hz, 1H), 4.26-4.16 (m, 1H), 3.44-3.23 (m, 2H), 3.20-3.06 (m, 2H), 2.72 (s, 3H), 2.11-1.88 (m, 2H), one NH not observed.

Step 4. Preparation of (S)-4-((1-benzylpyrrolidin-3-yl)(methyl)amino)-3-chloro-N-(1,2,4-thiadiazol-5-yl)benzenesulfonamide

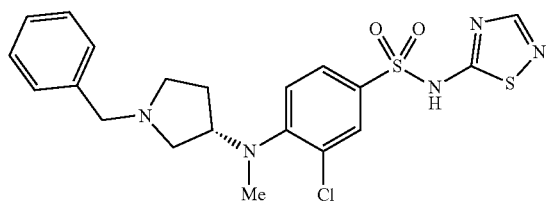 [SMILES: CN(c1ccc(S(=O)(=O)Nc2ncns2)cc1Cl)[C@H]1CCN(Cc2ccccc2)C1]

To a mixture of (S)-3-chloro-4-(methyl(pyrrolidin-3-yl)amino)-N-(1,2,4-thiadiazol-5-yl)benzenesulfonamide 2,2,2-trifluoroacetate (0.80 g, 1.6 mmol) in anhydrous N,N-dimethylformamide (8 mL) and anhydrous 1,2-dichloroethane (8 mL) was added benzaldehyde (0.2 mL, 2 mmol). The reaction mixture was stirred at ambient temperature for 10 minutes and then sodium triacetoxyborohydride (0.68 g, 3.2 mmol) was added to it. The reaction mixture was stirred at ambient temperature for 1.5 h. The reaction mixture was diluted with water (30 mL), saturated ammonium chloride solution (10 mL), and ethyl acetate (50 mL). The aqueous phase was extracted with ethyl acetate (2×30 mL), and dichloromethane (10×15 mL). The combined organic phases were washed with brine (30 mL), dried with anhydrous magnesium sulfate, and filtered. Concentration of the filtrate in vacuo and purification of the residue by column chromatography eluting with a gradient of 0 to 20% of methanol (containing 0.1% of ammonium hydroxide) in dichloromethane provided a residue which was triturated in methanol (10 mL) to afford the title compound as a colorless solid (0.355 g, 77% yield): ¹H NMR (300 MHz, DMSO-d₆) δ 10.07 (br s, 1H), 7.90 (s, 1H), 7.68 (d, J=2.1 Hz, 1H), 7.62 (dd, J=8.4, 2.1 Hz, 1H), 7.52-7.40 (m, J=2.7 Hz, 5H), 7.27 (d, J=8.5 Hz, 1H), 4.33 (s, 2H), 4.24-4.15 (m, 1H), 3.51-3.15 (m, 4H), 2.69 (s, 3H), 2.15-1.97 (m, 2H); MS (ES+) m/z 464.0 (M+1), 466.0 (M+1).

Step 5. Preparation of (S)-4-((1-benzylpyrrolidin-3-yl)(methyl)amino)-3-chloro-N-(1,2,4-thiadiazol-5-yl)benzenesulfonamide Hydrochloride

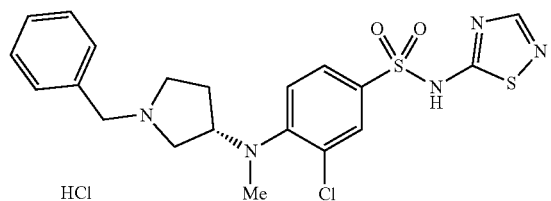 [SMILES: CN(c1ccc(S(=O)(=O)Nc2ncns2)cc1Cl)[C@H]1CCN(Cc2ccccc2)C1 ; Cl]

To (S)-4-((1-benzylpyrrolidin-3-yl)(methyl)amino)-3-chloro-N-(1,2,4-thiadiazol-5-yl)benzenesulfonamide (0.334 g, 0.720 mmol) was added a 5-10% solution of hydrogen chloride in methanol (2 mL) and the reaction mixture was stirred at ambient temperature for 30 minutes. Concentration in vacuo provided the title compound as a colorless solid (0.339 g, 94% yield): ¹H NMR (300 MHz, DMSO-d₆) δ11.33-10.82 (m, 1H), 8.43 (s, 1H), 7.73 (d, J=2.2 Hz, 1H), 7.68 (dd, J=8.4, 2.1 Hz, 1H), 7.62-7.53 (m, 2H), 7.47-7.41 (m, J=3.2 Hz, 3H), 7.33 (d, J=8.6 Hz, 1H), 4.49-4.16 (m, 3H), 3.54-3.00 (m, 5H), 2.76 (s, 3H), 2.20-2.00 (m, 2H); MS (ES+) m/z 464.0 (M+1), 466.0 (M+1).

Example 30

Synthesis of (S)-3-chloro-4-((1-(3-chlorobenzyl)pyrrolidin-3-yl)(methyl)amino)-N-(1,2,4-thiadiazol-5-yl)benzenesulfonamide

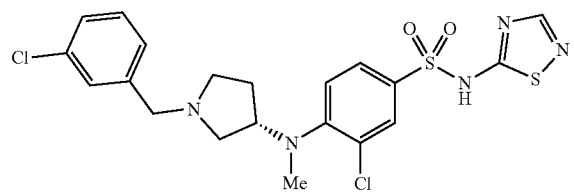 [SMILES: CN(c1ccc(S(=O)(=O)Nc2ncns2)cc1Cl)[C@H]1CCN(Cc2cccc(Cl)c2)C1]

Following the procedure as described for EXAMPLE 29, Step 4 and making non-critical variations as required to replace benzaldehyde with 3-chlorobenzaldehyde, and purification by column chromatography eluting with 0 to 20% of methanol (containing 0.2% of ammonium hydroxide) in dichloromethane, the title compound was obtained as a colorless solid (0.12 g, 47% yield): ¹H NMR (300 MHz, DMSO-d₆) δ 10.22 (br s, 1H), 7.85 (s, 1H), 7.64 (d, J=2.1

Hz, 1H), 7.59 (dd, J=8.4, 2.1 Hz, 1H), 7.47 (s, 1H), 7.41-7.34 (m, 3H), 7.20 (s, 1H), 4.12-4.04 (m, 1H), 3.98-3.89 (m, 2H), 3.04-2.75 (m, 4H), 2.67 (s, 3H), 2.11-1.99 (m, 1H), 1.93-1.81 (m, 1H); MS (ES+) m/z 498.0 (M+1), 500.0 (M+1).

Example 31

Synthesis of (S)-3-chloro-4-((1-(3-(difluoromethyl)benzyl)pyrrolidin-3-yl)(methyl)amino)-N-(1,2,4-thiadiazol-5-yl)benzenesulfonamide

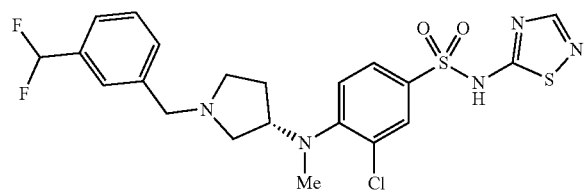 [SMILES: CN(c1ccc(S(=O)(=O)Nc2ncns2)cc1Cl)[C@H]1CCN(Cc2cccc(C(F)F)c2)C1]

Following the procedure as described for EXAMPLE 29, Step 4 and making non-critical variations as required to replace benzaldehyde with 3-(difluoromethyl)benzaldehyde, and purification by column chromatography eluting with 0 to 20% of methanol (containing 0.2% of ammonium hydroxide) in dichloromethane, the title compound was obtained as a colorless solid (0.085 g, 32% yield): $^1$H NMR (300 MHz, DMSO-$d_6$) δ 10.22 (br s, 1H), 7.87 (s, 1H), 7.66-7.54 (m, 6H), 7.25 (s, 1H), 7.05 (t, J=51.4 Hz, 1H), 4.19-4.09 (m, 3H), 3.46-3.32 (m, 1H), 3.22-2.93 (m, 3H), 2.68 (s, 3H), 2.14-2.03 (m, 1H), 1.98-1.86 (m, 1H); MS (ES+) m/z 514.0 (M+1), 516.0 (M+1).

Example 32

Synthesis of (S)-3-chloro-4-((1-(3-chloro-2-fluorobenzyl)pyrrolidin-3-yl)(methyl)amino)-N-(1,2,4-thiadiazol-5-yl)benzenesulfonamide

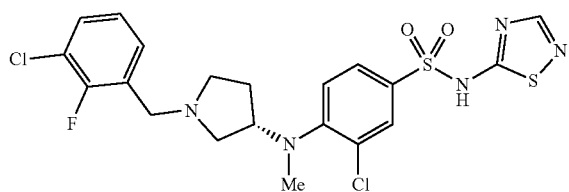 [SMILES: CN(c1ccc(S(=O)(=O)Nc2ncns2)cc1Cl)[C@H]1CCN(Cc2cccc(Cl)c2F)C1]

Following the procedure as described for EXAMPLE 29, Step 4 and making non-critical variations as required to replace benzaldehyde with 3-chloro-2-fluorobenzaldehyde, and purification by column chromatography eluting with 0 to 20% of methanol (containing 0.2% of ammonium hydroxide) in dichloromethane, the title compound was obtained as a colorless solid (0.145 g, 55% yield): $^1$H NMR (300 MHz, DMSO-$d_6$) δ 7.89 (s, 1H), 7.64 (d, J=2.1 Hz, 1H), 7.61-7.54 (m, 2H), 7.49-7.44 (m, 1H), 7.26 (dd, J=7.9, 0.8 Hz, 1H), 7.21 (d, J=8.5 Hz, 1H), 4.12-4.07 (m, 1H), 3.98 (s, 2H), 3.05-2.74 (m, 4H), 2.67 (s, 3H), 2.10-1.98 (m, 1H), 1.91-1.79 (m, 1H), NH not observed; MS (ES+) m/z 516.0 (M+1), 518.0 (M+1).

Example 33

Synthesis of (S)-3-chloro-4-((1-(5-chloro-2-fluorobenzyl)pyrrolidin-3-yl)(methyl)amino)-N-(1,2,4-thiadiazol-5-yl)benzenesulfonamide 2,2,2-trifluoroacetate

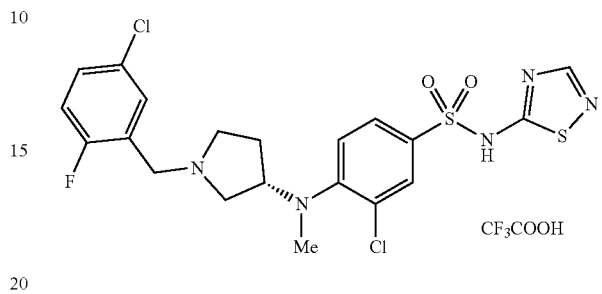

Following the procedure as described for EXAMPLE 29, Step 4 and making non-critical variations as required to replace benzaldehyde with 5-chloro-2-fluorobenzaldehyde, and purification by preparative reverse-phase HPLC eluting with a gradient of 10 to 60% of acetonitrile in water containing 0.1% of trifluoroacetic acid, the title compound was obtained as a colorless solid (0.085 g, 26% yield): $^1$H NMR (300 MHz, CD$_3$OD) δ 8.08 (s, 1H), 7.88 (d, J=2.2 Hz, 1H), 7.75 (dd, J=8.5, 2.2 Hz, 1H), 7.55 (dd, J=6.2, 2.6 Hz, 1H), 7.47 (ddd, J=8.9, 4.5, 2.7 Hz, 1H), 7.26-7.16 (m, 2H), 4.42 (s, 2H), 4.40-4.33 (m, 1H), 3.67-3.61 (m, 1H), 3.51-3.36 (m, 3H), 2.77 (s, 3H), 2.30-2.16 (m, 2H), NH and COOH not observed; MS (ES+) m/z 516.0 (M+1), 518.0 (M+1).

Example 34

Synthesis of (S)-3-chloro-4-((1-(2-fluoro-3-methylbenzyl)pyrrolidin-3-yl)(methyl)amino)-N-(1,2,4-thiadiazol-5-yl)benzenesulfonamide 2,2,2-trifluoroacetate

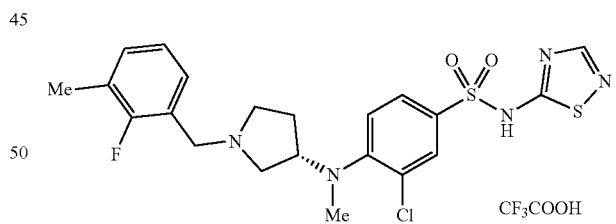

Following the procedure as described for EXAMPLE 29, Step 4 and making non-critical variations as required to replace benzaldehyde with 2-fluoro-3-methylbenzaldehyde, and purification by preparative reverse-phase HPLC eluting with a gradient of 10 to 60% of acetonitrile in water containing 0.1% of trifluoroacetic acid, the title compound was obtained as a colorless solid (0.085 g, 22% yield, check): $^1$H NMR (300 MHz, CD$_3$OD) δ 8.19 (s, 1H), 7.86 (d, J=2.2 Hz, 1H), 7.76 (dd, J=8.5, 2.2 Hz, 1H), 7.42-7.31 (m, 3H), 7.16 (t, J=7.6 Hz, 1H), 4.49 (s, 2H), 4.42-4.32 (m, 1H), 3.70-3.63 (m, 1H), 3.54-3.41 (m, 3H), 2.79 (s, 3H), 2.31-2.22 (m, 5H), NH and COOH not observed; MS (ES+) m/z 496.0 (M+1), 498.0 (M+1).

Example 35

Synthesis of (S)-3-chloro-4-((1-(2-fluoro-5-methyl-benzyl)pyrrolidin-3-yl)(methyl)amino)-N-(1,2,4-thiadiazol-5-yl)benzenesulfonamide

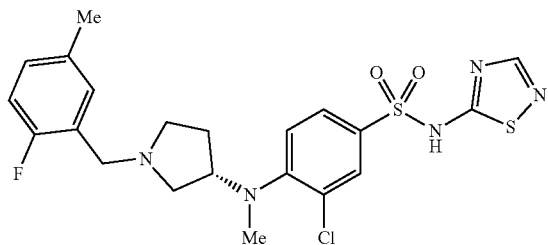 [SMILES: Cc1ccc(F)c(CN2CC[C@H](N(C)c3ccc(S(=O)(=O)Nc4ncns4)cc3Cl)C2)c1]

Following the procedure as described for EXAMPLE 29, Step 4 and making non-critical variations as required to replace benzaldehyde with 2-fluoro-5-methylbenzaldehyde, and purification by column chromatography eluting with 0 to 20% of methanol (containing 0.2% of ammonium hydroxide) in dichloromethane, the title compound was obtained as a colorless solid (0.085 g, 32% yield): $^1$H NMR (300 MHz, DMSO-$d_6$) δ 7.89 (s, 1H), 7.66 (d, J=2.1 Hz, 1H), 7.60 (dd, J=8.4, 2.1 Hz, 1H), 7.32 (dd, J=7.2, 1.8 Hz, 1H), 7.27-7.22 (m, 2H), 7.14 (dd, J=9.1, 9.1 Hz, 1H), 4.18-4.15 (m, 3H), 3.32-3.25 (m, 1H), 3.13-3.04 (m, 3H), 2.68 (s, 3H), 2.28 (s, 3H), 2.12-2.04 (m, 1H), 1.98-1.91 (m, 1H), NH and COOH not observed; MS (ES+) m/z 496.1 (M+1), 498.1 (M+1).

Example 36

Synthesis of (S)-4-((1-benzylpyrrolidin-3-yl)(ethyl)amino)-3-chloro-N-(1,2,4-thiadiazol-5-yl)benzenesulfonamide

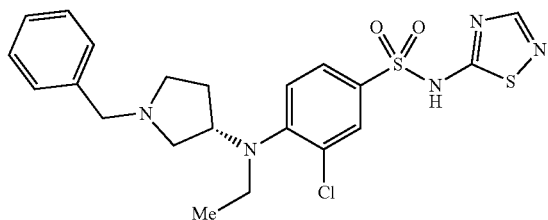 [SMILES: CCN(c1ccc(S(=O)(=O)Nc2ncns2)cc1Cl)[C@H]1CCN(Cc2ccccc2)C1]

Step 1. Preparation of tert-butyl (S)-3-((2-chloro-4-(N-(2,4-dimethoxybenzyl)-N-(1,2,4-thiadiazol-5-yl)sulfamoyl)phenyl)(ethyl)amino)pyrrolidine-1-carboxylate

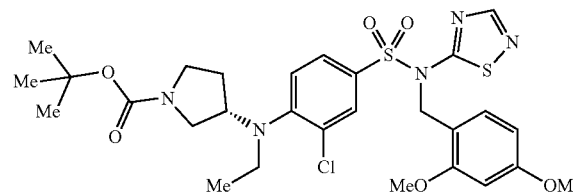

To a solution of tert-butyl (S)-3-((2-chloro-4-(N-(2,4-dimethoxybenzyl)-N-(1,2,4-thiadiazol-5-yl)sulfamoyl)phenyl)amino)pyrrolidine-1-carboxylate (0.94 g, 1.54 mmol) in anhydrous dimethyl sulfoxide (21 mL) was added anhydrous cesium carbonate (1.0 g, 3.08 mmol). The reaction mixture was stirred at ambient temperature for 2 h, and then iodoethane (0.19 mL, 2.31 mmol) was added dropwise to it. The reaction mixture was stirred at ambient temperature for 16 h. The mixture was diluted with ethyl acetate (50 mL), washed with water (50 mL), brine (3×50 mL), dried over anhydrous sodium sulfate, and filtered. Concentration of the filtrate in vacuo and purification of the residue by column chromatography eluting with a gradient of 0 to 100% of ethyl acetate in hexanes yielded the title compound as a colorless solid (0.77 mg, 78% yield). $^1$H NMR (300 MHz, CDCl$_3$) δ 8.16 (s, 1H), 7.61-7.56 (m, 2H), 7.03 (d, J=8.4 Hz, 2H), 6.31-6.28 (m, 2H), 5.26 (s, 2H), 4.01-3.93 (m, 1H), 3.73 (s, 3H), 3.69 (s, 3H), 3.66-3.43 (m, 2H), 3.30-3.09 (m, 4H), 2.00-1.94 (m, 1H), 1.90-1.77 (m, 1H), 1.43 (s, 9H), 0.92-0.88 (m, 3H); MS (ES+) m/z 638.2 (M+1), 640.1 (M+1).

Step 2. Preparation of (S)-3-chloro-4-(ethyl(pyrrolidin-3-yl)amino)-N-(1,2,4-thiadiazol-5-yl)benzenesulfonamide 2,2,2-trifluoroacetate

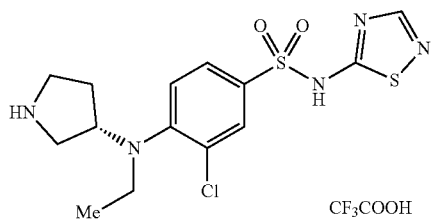 [SMILES: CCN(c1ccc(S(=O)(=O)Nc2ncns2)cc1Cl)[C@H]1CCNC1 ; "CF3COOH"]

Following the procedure as described for EXAMPLE 29, Step 3 and making non-critical variations as required to replace tert-butyl (S)-3-((2-chloro-4-(N-(2,4-dimethoxybenzyl)-N-(1,2,4-thiadiazol-5-yl)sulfamoyl)phenyl)(methyl)amino)pyrrolidine-1-carboxylate with tert-butyl (S)-3-((2-chloro-4-(N-(2,4-dimethoxybenzyl)-N-(1,2,4-thiadiazol-5-yl)sulfamoyl)phenyl)(ethyl)amino)pyrrolidine-1-carboxylate, the title compound was obtained as a brown foam (0.61 g, quantitative yield): $^1$H NMR (300 MHz, CD$_3$OD) δ 8.20 (s, 1H), 7.88 (d, J=2.2 Hz, 1H), 7.77 (dd, J=8.4, 2.2 Hz, 1H), 7.44 (d, J=8.5 Hz, 1H), 4.30-4.20 (m, 1H), 3.45-3.34 (m, 2H), 3.26-3.17 (m, 4H), 2.21-2.06 (m, 1H), 2.02-1.90 (m, 1H), 0.92 (t, J=7.1 Hz, 3H), NH and COOH not observed; MS (ES+) m/z 388.0 (M+1), 390.0 (M+1).

Step 3. Preparation of (S)-4-((1-benzylpyrrolidin-3-yl)(ethyl)amino)-3-chloro-N-(1,2,4-thiadiazol-5-yl)benzenesulfonamide

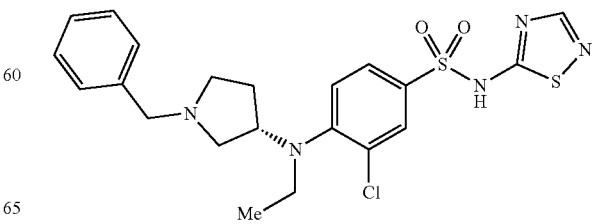

To a mixture of benzaldehyde (0.15 g, 1.08 mmol) and (S)-3-chloro-4-(ethyl(pyrrolidin-3-yl)amino)-N-(1,2,4-thiadiazol-5-yl)benzenesulfonamide 2,2,2-trifluoroacetate (0.30 g, 0.60 mmol) in anhydrous N,N-dimethylformamide (4 mL) and anhydrous 1,2-dichloroethane (4 mL) was added sodium triacetoxyborohydride (0.32 g, 1.50 mmol) and the reaction mixture was stirred at ambient temperature for 18 h. The mixture was diluted with ethyl acetate (50 mL), washed with saturated ammonium chloride (40 mL), and concentrated in vacuo. Purification of the residue by column chromatography eluting with a gradient of 0 to 20% of methanol (containing 0.2% of ammonium hydroxide) in dichloromethane provided the title compound as a colorless solid (0.11 g, 38% yield): $^1$H NMR (300 MHz, DMSO-$d_6$) δ 10.11 (br s, 1H), 7.85 (s, 1H), 7.67 (d, J=2.1 Hz, 1H), 7.60 (dd, J=8.2, 2.1 Hz, 1H), 7.45-7.36 (m, 5H), 7.31 (d, J=8.4 Hz, 1H), 4.24 (s, 2H), 4.16-4.03 (m, 1H), 3.14-3.30 (m, 2H), 3.24-3.00 (m, 4H), 2.14-2.00 (m, 1H), 1.93-1.79 (m, 1H), 0.77 (t, J=7.01 Hz, 3H); MS (ES+) m/z 478.1 (M+1), 480.1 (M+1).

Example 37

Synthesis of (S)-3-chloro-4-(ethyl(1-(3-methylbenzyl)pyrrolidin-3-yl)amino)-N-(1,2,4-thiadiazol-5-yl)benzenesulfonamide

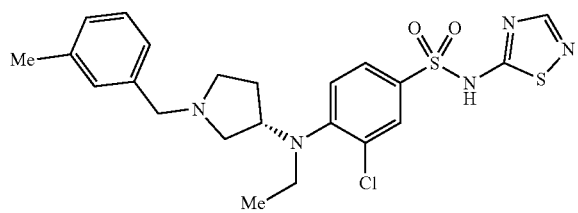 [SMILES: CCN(c1ccc(S(=O)(=O)Nc2ncns2)cc1Cl)[C@H]1CCN(Cc2cccc(C)c2)C1]

Following the procedure as described for EXAMPLE 36, Step 3 and making non-critical variations as required to replace benzaldehyde with 3-methylbenzaldehyde, the title compound was obtained as a colorless solid (0.11 g, 37% yield): $^1$H NMR (300 MHz, DMSO-$d_6$) δ 10.02 (br s, 1H), 7.85 (s, 1H), 7.67 (d, J=2.0 Hz, 1H), 7.60 (dd, J=8.4, 2.0 Hz, 1H), 7.34-7.16 (m, 5H), 4.21 (s, 2H), 4.15-4.03 (m, 1H), 3.42-3.31 (m, 1H), 3.27-2.97 (m, 5H), 2.26 (s, 3H), 2.12-1.99 (m, 1H), 1.92-1.78 (m, 1H), 0.77 (t, J=6.6 Hz, 3H); MS (ES+) m/z 492.1 (M+1), 494.1 (M+1).

Example 38

Synthesis of (S)-4-((1-benzylpyrrolidin-3-yl)(methyl)amino)-5-chloro-2-fluoro-N-(thiazol-4-yl)benzenesulfonamide 2,2,2-trifluoroacetate

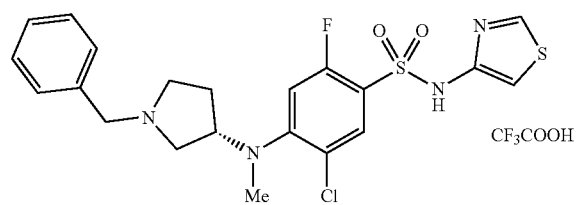 [SMILES: CN(c1cc(F)c(S(=O)(=O)Nc2cscn2)cc1Cl)[C@H]1CCN(Cc2ccccc2)C1 ; "CF3COOH"]

Step 1. Preparation of tert-butyl ((5-chloro-2,4-difluorophenyl)sulfonyl)(thiazol-4-yl)carbamate

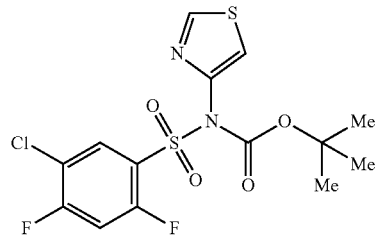 [SMILES: CC(C)(C)OC(=O)N(c1cscn1)S(=O)(=O)c1cc(Cl)c(F)cc1F]

To a solution of tert-butyl thiazol-4-ylcarbamate (160.0 g, 799.0 mmol) in anhydrous tetrahydrofuran (1500 mL) was added lithium bis(trimethylsilyl)amide (1 M solution in tetrahydron, 1120 mL) at −78° C. The reaction mixture was warmed to 5° C., stirred for 30 minutes, and cooled to −78° C. To it was then added dropwise a solution of 5-chloro-2,4-difluorobenzenesulfonyl chloride (355.3 g, 1440 mmol) in anhydrous tetrahydrofuran (500 mL) at −78° C. The reaction mixture was allowed to warm to ambient temperature and stirred for 12h. To it was then added saturated ammonium chloride (200 mL), and the mixture was extracted with ethyl acetate (3×1000 mL).

The combined organic phase was washed with brine (3×1000 mL), dried over anhydrous sodium sulfate, and filtered. Concentration of the filtrate in vacuo and trituration of the residue with methanol (500 mL) provided the title compound as a colorless solid (220.0 g, 67% yield): $^1$H NMR (400 MHz, DMSO-$d_6$) δ 9.14 (d, J=2.2 Hz, 1H), 8.25 (t, J=7.6 Hz, 1H), 8.06-7.94 (m, 2H), 1.28 (s, 9H); MS (ES+) m/z 310.8 (M−99), 312.8 (M−99).

Step 2. Preparation of (S)-4-((1-benzylpyrrolidin-3-yl)(methyl)amino)-5-chloro-2-fluoro-N-(thiazol-4-yl)benzenesulfonamide 2,2,2-trifluoroacetate

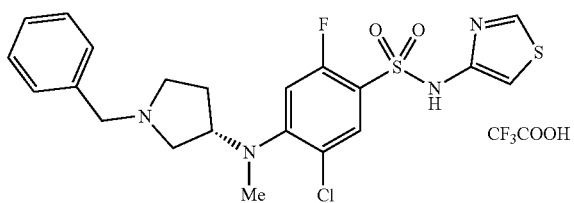 [SMILES: CN(c1cc(F)c(S(=O)(=O)Nc2cscn2)cc1Cl)[C@H]1CCN(Cc2ccccc2)C1 ; "CF3COOH"]

To a mixture of tert-butyl ((5-chloro-2,4-difluorophenyl)sulfonyl)(thiazol-4-yl)carbamate (prepared according to WO2010079443, 0.28 g, 0.67 mmol) in anhydrous dimethyl sulfoxide (3 mL) was added (S)-1-benzyl-N-methylpyrrolidin-3-amine (0.26 g, 1.34 mmol) and the reaction mixture was heated to 80° C. in a sealed tube for 30 minutes. The reaction mixture was diluted with ethyl acetate (50 mL), washed with saturated ammonium chloride (30 mL), brine (30 mL), dried over anhydrous sodium sulfate, and filtered. The filtrate was concentrated in vacuo. The obtained residue was dissolved in dichloromethane (10 mL) and trifluoroacetic acid (5 mL) was added to it. The reaction mixture was stirred at ambient temperature for 20 minutes and concentrated in vacuo. Purification of the residue by preparative reverse-phase HPLC, eluting with a gradient of 10 to 50% of acetonitrile in water containing 0.1% of trifluoroacetic acid, provided the title compound as a colorless solid (0.125 g, 39% yield): $^1$H NMR (300 MHz, DMSO-d$_6$) δ 11.36 (br s, 1H), 10.61 (br s, 0.5H), 10.35 (br s, 0.5H), 8.87 (d, J=2.2 Hz, 1H), 7.71 (d, J=7.6 Hz, 1H), 7.51-7.38 (m, 5H), 7.21-7.13 (m, 1H), 7.04 (d, J=2.2 Hz, 1H), 4.61-4.20 (m, 3H), 3.61-3.01 (m, 4H), 2.73 (d, J=20.0 Hz, 3H), 2.17-1.89 (m, 2H); MS (ES+) m/z 481.1 (M+1), 483.1 (M+1).

Example 39

Synthesis of (S)-4-((1-benzylpyrrolidin-3-yl)(methyl)amino)-5-chloro-2-fluoro-N-(thiazol-2-yl)benzenesulfonamide bis(trifluoroacetic acid) Salt

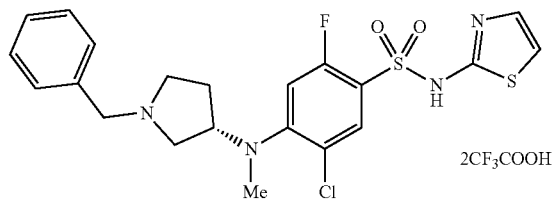 [SMILES: CN(c1cc(F)c(S(=O)(=O)Nc2nccs2)cc1Cl)[C@H]1CCN(Cc2ccccc2)C1 ; "2CF3COOH"]

Following the procedure as described for EXAMPLE 38, STEP 2 and making non-critical variations as required to replace tert-butyl ((5-chloro-2,4-difluorophenyl)sulfonyl)(thiazol-4-yl)carbamate with 5-chloro-N-(2,4-dimethoxybenzyl)-2,4-difluoro-N-(thiazol-2-yl)benzenesulfonamide, and purification by column chromatography eluting with 0 to 20% of methanol (containing 0.2% of ammonium hydroxide) in dichloromethane, the title compound was obtained as a colorless solid (0.40 g, 56% yield): $^1$H NMR (300 MHz, DMSO-d$_6$) δ 12.93 (br s, 1H), 10.98 (br s, 1H), 7.73 (d, J=7.4 Hz, 1H), 7.53-7.44 (m, 5H), 7.32 (d, J=4.6 Hz, 1H), 7.21 (d, J=11.9 Hz, 1H), 6.89 (d, J=4.6 Hz, 1H), 4.40-4.33 (m, 2H), 3.79-3.69 (m, 2H), 3.57-3.49 (m, 1H), 3.37-3.29 (m, 2H), 2.75 (s, 3H), 2.17-2.07 (m, 2H), one exchangeable proton not observed; $^{19}$F NMR (282 MHz, DMSO-d$_6$) δ −73.65 (s, 6F), −109.18 (s, 1F); MS (ES+) m/z 481.1 (M+1), 483.0 (M+1).

Example 40

Synthesis of (S)-4-((1-benzylpyrrolidin-3-yl)(methyl)amino)-5-chloro-2-fluoro-N-(6-fluoropyridin-2-yl)benzenesulfonamide bis(trifluoroacetic acid) Salt

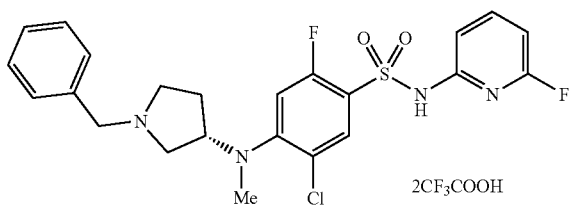 [SMILES: CN(c1cc(F)c(S(=O)(=O)Nc2cccc(F)n2)cc1Cl)[C@H]1CCN(Cc2ccccc2)C1 ; "2CF3COOH"]

Step 1. Preparation of 5-chloro-N-(2,4-dimethoxybenzyl)-2,4-difluoro-N-(6-fluoropyridin-2-yl)benzenesulfonamide

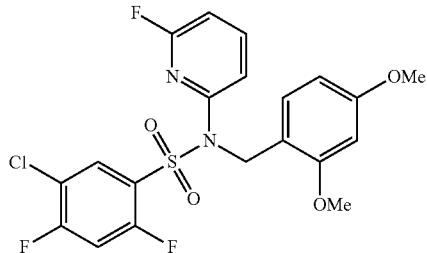 [SMILES: COc1ccc(CN(c2cccc(F)n2)S(=O)(=O)c2cc(Cl)c(F)cc2F)c(OC)c1]

To a solution of N-(2,4-dimethoxybenzyl)-6-fluoropyridin-2-amine (prepared according to WO2014066490, 20.00 g, 76.25 mmol) in anhydrous tetrahydrofuran (200 mL) was added a 1.6 M solution of methyl lithium in diethyl ether (66.7 mL, 106.7 mmol) dropwise at −78° C. The reaction mixture was allowed to warm to 0° C. and stirred for 30 minutes. The reaction mixture was cooled to −78° C. and a solution of 5-chloro-2,4-difluorobenzenesulfonyl chloride (33.9 g, 137.3 mmol) in anhydrous tetrahydrofuran (100 mL) was added dropwise to it. The reaction mixture was allowed to warm to ambient temperature and stirred for 12 h. The mixture was diluted with water (200 mL) and extracted with ethyl acetate (3×200 mL). The combined organic phase was washed with brine (50 mL), dried over anhydrous sodium sulfate, and filtered. Concentration of the filtrate in vacuo and trituration of the residue in a mixture of methanol and dichloromethane (20:1, 2×150 mL) provided the title compound as a colorless solid (12.1 g, 32% yield): $^1$H NMR (300 MHz, CDCl$_3$) δ 8.02 (t, J=8.0 Hz, 1H), 7.77-7.66 (m, 1H), 7.27-7.15 (m, 2H), 7.01 (t, J=8.0 Hz, 1H), 6.72 (dd, J=8.0, 2.8 Hz, 1H), 6.43-6.35 (m, 2H), 5.07 (s, 2H), 3.78 (s, 3H), 3.73 (s, 3H).

Step 2. Preparation of (S)-4-((1-benzylpyrrolidin-3-yl)(methyl)amino)-5-chloro-2-fluoro-N-(thiazol-2-yl)benzenesulfonamide bis(trifluoroacetic acid) Salt

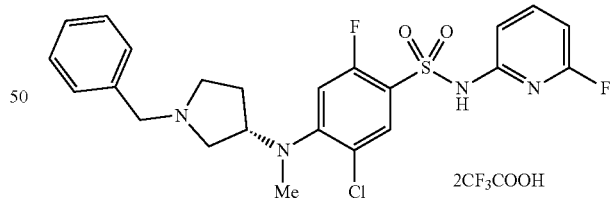

Following the procedure as described for EXAMPLE 38, STEP 2 and making non-critical variations as required to replace tert-butyl ((5-chloro-2,4-difluorophenyl)sulfonyl)(thiazol-4-yl)carbamate with 5-chloro-N-(2,4-dimethoxybenzyl)-2,4-difluoro-N-(6-fluoropyridin-2-yl)benzenesulfonamide, and purification by flash chromatography (0 to 20% methanol (+0.2% of ammonium hydroxide) in dichloromethane), the title compound was obtained as a colorless solid (0.40 g, 56% yield): $^1$H NMR (300 MHz, DMSO-d$_6$) δ 11.75 (br s, 1H), 10.63 (br s, 1H), 7.92-7.83 (m, 2H), 7.53-7.44 (m, 5H), 7.19 (d, J=12.4 Hz, 1H), 6.90 (dd, J=7.9, 2.1 Hz, 1H), 6.75 (dd, J=8.0, 2.5 Hz, 1H), 4.53-4.32 (m, 3H), 3.58-3.51 (m, 2H), 3.42-3.27 (m, 2H), 2.78 (s, 3H), 2.21-2.07 (m, 2H), one exchangeable proton not observed; $^{19}$F NMR (282 MHz, DMSO-$d_6$) δ −69.00 (s, 1F), −73.61 (s, 6F), −110.18 (s, 1F); MS (ES+) m/z 493.1 (M+1), 495.1 (M+1).

Example 41

Synthesis of (S)-4-((1-benzylpyrrolidin-3-yl)(methyl)amino)-3-chloro-N-(thiazol-4-yl)benzenesulfonamide 2,2,2-trifluoroacetate

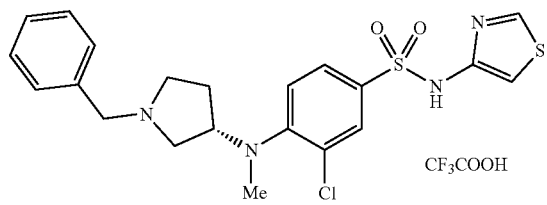 [SMILES: CN(c1ccc(S(=O)(=O)Nc2cscn2)cc1Cl)[C@H]1CCN(Cc2ccccc2)C1 ; "CF3COOH"]

Step 1. Preparation of tert-butyl ((3-chloro-4-fluorophenyl)sulfonyl)(thiazol-5-yl)carbamate

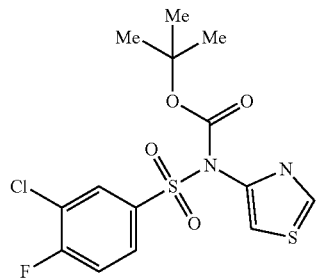

To a solution of tert-butyl thiazol-4-ylcarbamate (8.87 g, 44.3 mmol) in anhydrous tetrahydrofuran (220 mL) was added a 1 M solution of lithium bis(trimethylsilyl)amide in tetrahydrofuran (48.7 mL, 48.7 mmol) at −78° C. The reaction mixture was allowed to warm to ambient temperature and stirred for 1 h. The reaction mixture was cooled to −78° C., and a solution of 3-chloro-4-fluorobenzenesulfonyl chloride (6.93 mL, 48.7 mmol) in anhydrous tetrahydrofuran (17 mL) was added to it. The reaction mixture was allowed to warm to ambient temperature and stirred for 3 h. The mixture was diluted with ethyl acetate (350 mL), washed with saturated ammonium chloride (2×200 mL), brine (2×150 mL), dried over anhydrous sodium sulfate, and filtered. Concentration of the filtrate in vacuo and purification of the residue by column chromatography eluting with a gradient of 0 to 100% of ethyl acetate in hexanes provided the title compound as a colorless solid (13.9 g, 80% yield): $^1$H NMR (300 MHz, CDCl$_3$) δ 8.83-8.81 (m, 1H), 8.30-8.25 (m, 1H), 8.14-8.07 (m, 1H), 7.58-7.55 (m, 1H), 7.39-7.28 (m, 1H), 1.38 (s, 9H); MS (ES+) m/z 393.0 (M+1), 395.0 (M+1).

Step 2. Preparation of (S)-4-((1-benzylpyrrolidin-3-yl)(methyl)amino)-3-chloro-N-(thiazol-4-yl)benzenesulfonamide 2,2,2-trifluoroacetate

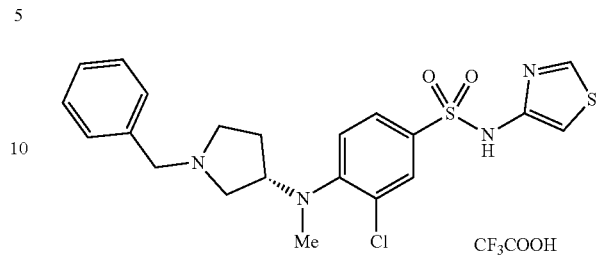

Following the procedure as described for EXAMPLE 38, STEP 2 and making non-critical variations as required to replace tert-butyl ((5-chloro-2,4-difluorophenyl)sulfonyl)(thiazol-4-yl)carbamate with tert-butyl ((3-chloro-4-fluorophenyl)sulfonyl)(thiazol-5-yl)carbamate, the title compound was obtained as a colorless solid (0.40 g, 56% yield): $^1$H NMR (300 MHz, CD$_3$OD) δ 8.71 (d, J=2.2 Hz, 1H), 7.87 (d, J=0.6 Hz, 1H), 7.72 (dd, J=8.5, 2.2 Hz, 1H), 7.51-7.44 (m, 5H), 7.07 (d, J=2.2 Hz, 1H), 4.43-4.40 (m, 2H), 4.38-4.28 (m, 2H), 3.64-3.38 (m, 4H), 2.79-2.77 (m, 3H), 2.35-2.10 (m, 2H), NH and COOH not observed; MS (ES+) m/z 463.1 (M+1), 465.1 (M+1).

Example 42

Synthesis of 3-chloro-4-(methyl((S)-1-((S)-1-phenylethyl)pyrrolidin-3-yl)amino)-N-(thiazol-2-yl)benzenesulfonamide

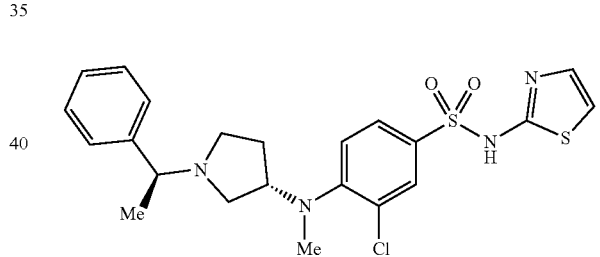

Step 1. Preparation of (S)-2-((tert-butoxycarbonyl)amino)butane-1,4-diyl dimethanesulfonate

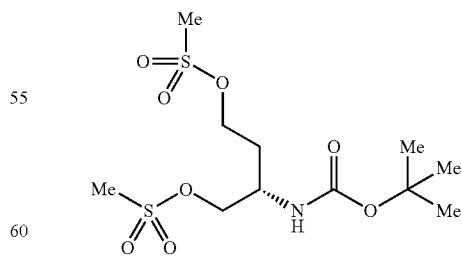

To a solution of tert-butyl (S)-(1,4-dihydroxybutan-2-yl)carbamate (5.0 g, 24.36 mmol) and triethylamine (17.0 mL, 121.8 mmol) in anhydrous dichloromethane (120 mL) was added methanesulfonyl chloride (4.15 mL, 53.59 mmol) at 0° C. The reaction mixture was stirred at for 1 h at 0° C. and then quenched by addition of water (50 mL) and saturated ammonium chloride (120 mL). The aqueous layer was extracted with dichloromethane (100 mL), and the combined organic layers were washed with brine (50 mL), dried over anhydrous sodium sulfate, and filtered. Concentration of the filtrate in vacuo provided the title compound as a colorless solid (8.70 g, 99% yield): $^1$H NMR (300 MHz, DMSO-$d_6$) δ 7.08 (d, J=8.4 Hz, 1H), 4.26-4.06 (m, 4H), 3.18 (s, 3H), 3.16 (s, 3H), 1.97-1.86 (m, 1H), 1.83-1.71 (m, 1H), 1.39 (s, 9H), NH not observed; MS (ES+) m/z 362.1 (M+1).

Step 2. Preparation of tert-butyl ((S)-1-((S)-1-phenylethyl)pyrrolidin-3-yl)carbamate

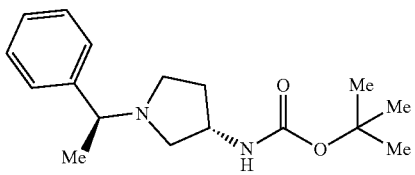 [SMILES: C[C@@H](c1ccccc1)N1CC[C@H](NC(=O)OC(C)(C)C)C1]

To a mixture of (S)-2-((tert-butoxycarbonyl)amino)butane-1,4-diyl dimethanesulfonate (2.63 g, 7.28 mmol) and N,N-diisopropylethylamine (6.34 mL, 36.4 mmol) in anhydrous dimethyl sulfoxide (12 mL) was added (S)-1-phenylethan-1-amine (0.93 mL, 7.28 mmol) and the reaction mixture was heated to 40° C. in a sealed tube for 18 h. The reaction mixture was diluted with ethyl acetate (130 mL), washed with saturated ammonium chloride (3×100 mL), brine (50 mL), dried over anhydrous sodium sulfate, and filtered. Concentration of the filtrate in vacuo and purification of the residue by column chromatography, eluting with 5% of methanol (containing 0.2% of ammonium hydroxide) in dichloromethane provided the title compound as a colorless solid (0.76 g, 36% yield): $^1$H NMR (300 MHz, CDCl$_3$) δ 7.36-7.25 (m, 5H), 4.86-4.81 (m, 1H), 4.18-4.07 (m, 1H), 3.22 (q, J=6.6 Hz, 1H), 2.97-2.88 (m, 1H), 2.57 (dd, J=9.9, 6.6 Hz, 1H), 2.36-2.20 (m, 3H), 1.71-1.57 (m, 1H), 1.43 (s, 9H), 1.39 (d, J=6.6 Hz, 3H); MS (ES+) m/z 291.2 (M+1).

Step 3. Preparation of (S)—N-methyl-1-((S)-1-phenylethyl)pyrrolidin-3-amine

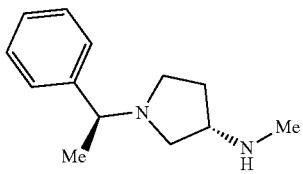 [SMILES: CN[C@H]1CCN([C@@H](C)c2ccccc2)C1]

To a solution of tert-butyl ((S)-1-((S)-1-phenylethyl)pyrrolidin-3-yl)carbamate (0.76 g, 2.62 mmol) in anhydrous tetrahydrofuran (40 mL) was added a 1.0 M solution of lithium aluminum hydride in tetrahydrofuran (5.24 mL, 5.24 mmol) and the reaction mixture was heated to reflux for 4 h. The reaction mixture was cooled to 0° C. and quenched by slow addition of 2.0 M sodium hydroxide (50 mL). The mixture was extracted with diethyl ether (2×60 mL). The combined organic phase was washed with 2.0 M sodium hydroxide (20 mL), brine (3×20 mL), dried over anhydrous sodium sulfate, and filtered. Concentration of the filtrate in vacuo provided the title compound as a colorless oil (0.46 g, 85% yield): $^1$H NMR (300 MHz, CDCl$_3$) δ 7.36-7.20 (m, 5H), 3.24-3.14 (m, 2H), 2.78-2.65 (m, 2H), 2.40-2.32 (m, 4H), 2.27 (dt, J=9.6, 4.5 Hz, 1H), 2.14-1.99 (m, 1H), 1.62-1.45 (m, 2H), 1.38 (d, J=6.6 Hz, 3H); MS (ES+) m/z 205.2 (M+1).

Step 4. Preparation of Synthesis of 3-chloro-4-(methyl((S)-1-((S)-1-phenylethyl)pyrrolidin-3-yl)amino)-N-(thiazol-2-yl)benzenesulfonamide

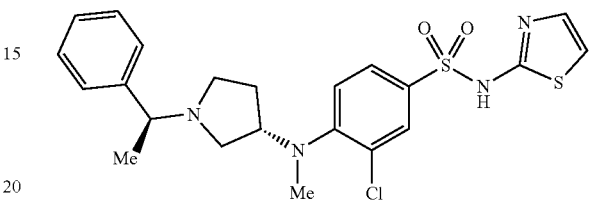

To a mixture of 3-chloro-N-(2,4-dimethoxybenzyl)-4-fluoro-N-(thiazol-2-yl)benzenesulfonamide (0.22 g, 0.50 mmol) and (S)—N-methyl-1-((S)-1-phenylethyl)pyrrolidin-3-amine (0.10 g, 0.5 mmol) in anhydrous dimethyl sulfoxide (5 mL) was added potassium carbonate (0.14 g, 1.0 mmol) and the reaction mixture was at 80° C. for 18 h. The reaction mixture was allowed to cool to ambient temperature and diluted with ethyl acetate (50 mL). The mixture washed with saturated ammonium chloride (50 mL), brine (30 mL), dried over anhydrous sodium sulfate, and filtered.

Concentration of the filtrate in vacuo provided a residue, which was dissolved in dichloromethane (20 mL). To it was added trifluoroacetic acid (8 mL) and the mixture was stirred at ambient temperature for 1 h. The mixture was concentrated in vacuo and methanol (20 mL) was added to it. Filtration and concentration of the filtrate in vacuo provided a residue, which was purified by column chromatography, eluting with 5% of methanol (containing 0.2% of ammonium hydroxide) in dichloromethane to afford the title compound as a colorless solid (0.07 g, 29% yield): $^1$H NMR (300 MHz, DMSO-$d_6$) δ 12.13 (br s, 1H), 7.68 (d, J=2.2 Hz, 1H), 7.63 (dd, J=8.5, 2.2 Hz, 1H), 7.44-7.31 (m, 5H), 7.27 (d, J=4.6 Hz, 1H), 7.23 (d, J=8.5 Hz, 1H), 6.84 (d, J=4.6 Hz, 1H), 4.20-4.10 (m, 1H), 3.81-3.75 (m, 2H), 3.08-3.03 (m, 2H), 2.78-2.69 (m, 4H), 2.06-2.01 (m, 1H), 1.95-1.84 (m, 1H), 1.43 (d, J=6.6 Hz, 3H); MS (ES+) m/z 477.1 (M+1), 479.1 (M+1).

Example 43

Synthesis of 3-chloro-2-fluoro-N-(6-fluoropyridin-2-yl)-4-(((S)-1-((S)-1-phenylethyl)pyrrolidin-3-yl)amino)benzenesulfonamide 2,2,2-trifluoroacetate

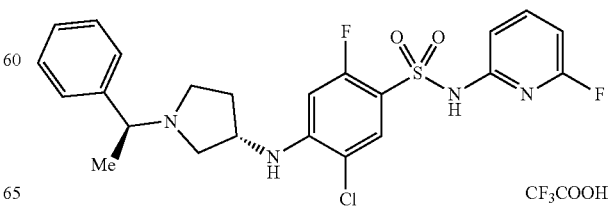

Following the procedure as described for EXAMPLE 42, Step 4 and making non-critical variations as required to replace 5-chloro-N-(2,4-dimethoxybenzyl)-2,4-difluoro-N-(thiazol-2-yl)benzenesulfonamide with 5-chloro-N-(2,4-dimethoxybenzyl)-2,4-difluoro-N-(6-fluoropyridin-2-yl)benzenesulfonamide, and purification by preparative reverse-phase HPLC, eluting with a gradient of 10 to 50% of acetonitrile in water containing 0.1% of trifluoroacetic acid, the title compound was obtained as a colorless solid (0.11 g, 43% yield): ¹H NMR (300 MHz, CD₃OD) δ 8.01-7.98 (m, 1H), 7.76 (dd, J=8.1, 8.1 Hz, 1H), 7.51-7.46 (m, 5H), 7.09-7.06 (m, 1H), 6.92 (dd, J=7.9, 1.9 Hz, 1H), 6.61 (dd, J=8.1, 2.6 Hz, 1H), 4.47-4.40 (m, 2H), 4.07-3.85 (m, 1H), 3.26-3.07 (m, 1H), 2.86-2.72 (m, 3H), 2.34-2.10 (m, 2H), 1.72 (d, J=6.8 Hz, 3H), NH and COOH not observed; MS (ES+) m/z 507.1 (M+1), 509.1 (M+1).

Example 44

Synthesis of 3-chloro-4-(methyl((S)-1-((R)-1-phenylethyl)pyrrolidin-3-yl)amino)-N-(thiazol-2-yl)benzenesulfonamide

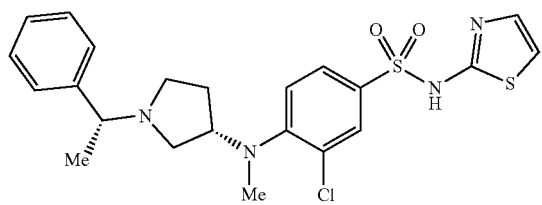 [SMILES: C[C@H](c1ccccc1)N1CC[C@H](N(C)c2ccc(S(=O)(=O)Nc3nccs3)cc2Cl)C1]

Step 1. Preparation of tert-butyl ((S)-1-((R)-1-phenylethyl)pyrrolidin-3-yl)carbamate

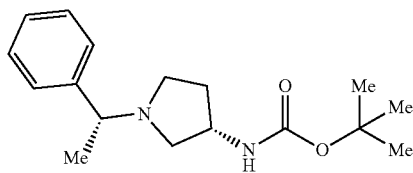 [SMILES: C[C@H](c1ccccc1)N1CC[C@H](NC(=O)OC(C)(C)C)C1]

Following the procedure as described for EXAMPLE 42, Step 2 and making non-critical variations as required to replace (S)-1-phenylethan-1-amine with (R)-1-phenylethan-1-amine, the title compound was obtained as a colorless solid (1.39 g, 66% yield): ¹H NMR (300 MHz, CDCl₃) δ 7.35-7.23 (m, 5H), 4.96-4.79 (m, 1H), 4.39-4.26 (m, 1H), 4.22-4.06 (m, 1H), 3.26-3.19 (m, 1H), 2.69-2.54 (m, 2H), 2.31-2.18 (m, 1H), 2.10-1.98 (m, 1H), 1.59-1.52 (m, 1H), 1.45 (s, 9H), 1.38 (d, J=6.5 Hz, 3H); MS (ES+) m/z 291.2 (M+1).

Step 2. Preparation of (S)—N-methyl-1-((R)-1-phenylethyl)pyrrolidin-3-amine

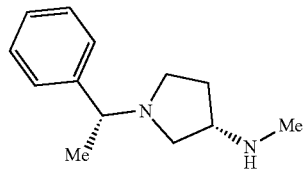 [SMILES: CN[C@H]1CCN([C@H](C)c2ccccc2)C1]

Following the procedure as described for EXAMPLE 42, Step 2 and making non-critical variations as required to replace tert-butyl ((S)-1-((S)-1-phenylethyl)-pyrrolidin-3-yl)carbamate with tert-butyl ((S)-1-((R)-1-phenylethyl)pyrrolidin-3-yl)carbamate, the title compound was obtained as a colorless oil (0.63 g, 64% yield): ¹H NMR (300 MHz, CDCl₃) δ 87.35-7.24 (m, 5H), 3.23-3.12 (m, 2H), 2.64-2.45 (m, 4H), 2.35 (s, 3H), 2.16-2.05 (m, 2H), 1.58-1.46 (m, 1H), 1.38 (d, J=6.6 Hz, 3H); MS (ES+) m/z 205.2 (M+1).

Step 3. Preparation of 3-chloro-4-(methyl((S)-1-((R)-1-phenylethyl)pyrrolidin-3-yl)amino)-N-(thiazol-2-yl)benzenesulfonamide

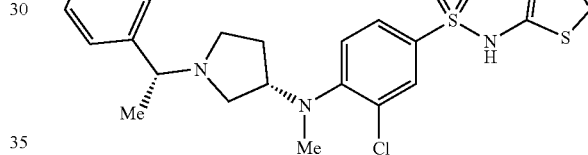

Following the procedure as described for EXAMPLE 42, Step 4 and making non-critical variations as required to replace (S)—N-methyl-1-((S)-1-phenylethyl)pyrrolidin-3-amine with (S)—N-methyl-1-((R)-1-phenylethyl)pyrrolidin-3-amine, the title compound was obtained as a colorless solid (0.11 g, 46% yield): ¹H NMR (300 MHz, DMSO-d₆) δ 12.03 (br s, 1H), 7.71 (d, J=2.2 Hz, 1H), 7.65 (dd, J=8.5, 2.2 Hz, 1H), 7.51-7.40 (m, 5H), 7.31-7.28 (m, 2H), 6.85 (d, J=4.6 Hz, 1H), 4.39-4.21 (m, 2H), 3.45-3.38 (m, 1H), 3.33-3.26 (m, 2H), 3.10-3.02 (m, 1H), 2.72 (s, 3H), 2.10-2.02 (m, 2H), 1.59 (d, J=6.7 Hz, 3H); MS (ES+) m/z 477.1 (M+1), 479.1 (M+1).

Example 45

Synthesis of 5-chloro-2-fluoro-N-(6-fluoropyridin-2-yl)-4-(methyl((S)-1-((R)-1-phenylethyl)pyrrolidin-3-yl)amino)benzenesulfonamide 2,2,2-trifluoroacetate

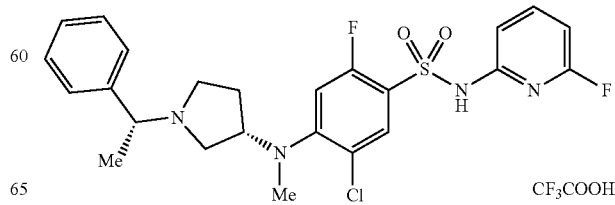

To a mixture of 5-chloro-N-(2,4-dimethoxybenzyl)-2,4-difluoro-N-(6-fluoropyridin-2-yl)benzenesulfonamide (0.22 g, 0.5 mmol) and (S)—N-methyl-1-((S)-1-phenylethyl)pyrrolidin-3-amine (0.10 g, 0.5 mmol) in anhydrous dimethyl sulfoxide (5 mL) was added potassium carbonate (0.14 g, 1.0 mmol) and the reaction mixture was headed at 80° C. for 18 h. The reaction mixture was allowed to cool to ambient temperature and diluted with ethyl acetate (50 mL). The mixture was washed with saturated ammonium chloride (50 mL), brine (30 mL), dried over anhydrous sodium sulfate, and filtered. Concentration of the filtrate in vacuo and purification of the residue by preparative reverse-phase HPLC eluting with a gradient of 10 to 50% of acetonitrile in water (containing 0.1% of trifluoroacetic acid) provided the title compound as a colorless solid (0.10 g, 39% yield): $^1$H NMR (300 MHz, CD$_3$OD) δ 8.02 (d, J=7.4 Hz, 1H), 7.78 (dd, J=8.1, 8.1 Hz, 1H), 7.48-7.43 (m, 5H), 7.13-7.05 (m, 1H), 6.94 (dd, J=7.9, 2.0 Hz, 1H), 6.63 (dd, J=8.1, 2.6 Hz, 1H), 4.57-4.28 (m, 2H), 3.89-3.44 (m, 2H), 3.15-3.03 (m, 2H), 2.85-2.74 (m, 3H), 2.31-2.09 (m, 2H), 1.74 (d, J=6.8 Hz, 3H), NH and COOH not observed; MS (ES+) m/z 507.1 (M+1), 509.1 (M+1).

Example 46

Synthesis of 4-((1-benzylpiperidin-4-yl)amino)-3-chloro-N-(1,2,4-thiadiazol-5-yl)benzenesulfonamide 2,2,2-trifluoroacetate

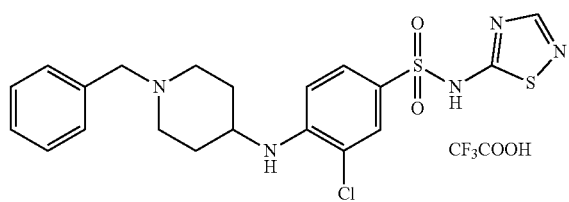 [SMILES: O=S(=O)(Nc1ncns1)c1ccc(NC2CCN(Cc3ccccc3)CC2)c(Cl)c1 ; "CF3COOH"]

Step 1. Preparation of 4-((1-benzylpiperidin-4-yl)amino)-3-chloro-N-(2,4-dimethoxybenzyl)-N-(1,2,4-thiadiazol-5-yl)benzenesulfonamide

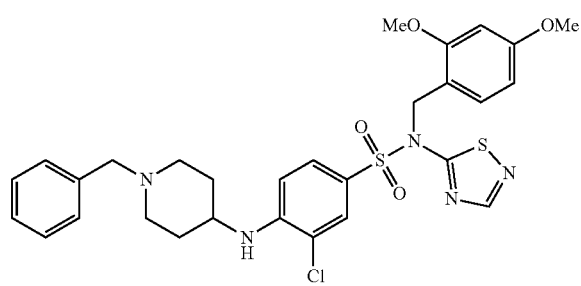 [SMILES: COc1ccc(CN(c2ncns2)S(=O)(=O)c2ccc(NC3CCN(Cc4ccccc4)CC3)c(Cl)c2)c(OC)c1]

To a solution of 3-chloro-N-(2,4-dimethoxybenzyl)-4-fluoro-N-(1,2,4-thiadiazol-5-yl)benzenesulfonamide (0.20 g, 0.45 mmol) and 1-benzylpiperidin-4-amine (0.09 mL, 0.45 mmol) in anhydrous dimethyl sulfoxide (1.8 mL) was added potassium carbonate (0.149 g, 1.1 mmol) and the reaction mixture was stirred at ambient temperature for 17 h. The mixture was diluted with ethyl acetate (5 mL) and water (5 mL) and the aqueous phase was extracted with ethyl acetate (2×5 mL). The combined organic extracts were washed with brine (2×5 mL), dried over anhydrous magnesium sulfate, filtered and the filtrate concentrated in vacuo. Purification of the residue by column chromatography eluting with a gradient of 30 to 50% of ethyl acetate in hexanes followed by 5% of methanol in dichloromethane afforded the title compound as a colorless oil (0.158 g, 57% yield): $^1$H NMR (300 MHz, CDCl$_3$) δ 8.13 (s, 1H), 7.57-7.50 (m, 2H), 7.38-7.25 (m, 5H), 7.03 (d, J=9.1 Hz, 1H), 6.53 (d, J=8.5 Hz, 1H), 6.36-6.29 (m, 2H), 5.18 (s, 2H), 4.83 (d, J=7.7 Hz, 1H), 3.75 (s, 3H), 3.73 (s, 3H), 3.53 (s, 2H), 3.45-3.29 (m, 1H), 2.90-2.78 (m, 2H), 2.25-2.11 (m, 2H), 2.05-1.94 (m, 2H), 1.65-1.50 (m, 2H); MS (ES+) m/z 614.2 (M+1), 616.2 (M+1).

Step 2. Preparation of 4-((1-benzylpiperidin-4-yl)amino)-3-chloro-N-(1,2,4-thiadiazol-5-yl)benzenesulfonamide 2,2,2-trifluoroacetate

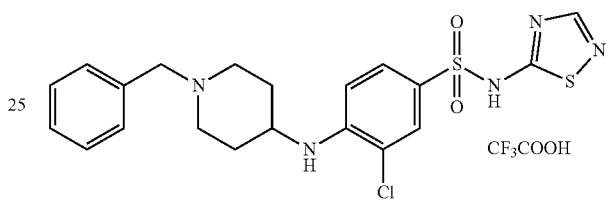

To a solution of 4-((1-benzylpiperidin-4-yl)amino)-3-chloro-N-(2,4-dimethoxybenzyl)-N-(1,2,4-thiadiazol-5-yl)benzenesulfonamide (0.158 g, 0.26 mmol) in dichloromethane (4 mL) was added trifluoroacetic acid (0.5 mL, 7 mmol) and the reaction mixture was stirred at ambient temperature for 15 minutes. The reaction mixture was concentrated in vacuo and methanol (4 mL) was added to the residue. The resulting mixture was filtered and the filtrate concentrated in vacuo to provide the title compound as a colorless solid (0.100 g, 68% yield): $^1$H NMR (300 MHz, DMSO-d$_6$) δ 9.68 (br s, 1H), 8.45 (s, 1H), 7.69-7.43 (m, 7H), 6.93 (d, J=8.9 Hz, 1H), 6.02 (d, J=7.6 Hz, 1H), 4.31 (s, 2H), 3.63 (br s, 1H), 3.44 (d, J=11.7 Hz, 2H), 3.13-2.95 (m, 2H), 2.15-2.01 (m, 2H), 1.87-1.67 (m, 2H), NH not observed; MS (ES+) m/z 464.0 (M+1), 466.0 (M+1).

Example 47

Synthesis of 4-((1-benzylpiperidin-4-yl)oxy)-5-chloro-2-fluoro-N-(thiazol-2-yl)benzenesulfonamide 2,2,2-trifluoroacetate

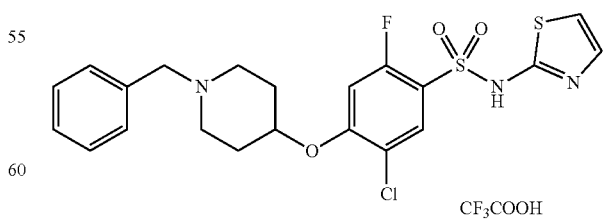

To a solution of 1-benzylpiperidin-4-ol (0.21 g, 1.09 mmol) and 5-chloro-N-(2,4-dimethoxybenzyl)-2,4-difluoro-N-(thiazol-2-yl)benzenesulfonamide (0.50 g, 1.09 mmol) in dimethyl sulfoxide (4.4 mL) was added cesium carbonate (0.86 g, 2.64 mmol) and the reaction mixture was stirred at ambient temperature for 17 h. The mixture was diluted with ethyl acetate (10 mL) and water (10 mL), and the aqueous phase was extracted with ethyl acetate (2×10 mL). The combined organic extracts were washed with brine (2×10 mL), dried over anhydrous magnesium sulfate, filtered, and the filtrate concentrated in vacuo. The residue was dissolved in dichloromethane (12 mL) and trifluoroacetic acid (2.0 mL, 26 mmol) was added to it. The reaction mixture was stirred at ambient temperature for 10 minutes and then concentrated in vacuo. The residue was triturated in methanol (7 mL), and the obtained suspension filtered. Concentration of the filtrate in vacuo and purification of the residue by column chromatography eluting with 0 to 10% of methanol in dichloromethane afforded the title compound as a colorless solid (0.27 g, 41% yield): $^1$H NMR (300 MHz, DMSO-$d_6$) δ 12.86 (br s, 1H), 10.13 (br s, 1H), 7.77 (d, J=7.1 Hz, 1H), 7.59-7.38 (m, 6H), 7.32 (d, J=3.7 Hz, 1H), 6.89 (d, J=3.7 Hz, 1H), 4.86 (br s, 1H), 4.37 (s, 2H), 3.19 (br s, 4H), 2.09 (br s, 4H); MS (ES+) m/z 482.0 (M+1), 484.0 (M+1).

Example 48

Synthesis of 3-chloro-4-((1-(4-methoxybenzyl)piperidin-4-yl)oxy)-N-(thiazol-2-yl)benzenesulfonamide

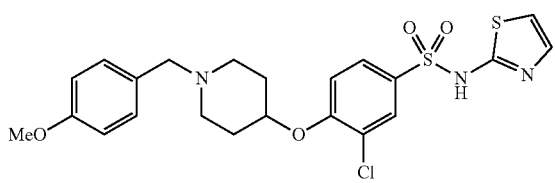 [SMILES: COc1ccc(CN2CCC(Oc3ccc(S(=O)(=O)Nc4nccs4)cc3Cl)CC2)cc1]

Following the procedure as described in Example 22, and making non-critical variations as required to replace 4-fluorobenzaldehyde with 4-methoxybenzaldehyde, and purification by column chromatography eluting with 0 to 20% of methanol, the title compound was obtained as a colorless solid (0.122 g, 40% yield): $^1$H NMR (300 MHz, DMSO-$d_6$) δ 12.01 (br s, 1H), 7.74 (d, J=2.3 Hz, 1H), 7.71-7.65 (m, 1H), 7.37-7.24 (m, 4H), 6.94 (s, 1H), 6.91 (s, 1H), 6.83 (d, J=4.6 Hz, 1H), 4.74-4.64 (m, 1H), 3.74 (s, 3H), 3.70 (s, 2H), 2.87-2.71 (m, 2H), 2.63-2.52 (m, 2H), 2.07-1.92 (m, 2H), 1.85-1.69 (m, 2H); MS (ES+) m/z 494.0 (M+1), 496.0 (M+1).

Example 49

Synthesis of 3-chloro-4-((1-(2,3-dihydro-1H-inden-1-yl)piperidin-4-yl)oxy)-N-(thiazol-2-yl)benzenesulfonamide 2,2,2-trifluoroacetate

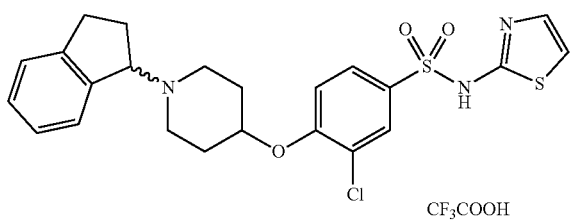 [SMILES: O=S(=O)(Nc1nccs1)c1ccc(OC2CCN(C3CCc4ccccc43)CC2)c(Cl)c1 ; "CF3COOH"]

Step 1. Preparation of 1-(2,3-dihydro-1H-inden-1-yl)piperidin-4-ol

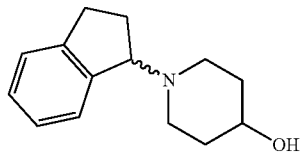 [SMILES: OC1CCN(C2CCc3ccccc32)CC1]

To a mixture of piperidin-4-ol (1.00 g, 9.90 mmol) and 2,3-dihydro-1H-inden-1-one (0.65 g, 4.9 mmol) in anhydrous tetrahydrofuran (40 mL) was added titanium(IV) isopropoxide (4.35 mL, 14.85 mmol) and the reaction mixture was heated to reflux for 4 h. The reaction mixture was allowed to cool to ambient temperature, sodium triacetoxyborohydride (4.20 g, 19.80 mmol) was added to it, and the reaction mixture was stirred at ambient temperature for 18 h. The reaction mixture was quenched by addition of 2.0 M sodium hydroxide (20 mL), and filtered. The filtrate was diluted with ethyl acetate (100 mL), washed with brine (3×60 mL), dried over anhydrous sodium sulfate, and filtered. Concentration of the filtrate in vacuo and purification of the residue by column chromatography eluting with a gradient of 0 to 20% of methanol (containing 0.2% of ammonium hydroxide) in dichloromethane provided the title compound as a clear oil (0.99 g, 93% yield): $^1$H NMR (300 MHz, CDCl$_3$) δ 7.43-7.37 (m, 1H), 7.24-7.20 (m, 3H), 4.44-4.38 (m, 1H), 3.74-3.67 (m, 1H), 2.99-2.78 (m, 3H), 2.72-2.66 (m, 1H), 2.41-2.33 (m, 2H), 2.16-2.07 (m, 2H), 1.98-1.91 (m, 2H), 1.69-1.55 (m, 3H); MS (ES+) m/z 218.2 (M+1).

Step 2. Preparation of 3-chloro-4-((1-(2,3-dihydro-1H-inden-1-yl)piperidin-4-yl)oxy)-N-(thiazol-2-yl) benzenesulfonamide 2,2,2-trifluoroacetate

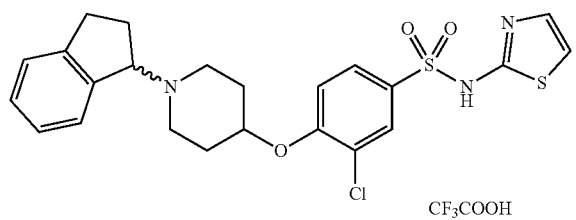 [SMILES: O=S(=O)(Nc1nccs1)c1ccc(OC2CCN(C3CCc4ccccc43)CC2)c(Cl)c1 ; "CF3COOH"]

To a mixture of 1-(2,3-dihydro-1H-inden-1-yl)piperidin-4-ol (0.33 g, 1.50 mmol) and 3-chloro-N-(2,4-dimethoxybenzyl)-4-fluoro-N-(thiazol-2-yl)benzenesulfonamide (0.44 g, 1.00 mmol) in anhydrous dimethyl sulfoxide (6 mL) was added cesium carbonate (0.49 g, 1.50 mmol) and the reaction mixture was stirred at ambient temperature for 18 h. The reaction mixture was diluted with ethyl acetate (80 mL), washed with brine (2×60 mL), dried over anhydrous sodium sulfate, and filtered.

Concentration of the filtrate in vacuo gave a residue which was dissolved in dichloromethane (20 mL). To this mixture was added trifluoroacetic acid (5 mL) and the reaction mixture was stirred at ambient temperature for 40 minutes. The mixture was concentrated in vacuo and the residue suspended in methanol (10 mL). Filtration and concentration of the filtrate gave a residue. The residue was purified by preparative reverse-phase HPLC eluting with a gradient of 10 to 50% of acetonitrile in water containing 0.1% of trifluoroacetic acid to provide the title compound as a colorless solid (0.04 g, 14% yield): ¹H NMR (300 MHz, CD₃OD) δ 7.82 (d, J=2.1 Hz, 1H), 7.78-7.70 (m, 1H), 7.62-7.56 (m, 1H), 7.47-7.30 (m, 3H), 7.23 (d, J=8.9 Hz, 1H), 7.08 (d, J=4.6 Hz, 1H), 6.70 (d, J=4.6 Hz, 1H), 5.03-4.93 (m, 2H), 3.62-3.44 (m, 1H), 3.39-3.31 (m, 1H), 3.26-3.12 (m, 2H), 3.09-2.94 (m, 2H), 2.68-2.32 (m, 3H), 2.29-2.03 (m, 3H), NH and COOH not observed; MS (ES+) m/z 490.0 (M+1), 492.0 (M+1).

Example 50

Synthesis of 4-((1-benzylazetidin-3-yl)amino)-3-chloro-N-(thiazol-2-yl)benzenesulfonamide 2,2,2-trifluoroacetate

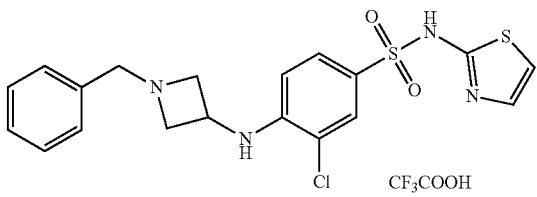 [SMILES: O=S(=O)(Nc1nccs1)c1ccc(NC2CN(Cc3ccccc3)C2)c(Cl)c1 ; "CF3COOH"]

Step 1. Preparation of tert-butyl 3-((2-chloro-4-(N-(2,4-dimethoxybenzyl)-N-(thiazol-2-yl)sulfamoyl)phenyl)amino)azetidine-1-carboxylate

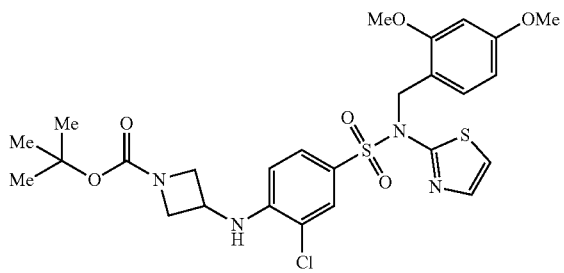 [SMILES: COc1ccc(CN(c2nccs2)S(=O)(=O)c2ccc(NC3CN(C(=O)OC(C)(C)C)C3)c(Cl)c2)c(OC)c1]

Following the procedure as described in Example 25, Step 1 and making non-critical variations as required to replace 3-amino-3-methyl-N-benzylazetidine with tert-butyl 3-aminoazetidine-1-carboxylate, the title compound was obtained as a colorless foam (1.3 g, 75% yield): ¹H NMR (300 MHz, CDCl₃) δ 7.70 (d, J=2.1 Hz, 1H), 7.60 (dd, J=8.7, 2.1 Hz, 1H), 7.42 (d, J=3.6 Hz, 1H), 7.19-7.16 (m, 1H), 7.02 (d, J=3.6 Hz, 1H), 6.39-6.36 (m, 3H), 5.12-5.10 (m, 1H), 5.06 (s, 2H), 4.40-4.34 (m, 2H), 4.29-4.25 (m, 1H), 3.85-3.79 (m, 2H), 3.78 (s, 3H), 3.75 (s, 3H), 1.47 (s, 9H).

Step 2. Preparation of 4-((1-benzylazetidin-3-yl)amino)-3-chloro-N-(thiazol-2-yl)benzenesulfonamide 2,2,2-trifluoroacetate

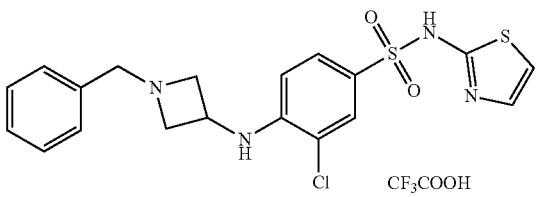 [SMILES: O=S(=O)(Nc1nccs1)c1ccc(NC2CN(Cc3ccccc3)C2)c(Cl)c1 ; "CF3COOH"]

To a solution of tert-butyl 3-((2-chloro-4-(N-(2,4-dimethoxybenzyl)-N-(thiazol-2-yl)sulfamoyl)phenyl)amino)azetidine-1-carboxylate (0.30 g, 0.504 mmol) in dichloromethane (6 mL) was added trifluoroacetic acid (3 mL) and the reaction mixture was stirred at ambient temperature for 1 h. The reaction mixture was concentrated in vacuo, the residue triturated in methanol (5 mL), and the obtained suspension filtered. The filtrate was concentrated in vacuo to provide an oil which was dissolved in tetrahydrofuran (2 mL). To this solution was added benzaldehyde (0.040 mL, 0.39 mmol) and sodium triacetoxyborohydride (0.105 g, 0.498 mmol). The reaction mixture was stirred at ambient temperature for 17 h and was then quenched by addition of water (5 mL). The mixture was extracted with ethyl acetate (2×5 mL). The combined organic phase was washed with brine (5 mL), dried with anhydrous magnesium sulfate, and filtered. Concentration of the filtrate in vacuo and purification of the residue by preparative reverse-phase HPLC eluting with a gradient of 20 to 80% of acetonitrile in water containing 0.1% of trifluoroacetic acid provided the title compound as a colorless solid (0.014 g, 5% yield): ¹H NMR (300 MHz, DMSO-d₆) δ 12.68 (br s, 1H), 10.28 (br s, 1H), 7.65 (d, J=2.1 Hz, 1H), 7.59-7.52 (m, 1H), 7.52-7.42 (m, 4H), 7.26 (d, J=4.6 Hz, 1H), 6.85-6.79 (m, 1H), 6.79-6.61 (m, 2H), 4.72-4.30 (m, 5H), 4.29-4.11 (m, 2H), 3.70-3.35 (m, 1H); MS (ES+) m/z 435.1 (M+1), 437.1 (M+1).

Example 51

Synthesis of 3-chloro-4-((1-(naphthalen-2-ylmethyl)piperidin-4-yl)oxy)-N-(thiazol-2-yl)benzenesulfonamide 2,2,2-trifluoroacetate

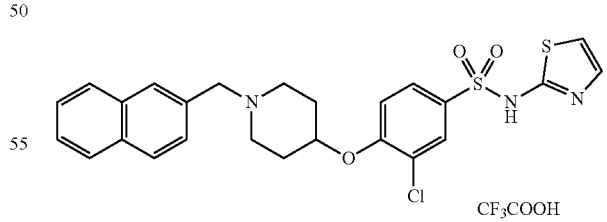

Following the procedure as described in EXAMPLE 22, and making non-critical variations as required to replace 4-fluorobenzaldehyde with 2-naphthaldehyde, the title compound was obtained as a colorless solid (0.177 g, 46% yield): ¹H NMR (300 MHz, CDCl₃) δ 8.73 (br s, 1H), 7.88 (d, J=2.2 Hz, 1H), 7.86-7.68 (m, 5H), 7.55-7.42 (m, 3H), 7.13 (d, J=4.6 Hz, 1H), 6.93 (d, J=8.9 Hz, 1H), 6.51 (d, J=4.6 Hz, 1H), 4.55 (s, 1H), 3.83 (s, 2H), 2.90-2.76 (m, 2H), 2.63

(br s, 2H), 2.18-2.02 (m, 2H), 2.01-1.87 (m, 2H), NH not observed; MS (ES+) m/z 514.0 (M+1), 516.0 (M+1).

Example 52

Synthesis of 3-chloro-4-((1-(1-phenylethyl)piperidin-4-yl)oxy)-N-(thiazol-2-yl)benzenesulfonamide

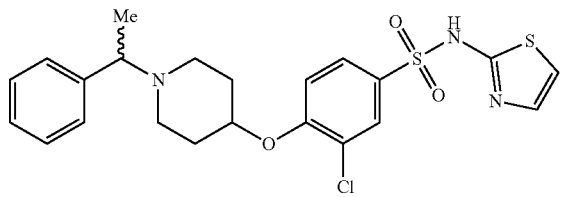 [SMILES: CC(c1ccccc1)N1CCC(Oc2ccc(S(=O)(=O)Nc3nccs3)cc2Cl)CC1]

Step 1. Preparation of 1-(1-phenylethyl)piperidin-4-ol

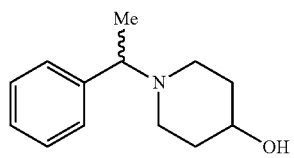 [SMILES: CC(c1ccccc1)N1CCC(O)CC1]

To a solution of piperidin-4-ol (1.0 g, 10 mmol) and acetophenone (0.78 mL, 6.7 mmol) in dichloromethane (2 mL) was added titanium(IV) isopropoxide (2.8 mL, 9.4 mmol). The reaction mixture was heated to 45° C. for 17 h and then a 1 M solution sodium cyanoborohydride in tetrahydrofuran (14.7 mL, 14.7 mmol) was added to it. The reaction mixture was stirred at 45° C. for an additional 3 h, allowed to cooled to ambient temperature, and quenched with water (250 mL). The resulting mixture was filtered and the filtrate extracted with dichloromethane (3×50 mL). The combined organic phase was washed with brine (50 mL), dried over anhydrous magnesium sulfate, filtered, and the filtrate concentrated in vacuo. Purification of the residue by column chromatography, eluting with 0 to 15% of methanol (containing 2% of ammonium hydroxide) in dichloromethane afforded the title compound as a yellow oil (0.710 g, 35% yield): $^1$H NMR (300 MHz, CDCl$_3$) δ 7.31 (s, 5H), 3.72-3.57 (m, 1H), 3.55-3.41 (m, 1H), 2.95-2.81 (m, 1H), 2.80-2.65 (m, 1H), 2.27-2.09 (m, 2H), 2.05 (br s, 1H), 2.00-1.81 (m, 2H), 1.69-1.47 (m, 2H), 1.41 (d, J=6.1 Hz, 3H); MS (ES+) m/z 206.2 (M+1).

Step 2. Preparation of 3-chloro-4-((1-(1-phenylethyl)piperidin-4-yl)oxy)-N-(thiazol-2-yl)benzenesulfonamide

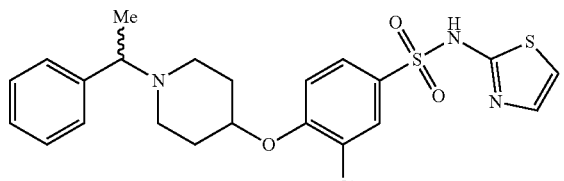

To a solution of 1-(1-phenylethyl)piperidin-4-ol (0.133 g, 0.650 mmol) and 3-chloro-N-(2,4-dimethoxybenzyl)-4-fluoro-N-(thiazol-2-yl)benzenesulfonamide (0.288 g, 0.650 mmol) in dimethyl sulfoxide (2.6 mL) was added cesium carbonate (0.509 g, 1.56 mmol) and the reaction mixture was stirred at ambient temperature for 17 h. The reaction mixture was diluted with ethyl acetate (5 mL) and water (5 mL) and the aqueous phase was extracted with ethyl acetate (2×5 mL). The combined organic phase was washed with brine (2×5 mL), dried over anhydrous magnesium sulfate, filtered, and the filtrate was concentrated in vacuo. The residue was dissolved in dichloromethane (7 mL) and trifluoroacetic acid (0.18 mL, 2.3 mmol) was added to it at 0° C. The reaction mixture was stirred for 20 minutes at 0° C. and then concentrated in vacuo. The residue was triturated in methanol (7 mL), and the resulting mixture was filtered. Concentration of the filtrate in vacuo and purification by preparative reverse-phase HPLC eluting with a gradient of 20 to 80% of acetonitrile in water containing 0.1% of trifluoroacetic acid afforded the title compound as a colorless solid (0.011 g, 4% yield): $^1$H NMR (300 MHz, DMSO-d$_6$) δ 8.18 (s, 1H), 7.69 (d, J=2.2 Hz, 1H), 7.61 (dd, J=2.2, 8.6 Hz, 1H), 7.33-7.29 (m, 4H), 7.24 (d, J=8.8 Hz, 1H), 7.10 (d, J=4.3 Hz, 1H), 6.65 (d, J=4.3 Hz, 1H), 4.57-4.45 (m, 1H), 3.51 (q, J=6.8 Hz, 1H), 2.75-2.55 (m, 2H), 2.32-2.18 (m, 2H), 1.96-1.83 (m, 2H), 1.71-1.56 (m, 2H), 1.30 (d, J=6.8 Hz, 3H), NH not observed; MS (ES+) m/z 478.1 (M+1), 480.1 (M+1).

Example 53

Synthesis of 4-((1-benzylpiperidin-4-yl)(methyl)amino)-5-chloro-2-fluoro-N-(thiazol-2-yl)benzenesulfonamide

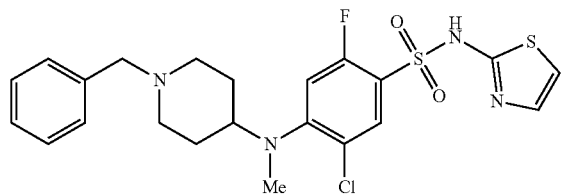 [SMILES: CN(c1cc(F)c(S(=O)(=O)Nc2nccs2)cc1Cl)C1CCN(Cc2ccccc2)CC1]

Following the procedure as described in EXAMPLE 47, and making non-critical variations as required to replace 1-benzylpiperidin-4-ol with 1-benzyl-N-methylpiperidin-4-amine, the title compound was obtained as a colorless solid (0.077 g, 24% yield): $^1$H NMR (300 MHz, DMSO-d$_6$) δ 7.69 (d, J=7.4 Hz, 1H), 7.40-7.31 (m, 5H), 7.29 (d, J=4.8 Hz, 1H), 7.11 (d, J=12.2 Hz, 1H), 6.86 (d, J=4.6 Hz, 1H), 3.70 (s, 2H), 3.47-3.32 (m, 1H), 3.00 (d, J=11.5 Hz, 2H), 2.67 (s, 3H), 2.28 (t, J=11.1 Hz, 2H), 1.95-1.74 (m, 2H), 1.74-1.60 (m, 2H), NH not observed; MS (ES+) m/z 495.1 (M+1), 497.1 (M+1).

Example 54

Synthesis of 5-chloro-2-fluoro-4-((1-(1-phenylethyl)piperidin-4-yl)oxy)-N-(thiazol-2-yl)benzenesulfonamide

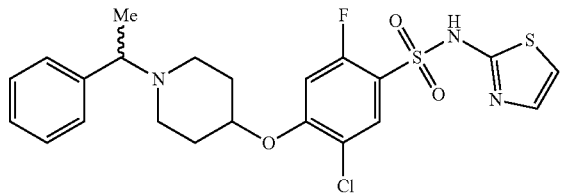 [SMILES: CC(c1ccccc1)N1CCC(Oc2cc(F)c(S(=O)(=O)Nc3nccs3)cc2Cl)CC1]

Following the procedure as described in EXAMPLE 52, Step 2, and making non-critical variations as required to replace 3-chloro-N-(2,4-dimethoxybenzyl)-4-fluoro-N-(thiazol-2-yl)benzenesulfonamide with 5-chloro-N-(2,4-dimethoxybenzyl)-2,4-difluoro-N-(thiazol-2-yl)benzenesulfonamide, the title compound was obtained as a colorless solid (0.017 g, 5% yield): $^1$H NMR (300 MHz, DMSO-$d_6$) δ 8.14 (s, 1H), 7.72 (d, J=7.6 Hz, 1H), 7.35-7.19 (m, 6H), 6.77 (d, J=4.5 Hz, 1H), 4.63-4.52 (m, 1H), 3.55 (q, J=6.6 Hz, 1H), 2.75-2.56 (m, 2H), 2.38-2.20 (m, 2H), 1.97-1.84 (m, 2H), 1.73-1.56 (m, 2H), 1.31 (d, J=6.8 Hz, 3H), NH not observed; MS (ES+) m/z 496.1 (M+1), 498.1 (M+1).

Example 55

Synthesis of (R)-3-chloro-4-((1-(1-phenylethyl)piperidin-4-yl)oxy)-N-(thiazol-2-yl)benzenesulfonamide 2,2,2-trifluoroacetate

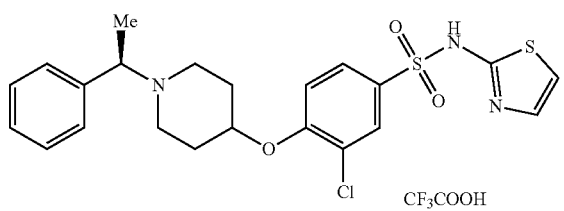

Step 1. Preparation of 1-ethyl-1-methyl-4-oxopiperidin-1-ium iodide

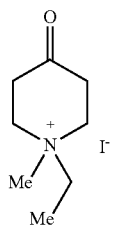

To a solution of 1-methylpiperidin-4-one (13.8 mL, 120 mmol) in butan-2-one (70 mL) was added iodoethane (10.6 mL, 132 mmol) and the reaction mixture was stirred at ambient temperature for 4 d. The mixture was filtered and the resulting solid was dried in vacuo to afford the title compound as an orange solid (27.8 g, 86% yield): $^1$H NMR (300 MHz, D$_2$O) δ 3.52-3.38 (m, 6H), 3.05 (s, 3H), 2.17-1.99 (m, 4H), 1.34 (t, J=7.3 Hz, 3H); MS (ES+) m/z 142.2 (M+1).

Step 2. Preparation of (R)-1-(1-phenylethyl)piperidin-4-one

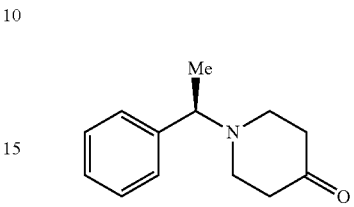

To a hot mixture of (R)-1-phenylethan-1-amine (0.7 mL, 6 mmol) and potassium carbonate (0.05 g, 0.37 mmol) in ethanol (6 mL) was added a solution of 1-ethyl-1-methyl-4-oxopiperidin-1-ium iodide (1.0 g, 3.7 mmol) in water (2.6 mL) and the reaction mixture was heated to reflux for 1.5 h. The reaction mixture was allowed to cool to ambient temperature and was then diluted with water (6 mL) and ethyl acetate (15 mL).

The aqueous phase was extracted with ethyl acetate (2×10 mL). The combined organic phase was washed with water (2×10 mL), brine (10 mL), dried over anhydrous magnesium sulfate, and filtered. The filtrate was concentrated in vacuo and the residue purified by column chromatography, eluting with a gradient of 0 to 80% of ethyl acetate (containing 10% of isopropanol and 10% of triethylamine) in hexanes, to afford the title compound as an oil (0.583 g, 77% yield): $^1$H NMR (300 MHz, CDCl$_3$) g 7.41-7.18 (m, 5H), 3.62 (q, J=6.8 Hz, 1H), 2.84-2.65 (m, 4H), 2.42 (t, J=6.0 Hz, 4H), 1.42 (d, J=6.8 Hz, 3H); MS (ES+) m/z 204.3 (M+1).

Step 3. Preparation of (R)-1-(1-phenylethyl)piperidin-4-ol

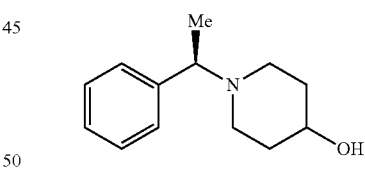

To a solution of (R)-1-(1-phenylethyl)piperidin-4-one (0.55 g, 2.71 mmol) in ethanol (27 mL) was added sodium borohydride (0.21 g, 5.42 mmol) and the reaction mixture was stirred at ambient temperature for 17 h. The reaction mixture was concentrated in vacuo, saturated ammonium chloride (5 mL) was slowly added to the residue, and the obtained mixture was extracted with ethyl acetate (3×5 mL). The combined organic phase was washed with brine (5 mL), dried over anhydrous magnesium sulfate, and filtered. Concentration of the filtrate in vacuo provided the title compound as a yellow oil (0.51 g, 91% yield): $^1$H NMR (300 MHz, CDCl$_3$) δ 7.37-7.20 (m, 5H), 3.73-3.57 (m, 1H), 3.47 (q, J=6.8 Hz, 1H), 2.94-2.82 (m, 1H), 2.79-2.67 (m, 1H), 2.24-2.07 (m, 2H), 1.99-1.82 (m, 2H), 1.70-1.47 (m, 2H), 1.41 (d, J=6.8 Hz, 3H), OH not observed; MS (ES+) m/z 206.3 (M+1).

Step 4. Preparation of (R)-3-chloro-4-((1-(1-phenylethyl)piperidin-4-yl)oxy)-N-(thiazol-2-yl)benzenesulfonamide 2,2,2-trifluoroacetate

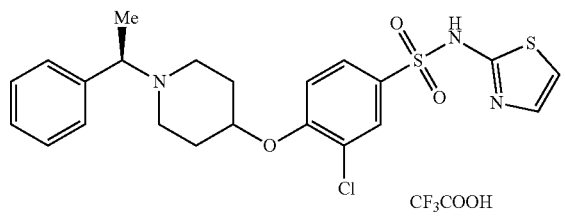 [SMILES: C[C@H](c1ccccc1)N1CCC(Oc2ccc(S(=O)(=O)Nc3nccs3)cc2Cl)CC1 ; "CF3COOH"]

Following the procedure as described in EXAMPLE 52, Step 2, and making non-critical variations as required to replace 1-(1-phenylethyl)piperidin-4-ol with (R)-1-(1-phenylethyl)piperidin-4-ol, the title compound was obtained as a colorless solid (0.046 g, 12% yield): $^1$H NMR (300 MHz, DMSO-$d_6$) δ 11.86 (br s, 1H), 7.74-7.63 (m, 2H), 7.46-7.30 (m, 6H), 7.27 (d, J=4.6 Hz, 1H), 6.84 (d, J=4.6 Hz, 1H), 4.77-4.64 (m, 1H), 4.17-3.97 (m, 1H), 2.98-2.61 (m, 4H), 2.11-1.94 (m, 2H), 1.90-1.72 (m, 2H), 1.49 (d, J=6.7 Hz, 3H), one exchangeable proton not observed; $^{19}$F NMR (282 MHz, DMSO-$d_6$) δ–77.4; MS (ES+) m/z 478.0 (M+1), 480.0 (M+1).

Example 56

Synthesis of (R)-5-chloro-2-fluoro-4-((1-(1-phenylethyl)piperidin-4-yl)oxy)-N-(thiazol-2-yl)benzenesulfonamide 2,2,2-trifluoroacetate

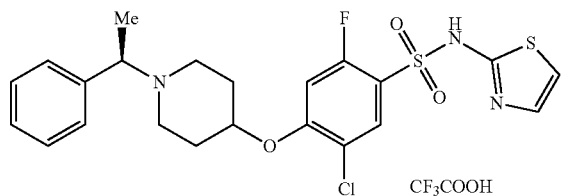

Step 1. Preparation of (R)-5-chloro-N-(2,4-dimethoxybenzyl)-2-fluoro-4-((1-(1-phenylethyl)piperidin-4-yl)oxy)-N-(thiazol-2-yl)benzenesulfonamide

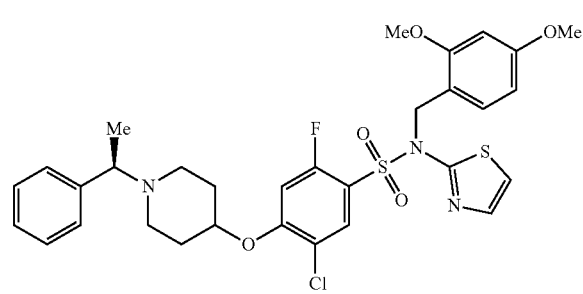 [SMILES: COc1ccc(CN(c2nccs2)S(=O)(=O)c2cc(Cl)c(OC3CCN([C@H](C)c4ccccc4)CC3)cc2F)c(OC)c1]

To a solution of (R)-1-(1-phenylethyl)piperidin-4-ol (0.13 g, 0.65 mmol) and 5-chloro-N-(2,4-dimethoxybenzyl)-2,4-difluoro-N-(thiazol-2-yl)benzenesulfonamide (0.30 g, 0.65 mmol) in anhydrous dimethyl sulfoxide (3 mL) was added cesium carbonate (0.51 g, 1.6 mmol) and the reaction mixture was stirred at ambient temperature for 17 h. The mixture was diluted with ethyl acetate (5 mL) and water (5 mL), and the aqueous phase was extracted with ethyl acetate (2×5 mL). The combined organic phase was washed with brine (5 mL), dried over anhydrous magnesium sulfate, filtered, and the filtrate concentrated in vacuo. The residue was purified by column chromatography eluting with 0 to 95% of ethyl acetate in hexanes to provide the title compound as a yellow oil (0.065 g, 15% yield): MS (ES+) m/z 646.1 (M+1), 648.1 (M+1).

Step 2. Preparation of (R)-5-chloro-2-fluoro-4-((1-(1-phenylethyl)piperidin-4-yl)oxy)-N-(thiazol-2-yl)benzenesulfonamide 2,2,2-trifluoroacetate

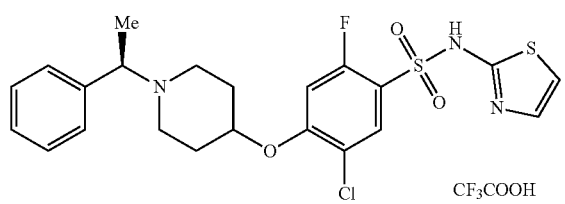 [SMILES: C[C@H](c1ccccc1)N1CCC(Oc2cc(F)c(S(=O)(=O)Nc3nccs3)cc2Cl)CC1 ; "CF3COOH"]

To a mixture of (R)-5-chloro-N-(2,4-dimethoxybenzyl)-2-fluoro-4-((1-(1-phenylethyl)piperidin-4-yl)oxy)-N-(thiazol-2-yl)benzenesulfonamide in dichloromethane (2 mL) was added trifluoroacetic acid (0.02 mL, 0.30 mmol) at 0° C. The reaction mixture was stirred at 0° C. for 15 minutes and then concentrated in vacuo. To the residue was added methanol (5 mL) and the mixture was filtered. Concentration of the filtrate in vacuo afforded the title compound as a colorless solid (0.043 g, 88% yield): $^1$H NMR (300 MHz, DMSO-$d_6$) δ 12.97 (br s, 1H), 9.79 (br s, 1H), 7.81-7.66 (m, 1H), 7.62-7.35 (m, 6H), 7.31 (d, J=4.6 Hz, 1H), 6.88 (d, J=4.6 Hz, 1H), 5.04-4.88 (m, 1H), 4.74-4.59 (m, 1H), 3.79-3.63 (m, 2H), 3.57-3.39 (m, 2H), 2.99-2.69 (m, 2H), 2.16-1.95 (m, 2H), 1.68 (d, J=6.9 Hz, 3H); MS (ES+) m/z 496.1 (M+1), 498.1 (M+1).

Example 57

Synthesis of (R)-3-chloro-4-((1-(1-phenylethyl)piperidin-4-yl)oxy)-N-(thiazol-4-yl)benzenesulfonamide 2,2,2-trifluoroacetate

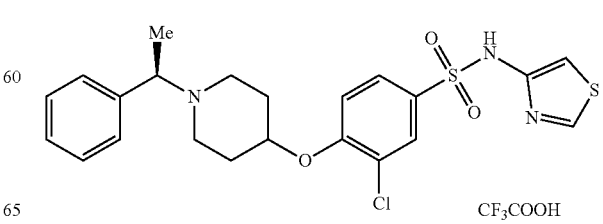

Step 1. Preparation of tert-butyl ((3-chloro-4-fluorophenyl)sulfonyl)(thiazol-4-yl)carbamate

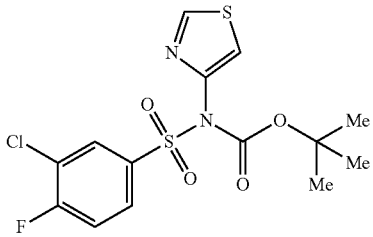 [SMILES: CC(C)(C)OC(=O)N(c1cscn1)S(=O)(=O)c1ccc(F)c(Cl)c1]

To a solution of tert-butyl thiazol-4-ylcarbamate (30.0 g, 150 mmol) in anhydrous tetrahydrofuran (400 mL) was added lithium bis(trimethylsilyl)amide (1 M solution in tetrahydrofuran, 210.0 mL, 210.0 mmol) at −78° C. The reaction mixture was warmed to 0° C., stirred for 1 h, and cooled to −78° C. To it was then added dropwise a solution of 3-chloro-4-fluorobenzenesulfonyl chloride (51.5 g, 225.0 mmol) in anhydrous tetrahydrofuran (100 mL) at −78° C. The reaction mixture was allowed to warm to ambient temperature and stirred for 2 h. The mixture was then diluted with water (500 mL) and extracted with ethyl acetate (3×400 mL). The combined organic phase was washed with brine (100 mL), dried over anhydrous sodium sulfate, and filtered. Concentration of the filtrate in vacuo and trituration of the residue with methanol (2×200 mL) afforded the title compound as a colorless solid (47.0 g, 80% yield): $^1$H NMR (400 MHz, CDCl$_3$) δ 8.83 (d, J=2.0 Hz, 1H), 8.28 (dd, J=6.4, 2.0 Hz, 1H), 8.13-8.08 (m, 1H), 7.57 (d, J=2.0 Hz, 1H), 7.35 (t, J=8.4 Hz, 1H), 1.38 (s, 9H); MS (ES+) m/z 415.0 (M+23), 417.0 (M+23).

Step 2. Preparation of 3-chloro-4-fluoro-N-(thiazol-4-yl)benzenesulfonamide

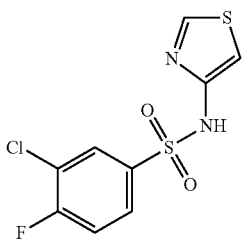 [SMILES: O=S(=O)(Nc1cscn1)c1ccc(F)c(Cl)c1]

To a solution of tert-butyl ((3-chloro-4-fluorophenyl)sulfonyl)(thiazol-4-yl)carbamate (1.0 g, 2.5 mmol) in dichloromethane (5 mL) was added trifluoroacetic acid (1.0 mL, 13 mmol) and the reaction mixture was stirred for 2 h. The reaction mixture was concentrated in vacuo and the residue was triturated in diethyl ether (5 mL) to provide a colorless solid (0.55 g, 74% yield): $^1$H NMR (300 MHz, DMSO-ds) δ 11.22 (s, 1H), 8.91 (d, J=2.2 Hz, 1H), 8.01 (dd, J=2.2, 6.8 Hz, 1H), 7.87-7.80 (m, 1H), 7.64 (t, J=8.9 Hz, 1H), 7.15 (d, J=2.2 Hz, 1H); MS (ES−) m/z 291.1 (M−1), 293.0 (M−1).

Step 3. Preparation of (R)-3-chloro-4-((1-(1-phenylethyl)piperidin-4-yl)oxy)-N-(thiazol-4-yl)benzenesulfonamide 2,2,2-trifluoroacetate

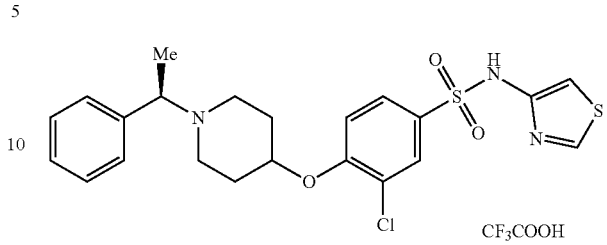

To a mixture of 3-chloro-4-fluoro-N-(thiazol-4-yl)benzenesulfonamide (0.06 g, 0.21 mmol) in anhydrous dimethyl sulfoxide (1.2 mL) and (R)-1-(1-phenylethyl)piperidin-4-ol (0.06 g, 0.30 mmol) was added cesium carbonate (0.51 g, 1.56 mmol) and a 60% dispersion of sodium hydride in mineral oil (0.025 g, 0.63 mmol). The reaction mixture was stirred at ambient temperature for 2 h and then quenched by addition of water (5 mL) and saturated ammonium chloride (5 mL). The mixture was extracted with ethyl acetate (3×5 mL) and the combined organic phase was washed with brine (5 mL), dried over anhydrous magnesium sulfate, and filtered. Concentration of the filtrate in vacuo and purification of the residue by preparative reverse-phase HPLC, eluting with a gradient of 12 to 54% of acetonitrile in water containing 0.1% of trifluoroacetic acid afforded the title compound as a colorless solid (0.030 g, 17% yield): $^1$H NMR (300 MHz, DMSO-d$_6$) δ 11.08 (s, 1H), 9.93-9.64 (m, 1H), 8.88 (s, 1H), 7.86-7.76 (m, 1H), 7.75-7.65 (m, 1H), 7.59-7.45 (m, 5H), 7.44-7.31 (m, 1H), 7.11-7.05 (m, 1H), 4.98 (s, 1H), 4.75-4.57 (m, 1H), 3.56-3.24 (m, 2H), 2.99-2.69 (m, 2H), 2.34-2.18 (m, 1H), 2.14-1.96 (m, 2H), 1.93-1.74 (m, 1H), 1.68 (d, J=6.8 Hz, 3H); MS (ES+) m/z 478.1 (M+1), 480.1 (M+1).

Example 58

Synthesis of (S)-3-chloro-4-((1-(1-phenylethyl)piperidin-4-yl)oxy)-N-(thiazol-2-yl)benzenesulfonamide 2,2,2-trifluoroacetate

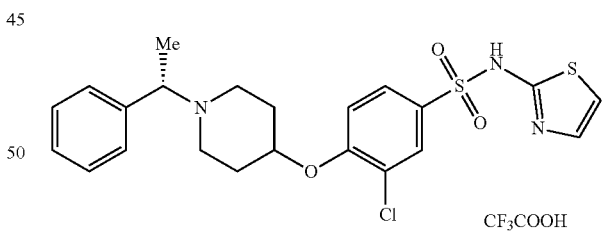

Step 1. Preparation of (S)-1-(1-phenylethyl)piperidin-4-one

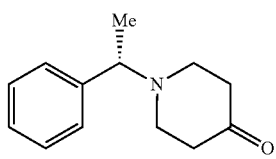

Following the procedure as described in EXAMPLE 55, Step 2 and making non-critical variations as required to replace (R)-1-phenylethan-1-amine with (S)-1-phenylethan-1-amine, the title compound was obtained as an yellow oil (1.17 g, 78% yield): $^1$H NMR (300 MHz, CDCl$_3$) δ 7.38-7.21 (m, 5H), 3.62 (q, J=6.8 Hz, 1H), 2.84-2.64 (m, 4H), 2.41 (t, J=6.0 Hz, 4H), 1.41 (d, J=6.8 Hz, 3H); MS (ES+) m/z 204.3 (M+1).

Step 2. Preparation of (S)-1-(1-phenylethyl)piperidin-4-ol

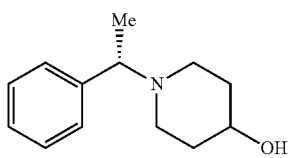 [SMILES: C[C@@H](c1ccccc1)N1CCC(O)CC1]

Following the procedure as described in EXAMPLE 55, Step 3 and making non-critical variations as required to replace (R)-1-(1-phenylethyl)piperidin-4-one with (S)-1-(1-phenylethyl)piperidin-4-one, the title compound was obtained as a yellow oil (1.15 g, 97% yield): $^1$H NMR (300 MHz, CDCl$_3$) δ 7.38-7.17 (m, 5H), 3.69-3.55 (m, 1H), 3.43 (q, J=6.8 Hz, 1H), 2.93-2.80 (m, 1H), 2.76-2.64 (m, 1H), 2.19-2.04 (m, 2H), 1.95-1.78 (m, 2H), 1.67-1.45 (m, 2H), 1.38 (d, J=6.8 Hz, 3H), OH not observed; MS (ES+) m/z 206.3 (M+1).

Step 3. Preparation of (S)-3-chloro-4-((1-(1-phenylethyl)piperidin-4-yl)oxy)-N-(thiazol-2-yl)benzenesulfonamide 2,2,2-trifluoroacetate

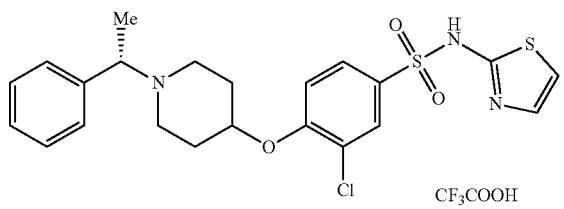 [SMILES: C[C@@H](c1ccccc1)N1CCC(Oc2ccc(S(=O)(=O)Nc3nccs3)cc2Cl)CC1 ; "CF3COOH"]

To a solution of 3-chloro-N-(2,4-dimethoxybenzyl)-4-fluoro-N-(thiazol-2-yl)benzenesulfonamide (0.300 g, 0.676 mmol) and (S)-1-(1-phenylethyl)piperidin-4-ol (0.137 g, 0.668 mmol) in N,N-dimethylformamide (6.5 mL) was added 60% sodium hydride in mineral oil (0.052 g, 1.3 mmol) and the reaction mixture was stirred at ambient temperature for 30 minutes. The reaction mixture was quenched by slow addition of saturated ammonium chloride (5 mL) and extracted with ethyl acetate (3×5 mL). The combined organic phase was washed with brine (5 mL), dried over anhydrous magnesium sulfate, filtered, and the filtrate concentrated in vacuo. The obtained residue was dissolved in dichloromethane (4 mL) and trifluoroacetic acid (0.6 mL, 6 mmol) was added to it. The reaction mixture was stirred at ambient temperature for 10 minutes, concentrated in vacuo, and methanol was added to the residue. The mixture was filtered and the filtrate concentrated in vacuo. Purification of the residue by preparative reverse-phase HPLC eluting with a gradient of 20 to 85% of acetonitrile in water containing 0.1% of trifluoroacetic acid afforded the title compound as a colorless solid (0.05 g, 13% yield): $^1$H NMR (300 MHz, DMSO-d$_6$) δ 12.81 (br s, 1H), 10.03-9.56 (m, 1H), 7.78-7.64 (m, 2H), 7.60-7.44 (m, 5H), 7.42-7.31 (m, 1H), 7.28 (d, J=4.6 Hz, 1H), 6.85 (d, J=4.6 Hz, 1H), 5.04-4.87 (m, 1H), 4.77-4.55 (m, 1H), 3.58-3.25 (m, 2H), 3.01-2.67 (m, 2H), 2.37-2.16 (m, 1H), 2.15-1.95 (m, 3H), 1.68 (d, J=6.9 Hz, 3H); MS (ES+) m/z 478.0 (M+1), 480.0 (M+1).

Example 59

Synthesis of 3-chloro-4-((1-(2-phenylpropan-2-yl)piperidin-4-yl)oxy)-N-(thiazol-2-yl)benzenesulfonamide 2,2,2-trifluoroacetate

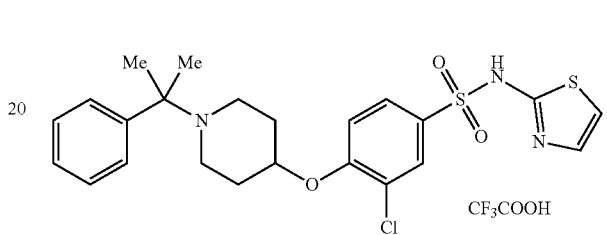

Step 1. Preparation of 1-(2-phenylpropan-2-yl)piperidin-4-one

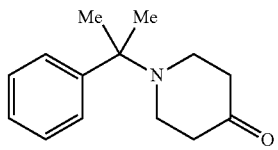 [SMILES: CC(C)(c1ccccc1)N1CCC(=O)CC1]

Following the procedure as described in EXAMPLE 55, Step 2 and making non-critical variations as required to replace (R)-1-phenylethan-1-amine with 2-phenylpropan-2-amine, the title compound was obtained as a yellow oil (0.56 g, 70% yield): $^1$H NMR (300 MHz, CDCl$_3$) δ7.63-7.54 (m, 2H), 7.38-7.20 (m, 3H), 2.77 (t, J=5.9 Hz, 4H), 2.41 (t, J=6.0 Hz, H), 1.40 (s, 6H); MS (ES+) m/z 218.3 (M+1).

Step 2. Preparation of 1-(2-phenyl propan-2-yl)piperidin-4-ol

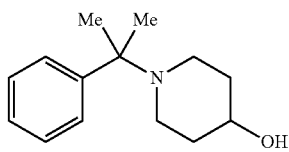 [SMILES: CC(C)(c1ccccc1)N1CCC(O)CC1]

Following the procedure as described in EXAMPLE 55, Step 3 and making non-critical variations as required to replace (R)-1-(1-phenylethyl)piperidin-4-one with 1-(2-phenylpropan-2-yl)piperidin-4-one, the title compound was obtained as a yellow oil (0.50 g, 88% yield): $^1$H NMR (300 MHz, CDCl$_3$) δ 7.63-7.46 (m, 2H), 7.36-7.26 (m, 2H), 7.25-7.16 (m, 1H), 3.78-3.56 (m, 1H), 2.87-2.63 (m, 2H), 2.32-2.10 (m, 2H), 1.96-1.77 (m, 2H), 1.62-1.43 (m, 2H), 1.35 (s, 6H), OH not observed; MS (ES+) m/z 220.3 (M+1).

147

Step 3. Preparation of 3-chloro-4-((1-(2-phenylpropan-2-yl)piperidin-4-yl)oxy)-N-(thiazol-2-yl)benzenesulfonamide 2,2,2-trifluoroacetate

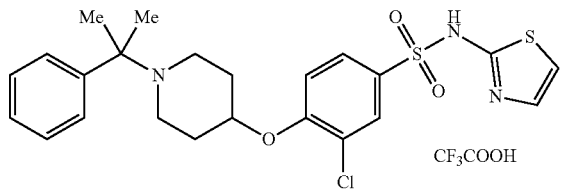 [SMILES: CC(C)(c1ccccc1)N1CCC(Oc2ccc(S(=O)(=O)Nc3nccs3)cc2Cl)CC1 ; "CF3COOH"]

Following the procedure as described in EXAMPLE 52, Step 2 and making non-critical variations as required to replace 1-(1-phenylethyl)piperidin-4-ol with 1-(2-phenylpropan-2-yl)piperidin-4-ol, the title compound was obtained as a colorless solid (0.116 g, 28% yield): $^1$H NMR (300 MHz, DMSO-$d_6$) δ 12.80 (br s, 1H), 9.40 (br s, 1H), 7.74-7.65 (m, 4H), 7.56-7.44 (m, 3H), 7.39-7.30 (m, 1H), 7.28 (d, J=4.6 Hz, 1H), 6.85 (d, J=4.6 Hz, 1H), 5.03-4.92 (m, 1H), 3.51-3.28 (m, 2H), 3.00-2.73 (m, 2H), 2.32-2.17 (m, 1H), 2.13-1.97 (m, 3H), 1.82 (s, 6H); MS (ES+) m/z 492.1 (M+1), 494.1 (M+1).

Example 60

Synthesis of 5-chloro-2-fluoro-4-((1-(2-phenylpropan-2-yl)piperidin-4-yl)oxy)-N-(thiazol-2-yl)benzenesulfonamide 2,2,2-trifluoroacetate

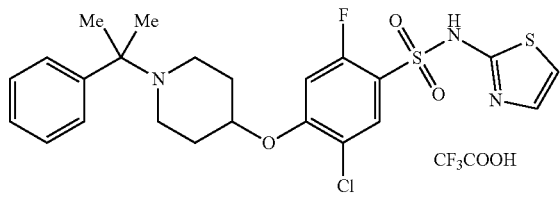 [SMILES: CC(C)(c1ccccc1)N1CCC(Oc2cc(F)c(S(=O)(=O)Nc3nccs3)cc2Cl)CC1 ; "CF3COOH"]

Step 1. Preparation of 5-chloro-N-(2,4-dimethoxybenzyl)-2-fluoro-4-((1-(2-phenylpropan-2-yl)piperidin-4-yl)oxy)-N-(thiazol-2-yl)benzenesulfonamide

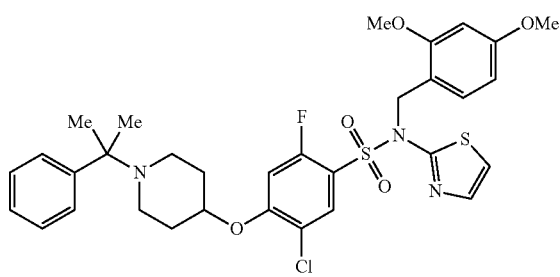 [SMILES: COc1ccc(CN(c2nccs2)S(=O)(=O)c2cc(Cl)c(OC3CCN(C(C)(C)c4ccccc4)CC3)cc2F)c(OC)c1]

To a solution of 1-(2-phenylpropan-2-yl)piperidin-4-ol (0.14 g, 0.65 mmol) and 5-chloro-N-(2,4-dimethoxybenzyl)-2,4-difluoro-N-(thiazol-2-yl)benzenesulfonamide (0.30 g, 0.65 mmol) in anhydrous dimethyl sulfoxide (3 mL) was added cesium carbonate (0.51 g, 1.6 mmol) and the reaction mixture was stirred at ambient temperature for 17 h. The mixture was diluted with ethyl acetate (5 mL) and water (5 mL), and the aqueous phase was extracted with ethyl acetate (2×5 mL). The combined organic phase washed with brine (5 mL), dried over anhydrous magnesium sulfate, filtered, and the filtrate was concentrated in vacuo. The residue was purified by column chromatography eluting with 0 to 90% of ethyl acetate in hexanes to provide the title compound as yellow oil (0.174 g, 40% yield): MS (ES+) m/z 660.2 (M+1), 662.1 (M+1).

Step 2. Preparation of 5-chloro-2-fluoro-4-((1-(2-phenylpropan-2-yl)piperidin-4-yl)oxy)-N-(thiazol-2-yl)benzenesulfonamide 2,2,2-trifluoroacetate

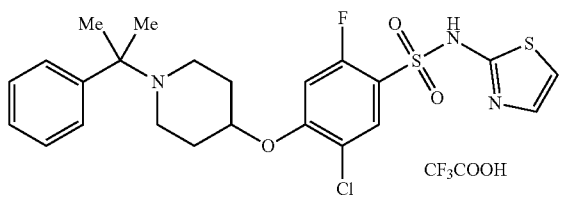

To a mixture of 5-chloro-N-(2,4-dimethoxybenzyl)-2-fluoro-4-((1-(2-phenylpropan-2-yl)piperidin-4-yl)oxy)-N-(thiazol-2-yl)benzenesulfonamide in dichloromethane (5 mL) was added trifluoroacetic acid (0.26 mL, 3.4 mmol). The reaction mixture was stirred at ambient temperature for 15 minutes and then concentrated in vacuo. To the residue was added methanol (5 mL) and the mixture was filtered. Concentration of the filtrate in vacuo provided a residue which was purified by preparative reverse-phase HPLC eluting with a gradient of 20 to 80% of acetonitrile in water containing 0.1% of trifluoroacetic acid to afford the title compound as a colorless solid (0.053 g, 40% yield): $^1$H NMR (300 MHz, DMSO-$d_6$) δ 12.96 (s, 1H), 9.48-9.31 (m, 1H), 7.80-7.65 (m, 3H), 7.57-7.45 (m, 3H), 7.45-7.35 (m, 1H), 7.32 (d, J=4.6 Hz, 1H), 6.89 (d, J=4.6 Hz, 1H), 5.02-4.91 (m, 1H), 3.56-3.43 (m, 1H), 3.41-3.28 (m, 1H), 2.94-2.73 (m, 2H), 2.32-2.18 (m, 1H), 2.14-1.97 (m, 3H), 1.83 (s, 6H); MS (ES+) m/z 510.1 (M+1), 512.1 (M+1).

Example 61

Synthesis of 4-((1-benzyl-3-methylpyrrolidin-3-yl)amino)-3-chloro-N-(thiazol-2-yl)benzenesulfonamide

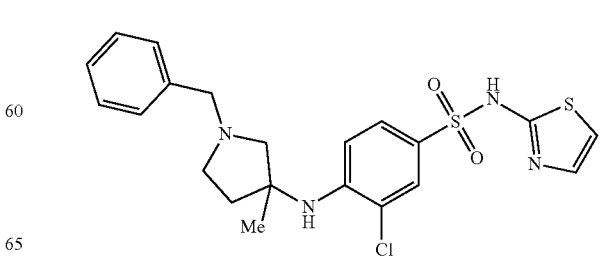

Step 1. Preparation of 4-bromo-3-chloro-N-(2,4-dimethoxybenzyl)-N-(thiazol-2-yl)benzenesulfonamide

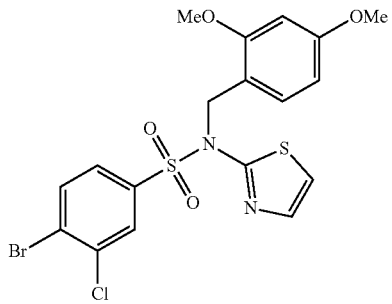 [SMILES: COc1ccc(CN(c2nccs2)S(=O)(=O)c2ccc(Br)c(Cl)c2)c(OC)c1]

Following the procedure as described in EXAMPLE 1, Step 1 and making non-critical variations as required to replace 3-chloro-4-fluorobenzenesulfonyl chloride with 4-bromo-3-chlorobenzenesulfonyl chloride, and purification by column chromatography, eluting with 20% of ethyl acetate in hexanes, the title compound was obtained as a colorless solid (0.50 g, 50% yield): $^1$H NMR (400 MHz, CDCl$_3$) 37.84 (d, J=2.0 Hz, 1H), 7.72 (d, J=8.0 Hz, 1H), 7.56 (dd, J=8.0, 2.0 Hz, 1H), 7.48 (d, J=4.0 Hz, 1H), 7.16-7.14 (m, 1H), 7.09 (d, J=4.0 Hz, 1H), 6.39-6.36 (m, 2H), 5.07 (s, 2H), 3.79 (s, 3H), 3.71 (s, 3H).

Step 2. Preparation of 4-((1-benzyl-3-methylpyrrolidin-3-yl)amino)-3-chloro-N-(2,4-dimethoxybenzyl)-N-(thiazol-2-yl)benzenesulfonamide

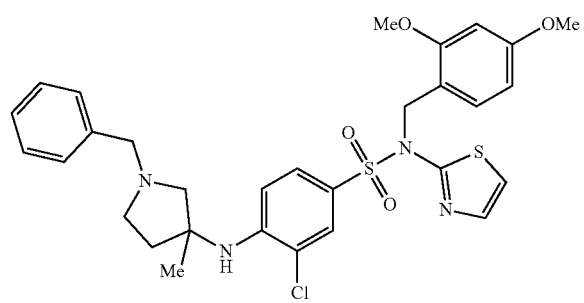 [SMILES: COc1ccc(CN(c2nccs2)S(=O)(=O)c2ccc(NC3(C)CCN(Cc4ccccc4)C3)c(Cl)c2)c(OC)c1]

To a mixture of 1-benzyl-3-methylpyrrolidin-3-amine (prepared according to WO2007117559, 0.10 g, 0.53 mmol) and 4-bromo-3-chloro-N-(2,4-dimethoxybenzyl)-N-(thiazol-2-yl)benzenesulfonamide (0.27 g, 0.53 mmol) in anhydrous toluene (5 mL) was added 4,5-bis(diphenylphosphino)-9,9-dimethylxanthene (0.091 g, 0.158 mmol), bis(dibenzylideneacetone)palladium(0) (0.060 g, 0.105 mmol), and cesium carbonate (0.17 g, 0.53 mmol) and the reaction mixture was heated to 100° C. for 12 h. The reaction mixture was poured into water (20 mL), and the mixture was extracted with ethyl acetate (3×20 mL). The combined organic phase was washed with brine (2×20 mL), dried over anhydrous sodium sulfate, and filtered. Concentration of the filtrate in vacuo and purification of the residue by preparative thin layer chromatography, eluting with 20% of ethyl acetate in hexanes afforded the title compound as a beige solid (0.25 g, 54% yield): MS (ES+) m/z 613.1 (M+1), 615.1 (M+1).

Step 3. Preparation of 4-((1-benzyl-3-methylpyrrolidin-3-yl)amino)-3-chloro-N-(thiazol-2-yl)benzenesulfonamide

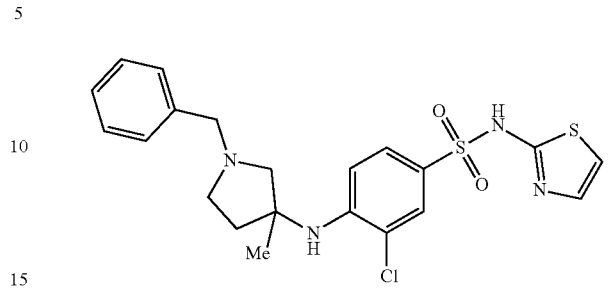

To a mixture of 4-((1-benzyl-3-methylpyrrolidin-3-yl)amino)-3-chloro-N-(2,4-dimethoxybenzyl)-N-(thiazol-2-yl)benzenesulfonamide (0.20 g, 0.33 mmol) in anhydrous dichloromethane (10 mL) was added trifluoroacetic acid (1 mL) and the reaction mixture was stirred at ambient temperature for 12 h. Concentration in vacuo and purification of the residue by preparative reverse-phase HPLC, eluting with a gradient of acetonitrile in water containing 0.2% of formic acid, provided the title compound as a colorless solid (0.12 g, 77% yield): $^1$H NMR (400 MHz, DMSO-d$_6$) δ 7.63 (d, J=2.0 Hz, 1H), 7.57 (dd, J=8.0, 2.0 Hz, 1H), 7.43-7.39 (m, 5H), 7.26 (d, J=4.0 Hz, 1H), 6.99 (d, J=8.0 Hz, 1H), 6.83 (d, J=4.0 Hz, 1H), 5.63 (s, 1H), 4.11 (s, 2H), 3.14 2.89 (m, 4H), 2.40 (m, 1H), 2.13-2.08 (m, 1H), 1.50 (s, 3H), NH not observed; MS (ES+) m/z 463.1 (M+1), 465.1 (M+1).

Example 62

Synthesis of (S)-3-chloro-4-(methyl(1-(2-phenylpropan-2-yl)pyrrolidin-3-yl)amino)-N-(thiazol-4-yl)benzenesulfonamide

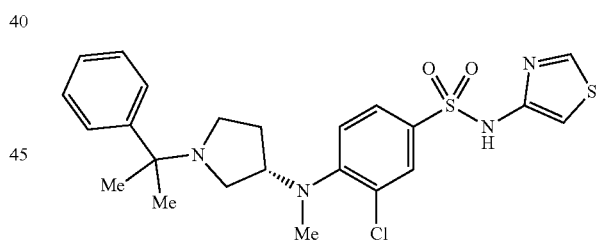

Step 1. Preparation of tert-butyl (S)-(1-(2-phenylpropan-2-yl)pyrrolidin-3-yl)carbamate

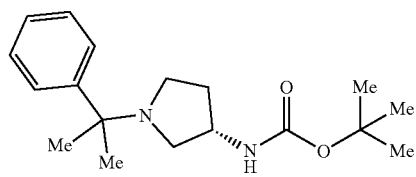 [SMILES: CC(C)(C)OC(=O)N[C@H]1CCN(C(C)(C)c2ccccc2)C1]

Following the procedure as described for EXAMPLE 42, Step 2 and making non-critical variations as required to replace (S)-1-phenylethan-1-amine with 2-phenylpropan-2-amine, and purification by trituration with ethyl acetate (10 mL), the title compound was obtained as a colorless solid (1.95 g, 73% yield): $^1$H NMR (300 MHz, CDCl$_3$) δ 87.52-7.50 (m, 2H), 7.38-7.31 (m, 2H), 7.26-7.20 (m, 1H), 4.84-4.79 (m, 1H), 4.38-4.25 (m, 2H), 4.12-4.05 (m, 1H), 3.07 (s, 3H), 3.06 (s, 3H), 2.73-2.68 (m, 1H), 2.48-2.42 (m, 1H), 2.15-1.97 (m, 2H), 1.45 (s, 9H); MS (ES+) m/z 305.4 (M+1).

Step 2. Preparation of (S)—N-methyl-1-(2-phenyl-propan-2-yl)pyrrolidin-3-amine

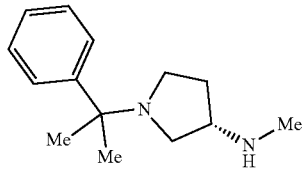 [SMILES: CN[C@H]1CCN(C(C)(C)c2ccccc2)C1]

Following the procedure as described for EXAMPLE 42, Step 3 and making non-critical variations as required to replace tert-butyl ((S)-1-((S)-1-phenylethyl)pyrrolidin-3-yl)carbamate with tert-butyl (S)-(1-(2-phenylpropan-2-yl)pyrrolidin-3-yl)carbamate, the title compound was obtained as a colorless oil (0.55 g, 39% yield): MS (ES+) m/z 219.2 (M+1).

Step 3. Preparation of tert-butyl ((4-bromo-3-chlorophenyl)sulfonyl)(thiazol-4-yl)carbamate

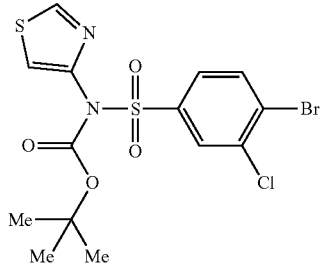 [SMILES: CC(C)(C)OC(=O)N(c1cscn1)S(=O)(=O)c1ccc(Br)c(Cl)c1]

To a solution of tert-butyl thiazol-4-ylcarbamate (25.0 g, 124.9 mmol) in anhydrous tetrahydrofuran (250 mL) was added a 1 M solution of lithium bis(trimethylsilyl)amide in tetrahydrofuran (174.8 mL, 174.8 mmol) at −78° C. The reaction mixture was allowed to warm to 0° C., stirred for 30 minutes at 0° C., and cooled to −78° C. To it was added a solution of 4-bromo-3-chlorobenzenesulfonyl chloride (47.1 g, 162.3 mmol) in anhydrous tetrahydrofuran (50 mL) at −78° C. The reaction mixture was allowed to warm to ambient temperature and stirred for 2 h. The mixture was diluted with water (500 mL) and extracted with ethyl acetate (3×500 mL). The combined organic phase was washed with brine (100 mL), dried over anhydrous sodium sulfate, and filtered. Concentration of the filtrate in vacuo and trituration of the residue with methanol (3×150 mL) afforded the title compound as a colorless solid (28.0 g, 49% yield): $^1$H NMR (400 MHz, CDCl$_3$) δ 8.73 (d, J=2.1 Hz, 1H), 8.16 (d, J=2.0 Hz, 1H), 7.87-7.81 (m, 1H), 7.78-7.73 (m, 1H), 7.48 (d, J=4.0 Hz, 1H), 1.29 (s, 9H).

Step 4. Preparation of 4-bromo-3-chloro-N-(thiazol-4-yl)benzenesulfonamide

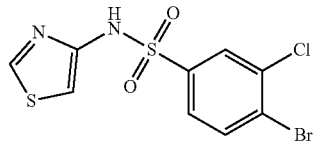 [SMILES: O=S(=O)(Nc1cscn1)c1ccc(Br)c(Cl)c1]

To tert-butyl ((4-bromo-3-chlorophenyl)sulfonyl)(thiazol-4-yl)carbamate (20.0 g, 44.1 mmol) was added a 4 M solution of hydrogen chloride in ethyl acetate (200 mL) and the mixture was stirred at ambient temperature for 72 h. Filtration and concentration of the filtrate in vacuo provided a residue, which was triturated with ethyl acetate (2×100 mL) to provide the title compound as a colorless solid (15.1 g, 97% yield): $^1$H NMR (400 MHz, CD$_3$OD) δ 8.84 (d, J=2.4 Hz, 1H), 7.97 (d, J=2.4 Hz, 1H), 7.87 (d, J=8.0 Hz, 1H), 7.65 (dd, J=12.0, 4.0 Hz, 1H), 7.16 (d, J=2.4 Hz, 1H), NH not observed; MS (ES+) m/z 352.9 (M+1), 355.0 (M+1).

Step 5. Preparation of (S)-3-chloro-4-(methyl(1-(2-phenylpropan-2-yl)pyrrolidin-3-yl)amino)-N-(thiazol-4-yl)benzenesulfonamide

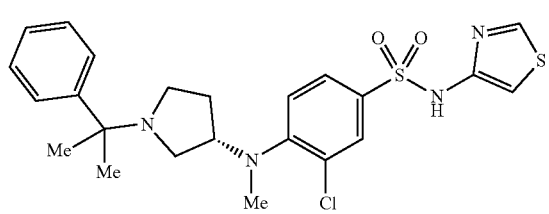 [SMILES: CN(c1ccc(S(=O)(=O)Nc2cscn2)cc1Cl)[C@H]1CCN(C(C)(C)c2ccccc2)C1]

To a mixture of 4-bromo-3-chloro-N-(thiazol-4-yl)benzenesulfonamide (0.89 g, 2.52 mmol), (S)—N-methyl-1-(2-phenylpropan-2-yl)pyrrolidin-3-amine (0.55 g, 2.52 mmol), 4,5-bis(diphenylphosphino)-9,9-dimethylxanthene (0.29 g, 0.50 mmol), and sodium tert-butoxide (0.73 g, 7.56 mmol) in anhydrous dioxane (32 mL) was added tris(dibenzylideneacetone)dipalladium(0) (0.23 g, 0.25 mmol). The resulting mixture was degassed by passing nitrogen through it and then heated to reflux for 18 h. The reaction mixture was concentrated in vacuo and the residue dissolved in methanol (40 mL). To this mixture was added 6.0 M hydrochloric acid (40 mL) and the reaction mixture was stirred for 30 minutes. Filtration and concentration of the filtrate in vacuo gave a residue which was purified by column chromatography eluting with 0 to 20% of methanol (containing 0.2% of ammonium hydroxide) in dichloromethane. The obtained residue was then purified by preparative reverse-phase HPLC eluting with a gradient of 10 to 45% of acetonitrile in water (containing 0.1% formic acid) to afford the title compound as a colorless solid (0.020 g, 2% yield): $^1$H NMR (300 MHz, DMSO-d$_6$) δ 11.31 (br s, 1H), 8.89 (d, J=2.1 Hz, 1H), 7.74 (d, J=2.3 Hz, 1H), 7.62 (dd, J=8.6, 2.3 Hz, 1H), 7.48 (dt, J=8.3, 1.7 Hz, 2H), 7.33-7.28 (m, 2H), 7.22-7.17 (m, 2H), 7.05 (d, J=2.2 Hz, 1H), 4.04-3.97 (m, 1H), 2.75 (s, 3H), 2.69-2.59 (m, 2H), 2.55-2.52 (m, 1H), 2.43-2.35 (m, 1H), 2.02-1.91 (m, 1H), 1.79-1.67 (m, 1H), 1.34 (s, 6H); MS (ES+) m/z 491.1 (M+1), 493.1 (M+1).

Example 63

Synthesis of 3-chloro-4-((1-(pyridin-4-ylmethyl)piperidin-4-yl)oxy)-N-(thiazol-2-yl)benzenesulfonamide

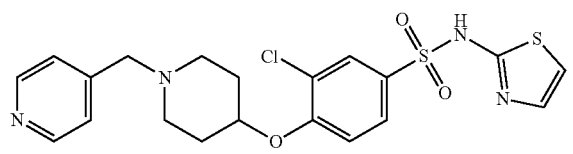 [SMILES: O=S(=O)(Nc1nccs1)c1ccc(OC2CCN(Cc3ccncc3)CC2)c(Cl)c1]

Following the procedure as described in Example 22, and making non-critical variations as required to replace 4-fluorobenzaldehyde with isonicotinaldehyde, and purification by column chromatography eluting with 0 to 20% of methanol, the title compound was obtained as a colorless solid (0.17 g, 36% yield). $^1$H NMR (300 MHz, DMSO-$d_6$) δ 12.67 (br s, 1H), 8.48-8.46 (m, 2H), 7.70 (d, J=2.2 Hz, 1H), 7.64 (dd, J=8.7, 2.3 Hz, 1H), 7.32-7.29 (m, 3H), 7.24-7.22 (m, 1H), 6.80-6.78 (m, 1H), 4.64-4.60 (m, 1H), 3.51 (s, 2H), 2.61-2.56 (m, 2H), 2.33-2.28 (m, 2H), 1.95-1.88 (m, 2H), 1.74-1.63 (m, 2H); MS (ES+) m/z 465.0 (M+1), 467.0 (M+1).

Example 64

Synthesis of 3-chloro-4-((1-(pyridin-3-ylmethyl)piperidin-4-yl)oxy)-N-(thiazol-2-yl)benzenesulfonamide

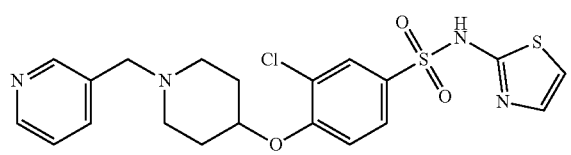 [SMILES: O=S(=O)(Nc1nccs1)c1ccc(OC2CCN(Cc3cccnc3)CC2)c(Cl)c1]

Following the procedure as described in Example 22, and making non-critical variations as required to replace 4-fluorobenzaldehyde with nicotinaldehyde, and purification by column chromatography eluting with 0 to 20% of methanol, the title compound was obtained as a colorless solid (0.18 mg, 39% yield). $^1$H NMR (300 MHz, DMSO-$d_6$) δ 8.47-8.42 (m, 2H), 7.70-7.66 (m, 2H), 7.64 (dd, J=8.7, 2.3 Hz, 1H), 7.34-7.28 (m, 2H), 7.21 (d, J=4.6 Hz, 1H), 6.78 (d, J=4.6 Hz, 1H), 4.64-4.57 (m, 1H), 3.51 (s, 2H), 2.61-2.55 (m, 2H), 2.33-2.26 (m, 2H), 1.93-1.87 (m, 2H), 1.71-1.61 (m, 2H); NH not observed; MS (ES+) m/z 465.0 (M+1), 467.0 (M+1).

Example 65

Synthesis of 3-chloro-4-((1-(pyridin-2-ylmethyl)piperidin-4-yl)oxy)-N-(thiazol-2-yl)benzenesulfonamide

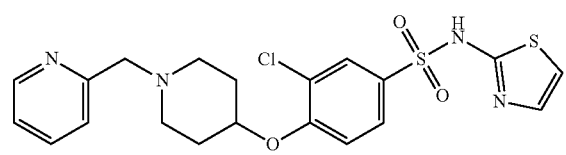 [SMILES: O=S(=O)(Nc1nccs1)c1ccc(OC2CCN(Cc3ccccn3)CC2)c(Cl)c1]

Following the procedure as described in Example 22, and making non-critical variations as required to replace 4-fluorobenzaldehyde with picolinaldehyde, and purification by column chromatography eluting with 0 to 20% of methanol, the title compound was obtained as a colorless solid (0.20 mg, 43% yield). $^1$H NMR (300 MHz, DMSO-$d_6$) δ 12.48 (br s, 1H), 8.47-8.45 (m, 1H), 7.77-7.70 (m, 2H), 7.64 (dd, J=8.7, 2.3 Hz, 1H), 7.42 (d, J=7.8 Hz, 1H), 7.31 (d, J=8.9 Hz, 1H), 7.25-7.21 (m, 2H), 6.78 (s, J=4.6 Hz, 1H), 4.65-4.58 (m, 1H), 3.63 (s, 2H), 2.71-2.64 (m, 2H), 2.42-2.34 (m, 2H), 1.97-1.90 (m, 2H), 1.74-1.63 (m, 2H); MS (ES+) m/z 465.0 (M+1), 467.0 (M+1).

Example 66

Synthesis of (R)-4-((1-benzylpyrrolidin-3-yl)amino)-3-chloro-N-(1,2,4-thiadiazol-5-yl)benzenesulfonamide 2,2,2-trifluoroacetate

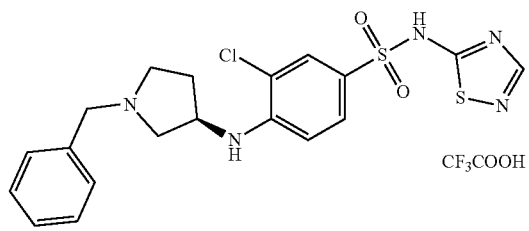 [SMILES: O=S(=O)(Nc1ncns1)c1ccc(N[C@@H]2CCN(Cc3ccccc3)C2)c(Cl)c1 ; "CF3COOH"]

Step 1. Preparation of (R)-4-((1-benzylpyrrolidin-3-yl)amino)-3-chloro-N-(2,4-dimethoxybenzyl)-N-(1,2,4-thiadiazol-5-yl)benzenesulfonamide

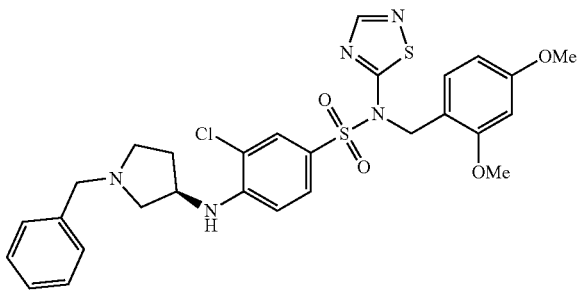 [SMILES: COc1ccc(CN(c2ncns2)S(=O)(=O)c2ccc(N[C@@H]3CCN(Cc4ccccc4)C3)c(Cl)c2)c(OC)c1]

To a mixture of 3-chloro-N-(2,4-dimethoxybenzyl)-4-fluoro-N-(1,2,4-thiadiazol-5-yl)benzenesulfonamide (0.40 g, 0.90 mmol) and anhydrous potassium carbonate (0.31 g, 2.25 mmol) in anhydrous dimethyl sulfoxide (2 mL) was added (R)-1-benzylpyrrolidin-3-amine (0.16 g, 0.90 mmol) and the reaction mixture was stirred at ambient temperature for 16 h. The mixture was diluted with ethyl acetate (50 mL), washed with water (20 mL), brine (3×50 mL), dried over anhydrous sodium sulfate, and filtered. Concentration in vacuo and purification of the residue by column chromatography eluting with a gradient of 0 to 5% of methanol in dichloromethane afforded the title compound as a colorless solid (0.54 g, quantitative yield): $^1$H NMR (300 MHz, CD$_3$OD) δ8.16 (s, 1H), 7.43 (dd, J=8.8, 2.3 Hz, 1H), 7.34-7.22 (m, 6H), 6.90 (d, J=8.1 Hz, 1H), 6.60 (d, J=8.9 Hz, 1H), 6.29-6.25 (m, 2H), 5.21 (s, 2H), 4.13-4.05 (m, 1H), 3.69 (s, 3H), 3.66 (s, 2H), 3.60 (s, 3H), 2.88-2.80 (m, 2H), 2.61 (dd, J=10.1, 3.8 Hz, 1H), 2.54-2.46 (m, 1H), 2.42-2.31 (m, 1H), 1.77-1.66 (m, 1H), NH not observed; MS (ES+) m/z 600.1 (M+1), 602.1 (M+1).

Step 2. Preparation of (R)-4-((1-benzylpyrrolidin-3-yl)amino)-3-chloro-N-(1,2,4-thiadiazol-5-yl)benzenesulfonamide 2,2,2-trifluoroacetate

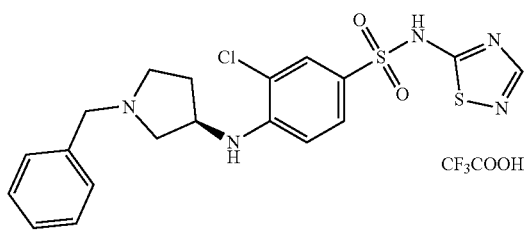 [SMILES: O=S(=O)(Nc1ncns1)c1ccc(N[C@@H]2CCN(Cc3ccccc3)C2)c(Cl)c1 ; "CF3COOH"]

To a solution of (R)-4-((1-benzylpyrrolidin-3-yl)amino)-3-chloro-N-(2,4-dimethoxybenzyl)-N-(1,2,4-thiadiazol-5-yl)benzenesulfonamide (0.14 g, 0.23 mmol) in dichloromethane (1.4 mL) was added trifluoroacetic acid (0.8 mL). The reaction mixture was stirred at ambient temperature for 30 minutes and then concentrated in vacuo. To the residue was added methanol (20 mL) and the obtained suspension was filtered.

The filtrate was concentrated in vacuo to give the title compound as a beige solid (0.11 g, 82% yield). $^1$H NMR (300 MHz, CD$_3$OD) δ 8.14 (s, 1H), 7.71 (d, J=2.1 Hz, 1H), 7.64 (dd, J=8.7, 2.1 Hz, 1H), 7.51-7.45 (m, 5H), 6.78 (d, J=8.8 Hz, 1H), 4.48-4.44 (m, 1H), 4.43-4.42 (m, 2H), 3.77-3.68 (m, 1H), 3.63-3.51 (m, 1H), 3.48-3.37 (m, 2H), 2.67-2.56 (m, 1H), 2.18-2.07 (m, 1H), 2 NH and COOH not observed; MS (ES+) m/z 450.0 (M+1) 452.0 (M+1).

Example 67

Synthesis of (S)-4-((1-benzylpyrrolidin-3-yl)amino)-3-chloro-N-(1,2,4-thiadiazol-5-yl)benzenesulfonamide 2,2,2-trifluoroacetate

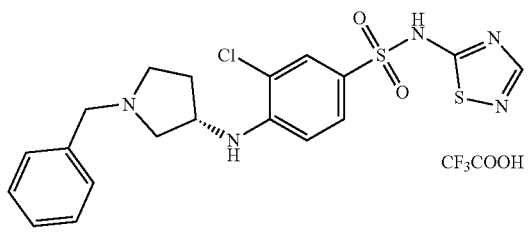 [SMILES: O=S(=O)(Nc1ncns1)c1ccc(N[C@H]2CCN(Cc3ccccc3)C2)c(Cl)c1 ; "CF3COOH"]

Step 1. Preparation of tert-butyl (S)-(1-benzylpyrrolidin-3-yl)carbamate

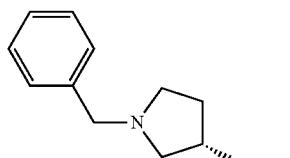

To a solution of tert-butyl (S)-pyrrolidin-3-ylcarbamate (0.30 g, 1.60 mmol) in anhydrous 1,2-dichloroethane (2 mL) and anhydrous N,N-dimethylformamide (2 mL) was added benzaldehyde (0.26 g, 2.40 mmol). The reaction mixture was stirred at ambient temperature for 10 minutes and then sodium triacetoxyborohydride (0.68 g, 3.20 mmol) was added to it. The reaction mixture was stirred at ambient temperature for 5 h. After dilution with ethyl acetate (50 mL), the mixture was washed with brine (3×50 mL), dried over anhydrous sodium sulfate, and filtered. Concentration of the filtrate in vacuo provided the title compound as colorless oil (0.37 g, 84% yield). $^1$H NMR (300 MHz, CDCl$_3$) 37.58-7.53 (m, 2H), 7.46-7.39 (m, 3H), 4.55-4.49 (m, 1H), 4.16 (s, 2H), 3.67-3.52 (m, 1H), 3.40-3.36 (m, 1H), 3.12-3.06 (m, 1H), 2.91-2.81 (m, 1H), 2.52-2.40 (m, 1H), 2.25-2.12 (m, 1H), 1.39 (s, 9H), NH not observed; MS (ES+) m/z 277.2 (M+1).

Step 2. Preparation of (S)-1-benzylpyrrolidin-3-amine

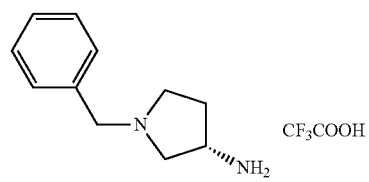 [SMILES: N[C@H]1CCN(Cc2ccccc2)C1 ; "CF3COOH"]

To a solution of tert-butyl (S)-(1-benzylpyrrolidin-3-yl)carbamate (0.37 g, 1.34 mmol) in dichloromethane (20 mL) was added trifluoroacetic acid (4.0 mL). The reaction mixture was stirred at ambient temperature for 1.5 h and concentrated in vacuo to give the title compound as beige oil 0.39 g, quantitative yield): MS (ES+) m/z 177.2 (M+1).

Step 3. Preparation of (S)-4-((1-benzylpyrrolidin-3-yl)amino)-3-chloro-N-(2,4-dimethoxybenzyl)-N-(1,2,4-thiadiazol-5-yl)benzenesulfonamide

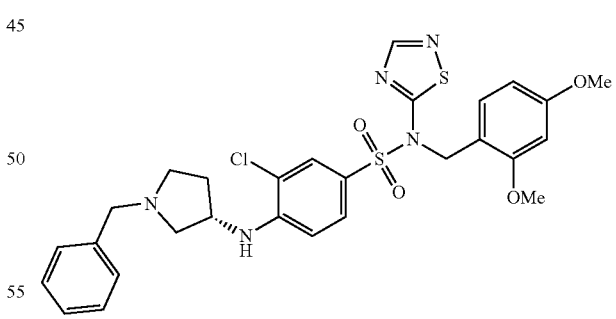

Following the procedure as described in Example 66 Step 1 and making non-critical variations as required to replace (R)-1-benzylpyrrolidin-3-amine with (S)-1-benzylpyrrolidin-3-amine 2,2,2-trifluoroacetate, the title compound was obtained as white solid (0.43 g, 79% yield): $^1$H NMR (300 MHz, CD$_3$OD) δ 8.20 (s, 1H), 7.47 (dd, J=8.9, 2.3 Hz, 1H), 7.39-7.33 (m, 5H), 7.32-7.26 (m, 2H), 6.94 (d, J=8.1 Hz, 1H), 6.64 (d, J=8.9 Hz, 1H), 6.33-6.28 (m, 2H), 5.25 (s, 2H), 4.17-4.09 (m, 1H), 3.73 (s, 3H), 3.69 (s, 2H), 3.63 (s, 3H), 2.89-2.84 (m, 2H), 2.65 (dd, J=10.1, 3.8 Hz, 1H), 2.54 (d, J=7.5 Hz, 1H), 2.40 (d, J=8.3 Hz, 1H), sulfonamide NH not observed; MS (ES+) m/z 600.1 (M+1), 602.1 (M+1).

Step 4. Preparation of (S)-4-((1-benzylpyrrolidin-3-yl)amino)-3-chloro-N-(1,2,4-thiadiazol-5-yl)benzenesulfonamide 2,2,2-trifluoroacetate

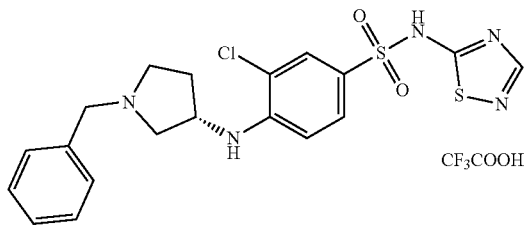 [SMILES: O=S(=O)(Nc1ncns1)c1ccc(N[C@H]2CCN(Cc3ccccc3)C2)c(Cl)c1 ; "CF3COOH"]

Following the procedure as described in Example 66 Step 2 and making non-critical variations as required to replace (R)-4-((1-benzylpyrrolidin-3-yl)amino)-3-chloro-N-(2,4-dimethoxybenzyl)-N-(1,2,4-thiadiazol-5-yl)benzenesulfonamide with (S)-4-((1-benzylpyrrolidin-3-yl)amino)-3-chloro-N-(2,4-dimethoxybenzyl)-N-(1,2,4-thiadiazol-5-yl) benzenesulfonamide, the title compound was obtained a colorless solid 0.10 mg, quantitative yield): $^1$H NMR (300 MHz, CD$_3$OD) δ 8.14 (s, 1H), 7.71 (d, J=2.1 Hz, 1H), 7.64 (dd, J=8.7, 2.1 Hz, 1H), 7.51-7.45 (m, 5H), 6.78 (d, J=8.8 Hz, 1H), 4.49-4.45 (m, 1H), 4.42-4.42 (m, 2H), 3.77-3.68 (m, 1H), 3.63-3.52 (m, 1H), 3.49-3.35 (m, 2H), 2.67-2.54 (m, 1H), 2.18-2.06 (m, 1H), 2 NH and COOH not observed; MS (ES+) m/z 450.0 (M+1), 452.0 (M+1).

Example 68

Synthesis of (R)-4-((1-benzylpyrrolidin-3-yl)(methyl)amino)-3-chloro-N-(1,2,4-thiadiazol-5-yl)benzenesulfonamide 2,2,2-trifluoroacetate

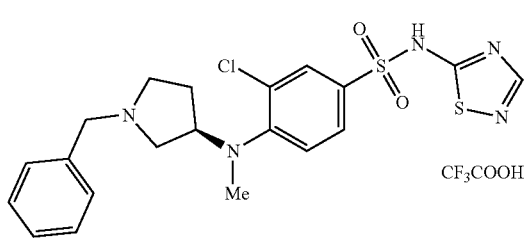 [SMILES: CN(c1ccc(S(=O)(=O)Nc2ncns2)cc1Cl)[C@@H]1CCN(Cc2ccccc2)C1 ; "CF3COOH"]

Step 1. Preparation of (R)-4-((1-benzylpyrrolidin-3-yl)(methyl)amino)-3-chloro-N-(2,4-dimethoxybenzyl)-N-(1,2,4-thiadiazol-5-yl)benzenesulfonamide

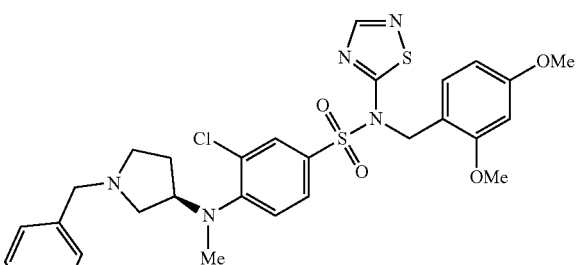

To a mixture of (R)-4-((1-benzylpyrrolidin-3-yl)amino)-3-chloro-N-(2,4-dimethoxybenzyl)-N-(1,2,4-thiadiazol-5-yl)benzenesulfonamide (0.37 g, 0.62 mmol) in anhydrous tetrahydrofuran (9.0 mL) was added a 60% dispersion of sodium hydride in mineral oil (0.027 g, 0.68 mmol) at 0° C. The reaction mixture was allowed to warm to ambient temperature and stirred for 1h. The reaction mixture was then cooled to 0° C. and a 0.5 M solution of iodomethane in anhydrous tetrahydrofuran (1.0 mL, 0.50 mmol) was added to it. The reaction mixture was allowed to warm to ambient temperature, stirred for 16 h, and quenched by addition of water (10 mL). After dilution with ethyl acetate (50 mL), the organic phase was washed with brine (3×50 mL), dried over anhydrous sodium sulfate, and concentrated in vacuo. The residue was purified by preparative reverse-phase HPLC eluting with eluting with a gradient of 15 to 92% of acetonitrile in water (containing 0.2% of ammonium hydroxide) to provide the title compound as a colorless solid (0.012 g, 3% yield): MS (ES+) m/z 614.1 (M+1), 616.1 (M+1).

Step 2. Preparation of (R)-4-((1-benzylpyrrolidin-3-yl)(methyl)amino)-3-chloro-N-(1,2,4-thiadiazol-5-yl)benzenesulfonamide 2,2,2-trifluoroacetate

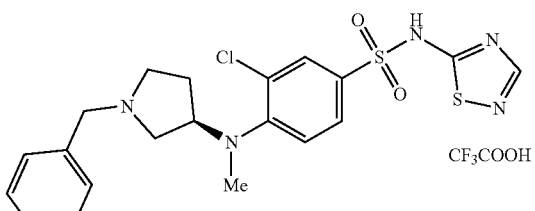

Following the procedure as described in Example 66 Step 2 and making non-critical variations as required to replace (R)-4-((1-benzylpyrrolidin-3-yl)amino)-3-chloro-N-(2,4-dimethoxybenzyl)-N-(1,2,4-thiadiazol-5-yl)benzenesulfonamide with (R)-4-((1-benzylpyrrolidin-3-yl)(methyl)amino)-3-chloro-N-(2,4-dimethoxybenzyl)-N-(1,2,4-thiadiazol-5-yl)benzenesulfonamide, the title compound was obtained as a colorless solid 0.02 g, quantitative yield): $^1$H NMR (300 MHz, CD$_3$OD) δ 8.16 (br s, 1H), 7.86 (d, J=2.1 Hz, 1H), 7.75 (dd, J=8.5, 2.1 Hz, 1H), 7.45 (s, 5H), 7.32 (d, J=8.5 Hz, 1H), 4.39 (s, 2H), 4.34-4.28 (m, 1H), 3.61-3.52 (m, 1H), 3.48-3.34 (m, 2H), 3.24-3.20 (m, 1H), 2.77 (s, 3H), 2.29-2.12 (m, 2H), NH and COOH not observed; MS (ES+) m/z 464.0 (M+1), 466.0 (M+1).

Example 69

Synthesis of (R)-3-chloro-4-((1-(3-chlorobenzyl)pyrrolidin-3-yl)amino)-N-(thiazol-2-yl) benzenesulfonamide

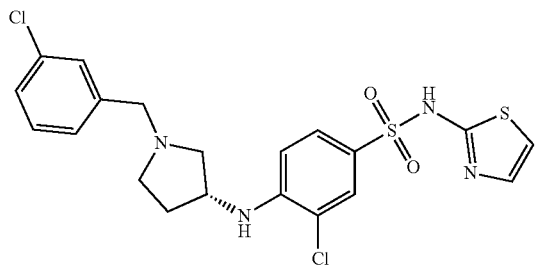 [SMILES: O=S(=O)(Nc1nccs1)c1ccc(N[C@@H]2CCN(Cc3cccc(Cl)c3)C2)c(Cl)c1]

Step 1. Preparation of tert-butyl (R)-3-((2-chloro-4-(N-(2,4-dimethoxybenzyl)-N-(thiazol-2-yl)sulfamoyl)phenyl)amino)pyrrolidine-1-carboxylate

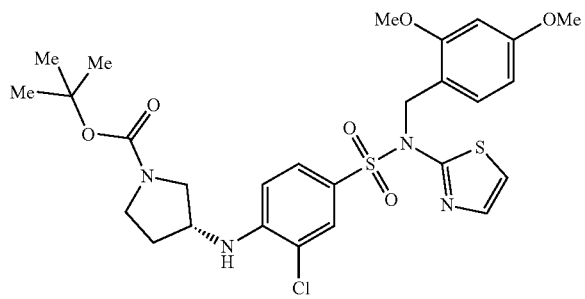 [SMILES: COc1ccc(CN(c2nccs2)S(=O)(=O)c2ccc(N[C@@H]3CCN(C(=O)OC(C)(C)C)C3)c(Cl)c2)c(OC)c1]

To a suspension of 3-chloro-N-(2,4-dimethoxybenzyl)-4-fluoro-N-(thiazol-2-yl) benzenesulfonamide (1.08 g, 2.44 mmol) and tert-butyl (R)-3-aminopyrrolidine-1-carboxylate (0.500 g, 2.68 mmol) in anhydrous dimethyl sulfoxide (10 mL) was added potassium carbonate (0.843 g, 6.10 mmol) and the reaction mixture was stirred at ambient temperature for 18 h. The reaction mixture was diluted with ethyl acetate (50 mL) and water (20 mL) and the aqueous phase was extracted with ethyl acetate (2×50 mL). The combined organic phases were washed with brine (3×20 mL), dried over anhydrous sodium sulfate, and filtered. Concentration of the filtrate in vacuo and purification of the residue by column chromatography eluting with a gradient of 0 to 50% of ethyl acetate in hexanes afforded the title compound as a colorless foam (0.72 g, 48% yield): MS (ES+) m/z 609.1 (M+1), 611.1 (M+1).

Step 2. Preparation of (R)-3-chloro-4-(pyrrolidin-3-ylamino)-N-(thiazol-2-yl)benzenesulfonamide 2,2,2-trifluoroacetate

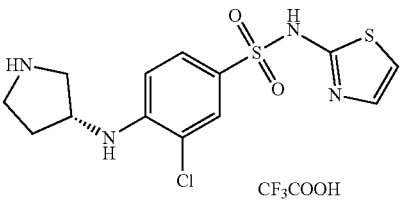 [SMILES: O=S(=O)(Nc1nccs1)c1ccc(N[C@@H]2CCNC2)c(Cl)c1 ; "CF3COOH"]

To a solution of tert-butyl (R)-3-((2-chloro-4-(N-(2,4-dimethoxybenzyl)-N-(thiazol-2-yl)sulfamoyl) phenyl)amino)pyrrolidine-1-carboxylate (0.72 g, 1.17 mmol) in anhydrous dichloromethane (7.5 mL) was added trifluoroacetic acid (3 mL) and the reaction mixture was stirred at ambient temperature for 3 h. The reaction mixture was concentrated in vacuo and the residue was suspended in methanol (20 mL). The mixture was stirred at ambient temperature for 16 h, filtered, and the residue was washed with methanol (2×15 mL). Concentration of the filtrate in vacuo afforded (R)-3-chloro-4-(pyrrolidin-3-ylamino)-N-(thiazol-2-yl)benzenesulfonamide 2,2,2-trifluoroacetate beige foam (0.52 g, 94% yield): MS (ES+) m/z 359.0 (M+1), 361.0 (M+1).

Step 3. Preparation of (R)-3-chloro-4-((1-(3-chlorobenzyl)pyrrolidin-3-yl)amino)-N-(thiazol-2-yl)benzenesulfonamide

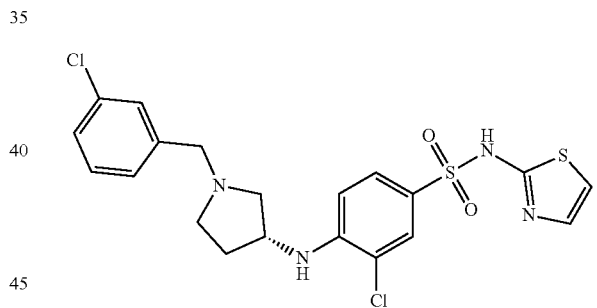

To a solution of (R)-3-chloro-4-(pyrrolidin-3-ylamino)-N-(thiazol-2-yl)benzenesulfonamide 2,2,2-trifluoroacetate (0.170 g, 0.36 mmol) in anhydrous 1,2-dichloroethane (2 mL) and anhydrous N,N-dimethylformamide (2 mL) was added 3-chlorobenzaldehyde (0.15 g, 1.08 mmol). The reaction mixture was stirred for 15 minutes and then sodium triacetoxyborohydride (0.23 g, 1.08 mmol) was added to it. The reaction mixture was stirred at ambient temperature for 16 h. The reaction mixture was diluted with ethyl acetate (50 mL) and washed with brine (2×25 mL). The combined aqueous layers were extracted with ethyl acetate (3×75 mL). The combined organic phase was dried over anhydrous sodium sulfate, filtered, and the filtrate concentrated in vacuo. The residue was purified by column chromatography, eluting with a gradient of 0 to 5% of methanol (containing 0.2% of ammonium hydroxide) in dichloromethane to afford the title compound as a colorless solid (0.136 g, 78% yield): $^1$H NMR (300 MHz, DMSO-$d_6$) δ 12.53 (br s, 1H), 7.58 (d, J=2.2 Hz, 1H), 7.52 (dd, J=2.1, 8.5 Hz, 1H), 7.38-7.35 (m, 1H), 7.32-7.26 (m, 2H), 7.23 (d, J=4.6 Hz, 1H), 6.82-6.77

(m, 2H), 5.72 (d, J=7.0 Hz, 1H), 4.09-4.02 (m, 1H), 3.63 (s, 2H), 3.41-3.28 (m, 1H), 2.83 (dd, J=6.7, 9.4 Hz, 1H), 2.72-2.64 (m, 1H), 2.53-2.44 (m, 2H), 2.29-2.17 (m, 1H), 1.81-1.71 (m, 1H); (ES-) m/z 481.0 (M−1), 483.0 (M−1).

Example 70

Synthesis of (R)-3-chloro-4-((1-(3-methylbenzyl) pyrrolidin-3-yl)amino)-N-(thiazol-2-yl) benzenesulfonamide

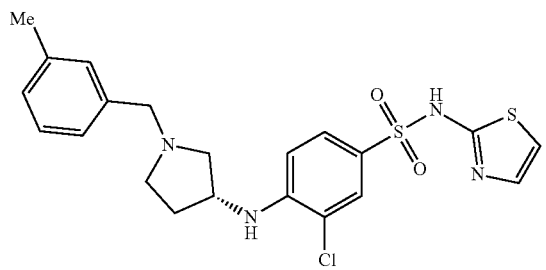 [SMILES: Cc1cccc(CN2CC[C@@H](Nc3ccc(S(=O)(=O)Nc4nccs4)cc3Cl)C2)c1]

Following the procedure as described in Example 69 Step 3 and making non-critical variations as required to replace 3-chlorobenzaldehyde with 3-methylbenzaldehyde, the title compound was obtained as a colorless solid 0.085 g, 51% yield): $^1$H NMR (300 MHz, DMSO-$d_6$) δ 12.44 (br s, 1H), 7.57 (d, J=2.1 Hz, 1H), 7.51 (dd, J=2.1, 8.6 Hz, 1H), 7.22-7.04 (m, 4H), 6.82-6.75 (m, 2H), 5.70 (d, J=7.0 Hz, 1H), 4.10-3.99 (m, 1H), 3.60 (s, 2H), 3.43-3.24 (m, 1H), 2.88-2.79 (m, 1H), 2.74-2.63 (m, 1H), 2.57-2.41 (m, 2H), 2.34-2.23 (m, 1H), 2.27 (s, 3H), 1.81-1.70 (m, 1H); MS (ES+) m/z 463.0 (M+1), 465.0 (M+1).

Example 71

Synthesis of (R)-3-chloro-4-((1-(2-fluorobenzyl) pyrrolidin-3-yl)amino)-N-(thiazol-2-yl) benzenesulfonamide

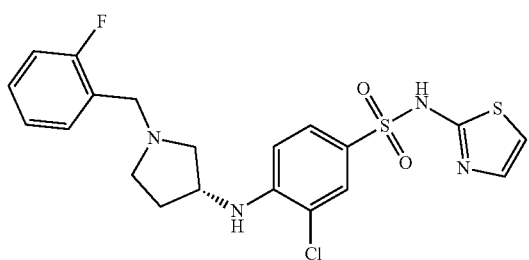 [SMILES: O=S(=O)(Nc1nccs1)c1ccc(N[C@@H]2CCN(Cc3ccccc3F)C2)c(Cl)c1]

Following the procedure as described in Example 69 Step 3 and making non-critical variations as required to replace 3-chlorobenzaldehyde with 2-fluorobenzaldehyde, the title compound was obtained as colorless solid (0.138 g, 82% yield): $^1$H NMR (300 MHz, DMSO-$d_6$) δ $^1$H NMR (300 MHz, DMSO-$d_6$) δ 12.44 (br s, 1H), 7.58 (d, J=2.1 Hz, 1H), 7.52 (dd, J=2.2, 8.6 Hz, 1H), 7.44-7.38 (m, 1H), 7.35-7.27 (m, 1H), 7.15-7.12 (m, 2H), 6.80 (d, J=8.8 Hz, 1H), 6.78 (d, J=4.6 Hz, 1H), 5.72 (d, J=7.0 Hz, 1H), 4.08-4.00 (m, 1H), 3.67 (s, 2H), 3.38-3.30 (m, 1H), 2.89-2.84 (m, 1H), 2.73-2.65 (m, 1H), 2.53-2.46 (m, 2H), 2.28-2.16 (m, 1H), 1.81-1.70 (m, 1H); MS (ES+) m/z 467.0 (M+1), 469.0 (M+1).

Example 72

Synthesis of 4-((cis-1-benzyl-2-methylpiperidin-4-yl)oxy)-3-chloro-N-(thiazol-2-yl)benzenesulfonamide

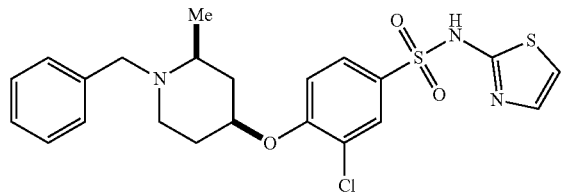 [SMILES: C[C@H]1C[C@@H](Oc2ccc(S(=O)(=O)Nc3nccs3)cc2Cl)CCN1Cc1ccccc1]

Step 1. Preparation of tert-butyl cis-4-hydroxy-2-methylpiperidine-1-carboxylate

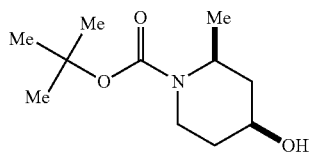 [SMILES: C[C@H]1C[C@@H](O)CCN1C(=O)OC(C)(C)C]

To a solution of tert-butyl 2-methyl-4-oxopiperidine-1-carboxylate (1.5 g, 7.03 mmol) in anhydrous tetrahydrofuran (110 mL) was added a 1.0 M solution of lithium tri-sec-butylborohydride in tetrahydrofuran (8.10 mL, 8.1 mmol) at −78° C. The reaction mixture was stirred at −78° C. for 20 minutes before it was quenched by addition of methanol (15 mL). The reaction mixture was diluted with water (300 mL) and dichloromethane (300 mL) and allowed to warm to ambient temperature. The aqueous layer was extracted with dichloromethane (2×150 mL). The combined organic phases were washed with brine (50 mL), dried over anhydrous sodium sulfate, filtered, and the filtrate concentrated in vacuo. The residue was purified by column chromatography eluting with a gradient of 0 to 40% of ethyl acetate in hexanes to yield the title compound as a colorless solid (1.08 g, 71% yield): $^1$H NMR (300 MHz, CDCl$_3$) δ 4.32-4.23 (m, 1H), 4.20-4.13 (m, 1H), 3.84-3.77 (m, 1H), 3.24 (ddd, J=13.6, 11.1, 4.7 Hz, 1H), 1.84 (ddd, J=14.4, 6.6, 3.3 Hz, 1H), 1.77-1.60 (m, 3H), 1.58-1.51 (m, 1H), 1.44 (s, 9H), 1.31 (d, J=7.1 Hz, 3H); MS (ES+) m/z 216.3.

Step 2. Preparation of tert-butyl cis-4-(2-chloro-4-(N-(2,4-dimethoxybenzyl)-N-(thiazol-2-yl)sulfamoyl)phenoxy)-2-methylpiperidine-1-carboxylate

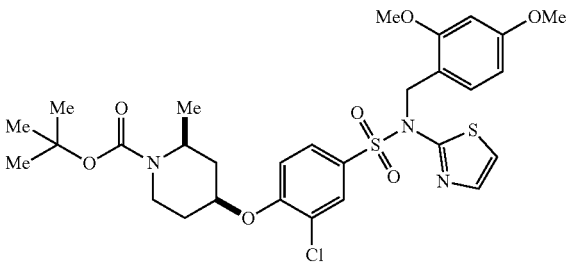 [SMILES: COc1ccc(CN(c2nccs2)S(=O)(=O)c2ccc(O[C@H]3CCN(C(=O)OC(C)(C)C)[C@@H](C)C3)c(Cl)c2)c(OC)c1]

To a mixture of 3-chloro-N-(2,4-dimethoxybenzyl)-4-fluoro-N-(thiazol-2-yl) benzenesulfonamide (1.1 g, 2.49 mmol) and tert-butyl cis-4-hydroxy-2-methylpiperidine-1-carboxylate (0.535 g, 2.49 mmol) in anhydrous dimethyl sulfoxide (15 mL) was added cesium carbonate (2.03 g, 6.23 mmol) and the reaction mixture was stirred at ambient temperature for 18 h. The reaction mixture was diluted with ethyl acetate (50 mL) and water (20 mL). The aqueous phase was extracted with ethyl acetate (2×50 mL). The combined organic phases were washed with brine (3×20 mL), dried over anhydrous sodium sulfate, filtered, and the filtrate was concentrated in vacuo. The residue was purified by column chromatography eluting with a gradient of 0 to 50% of ethyl acetate in hexanes to afford the title compound as a yellowish foam (1.14 g, 72% yield): MS (ES+) m/z 638.1 (M+1).

Step 3. Preparation of 3-chloro-4-((cis-2-methylpiperidin-4-yl)oxy)-N-(thiazol-2-yl)benzenesulfonamide 2,2,2-trifluoroacetate

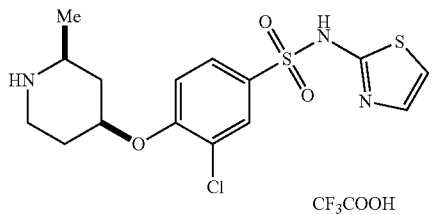 [SMILES: C[C@H]1C[C@@H](Oc2ccc(S(=O)(=O)Nc3nccs3)cc2Cl)CCN1 ; "CF3COOH"]

CF$_3$COOH

To a solution of tert-butyl cis-4-(2-chloro-4-(N-(2,4-dimethoxybenzyl)-N-(thiazol-2-yl)sulfamoyl)phenoxy)-2-methylpiperidine-1-carboxylate (1.14 g, 1.79 mmol) in dichloromethane (12 mL) was added trifluoroacetic acid (5 mL) and the reaction mixture was stirred at ambient temperature for 3 h. The reaction mixture was concentrated in vacuo and the residue was diluted with methanol (20 mL). The mixture was stirred at ambient temperature for 16 h and the filtered. The residue was rinsed with methanol (2×15 mL) and the filtrate was concentrated in vacuo to afford the title compound as a beige solid (0.90 g, quantitative yield): MS (ES+) m/z 388.2 (M+1), 390.2 (M+1).

Step 4. Preparation of 4-((cis-1-benzyl-2-methylpiperidin-4-yl)oxy)-3-chloro-N-(thiazol-2-yl)benzenesulfonamide

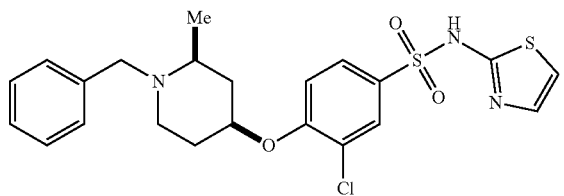 [SMILES: C[C@H]1C[C@@H](Oc2ccc(S(=O)(=O)Nc3nccs3)cc2Cl)CCN1Cc1ccccc1]

To a solution of 3-chloro-4-((cis-2-methylpiperidin-4-yl)oxy)-N-(thiazol-2-yl)benzenesulfonamide 2,2,2-trifluoroacetate (0.4 g, 0.825 mmol) in anhydrous 1,2-dichloroethane (5 mL) and anhydrous N,N-dimethylformamide (5 mL) was added benzaldehyde (0.21 mL, 2.06 mmol). The reaction mixture was stirred for 15 minutes and then sodium triacetoxyborohydride (0.525 g, 2.49 mmol) was added to it. The reaction mixture was stirred at ambient temperature for 16 h.

The reaction mixture was diluted with ethyl acetate (75 mL) and washed with brine (2×50 mL). The combined aqueous layers were extracted with ethyl acetate (3×100 mL). The combined organic phase was dried over anhydrous sodium sulfate, filtered, and the filtrate concentrated in vacuo. The residue was purified by column chromatography, eluting with a gradient of 0 to 5% of methanol (containing 0.2% of ammonium hydroxide) in dichloromethane to afford the title compound as a colorless solid (0.214 g, 54% yield): $^1$H NMR (300 MHz, DMSO-d$_6$) δ 12.26 (br s, 1H), 7.73 (d, J=2.3 Hz, 1H), 7.66 (dd, J=8.7, 2.3 Hz, 1H), 7.38-7.21 (m, 7H), 6.82 (d, J=4.5 Hz, 1H), 4.57-4.47 (m, 1H), 4.03 (d, J=13.6 Hz, 1H), 3.24 (d, J=13.6 Hz, 1H), 2.78 (dt, J=12.1, 3.7 Hz, 1H), 2.54-2.46 (m, 1H), 2.17-1.95 (m, 3H), 1.55-1.38 (m, 2H), 1.20 (d, J=6.2 Hz, 3H); MS (ES+) m/z 478.0 (M+1), 480.0 (M+1).

Example 73

Synthesis of 4-((trans-1-benzyl-2-methylpiperidin-4-yl)oxy)-3-chloro-N-(thiazol-2-yl)benzenesulfonamide

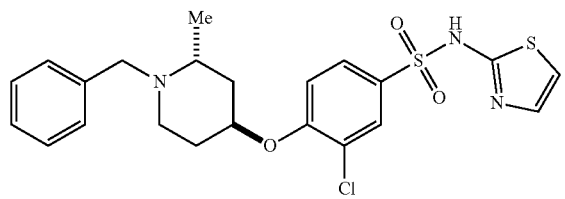 [SMILES: C[C@@H]1C[C@@H](Oc2ccc(S(=O)(=O)Nc3nccs3)cc2Cl)CCN1Cc1ccccc1]

Step 1. Preparation of tert-butyl trans-4-hydroxy-2-methylpiperidine-1-carboxylate

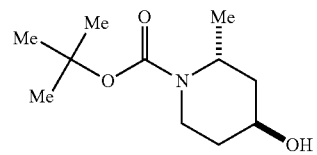 [SMILES: C[C@@H]1C[C@@H](O)CCN1C(=O)OC(C)(C)C]

To a solution of tert-butyl 2-methyl-4-oxopiperidine-1-carboxylate (1.5 g, 7.03 mmol) in anhydrous ethanol (30 mL)) was added sodium borohydride (0.4 g, 10.55 mmol) and the reaction mixture was stirred at ambient temperature for 2 h. The reaction mixture was concentrated in vacuo and the residue was diluted with water (15 mL) and a mixture of hexanes and ethyl acetate (1:1, 30 mL). The aqueous layer was extracted with a mixture of hexanes and ethyl acetate (1:1, 3×50 mL). The combined organic phases were washed with brine (50 mL), dried over anhydrous sodium sulfate, filtered, and the filtrate was concentrated in vacuo. Purification of the residue by column chromatography eluting with a gradient of 0 to 40% of ethyl acetate in hexanes afforded the title compound as a colorless solid (0.627 g, 41% yield); $^1$H NMR (300 MHz, CDCl$_3$) 94.51-4.42 (m, 1H), 4.06-3.87 (m, 2H), 2.85 (dt, J=13.5, 2.8 Hz, 1H), 2.14-1.96 (m, 1H), 1.94-1.77 (m, 2H), 1.56-1.45 (m, 1H), 1.42 (s, 9H), 1.41-1.22 (m, 1H), 1.12 (d, J=7.1 Hz, 3H); MS (ES+) m/z 216.3 (M+1).

Step 2. Preparation of tert-butyl trans-4-(2-chloro-4-(N-(2,4-dimethoxybenzyl)-N-(thiazol-2-yl)sulfamoyl)phenoxy)-2-methylpiperidine-1-carboxylate

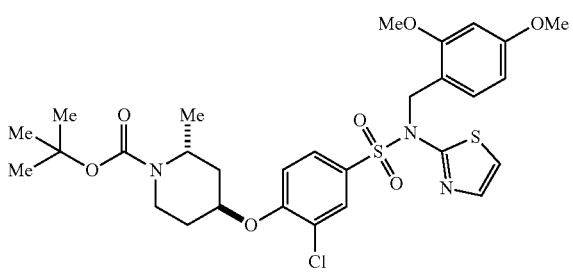 [SMILES: COc1ccc(CN(c2nccs2)S(=O)(=O)c2ccc(O[C@H]3CCN(C(=O)OC(C)(C)C)[C@H](C)C3)c(Cl)c2)c(OC)c1]

Following the procedure as described in Example 72, Step 2 and making non-critical variations as required to replace tert-butyl cis-4-hydroxy-2-methylpiperidine-1-carboxylate with tert-butyl trans-4-hydroxy-2-methylpiperidine-1-carboxylate, the title compound was obtained as a yellowish foam (1.02 g, 71% yield): MS (ES+) m/z 638.1 (M+1).

Step 3. Preparation of 3-chloro-4-((trans-2-methylpiperidin-4-yl)oxy)-N-(thiazol-2-yl)benzenesulfonamide 2,2,2-trifluoroacetate

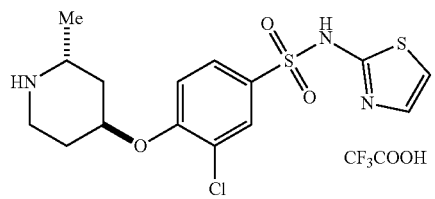 [SMILES: C[C@@H]1C[C@@H](Oc2ccc(S(=O)(=O)Nc3nccs3)cc2Cl)CCN1 ; "CF3COOH"]

Following the procedure as described in Example 72, Step 3 and making non-critical variations as required to replace tert-butyl cis-4-(2-chloro-4-(N-(2,4-dimethoxybenzyl)-N-(thiazol-2-yl)sulfamoyl)phenoxy)-2-methylpiperidine-1-carboxylate with tert-butyl trans-4-(2-chloro-4-(N-(2,4-dimethoxybenzyl)-N-(thiazol-2-yl)sulfamoyl)phenoxy)-2-methylpiperidine-1-carboxylate, the title compound was obtained as beige solid (0.925 g, quantitative yield): MS (ES+) m/z 388.2 (M+1), 390.2 (M+1).

Step 4. Preparation of 4-((trans-1-benzyl-2-methylpiperidin-4-yl)oxy)-3-chloro-N-(thiazol-2-yl)benzenesulfonamide

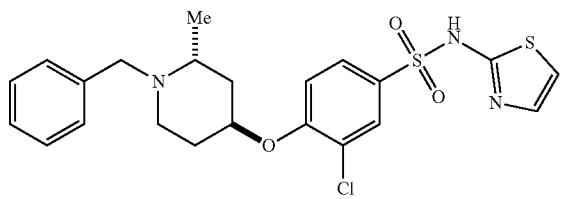 [SMILES: C[C@@H]1C[C@@H](Oc2ccc(S(=O)(=O)Nc3nccs3)cc2Cl)CCN1Cc1ccccc1]

Following the procedure as described in Example 72, Step 4 and making non-critical variations as required to replace 3-chloro-4-((cis-2-methylpiperidin-4-yl)oxy)-N-(thiazol-2-yl)benzenesulfonamide 2,2,2-trifluoroacetate with 3-chloro-4-((trans-2-methylpiperidin-4-yl)oxy)-N-(thiazol-2-yl)benzenesulfonamide 2,2,2-trifluoroacetate, the title compound was obtained as a colorless solid (0.095 g, 24% yield): $^1$H NMR (300 MHz, DMSO-$d_6$) δ 12.17 (br s, 1H), 7.73 (d, J=2.3 Hz, 1H), 7.68 (dd, J=8.6, 2.3 Hz, 1H), 7.45-7.31 (m, 6H), 7.26 (d, J=4.6 Hz, 1H), 6.83 (d, J=4.6 Hz, 1H), 4.90-4.89 (m, 1H), 4.18 (d, J=13.5 Hz, 1H), 3.65 (d, J=13.5 Hz, 1H), 3.07-3.01 (m, 1H), 2.78-2.73 (m, 1H), 2.64-2.56 (m, 1H), 2.01-1.78 (m, 4H), 1.28 (d, J=6.3 Hz, 3H); MS (ES+) m/z 478.0 (M+1), 480.0 (M+1).

Example 74

Synthesis of 4-((trans-1-benzyl-4-methylpyrrolidin-3-yl)amino)-3-chloro-N-(thiazol-2-yl)benzenesulfonamide

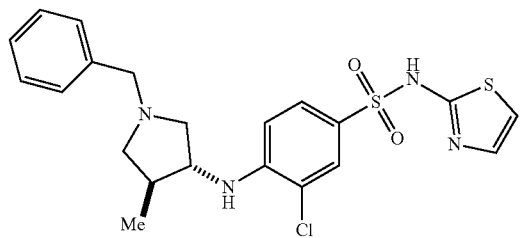 [SMILES: C[C@H]1CN(Cc2ccccc2)C[C@@H]1Nc1ccc(S(=O)(=O)Nc2nccs2)cc1Cl]

Step 1. Preparation of tert-butyl trans-3-((2-chloro-4-(N-(2,4-dimethoxybenzyl)-N-(thiazol-2-yl)sulfamoyl)phenyl)amino)-4-methylpyrrolidine-1-carboxylate

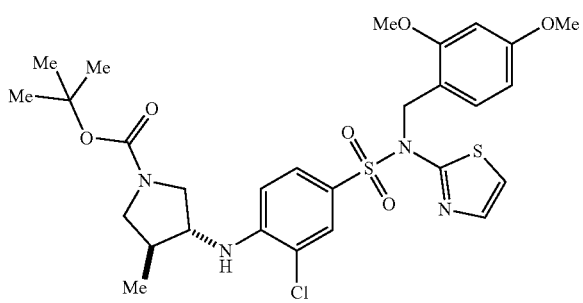 [SMILES: COc1ccc(CN(c2nccs2)S(=O)(=O)c2ccc(N[C@H]3CN(C(=O)OC(C)(C)C)C[C@@H]3C)c(Cl)c2)c(OC)c1]

Following the procedure as described in Example 72, Step 2 and making non-critical variations as required to replace tert-butyl cis-4-hydroxy-2-methylpiperidine-1-carboxylate with tert-butyl trans-3-amino-4-methylpyrrolidine-1-carboxylate, the title compound was obtained as a yellowish foam (0.927 g, 66% yield): MS (ES+) m/z 623.1 (M+1), 625.1 (M+1).

Step 2. Preparation of 3-chloro-4-((trans-4-methylpyrrolidin-3-yl)amino)-N-(thiazol-2-yl)benzenesulfonamide 2,2,2-trifluoroacetate

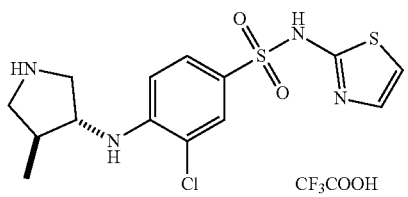 [SMILES: C[C@H]1CNC[C@@H]1Nc1ccc(S(=O)(=O)Nc2nccs2)cc1Cl ; "CF3COOH"]

Following the procedure as described in Example 72, Step 3 and making non-critical variations as required to replace tert-butyl cis-4-(2-chloro-4-(N-(2,4-dimethoxybenzyl)-N-(thiazol-2-yl)sulfamoyl)phenoxy)-2-methylpiperidine-1-carboxylate with tert-butyl trans-3-((2-chloro-4-(N-(2,4-dimethoxybenzyl)-N-(thiazol-2-yl)sulfamoyl)phenyl)amino)-4-methylpyrrolidine-1-carboxylate, the title compound was obtained as a beige solid (0.734 g, quantitative yield): MS (ES+) m/z 373.0 (M+1), 375.0 (M+1).

Step 3. Preparation of 4-((trans-1-benzyl-4-methylpyrrolidin-3-yl)amino)-3-chloro-N-(thiazol-2-yl)benzenesulfonamide

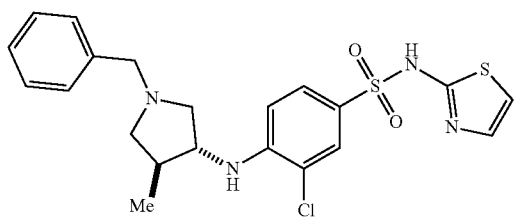 [SMILES: C[C@H]1CN(Cc2ccccc2)C[C@@H]1Nc1ccc(S(=O)(=O)Nc2nccs2)cc1Cl]

Following the procedure as described in Example 72, Step 4 and making non-critical variations as required to replace 3-chloro-4-((cis-2-methylpiperidin-4-yl)oxy)-N-(thiazol-2-yl)benzenesulfonamide 2,2,2-trifluoroacetate with 3-chloro-4-((trans-4-methylpyrrolidin-3-yl)amino)-N-(thiazol-2-yl)benzenesulfonamide 2,2,2-trifluoroacetate, the title compound was obtained as colorless solid (0.059 g, 20% yield): $^1$H NMR (300 MHz, DMSO-$d_6$) δ 7.57 (d, J=2.2 Hz, 1H), 7.52 (dd, J=8.6, 2.1 Hz, 1H), 7.32-7.28 (m, 4H), 7.27-7.20 (m, 2H), 6.79 (d, J=8.7 Hz, 1H), 6.77 (d, J=4.6 Hz, 1H), 5.72 (d, J=7.5 Hz, 1H), 3.85-3.11 (m, 1H), 3.68-3.55 (m, 2H), 2.98-2.89 (s, 1H), 2.88-2.80 (m, 1H), 2.58-2.51 (m, 1H), 2.34-2.26 (m, 1H), 2.11-2.06 (m, 1H), 1.06 (d, J=6.8 Hz, 3H), sulfonamide NH not observed; MS (ES+) m/z 463.0 (M+1), 465.0 (M+1).

Example 75

Synthesis of 4-((cis-1-benzyl-4-methylpyrrolidin-3-yl)amino)-3-chloro-N-(thiazol-2-yl)benzenesulfonamide

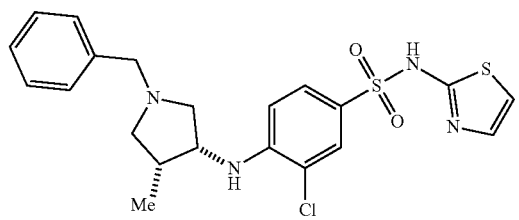 [SMILES: C[C@@H]1CN(Cc2ccccc2)C[C@@H]1Nc1ccc(S(=O)(=O)Nc2nccs2)cc1Cl]

Step 1. Preparation of tert-butyl cis-3-((2-chloro-4-(N-(2,4-dimethoxybenzyl)-N-(thiazol-2-yl)sulfamoyl)phenyl)amino)-4-methylpyrrolidine-1-carboxylate

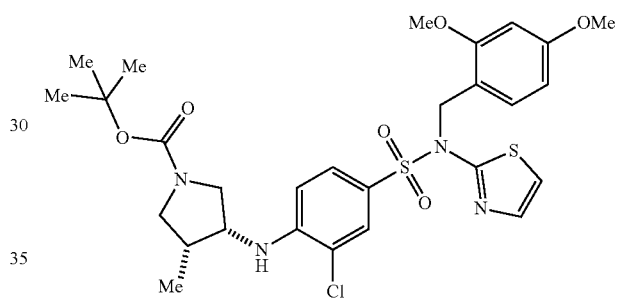

Following the procedure as described in Example 72, Step 2 and making non-critical variations as required to replace tert-butyl cis-4-hydroxy-2-methylpiperidine-1-carboxylate with tert-butyl cis-3-amino-4-methylpyrrolidine-1-carboxylate, the title compound was obtained as a yellowish foam (0.683 g, 48% yield): MS (ES+) m/z 623.1 (M+1), 625.1 (M+1).

Step 2. Preparation of 3-chloro-4-(((3R,4S)-4-methylpyrrolidin-3-yl)amino)-N-(thiazol-2-yl)benzenesulfonamide 2,2,2-trifluoroacetate

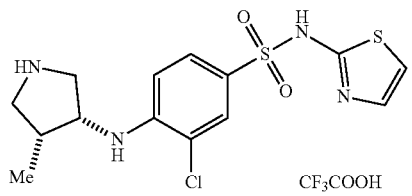

Following the procedure as described in Example 72, Step 3 and making non-critical variations as required to replace tert-butyl cis-4-(2-chloro-4-(N-(2,4-dimethoxybenzyl)-N-(thiazol-2-yl)sulfamoyl)phenoxy)-2-methylpiperidine-1-carboxylate with tert-butyl cis-3-((2-chloro-4-(N-(2,4-dimethoxybenzyl)-N-(thiazol-2-yl)sulfamoyl)phenyl)amino)-4-methylpyrrolidine-1-carboxylate, the title compound was obtained as a beige solid (0.561 g, quantitative yield): MS (ES+) m/z 373.0 (M+1), 375.1 (M+1).

Step 3. Preparation of 4-((cis-1-benzyl-4-methylpyrrolidin-3-yl)amino)-3-chloro-N-(thiazol-2-yl)benzenesulfonamide

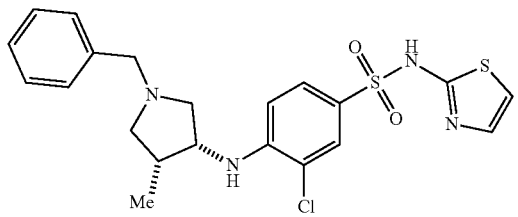 [SMILES: C[C@@H]1CN(Cc2ccccc2)C[C@@H]1Nc1ccc(S(=O)(=O)Nc2nccs2)cc1Cl]

Following the procedure as described in Example 72, Step 4 and making non-critical variations as required to replace of 3-chloro-4-((cis-2-methylpiperidin-4-yl)oxy)-N-(thiazol-2-yl)benzenesulfonamide 2,2,2-trifluoroacetate with 3-chloro-4-(((3R,4S)-4-methylpyrrolidin-3-yl)amino)-N-(thiazol-2-yl)benzenesulfonamide 2,2,2-trifluoroacetate, the title compound was obtained as a colorless solid (0.032 g, 11% yield): $^1$H NMR (300 MHz, DMSO-d$_6$) δ 7.58 (d, J=2.2 Hz, 1H), 7.51 (dd, J=8.7, 2.1 Hz, 1H), 7.34-7.30 (m, 4H), 7.29-7.21 (m, 2H), 6.87 (d, J=8.9 Hz, 1H), 6.78 (d, J=4.6 Hz, 1H), 5.57 (d, J=8.4 Hz, 1H), 4.19-4.09 (m, 1H), 3.70-3.57 (m, 2H), 3.68-3.12 (m, 1H), 3.02 (dd, J=9.3, 7.0 Hz, 1H), 2.95-2.89 (m, 1H), 2.61-2.53 (m, 1H), 2.19 (dd, J=8.9, 7.6 Hz, 1H), 0.77 (d, J=7.1 Hz, 3H), sulfonamide NH not observed; MS (ES+) m/z 463.0 (M+1), 465.0 (M+1).

Example 76

Synthesis of 4-((1-benzylazetidin-3-yl)oxy)-3-chloro-N-(thiazol-2-yl)benzenesulfonamide

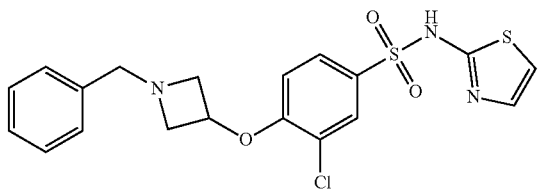 [SMILES: O=S(=O)(Nc1nccs1)c1ccc(OC2CN(Cc3ccccc3)C2)c(Cl)c1]

Step 1. Preparation of tert-butyl 3-(2-chloro-4-(N-(2,4-dimethoxybenzyl)-N-(thiazol-2-yl)sulfamoyl)phenoxy)azetidine-1-carboxylate

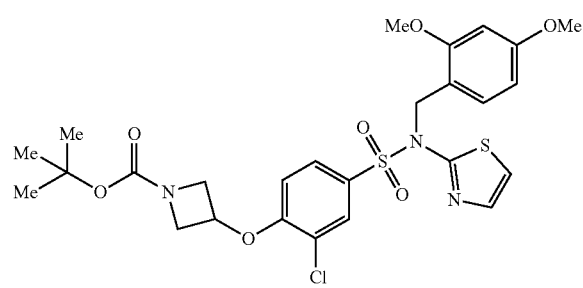 [SMILES: COc1ccc(CN(c2nccs2)S(=O)(=O)c2ccc(OC3CN(C(=O)OC(C)(C)C)C3)c(Cl)c2)c(OC)c1]

To a solution of 3-chloro-N-(2,4-dimethoxybenzyl)-4-fluoro-N-(thiazol-2-yl)benzenesulfonamide (1.02 g, 2.31 mmol) and tert-butyl 3-hydroxyazetidine-1-carboxylate (0.400 g, 2.31 mmol) in anhydrous N,N-dimethylformamide (20 mL) was added a dispersion of 60% of sodium hydride in mineral oil (0.185 g, 4.62 mmol) and the reaction mixture was stirred at ambient temperature for 30 minutes. The reaction mixture then added slowly to a rapidly stirred saturated ammonium chloride solution (150 mL). The resulting slurry was filtered and the precipitate was dried in vacuo to give the title compound as a pale yellow solid (1.43 g, quantitative yield): $^1$H-NMR (300 MHz, DMSO-d$_6$): 97.81 (d, J=2.3 Hz, 1H), 7.72 (dd, J=8.7, 2.3 Hz, 1H), 7.46 (q, J=4.3 Hz, 2H), 7.04 (dd, J=15.3, 8.6 Hz, 2H), 6.48 (d, J=2.3 Hz, 1H), 6.42 (dd, J=8.5, 2.3 Hz, 1H), 5.19-5.15 (m, 1H), 4.97 (s, 2H), 4.37-4.31 (m, 2H), 3.87-3.83 (m, 2H), 3.71 (s, 3H), 3.67 (s, 3H), 1.39 (s, 9H); MS (ES+) m/z 596.0 (M+1), 597.0 (M+1).

Step 2. Preparation of 4-(azetidin-3-yloxy)-3-chloro-N-(thiazol-2-yl)benzenesulfonamide 2,2,2-trifluoroacetate

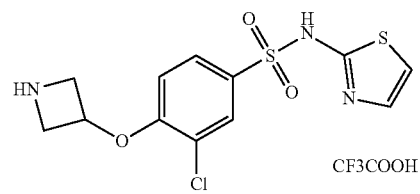 [SMILES: O=S(=O)(Nc1nccs1)c1ccc(OC2CNC2)c(Cl)c1 ; "CF3COOH"]

Following the procedure as described in Example 72, Step 3 and making non-critical variations as required to replace tert-butyl cis-4-(2-chloro-4-(N-(2,4-dimethoxybenzyl)-N-(thiazol-2-yl)sulfamoyl)phenoxy)-2-methylpiperidine-1-carboxylate with tert-butyl 3-(2-chloro-4-(N-(2,4-dimethoxybenzyl)-N-(thiazol-2-yl)sulfamoyl)phenoxy)azetidine-1-carboxylate, the title compound was obtained as a beige foam (0.729 g, quantitative yield): MS (ES+) m/z 346.0 (M+1), 348.0 (M+1).

Step 3. Preparation of 4-((1-benzylazetidin-3-yl)oxy)-3-chloro-N-(thiazol-2-yl)benzenesulfonamide

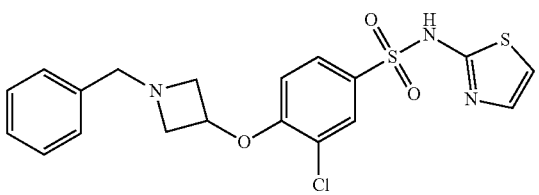 [SMILES: O=S(=O)(Nc1nccs1)c1ccc(OC2CN(Cc3ccccc3)C2)c(Cl)c1]

Following the procedure as described in Example 72, Step 4 and making non-critical variations as required to replace 3-chloro-4-((cis-2-methylpiperidin-4-yl)oxy)-N-(thiazol-2-yl)benzenesulfonamide 2,2,2-trifluoroacetate with 4-(azetidin-3-yloxy)-3-chloro-N-(thiazol-2-yl)benzenesulfonamide 2,2,2-trifluoroacetate, the title compound was obtained as a colorless solid (0.073 g, 31% yield): $^1$H-NMR (300 MHz, DMSO-d$_6$): δ 7.76 (d, J=2.2 Hz, 1H), 7.66 (dd, J=8.6, 2.3 Hz, 1H), 7.35-7.23 (m, 6H), 7.05 (d, J=8.7 Hz, 1H), 6.83 (d, J=4.6 Hz, 1H), 5.00-4.93 (m, 1H), 3.82-3.77 (m, 2H), 3.69

(s, 2H), 3.18-3.13 (m, 2H), sulfonamide NH not observed; MS (ES+) m/z 436.0 (M+1), 438.0 (M+1).

Example 77

Synthesis of 4-((1-benzylpiperidin-4-yl)oxy)-3-chloro-N-(6-fluoropyridin-2-yl)benzenesulfonamide 2,2,2-trifluoroacetate

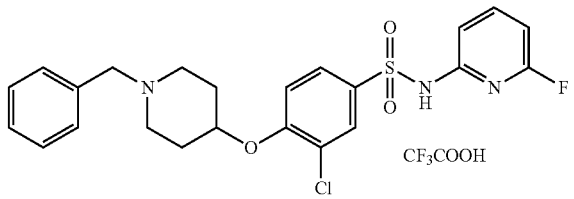

Step 1. Synthesis of 3-chloro-N-(2,4-dimethoxybenzyl)-4-fluoro-N-(6-fluoropyridin-2-yl)benzenesulfonamide

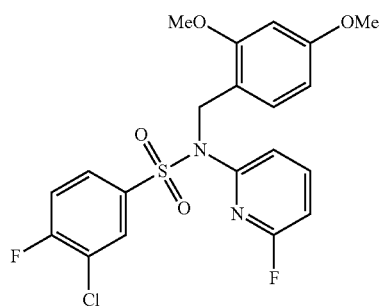

Following the procedure as described in Example 40, Step 1 and making non-critical variations as required to replace 5-chloro-2,4-difluorobenzenesulfonyl chloride with 3-chloro-4-fluorobenzenesulfonyl chloride and purification by column chromatography eluting with a gradient of 5 to 20% of ethyl acetate in hexanes, the title compound was obtained as yellowish oil (2.71 g, 75% yield): $^1$H NMR (300 MHz, CDCl$_3$) δ 7.84 (ddd, J=6.7, 2.3 Hz, 1H), 7.78-7.68 (m, 2H), 7.28-7.24 (m, 1H), 7.20 (d, J=8.2 Hz, 2H), 6.77-6.73 (m, 1H), 6.41-6.35 (m, 2H), 4.95 (s, 2H), 3.78 (s, 3H), 3.67 (s, 3H); $^{19}$F NMR (282 MHz, CDCl$_3$) δ −67.5 (s, 1F), −107.1 (s, 1F); MS (ES+) m/z 477.1 (M+23), 479.0 (M+23).

Step 2. Synthesis of 4-((1-benzylpiperidin-4-yl)oxy)-3-chloro-N-(6-fluoropyridin-2-yl)benzenesulfonamide 2,2,2-trifluoroacetate

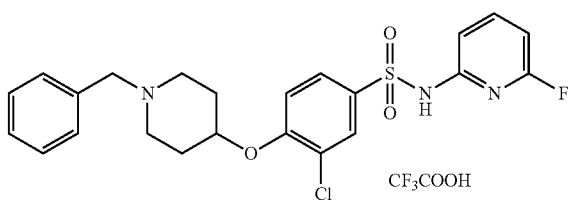

To a mixture of 1-benzylpiperidin-4-ol (0.231 g, 1.21 mmol) in anhydrous N,N-dimethylformamide (10 mL) was added a 60% dispersion of sodium hydride in mineral oil (0.054 g, 1.32 mmol) at 0° C. The reaction mixture was allowed to warm to ambient temperature and stirred for 2 h. After cooling to 0° C., 3-chloro-N-(2,4-dimethoxybenzyl)-4-fluoro-N-(6-fluoropyridin-2-yl)benzenesulfonamide (0.50 g, 1.1 mmol) was added to it. The reaction mixture was allowed to warm up to ambient temperature, stirred for 3 h, and quenched by addition of water (10 mL). The mixture was extracted with ethyl acetate (50 mL) and the organic layer was washed with brine (3×50 mL), dried over anhydrous sodium sulfate, and filtered. Concentration of the filtrate in vacuo provided a residue which was dissolved in dichloromethane (10 mL) and trifluoroacetic acid (4 mL) was added to it. The reaction mixture was stirred at ambient temperature for 1 h and then concentrated in vacuo. To the residue was added methanol (10 mL) and the mixture was filtered. Concentration of the filtrate in vacuo and purification of the residue by preparative reverse-phase HPLC, eluting with a gradient of 10 to 40% of acetonitrile in water containing 0.1% of trifluoroacetic acid, afforded the title compound as a colorless solid (0.333 g, 51% yield): $^1$H NMR (300 MHz, CD$_3$OD) δ 8.01 (s, 1H), 7.89 (dd, J=8.8, 2.3 Hz, 1H), 7.74 (t, J=7.9 Hz, 1H), 7.53-7.47 (m, 5H), 7.31-7.25 (m, 1H), 6.94 (d, J=7.9 Hz, 1H), 6.59 (d, J=8.0 Hz, 1H), 4.96 (br s, 1H), 4.36 (s, 2H), 3.61-3.39 (m, 2H), 3.25-3.11 (m, 2H), 2.43-2.36 (m, 1H), 2.26-2.01 (m, 2H), 2.00-1.86 (m, 1H), sulfonamide NH and CF$_3$COOH not observed; $^{19}$F NMR (282 MHz, CD$_3$OD) δ 70.5 (s, 1F), 76.8 (s, 3F); MS (ES+) m/z 476.0 (M+1), 478.0 (M+1).

Example 78

Synthesis of 4-((1-benzylpiperidin-4-yl)oxy)-5-chloro-2-fluoro-N-(6-fluoropyridin-2-yl)benzenesulfonamide 2,2,2-trifluoroacetate

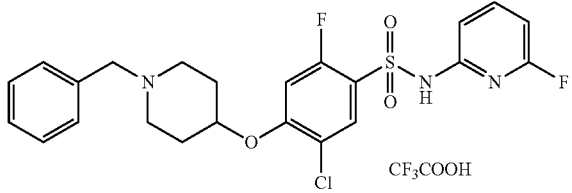

Following the procedure as described in Example 77, Step 2 and making non-critical variations as required to replace 3-chloro-N-(2,4-dimethoxybenzyl)-4-fluoro-N-(6-fluoropyridin-2-yl)benzenesulfonamide with 5-chloro-N-(2,4-dimethoxybenzyl)-2,4-difluoro-N-(6-fluoropyridin-2-yl)benzenesulfonamide, the title compound was obtained as a colorless solid (0.015 g, 3% yield): $^1$H NMR (300 MHz, CD$_3$OD) δ 8.15 (s, 1H), 7.78 (t, J=7.8 Hz, 1H), 7.56-7.48 (m, 5H), 7.26 (s, 1H), 6.93 (d, J=7.9 Hz, 1H), 6.63 (d, J=8.0 Hz, 1H), 4.99 (br s, 1H), 4.33 (s, 2H), 3.60-3.51 (m, 2H), 3.36-3.21 (m, 2H), 2.32-2.26 (m, 2H), 2.10-1.99 (m, 2H), sulfonamide NH and CF$_3$COOH not observed; $^{19}$F NMR (282-MHz, CD$_3$O) δ 70.4 (s, 1F), 77.0 (s, 3F), 105.0 (s, 1F); MS (ES+) m/z 494.0 (M+1), 496.0 (M+1).

Examples 79-100

In a similar manner as described in the Examples and in the Reaction Schemes above, utilizing the appropriately substituted starting materials and intermediates, the following compounds were prepared:

| Example No. | Name | MS (ES+) m/z |
|---|---|---|
| 79 | (R)-4-(1-benzylpyrrolidin-3-ylamino)-3-chloro-N-(thiazol-2-yl)benzenesulfonamide | 449.0 (M + 1), 451.0 (M + 1) |
| 80 | (S)-4-((1-benzylpyrrolidin-3-yl)(methyl)amino)-3-chloro-N-(thiazol-2-yl)benzenesulfonamide | 463.0 (M + 1), 465.0 (M + 1) |
| 81 | 3-chloro-4-(1-(3-fluorobenzyl)piperidin-4-yloxy)-N-(thiazol-2-yl)benzenesulfonamide | 482.0 (M + 1), 484.0 (M + 1) |
| 82 | 3-chloro-4-(1-((6-methylpyridin-2-yl)methyl)piperidin-4-yloxy)-N-(thiazol-2-yl)benzenesulfonamide | 479.0 (M + 1), 480.9 (M + 1) |
| 83 | (S)-3-chloro-4-(methyl(1-(3-methylbenzyl)pyrrolidin-3-yl)amino)-N-(1,2,4-thiadiazol-5-yl)benzenesulfonamide | 478.0 (M + 1), 480.0 (M + 1) |
| 84 | 3-chloro-4-(1-(3-methoxybenzyl)piperidin-4-yloxy)-N-(thiazol-2-yl)benzenesulfonamide | 494.0 (M + 1), 496.0 (M + 1) |
| 85 | 3-chloro-4-(1-(3-chlorobenzyl)piperidin-4-yloxy)-N-(thiazol-2-yl)benzenesulfonamide | 498.0 (M + 1), 500.0 (M + 1) |
| 86 | (S)-5-chloro-2-fluoro-4-(1-(3-methylbenzyl)pyrrolidin-3-ylamino)-N-(thiazol-2-yl)benzenesulfonamide | 481.0 (M + 1), 483.0 (M + 1) |
| 87 | (S)-4-(1-benzylpyrrolidin-3-ylamino)-5-chloro-2-fluoro-N-(thiazol-2-yl)benzenesulfonamide | 467.0 (M + 1), 469.0 (M + 1) |
| 88 | (R)-5-chloro-2-fluoro-4-(1-(3-methylbenzyl)pyrrolidin-3-ylamino)-N-(thiazol-2-yl)benzenesulfonamide | 481.0 (M + 1), 483.0 (M + 1) |
| 89 | (R)-4-(1-benzylpyrrolidin-3-ylamino)-5-chloro-2-fluoro-N-(thiazol-2-yl)benzenesulfonamide | 467.0 (M + 1), 469.0 (M + 1) |
| 90 | 3-chloro-4-(1-(2-fluorobenzyl)piperidin-4-yloxy)-N-(thiazol-2-yl)benzenesulfonamide | 482.0 (M + 1), 484.0 (M + 1) |
| 91 | 3-chloro-4-(1-(2-methylbenzyl)piperidin-4-yloxy)-N-(thiazol-2-yl)benzenesulfonamide | 478.0 (M + 1), 480.0 (M + 1) |
| 92 | 3-chloro-4-(1-(3-methylbenzyl)piperidin-4-yloxy)-N-(thiazol-2-yl)benzenesulfonamide | 478.0 (M + 1), 480.0 (M + 1) |
| 93 | 3-chloro-4-(1-(3,4-dimethylbenzyl)piperidin-4-yloxy)-N-(thiazol-2-yl)benzenesulfonamide | 492.1 (M + 1), 494.0 (M + 1) |
| 94 | 3-chloro-4-(1-(3,5-dimethylbenzyl)piperidin-4-yloxy)-N-(thiazol-2-yl)benzenesulfonamide | 492.0 (M + 1), 494.0 (M + 1) |
| 95 | 4-(1-benzylpiperidin-4-yloxy)-3-chloro-N-(thiazol-2-yl)benzenesulfonamide 2,2,2-trifluoroacetate | 464.0 (M + 1), 466.0 (M + 1) |
| 96 | (R)-4-(1-benzylpyrrolidin-3-yloxy)-3-chloro-N-(1,2,4-thiadiazol-5-yl)benzenesulfonamide 2,2,2-trifluoroacetate | 451.1 (M + 1), 453.1 (M + 1) |
| 97 | (S)-4-(1-benzylpyrrolidin-3-yloxy)-3-chloro-N-(1,2,4-thiadiazol-5-yl)benzenesulfonamide 2,2,2-trifluoroacetate | 451.1 (M + 1), 453.1 (M + 1) |
| 98 | (R)-3-chloro-4-(1-(3,5-dimethylbenzyl)pyrrolidin-3-yloxy)-N-(1,2,4-thiadiazol-5-yl)benzenesulfonamide 2,2,2-trifluoroacetate | 479.1 (M + 1), 481.1 (M + 1) |
| 99 | (S)-3-chloro-4-(1-(3,5-dimethylbenzyl) pyrrolidin-3-yloxy)-N-(1,2,4-thiadiazol-5-yl)benzenesulfonamide 2,2,2-trifluoroacetate | 479.1 (M + 1), 481.1 (M + 1) |
| 100 | 4-(1-benzylpiperidin-4-yloxy)-3-chloro-N-(1,2,4-thiadiazol-5-yl)benzenesulfonamide 2,2,2-trifluoroacetate | 465.0 (M + 1), 467.1 (M + 1) |

Example 101

Synthesis of (S)-4-((1-benzylpyrrolidin-3-yl)(methyl)amino)-2-fluoro-5-methyl-N-(thiazol-4-yl)benzenesulfonamide Formate

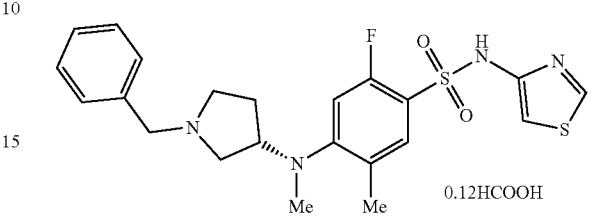

Step 1. Preparation of tert-butyl (S)-3-((4-(N-(tert-butoxycarbonyl)-N-(thiazol-4-yl)sulfamoyl)-2-chloro-5-fluorophenyl)amino)pyrrolidine-1-carboxylate

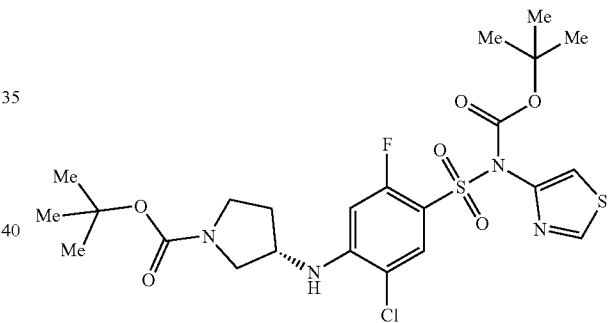

To a solution of tert-butyl ((5-chloro-2,4-difluorophenyl)sulfonyl)(thiazol-4-yl)carbamate (7.49 g, 18.3 mmol) in anhydrous dimethyl sulfoxide (37 mL) was added triethylamine (3.1 mL, 21.9 mmol) followed by tert-butyl (S)-3-aminopyrrolidine-1-carboxylate (4.08 g, 21.9 mmol). The reaction mixture was stirred at ambient temperature for 16 h and then diluted with water (150 mL). The resulting solid was filtered off and rinsed with water (300 mL) to give the title compound as a tan solid, which was used without further purification (yield not determined). An analytically pure sample was obtained through purification by column chromatography, eluting with a gradient of 20 to 80% of ethyl acetate in hexanes, to give the title compound as a colorless solid: $^1$H-NMR (300 MHz, CDCl$_3$) δ 8.81 (d, J=2.3 Hz, 1H), 7.99 (d, J=7.1 Hz, 1H), 7.53 (d, J=2.2 Hz, 1H), 6.42 (d, J=12.2 Hz, 1H), 5.05-5.02 (m, 1H), 4.09-4.06 (m, 1H), 3.79-3.77 (m, 1H), 3.58-3.54 (m, 2H), 3.43-3.28 (m, 1H), 2.34-2.27 (m, 1H), 2.03-1.96 (m, 1H), 1.50 (s, 9H), 1.40 (s, 9H); MS (ES+) m/z 577.3 (M+1), 579.3 (M+1).

Step 2. Preparation of tert-butyl (S)-3-((4-(N-(tert-butoxycarbonyl)-N-(thiazol-4-yl)sulfamoyl)-5-fluoro-2-methylphenyl)amino)pyrrolidine-1-carboxylate

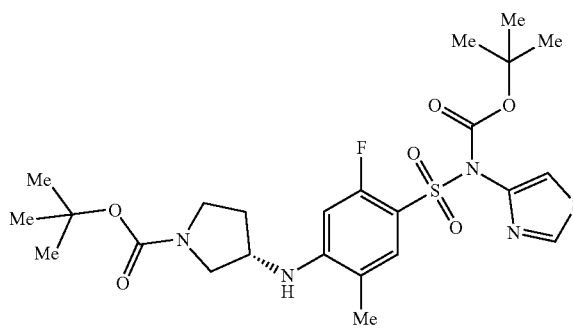

To a mixture of tert-butyl (S)-3-((4-(N-(tert-butoxycarbonyl)-N-(thiazol-4-yl)sulfamoyl)-2-chloro-5-fluorophenyl)amino)pyrrolidine-1-carboxylate (12.0 g, 13.2 mmol) in 1,4-dioxane (132 mL) was added methylboronic acid (7.89 g, 131.6 mmol), palladium acetate (0.44 g, 2.0 mmol), potassium phosphate (14.00 g, 65.8 mmol), and tricyclohexylphosphonium tetrafluoroborate (1.45 g, 4.0 mmol). The resulting mixture was degassed by passing a stream of dry argon through it for 15 minutes, and then heated at 90° C. for 4 h. The reaction mixture was allowed to cool to ambient temperature and filtered through a pad of Celite. The filter pad was washed with ethyl acetate (300 mL) and the combined filtrate concentrated in vacuo. Purification of the residue by column chromatography, eluting with a gradient of 15 to 65% of ethyl acetate in hexanes, afforded the title compound as a colorless sold (5.1 g, 70% yield): $^{1}$H-NMR (300 MHz, CDCl$_3$) δ 8.80 (d, J=2.3 Hz, 1H), 7.72 (d, J=8.3 Hz, 1H), 7.52 (d, J=2.2 Hz, 1H), 6.34 (d, J=12.7 Hz, 1H), 4.22 (d, J=5.2 Hz, 1H), 4.08-4.05 (m, 1H), 3.79-3.75 (m, 1H), 3.55-3.50 (m, 2H), 3.41-3.24 (m, 1H), 2.34-2.23 (m, 1H), 2.13 (s, 3H), 1.99-1.94 (m, 1H), 1.49 (s, 9H), 1.37 (s, 9H); MS (ES+) m/z 557.3 (M+1).

Step 3. Preparation of tert-butyl (S)-3-((4-(N-(tert-butoxycarbonyl)-N-(thiazol-4-yl)sulfamoyl)-5-fluoro-2-methylphenyl)(methyl)amino)pyrrolidine-1-carboxylate

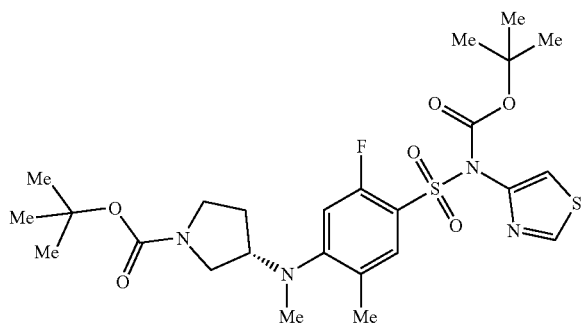 [SMILES: Cc1cc(S(=O)(=O)N(C(=O)OC(C)(C)C)c2cscn2)c(F)cc1N(C)[C@H]1CCN(C(=O)OC(C)(C)C)C1]

To a solution of tert-butyl (S)-3-((4-(N-(tert-butoxycarbonyl)-N-(thiazol-4-yl)sulfamoyl)-5-fluoro-2-methylphenyl)amino)pyrrolidine-1-carboxylate (5.0 g, 9.0 mmol) in anhydrous N,N-dimethylformamide (18 mL) was added methyl iodide (1.1 mL, 18.2 mmol) followed by sodium hydride (0.55 g of a 60% dispersion in mineral oil, 13.6 mmol), and the reaction mixture was stirred at ambient temperature for 18 h. HPLC analysis showed incomplete conversion, and more methyl iodide (1.0 mL, 16.1 mmol), followed by sodium hydride (0.50 g of a 60% dispersion in mineral oil, 12.5 mmol) was added to the reaction mixture. After 2 h, the reaction mixture was quenched by addition of saturated ammonium chloride and extracted with dichloromethane (3×75 mL). The combined organic extracts were washed with 5% aqueous lithium chloride solution (2×75 mL), dried over anhydrous magnesium sulfate, and filtered. Concentration of the filtrate in vacuo and purification of the residue by column chromatography, eluting with a gradient of 5 to 45% of ethyl acetate in hexanes, afforded the title compound as orange oil (4.1 g, 80% yield): MS (ES+) m/z 571.3 (M+1).

Step 4. Preparation of (S)-4-((1-benzylpyrrolidin-3-yl)(methyl)amino)-2-fluoro-5-methyl-N-(thiazol-4-yl)benzenesulfonamide formate

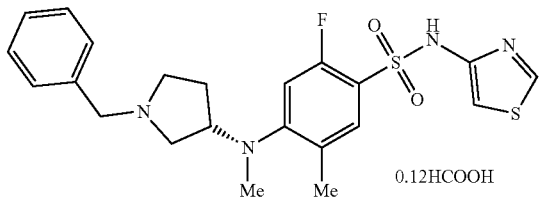

A solution of tert-butyl (S)-3-((4-(N-(tert-butoxycarbonyl)-N-(thiazol-4-yl)sulfamoyl)-5-fluoro-2-methylphenyl)(methyl)amino)pyrrolidine-1-carboxylate (4.12 g, 8.8 mmol) in anhydrous dichloromethane (10 mL) was treated with trifluoroacetic acid (6.8 mL, 87.8 mmol), and the resulting mixture was stirred at ambient temperature for 16 h. Concentration in vacuo provided a brown solid, which was suspended in N,N-dimethylformamide (18 mL). An aliquot of 11 mL of this solution was treated with benzaldehyde (1.1 g, 10.4 mmol) and sodium triacetoxyborohydride (3.32 g, 15.7 mmol). The reaction mixture was stirred at ambient temperature for 16 h, then quenched by addition of 5% aqueous lithium chloride, and extracted with ethyl acetate (3×75 mL). The combined organic layers were dried over anhydrous magnesium sulfate and filtered. Concentration of the filtrate in vacuo and purification of the residue by preparative reverse-phase HPLC, eluting with a gradient of acetonitrile in water containing 0.5% formic acid, provided the title compound as a colorless solid (0.54 g, 14% yield): $^{1}$H-NMR (300 MHz, DMSO-d$_6$) δ 8.87 (d, J=2.1 Hz, 1H), 8.17 (s, 0.12H), 7.58 (d, J=8.5 Hz, 1H), 7.38-7.34 (m, 5H), 6.98-6.96 (m, 1H), 6.95 (d, J=11.0 Hz, 1H), 4.04-3.89 (m, 3H), 3.02-2.96 (m, 2H), 2.91-2.86 (m, 1H), 2.80-2.76 (m, 1H), 2.64 (s, 3H), 2.20 (s, 3H), 2.07-2.02 (m, 1H), 1.91-1.84 (m, 1H), NH and COOH not observed; $^{13}$C NMR (75 MHz, DMSO-d$_6$) δ 157.44 (d, J=252.6 Hz), 157.8 (d, J=8.4 Hz), 153.5, 147.9, 135.5, 132.5 (d, J=4.6 Hz), 129.8, 129.0, 128.5, 127.5 (d, J=3.0 Hz), 120.2 (d, J=14.2 Hz), 108.8 (d, J=22.0 Hz), 103.0, 60.2, 58.9, 55.7, 53.0, 36.6, 27.6, 18.6; MS (ES+) m/z 461.2 (M+1).

Example 102

Synthesis of (S)-4-((1-benzylpyrrolidin-3-yl)(methyl)amino)-3-chloro-2,6-difluoro-N-(thiazol-4-yl)benzenesulfonamide Formate

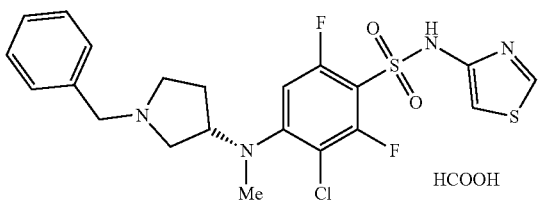

Step 1. Preparation of 3-chloro-2,4,6-trifluorobenzenesulfonyl Chloride

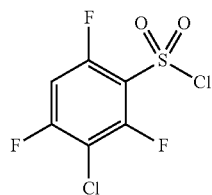 [SMILES: O=S(=O)(Cl)c1c(F)cc(F)c(Cl)c1F]

To chlorosulfonic acid (18.0 mL, 270.3 mmol) was added 2-chloro-1,3,5-trifluorobenzene (7.20 g, 43.3 mmol) at 0° C. The resulting mixture was stirred for 18 h at ambient temperature and then heated to 65° C. The reaction mixture was allowed to cool to ambient temperature and then added dropwise to a mixture of ice (400 g) and concentrated hydrochloric acid (125 mL), maintaining a temperature below 5° C. After the addition was complete, the mixture was vigorously stirred at 0° C. for 1 h. The precipitate was filtered off and rinsed with water (250 mL) to provide the title compound as a colorless amorphous solid (8.02 g, 70% yield): $^1$H NMR (300 MHz, CDCl$_3$) δ 7.07 (ddd, J=9.8, 8.3, 2.3 Hz, 1H).

Step 2. Preparation of tert-butyl ((3-chloro-2,4,6-trifluorophenyl)sulfonyl)(thiazol-4-yl)carbamate

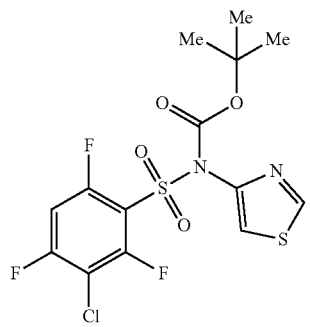 [SMILES: CC(C)(C)OC(=O)N(c1cscn1)S(=O)(=O)c1c(F)cc(F)c(Cl)c1F]

To a solution of tert-butyl thiazol-4-ylcarbamate (3.32 g, 16.6 mmol) in anhydrous tetrahydrofuran (210 mL) was added a 1 M solution of lithium bis(trimethylsilyl)amide in tetrahydrofuran (16.6 mL, 16.6 mmol) at 0° C. The reaction mixture was stirred at 0° C. for 1 h, cooled to −78° C., and a solution of 3-chloro-2,4,6-trifluorobenzenesulfonyl chloride (4.00 g, 15.09 mmol) in anhydrous tetrahydrofuran (15 mL) was then added dropwise to it. The reaction mixture was allowed to warm to ambient temperature and stirred for 16 h. The reaction mixture was concentrated in vacuo to a volume of approximately 50 mL. After dilution with ethyl acetate (160 mL), the organic layer was washed with saturated ammonium chloride (150 mL), saturated sodium bicarbonate (150 mL), brine (50 mL), and dried over anhydrous sodium sulfate. Filtration and concentration of the filtrate in vacuo provided a residue which was purified by column chromatography, eluting with a gradient of 10 to 50% of ethyl acetate in hexanes, to provide the title compound as a colorless solid (3.35 g, 52% yield): $^1$H NMR (300 MHz, CDCl$_3$) δ 8.83 (d, J=2.2 Hz, 1H), 7.55 (d, J=2.2 Hz, 1H), 6.99 (ddd, J=10.0, 8.2, 2.0 Hz, 1H), 1.40 (s, 9H); MS (ES+) m/z 329.0 (M−100), 331.0 (M−100).

Step 3. Preparation of tert-butyl (S)-3-((4-(N-(tert-butoxycarbonyl)-N-(thiazol-4-yl)sulfamoyl)-2-chloro-3,5-difluorophenyl)amino)pyrrolidine-1-carboxylate

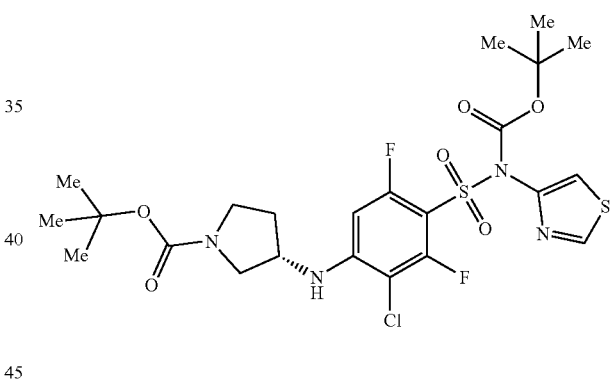

To a solution of tert-butyl ((3-chloro-2,4,6-trifluorophenyl)sulfonyl)(thiazol-4-yl)carbamate (1.53 g, 3.57 mmol) in anhydrous N,N-dimethylformamide (25 mL) was added cesium carbonate (1.16 g, 3.57 mmol) and tert-butyl (S)-3-aminopyrrolidine-1-carboxylate (0.66 g, 3.57 mmol) at −42° C. The reaction mixture was stirred at −42° C. for 1 h and then at 0° C. for 2 h. The reaction mixture was diluted with ethyl acetate (80 mL), washed with saturated ammonium chloride (2×50 mL), brine (50 mL), dried over anhydrous sodium sulfate, and filtered. Concentration of the filtrate in vacuo and purification of the residue by column chromatography, eluting with a gradient of 10 to 60% of ethyl acetate in hexanes, afforded the title compound as a colorless foam (1.54 g, 73% yield): $^1$H NMR (300 MHz, CDCl$_3$) δ 8.80 (d, J=2.3 Hz, 1H), 7.52 (d, J=2.2 Hz, 1H), 6.30 (dd, J=12.6, 1.6 Hz, 1H), 5.17-5.13 (m, 1H), 4.09-4.05 (m, 1H), 3.81-3.74 (m, 1H), 3.58-3.49 (m, 2H), 3.42-3.29 (m, 1H), 2.36-2.24 (m, 1H), 2.02-1.97 (m, 1H), 1.49 (s, 9H), 1.40 (s, 9H); MS (ES−) m/z 593.4 (M−1), 595.4 (M−1).

Step 4. Preparation of tert-butyl (S)-3-((4-(N-(tert-butoxycarbonyl)-N-(thiazol-4-yl)sulfamoyl)-2-chloro-3,5-difluorophenyl)(methyl)amino)pyrrolidine-1-carboxylate

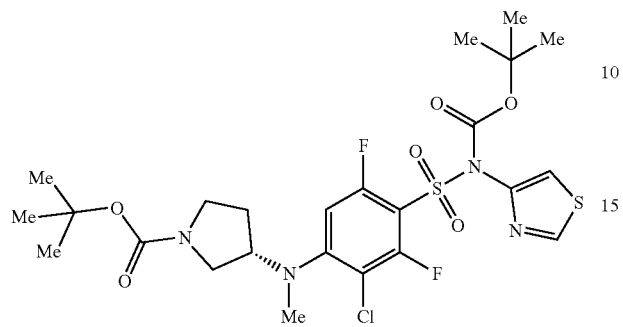

To a solution of tert-butyl (S)-3-((4-(N-(tert-butoxycarbonyl)-N-(thiazol-4-yl)sulfamoyl)-2-chloro-3,5-difluorophenyl)amino)pyrrolidine-1-carboxylate (1.50 g, 2.52 mmol) and methyl iodide (0.19 mL, 3.02 mmol) in anhydrous N,N-dimethylformamide (20 mL) was added a 60% dispersion of sodium hydride in mineral oil (0.21 g, 30.2 mmol) at 0° C. The resulting mixture was stirred at 0° C. for 1 h and then quenched by slow addition of water (5 mL). The mixture was diluted with ethyl acetate (80 mL), washed with saturated ammonium chloride (2×50 mL), brine (30 mL), and dried over anhydrous sodium sulfate. Filtration and concentration of the filtrate in vacuo provided a residue which was purified by column chromatography, eluting with a gradient of 10 to 60% of ethyl acetate in hexanes, to provide the title compound as a colorless foam (1.26 g, 82% yield): $^1$H NMR (300 MHz, CDCl$_3$) δ 8.81 (d, J=2.3 Hz, 1H), 7.54 (d, J=2.2 Hz, 1H), 6.65 (dd, J=12.4, 1.4 Hz, 1H), 4.33-4.27 (m, 1H), 3.67-3.59 (m, 2H), 3.38-3.30 (m, 2H), 2.88 (s, 3H), 2.14-2.08 (m, 2H), 1.48 (s, 10H), 1.40 (s, 9H); MS (ES+) m/z 631.4 (M+23), 633.4 (M+23).

Step 5. Preparation of (S)-3-chloro-2,6-difluoro-4-(methyl(pyrrolidin-3-yl)amino)-N-(thiazol-4-yl)benzenesulfonamide 2,2,2-trifluoroacetate

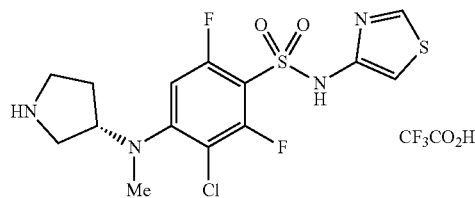 [SMILES: CN(c1cc(F)c(S(=O)(=O)Nc2cscn2)c(F)c1Cl)[C@H]1CCNC1 ; "CF3CO2H"]

To a solution of tert-butyl (S)-3-((4-(N-(tert-butoxycarbonyl)-N-(thiazol-4-yl)sulfamoyl)-2-chloro-3,5-difluorophenyl)(methyl)amino)pyrrolidine-1-carboxylate (1.26 g, 2.07 mmol) in dichloromethane (10 mL) was added trifluoroacetic acid (10 mL). The resulting mixture was stirred for 2 h and then concentrated in vacuo to provide the title compound as a yellowish foam (1.08 g, quantitative yield): MS (ES+) m/z 409.2 (M+1), 411.2 (M+1).

Step 6. Preparation of (S)-4-((1-benzylpyrrolidin-3-yl)(methyl)amino)-3-chloro-2,6-difluoro-N-(thiazol-4-yl)benzenesulfonamide Formate

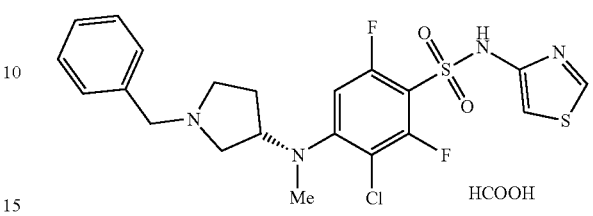

To a mixture of (S)-3-chloro-2,6-difluoro-4-(methyl(pyrrolidin-3-yl)amino)-N-(thiazol-4-yl)benzenesulfonamide 2,2,2-trifluoroacetate (0.40 g, 0.76 mmol) and benzaldehyde (0.16 mL, 1.52 mmol) in dichloromethane (5 mL) and N,N-dimethylformamide (5 mL) was added sodium triacetoxyborohydride (0.32 g, 1.52 mmol). The reaction mixture was stirred at ambient temperature for 16 h, then quenched by addition of 2 M sodium hydroxide (15 mL), and extracted with ethyl acetate (50 mL). The aqueous layer was diluted with saturated ammonium chloride (30 mL) and extracted with ethyl acetate (50 mL). The combined organic layers were washed with saturated ammonium chloride (30 mL), brine (30 mL), dried over anhydrous sodium sulfate, and filtered. Concentration of the filtrate in vacuo afforded a residue which was purified by column chromatography, eluting with a gradient of 10 to 65% of ethyl acetate (containing 20% of ethanol and 0.1% of ammonium hydroxide) in hexanes. The purified residue was then dissolved in methanol (15 mL) and formic acid (0.5 mL). Filtration and concentration of the filtrate provided the title compound as a colorless foam (0.09 g, 22% yield): $^1$H NMR (300 MHz, DMSO-d$_6$+25% CD$_3$OD) δ 8.81 (d, J=2.2 Hz, 1H), 8.12 (s, 0.6H), 7.30 (d, J=4.2 Hz, 4H), 7.27-7.21 (m, 1H), 6.94 (d, J=2.2 Hz, 1H), 6.84-6.77 (m, 1H), 4.29-4.25 (m, 1H), 3.69 (d, J=12.9 Hz, 1H), 3.57 (d, J=13.1 Hz, 1H), 2.83 (s, 3H), 2.80-2.70 (m, 2H), 2.65-2.58 (m, 1H), 2.43-2.34 (m, 1H), 2.16-2.05 (m, 1H), 1.91-1.79 (m, 1H), NH and COOH not observed; MS (ES+) m/z 499.1 (M+1), 501.1 (M+1).

Example 103

Synthesis of (S)-4-((1-benzylpyrrolidin-3-yl)(methyl)amino)-2,6-difluoro-3-methyl-N-(thiazol-4-yl)benzenesulfonamide 2,2,2-trifluoroacetate

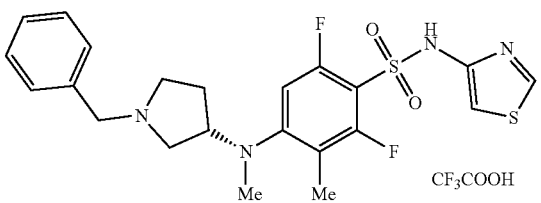

Step 1. Preparation of tert-butyl (S)-3-((3,5-difluoro-2-methyl-4-(N-(thiazol-4-yl)sulfamoyl)phenyl)amino)pyrrolidine-1-carboxylate

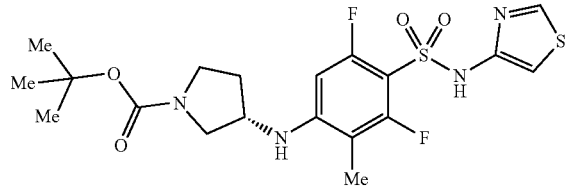 [SMILES: Cc1c(N[C@H]2CCN(C(=O)OC(C)(C)C)C2)cc(F)c(S(=O)(=O)Nc2cscn2)c1F]

To a mixture of tert-butyl (S)-3-((4-(N-(tert-butoxycarbonyl)-N-(thiazol-4-yl)sulfamoyl)-2-chloro-3,5-difluorophenyl)amino)pyrrolidine-1-carboxylate (2.04 g, 3.43 mmol) and methylboronic acid (4.11 g, 68.6 mmol) in anhydrous 1,4-dioxane (35 mL) was added potassium phosphate tribasic (7.28 g, 34.3 mmol), and the mixture was degassed by passing a stream of nitrogen through it for 15 minutes. To the mixture was then added tricyclohexylphosphine tetrafluoroborate (0.76 g, 2.05 mmol) and palladium acetate (0.23 g, 1.03 mmol), and the resulting mixture was heated to reflux for 16 h. The reaction mixture was allowed to cool to ambient temperature, diluted with ethyl acetate (100 mL) and saturated ammonium chloride (100 mL), and filtered. The filtrate was collected and the layers were separated. The organic layer was washed with saturated ammonium chloride (80 mL), brine (50 mL), dried over anhydrous sodium sulfate, and filtered. Concentration of the filtrate in vacuo and purification of the residue by column chromatography, eluting with a gradient of 10 to 65% of ethyl acetate in hexanes, afforded the title compound as a brownish foam (1.25 g, 77% yield): $^1$H NMR (300 MHz, CDCl$_3$) 11.06 (s, 1H), 8.77 (d, J=2.3 Hz, 1H), 6.98 (d, J=2.1 Hz, 1H), 6.15-6.03 (m, 1H), 4.28-4.26 (m, 1H), 4.03-3.99 (m, 1H), 3.76-3.66 (m, 1H), 3.54-3.43 (m, 2H), 3.35-3.22 (m, 1H), 2.29-2.16 (m, 1H), 1.99-1.88 (m, 4H), 1.47 (s, 9H); MS (ES-) m/z 473.2 (M-1).

Step 2. Preparation of (S)-2,6-difluoro-3-methyl-4-(pyrrolidin-3-ylamino)-N-(thiazol-4-yl)benzenesulfonamide 2,2,2-trifluoroacetate

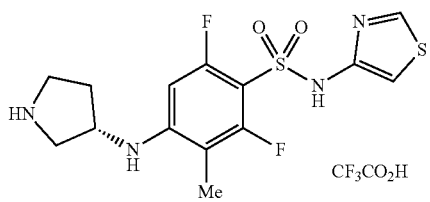 [SMILES: Cc1c(N[C@H]2CCNC2)cc(F)c(S(=O)(=O)Nc2cscn2)c1F ; "CF3CO2H"]

Following the procedure as described in Example 102, Step 5 and making non-critical variations as required to replace of tert-butyl (S)-3-((4-(N-(tert-butoxycarbonyl)-N-(thiazol-4-yl)sulfamoyl)-2-chloro-3,5-difluorophenyl)(methyl)amino)pyrrolidine-1-carboxylate with tert-butyl (S)-3-((3,5-difluoro-2-methyl-4-(N-(thiazol-4-yl)sulfamoyl)phenyl)amino)pyrrolidine-1-carboxylate, the title compound was obtained as a yellowish foam (1.28 g, quantitative yield): MS (ES+) m/z 375.2 (M+1).

Step 3. Preparation of (S)-4-((1-benzylpyrrolidin-3-yl)amino)-2,6-difluoro-3-methyl-N-(thiazol-4-yl)benzenesulfonamide

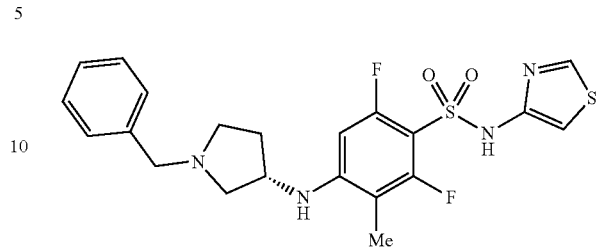

Following the procedure as described in Example 102, Step 6 and making non-critical variations as required to replace of (S)-3-chloro-2,6-difluoro-4-(methyl(pyrrolidin-3-yl)amino)-N-(thiazol-4-yl)benzenesulfonamide 2,2,2-trifluoroacetate with (S)-2,6-difluoro-3-methyl-4-(pyrrolidin-3-ylamino)-N-(thiazol-4-yl)benzenesulfonamide 2,2,2-trifluoroacetate, the title compound was obtained as a colorless foam (0.34 g, 89% yield): MS (ES+) m/z 465.3 (M+1).

Step 4. Preparation of (S)-4-((1-benzylpyrrolidin-3-yl)(methyl)amino)-2,6-difluoro-3-methyl-N-(thiazol-4-yl)benzenesulfonamide 2,2,2-trifluoroacetate

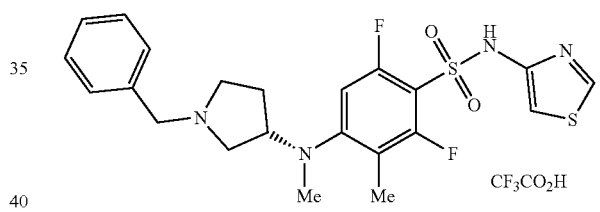

To a solution of (S)-4-((1-benzylpyrrolidin-3-yl)amino)-2,6-difluoro-3-methyl-N-(thiazol-4-yl)benzenesulfonamide (0.19 g, 0.40 mmol) in trifluoroacetic acid (1.8 mL) was added sodium triacetoxyborohydride (0.25 g, 1.20 mmol) at 0° C. The resulting mixture was stirred at 0° C. for 10 minutes, and then paraformaldehyde was added (24 mg, 0.80 mmol) to it. The reaction mixture was stirred at 0° C. for 15 minutes and then concentrated in vacuo. To the residue was added 2 M sodium hydroxide (15 mL) and brine (15 mL), and the mixture was extracted with ethyl acetate (50 mL). The aqueous layer was diluted with saturated ammonium chloride (50 mL) and then extracted with ethyl acetate (50 mL). The combined organic layers were washed with saturated ammonium chloride (30 mL), brine (30 mL), dried over anhydrous sodium sulfate, and filtered. Concentration of the filtrate in vacuo and purification of the residue by preparative reverse-phase HPLC, eluting with a gradient of 7 to 50% of acetonitrile in water containing 0.1% of trifluoroacetic acid, afforded the title compound as a colorless solid (0.045 g, 19% yield): $^1$H NMR (300 MHz, DMSO-d$_6$) δ 11.48 (br s, 1H), 10.59 (br s, 1H), 8.91 (d, J=2.1 Hz, 1H), 7.50-7.45 (m, 5H), 6.99 (d, J=2.2 Hz, 1H), 6.89-6.83 (m, 1H), 4.40-4.34 (m, 3H), 4.08-3.89 (m, 4H), 2.70-2.63 (m, 3H), 2.16-1.98 (m, 5H); MS (ES+) m/z 479.3 (M+1).

Example 104

Synthesis of (S)-2,6-difluoro-3-methyl-4-(methyl(1-((6-methylpyridin-2-yl)methyl)pyrrolidin-3-yl)amino)-N-(thiazol-4-yl)benzenesulfonamide Formate

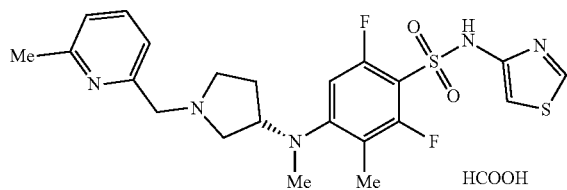

To a solution of (S)-2,6-difluoro-3-methyl-4-(pyrrolidin-3-ylamino)-N-(thiazol-4-yl)benzenesulfonamide 2,2,2-trifluoroacetate (0.63 g, 1.30 mmol) and 6-methylpicolinaldehyde (0.17 g, 1.43 mmol) in dichloromethane (20 mL) and isopropanol (5 mL) was added sodium triacetoxyborohydride (0.55 g, 2.60 mmol). The resulting mixture was stirred for 1 h and then concentrated in vacuo. The residue was dissolved in trifluoroacetic acid (5 mL), cooled to 0° C., and sodium triacetoxyborohydride (2.20 g, 10.4 mmol) was added to it. The reaction mixture was stirred for 10 minutes at 0° C. and then paraformaldehyde was added (0.16 g, 5.20 mmol) to it. The resulting mixture was stirred at 0° C. for 15 minutes and then concentrated in vacuo. To the residue was added 2 M sodium hydroxide (50 mL) and dichloromethane (15 mL) and the mixture was extracted with ethyl acetate (75 mL). The aqueous layer was diluted with saturated ammonium chloride (50 mL) and extracted with ethyl acetate (75 mL). The combined organic layers were washed with saturated ammonium chloride (50 mL), brine (50 mL), dried over anhydrous sodium sulfate, and filtered. Filtration and concentration of the filtrate in vacuo provided a residue which was purified by preparative reverse-phase HPLC, eluting with a gradient of 7 to 50% of acetonitrile in water containing 0.5% of formic acid, to afford the title compound as a colorless solid (0.045 g, 19% yield): $^1$H NMR (300 MHz, DMSO-$d_6$) δ 8.89 (d, J=2.2 Hz, 1H), 8.17 (s, 0.8H), 7.64 (t, J=7.7 Hz, 1H), 7.21 (d, J=7.6 Hz, 1H), 7.10 (d, J=7.5 Hz, 1H), 6.93 (d, J=2.2 Hz, 1H), 6.72 (dd, J=13.4, 1.4 Hz, 1H), 4.03-3.93 (m, 1H), 3.72 (d, J=14.0 Hz, 1H), 3.62 (d, J=14.0 Hz, 1H), 2.81-2.80 (m, 1H), 2.71 (s, 3H), 2.68-2.59 (m, 2H), 2.46-2.37 (m, 4H), 2.11-1.99 (m, 4H), 1.86-1.75 (m, 1H), NH and COOH not observed; MS (ES+) m/z 494.3 (M+1).

Example 105

Synthesis of 4-((1-benzylpiperidin-4-yl)oxy)-3-chloro-2,6-difluoro-N-(thiazol-4-yl)benzenesulfonamide Formate

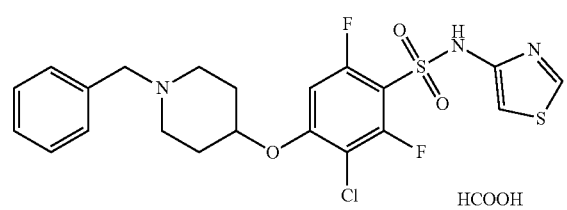 [SMILES: O=S(=O)(Nc1cscn1)c1c(F)cc(OC2CCN(Cc3ccccc3)CC2)c(Cl)c1F ; "HCOOH"]

Step 1. Preparation of tert-butyl ((4-((1-benzylpiperidin-4-yl)oxy)-3-chloro-2,6-difluorophenyl)sulfonyl)(thiazol-4-yl)carbamate

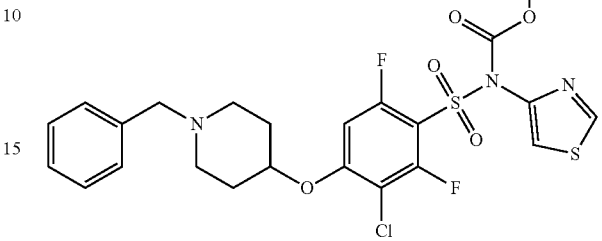

To a solution of 1-benzylpiperidin-4-ol (0.94 g, 4.90 mmol) and tert-butyl ((3-chloro-2,4,6-trifluorophenyl)sulfonyl)(thiazol-4-yl)carbamate (2.10 g, 4.90 mmol) in anhydrous N,N-dimethylformamide (25 mL) was added a 60% dispersion of sodium hydride in mineral oil (0.20 g, 4.90 mmol) at 0° C. The reaction mixture was allowed to warm to ambient temperature and stirred for 1 h, diluted with ethyl acetate (80 mL), and then quenched by slow addition of water (50 mL). The mixture was washed with saturated ammonium chloride (2×50 mL), brine (2×30 mL), dried over anhydrous sodium sulfate, and filtered. Concentration of the filtrate in vacuo and purification of the residue by column chromatography, eluting with a gradient of 10 to 65% of ethyl acetate (containing 20% of ethanol and 0.1% of ammonium hydroxide) in hexanes, provided the title compound as a colorless foam (0.62 g, 21% yield): $^1$H NMR (300 MHz, CDCl$_3$) δ 8.82 (d, J=2.3 Hz, 1H), 7.54 (d, J=2.2 Hz, 1H), 7.35 (d, J=4.3 Hz, 4H), 7.33-7.29 (m, 1H), 6.62 (dd, J=12.2, 1.9 Hz, 1H), 4.57-4.49 (m, 1H), 3.58 (s, 2H), 2.77-2.69 (m, 2H), 2.49-2.43 (m, 2H), 2.11-2.02 (m, 2H), 2.00-1.91 (m, 2H), 1.40 (s, 9H); MS (ES+) m/z 600.2 (M+1), 602.2 (M+1).

Step 2. Preparation of 4-((1-benzylpiperidin-4-yl)oxy)-3-chloro-2,6-difluoro-N-(thiazol-4-yl)benzenesulfonamide Formate

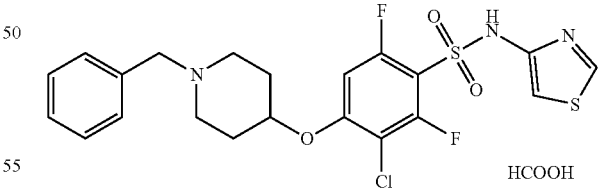

To a solution of tert-butyl ((4-((1-benzylpiperidin-4-yl)oxy)-3-chloro-2,6-difluorophenyl)sulfonyl)(thiazol-4-yl)carbamate (0.21 g, 0.35 mmol) in dichloromethane (3 mL) was added trifluoroacetic acid (2 mL) and the reaction mixture was stirred at ambient temperature for 3 h. The mixture was concentrated in vacuo, and the residue purified by preparative reverse-phase HPLC, eluting with a gradient of 7 to 50% of acetonitrile in water containing 0.5% of formic acid, to afford the title compound as a colorless solid (0.045 g, 19% yield): $^1$H NMR (300 MHz, DMSO-$d_6$) δ 8.89

(d, J=2.2 Hz, 1H), 8.15 (s, 1H), 7.35-7.24 (m, 6H), 7.00 (d, J=2.2 Hz, 1H), 4.76-4.69 (m, 1H), 3.60 (s, 2H), 2.70-2.64 (m, 2H), 2.46-2.39 (m, 2H), 1.99-1.91 (m, 2H), 1.78-1.68 (m, 2H), NH and COOH not observed; MS (ES+) m/z 500.2 (M+1), 502.2 (M+1).

Example 106

Synthesis of 4-((1-benzylpiperidin-4-yl)oxy)-2,6-difluoro-3-methyl-N-(thiazol-4-yl)benzenesulfonamide Formate

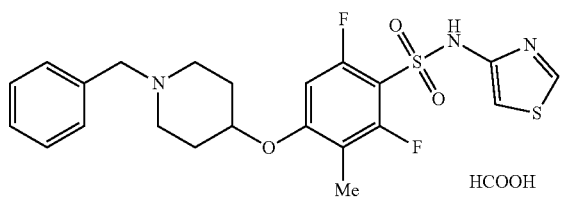 [SMILES: Cc1c(OC2CCN(Cc3ccccc3)CC2)cc(F)c(S(=O)(=O)Nc2cscn2)c1F ; "HCOOH"]

To a mixture of tert-butyl ((4-((1-benzylpiperidin-4-yl)oxy)-3-chloro-2,6-difluorophenyl)sulfonyl)(thiazol-4-yl)carbamate (0.62 g, 1.03 mmol) and methylboronic acid (0.62 g, 10.3 mmol) in anhydrous 1,4-dioxane (16 mL) was added potassium phosphate tribasic (1.09 g, 5.15 mmol) and the mixture was degassed by passing a stream of nitrogen through it for 15 minutes. To the mixture was then added tricyclohexylphosphine tetrafluoroborate (0.15 g, 0.41 mmol) and palladium acetate (0.046 g, 0.21 mmol), and the resulting mixture was heated to reflux for 6 h. The mixture was diluted with saturated ammonium chloride (50 mL) and extracted with ethyl acetate (80 mL). The organic layer was washed with saturated ammonium chloride (50 mL), brine (50 mL), dried over anhydrous sodium sulfate, and filtered. The filtrate was concentrated in vacuo and the residue purified by column chromatography, eluting with a gradient of 10 to 65% of ethyl acetate (containing 20% of ethanol and 0.1% of ammonium hydroxide) in hexanes. Additional purification by preparative reverse-phase HPLC, eluting with a gradient of 7 to 50% of acetonitrile in water containing 0.5% of formic acid, afforded the title compound as a colorless solid (0.14 g, 27% yield): $^1$H NMR (300 MHz, DMSO-$d_6$) δ 8.89 (d, J=2.2 Hz, 1H), 8.17 (s, 1H), 7.36-7.29 (m, 4H), 7.25 (dddd, J=5.2, 5.0, 2.4, 1.8 Hz, 1H), 7.00 (dd, J=13.1, 1.3 Hz, 1H), 6.94 (d, J=2.2 Hz, 1H), 4.65-4.57 (m, 1H), 3.52 (s, 2H), 2.63-2.55 (m, 2H), 2.37-2.30 (m, 2H), 1.98 (d, J=1.8 Hz, 3H), 1.94-1.88 (m, 2H), 1.71-1.64 (m, 2H), NH and COOH not observed; MS (ES+) m/z 480.3 (M+1).

Example 107

Synthesis of (S)-2-fluoro-4-((1-((2-isopropylthiazol-4-yl)methyl)pyrrolidin-3-yl)(methyl)amino)-5-methyl-N-(thiazol-4-yl)benzenesulfonamide 2,2,2-trifluoroacetate

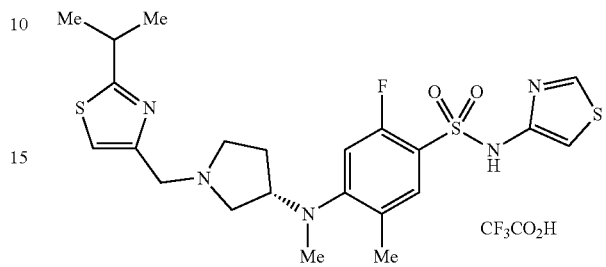

Step 1. Preparation of 5-chloro-2,4-difluoro-N-(thiazol-4-yl)benzenesulfonamide

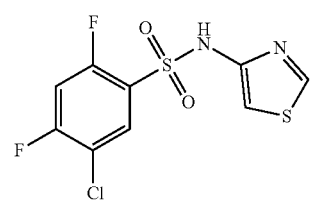 [SMILES: O=S(=O)(Nc1cscn1)c1cc(Cl)c(F)cc1F]

To a solution of tert-butyl ((5-chloro-2,4-difluorophenyl)sulfonyl)(thiazol-4-yl)carbamate (37.0 g, 90.1 mmol) in dichloromethane (400 mL) was added trifluoroacetic acid (200 mL) and the reaction mixture was stirred at ambient temperature for 1 h. Concentration in vacuo provided a residue which was triturated in ethyl acetate (100 mL) to give the title compound as a colorless solid (25.0 g, 89% yield): $^1$H NMR (400 MHz, CDCl$_3$) δ 8.75 (s, 1H), 8.00 (t, J=7.2 Hz, 1H), 7.07 (s, 1H), 7.02 (t, J=8.8 Hz, 1H), NH not observed.

Step 2. Preparation of 5-chloro-2,4-difluoro-N-(4-methoxybenzyl)-N-(thiazol-4-yl)benzenesulfonamide

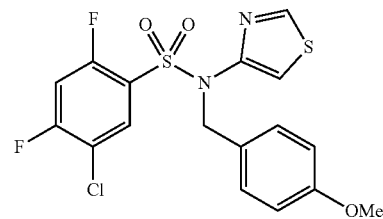 [SMILES: COc1ccc(CN(c2cscn2)S(=O)(=O)c2cc(Cl)c(F)cc2F)cc1]

To a solution of 5-chloro-2,4-difluoro-N-(thiazol-4-yl)benzenesulfonamide (50.00 g, 161.00 mmol) in anhydrous N,N-dimethylformamide (500 mL), was added 4-methoxybenzyl chloride (30.20 g, 193.40 mmol) and sodium bicarbonate (69.08 g, 803.85 mmol). The resulting solution was stirred at 50° C. for 16 h, and then cooled to ambient temperature and diluted with cold water (2000 mL). The supernatant was decanted, and the residue was stirred with water (1000 mL) for 2 h until a yellow solid formed. The solid was collected by filtration and dried in vacuo to obtain the title compound as pale yellow solid (63.80 g, 92% yield): $^1$H NMR (300 MHz, CDCl$_3$) δ 8.57 (d, J=2.3 Hz, 1H), 7.81 (dd, J=7.7, 7.1 Hz, 1H), 7.22 (d, J=14.5 Hz, 2H), 7.18 (d, J=2.3 Hz, 1H), 7.03 (t, J=8.8 Hz, 1H), 6.81-6.76 (m, 2H), 5.01 (s, 2H), 3.76 (d, J=10.2 Hz, 3H).

Step 3. Preparation of tert-butyl (S)-3-((2-chloro-5-fluoro-4-(N-(4-methoxybenzyl)-N-(thiazol-4-yl) sulfamoyl)phenyl)amino)pyrrolidine-1-carboxylate

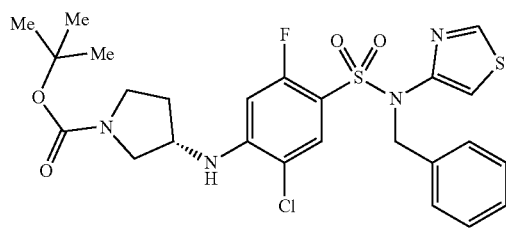

To a solution of 5-chloro-2,4-difluoro-N-(4-methoxybenzyl)-N-(thiazol-4-yl)benzenesulfonamide (15.00 g, 34.95 mmol) and potassium carbonate (15.00 g, 108.62 mmol) in anhydrous N,N-dimethylformamide (100 mL) was added a solution of (S)-1-tert-butoxycarbonyl-3-aminopyrrolidine (6.50 g, 34.90 mmol) dropwise at 0° C. The reaction mixture was slowly warmed to ambient temperature and stirred for 24 h. The reaction mixture was poured onto ice to provide a gum, which was triturated in water (400 mL) and then dissolved in ethyl acetate (100 mL). The organic phase was washed with water (3×150 mL), brine (3×100 mL), dried over anhydrous sodium sulfate, and filtered. Concentration of the filtrate in vacuo provided a pale yellow solid, which was directly used without further purification (18.60 g, 89% yield).

Step 5. Preparation of tert-butyl (S)-3-((5-fluoro-4-(N-(4-methoxybenzyl)-N-(thiazol-4-yl)sulfamoyl)-2-methylphenyl)amino)pyrrolidine-1-carboxylate

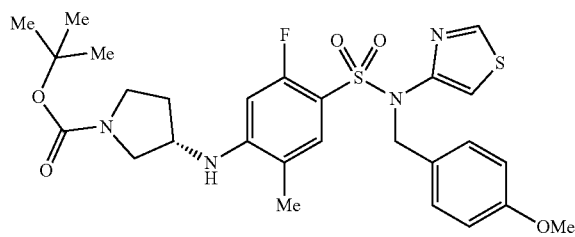 [SMILES: COc1ccc(CN(c2cscn2)S(=O)(=O)c2cc(C)c(N[C@H]3CCN(C(=O)OC(C)(C)C)C3)cc2F)cc1]

To a solution of tert-butyl (S)-3-((2-chloro-5-fluoro-4-(N-(4-methoxybenzyl)-N-(thiazol-4-yl)sulfamoyl)phenyl) amino)pyrrolidine-1-carboxylate (12.80 g, 21.50 mmol) in anhydrous 1,4-dioxane (425 mL) was added palladium(II) acetate (0.48 g, 2.15 mmol), tricyclohexylphosphonium tetrafluoroborate (1.58 g, 4.30 mmol), methylboronic acid (10.15 g, 169.44 mmol) and tripotassium phosphate (18.20 g, 85.74 mmol). The mixture was degassed by sparging with argon, and then heated to reflux for 6 h. After cooling to ambient temperature, the mixture was filtered through a pad of Celite. The filter pad was washed with ethyl acetate (500 mL), and the combined filtrate was concentrated to a volume of about 150 mL. The organic phase was washed with saturated aqueous ammonium chloride (2×250 mL), brine (100 mL), and dried over anhydrous sodium sulfate. Filtration and concentration of the filtrate in vacuo provided the title compound as a brown foam, which was used without further purification (13.0 g, quantitative yield): MS (ES-) m/z 575.2 (M-1).

Step 6. Preparation of tert-butyl (S)-3-((5-fluoro-4-(N-(4-methoxybenzyl)-N-(thiazol-4-yl)sulfamoyl)-2-methylphenyl)(methyl)amino)pyrrolidine-1-carboxylate

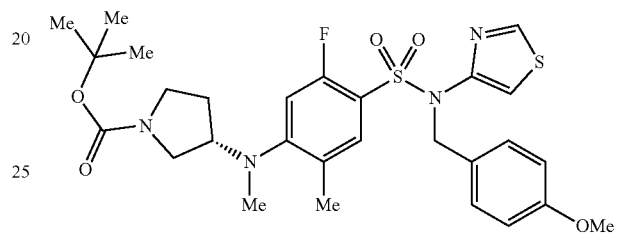

To a solution of tert-butyl (S)-3-((5-fluoro-4-(N-(4-methoxybenzyl)-N-(thiazol-4-yl)sulfamoyl)-2-methylphenyl)amino)pyrrolidine-1-carboxylate (3.26 g, 5.66 mmol) in N,N-dimethylformamide (28 mL) was added iodomethane (0.70 mL, 11.32 mmol) followed by sodium hydride (0.45 g, 11.32 mmol). The solution was stirred for 1 h, then diluted with saturated ammonium chloride (30 mL), and extracted with ethyl acetate (3×50 mL). The combined organic extracts were washed with brine (50 mL), dried over anhydrous magnesium sulfate, and filtered. Concentration of the filtrate in vacuo and purification of the residue by column chromatography, eluting with a gradient of 10 to 50% of ethyl acetate in heptane, provided the title compound as a light brown solid (2.77 g, 83% yield): $^1$H-NMR (300 MHz, CDCl$_3$) δ 8.56 (d, J=2.0 Hz, 1H), 7.52 (d, J=8.1 Hz, 1H), 7.29-7.20 (m, 3H), 6.81-6.75 (m, 3H), 5.03 (s, 2H), 3.81-3.71 (m, 4H), 3.65-3.47 (m, 2H), 3.34-3.19 (m, 2H), 2.65 (s, 3H), 2.22 (s, 3H), 2.04-1.88 (m, 2H), 1.47 (s, 9H); MS (ES+) m/z 591.2 (M+1).

Step 7. Preparation of (S)-2-fluoro-5-methyl-4-(methyl(pyrrolidin-3-yl)amino)-N-(thiazol-4-yl)benzenesulfonamide 2,2,2-trifluoroacetate

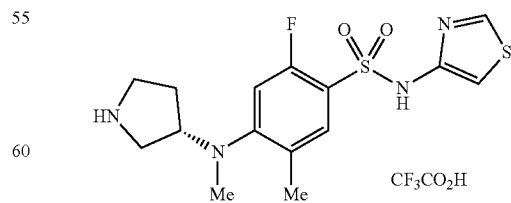

To a solution of tert-butyl (S)-3-((5-fluoro-4-(N-(4-methoxybenzyl)-N-(thiazol-4-yl)sulfamoyl)-2-methylphenyl)(methyl)amino)pyrrolidine-1-carboxylate (2.77 g, 4.70 mmol) in dichloromethane (32 mL) was added trifluoroacetic acid (3.60 mL, 46.98 mmol) and the solution was stirred for 2 h. The volatiles were removed in vacuo and the resulting residue was triturated in methanol (50 mL). Filtration and concentration of the filtrate in vacuo provided a residue, which was triturated in diethyl ether (50 mL) to afford the title compound as a tan solid (2.16 g, 95% yield): MS (ES+) m/z 371.1 (M+1).

Step 8. Preparation of (S)-2-fluoro-4-((1-((2-isopropylthiazol-4-yl)methyl)pyrrolidin-3-yl)(methyl) amino)-5-methyl-N-(thiazol-4-yl)benzenesulfonamide 2,2,2-trifluoroacetate

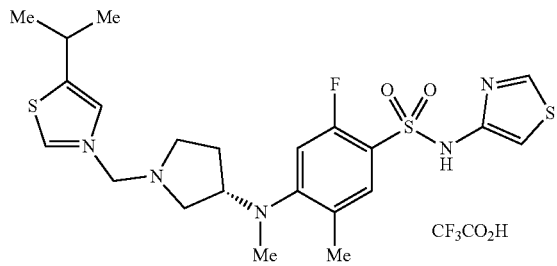

To a solution of (S)-2-fluoro-5-methyl-4-(methyl(pyrrolidin-3-yl)amino)-N-(thiazol-4-yl)benzenesulfonamide 2,2,2-trifluoroacetate (0.081 g, 0.17 mmol) in anhydrous N,N-dimethylformamide (1.7 mL) and anhydrous 1,2-dichloroethane (1.0 mL) was added 2-isopropylthiazole-4-carbaldehyde (0.039 g, 0.25 mmol) and sodium triacetoxyborohydride (0.071 g, 0.33 mmol). The reaction mixture was stirred at ambient temperature for 18 hours. The mixture was then diluted with 1 M sodium hydroxide (0.30 mL) and stirred for 1 h. The mixture was diluted with saturated ammonium chloride (6 mL) and extracted with ethyl acetate (2×5 mL). The combined organic layers were concentrated in vacuo and purified by reverse-phase HPLC, eluting with a gradient of acetonitrile in water containing 0.1% of trifluoroacetic acid, to afford the title compound as a colorless solid (0.052 g, 49% yield): $^1$H NMR (300 MHz, DMSO-$d_6$) δ 11.25 (s, 1H), 10.47-10.30 (m, 1H), 8.89 (d, J=2.2 Hz, 1H), 7.64-7.57 (m, 2H), 7.05 (d, J=12.4 Hz, 1H), 7.00 (d, J=2.1 Hz, 1H), 4.42-4.37 (m, 2H), 4.19-4.11 (m, 2H), 3.51-3.34 (m, 5H), 2.62 (s, 3H), 2.45-2.42 (m, 1H), 2.22 (s, 3H), 2.07-2.00 (m, 2H), 1.16-1.12 (m, 2H), 0.94 (dt, J=2.6, 2.1 Hz, 2H); MS (ES+) m/z 510.1 (M+1).

Examples 108-127

In a similar manner as described in the EXAMPLE 107, utilizing the appropriately substituted starting materials and intermediates, the following compounds were prepared:

| Example No. | Name | MS (ES+) m/z | $^1$H NMR |
|---|---|---|---|
| 108 | (S)-2-fluoro-5-methyl-4-(methyl(1-((1-(2,2,2-trifluoroethyl)-1H-pyrazol-5-yl)methyl)pyrrolidin-3-yl)amino)-N-(thiazol-4-yl)benzenesulfonamide | 533.4 (M + 1) | (400 MHz, CDCl$_3$) δ 8.60 (d, J = 2.4 Hz, 1H), 8.37 (br s, 1H), 7.61 (d, J = 8.4 Hz, 1H), 7.52 (d, J = 1.8 Hz, 1H), 7.01 (d, J = 2.4 Hz, 1H), 6.67 (d, J = 12.4 Hz, 1H), 6.19 (d, J = 1.8 Hz, 1H), 4.99 (dq, J = 4.4, 8.6 Hz, 2H), 3.94-3.81 (m, 1H), 3.67 (d, J = 2.8 Hz, 2H), 2.71 (td, J = 4.2, 8.8 Hz, 1H), 2.66 (s, 3H), 2.61 (d, J = 6.4 Hz, 2H), 2.48-2.38 (m, 1H), 2.24 (s, 3H), 2.14-2.03 (m, 1H), 1.89-1.78 (m, 1H). |
| 109 | 2-fluoro-5-methyl-4-(methyl((S)-1-((1s,3R)-3-phenylcyclobutyl)-pyrrolidin-3-yl)amino)-N-(thiazol-4-yl)benzenesulfonamide formate | 501.2 (M + 1) | (400 MHz, DMSO-$d_6$) δ 8.85 (d, J = 2.1 Hz, 1H), 8.21 (s, 1H), 7.54 (dd, J = 8.4, 0.3 Hz, 1H), 7.31-7.15 (m, 5H), 6.90 (d, J = 12.6 Hz, 1H), 6.87-6.86 (m, 1H), 3.92-3.85 (m, 1H), 3.17-3.11 (m, 1H), 2.89-2.84 (m, 1H), 2.67 (d, J = 1.7 Hz, 1H), 2.64 (s, 3H), 2.59 (d, J = 0.4 Hz, 1H), 2.42-2.33 (m, 4H), 2.21 (s, 3H), 2.00-1.89 (m, 3H), 1.75-1.71 (m, 1H). |
| 110 | (S)-2-fluoro-5-methyl-4-(methyl(1-((2-methylthiazol-4-yl)methyl)pyrrolidin-3-yl)amino)-N-(thiazol-4-yl)benzenesulfonamide formate | 482.1 (M + 1) | (400 MHz, CD$_3$OD) δ 8.72 (d, J = 2.2 Hz, 1H), 8.42 (br s, 1H), 7.67 (d, J = 8.3 Hz, 1H), 7.40 (s, 1H), 7.00 (d, J = 2.2 Hz, 1H), 6.95 (d, J = 12.1 Hz, 1H), 4.10 (d, J = 5.3 Hz, 2H), 4.04-4.00 (m, 1H), 3.27-3.22 (m, 1H), 3.14-2.99 (m, 3H), 2.71 (s, 3H), 2.67 (s, 3H), 2.29 (s, 3H), 2.19-2.15 (m, 1H), 2.01-1.95 (m, 1H), NH and COOH not observed. |
| 111 | (S)-2-fluoro-5-methyl-4-(methyl(1-((1-methyl-1H-pyrazol-3-yl)methyl)pyrrolidin-3-yl)amino)-N-(thiazol-4-yl)benzenesulfonamide formate | 465.2 (M + 1) | (400 MHz, CD$_3$OD) δ 8.72 (d, J = 1.7 Hz, 1H), 8.51 (s, 1H), 7.67 (d, J = 8.2 Hz, 1H), 7.59 (d, J = 0.3 Hz, 1H), 6.99 (d, J = 1.7 Hz, 1H), 6.95 (d, J = |

-continued

| Example No. | Name | MS (ES+) m/z | ¹H NMR |
|---|---|---|---|
| | | | 12.2 Hz, 1H), 6.34 (d, J = 1.6 Hz, 1H), 4.08-3.99 (m, 3H), 3.89 (s, 3H), 3.55-3.45 (m, 1H), 3.19-3.07 (m, 2H), 3.03-2.99 (m, 1H), 2.65 (s, 3H), 2.28 (s, 3H), 2.22-2.13 (m, 1H), 2.00-1.94 (m, 1H), NH and COOH not observed. |
| 112 | (S)-4-((1-(2-(difluoromethyl)benzyl)-pyrrolidin-3-yl)(methyl)amino)-2-fluoro-5-methyl-N-(thiazol-4-yl)benzenesulfonamide | 511.2 (M + 1) | (400 MHz, CD₃OD) δ 8.70 (d, J = 2.2 Hz, 1H), 7.63-7.59 (m, 2H), 7.47-7.40 (m, 3H), 7.20 (d, J = 55.6 Hz, 1H), 6.97 (d, J = 2.2 Hz, 1H), 6.82 (d, J = 12.5 Hz, 1H), 3.98-3.91 (m, 1H), 3.79 (d, J = 3.3 Hz, 2H), 2.80-2.75 (m, 1H), 2.71-2.65 (m, 5H), 2.49 (q, J = 8.3 Hz, 1H), 2.26 (s, 3H), 2.11-2.06 (m, 1H), 1.89-1.83(m, 1H), NH not observed. |
| 113 | (S)-2-fluoro-4-((1-(2-hydroxybenzyl)-pyrrolidin-3-yl)(methyl)amino)-5-methyl-N-(thiazol-4-yl)benzenesulfonamide | 477.1 (M + 1) | (300 MHz, DMSO-d₆) δ 10.80 (s, 1H), 8.86 (d, J = 2.2 Hz, 1H), 7.55 (dd, J = 8.6, 0.4 Hz, 1H), 7.12-7.05 (m, 2H), 6.94-6.90 (m, 2H), 6.76-6.72 (m, 2H), 4.00-3.91 (m, 1H), 3.69 (s, 2H), 2.78-2.61 (m, 6H), 2.47-2.40 (m, 1H), 2.21 (s, 3H), 2.09-1.98 (m, 1H), 1.83-1.72 (m, 1H), one exchangeable proton not observed. |
| 114 | (S)-2-fluoro-4-((1-(3-hydroxybenzyl)-pyrrolidin-3-yl)(methyl)amino)-5-methyl-N-(thiazol-4-yl)benzenesulfonamide | 477.1 (M + 1) | (300 MHz, DMSO-d₆) δ 11.10 (s, 1H), 9.34 (s, 1H), 8.87 (d, J = 2.2 Hz, 1H), 7.55-7.52 (m, 1H), 7.09 (t, J = 7.8 Hz, 1H), 6.95 (d, J = 2.2 Hz, 1H), 6.88 (d, J = 12.8 Hz, 1H), 6.73-6.70 (m, 2H), 6.65-6.61 (m, 1H), 3.97-3.87 (m, 1H), 3.60-3.43 (m, 2H), 2.72-2.57 (m, 6H), 2.45-2.36 (m, 1H), 2.20 (s, 3H), 2.04-1.96 (m, 1H), 1.81-1.70 (m, 1H) |
| 115 | (S)-2-fluoro-5-methyl-4-(methyl(1-phenethylpyrrolidin-3-yl)amino)-N-(thiazol-4-yl)benzenesulfonamide | 475.2 (M + 1) | (400 MHz, CD₃OD) δ 8.71 (d, J = 2.2 Hz, 1H), 7.67 (d, J = 8.4 Hz, 1H), 7.32-7.22 (m, 5H), 6.97-6.92 (m, 2H), 4.03-4.00 (m, 1H), 3.23-3.18 (m, 1H), 3.14-3.04 (m, 4H), 2.98-2.90 (m, 3H), 2.67 (s, 3H), 2.29 (s, 3H), 2.22-2.15 (m, 1H), 2.01-1.94 (m, 1H), NH not observed. |
| 116 | (S)-2-fluoro-4-((1-((3-isopropoxypyridin-2-yl)methyl)pyrrolidin-3-yl)(methyl)amino)-5-methyl-N-(thiazol-4-yl)benzenesulfonamide formate | 520.3 (M + 1) | (400 MHz, CD₃OD) δ 8.71 (d, J = 2.1 Hz, 1H), 8.55 (s, 1H), 8.12-8.11 (m, 1H), 7.67 (d, J = 8.2 Hz, 1H), 7.48-7.46 (m, 1H), 7.34 (dd, J = 8.4, 4.7 Hz, 1H), 6.98 (d, J = 2.3 Hz, 1H), 6.94 (d, J = 12.1 Hz, 1H), 4.73-4.69 (m, 1H), 4.16 (s, 2H), 4.02-3.98 (m, 1H), 3.28-3.22 (m, 1H), 3.15-3.13 (m, 2H), 3.02-2.99 (m, 1H), 2.67 (s, 3H), 2.29 (s, 3H), 2.19-2.15 (m, 1H), 2.00-1.96 (m, 1H), 1.35 (d, J = 6.0 Hz, 6H), NH and COOH not observed. |
| 117 | 2-fluoro-5-methyl-4-(methyl((S)-1-((1r,3S)-3-phenylcyclobutyl)-pyrrolidin-3-yl)amino)-N-(thiazol-4-yl)benzenesulfonamide formate | 501.2 (M + 1) | (400 MHz, CD₃OD) δ 8.72 (d, J = 2.2 Hz, 1H), 8.43 (s, 1H), 7.71 (d, J = 8.2 Hz, 1H), 7.35-7.23 (m, 5H), 7.05-7.01 (m, 2H), 4.14-4.10 (m, 1H), 3.90-3.86 (m, 1H), 3.71-3.67 (m, 1H), 3.46-3.40 (m, 3H), 3.24- |

| Example No. | Name | MS (ES+) m/z | ¹H NMR |
|---|---|---|---|
| | | | 3.19 (m, 1H), 2.78-2.72 (m, 2H), 2.69 (s, 3H), 2.55-2.50 (m, 1H), 2.32 (d, J = 5.7 Hz, 3H), 2.30-2.25 (m, 2H), 2.13-2.07 (m, 1H), NH and COOH not observed. |
| 118 | (S)-2-fluoro-5-methyl-4-(methyl(1-((1-(2,2,2-trifluoroethyl)-1H-pyrazol-3-yl)methyl)pyrrolidin-3-yl)amino)-N-(thiazol-4-yl)benzenesulfonamide | 533.4 (M + 1) | (400 MHz, CD₃OD) δ 8.70 (d, J = 2.4 Hz, 1H), 7.71 (d, J = 2.4 Hz, 1H), 7.62 (d, J = 8.4 Hz, 1H), 6.93 (d, J = 2.2 Hz, 1H), 6.86 (d, J = 12.4 Hz, 1H), 6.38 (d, J = 2.4 Hz, 1H), 4.94-4.91 (m, 2H), 3.94-3.85 (m, 1H), 3.76-3.61 (m, 2H), 2.87 (dd, J = 7.6, 10.0 Hz, 1H), 2.70 (br t, J = 7.2 Hz, 2H), 2.64 (s, 3H), 2.58 (dd, J = 6.2, 10.0 Hz, 1H), 2.26 (s, 3H), 2.07 (qd, J = 6.8, 15.4 Hz, 1H), 1.82 (qd, J = 6.8, 13.4 Hz, 1H), NH not observed. |
| 119 | (S)-2-fluoro-4-((1-(2-methoxybenzyl)-pyrrolidin-3-yl)(methyl)amino)-5-methyl-N-(thiazol-4-yl)benzenesulfonamide formate | 491.2 (M + 1) | (400 MHz, CD₃OD) δ 8.72 (d, J = 2.1 Hz, 1H), 8.52 (s, 1H), 7.70 (d, J = 8.3 Hz, 1H), 7.46-7.42 (m, 1H), 7.36 (d, J = 7.6 Hz, 1H), 7.08 (d, J = 8.5 Hz, 1H), 7.03-6.97 (m, 3H), 4.24 (s, 2H), 4.09-4.05 (m, 1H), 3.87 (s, 3H), 3.44-3.39 (m, 1H), 3.30-3.24 (m, 2H), 3.14-3.10 (m, 1H), 2.67 (s, 3H), 2.29 (s, 3H), 2.24-2.20 (m, 1H), 2.10-2.06 (m, 1H), NH and COOH not observed. |
| 120 | (S)-2-fluoro-4-((1-((3-methoxypyridin-2-yl)methyl)pyrrolidin-3-yl)(methyl)amino)-5-methyl-N-(thiazol-4-yl)benzenesulfonamide formate | 492.1 (M + 1) | (400 MHz, CD₃OD) δ 8.71 (d, J = 2.2 Hz, 1H), 8.47 (s, 1H), 8.18 (dd, J = 4.7, 1.1 Hz, 1H), 7.70 (dd, J = 8.1, 0.3 Hz, 1H), 7.52-7.50 (m, 1H), 7.42 (dd, J = 8.4, 4.6 Hz, 1H), 7.02-6.99 (m, 2H), 4.43 (s, 2H), 4.13-4.09 (m, 1H), 3.92 (s, 3H), 3.50-3.37 (m, 4H), 2.69 (s, 3H), 2.32-2.31 (m, 3H), 2.29-2.24 (m, 1H), 2.13-2.09 (m, 1H), NH and COOH not observed. |
| 121 | (S)-2-fluoro-5-methyl-4-(methyl(1-((5-methylisothiazol-3-yl)methyl)pyrrolidin-3-yl)amino)-N-(thiazol-4-yl)benzenesulfonamide formate | 482.1 (M + 1) | (400 MHz, CD₃OD) δ 8.71 (d, J = 2.2 Hz, 1H), 8.47 (s, 1H), 7.64 (d, J = 8.3 Hz, 1H), 7.09 (s, 1H), 6.98 (d, J = 2.2 Hz, 1H), 6.91 (d, J = 12.3 Hz, 1H), 4.01-3.90 (m, 3H), 3.06-3.01 (m, 1H), 2.97-2.93 (m, 1H), 2.89-2.81 (m, 2H), 2.67 (s, 3H), 2.61 (s, 3H), 2.28 (s, 3H), 2.17-2.11 (m, 1H), 1.96-1.89 (m, 1H), NH and COOH not observed. |
| 122 | (S)-2-fluoro-5-methyl-4-(methyl(1-(pyrazolo [1,5-a]pyridin-2-ylmethyl)pyrrolidin-3-yl)amino)-N-(thiazol-4-yl)benzenesulfonamide | 501.3 (M + 1) | (400 MHz, CD₃OD) δ 8.70(d, J = 2.2 Hz 1H), 8.51 (d, J = 7.0 Hz, 1H), 7.65 (dd, J = 8.6, 4.3 Hz, 2H), 7.28-7.21 (m, 1H), 6.99 (d, J = 2.2 Hz, 1H), 6.96-6.90 (m, 2H), 6.64 (s, 1H), 4.30-4.21 (m, 2H), 4.04-4.01 (m, 1H), 3.31-3.28 (m, 1H), 3.21-3.13 (m, 2H), 3.10-3.06 (m, 1H), 2.66 (s, 3H), 2.25 (s, 3H), 2.22-2.16 (m, 1H), 2.02-1.97 (m, 1H), NH not observed. |
| 123 | (S)-4-((1-(cyclohexylmethyl)-pyrrolidin-3-yl)(methyl)amino)-2-fluoro-5-methyl-N-(thiazol-4-yl)benzenesulfonamide | 467.3 (M + 1) | (400 MHz, CDCl₃) δ 8.63 (d, J = 2.3 Hz, 1H), 7.64 (d, J = 8.4 Hz, 1H), 7.02 (d, J = 2.2 Hz, 1H), 6.74 (d, J = 11.9 Hz, 1H), |

-continued

| Example No. | Name | MS (ES+) m/z | ¹H NMR |
|---|---|---|---|
| | | | 4.02-3.98 (m, 1H), 2.68 (s, 4H), 2.63-2.58 (m, 2H), 2.26-2.20 (m, 4H), 2.20-2.16 (m, 1H), 1.82-1.70 (m, 5H), 1.63-1.49 (m, 2H), 1.28-1.18 (m, 4H), 0.99-0.94 (m, 3H), NH not observed. |
| 124 | (S)-2-fluoro-5-methyl-4-(methyl(1-neopentylpyrrolidin-3-yl)amino)-N-(thiazol-4-yl)benzenesulfonamide formate | 441.1 (M + 1) | (400 MHz, CD₃OD) δ 8.72(d, J = 2.2 Hz, 1H), 8.51 (s, 1H), 7.66 (d, J = 8.4 Hz, 1H), 6.99 (d, J = 2.2 Hz, 1H), 6.94 (d, J = 12.3 Hz, 1H), 4.03-3.99 (m, 1H), 3.19-3.16 (m, 2H), 3.07-3.02 (m, 2H), 2.72 (s, 3H), 2.70-2.68 (m, 2H), 2.29 (s, 3H), 2.19-2.11 (m, 1H), 2.02-1.95 (m, 1H), 1.01 (s, 9H), NH and COOH not observed. |
| 125 | (S)-4-((1-(3,3-dimethylbutyl)-pyrrolidin-3-yl)(methyl)amino)-2-fluoro-5-methyl-N-(thiazol-4-yl)benzenesulfonamide formate | 455.1 | (400 MHz, CD₃OD) δ 8.70(s, 1H), 8.51 (s, 1H), 7.67 (d, J = 8.0 Hz, 1H), 6.98-6.96 (m, 2H), 4.05-4.01 (m, 1H), 3.28-2.95 (m, 6H), 2.66 (s, 3H), 2.29 (s, 3H), 2.23-2.18 (m, 1H), 2.01-1.96 (m, 1H), 1.56-1.52 (m, 2H), 0.96-0.92 (m, 9H), NH and COOH not observed. |
| 126 | (S)-2-fluoro-4-((1-(4-hydroxybenzyl)-pyrrolidin-3-yl)(methyl)amino)-5-methyl-N-(thiazol-4-yl)benzenesulfonamide | 477.1 (M + 1) | (300 MHz, DMSO-d₆) δ 11.10 (s, 1H), 9.35 (d, J = 0.5 Hz, 1H), 8.86 (d, J = 2.2 Hz, 1H), 7.53 (dd, J = 8.6, 0.5 Hz, 1H), 7.09 (d, J = 8.5 Hz, 2H), 6.94 (d, J = 2.2 Hz, 1H), 6.88 (d, J = 12.8 Hz, 1H), 6.72-6.67 (m, 2H), 3.95-3.86 (m, 1H), 3.59-3.43 (m, 2H), 2.74-2.55 (m, 6H), 2.38-2.37 (m, 1H), 2.19 (s, 3H), 2.05-1.93 (m, 1H), 1.80-1.67(m, 1H) |
| 127 | (S)-2-fluoro-4-((1-(2-fluoro-3-methylbenzyl)pyrrolidin-3-yl)(methyl)amino)-5-methyl-N-(thiazol-4-yl)benzenesulfonamide 2,2,2-trifluoroacetate | 493.2 (M + 1) | (300 MHz, DMSO-d₆) δ 11.24 (s, 1H), 10.42-10.47 (m, 1H), 8.89 (d, J = 2.2 Hz, 1H), 7.61 (dd, J = 8.5, 0.5 Hz, 1H), 7.40 (t, J = 7.5 Hz, 2H), 7.19 (d, J = 7.6 Hz, 1H), 7.03 (d, J = 12.4 Hz, 1H), 6.99 (d, J = 2.2 Hz, 1H), 4.43 (d, J = 12.1 Hz, 2H), 4.14 (m, 1H), 3.65-3.09 (m, 4H), 2.64 (d, J = 16.1 Hz, 3H), 2.26-1.92 (m, 8H). |

Examples 128-154

In a similar manner as described in the EXAMPLE 107, utilizing the appropriately substituted starting materials and intermediates, the following compounds were prepared:

| Example No. | Name | MS (ES+) m/z |
|---|---|---|
| 128 | 4-(((S)-1-((S)-2,3-dihydro-1H-inden-1-yl)pyrrolidin-3-yl)(methyl)amino)-2-fluoro-5-methyl-N-(thiazol-4-yl)benzenesulfonamide | 487.2 (M + 1) |
| 129 | (S)-2-fluoro-5-methyl-4-(methyl(1((4-methylthiazol-2-yl)methyl)pyrrolidin-3-yl)amino)-N-(thiazol-4-yl)benzenesulfonamide | 482.1 (M + 1) |
| 130 | (S)-2-fluoro-4-((1-((3-fluoro-6-methylpyridin-2-yl)methyl)pyrrolidin-3-yl)(methyl)amino)-5-methyl-N-(thiazol-4-yl)benzenesulfonamide | 494.2 (M + 1) |
| 131 | (S)-2-fluoro-5-methyl-4-(methyl(1-((2-methyloxazol-4-yl)methyl)pyrrolidin-3-yl)amino)-N-(thiazol-4-yl)benzenesulfonamide | 466.1 (M + 1) |
| 132 | (S)-2-fluoro-5-methyl-4-(methyl(1-((5-methylfuran-2-yl)methyl)pyrrolidin-3-yl)amino)-N-(thiazol-4-yl)benzenesulfonamide | 465.1 (M + 1) |
| 133 | (S)-2-fluoro-4-((1-((2-isopropyloxazol-4-yl)methyl)pyrrolidin-3-yl)(methyl)amino)-5-methyl-N-(thiazol-4-yl)benzenesulfonamide | 494.1 (M + 1) |
| 134 | (S)-4-((1-((4-cyclopropylthiazol-2-yl)methyl)pyrrolidin-3-yl)(methyl)amino)-2-fluoro-5-methyl-N-(thiazol-4-yl)benzenesulfonamide | 508.1 (M + 1) |
| 135 | (S)-2-fluoro-5-methyl-4-(methyl(1-((2-phenylthiazol-4-yl)methyl)pyrrolidin-3-yl)amino)-N-(thiazol-4-yl)benzenesulfonamide | 544.1 (M + 1) |

| Example No. | Name | MS (ES+) m/z |
|---|---|---|
| 136 | (S)-2-fluoro-5-methyl-4-(methyl(1-(thiazol-2-ylmethyl)pyrrolidin-3-yl)amino)-N-(thiazol-4-yl)benzenesulfonamide | 467.9 (M + 1) |
| 137 | (S)-2-fluoro-5-methyl-4-(methyl(1-((2-(trifluoromethyl)thiazol-4-yl)methyl)pyrrolidin-3-yl)amino)-N-(thiazol-4-yl)benzenesulfonamide | 536.1 (M + 1) |
| 138 | (S)-4-((1-((2-cyclopropylthiazol-4-yl)methyl)pyrrolidin-3-yl)(methyl)amino)-2-fluoro-5-methyl-N-(thiazol-4-yl)benzenesulfonamide | 508.1 (M + 1) |
| 139 | (S)-2-fluoro-5-methyl-4-(methyl(1-((4-methyloxazol-2-yl)methyl)pyrrolidin-3-yl)amino)-N-(thiazol-4-yl)benzenesulfonamide | 466.1 (M + 1) |
| 140 | (S)-2-fluoro-5-methyl-4-(methyl(1-(thiazol-4-ylmethyl)pyrrolidin-3-yl)amino)-N-(thiazol-4-yl)benzenesulfonamide | 468.1 (M + 1) |
| 141 | (S)-4-((1-((1,5-dimethyl-1H-pyrazol-3-yl)methyl)pyrrolidin-3-yl)(methyl)amino)-2-fluoro-5-methyl-N-(thiazol-4-yl)benzenesulfonamide | 479.1 (M + 1) |
| 142 | (S)-2-fluoro-5-methyl-4-(methyl(1-((5-(trifluoromethyl)furan-2-yl)methyl)pyrrolidin-3-yl)amino)-N-(thiazol-4-yl)benzenesulfonamide | 518.8 (M + 1) |
| 143 | (S)-2-fluoro-5-methyl-4-(methyl(1-(oxazol-4-ylmethyl)pyrrolidin-3-yl)amino)-N-(thiazol-4-yl)benzenesulfonamide | 452.1 (M + 1) |
| 144 | (S)-4((1-(benzo[d]thiazol-2-ylmethyl)pyrrolidin-3-yl)(methyl)amino)-2-fluoro-5-methyl-N-(thiazol-4-yl)benzenesulfonamide | 518.1 (M + 1) |
| 145 | (S)-2-fluoro-4-((1-((4-isopropylthiazol-2-yl)methyl)pyrrolidin-3-yl)(methyl)amino)-5-methyl-N-(thiazol-4-yl)benzenesulfonamide | 510.2 (M + 1) |
| 146 | (S)-4-((1-((5-chlorothiazol-2-yl)methyl)pyrrolidin-3-yl)(methyl)amino)-2-fluoro-5-methyl-N-(thiazol-4-yl)benzenesulfonamide | 502.1 (M + 1), 504.1 (M + 1) |
| 147 | (S)-4-((1-((1-(difluoromethyl)-1H-pyrazol-3-yl)methyl)pyrrolidin-3-yl)(methyl)amino)-2-fluoro-5-methyl-N-(thiazol-4-yl)benzenesulfonamide | 501.1 (M + 1) |
| 148 | (S)-2-fluoro-5-methyl-4-(methyl(1-(2-methylbenzyl)pyrrolidin-3-yl)amino)-N-(thiazol-4-yl)benzenesulfonamide | 475.3 (M + 1) |
| 149 | (S)-4-((1-(2,3-dihydro-1H-inden-2-yl)pyrrolidin-3-yl)(methyl)amino)-2-fluoro-5-methyl-N-(thiazol-4-yl)benzenesulfonamide | 487.0 (M + 1) |
| 150 | (S)-4-((1-((1,4-dimethyl-1H-imidazol-2-yl)methyl)pyrrolidin-3-yl)(methyl)amino)-2-fluoro-5-methyl-N-(thiazol-4-yl)benzenesulfonamide | 479.2 (M + 1) |
| 151 | (S)-2-fluoro-5-methyl-4-(methyl(1-((4,5,6,7-tetrahydropyrazolo[1,5-a]pyridin-2-yl)methyl)pyrrolidin-3-yl)amino)-N-(thiazol-4-yl)benzenesulfonamide | 505.2 (M + 1) |
| 152 | (S)-2-fluoro-5-methyl-4-(methyl(1-((4-(trifluoromethyl)thiazol-2-yl)methyl)pyrrolidin-3-yl)amino)-N-(thiazol-4-yl)benzenesulfonamide | 536.1 (M + 1) |
| 153 | (S)-4-((1-((1-(2,2-difluoroethyl)-1H-pyrazol-3-yl)methyl)pyrrolidin-3-yl)(methyl)amino)-2-fluoro-5-methyl-N-(thiazol-4-yl)benzenesulfonamide 2,2,2-trifluoroacetate | 515.0 (M + 1) |
| 154 | (S)-2-fluoro-5-methyl-4-(methyl(1-((2-methyl-5-(trifluoromethyl)oxazol-4-yl)methyl)pyrrolidin-3-yl)amino)-N-(thiazol-4-yl)benzenesulfonamide 2,2,2-trifluoroacetate | 534.2 (M + 1) |

Example 155

Synthesis of (S)-2-fluoro-4-((1-(2-fluorobenzyl)pyrrolidin-3-yl)(methyl)amino)-5-methyl-N-(thiazol-4-yl)benzenesulfonamide

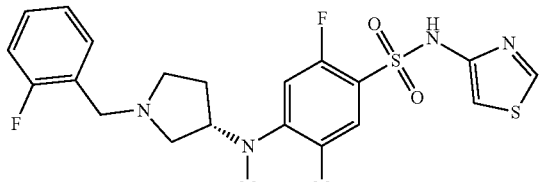

Step 1. Preparation of tert-butyl (S)-3-((5-fluoro-2-methyl-4-(N-(thiazol-4-yl)sulfamoyl)phenyl)amino) pyrrolidine-1-carboxylate

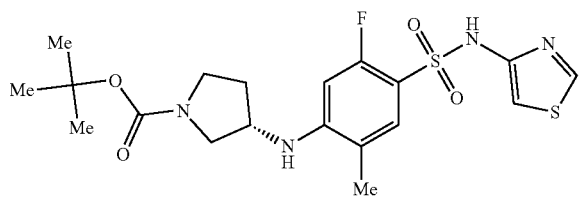 [SMILES: Cc1cc(S(=O)(=O)Nc2cscn2)c(F)cc1N[C@H]1CCN(C(=O)OC(C)(C)C)C1]

To a solution of tert-butyl (S)-3-((4-(N-(tert-butoxycarbonyl)-N-(thiazol-4-yl)sulfamoyl)-2-chloro-5-fluorophenyl)amino)pyrrolidine-1-carboxylate (8.58 g, 14.87 mmol) in anhydrous 1,4-dioxane (149 mL) was added methylboronic acid (10.15 g, 169.44 mmol) and tripotassium phosphate (18.20 g, 85.74 mmol). The mixture was degassed by sparging with argon before palladium(II) acetate (0.48 g, 2.15 mmol) and tricyclohexylphosphonium tetrafluoroborate (1.58 g, 4.30 mmol) were added to it. The resulting suspension was heated to 115° C. for 4 h. After cooling to ambient temperature, the mixture was filtered through a pad of Celite. The filter pad was washed with ethyl acetate (200 mL), and the combined filtrate was concentrated in vacuo. The residue was diluted with ethyl acetate (100 mL) and then washed with water (50 mL) and brine (50 mL). The organic layer was dried over anhydrous sodium sulfate, filtered, and concentrated in vacuo. The residue was purified by column chromatography, eluting with a gradient of 0-60% of ethyl acetate (containing 10% isopropyl alcohol and 10% triethylamine) in hexanes to afford tert-butyl (S)-3-((4-(N-(tert-butoxycarbonyl)-N-(thiazol-4-yl)sulfamoyl)-5-fluoro-2-methylphenyl)amino)pyrrolidine-1-carboxylate as pale brown solid (5.13 g, 62% yield) and the title compound as pale brown solid (1.84 g, 27% yield). Characterization data for tert-butyl (S)-3-((4-(N-(tert-butoxycarbonyl)-N-(thiazol-4-yl)sulfamoyl)-5-fluoro-2-methylphenyl)amino)pyrrolidine-1-carboxylate: $^1$H-NMR (300 MHz, CDCl$_3$) δ 8.79 (d, J=2.3 Hz, 1H), 7.70 (dd, J=8.0, 0.8 Hz, 1H), 7.51 (dd, J=2.3, 0.5 Hz, 1H), 6.33 (d, J=12.7 Hz, 1H), 4.08-4.03 (m, 1H), 3.79-3.73 (m, 1H), 3.54-3.48 (m, 2H), 3.33-3.27 (m, 1H), 2.34 (d, J=7.8 Hz, 1H), 2.12 (s, 3H), 1.92 (dt, J=0.8, 0.4 Hz, 1H), 1.48 (s, 9H), 1.35 (s, 9H), NH not observed; MS (ES+) m/z 557.2 (M+1), 558.3 (M+1). Characterization data for tert-butyl (S)-3-((5-fluoro-2-methyl-4-

(N-(thiazol-4-yl)sulfamoyl)phenyl)amino)pyrrolidine-1-carboxylate: ¹H NMR (300 MHz, CDCl₃) s 8.66 (td, J=1.1, 0.6 Hz, 1H), 7.51 (dd, J=8.0, 0.7 Hz, 1H), 6.98 (dt, J=1.6, 0.4 Hz, 1H), 6.29 (d, J=12.8 Hz, 1H), 4.05-3.98 (m, 1H), 3.76-3.70 (m, 1H), 3.54-3.47 (m, 2H), 3.30-3.25 (m, 1H), 2.29-2.20 (m, 1H), 2.07 (s, 3H), 1.96-1.89 (m, 1H), 1.48 (s, 9H), NH not observed; MS (ES+) m/z 457.1 (M+1), 458.1 (M+1); MS (ES-) m/z 455.3 (M-1), 456.2 (M-1).

Step 2. Preparation of (S)-2-fluoro-5-methyl-4-(pyrrolidin-3-ylamino)-N-(thiazol-4-yl)benzenesulfonamide 2,2,2-trifluoroacetate

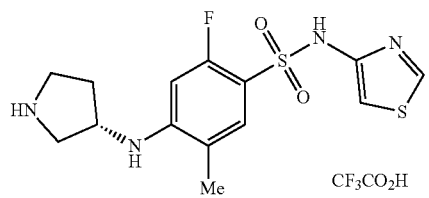 [SMILES: Cc1cc(S(=O)(=O)Nc2cscn2)c(F)cc1N[C@H]1CCNC1 ; "CF3CO2H"]

To a solution of tert-butyl (S)-3-((5-fluoro-2-methyl-4-(N-(thiazol-4-yl)sulfamoyl)phenyl)amino)pyrrolidine-1-carboxylate (0.900 g, 1.97 mmol) in dichloromethane (30 mL) was added trifluoroacetic acid (7 mL) and the reaction was stirred at ambient temperature for 3 h. The reaction mixture was concentrated under reduced pressure and the residue was triturated with diethyl ether (10 mL). The resulting suspension was filtered to yield the title compound as a pale yellow solid (0.805 g, 87% yield) which was used without further purification: MS (ES+) m/z 357.2 (M+1), 358.2 (M+1).

Step 3. Preparation of (S)-2-fluoro-4-((1-(2-fluorobenzyl)pyrrolidin-3-yl)amino)-5-methyl-N-(thiazol-4-yl)benzenesulfonamide

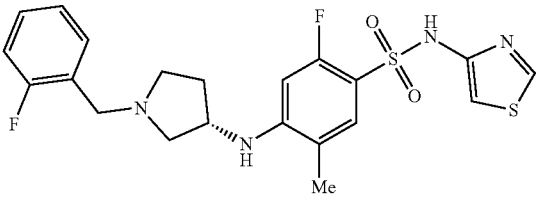 [SMILES: Cc1cc(S(=O)(=O)Nc2cscn2)c(F)cc1N[C@H]1CCN(Cc2ccccc2F)C1]

To a solution of (S)-2-fluoro-5-methyl-4-(pyrrolidin-3-ylamino)-N-(thiazol-4-yl)benzenesulfonamide 2,2,2-trifluoroacetate (0.250 g, 0.531 mmol) in anhydrous 1,2-dichloroethane (4.5 mL) and anhydrous N,N-dimethylformamide (4.5 mL) was added 2-fluorobenzaldehyde (0.170 mL, 1.59 mmol). After 15 minutes, sodium triacetoxyborohydride (0.338 g, 1.59 mmol) was added and the reaction was stirred at ambient temperature for 16 h. The reaction was diluted with ethyl acetate (50 mL) and washed with brine (2×25 mL). The aqueous layers were extracted with ethyl acetate (3×75 mL). The combined organic layers were dried over anhydrous sodium sulfate, and filtered. Concentration of the filtrate in vacuo and purification of the residue by column chromatography, eluting with a gradient of 0-5% of methanol (containing 2% of ammonium hydroxide) in dichloromethane, provided the title compound as a pale yellow solid (0.209 g, 85% yield): MS (ES+) m/z 465.2 (M+1), 466.1 (M+1); (ES-) m/z 463.2 (M-1), 464.2 (M-1).

Step 4. Preparation of (S)-2-fluoro-4-((1-(2-fluorobenzyl)pyrrolidin-3-yl)(methyl)amino)-5-methyl-N-(thiazol-4-yl)benzenesulfonamide

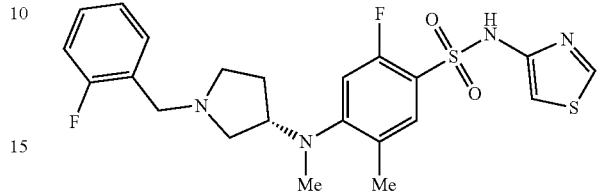

To a cooled (0° C.) solution of (S)-2-fluoro-4-((1-(2-fluorobenzyl)pyrrolidin-3-yl)amino)-5-methyl-N-(thiazol-4-yl)benzenesulfonamide (0.209 g, 0.450 mmol) in trifluoroacetic acid (4.5 mL) was added sodium triacetoxyborohydride (0.286 g, 1.35 mmol). The resulting mixture was stirred at 0° C. for 10 minutes before paraformaldehyde (0.020 g, 0.68 mmol) was added to it. The reaction mixture was stirred at 0° C. for 45 minutes and then concentrated in vacuo. To the residue was added 2 M sodium hydroxide (15 mL) and brine (15 mL), and the mixture was extracted with ethyl acetate (50 mL). The aqueous layer was diluted with saturated ammonium chloride (50 mL) and then extracted with ethyl acetate (50 mL). The combined organic layers were washed with saturated ammonium chloride (30 mL), brine (30 mL), dried over anhydrous sodium sulfate, and filtered. Concentration of the filtrate in vacuo and purification of the residue by column chromatography, eluting with a gradient of 0-5% of methanol (containing 2% of ammonium hydroxide in dichloromethane, provided the title compound as a pale yellow solid (0.093 g, 43% yield) ¹H NMR (300 MHz, CDCl₃) δ 8.71 (d, J=2.3 Hz, 1H), 7.60 (dd, J=8.4, 0.5 Hz, 1H), 7.48-7.43 (m, 1H), 7.31-7.24 (m, 1H), 7.13 (td, J=7.5, 1.2 Hz, 1H), 7.04 (ddd, J=9.9, 8.4, 1.3 Hz, 1H), 6.90 (d, J=2.3 Hz, 1H), 6.63 (d, J=12.3 Hz, 1H), 3.96-3.88 (m, 1H), 3.88-3.75 (m, 2H), 2.93-2.68 (m, 4H), 2.64 (s, 3H), 2.21 (d, J=4.3 Hz, 3H), 2.16-2.04 (m, 1H), 1.90-1.83 (m, 1H), NH not observed; MS (ES+) m/z 479.2 (M+1); MS (ES-) m/z 477.3 (M-1).

Examples 156-157

In a similar manner as described in the EXAMPLE 155, Step 3 to Step 4, utilizing the appropriately substituted starting materials and intermediates, the following compounds were prepared:

| Example No | Name | MS (ES+) m/z | ¹H NMR |
|---|---|---|---|
| 156 | (S)-4-((1-(2,3-difluorobenzyl)pyrrolidin-3-yl)(methyl)amino)-2-fluoro-5-methyl-N-(thiazol-4-yl)benzenesulfonamide | 497.2 (M + 1) | (300 MHz, CDCl₃) δ 8.74 (d, J = 2.3 Hz, 1H), 7.60 (dd, J = 8.4, 0.5 Hz, 1H), 7.19-7.15 (m, 1H), 7.09-7.03 (m, 2H), 6.88 (d, J = 2.3 Hz, 1H), 6.61 (d, J = 12.3 Hz, 1H), 3.93-3.83 (m, 1H), 3.79-3.68 (m, 2H), 2.80-2.57 (m, 7H), 2.22 (s, 3H), 2.13-2.02 (m, 1H), 1.89-1.80 (m, 1H), NH not observed. |

| Example No | Name | MS (ES+) m/z | ¹H NMR |
|---|---|---|---|
| 157 | (S)-2-fluoro-4-((1-(3-fluorobenzyl)pyrrolidin-3-yl)(methyl)amino)-5-methyl-N-(thiazol-4-yl)benzenesulfonamide | 479.2 (M + 1) | (300 MHz, CDCl₃) δ 8.70 (d, J = 2.2 Hz, 1H), 7.59 (d, J = 8.3 Hz, 1H), 7.31-7.24 (m, 1H), 7.12-7.04 (m, 2H), 6.98-6.90 (m, 2H), 6.62 (d, J = 12.3 Hz, 1H), 3.94-3.84 (m, 1H), 3.64 (q, J = 18.7 Hz, 2H), 2.78-2.51 (m, 6H), 2.22-2.14 (m, 3H), 2.14-2.00 (m, 1H), 1.91-1.79 (m, 1H), NH not observed. |

Example 158

Synthesis of (S)-4-((1-benzyl-3-methylpyrrolidin-3-yl)oxy)-2,6-difluoro-3-methyl-N-(thiazol-4-yl)benzenesulfonamide Formate

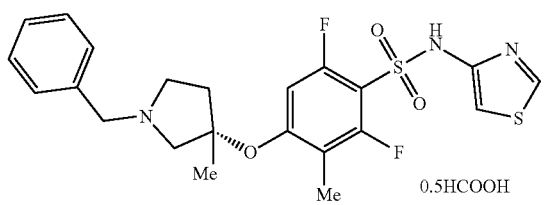 [SMILES: Cc1c(O[C@@]2(C)CCN(Cc3ccccc3)C2)cc(F)c(S(=O)(=O)Nc2cscn2)c1F]

Step 1. Preparation of (S)-1-benzyl-3-methylpyrrolidin-3-ol

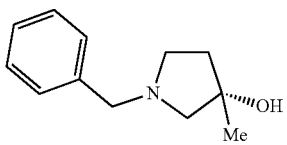 [SMILES: C[C@]1(O)CCN(Cc2ccccc2)C1]

To a mixture of benzaldehyde (3.0 g, 29.7 mmol) and (S)-3-methylpyrrolidin-3-ol (1.0 g, 9.90 mmol) in anhydrous N,N-dimethylformamide (10 mL) and anhydrous 1,2-dichloroethane (10 mL) was added sodium triacetoxyborohydride (6.29 g, 29.7 mmol) and the reaction mixture was stirred at ambient temperature for 18 h. The reaction mixture was cooled to 0° C. and quenched with methanol (5 mL) and 1 M hydrochloric acid (10 mL). To it was added diethyl ether (30 mL) and water (30 mL). The aqueous layer was adjusted with 1 M solution of sodium hydroxide to pH 9-10 and extracted with ethyl acetate (3×30 mL). The combined organic phase was washed with brine (40 mL), and concentrated in vacuo. Purification of the residue by column chromatography, eluting with a gradient of 0 to 80% of ethyl acetate (containing 10% of 2-propanol and 10% triethylamine) in heptane, provided the title compound as a pink oil (1.4 g, 76% yield): ¹H NMR (300 MHz, CDCl₃) δ 7.33-7.24 (m, 5H), 3.66 (s, 2H), 3.03-2.96 (m, 1H), 2.75 (dd, J=9.6, 0.6 Hz, 1H), 2.41-2.33 (m, 1H), 2.28-2.25 (m, 1H), 1.93-1.87 (m, 2H), 1.34 (s, 3H), OH not observed; MS (ES+) m/z 192.3 (M+1).

Step 2. Preparation of tert-butyl (S)-((4-((1-benzyl-3-methylpyrrolidin-3-yl)oxy)-3-chloro-2,6-difluorophenyl)sulfonyl)(thiazol-4-yl)carbamate

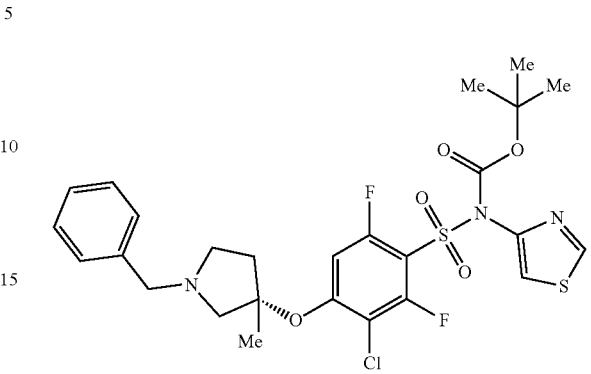

Following the procedure as described in Example 105, Step 1 and making variations as required to replace 1-benzylpiperidin-4-ol with (S)-1-benzyl-3-methylpyrrolidin-3-ol, the title compound was obtained as an orange oil (0.15 g, 17% yield): MS (ES+) m/z 600.1 (M+1), 602.1 (M+1).

Step 3. Preparation of (S)-4-((1-benzyl-3-methylpyrrolidin-3-yl)oxy)-2,6-difluoro-3-methyl-N-(thiazol-4-yl)benzenesulfonamide Formate

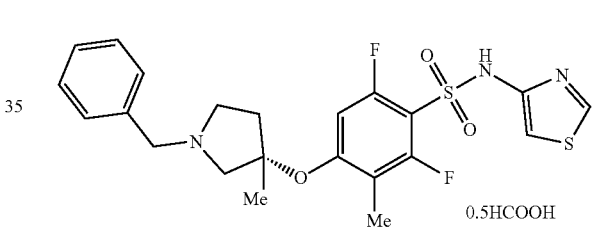

To a mixture of tert-butyl (S)-((4-((1-benzyl-3-methylpyrrolidin-3-yl)oxy)-3-chloro-2,6-difluorophenyl)sulfonyl)(thiazol-4-yl)carbamate (0.15 g, 0.25 mmol) and methylboronic acid (0.081 g, 13.6 mmol) in anhydrous 1,4-dioxane (5 mL) was added potassium phosphate tribasic (0.16 g, 0.74 mmol) and the mixture was degassed by passing a stream of argon through it for 15 minutes. To the mixture was then added tricyclohexylphosphine tetrafluoroborate (0.027 g, 0.07 mmol) and palladium(II) acetate (0.008 g, 0.04 mmol), and the resulting mixture was heated in a microwaved at 101° C. for 2 h. The mixture was filtered and the filtrate was concentrated in vacuo. The obtained residue was dissolved in ethyl acetate (30 mL) and the mixture was diluted with saturated ammonium chloride (50 mL). The aqueous phase was extracted with ethyl acetate (2×30 mL). The combined organic phase was washed with brine (50 mL), dried over anhydrous sodium sulfate, and filtered. The filtrate was concentrated in vacuo to provide crude tert-butyl (S)-((4-((1-benzyl-3-methylpyrrolidin-3-yl)oxy)-2,6-difluoro-3-methylphenyl)sulfonyl)(thiazol-4-yl)carbamate which was used directly without further purification. To a mixture of tert-butyl (S)-((4-((1-benzyl-3-methylpyrrolidin-3-yl)oxy)-2,6-difluoro-3-methylphenyl)sulfonyl)(thiazol-4-yl)carbamate (0.064 g, 0.11 mmol) in anhydrous dichloromethane (2 mL) was added trifluoroacetic acid (0.17 mL, 2.2 mmol) and the reaction mixture was stirred at ambient temperature for 4 h. The reaction mixture was concentrated in vacuo and the residue purified by preparative reverse-phase HPLC, eluting with a gradient of acetonitrile in water containing 0.5% of formic acid, to afford the title compound as a colorless solid (0.012 g, 5% yield over 2 steps): $^1$H NMR (300 MHz, DMSO-$d_6$) δ 8.82 (d, J=2.1 Hz, 1H), 8.19 (s, 0.5H), 7.35-7.20 (m, 5H), 7.08-7.03 (m, 1H), 6.75-6.74 (m, 1H), 3.64 (d, J=13.2 Hz, 1H), 3.53 (d, J=13.2 Hz, 1H), 2.91 (d, J=10.6 Hz, 1H), 2.79-2.70 (m, 1H), 2.59 (d, J=10.4 Hz, 1H), 2.55-2.47 (m, 1H), 2.28-2.18 (m, 1H), 2.04-1.99 (m, 1H), 1.94 (d, J=2.0 Hz, 3H), 1.53 (s, 3H), NH and COOH not observed; MS (ES+) m/z 480.1 (M+1).

Example 159

Synthesis of (S)-4-((1-benzyl-3-methylpyrrolidin-3-yl)oxy)-2-fluoro-5-methyl-N-(thiazol-4-yl)benzenesulfonamide Formate

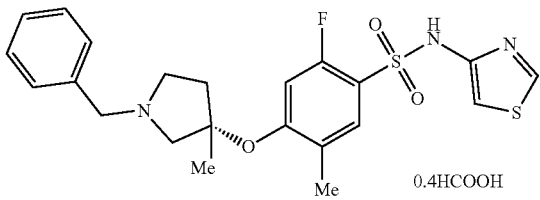 [SMILES: Cc1cc(S(=O)(=O)Nc2cscn2)c(F)cc1O[C@@]1(C)CCN(Cc2ccccc2)C1]

Step 1. Preparation of (S)-4-((1-benzyl-3-methylpyrrolidin-3-yl)oxy)-5-chloro-2-fluoro-N-(thiazol-4-yl)benzenesulfonamide

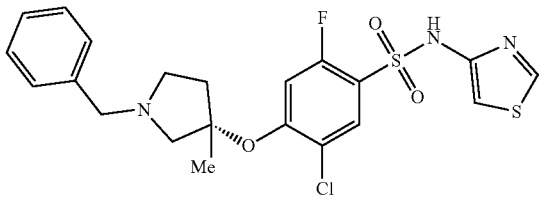 [SMILES: C[C@]1(Oc2cc(F)c(S(=O)(=O)Nc3cscn3)cc2Cl)CCN(Cc2ccccc2)C1]

To a solution of (S)-1-benzyl-3-methylpyrrolidin-3-ol (0.30 g, 1.57 mmol) and tert-butyl ((5-chloro-2,4-difluorophenyl)sulfonyl)(thiazol-4-yl)carbamate (0.58 g, 1.42 mmol) in anhydrous N,N-dimethylformamide (14 mL) was added a 60% dispersion of sodium hydride in mineral oil (0.11 g, 2.85 mmol) at 0° C. The reaction mixture was allowed to warm to ambient temperature and stirred for 16 h, diluted with ethyl acetate (40 mL), and then quenched by slow addition of water (15 mL) and saturated ammonium chloride (20 mL). The aqueous phase was extracted with ethyl acetate (2×40 mL), and the combined organic phase was washed with brine (2×30 mL), dried over anhydrous sodium sulfate, and filtered. Concentration of the filtrate in vacuo and purification of the residue by column chromatography, eluting with a gradient of 0 to 80% of ethyl acetate (containing 10% triethylamine and 10% 2-propanol) in heptane, provided the title compound as an orange oil (0.45 g, 54% yield): MS (ES+) m/z 482.0 (M+1), 484.1 (M+1).

Step 2. Preparation of (S)-4-((1-benzyl-3-methylpyrrolidin-3-yl)oxy)-2-fluoro-5-methyl-N-(thiazol-4-yl)benzenesulfonamide Formate

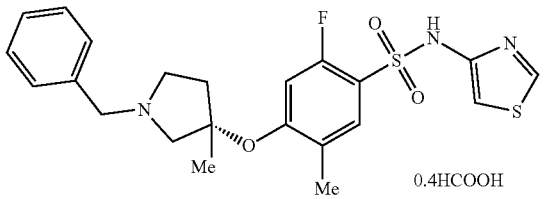 [SMILES: Cc1cc(S(=O)(=O)Nc2cscn2)c(F)cc1O[C@@]1(C)CCN(Cc2ccccc2)C1]

To a mixture of (S)-4-((1-benzyl-3-methylpyrrolidin-3-yl)oxy)-5-chloro-2-fluoro-N-(thiazol-4-yl)benzenesulfonamide (0.45 g, 0.94 mmol) and methylboronic acid (0.31 g, 51.5 mmol) in anhydrous 1,4-dioxane (9 mL) was added potassium phosphate tribasic (0.79 g, 3.74 mmol) and the mixture was degassed by passing a stream of argon through it for 15 minutes. To the mixture was then added tricyclohexylphosphine tetrafluoroborate (0.10 g, 0.28 mmol) and palladium acetate (0.032 g, 0.14 mmol), and the resulting mixture was heated in a microwave reactor to 101° C. for 2 h. The reaction mixture was allowed to cool to ambient temperature, and methylboronic acid (0.31 g, 51.5 mmol) was added to it. The reaction mixed was degassed by passing a stream of argon through it for 15 minutes, and tricyclohexylphosphine tetrafluoroborate (0.10 g, 0.28 mmol) and palladium(II) acetate (0.032 g, 0.14 mmol) were added to it. The reaction mixture was then heated in a microwave reactor to 101° C. for 90 minutes. The reaction mixture was allowed to cool to ambient temperature and filtered. The filtrate was concentrated in vacuo to provide a residue, which was dissolved in ethyl acetate (30 mL). To it was added saturated ammonium chloride (50 mL) and the mixture was extracted with ethyl acetate (2×30 mL). The combined organic phase was washed with brine (50 mL), dried over anhydrous sodium sulfate, and filtered. The filtrate was concentrated in vacuo and the residue purified by preparative reverse-phase HPLC, eluting with a gradient of acetonitrile in water containing 0.5% of formic acid, to afford the title compound as a colorless solid (0.020 g, 4% yield): $^1$H NMR (300 MHz, DMSO-$d_6$) δ 8.85 (d, J=2.2 Hz, 1H), 8.20 (s, 0.4H), 7.58 (dd, J=8.7, 0.6 Hz, 1H), 7.30-7.17 (m, 6H), 6.86 (d, J=2.2 Hz, 1H), 3.63 (d, J=13.0 Hz, 1H), 3.54 (d, J=13.0 Hz, 1H), 2.92-2.89 (m, 1H), 2.77-2.69 (m, 1H), 2.63-2.53 (m, 1H), 2.56-2.48 (m, 1H), 2.28-2.18 (m, 1H), 2.07 (s, 3H), 2.04-1.96 (m, 1H), 1.53 (s, 3H), NH and COOH not observed; MS (ES+) m/z 462.1 (M+1).

Example 160

Synthesis of (S)-5-chloro-4-((1-((6-(difluoromethyl)pyridin-2-yl)methyl)pyrrolidin-3-yl)(methyl)amino)-2-fluoro-N-(thiazol-4-yl)benzenesulfonamide

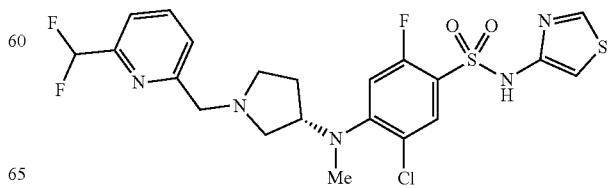

205

Step 1. Preparation of tert-butyl (S)-3-((4-(N-(tert-butoxycarbonyl)-N-(thiazol-4-yl)sulfamoyl)-2-chloro-5-fluorophenyl)(methyl)amino)pyrrolidine-1-carboxylate

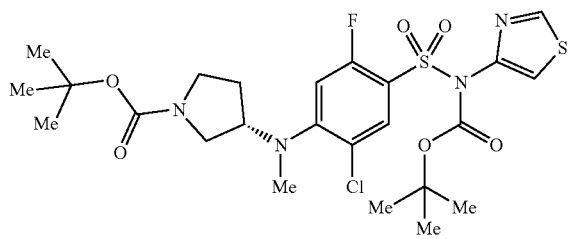 [SMILES: CN(c1cc(F)c(S(=O)(=O)N(C(=O)OC(C)(C)C)c2cscn2)cc1Cl)[C@H]1CCN(C(=O)OC(C)(C)C)C1]

Following the procedure as described for EXAMPLE 101, Step 4 and making non-critical variations as required to replace tert-butyl (S)-3-((4-(N-(tert-butoxycarbonyl)-N-(thiazol-4-yl)sulfamoyl)-5-fluoro-2-methylphenyl)amino)pyrrolidine-1-carboxylate with tert-butyl (S)-3-((4-(N-(tert-butoxycarbonyl)-N-(thiazol-4-yl)sulfamoyl)-2-chloro-5-fluorophenyl)amino)pyrrolidine-1-carboxylate, the title compound was obtained as a colorless foam (3.36 g, 85% yield): $^1$H NMR (300 MHz, CDCl$_3$) δ 8.81 (d, J=2.3 Hz, 1H), 8.07 (d, J=7.4 Hz, 1H), 7.54 (d, J=2.2 Hz, 1H), 6.83 (d, J=11.8 Hz, 1H), 4.27-4.23 (m, 1H), 3.65-3.58 (m, 2H), 3.35-3.31 (m, 2H), 2.85 (s, 3H), 2.09 (td, J=7.9, 2.7 Hz, 2H), 1.48 (s, 9H), 1.39 (s, 9H); MS (ES+) m/z 613.4 (M+23), 615.4 (M+23).

Step 2. Preparation of (S)-5-chloro-2-fluoro-4-(methyl(pyrrolidin-3-yl)amino)-N-(thiazol-4-yl)benzenesulfonamide 2,2,2-trifluoroacetate

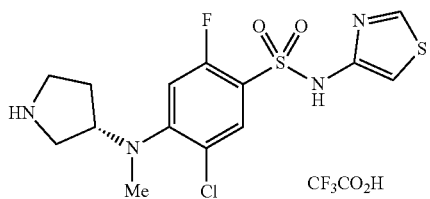 [SMILES: CN(c1cc(F)c(S(=O)(=O)Nc2cscn2)cc1Cl)[C@H]1CCNC1 ; "CF3CO2H"]

Following the procedure as described for EXAMPLE 253, Step 2 and making non-critical variations as required to replace tert-butyl (S)-3-((2-chloro-4-(N-(thiazol-4-yl)sulfamoyl)phenyl)(methyl)amino)pyrrolidine-1-carboxylate with tert-butyl (S)-3-((4-(N-(tert-butoxycarbonyl)-N-(thiazol-4-yl)sulfamoyl)-2-chloro-5-fluorophenyl)(methyl)amino)pyrrolidine-1-carboxylate, the title compound was obtained as a colorless foam (1.68 g, quantitative yield): MS (ES+) m/z 391.2 (M+1), 393.2 (M+1).

Step 3. Preparation of 2-bromo-6-(difluoromethyl)pyridine

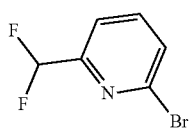

To a solution of 6-bromopicolinaldehyde (2.10 g, 11.29 mmol) in dichloromethane (20 mL) was added diethylaminosulfur trifluoride (1.94 mL, 14.68 mmol) at 0° C. The reaction mixture was allowed to warm to ambient temperature and stirred for 18 h, and then poured into an ice cold solution of saturated sodium bicarbonate (300 mL). The mixture was extracted with ethyl acetate (2×120 mL). The combined organic phase was washed with saturated sodium bicarbonate (80 mL), brine (2×50 mL), dried over anhydrous sodium sulfate, and filtered. Concentration of the filtrate in vacuo afforded the title compound as a brown oil (2.17 g, 89% yield): $^1$H NMR (300 MHz, CDCl$_3$) δ 7.75-7.70 (m, 1H), 7.65-7.60 (m, 2H), 6.60 (t, J=55.1 Hz, 1H).

Step 4. Preparation of 6-(difluoromethyl)picolinaldehyde

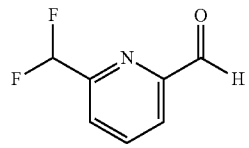

To a solution of 2-bromo-6-(difluoromethyl)pyridine (2.17 g, 10.53 mmol) in anhydrous tetrahydrofuran (50 mL) was added a 1.3 M solution of isopropylmagnesium chloride lithium chloride complex in tetrahydrofuran (54.24 mL, 41.72 mmol) at −42° C. The reaction mixture was allowed to warm to ambient temperature and stirred for 1 h, then cooled to −42° C., and anhydrous N,N-dimethylformamide (50 mL) was added to it. The reaction mixture was allowed to warm to ambient temperature, stirred for 18 h, and then diluted with ethyl acetate (140 mL). The mixture was washed with 1 M aqueous hydrochloric acid (2×60 mL), saturated ammonium chloride (60 mL), brine (60 mL), dried over anhydrous sodium sulfate, and filtered. Concentration of the filtrate in vacuo afforded the title compound as a brown oil (1.55 g, 95% yield): $^1$H NMR (300 MHz, CDCl$_3$) δ 10.08 (s, 1H), 8.09-8.05 (m, 2H), 7.91-7.85 (m, 1H), 6.73 (t, J=55.1 Hz, 2H).

Step 5. Preparation of (S)-5-chloro-4-((1-((6-(difluoromethyl)pyridin-2-yl)methyl)-pyrrolidin-3-yl)(methyl)amino)-2-fluoro-N-(thiazol-4-yl)benzenesulfonamide

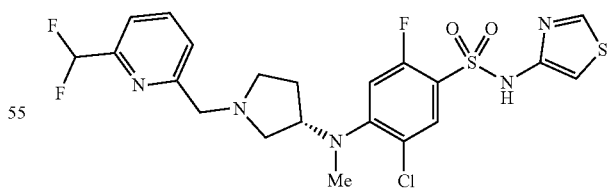

To a mixture of (S)-5-chloro-2-fluoro-4-(methyl(pyrrolidin-3-yl)amino)-N-(thiazol-4-yl)benzenesulfonamide 2,2,2-trifluoroacetate (0.51 g, 1.00 mmol) and 6-(difluoromethyl)picolinaldehyde (0.24 g, 1.5 mmol) in dichloromethane (8 mL) and N,N-dimethylformamide (8 mL) was added sodium triacetoxyborohydride (0.42 g, 2.00 mmol). The reaction mixture was stirred for 3 h and then diluted with ethyl acetate (60 mL). The mixture was washed with a 1:1 mixture of 1 M aqueous sodium hydroxide and brine (60 mL), saturated ammonium chloride (30 mL), brine (30 mL), dried over anhydrous sodium sulfate, and filtered. Concentration of the filtrate in vacuo and purification of the residue by column chromatography, eluting with a gradient of 10 to 60% of ethyl acetate (containing 20% of ethanol and 0.1% of ammonium hydroxide) in hexanes, afforded the title compound as a colorless solid (0.32 g, 60% yield): $^1$H NMR (300 MHz, DMSO-$d_6$) δ 8.76 (d, J=2.3 Hz, 1H), 7.86-7.80 (m, 2H), 7.54 (d, J=7.7 Hz, 2H), 6.92 (d, J=2.3 Hz, 1H), 6.82-6.44 (m, 2H), 4.32-4.22 (m, 1H), 3.90 (d, J=14.1 Hz, 1H), 3.75 (d, J=14.0 Hz, 1H), 2.93-2.90 (m, 1H), 2.85 (s, 3H), 2.81-2.67 (m, 2H), 2.61-2.50 (m, 1H), 2.22-2.11 (m, 1H), 2.00-1.88 (m, 1H), NH not observed; MS (ES+) m/z 532.4 (M+1), 534.2 (M+1).

Example 161

Synthesis of (S)-5-chloro-2-fluoro-4-((1-(3-(2-hydroxypropan-2-yl)benzyl)pyrrolidin-3-yl)(methyl)amino)-N-(thiazol-4-yl)benzenesulfonamide Formate

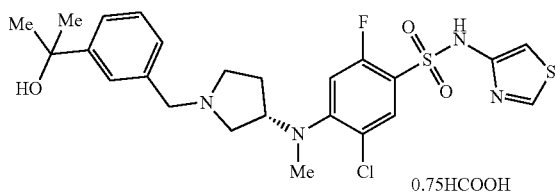 [SMILES: CN(c1cc(F)c(S(=O)(=O)Nc2cscn2)cc1Cl)[C@H]1CCN(Cc2cccc(C(C)(C)O)c2)C1]

Step 1. Preparation of (S)-methyl 3-((3-((2-chloro-5-fluoro-4-(N-(thiazol-4-yl)sulfamoyl)phenyl)(methyl)amino)pyrrolidin-1-yl)methyl)benzoate

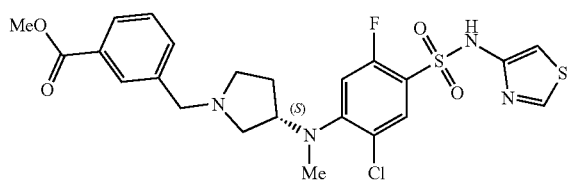

To a mixture of methyl 3-formylbenzoate (0.0900 g, 0.548 mmol), (S)-5-chloro-2-fluoro-4-(methyl(pyrrolidin-3-yl)amino)-N-(thiazol-4-yl)benzenesulfonamide hydrochloride salt (0.195 g, 0.456 mmol) in tetrahydrofuran (2 mL) was added sodium triacetoxyborohydride (0.193 g, 0.913 mmol) and the reaction mixture was stirred at ambient temperature for 2 h. Additional sodium triacetoxyborohydride (0.097 g, 0.456 mmol) was added and the reaction mixture was stirred at ambient temperature for 12 h. Concentration in vacuo and purification of the residue by preparative reverse phase HPLC, using acetonitrile in water containing 0.225% of formic acid as eluent, afforded the title compound as a colorless solid (0.129 g, 52% yield): MS (ES+) m/z 539.0 (M+1), 541.0 (M+1).

Step 2. Preparation of (S)-5-chloro-2-fluoro-4-((1-(3-(2-hydroxypropan-2-yl)benzyl)pyrrolidin-3-yl)(methyl)amino)-N-(thiazol-4-yl)benzenesulfonamide formate

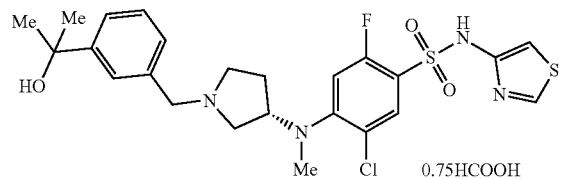 [SMILES: CN(c1cc(F)c(S(=O)(=O)Nc2cscn2)cc1Cl)[C@H]1CCN(Cc2cccc(C(C)(C)O)c2)C1]

To a solution of methylmagnesium bromide (3 M in tetrahydrofuran, 0.717 mL, 2.15 mmol) was added a solution of (S)-methyl 3-((3-((2-chloro-5-fluoro-4-(N-(thiazol-4-yl)sulfamoyl)phenyl)(methyl)amino)pyrrolidin-1-yl)methyl)benzoate (0.129 g, 0.239 mmol) in anhydrous tetrahydrofuran (2 mL) at 0° C. The reaction mixture was allowed to warm to ambient temperature, stirred for 2 h, and then quenched with aqueous ammonium chloride (5 mL). The mixture was extracted with ethyl acetate (2×30 mL). The combined organic layers were dried over anhydrous sodium sulfate, filtered, and the filtrate concentrated in vacuo. Purification of the residue by preparative reverse phase HPLC, using acetonitrile in water containing 0.225% formic acid as eluent, afforded the title compound as a colorless solid (0.089 g, 68% yield): $^1$H NMR (400 MHz, CD$_3$OD) δ 8.73 (d, J=2.0 Hz, 1H), 8.45 (br s, 0.75H), 7.82 (d, J=7.2 Hz, 1H), 7.59 (s, 1H), 7.52 (br d, J=8.4 Hz, 1H), 7.38 (t, J=7.6 Hz, 1H), 7.29 (br d, J=7.2 Hz, 1H), 7.08-7.02 (m, 2H), 4.62 (br s, 1H), 4.36-4.33 (m, 1H), 4.08 (q, J=12.8 Hz, 2H), 3.30-2.98 (m, 5H), 2.84 (s, 3H), 2.31-2.00 (m, 2H), 1.55 (s, 6H), NH and COOH not observed; MS (ES+) m/z 539.0 (M+1), 541.0 (M+1).

Example 162

Synthesis of 5-chloro-4-(((3R,4S)-1-(3-(difluoromethyl)benzyl)-3-fluoropiperidin-4-yl)oxy)-2-fluoro-N-(thiazol-4-yl)benzenesulfonamide

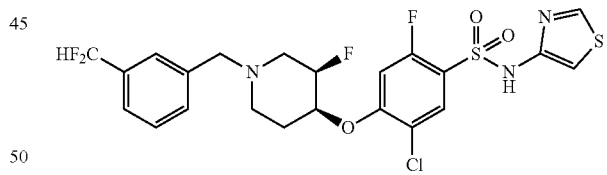

Step 1. Preparation of 5-chloro-2-fluoro-4-(((3R,4S)-3-fluoropiperidin-4-yl)oxy)-N-(thiazol-4-yl)benzenesulfonamide 2,2,2-trifluoroacetate

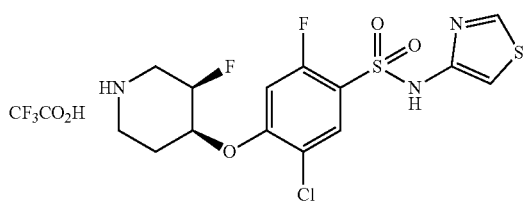

To a solution of tert-butyl (3R,4S)-3-fluoro-4-hydroxypiperidine-1-carboxylate (0.267 g. 1.22 mmol) and tert-butyl ((5-chloro-2,4-difluorophenyl)sulfonyl)(thiazol-4-yl)carbamate (0.500 g, 1.22 mmol) in anhydrous N,N-dimethylformamide (10 mL) was added sodium hydride (60% dispersion in mineral oil, 0.146 g, 3.65 mmol) and the suspension was stirred at ambient temperature for 1 h. Saturated ammonium chloride solution (10 mL) was added follow by water (10 mL) and ethyl acetate (20 mL). The layers were separated and the aqueous phase was extracted with ethyl acetate (3×20 mL). The combined organic phase was washed with brine (20 mL), dried over anhydrous sodium sulfate, and filtered. Concentration of the filtrate in vacuo provided a residue which was purified by column chromatography, eluting with a gradient of 0-60% of ethyl acetate in hexanes. The purified residue was then dissolved in dichloromethane (10 mL) and trifluoroacetic acid (2 mL) was added to it. The reaction mixture was stirred at ambient temperature for 20 h. Concentration in vacuo yielded the title compound as a colorless oil (0.664 g, quantitative yield): MS (ES+) m/z 408.2 (M+1), 410.2 (M+1).

Step 2. Preparation of 5-chloro-4-(((3R,4S)-1-(3-(difluoromethyl)benzyl)-3-fluoropiperidin-4-yl)oxy)-2-fluoro-N-(thiazol-4-yl)benzenesulfonamide

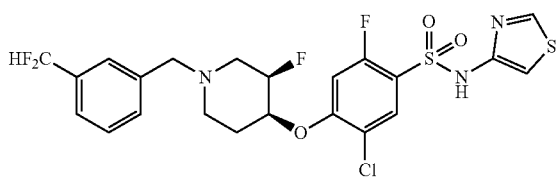

To a solution of 5-chloro-2-fluoro-4-(((3R,4S)-3-fluoropiperidin-4-yl)oxy)-N-(thiazol-4-yl)benzenesulfonamide 2,2,2-trifluoroacetate (0.332 g, 0.637 mmol) and 3-(difluoromethyl)benzaldehyde (0.100 g, 0.637 mmol) in anhydrous tetrahydrofuran (4 mL) was added sodium triacetoxyborohydride (0.268 g, 1.27 mmol). The mixture was stirred at ambient temperature for 2 h. Saturated aqueous ammonium chloride solution (5 mL) and ethyl acetate (5 mL) were added to the mixture and the layers were separated. The aqueous phase was extracted with ethyl acetate (3×5 mL). The combined organic phase was washed with brine (5 mL), dried over anhydrous sodium sulfate, and filtered. Concentration of the filtrate in vacuo and purification of the residue by column chromatography, eluting with a gradient of 0-20% methanol in dichloromethane, yielded the title compound as a colorless solid (0.152 g, 43% yield): $^1$H-NMR (300 MHz, DMSO-$d_6$) δ 8.90 (s, 1H), 7.95-7.91 (m, 1H), 7.63-7.44 (m, 5H), 7.36-6.80 (m, 1H), 7.23-7.06 (m, 1H), 5.35-4.49 (m, 1H), 4.97-4.83 (m, 1H), 3.80 (s, 2H), 2.88-2.73 (m, 1H), 2.72-2.54 (m, 2H), 2.54-2.22 (m, 1H), 1.85-1.68 (m, 2H), NH not observed; MS (ES+) m/z 548.2 (M+1), 550.2 (M+1).

Example 163

Synthesis of (S)-5-chloro-4-((1-((6-(difluoromethyl)-3-fluoropyridin-2-yl)methyl)pyrrolidin-3-yl)(methyl)amino)-2-fluoro-N-(thiazol-4-yl)benzenesulfonamide formate

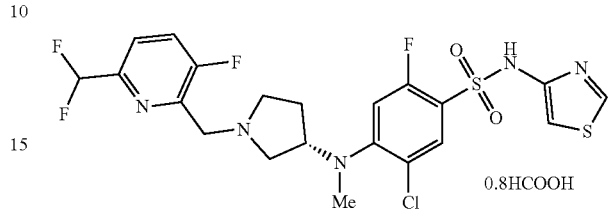

Step 1. Preparation of (6-bromo-5-fluoropyridin-2-yl)methanol

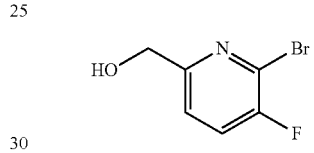

To a solution of 6-bromo-5-fluoropicolinic acid (4.50 g, 20.5 mmol) in anhydrous tetrahydrofuran (60 mL) was added borane dimethyl sulfide complex (10 M, 5.11 mL, 51.1 mmol) at 0° C. The mixture was then heated to 80° C. for 2 h. After cooling to ambient temperature, the reaction mixture was quenched with methanol (30 mL) and concentrated in vacuo to provide the title compound as a colorless oil (4.0 g, 95% yield): MS (ES+) m/z 205.9 (M+1), 207.9 (M+1).

Step 2. Preparation of 6-bromo-5-fluoropicolinaldehyde

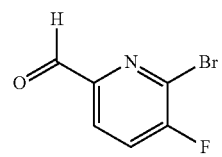

To a solution of (6-bromo-5-fluoropyridin-2-yl)methanol (4.00 g, 19.4 mmol) in chloroform (60 mL) was added manganese dioxide (8.44 g, 97.1 mmol) and the resulting mixture was heated to reflux for 12 h. After cooling to ambient temperature, the reaction mixture was filtered and the filtrate was concentrated under reduced pressure. Purification of the residue by column chromatography, eluting with a gradient of 2-10% of ethyl acetate in petroleum ether, afforded the title compound as a yellow solid (3.00 g, 76% yield): $^1$H NMR (400 MHz, CDCl$_3$) 310.00 (s, 1H), 8.00 (ddd, J=1.6, 3.6, 8.4 Hz, 1H), 7.68-7.54 (m, 1H).

Step 3. Preparation of 2-bromo-6-(difluoromethyl)-3-fluoropyridine

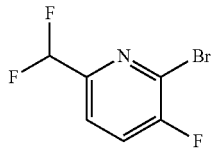

To a solution of 6-bromo-5-fluoropicolinaldehyde (2.90 g, 14.2 mmol) in dichloromethane (50 mL) was added diethylaminosulfur trifluoride (4.58 g, 28.4 mmol) in portions at 0° C. The reaction mixture was then stirred at ambient temperature for 1 h. The reaction mixture was poured slowly into ice water (50 mL) and extracted with dichloromethane (2×50 mL). The combined organic layers were washed with brine (50 mL), dried over anhydrous sodium sulfate, filtered and concentrated under reduced pressure. The residue was purified by column chromatography, eluting with 2% of ethyl acetate in petroleum ether, to afford the title compound as a light yellow oil (2.00 g, 62% yield): $^1$H NMR (400 MHz, CDCl$_3$) δ 7.73-7.63 (m, 1H), 7.63-7.49 (m, 1H), 6.62 (t, J=55.0 Hz, 1H).

Step 4. Preparation of methyl 6-(difluoromethyl)-3-fluoropicolinate

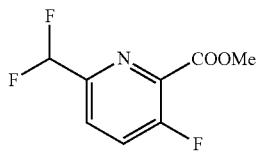

To a solution of 2-bromo-6-(difluoromethyl)-3-fluoropyridine (1.80 g, 7.96 mmol) in methanol (30 mL) was added [1,1'-bis(diphenylphosphino)ferrocene]dichloro-palladium(II) (0.291 g, 0.398 mmol) and N,N-diisopropylethylamine (2.06 g, 15.9 mmol, 2.78 mL). The resulting mixture was heated to 60° C. under a CO atmosphere (50 psi) for 12 h. After cooling to ambient temperature, the reaction mixture was filtered and the filtrate was concentrated under reduced pressure. The residue was purified by column chromatography, eluting with 17% of ethyl acetate in petroleum ether, to afford the title compound as an yellow oil (1.30 g, 79% yield): $^1$H NMR (400 MHz, CDCl$_3$), 7.90 (dd, J=3.6, 8.8 Hz, 1H), 7.79-7.68 (m, 1H), 6.74 (t, J=54.8 Hz, 1H), 4.05 (s, 3H).

Step 5. Preparation of (6-(difluoromethyl)-3-fluoropyridin-2-yl)methanol

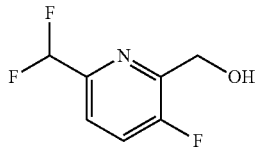

To a cooled (0° C.) solution of methyl 6-(difluoromethyl)-3-fluoropicolinate (1.30 g, 6.34 mmol) and calcium chloride (1.76 g, 15.9 mmol) in anhydrous methanol (20 mL) and anhydrous tetrahydrofuran (10 mL) was added sodium borohydride (4.41 g, 117 mmol) portionwise. The resulting mixture was stirred at 0° C. for 2 h, and then water (10 mL) was added to it. Concentration in vacuo provided a residue which was dissolved in water (10 mL) and extracted with ethyl acetate (3×20 mL). The combined organic extracts were dried over anhydrous magnesium sulfate and filtered. Concentration of the filtrate in vacuo provided the title compound as a colorless oil (1.00 g, 89% yield): $^1$H NMR (400 MHz, CDCl$_3$) δ 7.66 (dd, J=3.8, 8.4 Hz, 1H), 7.60-7.51 (m, 1H), 6.68 (t, J=55.2 Hz, 1H), 4.90 (d, J=4.4 Hz, 2H), 3.60 (t, J=5.2 Hz, 1H).

Step 6. Preparation of 6-(difluoromethyl)-3-fluoropicolinaldehyde

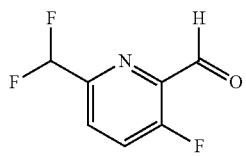 [SMILES: O=Cc1nc(C(F)F)ccc1F]

To a solution of (6-(difluoromethyl)-3-fluoropyridin-2-yl)methanol (1.00 g, 5.65 mmol) in chloroform (30 mL) was added manganese dioxide (2.46 g, 28.3 mmol) and the mixture was heated to reflux for 12 h. After cooling to ambient temperature, the reaction mixture was filtered and the filtrate was concentrated under reduced pressure. The residue was purified by column chromatography, eluting with a gradient of 5-9% of ethyl acetate in petroleum ether, to afford the title compound as an yellow oil (0.70 g, 71% yield): $^1$H NMR (400 MHz, CDCl$_3$) δ 10.22 (s, 1H), 7.95 (dd, J=3.6, 8.8 Hz, 1H), 7.77 (t, J=9.2 Hz, 1H), 6.75 (t, J=55.0 Hz, 1H).

Step 7. Preparation of (S)-5-chloro-4-((1-((6-(difluoromethyl)-3-fluoropyridin-2-yl)methyl)pyrrolidin-3-yl)(methyl)amino)-2-fluoro-N-(thiazol-4-yl)benzenesulfonamide Formate

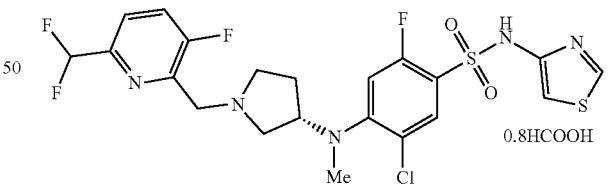

To a solution of (S)-5-chloro-2-fluoro-4-(methyl(pyrrolidin-3-yl)amino)-N-(thiazol-4-yl)benzenesulfonamide (0.100 g, 0.234 mmol) and 6-(difluoromethyl)-3-fluoropicolinaldehyde (0.102 g, 0.585 mmol) in dichloromethane (5 mL) was added acetic acid (0.50 mL) and sodium triacetoxyborohydride (0.148 g, 0.702 mmol) portionwise and the resulting mixture was stirred at ambient temperature for 1 h. Concentration in vacuo and purification of the residue by preparative reverse phase HPLC, using acetonitrile in water containing 0.225% formic acid as eluent, afforded the title compound as a colorless solid (0.017 g, 13% yield): $^1$H NMR (400 MHz, CD$_3$OD), 8.74 (d, J=2.2 Hz, 1H), 8.40 (br s, 0.8H), 7.83-7.71 (m, 3H), 7.04 (d, J=2.2 Hz, 1H), 7.00 (d, J=12.0 Hz, 1H), 6.75 (t, J=55.2 Hz, 1H), 4.35-4.26 (m, 1H), 4.16-4.02 (m, 2H), 3.09-2.96 (m, 3H), 2.92-2.84 (m, 1H), 2.83 (s, 3H), 2.22-2.12 (m, 1H), 2.05-1.92 (m, 1H), NH and COOH not observed; MS (ES+) m/z 549.9 (M+1), 551.9 (M+1).

Examples 164-194

In a similar manner as described in the EXAMPLE 163, utilizing the appropriately substituted starting materials and intermediates, the following compounds were prepared:

| Example No. | Name | MS (ES+) m/z | $^1$H NMR |
|---|---|---|---|
| 164 | (S)-5-chloro-2-fluoro-4-(methyl(1-((5-(trifluoromethyl)furan-2-yl)methyl)pyrrolidin-3-yl)amino)-N-(thiazol-4-yl)benzene-sulfonamide 2,2,2-trifluoroacetate | 539.2 (M + 1) | (300 MHz, DMSO-d$_6$) δ 11.39 (s, 1H), 8.91 (dd, J = 2.1, 0.7 Hz, 1H), 7.76 (d, J = 7.5 Hz, 1H), 7.33-7.31 (m, 1H), 7.22 (d, J = 12.0 Hz, 1H), 7.08 (d, J = 2.1 Hz, 1H), 6.92 (d, J = 3.5 Hz, 1H), 4.59 (s, 2H), 4.53-4.25 (m, 1H), 3.70-3.13 (m, 4H), 2.77 (s, 3H), 2.22-2.05 (m, 2H), NH not observed. |
| 165 | (S)-4-((1-((1-benzyl-1H-pyrazol-4-yl)methyl)pyrrolidin-3-yl)(methyl)amino)-5-chloro-2-fluoro-N-(thiazol-4-yl)benzene-sulfonamide formate | 561.1 (M + 1), 563.1 (M + 1) | (400 MHz, CD$_3$OD) δ 8.72 (d, J = 2.2 Hz, 1H), 8.48 (d, J = 0.5 Hz, 1H), 7.83-7.81 (m, 2H), 7.60 (s, 1H), 7.36-7.31 (m, 3H), 7.26-7.23 (m, 2H), 7.05-7.01 (m, 2H), 5.35 (s, 2H), 4.31 (quintet, J = 7.5 Hz, 1H), 4.06-3.98 (m, 2H), 3.28 (dd, J = 11.4, 7.9 Hz, 1H), 3.17-3.13 (m, 1H), 3.08-3.04 (m, 2H), 2.79 (s, 3H), 2.23-2.15 (m, 1H), 2.11-2.04 (m, 1H), NH and COOH not observed. |
| 166 | (S)-5-chloro-4-((1-(2,3-dihydro-1H-inden-2-yl)pyrrolidin-3-yl)(methyl)amino)-2-fluoro-N-(thiazol-4-yl)benzene-sulfonamide formate | 507.0 (M + 1), 509.0 (M + 1) | (400 MHz, CD$_3$OD) δ 8.74 (d, J = 2.1 Hz, 1H), 8.43 (d, J = 2.6 Hz, 1H), 7.84 (d, J = 7.4 Hz, 1H), 7.24-7.18 (m, 4H), 7.10-7.05 (m, 2H), 4.40-4.35 (m, 1H), 3.73-3.71 (m, 1H), 3.42-3.37 (m, 1H), 3.30-3.26 (m, 3H), 3.19-3.14 (m, 2H), 3.11-3.04 (m, 2H), 2.85 (s, 3H), 2.26-2.22 (m, 1H), 2.14-2.11 (m, 1H), NH and COOH not observed. |
| 167 | (S)-5-chloro-2-fluoro-4-((1-(2-fluoro-4-methylbenzyl)pyrrolidin-3-yl)(methyl)amino)-N-(thiazol-4-yl)benzene-sulfonamide | 513.2 (M + 1), 515.2 (M + 1). | (300 MHz, DMSO-d$_6$) δ 11.22 (br s, 1H), 8.90 (d, J = 2.2 Hz, 1H), 7.68 (d, J = 7.6 Hz, 1H), 7.31-7.25 (m, 1H), 7.10-6.98 (m, 4H), 4.22-4.16 (m, 1H), 3.67-3.58 (m, 2H), 2.77-2.63 (m, 5H), 2.46-2.36 (m, 2H), 2.29 (s, 3H), 2.09-2.01 (m, 1H), 1.85-1.73 (m, 1H). |
| 168 | (S)-5-chloro-4-((1-(3-(difluoromethoxy)benzyl)-pyrrolidin-3-yl)(methyl)amino)-2-fluoro-N-(thiazol-4-yl)benzene-sulfonamide formate | 546.9 (M + 1), 548.9 (M + 1) | (400 MHz; CD$_3$OD) δ 8.73 (d, J = 2.2 Hz, 1H), 8.43 (s, 1H), 7.79 (d, J = 7.5 Hz, 1H), 7.41 (t, J = 7.9 Hz, 1H), 7.26 (d, J = 7.7 Hz, 1H), 7.21 (s, 1H), 7.12 (d, J = 8.1 Hz, 1H), 7.03 (d, J = 2.2 Hz, 1H), 7.01 (s, 1H), 6.76 (t, J = 74.1 Hz, 1H), 4.34-4.27 (m, 1H), 3.90-3.87 (m, 1H), 3.82-3.77 (m, 1H), 2.97-2.88 (m, 3H), 2.85 (s, 3H), 2.77-2.72 (m, 1H), 2.21-2.13 (m, 1H), 2.03-1.97 (m, 1H), NH and COOH not observed. |
| 169 | (S)-5-chloro-4-((1-(2-chloro-6-fluorobenzyl)pyrrolidin-3-yl)(methyl)amino)-2-fluoro-N-(thiazol-4-yl)benzene-sulfonamide 2,2,2-trifluoroacetate | 533.2 (M + 1), 535.2 (M + 1) | (300 MHz, DMSO-d$_6$) δ 11.30 (s, 1H), 8.90 (dd, J = 2.2, 0.7 Hz, 1H), 7.68 (d, J = 7.6 Hz, 1H), 7.38-7.30 (m, 2H), 7.21 (td, J = 8.5, 1.9 Hz, 1H), 7.07-7.03 (m, 2H), 4.21-4.12 (m, 1H), 3.71 (s, 2H), 2.70-2.61 (m, 6H), 2.41-2.31 (m, 1H), 2.11-1.97 (m, 1H), 1.79-1.67 (m, 1H), NH not observed. |
| 170 | (S)-5-chloro-2-fluoro-4-(methyl(1-(quinolin-8-ylmethyl)-pyrrolidin-3-yl)amino)-N-(thiazol-4- | 532.0 (M + 1), 534.0 (M + 1) | (400 MHz, CD$_3$OD) δ 8.96 (dd, J = 4.2, 1.7 Hz, 1H), 8.71 (d, J = 2.2 Hz, 1H), 8.53 (dq, J = 1.4, 0.5 Hz, 1H), 8.41 (dd, J = 8.3, |

-continued

| Example No. | Name | MS (ES+) m/z | ¹H NMR |
|---|---|---|---|
| | yl)benzene-sulfonamide formate | | 1.7 Hz, 1H), 8.02-8.00 (m, 1H), 7.88-7.86 (m, 1H), 7.83 (d, J = 7.4 Hz, 1H), 7.66-7.59 (m, 2H), 7.05 (d, J = 11.8 Hz, 1H), 6.96 (d, J = 2.2 Hz, 1H), 4.72 (s, 2H), 4.37-4.34 (m, 1H), 3.29-3.14 (m, 4H), 2.83 (s, 3H), 2.26-2.12 (m, 2H), NH and COOH not observed. |
| 171 | (S)-5-chloro-2-fluoro-4-(methyl(1-(4-propylbenzyl)-pyrrolidin-3-yl)amino)-N-(thiazol-4-yl)benzene-sulfonamide | 523.1 (M + 1) | (400 MHz, CD$_3$OD) δ 8.72 (d, J = 1.7 Hz, 1H), 7.81 (d, J = 7.4 Hz, 1H), 7.32 (d, J = 7.8 Hz, 2H), 7.25-7.20 (m, 2H), 7.06-7.00 (m, 2H), 4.32 (t, J = 6.8 Hz, 1H), 4.03-3.94 (m, 2H), 3.19-2.98 (m, 4H), 2.82 (s, 3H), 2.62 (t, J = 7.6 Hz, 2H), 2.26-2.13 (m, 1H), 2.09-2.03 (m, 1H), 1.66 (sxt, J = 7.4 Hz, 2H), 0.95 (t, J = 7.2 Hz, 3H). |
| 172 | (S)-5-chloro-2-fluoro-4-((1-(2-fluoro-5-methylbenzyl)-pyrrolidin-3-yl)(methyl)amino)-N-(thiazol-4-yl)benzene-sulfonamide 2,2,2-trifluoroacetate | 513.2 (M + 1), 515.2 (M + 1) | (300 MHz, DMSO-d$_6$) δ 11.39 (s, 1H), 10.22-10.61 (m, 1H), 8.91 (d, J = 2.2 Hz, 1H), 7.75 (d, J = 7.5 Hz, 1H), 7.40-7.32 (m, 2H), 7.24-7.18 (m, 2H), 7.08 (d, J = 2.2 Hz, 1H), 4.59-4.27 (m, 3H), 3.41 (m, 4H), 2.77 (d, J = 14.9 Hz, 3H), 2.30 (s, 3H), 2.24-1.98 (m, 2H). |
| 173 | (S)-5-chloro-2-fluoro-4-((1-(2-fluoro-5-methoxybenzyl)-pyrrolidin-3-yl)(methyl)amino)-N-(thiazol-4-yl)benzene-sulfonamide 2,2,2-trifluoroacetate | 529.2 (M + 1), 531.2 (M + 1) | (300 MHz, DMSO-d$_6$) δ 11.26 (s, 1H), 10.24-10.55 (m, 1H), 8.91 (d, J = 2.2 Hz, 1H), 7.49 (d, J = 7.5 Hz, 1H), 7.29-7.03 (m, 5H), 4.80-4.54 (m, 3H), 3.82 (s, 3H), 3.48-3.15 (m, 4H), 2.77 (d, J = 14.9 Hz, 3H), 2.16-2.01 (m, 2H). |
| 174 | methyl (S)-3-((3-((2-chloro-5-fluoro-4-(N-(thiazol-4-yl)sulfamoyl)-phenyl)(methyl)-amino)pyrrolidin-1-yl)methyl)benzoate | 538.8 (M + 1) | (400 MHz, CD$_3$OD) δ 8.73 (d, J = 2.4 Hz, 1H), 8.06 (s, 1H), 7.98 (d, J = 7.6 Hz, 1H), 7.78 (d, J = 7.2 Hz, 1H), 7.64 (d, J = 6.0 Hz, 1H), 7.53-7.47 (m, 1H), 7.03 (d, J = 2.4 Hz, 1H), 6.98 (d, J = 12.4 Hz, 1H), 4.34-4.25 (m, 1H), 3.93 (s, 3H), 3.91-3.76 (m, 2H), 2.93-2.87 (m, 2H), 2.85 (s, 3H), 2.84-2.79 (m, 1H), 2.73-2.61 (m, 1H), 2.23-2.11 (m, 1H), 2.04-1.93 (m, 1H). |
| 175 | (S)-5-chloro-4-((1-(3,3-dimethylbutyl)-pyrrolidin-3-yl)(methyl)amino)-2-fluoro-N-(thiazol-4-yl)benzene-sulfonamide 2,2,2-trifluoroacetate | 477.2 (M + 1), 475.2 (M + 1) | (300 MHz, DMSO-d$_6$) δ 11.42-11.38 (br s, 1H), 10.11-9.88 (br s, 1H), 8.93-8.91 (m, 1H), 7.77-7.74 (m, 1H), 7.26-7.18 (m, 1H), 7.10-7.07 (m, 1H), 4.47-4.25 (m, 1H), 3.69-3.08 (m, 6H), 2.77 (m, 3H), 2.21-2.07 (m, 2H), 1.52-1.49 (m, 2H), 0.96-0.72 (m, 9H). |
| 176 | (S)-5-chloro-2-fluoro-4-((1-((3-methoxypyridin-2-yl)methyl)pyrrolidin-3-yl)(methyl)amino)-N-(thiazol-4-yl)benzene-sulfonamide formate | 512.1 (M + 1), 514.0 (M + 1). | (400 MHz, CD$_3$OD) δ 8.74 (d, J = 2.2 Hz, 1H), 8.39 (s, 1.3H), 8.21 (dd, J = 1.2, 4.6 Hz, 1H), 7.86 (d, J = 7.4 Hz, 1H), 7.54-7.50 (m, 1H), 7.45-7.41 (m, 1H), 7.13 (d, J = 11.6 Hz, 1H), 7.06 (d, J = 1.8 Hz, 1H), 4.53 (s, 2H), 4.44 (t, J = 7.2 Hz, 1H), 3.94 (s, 3H), 3.66-3.42 (m, 4H), 2.85 (s, 3H), 2.34-2.20 (m, 2H), NH and COOH not observed. |
| 177 | (S)-5-chloro-2-fluoro-4-((1-(3-isopropoxybenzyl)-pyrrolidin-3-yl)(methyl)amino)-N-(thiazol-4-yl)benzene-sulfonamide compound with triethylamine (1:0.35) | 539.3 (M + 1), 541.3 (M + 1) | ¹H NMR (300 MHz, DMSO-d$_6$) δ 8.91 (dd, J = 0.5, 2.2 Hz, 1H), 7.76-7.74 (m, 1H), 7.34 (td, J = 7.8, 0.4 Hz, 1H), 7.23-7.19 (m, 1H), 7.08-7.06 (m, 2H), 7.03-6.96 (m, 2H), 4.65-4.56 (m, 1H), 4.36-4.28 (m, 2H), 3.47-3.25 (m, 5H), 3.14-3.05 (m, 2H), 2.81-2.74 (m, 3H), 2.17-2.10 (m, 2H), |

| Example No. | Name | MS (ES+) m/z | ¹H NMR |
|---|---|---|---|
| | | | 1.26 (t, J = 6.1 Hz, 6H), 1.17 (t, J = 7.3 Hz, 3H), NH not observed. |
| 178 | (S)-4-((1-((6-bromopyridin-2-yl)methyl)pyrrolidin-3-yl)(methyl)amino)-5-chloro-2-fluoro-N-(thiazol-4-yl)benzene-sulfonamide | 560.1 (M + 1), 562.1 (M + 1). | (300 MHz, DMSO-$d_6$) δ 11.29 (s, 1H), 8.90 (d, J = 2.2 Hz, 1H), 7.74 (t, J = 7.7 Hz, 1H), 7.69 (d, J = 7.6 Hz, 1H), 7.52 (d, J = 7.9 Hz, 1H), 7.46 (d, J = 7.6 Hz, 1H), 7.07 (d, J = 12.4 Hz, 1H), 7.03 (dd, J = 2.1, 0.6 Hz, 1H), 4.28-4.16 (m, 1H), 3.74 (d, J = 14.3 Hz, 1H), 3.63 (d, J = 14.5 Hz, 1H), 2.81 (s, 3H), 2.79-2.69 (m, 2H), 2.65-2.59 (m, 1H), 2.45-2.36 (m, 1H), 2.14-2.04 (m, 1H), 1.88-1.78 (m, 1H). |
| 179 | (S)-5-chloro-2-fluoro-4-(methyl(1-phenethylpyrrolidin-3-yl)amino)-N-(thiazol-4-yl)benzene-sulfonamide formate | 495.0 (M + 1) | (400 MHz, CD$_3$OD) δ 8.74 (d, J = 2.2 Hz, 1H), 8.50 (s, 1H), 7.83 (d, J = 7.4 Hz, 1H), 7.35-7.20 (m, 5H), 7.08-7.00 (m, 2H), 4.33 (t, J = 7.4 Hz, 1H), 3.26-3.24 (m, 1H), 3.20-3.03 (m, 5H), 2.97-2.90 (m, 2H), 2.82 (s, 3H), 2.27-2.17 (m, 1H), 2.13-2.03 (m, 1H), NH and COOH not observed. |
| 180 | (S)-5-chloro-2-fluoro-4-((1-(4-fluorobenzyl)-pyrrolidin-3-yl)(methyl)amino)-N-(thiazol-4-yl)benzene-sulfonamide | 499.2 (M + 1), 501.2 (M + 1) | (300 MHz, DMSO-$d_6$) δ 11.33 (s, 1H), 8.88 (d, J = 2.2 Hz, 1H), 7.69 (d, J = 7.6 Hz, 1H), 7.36-7.32 (m, 2H), 7.13 (t, J = 8.9 Hz, 2H), 7.06 (d, J = 12.5 Hz, 1H), 7.00 (d, J = 2.2 Hz, 1H), 4.24-4.15 (m, 1H), 3.61 (d, J = 13.0 Hz, 1H), 3.50 (d, J = 13.1 Hz, 1H), 2.79 (s, 3H), 2.75-2.55 (m, 3H), 2.36-2.28 (m, 1H), 2.13-2.01 (m, 1H), 1.85-1.74 (m, 1H). |
| 181 | (S)-5-chloro-2-fluoro-4-(methyl(1-((1-methyl-1H-pyrrol-2-yl)methyl)pyrrolidin-3-yl)amino)-N-(thiazol-4-yl)benzene-sulfonamide | 484.0 (M + 1), 486.0 (M + 1) | (400 MHz, CD$_3$OD) δ 8.69 (d, J = 2.2 Hz, 1H), 7.77 (d, J = 7.5 Hz, 1H), 6.95-6.88 (m, 2H), 6.61 (t, J = 2.2 Hz, 1H), 5.96 (ddt, J = 4.5, 2.3, 1.8 Hz, 2H), 4.22-4.18 (m, 1H), 3.65 (s, 3H), 3.61 (t, J = 9.4 Hz, 2H), 2.81 (s, 3H), 2.77-2.69 (m, 3H), 2.52-2.46 (m, 1H), 2.18-2.09 (m, 1H), 1.92-1.87 (m, 1H), NH not observed. |
| 182 | (S)-4-((1-((1H-indol-3-yl)methyl)pyrrolidin-3-yl)(methyl)amino)-5-chloro-2-fluoro-N-(thiazol-4-yl)benzene-sulfonamide 2,2,2-trifluoroacetate | 520.2 (M + 1), 522.2 (M + 1) | (300 MHz, DMSO $d_6$) δ 11.53-11.49 (br s, 1H), 11.41-11.37 (br s, 1H), 10.28-9.99 (m, 1H), 8.91 (t, J = 2.2 Hz, 1H), 7.78-7.73 (m, 2H), 7.61-7.59 (m, 1H), 7.45-7.43 (m, 1H), 7.23-7.07 (m, 4H), 4.61-4.27 (m, 3H), 3.66-3.14 (m, 4H), 2.75 (d, J = 13.6 Hz, 3H), 2.20-2.02 (m, 2H). |
| 183 | (S)-5-chloro-2-fluoro-4-(methyl(1-((1-methyl-1H-pyrazol-3-yl)methyl)pyrrolidin-3-yl)amino)-N-(thiazol-4-yl)benzene-sulfonamide | 485.2 (M + 1), 487.3 (M + 1) | (300 MHz, DMSO-$d_6$) δ 8.74-8.72 (m, 1H), 7.86-7.82 (m, 1H), 7.42 (dd, J = 0.2, 1.8 Hz, 1H), 7.05 (d, J = 2.2 Hz, 1H), 6.80-6.75 (m, 1H), 6.51-6.49 (m, 1H), 4.39-4.37 (m, 1H), 4.33-4.29 (m, 2H), 4.16-3.65 (m, 5H), 3.93-3.89 (m, 3H), 2.81-2.74 (m, 3H), 2.27-2.13 (m, 1H), NH not observed. |
| 184 | (S)-5-chloro-2-fluoro-4-((1-(imidazo[1,5-a]pyridin-3-ylmethyl)pyrrolidin-3-yl)(methyl)amino)-N-(thiazol-4-yl)benzene-sulfonamide | 521.0 (M + 1), 523.0 (M + 1) | (300 MHz, CD$_3$OD) δ 8.70 (d, J = 2.2 Hz, 1H), 8.31 (dt, J = 6.2, 1.0 Hz, 1H), 7.75 (d, J = 7.5 Hz, 1H), 7.55-7.52 (m, 1H), 7.33 (d, J = 0.8 Hz, 1H), 6.93-6.89 (m, 2H), 6.84 (ddd, J = 9.2, 6.4, 0.9 Hz, 1H), 6.71 (ddd, J = 7.3, 6.3, 1.0 Hz, 1H), 4.28-4.21 (m, 1H), 4.10-4.02 (m, 2H), 2.79 (s, 3H), 2.78-2.74 (m, 1H), 2.72-2.66 (m, 2H), 2.49-2.43 (m, 1H), 2.15- |

| Example No. | Name | MS (ES+) m/z | ¹H NMR |
|---|---|---|---|
| | | | 2.11 (m, 1H), 1.93-1.88 (m, 1H), NH not observed. |
| 185 | (S)-5-chloro-2-fluoro-4-(methyl(1-((2-(trifluoromethyl)-pyridin-4-yl)methyl)pyrrolidin-3-yl)amino)-N-(thiazol-4-yl)benzene-sulfonamide | 550.0 (M + 1), 552.0 (M + 1) | (300 MHz, CD₃OD) δ 8.73 (d, J = 2.2 Hz, 1H), 8.66 (d, J = 5.0 Hz, 1H), 7.84 (s, 1H), 7.77 (d, J = 7.5 Hz, 1H), 7.67 (dd, J = 4.8, 0.3 Hz, 1H), 7.02 (d, J = 2.2 Hz, 1H), 6.96 (d, J = 12.1 Hz, 1H), 4.33-4.26 (m, 1H), 3.83 (d, J = 14.4 Hz, 1H), 3.74 (d, J = 14.5 Hz, 1H), 2.88 (s, 3H), 2.86-2.77 (m, 2H), 2.71 (dd, J = 10.0, 7.8 Hz, 1H), 2.54-2.48 (m, 1H), 2.23-2.14 (m, 1H), 2.01-1.92 (m, 1H), NH not observed. |
| 186 | (S)-5-chloro-2-fluoro-4-((1-(isoquinolin-8-ylmethyl)pyrrolidin-3-yl)(methyl)amino)-N-(thiazol-4-yl)benzene-sulfonamide 2,2,2-trifluoroacetate | 532.2 (M + 1), 534.2 (M + 1) | (300 MHz, DMSO d₆) δ 11.40-11.39 (br s, 1H), 10.74-10.37 (br s, 1H), 9.97 (s, 1H), 8.91 (d, J = 2.0 Hz, 1H), 8.71 (d, J = 5.9 Hz, 1H), 8.25-8.20 (m, 2H), 8.02 (q, J = 3.0 Hz, 2H), 7.76-7.73 (m, 1H), 7.20 (d, J = 12.1 Hz, 1H), 7.08-7.07 (m, 1H), 5.09-5.04 (m, 2H), 4.57-4.30 (m, 1H), 3.68-3.64 (m, 1H), 3.56-3.43 (m, 3H), 2.89-2.72 (m, 3H), 2.24-2.06 (m, 2H). |
| 187 | (S)-5-chloro-2-fluoro-4-(methyl(1-((6-(trifluoromethyl)-pyridin-2-yl)methyl)pyrrolidin-3-yl)amino)-N-(thiazol-4-yl)benzene-sulfonamide | 550.2 (M + 1), 552.2 (M + 1) | (300 MHz, DMSO-d₆) δ 8.82-8.80 (br s, 1H), 8.21 (br s, 1H), 8.07 (t, J = 7.7 Hz, 1H), 7.78-7.73 (m, 2H), 7.67 (dd, J = 7.5, 0.3 Hz, 1H), 7.05-7.00 (m, 1H), 6.77-6.76 (m, 1H), 4.18-4.16 (m, 1H), 3.84 (d, J = 13.8 Hz, 1H), 3.72 (d, J = 14.4 Hz, 1H), 2.77 (s, 3H), 2.72-2.62 (m, 2H), 2.48-2.39 (m, 2H), 2.10-2.03 (m, 1H), 1.85-1.77 (m, 1H). |
| 188 | (S)-5-chloro-4-((1-(4-chlorobenzyl)-pyrrolidin-3-yl)(methyl)amino)-2-fluoro-N-(thiazol-4-yl)benzene-sulfonamide | 515.2 (M + 1), 517.2 (M + 1) | (300 MHz, DMSO-d₆) δ 11.33 (s, 1H), 8.89 (d, J = 2.2 Hz, 1H), 7.69 (d, J = 7.6 Hz, 1H), 7.39-7.31 (m, 4H), 7.06 (d, J = 12.5 Hz, 1H), 7.01 (d, J = 2.2 Hz, 1H), 4.24-4.15 (m, 1H), 3.62 (d, J = 13.3 Hz, 1H), 3.50 (d, J = 13.3 Hz, 1H), 2.79 (s, 3H), 2.75-2.54 (m, 3H), 2.36-2.28 (m, 1H), 2.13-2.01 (m, 1H), 1.86-1.74 (m, 1H). |
| 189 | (S)-5-chloro-2-fluoro-4-(methyl(1-((5-methylthiophen-2-yl)methyl)pyrrolidin-3-yl)amino)-N-(thiazol-4-yl)benzene-sulfonamide formate | 501.0 (M + 1), 503.0 (M + 1) | (400 MHz, CD₃OD) δ 8.73 (d, J = 2.2 Hz, 1H), 8.51-8.50 (m, 1H), 7.78 (d, J = 7.5 Hz, 1H), 7.03-6.96 (m, 2H), 6.79 (d, J = 3.3 Hz, 1H), 6.64-6.63 (m, 1H), 4.30-4.23 (m, 1H), 3.94 (d, J = 13.9 Hz, 1H), 3.85-3.82 (m, 1H), 2.95-2.81 (m, 6H), 2.73-2.67 (m, 1H), 2.45 (s, 3H), 2.18-2.10 (m, 1H), 2.01-1.94 (m, 1H), NH and COOH not oberved. |
| 190 | (S)-4-((1-((1H-indol-5-yl)methyl)pyrrolidin-3-yl)(methyl)amino)-5-chloro-2-fluoro-N-(thiazol-4-yl)benzene-sulfonamide formate | 520.0 (M + 1), 522.0 (M + 1) | (300 MHz, CD₃OD) δ 8.68 (d, J = 2.2 Hz, 1H), 8.54 (s, 1H), 7.83 (d, J = 7.4 Hz, 1H), 7.64 (s, 1H), 7.44 (d, J = 8.3 Hz, 1H), 7.31 (d, J = 3.2 Hz, 1H), 7.17 (dd, J = 8.4, 1.6 Hz, 1H), 7.05 (d, J = 11.8 Hz, 1H), 6.98 (d, J = 2.2 Hz, 1H), 6.49 (dd, J = 3.1, 0.6 Hz, 1H), 4.38-4.30 (m, 1H), 4.26-4.19 (m, 2H), 3.40-3.35 (m, 1H), 3.27-3.21 (m, 1H), 3.19-3.12 (m, 2H), 2.81 (s, 3H), 2.25-2.08 (m, 2H), NH(s) and COOH not observed. |
| 191 | (S)-5-chloro-2-fluoro-4-((1-(2-fluoro-3-methylbenzyl)-pyrrolidin-3-yl) | MS (ES+) m/z | (300 MHz, DMSO-d₆) δ 11.25 (br s, 1H), 8.90 (d, J = 2.2 Hz, 1H), 7.69 (d, J = 7.6 Hz, 1H), 7.25- |

| Example No. | Name | MS (ES+) m/z | ¹H NMR |
|---|---|---|---|
| | (methyl)amino)-N-(thiazol-4-yl)benzene-sulfonamide | 513.2 (M + 1), 515.2 (M + 1). | 7.15 (m, 2H), 7.10-7.03 (m, 3H), 4.23-4.16 (m, 1H), 3.65-3.61 (m, 2H), 2.78-2.62 (m, 5H), 2.45-2.34 (m, 2H), 2.23-2.22 (m, 3H), 2.11-2.01 (m, 1H), 1.84-1.75 (m, 1H). |
| 192 | (S)-5-chloro-2-fluoro-4-(methyl(1-((6-methylpyridin-2-yl)methyl)pyrrolidin-3-yl)amino)-N-(thiazol-4-yl)benzene-sulfonamide | 496.3 (M + 1), 498.2 (M + 1) | (300 MHz, DMSO-$d_6$) δ 11.31 (s, 1H), 8.89 (d, J = 2.2 Hz, 1H), 7.69 (d, J = 7.6 Hz, 1H), 7.64 (t, J = 7.7 Hz, 1H), 7.22 (d, J = 7.6 Hz, 1H), 7.09 (t, J = 9.5 Hz, 2H), 7.01 (d, J = 2.2 Hz, 1 H), 4.26-4.17 (m, 1H), 3.73 (d, J = 13.9 Hz, 1H), 3.61 (d, J = 14.0 Hz, 1H), 2.81 (s, 3H), 2.78-2.60 (m, 3H), 2.43 (d, J = 6.3 Hz, 4H), 2.15-2.03 (m, 1H), 1.88-1.79 (m, 1H). |
| 193 | (S)-5-chloro-4-((1-(3-(difluoromethyl)benzyl)-pyrrolidin-3-yl)(methyl)amino)-2-fluoro-N-(thiazol-4-yl)benzene-sulfonamide | 531.2 (M + 1), 533.2 (M + 1) | (300 MHz, DMSO-$d_6$) δ 11.28 (s, 1H), 8.89 (d, J = 2.2 Hz, 1H), 7.69 (d, J = 7.6 Hz, 1H), 7.51-7.44 (m, 4H), 7.21-6.84 (m, 3H), 4.25-4.16 (m, 1H), 3.70 (d, J = 13.3 Hz, 1H), 3.58 (d, J = 13.4 Hz, 1H), 2.80 (s, 3H), 2.76-2.55 (m, 3H), 2.40-2.30 (m, 1H), 2.14-2.02 (m, 1H), 1.87-1.75 (m, 1H). |
| 194 | (S)-5-chloro-2-fluoro-4-((1-((6-methoxypyridin-2-yl)methyl)pyrrolidin-3-yl)(methyl)amino)-N-(thiazol-4-yl)benzene-sulfonamide | 512.0 ((M + 1), 514.0 (M + 1) | (400 MHz, CD$_3$OD) δ 8.73 (d, J = 2.0 Hz, 1H), 8.49 (s, 1H), 7.83 (d, J = 7.2 Hz, 1H), 7.70 (dd, J = 8.4, 7.2 Hz, 1H), 7.06-7.00 (m, 3H), 6.76 (d, J = 8.8Hz, 1H), 4.34 (quin, J = 8.4 Hz, 1H), 4.07-3.94 (m, 2H), 3.91 (s, 3H), 3.23-2.99 (m, 4H), 2.85 (s, 3H), 2.22-2.19 (m, 1H), 2.09-2.06 (m, 1H). |

Examples 195-220

In a similar manner as described in the EXAMPLE 163, utilizing the appropriately substituted starting materials and intermediates, the following compounds were prepared:

| Example No. | Name | MS (ES+) m/z |
|---|---|---|
| 195 | (S)-5-chloro-4-((1-(5-chloro-2-fluorobenzyl)pyrrolidin-3-yl)(methyl)amino)-2-fluoro-N-(thiazol-4-yl)benzenesulfonamide | 532.9 (M + 1), 534.9 (M + 1) |
| 196 | (S)-5-chloro-2-fluoro-4-(methyl(1-(3-phenylpropyl)pyrrolidin-3-yl)amino)-N-(thiazol-4-yl)benzenesulfonamide | 509.2 (M + 1), 511.2 (M + 1) |
| 197 | (S)-5-chloro-4-((1-(2,5-dichlorobenzyl)pyrrolidin-3-yl)(methyl)amino)-2-fluoro-N-(thiazol-4-yl)benzenesulfonamide | 549.0 (M + 1), 551.0 (M + 1), 553.0 (M + 1) |
| 198 | (S)-5-chloro-4-((1-(2-chlorobenzyl)pyrrolidin-3-yl)(methyl)amino)-2-fluoro-N-(thiazol-4-yl)benzenesulfonamide | 515.0 (M + 1), 517.0 (M + 1) |
| 199 | (S)-5-chloro-4-((1-(4-(dimethylamino)benzyl)pyrrolidin-3-yl)(methyl)amino)-2-fluoro-N-(thiazol-4-yl)benzenesulfonamide | 524.0 (M + 1), 526.0 (M + 1) |
| 200 | (S)-4-((1-(2-(benzyloxy)ethyl)pyrrolidin-3-yl)(methyl)amino)-5-chloro-2-fluoro-N-(thiazol-4-yl)benzenesulfonamide | 525.0 (M + 1), 527.0 (M + 1) |
| 201 | (S)-5-chloro-2-fluoro-4-(methyl(1-(4-methylbenzyl)pyrrolidin-3-yl)amino)-N-(thiazol-4-yl)benzenesulfonamide | 495.1 (M + 1), 497.0 (M + 1) |
| 202 | (S)-4-((1-((1H-pyrrol-2-yl)methyl)pyrrolidin-3-yl)(methyl)amino)-5-chloro-2-fluoro-N-(thiazol-4-yl)benzenesulfonamide | 470.0 (M + 1), 472.0 (M + 1) |
| 203 | (S)-5-chloro-4-((1-(2,6-dimethylbenzyl)pyrrolidin-3-yl)(methyl)amino)-2-fluoro-N-(thiazol-4-yl)benzenesulfonamide | 509.0 (M + 1), 511.0 (M + 1) |
| 204 | (S)-5-chloro-2-fluoro-4-(methyl(1-((5-methylfuran-2-yl)methyl)pyrrolidin-3-yl)amino)-N-(thiazol-4-yl)benzenesulfonamide | 485.1 (M + 1), 487.1 (M + 1) |
| 205 | (S)-5-chloro-4-((1-(3-chloro-2-fluorobenzyl)pyrrolidin-3-yl)(methyl)amino)-2-fluoro-N-(thiazol-4-yl)benzenesulfonamide | 532.9 (M + 1), 534.9 (M + 1) |
| 206 | (S)-5-chloro-2-fluoro-4-((1-(2-methoxybenzyl)pyrrolidin-3-yl)(methyl)amino)-N-(thiazol-4-yl)benzenesulfonamide | 511.0 (M + 1), 513.0 (M + 1) |
| 207 | (S)-5-chloro-4-((1-(2,5-difluorobenzyl)pyrrolidin-3-yl)(methyl)amino)-2-fluoro-N-(thiazol-4-yl)benzenesulfonamide | 516.9 (M + 1), 518.9 (M + 1) |

-continued

| Example No. | Name | MS (ES+) m/z |
|---|---|---|
| 208 | (S)-5-chloro-4-((1-(3-chlorobenzyl)pyrrolidin-3-yl)(methyl)amino)-2-fluoro-N-(thiazol-4-yl)benzenesulfonamide | 515.0 (M + 1), 517.0 (M + 1) |
| 209 | (S)-5-chloro-2-fluoro-4-((1-(2-hydroxybenzyl)pyrrolidin-3-yl)(methyl)amino)-N-(thiazol-4-yl)benzenesulfonamide | 497.0 (M + 1), 499.0 (M + 1) |
| 210 | (S)-5-chloro-4-((1-(2-(difluoromethoxy)benzyl)pyrrolidin-3-yl)(methyl)amino)-2-fluoro-N-(thiazol-4-yl)benzenesulfonamide | 547.0 (M + 1), 549.0 (M + 1) |
| 211 | (S)-5-chloro-2-fluoro-4-((1-(4-fluoro-3-methylbenzyl)pyrrolidin-3-yl)(methyl)amino)-N-(thiazol-4-yl)benzenesulfonamide | 513.0 (M + 1), 515.0 (M + 1) |
| 212 | (S)-5-chloro-2-fluoro-4-((1-(3-fluorobenzyl)pyrrolidin-3-yl)(methyl)amino)-N-(thiazol-4-yl)benzenesulfonamide | 499.0 (M + 1), 501.0 (M + 1) |
| 213 | (S)-5-chloro-4-((1-(2,3-difluorobenzyl)pyrrolidin-3-yl)(methyl)amino)-2-fluoro-N-(thiazol-4-yl)benzenesulfonamide | 517.0 (M + 1), 519.0 (M + 1) |
| 214 | (S)-5-chloro-2-fluoro-4-(methyl(1-(3-(trifluoromethyl)benzyl)pyrrolidin-3-yl)amino)-N-(thiazol-4-yl)benzenesulfonamide | 549.0 (M + 1), 551.0 (M + 1) |
| 215 | (S)-5-chloro-2-fluoro-4-(methyl(1-(thiophen-2-ylmethyl)pyrrolidin-3-yl)amino)-N-(thiazol-4-yl)benzenesulfonamide | 486.9 (M + 1), 488.9 (M + 1) |
| 216 | (S)-5-chloro-2-fluoro-4-(methyl(1-((4-methylpyridin-2-yl)methyl)pyrrolidin-3-yl)amino)-N-(thiazol-4-yl)benzenesulfonamide | 495.8 (M + 1), 497.8 (M + 1) |
| 217 | (S)-4-((1-(4-bromobenzyl)pyrrolidin-3-yl)(methyl)amino)-5-chloro-2-fluoro-N-(thiazol-4-yl)benzenesulfonamide | 558.8 (M + 1), 560.9 (M + 1) |
| 218 | (S)-5-chloro-2-fluoro-4-((1-(2-fluorobenzyl)pyrrolidin-3-yl)(methyl)amino)-N-(thiazol-4-yl)benzenesulfonamide | 499.0 (M + 1), 501.0 (M + 1) |
| 219 | (S)-5-chloro-2-fluoro-4-((1-(3-methoxybenzyl)pyrrolidin-3-yl)(methyl)amino)-N-(thiazol-4-yl)benzenesulfonamide | 510.8 (M + 1), 512.8 (M + 1) |
| 220 | (S)-5-chloro-2-fluoro-4-((1-(3-fluoro-2-methylbenzyl)pyrrolidin-3-yl)(methyl)amino)-N-(thiazol-4-yl)benzenesulfonamide | 513.0 (M + 1), 515.0 (M + 1) |

Example 221

Synthesis of (S)-3-chloro-4-((1-(1-phenylethyl)piperidin-4-yl)oxy)-N-(1,2,4-thiadiazol-5-yl)benzenesulfonamide 2,2,2-trifluoroacetate

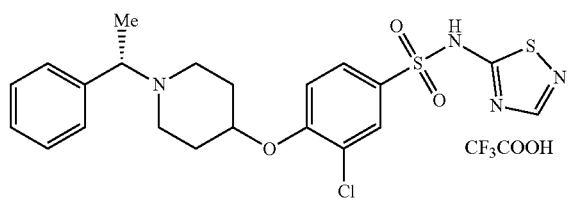 [SMILES: C[C@@H](c1ccccc1)N1CCC(Oc2ccc(S(=O)(=O)Nc3ncns3)cc2Cl)CC1 ; "CF3COOH"]

Following the procedure as described for EXAMPLE 58, Step 3 and making non-critical variations as required to replace 3-chloro-N-(2,4-dimethoxybenzyl)-4-fluoro-N-(thiazol-2-yl)benzenesulfonamide with 3-chloro-N-(2,4-dimethoxybenzyl)-4-fluoro-N-(1,2,4-thiadiazol-5-yl)benzenesulfonamide, the title compound was obtained as a colorless solid (0.025 g, 6% yield): ¹H NMR (300 MHz, DMSO-d₆) δ 9.87 (br s, 1H), 7.78-7.66 (m, 2H), 7.60-7.44 (m, 6H), 7.44-7.29 (m, 1H), 5.05-4.92 (m, 1H), 4.76-4.58 (m, 1H), 3.82-3.23 (m, 2H), 3.02-2.70 (m, 2H), 2.40-1.76 (m, 4H), 1.68 (d, J=7.0 Hz, 3H), NH not observed; MS (ES+) m/z 479.0 (M+1), 481.0 (M+1).

Example 222

Synthesis of (R)-5-chloro-2-fluoro-4-((1-(1-phenylethyl)piperidin-4-yl)oxy)-N-(thiazol-4-yl)benzenesulfonamide 2,2,2-trifluoroacetate

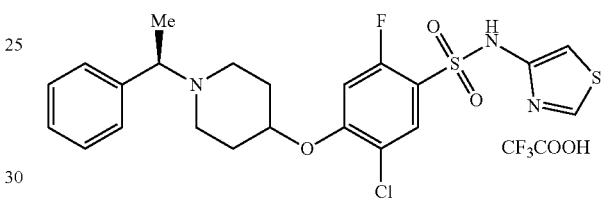

Following the procedure as described for EXAMPLE 57, Step 3 and making non-critical variations as required to replace 3-chloro-4-fluoro-N-(thiazol-4-yl)benzenesulfonamide with 5-chloro-2,4-difluoro-N-(thiazol-4-yl)benzenesulfonamide, the title compound was obtained as a colorless solid (0.04 g, 9% yield): ¹H NMR (300 MHz, DMSO-d₆) δ 11.37-11.35 (m, 1H), 9.93-9.68 (m, 1H), 8.89 (d, J=2.2 Hz, 1H), 7.81-7.74 (m, 1H), 7.62-7.40 (m, 5H), 7.07 (s, 1H), 4.98-4.96 (m, 1H), 4.69-4.62 (m, 1H), 3.74-3.68 (m, 1H), 3.59-3.28 (m, 2H), 2.92-2.71 (m, 2H), 2.31-2.22 (m, 1H), 2.13-1.99 (m, 2H), 1.68 (d, J=6.9 Hz, 3H); MS (ES+) m/z 496.1 (M+1), 498.1 (M+1).

Example 223

Synthesis of 4-((1-benzylpiperidin-4-yl)oxy)-2,6-difluoro-3-methyl-N-(thiazol-2-yl)benzenesulfonamide 2,2,2-trifluoroacetate

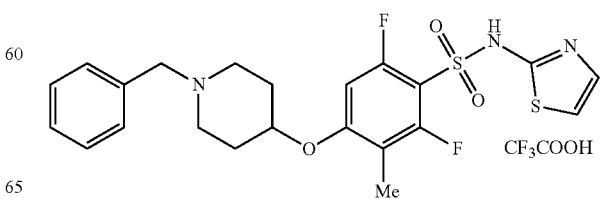

Step 1. Preparation of 3-chloro-N-(2,4-dimethoxy-benzyl)-2,4,6-trifluoro-N-(thiazol-2-yl)benzenesulfonamide

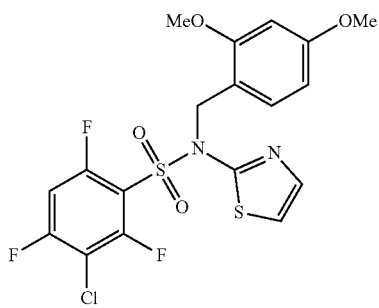 [SMILES: COc1ccc(CN(c2nccs2)S(=O)(=O)c2c(F)cc(F)c(Cl)c2F)c(OC)c1]

To a solution of N-(2,4-dimethoxybenzyl)thiazol-2-amine (4.11 g, 16.4 mmol) in anhydrous tetrahydrofuran (150 mL) was added a 1.0 M solution of lithium bis(trimethylsilyl)amide in tetrahydrofuran (16.40 mL, 16.40 mmol) at −78° C. The reaction mixture was allowed to warm to ambient temperature, stirred for 1 h, and then cooled to −78° C. To it was added a solution of 3-chloro-2,4,6-trifluorobenzenesulfonyl chloride (3.96 g, 14.90 mmol) in tetrahydrofuran (75 mL) −78° C. The reaction mixture was stirred at −78° C. for 1 h and then at ambient temperature for 18 h. The mixture was diluted with saturated ammonium chloride (100 mL) and extracted with ethyl acetate (2×100 mL). The combined organic fractions were washed with brine (100 mL), dried over anhydrous magnesium sulfate, and filtered. The filtrate was concentrated in vacuo and the residue purified by column chromatography, eluting with a gradient of 0 to 30% of ethyl acetate in pentane, to afford the title compound as a colorless solid (3.48 g, 49% yield): $^1$H NMR (300 MHz, CDCl$_3$) δ 87.44 (d, J=3.6 Hz, 1H), 7.21 (d, J=8.2 Hz, 1H), 7.04 (d, J=3.6 Hz, 1H), 6.90-6.82 (m, 1H), 6.39-6.36 (m, 2H), 5.21 (s, 2H), 3.76 (s, 3H), 3.74 (s, 3H).

Step 2. Preparation of tert-butyl 4-(2-chloro-4-(N-(2,4-dimethoxybenzyl)-N-(thiazol-2-yl)sulfamoyl)-3,5-difluorophenoxy)piperidine-1-carboxylate

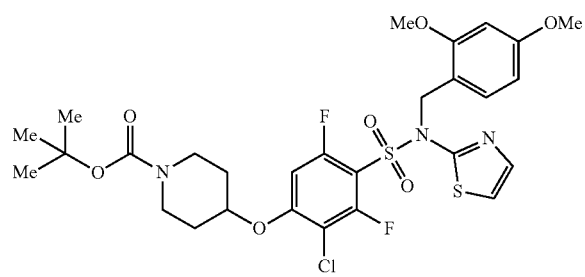 [SMILES: COc1ccc(CN(c2nccs2)S(=O)(=O)c2c(F)cc(OC3CCN(C(=O)OC(C)(C)C)CC3)c(Cl)c2F)c(OC)c1]

To a solution of tert-butyl 4-hydroxypiperidine-1-carboxylate (0.42 g, 2.10 mmol) and 3-chloro-N-(2,4-dimethoxybenzyl)-2,4,6-trifluoro-N-(thiazol-2-yl)benzenesulfonamide (1.00 g, 2.10 mmol) in anhydrous N,N-dimethylformamide (20 mL) was added a dispersion of 60% sodium hydride in mineral oil (0.17 g, 4.2 mmol) at ambient temperature. The reaction mixture was stirred for 18 h, and then quenched with saturated ammonium chloride (80 mL). The mixture was extracted with ethyl acetate (3×80 mL). The combined organic fractions were washed with brine (2×80 mL), dried over anhydrous magnesium sulfate, and filtered. The filtrate was concentrated in vacuo and purified by column chromatography, eluting with a gradient of 0 to 50% of ethyl acetate in heptane, to afford the title compound as a colorless solid (0.97 g, 70% yield): $^1$H NMR (300 MHz, CDCl$_3$) δ 87.43-7.42 (m, 1H), 7.21 (d, J=7.9 Hz, 1H), 7.01 (d, J=3.6 Hz, 1H), 6.53-6.47 (m, 1H), 6.39-6.36 (m, 2H), 5.23 (s, 2H), 4.60-4.56 (m, 1H), 3.75 (s, 3H), 3.74 (s, 3H), 3.58-3.51 (m, 4H), 1.94-1.81 (m, 4H), 1.47 (s, 9H).

Step 3. Preparation of tert-butyl 4-(4-(N-(2,4-dimethoxybenzyl)-N-(thiazol-2-yl)sulfamoyl)-3,5-difluoro-2-methylphenoxy)piperidine-1-carboxylate

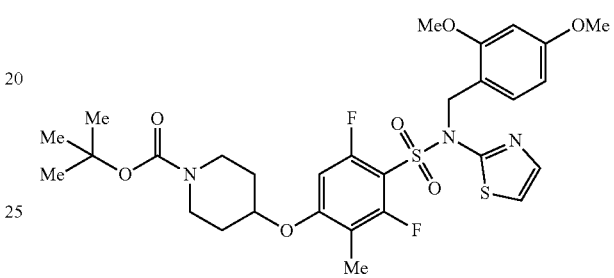

To a mixture of tert-butyl 4-(2-chloro-4-(N-(2,4-dimethoxybenzyl)-N-(thiazol-2-yl)sulfamoyl)-3,5-difluorophenoxy)piperidine-1-carboxylate (0.97 g, 1.50 mmol), methylboronic acid (0.88 g, 14.7 mmol), and potassium phosphate (1.59 g, 7.50 mmol) in anhydrous dioxane (30 mL) was added palladium acetate (0.10 g, 0.44 mmol) and tricyclohexylphosphonium tetrafluoroborate (0.32 g, 0.88 mmol). The resulting mixture was degassed and sparging with nitrogen and heated to reflux for 4 h. The reaction mixture was then allowed to cool to ambient temperature and stirred for 18 h. After concentration in vacuo, the residue was diluted with water (100 mL) and the mixture was extracted with ethyl acetate (4×50 mL). The combined organic fractions were washed with brine (100 mL), dried over anhydrous magnesium sulfate, and filtered. The filtrate was concentrated in vacuo and the residue purified by column chromatography, eluting with a gradient of 0 to 6% of ethyl acetate (containing 20% of ethanol and 0.1% of ammonium hydroxide) in heptane, to afford the title compound as a greyish oil (0.93 g, 97% yield): MS (ES+) m/z 640.5 (M+1).

Step 4. Preparation of 2,6-difluoro-3-methyl-4-(piperidin-4-yloxy)-N-(thiazol-2-yl)benzenesulfonamide 2,2,2-trifluoroacetate

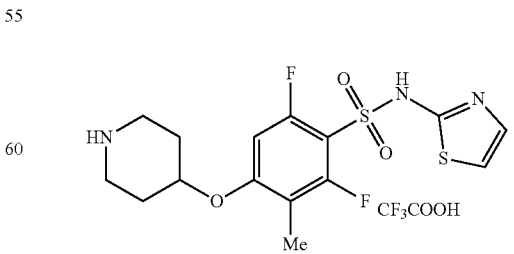

To a solution of tert-butyl 4-(4-(N-(2,4-dimethoxybenzyl)-N-(thiazol-2-yl)sulfamoyl)-3,5-difluoro-2-methylphenoxy)piperidine-1-carboxylate (0.93 g, 1.45 mmol) in dichloromethane (4 mL) was added trifluoroacetic acid (4 mL). The mixture was stirred 4 h and then concentrated in vacuo. The residue was triturated with methanol (20 mL). Filtration and concentration of the filtrate in vacuo afforded a pink solid (0.73 g, quantitative yield): MS (ES+) m/z 390.2 (M+1).

Step 5. Preparation of 4-((1-benzylpiperidin-4-yl)oxy)-2,6-difluoro-3-methyl-N-(thiazol-2-yl)benzenesulfonamide 2,2,2-trifluoroacetate

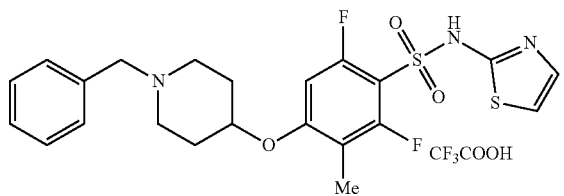 [SMILES: Cc1c(OC2CCN(Cc3ccccc3)CC2)cc(F)c(S(=O)(=O)Nc2nccs2)c1F ; "CF3COOH"]

Following the procedure as described for EXAMPLE 2 and making non-critical variations as required to replace 3-chloro-4-((3,3-dimethylpiperidin-4-yl)oxy)-N-(1,2,4-thiadiazol-5-yl)benzenesulfonamide 2,2,2-trifluoroacetate with 2,6-difluoro-3-methyl-4-(piperidin-4-yloxy)-N-(thiazol-2-yl)benzenesulfonamide 2,2,2-trifluoroacetate, afforded the title compound as a colorless solid (0.05 g, 14% yield): $^1$H NMR (300 MHz, DMSO-$d_6$) δ 12.97-12.88 (m, 1H), 9.81-9.62 (m, 1H), 7.63-7.47 (m, 5H), 7.35-7.28 (m, 1H), 7.06-6.88 (m, 2H), 4.38 (t, J=0.4 Hz, 2H), 3.50-3.42 (m, 1H), 3.34-3.00 (m, 4H), 2.28-1.72 (m, 7H); MS (ES+) m/z 480.3 (M+1).

Example 224

Synthesis of (S)-2,6-difluoro-3-methyl-4-(methyl(1-((6-(trifluoromethyl)pyridin-2-yl)methyl)pyrrolidin-3-yl)amino)-N-(thiazol-4-yl)benzenesulfonamide 2,2,2-trifluoroacetate

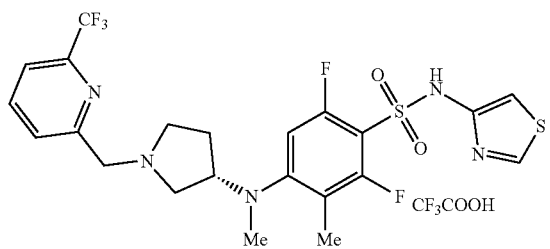 [SMILES: Cc1c(N(C)[C@H]2CCN(Cc3cccc(C(F)(F)F)n3)C2)cc(F)c(S(=O)(=O)Nc2cscn2)c1F ; "CF3COOH"]

Step 1. Preparation of 3-bromo-2,4,6-trifluorobenzene-1-sulfonyl Chloride

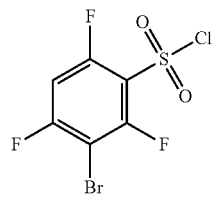

To 2-bromo-1,3,5-trifluorobenzene (50.00 g, 236.00 mmol) was added chlorosulfonic acid (250 mL) and the reaction mixture was heated to 80° C. for 12 h. The mixture was poured onto ice-water and extracted with ethyl acetate (2×500 mL). The combined organic phase was dried over anhydrous sodium sulfate, filtered and the filtrate concentrated in vacuo. Purification of the residue was purified by column chromatography, eluting with petroleum ether, provided the title compound as a yellow oil (51.00 g, 70% yield): $^1$H NMR (400 MHz, CDCl$_3$) δ 7.03 (ddd, J=9.8, 7.8, 2.2 Hz, 1H).

Step 2. Preparation of tert-butyl ((3-bromo-2,4,6-trifluorophenyl)sulfonyl)(thiazol-4-yl)carbamate

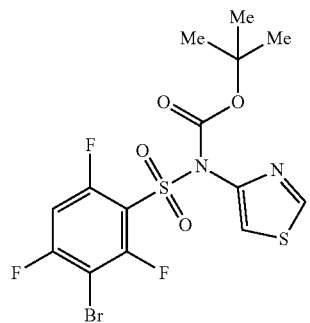 [SMILES: CC(C)(C)OC(=O)N(c1cscn1)S(=O)(=O)c1c(F)cc(F)c(Br)c1F]

To a solution of tert-butyl thiazol-4-ylcarbamate (26.90 g, 134.00 mmol) in anhydrous tetrahydrofuran (500 mL) was added lithium bis(trimethylsilyl)amide (1 M in tetrahydrofuran, 168 mL, 168.0 mmol) at −78° C. The reaction mixture was stirred at −78° C. for 20 minutes, after which a solution of 3-bromo-2,4,6-trifluorobenzene-1-sulfonyl chloride (50.00 g, 161.00 mmol) in anhydrous tetrahydrofuran (100 mL) was added dropwise at −78° C. The reaction mixture was allowed to warm to ambient temperature and stirred for 12 h. The reaction mixture was concentrated in vacuo and the residue was diluted with ethyl acetate (3×400 mL). The organic phase was washed with water (3×400 mL), dried over anhydrous sodium sulfate, and filtered. Concentration of the filtrate in vacuo and trituration of the residue in methanol (100 mL) afforded the title compound as a colorless solid (40.00 g, 62% yield): $^1$H NMR (400 MHz, CDCl$_3$) 98.81 (d, J=2.3 Hz, 1H), 7.54 (d, J=2.2 Hz, 1H), 6.97 (ddd, J=9.8, 8.0, 2.2 Hz, 1H), 1.47-1.34 (m, 9H); MS (ES+) m/z 496.9 (M+23).

Step 3. Preparation of tert-butyl (S)-3-((2-bromo-4-(N-(tert-butoxycarbonyl)-N-(thiazol-4-yl)sulfamoyl)-3,5-difluorophenyl)amino)pyrrolidine-1-carboxylate

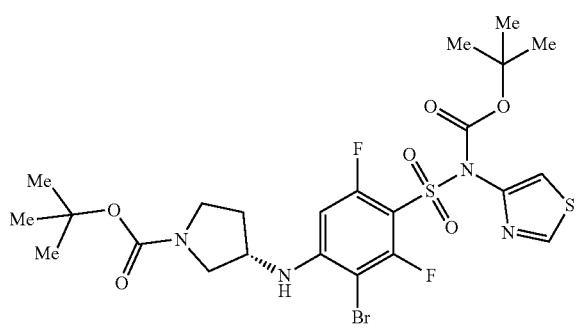 [SMILES: CC(C)(C)OC(=O)N1CC[C@H](Nc2cc(F)c(S(=O)(=O)N(C(=O)OC(C)(C)C)c3cscn3)c(F)c2Br)C1]

To a solution of tert-butyl ((3-bromo-2,4,6-trifluorophenyl)sulfonyl)(thiazol-4-yl)carbamate (38.1 g, 80.6 mmol) and triethylamine (34.0 mL, 241.8 mmol) in anhydrous N,N-dimethylformamide (250 mL) was added tert-butyl (S)-3-aminopyrrolidine-1-carboxylate (15.0 g, 80.6 mmol). The reaction mixture was stirred for 18 h and then diluted with ethyl acetate (1000 mL). The mixture was washed with saturated ammonium chloride (2×250 mL), brine (2×100 mL), dried over anhydrous sodium sulfate, and filtered. The filtrate was concentrated in vacuo and the residue was purified by column chromatography, eluting with a gradient of 10 to 80% of ethyl acetate in hexanes, to afford the title compound as a colorless solid (12.6 g, 25% yield): MS (ES+) m/z 639.2 (M+1), 641.2 (M+1).

Step 4. Preparation of (S)-3-bromo-2,6-difluoro-4-(pyrrolidin-3-ylamino)-N-(thiazol-4-yl)benzenesulfonamide 2,2,2-trifluoroacetate

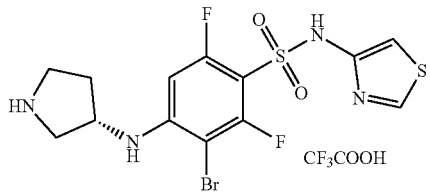 [SMILES: O=S(=O)(Nc1cscn1)c1c(F)cc(N[C@H]2CCNC2)c(Br)c1F ; "CF3COOH"]

To a solution of tert-butyl (S)-3-((2-bromo-4-(N-(tert-butoxycarbonyl)-N-(thiazol-4-yl)sulfamoyl)-3,5-difluorophenyl)amino)pyrrolidine-1-carboxylate (12.6 g, 19.70 mmol) in dichloromethane (50 mL) was added trifluoroacetic acid (25 mL). The mixture was stirred for 4 h and then concentrated in vacuo. The residue was triturated with methanol (75 mL) to afford the title compound as an off white solid (8.20 g, 75% yield): MS (ES+) m/z 439.0 (M+1), 441.0 (M+1).

Step 5. Preparation of (S)-3-bromo-2,6-difluoro-N-(thiazol-4-yl)-4-((1-((6-(trifluoromethyl)pyridin-2-yl)methyl)pyrrolidin-3-yl)amino)benzenesulfonamide

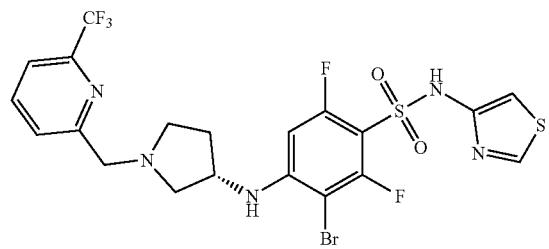 [SMILES: O=S(=O)(Nc1cscn1)c1c(F)cc(N[C@H]2CCN(Cc3cccc(C(F)(F)F)n3)C2)c(Br)c1F]

To a mixture of (S)-3-bromo-2,6-difluoro-4-(pyrrolidin-3-ylamino)-N-(thiazol-4-yl)benzenesulfonamide 2,2,2-trifluoroacetate (0.80 g, 1.45 mmol) and 6-(trifluoromethyl)picolinaldehyde (0.38 g, 2.18 mmol) in anhydrous N,N-dimethylformamide (5 mL) and anhydrous dichloromethane (5 mL) was added sodium triacetoxyborohydride (0.46 g, 2.18 mmol). The mixture was stirred at ambient temperature for 18 h and then quenched with 2 M aqueous sodium hydroxide (8 mL) and brine (8 mL). The mixture was extracted with ethyl acetate (3×25 mL). The combined organic phase was washed with brine (25 mL), dried over anhydrous magnesium sulfate, and filtered. The filtrate was concentrated in vacuo to afford the title compound as an orange oil (0.87 g, quantitative yield): $^1$H NMR (300 MHz, DMSO-$d_6$) δ 11.34 (s, 1H), 8.90 (d, J=2.2 Hz, 1H), 8.12-8.04 (m, 2H), 7.79-7.74 (m, 4H), 6.96 (d, J=2.2 Hz, 1H), 6.63 (dd, J=14.0, 1.4 Hz, 1H), 6.21-6.18 (m, 1H), 4.14-4.11 (m, 1H), 3.83 (s, 2H), 2.30-2.19 (m, 2H), 1.82-1.72 (m, 1H); MS (ES+) m/z 598.2 (M+1), 600.3 (M+1).

Step 6. Preparation of (S)-2,6-difluoro-3-methyl-N-(thiazol-4-yl)-4-((1-((6-(trifluoromethyl)pyridin-2-yl)methyl)pyrrolidin-3-yl)amino)benzenesulfonamide

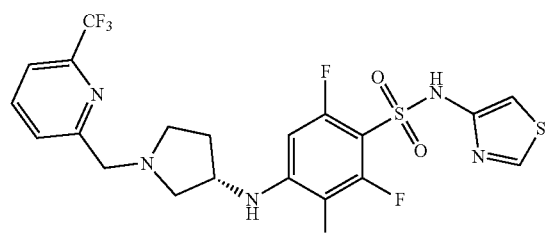

To a mixture of (S)-3-bromo-2,6-difluoro-N-(thiazol-4-yl)-4-((1-((6-(trifluoromethyl)pyridin-2-yl)methyl)pyrrolidin-3-yl)amino)benzenesulfonamide (0.87 g, 1.45 mmol), methylboronic acid (0.52 g, 8.70 mmol), and potassium phosphate (0.92 g, 4.35 mmol) in anhydrous dioxane (14 mL) was added tetrakis(triphenylphosphine)palladium(0) (0.16 g, 0.14 mmol). The reaction mixture was degassed by sparging with nitrogen and heated to reflux for 6 h. After cooling to ambient temperature, additional methylboronic acid (0.52 g, 8.70 mmol), potassium phosphate (0.92 g, 4.35 mmol), and tetrakis(triphenylphosphine)palladium(0) (0.16 g, 0.14 mmol) was added. The reaction mixture was heated to reflux for 6 h and then allowed to cool to ambient temperature. The mixture was filtered through a pad of celite and the filtrate was concentrated in vacuo. Purification of the residue by column chromatography, eluting with a gradient of 0 to 10% of methanol in dichloromethane, afforded the title compound as a greyish oil (0.72 g, quantitative yield): MS (ES+) m/z 534.4 (M+1).

Step 7. Preparation of (S)-2,6-difluoro-3-methyl-4-(methyl(1-((6-(trifluoromethyl)pyridin-2-yl)methyl)pyrrolidin-3-yl)amino)-N-(thiazol-4-yl)benzenesulfonamide 2,2,2-trifluoroacetate

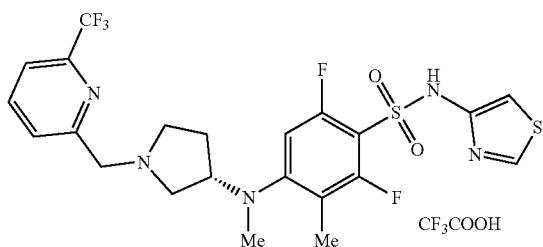 [SMILES: Cc1c(N(C)[C@H]2CCN(Cc3cccc(C(F)(F)F)n3)C2)cc(F)c(S(=O)(=O)Nc2cscn2)c1F ; "CF3COOH"]

Following the procedure as described for EXAMPLE 155, Step 4 and making non-critical variations as required to replace (S)-2-fluoro-4-((1-(2-fluorobenzyl)pyrrolidin-3-yl)amino)-5-methyl-N-(thiazol-4-yl)benzenesulfonamide with (S)-2,6-difluoro-3-methyl-N-(thiazol-4-yl)-4-((1-((6-(trifluoromethyl)pyridin-2-yl)methyl)pyrrolidin-3-yl)amino)benzenesulfonamide, and purification by preparative reverse-phase HPLC, eluting with a gradient of 10 to 50% of acetonitrile in water containing 0.1% of trifluoroacetic acid, afforded the title compound as a colorless solid (0.070 g, 6% yield): $^1$H NMR (300 MHz, DMSO-$d_6$) δ 11.49 (d, J=0.4 Hz, 1H), 10.58-10.40 (m, 1H), 8.90 (d, J=2.2 Hz, 1H), 8.23 (td, J=0.4, 7.8 Hz, 1H), 7.99 (d, J=7.8 Hz, 1H), 7.84 (d, J=7.8 Hz, 1H), 6.98 (d, J=2.2 Hz, 1H), 6.90-6.85 (m, 1H), 4.73-4.67 (m, 2H), 4.30-4.07 (m, 1H), 3.76-3.12 (m, 4H), 2.70-2.66 (m, 3H), 2.28-2.01 (m, 5H); MS (ES+) m/z 548.2 (M+1).

Example 225

Synthesis of (R)-4-((1-benzyl-3-methylpyrrolidin-3-yl)amino)-3-chloro-N-(thiazol-4-yl)benzenesulfonamide Formate

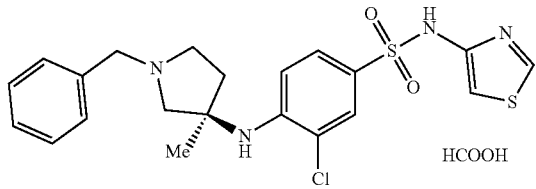 [SMILES: C[C@@]1(Nc2ccc(S(=O)(=O)Nc3cscn3)cc2Cl)CCN(Cc2ccccc2)C1 ; "HCOOH"]

Step 1. Preparation of tert-butyl (4-bromo-3-chlorophenyl)sulfonyl(thiazol-4-yl)carbamate

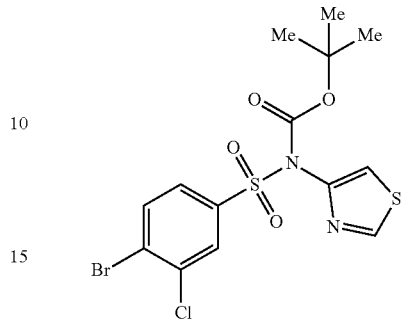

To a mixture of tert-butyl thiazol-4-ylcarbamate (26.5 g, 132.3 mmol) in anhydrous tetrahydrofuran (300 mL) was added a 1 M solution of lithium bis(trimethylsilyl)amide in tetrahydrofuran (185.3 mL, 185.3 mmol) at −78° C. The reaction mixture was allowed to warm to 0° C. and stirred for 1 h. After cooling the reaction mixture to −78° C., a solution of 4-bromo-3-chlorobenzenesulfonyl chloride (49.88 g, 172.0 mmol) in anhydrous tetrahydrofuran (200 mL) was added to it. The reaction mixture was allowed to warm to ambient temperature, stirred for 3 h, and then quenched by addition of saturated sodium bicarbonate solution (100 mL). The mixture was diluted with water (300 mL) and extracted with ethyl acetate (3×300 mL). The combined organic phase was washed with brine (100 mL), dried over anhydrous sodium sulfate, and filtered. Concentration of the filtrate in vacuo and trituration of the residue in methanol (200 mL) provided the title compound as a colorless solid (35.0 g, 58% yield): $^1$H NMR (400 MHz, CDCl$_3$) δ 8.85-8.78 (d, J=2.0 Hz, 1H), 8.28-8.21 (d, J=4.0 Hz, 1H), 7.95-7.89 (m, 1H), 7.87-7.83 (m, 1H), 7.59-7.55 (d, J=4.0 Hz, 1H), 1.38 (s, 9H); MS (ES+) m/z 352.9 (M−99), 354.9 (M−99).

Step 2. Preparation of tert-butyl (R)-((4-((1-benzyl-3-methylpyrrolidin-3-yl)amino)-3-chlorophenyl)sulfonyl)(thiazol-4-yl)carbamate

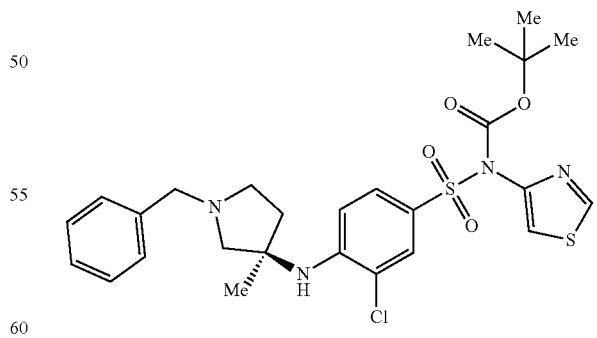

To a mixture of (R)-1-benzyl-3-methylpyrrolidin-3-amine (prepared according to WO 2013063459, 0.230 g, 1.2 mmol) and tert-butyl (4-bromo-3-chlorophenyl)sulfonyl(thiazol-4-yl)carbamate (0.548 g, 1.2 mmol) in anhydrous toluene (5 mL) was added 4,5-bis(diphenylphosphino)-9,9-dimethylxanthene (0.21 g, 0.363 mmol), cesium carbonate (1.20 g, 3.6 mmol), and bis(dibenzylideneacetone)palladium(0) (0.139 g, 0.242 mmol) and the reaction mixture was heated to 100° C. for 12 h. After cooling to ambient temperature, water (10 mL) was added and the mixture was extracted with ethyl acetate (3×10 mL). The combined organic layers were washed with brine (3×10 mL), dried over anhydrous sodium sulfate, and filtered. Concentration of the filtrate in vacuo and purification of the residue by column chromatography, eluting with a gradient of 10-50% of ethyl acetate in petroleum ether, afforded the title compound as a yellow solid (0.400 g, 54% yield): MS (ES+) m/z 563.2 (M+1), 565.2 (M+1).

Step 3. Preparation of (R)-4-((1-benzyl-3-methylpyrrolidin-3-yl)amino)-3-chloro-N-(thiazol-4-yl)benzenesulfonamide Formate

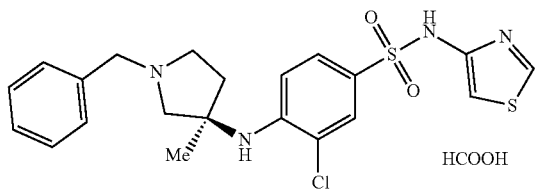 [SMILES: C[C@@]1(Nc2ccc(S(=O)(=O)Nc3cscn3)cc2Cl)CCN(Cc2ccccc2)C1 ; "HCOOH"]

To tert-butyl (R)-((4-((1-benzyl-3-methylpyrrolidin-3-yl)amino)-3-chlorophenyl)sulfonyl)(thiazol-4-yl)carbamate (0.400 g, 0.71 mmol) was added a 4 M solution of hydrogen chloride in dioxane (10 mL) and the reaction mixture was stirred at ambient temperature for 12 h. Concentration in vacuo and purification of the residue by preparative reverse-phase HPLC, eluting with a gradient of acetonitrile in water containing 0.225% of formic acid, provided the title compound as a colorless solid (0.021 g, 6% yield): $^1$H NMR (400 MHz, DMSO-$d_6$) δ 8.87 (d, J=2.0 Hz, 1H), 8.23 (s, 1H), 7.66 (d, J=2.4 Hz, 1H), 7.54 (dd, J=2.4, 8.8 Hz, 1H), 7.30 (d, J=4.4 Hz, 4H), 7.23 (qd, J=4.2, 8.4 Hz, 1H), 7.08 (d, J=8.8 Hz, 1H), 6.99 (d, J=2.0 Hz, 1H), 5.48 (s, 1H), 3.65-3.53 (m, 1H), 2.78 (d, J=9.6 Hz, 1H), 2.73-2.65 (m, 1H), 2.58-2.52 (m, 3H), 2.19-2.08 (m, 1H), 1.86 (ddd, J=5.2, 7.2, 12.6 Hz, 1H), 1.44 (s, 3H), NH and COOH not observed; MS (ES+) m/z 463.0.

Example 226

Synthesis of (S)-4-((1-benzyl-3-methylpyrrolidin-3-yl)amino)-3-chloro-N-(thiazol-4-yl)benzenesulfonamide Formate

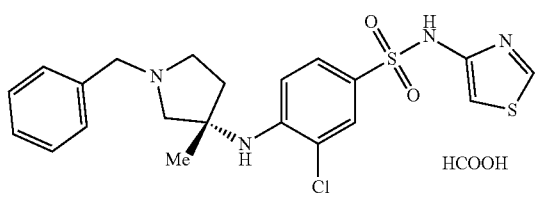 [SMILES: C[C@]1(Nc2ccc(S(=O)(=O)Nc3cscn3)cc2Cl)CCN(Cc2ccccc2)C1 ; "HCOOH"]

Step 1. Preparation of (S)—N-(1-benzyl-3-methylpyrrolidin-3-yl)acetamide (2R,3R)-2,3-bis((4-methoxybenzoyl)oxy)succinate

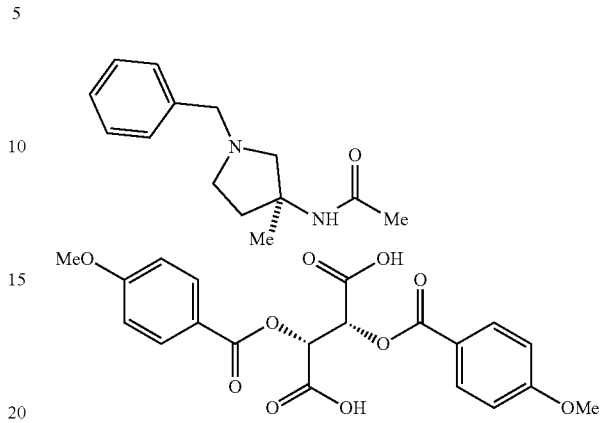

To a solution of (−)—O,O'-di-p-toluoyl-L-tartaric acid (11.5 g, 27.7 mmol) in ethanol (200 ml) was added N-(1-benzyl-3-methylpyrrolidin-3-yl)acetamide (9.0 g, 38.7 mmol). The mixture was stirred at 10° C. for 15 minutes, and then heated to 70° C. for 10 minutes. The reaction mixture was allowed to warm to ambient temperature and stirred for 48 h. The resultant solid was filtered off, the filter cake washed with ethanol (100 ml) and dried under reduced pressure to provide a colorless solid. The solid was dissolved in ethanol (100 mL), heated to reflux for 30 minutes, and allowed to cool to ambient temperature. The obtained precipitate was filtered off and to give a colorless solid. The recrystallization step was repeated twice to provide the title compound as a colorless solid (20.9 g, 33% yield): $^1$H NMR (400 MHz, DMSO-$d_6$) δ 8.07 (s, 1H), 7.94 (d, J=8.8 Hz, 4H), 7.44-7.38 (m, 2H), 7.36-7.25 (m, 3H), 7.06 (d, J=8.8 Hz, 4H), 5.69 (s, 2H), 4.12-4.02 (m, 2H), 3.83 (s, 6H), 3.24 (d, J=11.4 Hz, 1H), 3.10 (d, J=6.4 Hz, 2H), 2.97 (d, J=11.4 Hz, 1H), 2.14 (td, J=12.8, 6.4 Hz, 1H), 1.88-1.77 (m, 1H), 1.74 (s, 3H), 1.29 (s, 3H), two COOH not observed.

Step 2. Preparation of (S)—N-(1-benzyl-3-methylpyrrolidin-3-yl)acetamide

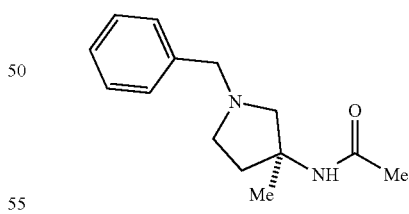

To a mixture of (S)—N-(1-benzyl-3-methylpyrrolidin-3-yl)acetamide (2R,3R)-2,3-bis((4-methoxybenzoyl)oxy)succinate (6.0 g, 9.2 mmol) in water (40 mL) was added and potassium carbonate (3.8 g, 27.6 mmol) and the mixture was stirred at 10° C. for 2 h. The mixture was extracted with ethyl acetate (3×50 mL). The combined organic phase was washed with brine (3×50 mL), dried over anhydrous sodium sulfate, and filtered. Concentration of the filtrate under reduced pressure afforded (S)—N-(1-benzyl-3-methylpyrrolidin-3-yl)acetamide as a yellow solid (2.0 g, 93% yield, 100% ee). Enantiopurity was determined by supercritical fluid chromatography, using 5-40% of isopropanol (containing 0.05% of diethylamine) in supercritical carbon dioxide as eluent at a flowrate of 3 mL/min and a Chiralpak IC-3 column (100×4.6 mm, 3 μm). Data for (S)—N-(1-benzyl-3-methylpyrrolidin-3-yl)acetamide: $^1$H NMR (400 MHz, DMSO-d$_6$) δ 7.77 (s, 1H), 7.33-7.26 (m, 4H), 7.25-7.19 (m, 1H), 3.59-3.46 (m, 2H), 2.65-2.60 (m, 1H), 2.59-2.51 (m, 2H), 2.49-2.43 (m, 1H), 2.07-1.95 (m, 1H), 1.75 (s, 3H), 1.74-1.66 (m, 1H), 1.33 (s, 3H).

Step 3. Preparation of (S)-1-benzyl-3-methylpyrrolidin-3-amine

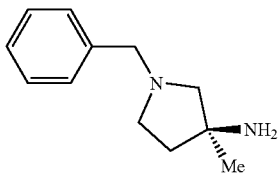 [SMILES: C[C@]1(N)CCN(Cc2ccccc2)C1]

To a (S)—N-(1-benzyl-3-methylpyrrolidin-3-yl)acetamide (1.5 g, 6.4 mmol) was added 6 M hydrochloric acid (5 mL) and the mixture was heated to 100° C. for 36 h. After cooling to ambient temperature, the mixture was adjusted to pH 11-12 with sodium hydroxide, and then extracted with ethyl acetate (3×10 mL). The combined organic phase was washed with brine (3×10 mL), dried over anhydrous sodium sulfate, and filtered. Concentration of the filtrate in vacuo afforded the title compound as a dark oil (1.0 g, 83% yield): $^1$H NMR (400 MHz, CDCl$_3$) δ 7.30-7.16 (m, 5H), 3.60-3.50 (m, 2H), 2.80 (dt, J=8.8, 5.2 Hz, 1H), 2.44 (d, J=9.0 Hz, 1H), 2.37 (dt, J=9.0, 6.8 Hz, 1H), 2.26 (d, J=9.0 Hz, 1H), 1.78 (ddd, J=13.2, 8.4, 5.0 Hz, 1H), 1.69-1.60 (m, 1H), 1.20 (s, 3H), NH not observed.

Step 4. Preparation of tert-butyl (S)-((4-((1-benzyl-3-methylpyrrolidin-3-yl)amino)-3-chlorophenyl)sulfonyl)(thiazol-4-yl)carbamate

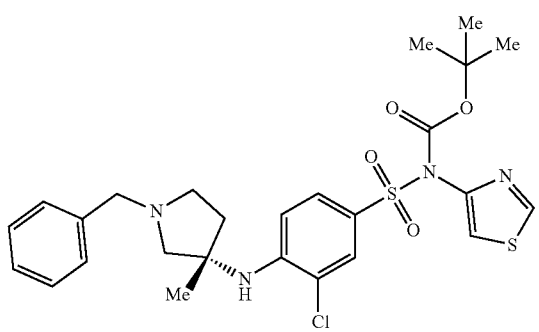 [SMILES: CC(C)(C)OC(=O)N(c1cscn1)S(=O)(=O)c1ccc(N[C@@]2(C)CCN(Cc3ccccc3)C2)c(Cl)c1]

Following the procedure as described in EXAMPLE 225, Step 2 and making non-critical variations to replace (R)-1-benzyl-3-methylpyrrolidin-3-amine with (S)-1-benzyl-3-methylpyrrolidin-3-amine, the title compound was obtained as a yellow solid (0.015 g, 5% yield): MS (ES+) m/z 563.1 (M+1), 565.1 (M+1).

Step 5. Preparation of (S)-4-((1-benzyl-3-methylpyrrolidin-3-yl)amino)-3-chloro-N-(thiazol-4-yl)benzenesulfonamide Formate

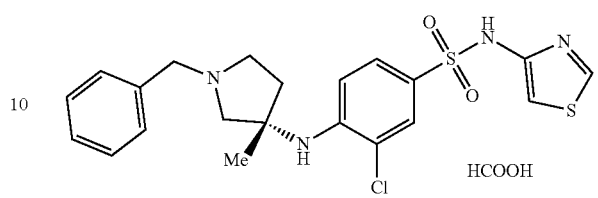

Following the procedure as described in EXAMPLE 225, Step 3 and making non-critical variations to replace tert-butyl (R)-((4-((1-benzyl-3-methylpyrrolidin-3-yl)amino)-3-chlorophenyl)sulfonyl)(thiazol-4-yl)carbamate with tert-butyl (S)-((4-((1-benzyl-3-methylpyrrolidin-3-yl)amino)-3-chlorophenyl)sulfonyl)(thiazol-4-yl)carbamate, the title compound was obtained as a colorless solid (0.027 g, 54% yield): $^1$H NMR (400 MHz, DMSO-d$_6$) δ 8.87 (d, J=2.1 Hz, 1H), 8.25 (s, 1H), 7.65 (d, J=2.4 Hz, 1H), 7.54 (dd, J=2.0, 8.8 Hz, 1H), 7.31 (d, J=4.4 Hz, 4H), 7.27-7.20 (m, 1H), 7.08 (d, J=8.8 Hz, 1H), 6.97 (s, 1H), 5.48 (s, 1H), 3.68-3.51 (m, 1H), 2.78 (d, J=9.8 Hz, 1H), 2.73-2.68 (m, 1H), 2.59-2.53 (m, 2H), 2.18-2.09 (m, 1H), 1.90-1.82 (m, 1H), 1.44 (s, 3H), NH and COOH not observed; MS (ES+) m/z 463.2 (M+1), 465.2 (M+1).

Example 227

Synthesis of (R)-3-chloro-2-fluoro-4-((1-(1-phenylethyl)piperidin-4-yl)oxy)-N-(thiazol-4-yl)benzenesulfonamide Formate

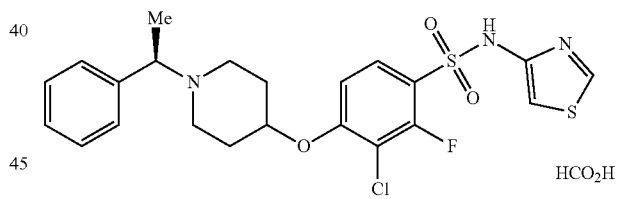

Step 1. Preparation of tert-butyl ((3-chloro-2,4-difluorophenyl)sulfonyl)(thiazol-4-yl)carbamate

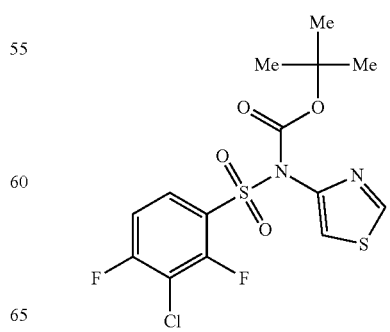

To a solution of tert-butyl N-thiazol-4-ylcarbamate (110 g, 549 mmol) in anhydrous tetrahydrofuran (1000 mL) was added lithium bis(trimethylsilyl)amide (1 M in tetrahydrofuran, 659 mL, 659 mmol) at −78° C. The mixture was warmed to 5° C. before a cooled (−78° C.) solution of 3-chloro-2,4-difluoro-benzenesulfonyl chloride (163 g, 659 mmol) in tetrahydrofuran (300 mL) was added dropwise to it. The reaction mixture was allowed to warm to ambient temperature and stirred for 12 h. After dilution with saturated aqueous ammonium chloride (200 mL), the mixture was extracted with ethyl acetate (3×1000 mL). The combined organic layers were washed with brine (3×1000 mL), dried over anhydrous sodium sulfate, and filtered. Concentration of the filtrate in vacuo and trituration of the residue with methanol (300 mL) afforded the title compound as a colorless solid (75 g, 33% yield) $^1$H NMR (400 MHz, CDCl$_3$) δ 9.14 (s, 1H), 8.26-8.09 (m, 1H), 8.03 (s, 1H), 7.66 (t, J=8.6 Hz, 1H), 1.27 (s, 9H); MS (ES+) m/z 432.8 (M+23), 434.8 (M+23).

Step 2. Preparation of 3-chloro-2,4-difluoro-N-(thiazol-4-yl)benzenesulfonamide

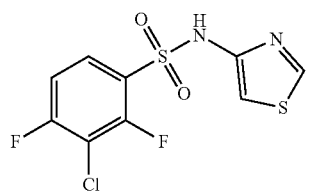 [SMILES: O=S(=O)(Nc1cscn1)c1ccc(F)c(Cl)c1F]

To a solution of tert-butyl ((3-chloro-2,4-difluorophenyl)sulfonyl)(thiazol-4-yl)carbamate (2.50 g, 6.09 mmol) in dichloromethane (15 mL) was added trifluoroacetic acid (7 mL) and the reaction mixture was stirred at ambient temperature for 2 h. Concentration in vacuo and trituration of the residue with diethyl ether (25 mL) afforded the title compound as a pale yellow solid (1.74 g, 92% yield) which was used without further purification: MS (ES+) m/z 311.1 (M+1), 313.1 (M+1).

Step 3. Preparation of (R)-3-chloro-2-fluoro-4-((1-(1-phenylethyl)piperidin-4-yl)oxy)-N-(thiazol-4-yl)benzenesulfonamide Formate

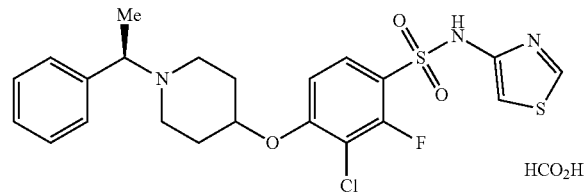 [SMILES: C[C@H](c1ccccc1)N1CCC(Oc2ccc(S(=O)(=O)Nc3cscn3)c(F)c2Cl)CC1 ; "HCO2H"]

To a solution of 3-chloro-2,4-difluoro-N-(thiazol-4-yl)benzenesulfonamide (0.241 g, 0.774 mmol) and (R)-1-(1-phenylethyl)piperidin-4-ol (0.159 g, 0.774 mmol) in anhydrous N,N-dimethylformamide (3 mL) was added a dispersion of 60% of sodium hydride in mineral oil (0.092 g, 2.32 mmol) and the reaction mixture was stirred at ambient temperature for 16 h. The reaction mixture was then added slowly to rapidly stirred saturated aqueous ammonium chloride solution (100 mL). The resulting slurry was filtered and the obtained solid purified by reverse-phase HPLC, using a gradient of acetonitrile in water (containing 0.5% of formic acid) to yield the title compound as a colorless solid (0.010 g, 2.6% yield) $^1$H NMR (300 MHz, DMSO-d$_6$), 8.75 (d, J=2.1 Hz, 1H), 8.20 (s, 1H), 7.64 (t, J=8.6 Hz, 1H), 7.32-7.30 (m, 4H), 7.25-7.21 (m, 1H), 7.11-7.08 (m, 1H), 6.62 (t, J=0.3 Hz, 1H), 4.60-4.54 (m, 1H), 3.53-3.46 (m, 1H), 2.73-2.55 (m, 2H), 2.30-2.19 (m, 2H), 1.94-1.86 (m, 2H), 1.69-1.59 (m, 2H), 1.30 (d, J=6.8 Hz, 3H), NH and COOH not observed; MS (ES+) m/z 496.2 (M+1), 498.2 (M+1).

Example 228

Synthesis of rac-4-((1-benzyl-3-methylpyrrolidin-3-yl)oxy)-2,6-difluoro-3-methyl-N-(thiazol-2-yl)benzenesulfonamide 2,2,2-trifluoroacetate

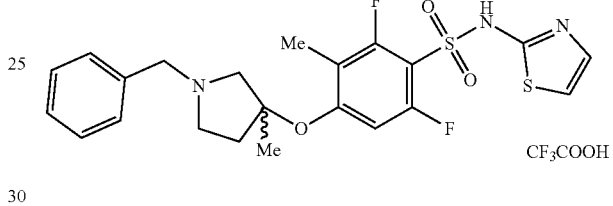

Step 1. Preparation of rac-tert-butyl 3-(2-chloro-4-(N-(2,4-dimethoxybenzyl)-N-(thiazol-2-yl)sulfamoyl)-3,5-difluorophenoxy)-3-methylpyrrolidine-1-carboxylate

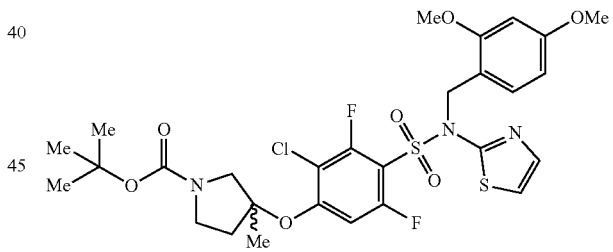

To a mixture of tert-butyl 3-hydroxy-3-methylpyrrolidine-1-carboxylate (prepared according to WO 2015035278, 1.19 g, 5.91 mmol) and 3-chloro-N-(2,4-dimethoxybenzyl)-2,4,6-trifluoro-N-(thiazol-2-yl)benzenesulfonamide (2.83 g, 5.91 mmol) in anhydrous N,N-dimethylformamide (10 mL) was added sodium hydride (60% dispersion in mineral oil, 0.496 g, 12.41 mmol) at 0° C. The mixture was stirred at ambient temperature for 48 h, cooled to 0° C., and diluted with saturated ammonium solution (40 mL). The mixture was extracted with ethyl acetate (3×60 mL). The combined organic layers were washed with water (80 mL), brine (80 mL), dried over anhydrous magnesium sulfate, and filtered. Concentration of the filtrate in vacuo and purification of the residue by column chromatography, eluting with a gradient of 0% to 50% of acetone in heptane, afforded the title compound as a colorless solid (0.22 g, 6% yield): MS (ES−) m/z 508.2 (M−151), 510.2 (M−151).

Step 2. Preparation of tert-butyl 3-(4-(N-(2,4-dimethoxybenzyl)-N-(thiazol-2-yl)sulfamoyl)-3,5-difluoro-2-methylphenoxy)-3-methylpyrrolidine-1-carboxylate

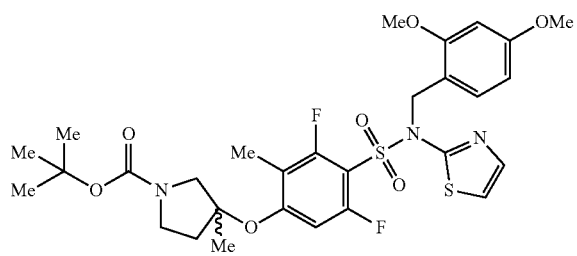 [SMILES: COc1ccc(CN(c2nccs2)S(=O)(=O)c2c(F)cc(OC3(C)CCN(C(=O)OC(C)(C)C)C3)c(C)c2F)c(OC)c1]

To a mixture of tert-butyl 3-(2-chloro-4-(N-(2,4-dimethoxybenzyl)-N-(thiazol-2-yl)sulfamoyl)-3,5-difluorophenoxy)-3-methylpyrrolidine-1-carboxylate (0.22 g, 0.33 mmol) and methylboronic acid (0.11 g, 1.83 mmol) in anhydrous 1,4-dioxane (10 mL) was added potassium phosphate tribasic (0.21 g, 0.99 mmol) and the mixture was degassed by sparging with argon for 15 minutes. To it was then added tricyclohexylphosphine tetrafluoroborate (0.049 g, 0.132 mmol) and palladium(II) acetate (0.015 g, 0.07 mmol) and the reaction mixture was heated in a microwave reactor to 101° C. for 12 minutes. The reaction mixture was then removed from the microwave reactor, and then heated to 100° C. for 4 h. The reaction mixture was allowed to cool to ambient temperature, and filtered through a pad of diatomaceous earth. The filter pad was washed with ethyl acetate (2×15 mL) and the combined filtrate was concentrated in vacuo. The residue was diluted with saturated aqueous ammonium chloride solution (15 mL), and extracted with ethyl acetate (3×20 mL). The combined organic layers were washed with brine (25 mL), dried over anhydrous magnesium sulfate, and filtered. Concentration of the residue in vacuo and purification of the residue by column chromatography, eluting with a gradient of 0 to 50% of ethyl acetone in heptane, afforded the title compound as a colorless solid (0.065 g, 31% yield): MS (ES+) m/z 640.3 (M+1).

Step 3. Preparation of rac-2,6-difluoro-3-methyl-4-((3-methylpyrrolidin-3-yl)oxy)-N-(thiazol-2-yl)benzenesulfonamide 2,2,2-trifluoroacetate

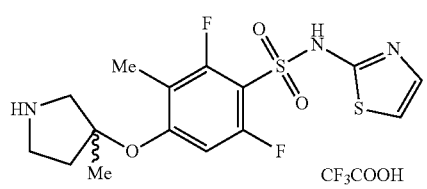

Following the procedure as described for EXAMPLE 1, Step 4 and making non-critical variations as required to replace tert-butyl 4-(2-chloro-4-(N-(2,4-dimethoxybenzyl)-N-(1,2,4-thiadiazol-5-yl)sulfamoyl)phenoxy)-3,3-dimethylpiperidine-1-carboxylate with tert-butyl 3-(4-(N-(2,4-dimethoxybenzyl)-N-(thiazol-2-yl)sulfamoyl)-3,5-difluoro-2-methylphenoxy)-3-methylpyrrolidine-1-carboxylate, the title compound was obtained as a colorless solid (0.051 g, quantitative yield): MS (ES+) m/z 390.1 (M+1).

Step 4. Preparation of rac 4-((1-benzyl-3-methylpyrrolidin-3-yl)oxy)-2,6-difluoro-3-methyl-N-(thiazol-2-yl)benzenesulfonamide 2,2,2-trifluoroacetate

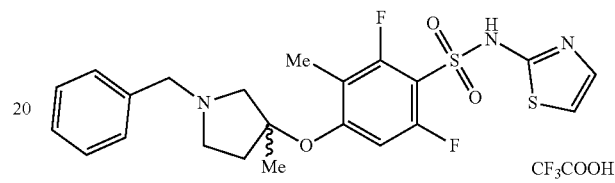

Following the procedure as described for EXAMPLE 36, Step 3 and making non-critical variations as required to replace (S)-3-chloro-4-(ethyl(pyrrolidin-3-yl)amino)-N-(1,2,4-thiadiazol-5-yl)benzenesulfonamide 2,2,2-trifluoroacetate with 2,6-difluoro-3-methyl-4-((3-methylpyrrolidin-3-yl)oxy)-N-(thiazol-2-yl)benzenesulfonamide 2,2,2-trifluoroacetate, and purification by the title compound was preparative reverse-phase HPLC, eluting with a gradient of acetonitrile in water containing 0.1% of trifluoroacetic acid, the title compound was obtained as a colorless solid (0.026 g, 43% yield): $^1$H NMR (300 MHz, DMSO-$d_6$) δ 12.96 (s, 1H), 10.51 (s, 1H), 7.60-7.39 (m, 5H), 7.33 (d, J=4.6 Hz, 1H), 6.98-6.86 (m, 2H), 4.40 (s, 2H), 4.00-3.20 (m, 4H), 2.68-2.09 (m, 2H), 2.03-1.94 (m, 3H), 1.61 (s, 3H); MS (ES+) m/z 480.3 (M+1).

Example 229

Synthesis of (S)-4-((1-benzylpyrrolidin-3-yl)(methyl)amino)-2-fluoro-N-(isoxazol-3-yl)-5-methylbenzenesulfonamide 2,2,2-trifluoroacetate

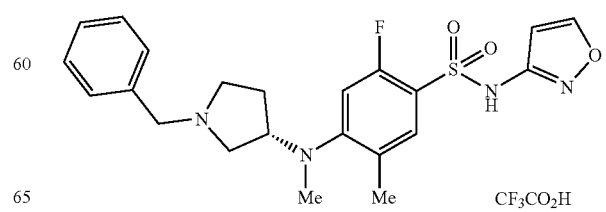

Step 1. Preparation of tert-butyl ((5-chloro-2,4-difluorophenyl)sulfonyl)(isoxazol-3-yl)carbamate

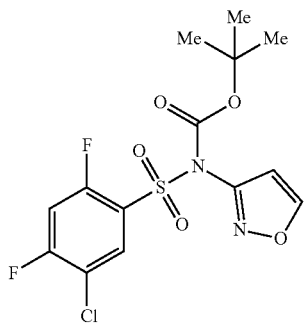 [SMILES: CC(C)(C)OC(=O)N(c1ccon1)S(=O)(=O)c1cc(Cl)c(F)cc1F]

To a solution of tert-butyl isoxazol-3-ylcarbamate (10.00 g, 54.30 mmol) in anhydrous tetrahydrofuran (200 mL) was added a 1 M solution of lithium bis(trimethylsilyl)amide in tetrahydrofuran (81.5 mL, 81.50 mmol) at −78° C. The reaction was stirred for 30 minutes at −78° C. and then a solution of 5-chloro-2,4-difluorobenzenesulfonyl chloride (13.40 g, 54.30 mmol) in anhydrous tetrahydrofuran (50 mL) was added to it dropwise. The reaction solution was allowed to warm to ambient temperature and stirred for 16 h. The reaction mixture was diluted with ethyl acetate (200 mL), and then washed with saturated ammonium chloride (100 mL) and brine (100 mL). The organic layer was dried over anhydrous sodium sulfate and filtered. The filtrate was concentrated in vacuo and the resulting residue was triturated with diethyl ether (75 mL) to afford the title compound as a pale yellow solid (6.21 g, 29% yield): $^1$H NMR (300 MHz, DMSO-$d_6$) δ 9.15 (d, J=2.2 Hz, 1H), 8.25 (dd, J=7.5, 7.5 Hz, 1H), 8.05 (dd, J=10.0, 9.5 Hz, 1H), 6.92 (s, 1H), 1.31 (s, 9H); MS (ES+) m/z 395.1 (M+1), 396.1 (M+1).

Step 2. Preparation of tert-butyl (S)-((4-((1-benzylpyrrolidin-3-yl)amino)-5-chloro-2-fluorophenyl)sulfonyl)(isoxazol-3-yl)carbamate

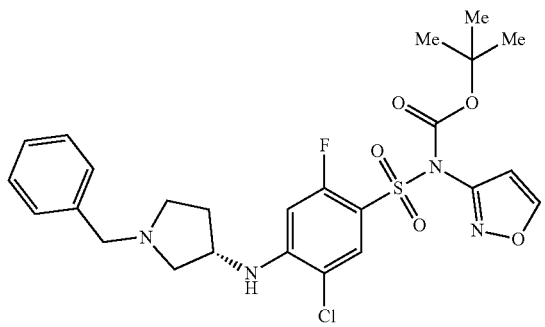 [SMILES: CC(C)(C)OC(=O)N(c1ccon1)S(=O)(=O)c1cc(Cl)c(N[C@H]2CCN(Cc3ccccc3)C2)cc1F]

To a solution of tert-butyl ((5-chloro-2,4-difluorophenyl)sulfonyl)(isoxazol-3-yl)carbamate (6.21 g, 15.80 mmol) in anhydrous N,N-dimethylformamide (200 mL) was added N,N-diisopropylethylamine (8.20 mL, 47.30 mmol) followed by (S)-1-benzylpyrrolidin-3-amine (2.78 g, 15.80 mmol) at 0° C. over a period of 30 minutes. The reaction mixture was stirred at ambient temperature for 16 h and then diluted with ethyl acetate (200 mL) and washed with saturated ammonium chloride (3×100 mL) and brine (200 mL). The organic layer was dried over anhydrous sodium sulfate and filtered. The filtrate was concentrated in vacuo and the residue purified by column chromatography, eluting with a gradient of 20 to 60% of ethyl acetate in heptane, to afford the title compound as brown gum (4.82 g, 56% yield): MS (ES+) m/z 551.2 (M+1), 553.2 (M+1).

Step 3. Preparation of tert-butyl (S)-((4-((1-benzylpyrrolidin-3-yl)amino)-2-fluoro-5-methylphenyl)sulfonyl)(isoxazol-3-yl)carbamate

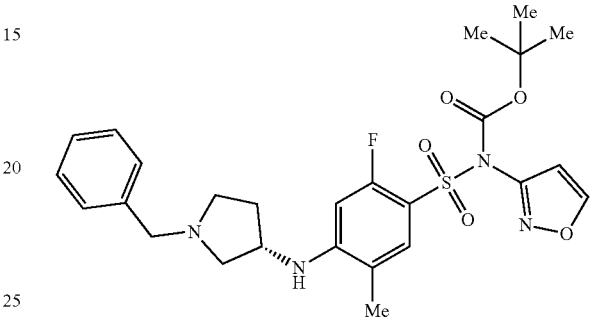

To a mixture of tert-butyl (S)-3-((4-(N-(tert-butoxycarbonyl)-N-(thiazol-4-yl)sulfamoyl)-2-chloro-3,5-difluorophenyl)amino)pyrrolidine-1-carboxylate (4.82 g, 8.76 mmol), methyl boronic acid (4.13 g, 70.10 mmol), potassium phosphate tribasic (7.43 g, 35.10 mmol), tricyclohexylphosphine tetrafluoroborate (0.64 g, 1.75 mmol) and palladium acetate (0.19 g, 0.08 mmol) was added 1,4-dioxane (150 mL). The resulting mixture degassed by sparging with nitrogen for 15 minutes and then heated to reflux for 8 h. After cooling to ambient temperature, the reaction mixture was filtered through a pad of Celite. The filtrate was diluted with ethyl acetate (150 mL), washed with saturated ammonium chloride (100 mL) and brine (100 mL), dried over anhydrous sodium sulfate, and filtered. Concentration of the filtrate in vacuo and purification of the residue by column chromatography, eluting with a gradient of 20 to 60% of ethyl acetate in heptane, afforded the title compound as a brown gum (3.50 g, 75% yield): MS (ES+) m/z 531.2 (M+1).

Step 4. Preparation of (S)-4-((1-benzylpyrrolidin-3-yl)(methyl)amino)-2-fluoro-N-(isoxazol-3-yl)-5-methylbenzenesulfonamide 2,2,2-trifluoroacetate

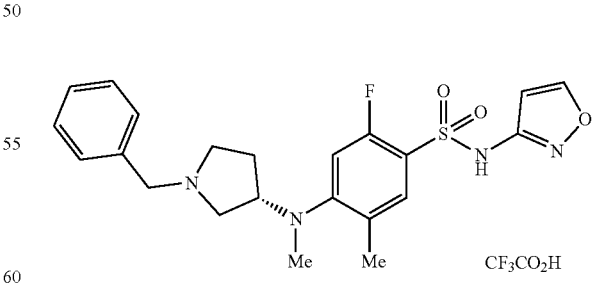

Following the procedure as described in EXAMPLE 103, Step 4 and making non-critical variations to replace (S)-4-((1-benzylpyrrolidin-3-yl)amino)-2,6-difluoro-3-methyl-N-(thiazol-4-yl)benzenesulfonamide with tert-butyl (S)-((4-((1-benzylpyrrolidin-3-yl)amino)-2-fluoro-5-methylphenyl)sulfonyl)(isoxazol-3-yl)carbamate, the title compound was obtained as a colorless solid (0.039 g, 9% yield): $^1$H NMR (300 MHz, DMSO-$d_6$) δ 11.80 (br s, 1H), 10.36-10.16 (m, 1H), 8.73 (d, J=1.8 Hz, 1H), 7.66 (d, J=8.5 Hz, 1H), 7.50-7.45 (m, 5H), 7.07 (d, J=12.6 Hz, 1H), 6.38 (d, J=1.8 Hz, 1H), 4.41-4.35 (m, 2H), 4.24-4.04 (m, 1H), 3.42-3.20 (m, 4H), 2.69-2.62 (m, 3H), 2.35-2.15 (m, 3H), 2.15-2.03 (m, 2H); MS (ES+) m/z 445.4 (M+1).

Example 230

Synthesis of (S)-4-((1-benzylpyrrolidin-3-yl)(methyl)amino)-5-bromo-2-fluoro-N-(thiazol-4-yl)benzenesulfonamide 2,2,2-trifluoroacetate

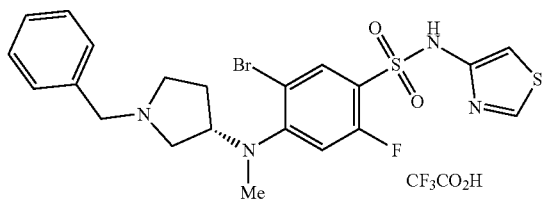 [SMILES: CN(c1cc(F)c(S(=O)(=O)Nc2cscn2)cc1Br)[C@H]1CCN(Cc2ccccc2)C1 ; "CF3CO2H"]

Step 1. Preparation of tert-butyl ((5-bromo-2,4-difluorophenyl)sulfonyl)(thiazol-4-yl)carbamate

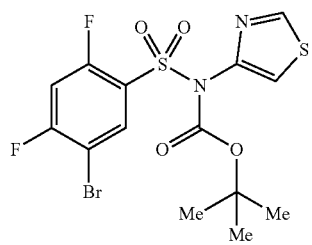 [SMILES: CC(C)(C)OC(=O)N(c1cscn1)S(=O)(=O)c1cc(Br)c(F)cc1F]

Following the procedure as described for EXAMPLE 102, Step 2 and making non-critical variations as required to replace 3-chloro-2,4,6-trifluorobenzenesulfonyl chloride with 5-bromo-2,4-difluorobenzenesulfonyl chloride and purification by trituration with methanol (50 mL), the title compound was obtained as a colorless solid (7.75 g, 75% yield): $^1$H NMR (300 MHz, CDCl$_3$) δ 8.82 (d, J=2.3 Hz, 1H), 8.39 (t, J=7.3 Hz, 1H), 7.55 (dd, J=2.2, 0.6 Hz, 1H), 7.09 (dd, J=9.3, 7.9 Hz, 1H), 1.39 (s, 9H).

Step 2. Preparation of 5-bromo-2,4-difluoro-N-(4-methoxybenzyl)-N-(thiazol-4-yl)benzenesulfonamide

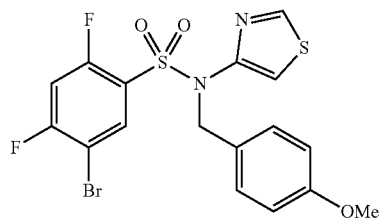

To a solution of tert-butyl ((5-bromo-2,4-difluorophenyl)sulfonyl)(thiazol-4-yl)carbamate (7.75 g, 17.02 mmol) in dichloromethane (10 mL) was added trifluoroacetic acid (10 mL). The reaction mixture was stirred at ambient temperature for 18 h and then concentrated in vacuo. The residue was dissolved in anyhydrous N,N-dimethylformamide (50 mL). To this mixture was then added sodium bicarbonate (7.15 g, 85.11 mmol) and 1-(chloromethyl)-4-methoxybenzene (4.62 mL, 34.04 mmol). The reaction mixture was heated to 45° C. for 18 h and then diluted with ethyl acetate (180 mL). The organic phase was washed with water (150 mL), saturated ammonium chloride (2×50 mL), brine (100 mL), dried over anhydrous sodium sulfate, and filtered. Concentration of the filtrate in vacuo and trituration of the residue with methanol (60 mL) afforded the title compound as a colorless solid (6.57 g, 81% yield): $^1$H NMR (300 MHz, CDCl$_3$) δ 8.59 (d, J=2.3 Hz, 1H), 7.96 (t, J=7.2 Hz, 1H), 7.25-7.19 (m, 3H), 7.01 (dd, J=9.3, 8.0 Hz, 1H), 6.81-6.77 (m, 2H), 5.02 (s, 2H), 3.78 (s, 3H); MS (ES+) m/z 475.2 (M+1), 477.2 (M+1).

Step 3. Preparation of tert-butyl (S)-3-((2-bromo-5-fluoro-4-(N-(4-methoxybenzyl)-N-(thiazol-4-yl)sulfamoyl)phenyl)amino)pyrrolidine-1-carboxylate

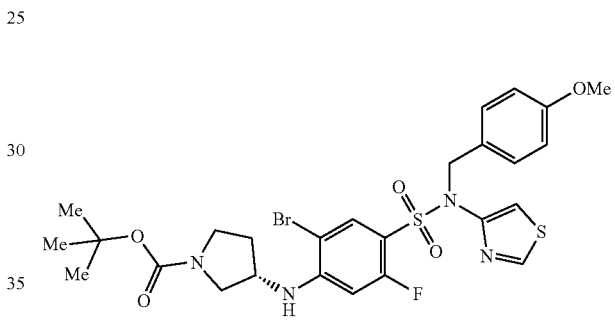

To a solution of 5-bromo-2,4-difluoro-N-(4-methoxybenzyl)-N-(thiazol-4-yl)benzenesulfonamide (10.00 g, 21.01 mmol) in anhydrous N,N-dimethylformamide (200 mL) was added potassium carbonate (7.26 g, 52.50 mmol) and (S)-1-benzylpyrrolidin-3-amine (3.91 g, 21.00 mmol). The solution was stirred at 40° C. for 16 h, and then diluted with water (800 mL). The resulting precipitate was collected by filtration, and washed with water (500 mL), and dried under vacuum to provide the title compound as a brown gum (9.80 g, 73% yield): MS (ES+) m/z 681.1 (M+1), 683.1 (M+1).

Step 4. Preparation of tert-butyl (S)-3-((2-bromo-5-fluoro-4-(N-(4-methoxybenzyl)-N-(thiazol-4-yl)sulfamoyl)phenyl)(methyl)amino)pyrrolidine-1-carboxylate

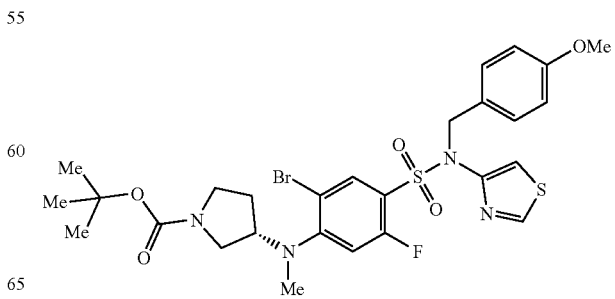

To a solution of tert-butyl (S)-3-((2-bromo-5-fluoro-4-(N-(4-methoxybenzyl)-N-(thiazol-4-yl)sulfamoyl)phenyl)amino)pyrrolidine-1-carboxylate (0.50 g, 0.78 mmol) in N,N-dimethylformamide (2 mL) was added iodomethane (0.49 mL, 7.80 mmol), followed by sodium hydride (0.094 g, 2.34 mmol). The reaction mixture was stirred at ambient temperature for 16 h, and then quenched by addition of water (5 mL). The precipitated solid was filtered off, and then suspended in ethyl acetate (50 mL). The resulting mixture was dried over anhydrous magnesium sulfate and filtered. Concentration of the filtrate in vacuo afforded the title compound as a brown solid (0.51 g, quantitative yield), which was used without further purification: MS (ES+) m/z 655.1 (M+1), 657.1 (M+1).

Step 5. Preparation of (S)-4-((1-benzylpyrrolidin-3-yl)(methyl)amino)-5-bromo-2-fluoro-N-(thiazol-4-yl)benzenesulfonamide 2,2,2-trifluoroacetate

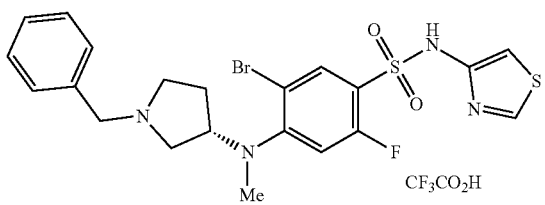 [SMILES: CN(c1cc(F)c(S(=O)(=O)Nc2cscn2)cc1Br)[C@H]1CCN(Cc2ccccc2)C1 ; "CF3CO2H"]

To a solution of tert-butyl (S)-3-((2-bromo-5-fluoro-4-(N-(4-methoxybenzyl)-N-(thiazol-4-yl)sulfamoyl)phenyl)(methyl)amino)pyrrolidine-1-carboxylate (0.51 g, 0.78 mmol) in dichloromethane (1 mL) was added trifluoroacetic acid (2.1 mL) and the resulting solution was heated to reflux for 1.5 h. The reaction mixture was cooled to ambient temperature and then concentrated in vacuo to provide a residue. To the residue was added N,N-dimethylformamide (2 mL), benzaldehyde (0.16 g, 1.56 mmol) and sodium triacetoxyborohydride (0.50 g, 2.34 mmol). The reaction mixture was stirred at ambient temperature for 16 h. The reaction mixture was then quenched by addition of 5% aqueous lithium chloride (10 mL) and extracted with ethyl acetate (3×25 mL). The combined organic extracts were dried over anhydrous magnesium sulfate and filtered. Concentration of the filtrate in vacuo and purification of the residue by reverse-phase HPLC, eluting with gradient of acetonitrile in water containing 0.1% of trifluoroacetic acid, provided the title compound as a colorless solid (0.050 g, 10% yield): $^1$H NMR (300 MHz, DMSO-$d_6$) δ 11.41 (s, 1H), 9.97 (s, 1H), 8.92 (d, J=2.2 Hz, 1H), 7.93 (d, J=7.7 Hz, 1H), 7.48-7.46 (m, 5H), 7.30 (s, 1H), 7.10 (d, J=2.1 Hz, 1H), 4.45-4.35 (m, 3H), 3.55-3.37 (m, 4H), 2.85-2.60 (m, 3H), 2.21-2.12 (m, 2H); MS (ES+) m/z: 525.0 (M+1), 527.0 (M+1).

Example 231

Synthesis of 4-(((3S,5S)-1-benzyl-5-methylpyrrolidin-3-yl)(methyl)amino)-5-chloro-2-fluoro-N-(thiazol-4-yl)benzenesulfonamide Formate

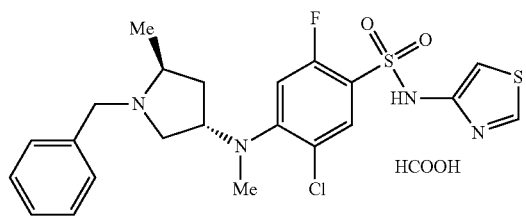 [SMILES: C[C@H]1C[C@H](N(C)c2cc(F)c(S(=O)(=O)Nc3cscn3)cc2Cl)CN1Cc1ccccc1 ; "HCOOH"]

Step 1. Preparation of tert-butyl (2S,4S)-4-((4-(N-(tert-butoxycarbonyl)-N-(thiazol-4-yl)sulfamoyl)-2-chloro-5-fluorophenyl)amino)-2-methylpyrrolidine-1-carboxylate

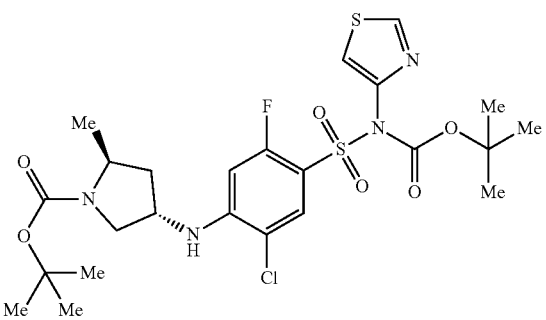 [SMILES: C[C@H]1C[C@H](Nc2cc(F)c(S(=O)(=O)N(C(=O)OC(C)(C)C)c3cscn3)cc2Cl)CN1C(=O)OC(C)(C)C]

To a solution of tert-butyl ((5-chloro-2,4-difluorophenyl)sulfonyl)(thiazol-4-yl)carbamate (1.71 g, 4.16 mmol) in anhydrous dimethyl sulfoxide (8 mL) was added tert-butyl (2S,4S)-4-amino-2-methylpyrrolidine-1-carboxylate (1.00 g, 4.99 mmol) followed by triethylamine (0.70 mL, 4.99 mmol). The resulting solution was stirred at ambient temperature for 16 h. The crude reaction mixture was purified by column chromatography, eluting with 0 to 100% of ethyl acetate in heptane, to provide the title compound as a colorless solid (1.62 g, 55% yield).

Step 2. Preparation of tert-butyl (2S,4S)-4-((4-(N-(tert-butoxycarbonyl)-N-(thiazol-4-yl)sulfamoyl)-2-chloro-5-fluorophenyl)(methyl)amino)-2-methylpyrrolidine-1-carboxylate

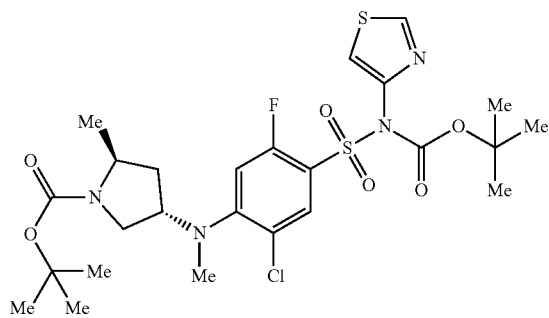 [SMILES: C[C@H]1C[C@H](N(C)c2cc(F)c(S(=O)(=O)N(C(=O)OC(C)(C)C)c3cscn3)cc2Cl)CN1C(=O)OC(C)(C)C]

Following the procedure as described in EXAMPLE 101, Step 3 and making non-critical variations to replace tert-butyl (S)-3-((4-(N-(tert-butoxycarbonyl)-N-(thiazol-4-yl)sulfamoyl)-5-fluoro-2-methylphenyl)amino)pyrrolidine-1-carboxylate with tert-butyl (2S,4S)-4-((4-(N-(tert-butoxycarbonyl)-N-(thiazol-4-yl)sulfamoyl)-2-chloro-5-fluorophenyl)amino)-2-methylpyrrolidine-1-carboxylate, the title compound was obtained as a brown solid (1.08 g, 65% yield): MS (ES+) m/z 605.3 (M+1), 607.4 (M+1).

Step 3. Preparation of 4-(((3S,5S)-1-benzyl-5-methylpyrrolidin-3-yl)(methyl)amino)-5-chloro-2-fluoro-N-(thiazol-4-yl)benzenesulfonamide Formate

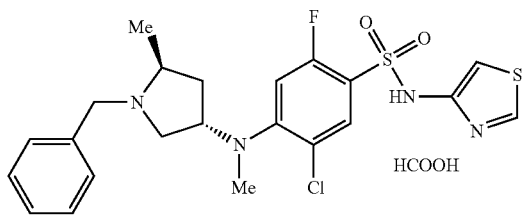 [SMILES: C[C@H]1C[C@H](N(C)c2cc(F)c(S(=O)(=O)Nc3cscn3)cc2Cl)CN1Cc1ccccc1 ; "HCOOH"]

Following the procedure as described in EXAMPLE 101, Step 4 and making non-critical variations to replace tert-butyl (S)-3-((4-(N-(tert-butoxycarbonyl)-N-(thiazol-4-yl)sulfamoyl)-5-fluoro-2-methylphenyl)(methyl)amino)pyrrolidine-1-carboxylate with tert-butyl (2S,4S)-4-((4-(N-(tert-butoxycarbonyl)-N-(thiazol-4-yl)sulfamoyl)-2-chloro-5-fluorophenyl)(methyl)amino)-2-methylpyrrolidine-1-carboxylate, the title compound was obtained as a colorless solid (0.46 g, 31% yield): $^1$H NMR (300 MHz, DMSO-$d_6$) δ 8.90 (d, J=2.1 Hz, 1H), 8.14 (s, 1H), 7.72 (d, J=7.5 Hz, 1H), 7.44-7.39 (m, 5H), 7.17 (d, J=12.0 Hz, 1H), 7.06 (d, J=2.1 Hz, 1H), 4.36 (d, J=12.5 Hz, 1H), 4.25-4.20 (m, 1H), 3.97-3.91 (m, 1H), 3.43-3.27 (m, 2H), 3.00-2.94 (m, 1H), 2.74 (s, 3H), 2.25-2.20 (m, 1H), 1.89-1.78 (m, 1H), 1.26 (d, J=6.1 Hz, 3H), NH and COOH not observed; MS (ES+) m/z 495.2, 497.2 (M+1). Note: acidic protons not observed.

Example 232

Synthesis of 3-chloro-4-((1-(3-(difluoromethyl)benzyl)piperidin-4-yl)oxy)-N-(thiazol-4-yl)benzenesulfonamide Formate

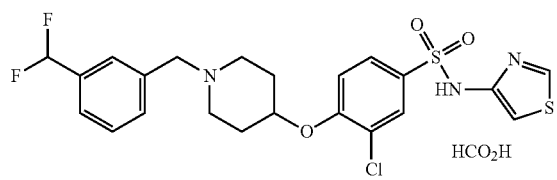 [SMILES: O=S(=O)(Nc1cscn1)c1ccc(OC2CCN(Cc3cccc(C(F)F)c3)CC2)c(Cl)c1 ; "HCO2H"]

Step 1. Preparation of tert-butyl 4-hydroxypiperidine-1-carboxylate

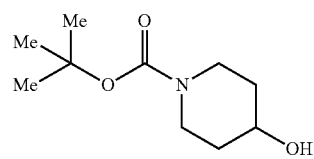 [SMILES: CC(C)(C)OC(=O)N1CCC(O)CC1]

To a solution of tert-butyl 4-oxopiperidine-1-carboxylate (2.00 g, 10.0 mmol) in methanol (2 mL) was added a solution of sodium borohydride (0.45 g, 12.1 mmol) in methanol (2 mL) at 0° C. The mixture was stirred at 0° C. for 1 h, quenched by addition of water (10 mL), and extracted with dichloromethane (3×20 mL). The combined organic extracts were washed with brine (2×10 mL), dried over anhydrous magnesium sulfate and filtered. The filtrate was concentrated to obtain the title compound as a yellow oil (1.70 g, 85% yield): $^1$H NMR (400 MHz, CD$_3$OD) δ 3.87-3.79 (m, 2H), 3.78-3.72 (m, 1H), 3.03 (br s, 2H), 1.86-1.76 (m, 2H), 1.45 (s, 9H), 1.44-1.33 (m, 2H), OH not observed.

Step 2. Preparation of tert-butyl 4-(4-(N-(tert-butoxycarbonyl)-N-(thiazol-4-yl)sulfamoyl)-2-chlorophenoxy)piperidine-1-carboxylate

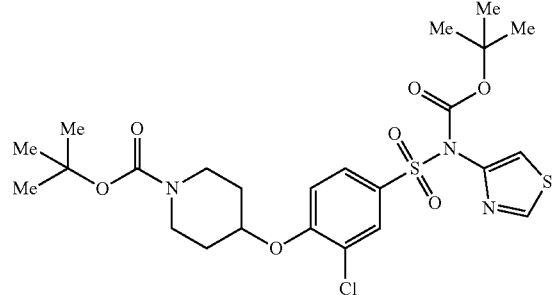 [SMILES: CC(C)(C)OC(=O)N1CCC(Oc2ccc(S(=O)(=O)N(C(=O)OC(C)(C)C)c3cscn3)cc2Cl)CC1]

To a mixture of a 60% dispersion of sodium hydride in mineral oil (0.087 g, 2.19 mmol) in anhydrous N,N-dimethylformamide (4 mL) was added a solution of tert-butyl 4-hydroxypiperidine-1-carboxylate (0.40 g, 1.99 mmol) in N,N-dimethylformamide (4 mL) at 0° C. The solution was stirred for 30 minutes at ambient temperature, and then a solution of tert-butyl (3-chloro-4-fluorophenyl)sulfonyl(thiazol-4-yl)carbamate (0.86 g, 2.19 mmol) in N,N-dimethylformamide (4 mL) was added to it dropwise. The mixture was stirred for 1 h at ambient temperature, and then the reaction was quenched by addition of saturated ammonium chloride (10 mL). The mixture was extracted with ethyl acetate (3×50 mL). The combined organic layers were washed with brine (2×20 mL), dried over anhydrous sodium sulfate, and filtered. Concentration of the filtrate in vacuo and purification of the residue by column chromatography, eluting with a gradient of 10 to 25% of ethyl acetate in petroleum ether, provided the title compound as a yellow solid (0.17 g, 15% yield): MS (ES+) m/z 596.0 (M+23), 598.0 (M+23).

Step 3. Preparation of 3-chloro-4-(piperidin-4-yloxy)-N-(thiazol-4-yl)benzenesulfonamide 2,2,2-trifluoroacetate

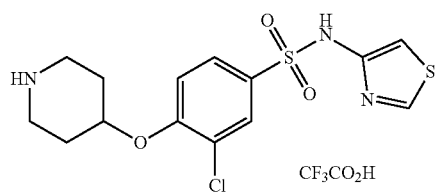 [SMILES: O=S(=O)(Nc1cscn1)c1ccc(OC2CCNCC2)c(Cl)c1 ; "CF3CO2H"]

To mixture of tert-butyl 4-(4-(N-(tert-butoxycarbonyl)-N-(thiazol-4-yl)sulfamoyl)-2-chlorophenoxy) piperidine-1-carboxylate (0.17 g, 0.30 mmol) dichloromethane (5 mL) was added trifluoroacetic acid (1 mL) and the reaction mixture was stirred at ambient temperature for 1 h. The mixture was then concentrated in vacuo to provide the title compound as a yellow solid (0.071 g, quantitative yield): MS (ES+) m/z 374.0 (M+1), 376.0 (M+1).

Step 4. Preparation of 3-chloro-4-((1-(3-(difluoromethyl)benzyl)piperidin-4-yl)oxy)-N-(thiazol-4-yl)benzenesulfonamide Formate

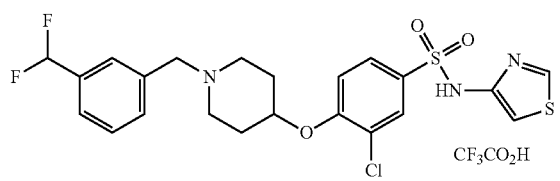 [SMILES: O=S(=O)(Nc1cscn1)c1ccc(OC2CCN(Cc3cccc(C(F)F)c3)CC2)c(Cl)c1 ; "CF3CO2H"]

To a solution of 3-chloro-4-(piperidin-4-yloxy)-N-(thiazol-4-yl)benzenesulfonamide 2,2,2-trifluoroacetate (0.48 g, 1.00 mmol) in anhydrous N,N-dimethylformamide (2.50 mL) was added 3-(difluoromethyl)benzaldehyde (0.23 g, 1.50 mmol) followed by sodium triacetoxyborohydride (0.64 g, 3.00 mmol). The reaction mixture was stirred at ambient temperature for 16 h and then concentrated in vacuo. The resulting residue was purified by column chromatography, eluting with a gradient of 10 to 100% of ethyl acetate in hexanes. Further purification by reverse-phase HPLC, eluting with a gradient of 20 to 50% of acetonitrile in water (containing 0.1% of formic acid), provided the title compound as a colorless solid (0.26 g, 51% yield): $^1$H NMR (300 MHz, DMSO-$d_6$), 58.89 (d, J=2.2 Hz, 1H), 8.15 (s, 1H), 7.84 (d, J=2.3 Hz, 1H), 7.72 (dd, J=8.8, 2.3 Hz, 1H), 7.64 (s, 1H), 7.59-7.54 (m, 3H), 7.39 (d, J=9.0 Hz, 1H), 7.09 (d, J=2.2 Hz, 1H), 7.05 (t, J=55.8 Hz, 1H), 4.77-4.75 (m, 1H), 3.98 (s, 2H), 2.94-2.87 (m, 2H), 2.77-2.71 (m, 2H), 2.03-2.00 (m, 2H), 1.86-1.80 (m, 2H), NH and COOH not observed; MS (ES+) m/z 513.9 (M+1), 515.9 (M+1).

Example 233

Synthesis of 4-((1-benzyl-3-methylazetidin-3-yl)amino)-2,6-difluoro-3-methyl-N-(thiazol-4-yl)benzenesulfonamide 2,2,2-trifluoroacetate

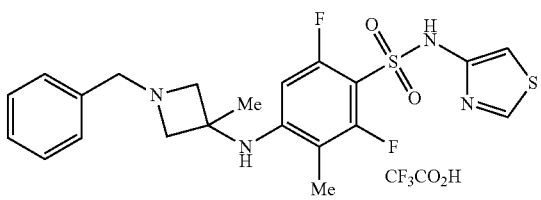

Step 1. Preparation of tert-butyl ((4-((1-benzyl-3-methylazetidin-3-yl)amino)-3-bromo-2,6-difluorophenyl)sulfonyl)(thiazol-4-yl)carbamate

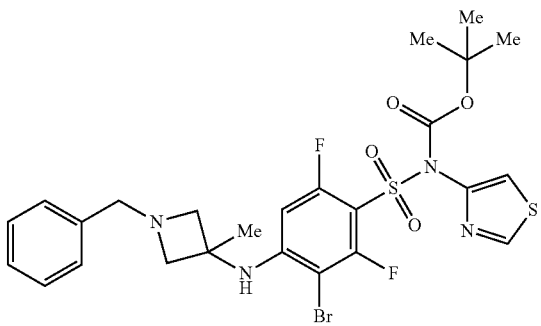

To a solution of tert-butyl ((3-bromo-2,4,6-trifluorophenyl)sulfonyl)(thiazol-4-yl)carbamate (1.07 g, 2.26 mmol) in anhydrous dimethyl sulfoxide (11 mL) was added potassium carbonate (0.47 g, 3.39 mmol) and 1-benzyl-3-methylazetidin-3-amine (0.40 g, 2.26 mmol). The reaction mixture was stirred at ambient temperature for 16 h, after which more 1-benzyl-3-methylazetidin-3-amine (0.30 g, 1.70 mmol) was added. The reaction mixture was then heated to 50° C. for 2 h. After cooling to ambient temperature, the mixture was diluted with brine (50 mL) and extracted with diethyl ether (5×50 mL). The combined organic extracts were washed with brine (50 mL), dried over anhydrous magnesium sulfate, and filtered. Concentration of the filtrate in vacuo and purification of the residue by column chromatography, eluting with a gradient of 20 to 100% of ethyl acetate in heptane, afforded the title compound as a colorless solid (1.02 g, 72% yield): MS (ES+) m/z 629.2 (M+1), 631.3 (M+1).

Step 2. Preparation of tert-butyl ((4-((1-benzyl-3-methylazetidin-3-yl)amino)-2,6-difluoro-3-methylphenyl)sulfonyl)(thiazol-4-yl)carbamate

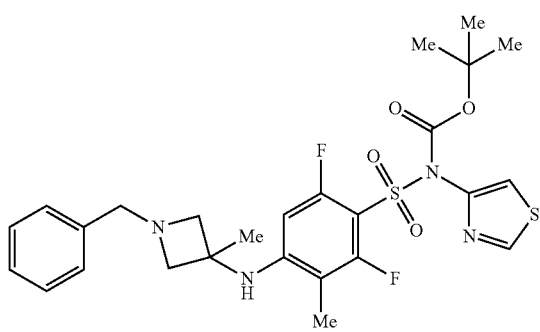 [SMILES: CC1(Nc2cc(F)c(S(=O)(=O)N(C(=O)OC(C)(C)C)c3cscn3)c(F)c2Br)CN(Cc2ccccc2)C1]

Following the procedure as described in EXAMPLE 224, Step 6 and making non-critical variations to (S)-3-bromo-2,6-difluoro-N-(thiazol-4-yl)-4-((1-((6-(trifluoromethyl)pyridin-2-yl)methyl)pyrrolidin-3-yl)amino)benzenesulfonamide with tert-butyl ((4-((1-benzyl-3-methylazetidin-3-yl)amino)-3-bromo-2,6-difluorophenyl)sulfonyl)-(thiazol-4-yl)carbamate, the title compound was obtained as a brown solid (0.45 g, 50% yield): MS (ES+) m/z 565.2 (M+1).

Step 3. Preparation of 4-((1-benzyl-3-methylazetidin-3-yl)amino)-2,6-difluoro-3-methyl-N-(thiazol-4-yl)benzenesulfonamide 2,2,2-trifluoroacetate

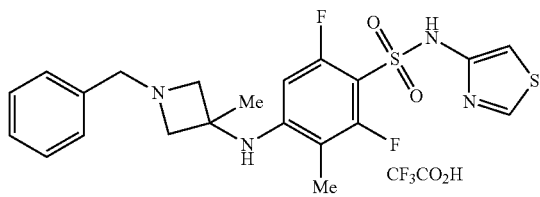

To a solution of tert-butyl ((4-((1-benzyl-3-methylazetidin-3-yl)amino)-2,6-difluoro-3-methylphenyl)sulfonyl)(thiazol-4-yl)carbamate (0.45 g, 0.80 mmol) in anhydrous dichloromethane (8 mL) was added trifluoroacetic acid (0.61 mL). The reaction mixture was stirred at ambient temperature for 16 h, and then concentrated in vacuo. The residue was triturated with methanol (2 mL) and filtered. Concentration of the filtrate in vacuo and purification of the residue by reverse-phase HPLC, eluting with a gradient of acetonitrile in water (containing 0.1% of trifluoroacetic acid) provided the title compound as a colorless solid (0.050 g, 11% yield): $^1$H NMR (300 MHz, DMSO-$d_6$) δ 11.29 (d, J=0.5 Hz, 1H), 10.80-10.59 (m, 1H), 8.91 (d, J=2.1 Hz, 1H), 7.48-7.43 (m, 5H), 6.91 (d, J=2.1 Hz, 1H), 5.96-5.91 (m, 1H), 4.41-4.40 (m, 2H), 4.26-4.21 (m, 4H), 1.96 (d, J=1.7 Hz, 3H), 1.54 (d, J=4.9 Hz, 3H), NH not observed; MS (ES+) m/z 465.2 (M+1).

Example 234

Synthesis of 3-chloro-4-((1-phenethylpiperidin-4-yl)oxy)-N-(thiazol-2-yl)benzenesulfonamide

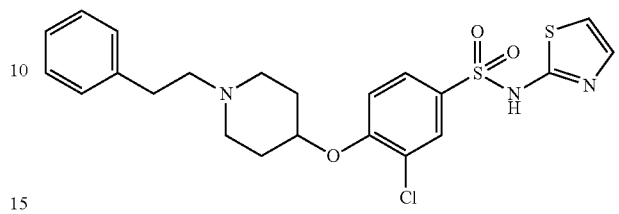

Following the procedure as described for EXAMPLE 5, Step 4 and making non-critical variations as required to replace 3-(difluoromethoxy)benzaldehyde with 2-phenylacetaldehyde, the title compound was obtained as a colorless solid (0.12 g, 41% yield): $^1$H NMR (300 MHz, DMSO-$d_6$) δ 12.13 (br s, 1H), 7.71 (d, J=2.2 Hz, 1H), 7.65 (dd, J=8.7, 2.2 Hz, 1H), 7.32 (d, J=8.8 Hz, 1H), 7.28-7.13 (m, 6H), 6.78 (d, J=4.5 Hz, 1H), 4.68-4.61 (m, 1H), 2.86-2.74 (m, 4H), 2.70-2.65 (m, 2H), 2.60-2.52 (m, 2H), 2.00-1.93 (m, 2H), 1.77-1.67 (m, 2H); MS (ES+) m/z: 478.0 (M+1), 480.0 (M+1).

Example 235

Synthesis of (S)-2,6-difluoro-4-((1-(3-fluorobenzyl)pyrrolidin-3-yl)(methyl)amino)-3-methyl-N-(thiazol-4-yl)benzenesulfonamide Formate

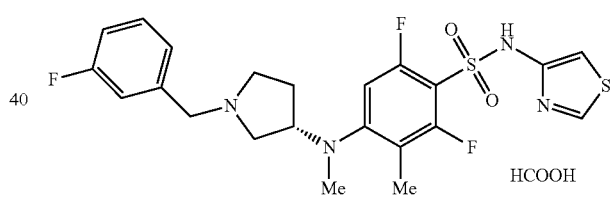

Step 1. Preparation of (S)-2,6-difluoro-4-((1-(3-fluorobenzyl)pyrrolidin-3-yl)amino)-3-methyl-N-(thiazol-4-yl)benzenesulfonamide

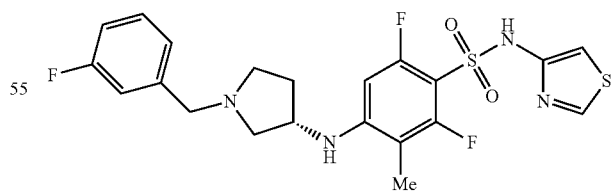

To a mixture of (S)-2,6-difluoro-3-methyl-4-(pyrrolidin-3-ylamino)-N-(thiazol-4-yl)benzenesulfonamide 2,2,2-trifluoroacetate (0.20 g, 0.41 mmol) and 3-fluorobenzaldehyde (0.087 mL, 0.82 mmol) in dichloromethane (2 mL) and N,N-dimethylformamide (1 mL) was added sodium triacetoxyborohydride (0.173 g, 0.82 mmol) and the reaction mixture was stirred at ambient temperature for 16 h. After addition of 2 M sodium hydroxide (3 mL) and brine (3 mL), the mixture was extracted with ethyl acetate (4 mL). The aqueous layer was diluted with saturated ammonium chloride (5 mL) and extracted with ethyl acetate (2×5 mL). The combined organic layers were washed with saturated ammonium chloride (2 mL), brine (3 mL), dried over anhydrous magnesium sulfate, and filtered. Concentration of the filtrate in vacuo afforded a residue which was purified by column chromatography, eluting with a gradient of 0 to 60% of ethyl acetate (containing 20% of ethanol and 0.1% of ammonium hydroxide) in hexanes, to provide the title compound as a colorless foam (0.18 g, 91% yield): MS (ES+) m/z 483.2 (M+1).

Step 2. Preparation of (S)-2,6-difluoro-4-((1-(3-fluorobenzyl)pyrrolidin-3-yl)(methyl)amino)-3-methyl-N-(thiazol-4-yl)benzenesulfonamide Formate

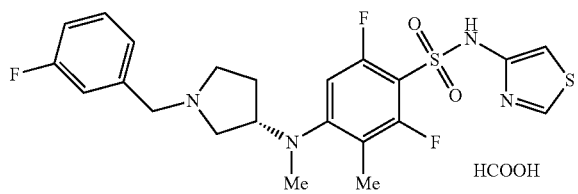 [SMILES: Cc1c(N(C)[C@H]2CCN(Cc3cccc(F)c3)C2)cc(F)c(S(=O)(=O)Nc2cscn2)c1F ; "HCOOH"]

To a mixture of (S)-2,6-difluoro-4-((1-(3-fluorobenzyl)pyrrolidin-3-yl)amino)-3-methyl-N-(thiazol-4-yl)benzenesulfonamide (0.152 g, 0.32 mmol) in 1,2-dichloroethane (1.5 mL) and trifluoroacetic acid (3.0 mL) was added sodium triacetoxyborohydride (0.208 g, 0.98 mmol) and the reaction mixture was stirred at ambient temperature for three days. The reaction mixture was concentrated under reduced pressure and the residue purified by column chromatography, eluting with a gradient of 0 to 100% of ethyl acetate (containing 20% of ethanol and 0.1% of ammonium hydroxide) in hexanes. Additional purification by preparative reverse-phase HPLC, eluting with a gradient of acetonitrile in water containing 0.5% of formic acid, afforded the title compound as a colorless solid (0.034 g, 20% yield): $^1$H NMR (300 MHz, DMSO-$d_6$) δ 8.89 (d, J=2.2 Hz, 1H), 8.15 (s, 0.9H), 7.38-7.32 (m, 1H), 7.18-7.03 (m, 3H), 6.93 (d, J=2.2 Hz, 1H), 6.71 (dd, J=13.4, 1.4 Hz, 1H), 4.01-3.91 (m, 1H), 3.63 (d, J=13.3 Hz, 1H), 3.53 (d, J=13.5 Hz, 1H), 2.76-2.53 (m, 6H), 2.38-2.28 (m, 1H), 2.10-1.98 (m, 4H), 1.85-1.72 (m, 1H), NH and COOH not observed; MS (ES+) m/z 497.3 (M+1).

Example 236

Synthesis of (S)-2,6-difluoro-4-((1-(2-fluorobenzyl)pyrrolidin-3-yl)(methyl)amino)-3-methyl-N-(thiazol-4-yl)benzenesulfonamide Formate

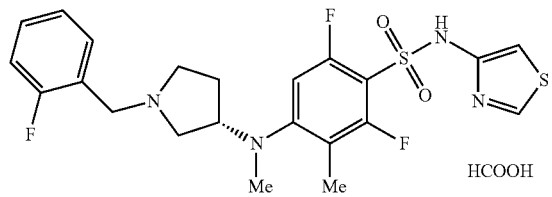 [SMILES: Cc1c(N(C)[C@H]2CCN(Cc3ccccc3F)C2)cc(F)c(S(=O)(=O)Nc2cscn2)c1F ; "HCOOH"]

Following the procedure as described for EXAMPLE 235, Step 3 to 4, and making non-critical variations as required to replace 3-fluorobenzaldehyde with 2-fluorobenzaldehyde, the title compound was obtained as a colorless solid (0.043 g, 28% yield): $^1$H NMR (300 MHz, DMSO-$d_6$) δ 8.89 (d, J=2.2 Hz, 1H), 8.14 (s, 1.3H), 7.41 (td, J=7.6, 1.8 Hz, 1H), 7.35-7.28 (m, 1H), 7.21-7.12 (m, 2H), 6.95 (d, J=2.2 Hz, 1H), 6.71 (dd, J=13.5, 1.4 Hz, 1H), 4.00-3.91 (m, 1H), 3.66 (d, J=13.7 Hz, 1H), 3.61 (d, J=13.7 Hz, 1H), 2.76-2.56 (m, 6H), 2.43-2.33 (m, 1H), 2.08-1.96 (m, 4H), 1.83-1.71 (m, 1H), NH and COOH not observed; MS (ES+) m/z 497.4 (M+1).

Example 237

Synthesis of (S)-4-((1-(2,3-difluorobenzyl)pyrrolidin-3-yl)(methyl)amino)-2,6-difluoro-3-methyl-N-(thiazol-4-yl)benzenesulfonamide Formate

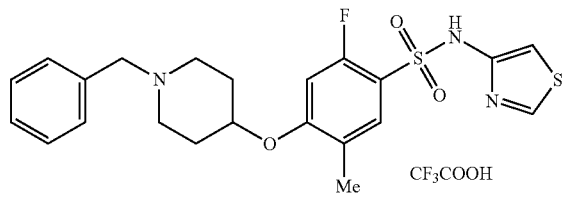

Following the procedure as described for EXAMPLE 235, Step 3 to 4, and making non-critical variations as required to replace 3-fluorobenzaldehyde with 2,3-difluorobenzaldehyde, the title compound was obtained as a colorless solid (0.046 g, 29% yield): $^1$H NMR (300 MHz, DMSO-$d_6$) δ 8.88 (d, J=2.2 Hz, 1H), 8.15 (s, 0.6H), 7.35-7.16 (m, 3H), 6.92 (d, J=2.2 Hz, 1H), 6.71 (dd, J=13.4, 1.3 Hz, 1H), 3.99-3.90 (m, 1H), 3.68 (dd, J=13.4, 1.2 Hz, 1H), 3.62 (dd, J=13.5, 1.1 Hz, 1H), 2.74-2.54 (m, 6H), 2.40-2.30 (m, 1H), 2.07-1.96 (m, 4H), 1.82-1.70 (m, 1H), NH and COOH not observed; MS (ES+) m/z 515.3 (M+1).

Example 238

Synthesis of 4-((1-benzylpiperidin-4-yl)oxy)-5-chloro-2-fluoro-N-(thiazol-4-yl)benzenesulfonamide 2,2,2-trifluoroacetate

255

Step 1. Preparation of tert-butyl ((4-((1-benzylpip-eridin-4-yl)oxy)-5-chloro-2-fluorophenyl)sulfonyl)(thiazol-4-yl)carbamate

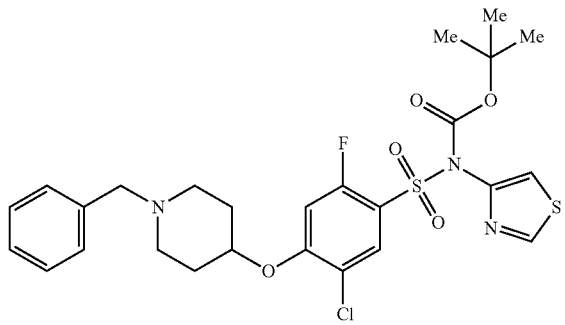 [SMILES: CC(C)(C)OC(=O)N(c1cscn1)S(=O)(=O)c1cc(Cl)c(OC2CCN(Cc3ccccc3)CC2)cc1F]

To a mixture of tert-butyl ((5-chloro-2,4-difluorophenyl)sulfonyl)(thiazol-4-yl)carbamate (0.821 g, 2.0 mmol) and 1-benzyl-4-hydroxypiperidine (0.383 g, 2.0 mmol) in anhydrous N,N-dimethylformamide (5 mL) was added a 60% dispersion of sodium hydride in mineral oil (0.088 g, 2.2 mmol) at 0° C. The reaction mixture was allowed to warm to ambient temperature and stirred for 4 h. After addition of saturated ammonium chloride solution (15 mL), the mixture was extracted with ethyl acetate (100 mL). The organic phase was washed with water (15 mL), brine (15 mL), and dried over anhydrous sodium sulfate. Filtration and concentration of the filtrate in vacuo provided a residue. Purification of the residue by column chromatography, eluting with a gradient of 0 to 100% of ethyl acetate (containing 10% isopropanol and 10% triethylamine) in hexanes, afforded the title compound as a colorless solid (0.850 g, 73% yield): MS (ES+) m/z 582.5 (M+1), 584.4 (M+1).

Step 2. Preparation of 4-((1-benzylpiperidin-4-yl)oxy)-5-chloro-2-fluoro-N-(thiazol-4-yl)benzene-sulfonamide 2,2,2-trifluoroacetate

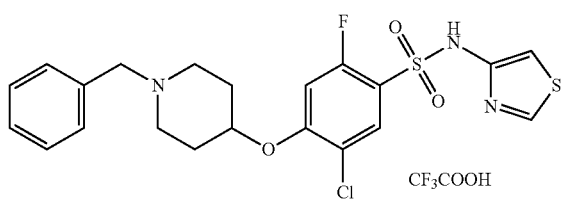

To a mixture of tert-butyl ((4-((1-benzylpiperidin-4-yl)oxy)-5-chloro-2-fluorophenyl)sulfonyl)(thiazol-4-yl)carbamate (0.150 g, 0.26 mmol) in dichloromethane (2 mL) was added trifluoroacetic acid (2 mL) and the reaction mixture was stirred at ambient temperature for 16 h. Concentration in vacuo and trituration of the residue in diethyl ether (15 mL) provided the title compound as a colorless solid (0.115 g, 92% yield): $^1$H NMR (300 MHz, DMSO-$d_6$) δ 11.10 (br s, 1H), 10.00 (br s, 1H), 8.91 (d, J=2.2 Hz, 1H), 7.81 (d, J=7.5 Hz, 1H), 7.57-7.44 (m, 6H), 7.08 (d, J=2.2 Hz, 1H), 5.00-4.69 (m, 1H), 4.36 (s, 2H), 3.58-2.63 (m, 4H), 2.25-1.79 (m, 4H); MS (ES+) m/z 482.3 (M+1), 484.3 (M+1).

256

Example 239

Synthesis of 4-((1-benzylpiperidin-4-yl)oxy)-2-fluoro-5-methyl-N-(thiazol-4-yl)benzenesulfonamide

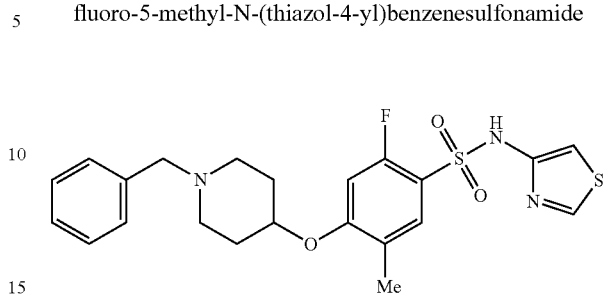

To a mixture of tert-butyl ((4-((1-benzylpiperidin-4-yl)oxy)-5-chloro-2-fluorophenyl)sulfonyl)(thiazol-4-yl)carbamate (0.70 g, 1.2 mmol) and methylboronic acid (0.359 g, 6.0 mmol) in anhydrous 1,4-dioxane (10 mL) was added potassium phosphate tribasic (1.27 g, 6.0 mmol), tricyclohexylphosphine tetrafluoroborate (0.177 g, 0.48 mmol) and palladium acetate (0.054 g, 0.24 mmol), and the mixture was degassed by passing a stream of nitrogen through it for 15 minutes. The resulting mixture was heated to 90-100° C. for 24 h. After cooling to ambient temperature, the mixture was diluted with ethyl acetate (50 mL) and filtered through a pad of Celite. The filter pad was washed with ethyl acetate (50 mL) and the combined filtrate concentrated in vacuo. The residue was dissolved in dichloromethane (10 mL), and trifluoroacetic acid (6 mL)) was added to it. The reaction mixture was stirred at ambient temperature for 6 h and then concentrated in vacuo. Purification of the residue by column chromatography, eluting with a gradient of 0 to 100% of ethyl acetate (containing 10% isopropanol and 10% triethylamine) in hexanes, afforded the title compound as an off-white solid (0.248 g, 45% yield): $^1$H NMR (300 MHz, DMSO-$d_6$) δ 38.82 (d, J=2.2 Hz, 1H), 7.57 (dd, J=8.6, 0.7 Hz, 1H), 7.35-7.22 (m, 5H), 7.05 (d, J=12.7 Hz, 1H), 6.77 (d, J=2.2 Hz, 1H), 4.57-4.52 (m, 1H), 3.48 (s, 2H), 2.76 (q, J=7.2 Hz, 3H), 2.61-2.53 (m, 2H), 2.33-2.26 (m, 2H), 2.09 (s, 3H), 1.93-1.85 (m, 2H), 1.71-1.61 (m, 2H), 1.05 (t, J=7.2 Hz, 4.5H), NH not observed; MS (ES+) m/z 462.3 (M+1).

Example 240

Synthesis of (S)-4-((1-(2,5-difluorobenzyl)pyrrolidin-3-yl)(methyl)amino)-2,6-difluoro-3-methyl-N-(thiazol-4-yl)benzenesulfonamide 2,2,2-trifluoroacetate

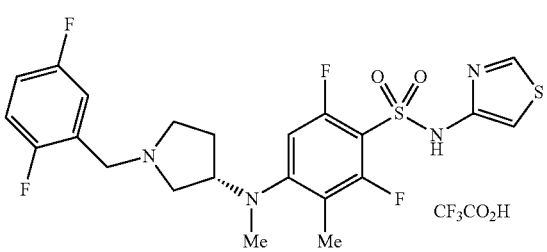 [SMILES: Cc1c(N(C)[C@H]2CCN(Cc3cc(F)ccc3F)C2)cc(F)c(S(=O)(=O)Nc2cscn2)c1F ; "CF3CO2H"]

Step 1. Preparation of (S)-4-((1-(2,5-difluorobenzyl)pyrrolidin-3-yl)amino)-2,6-difluoro-3-methyl-N-(thiazol-4-yl)benzenesulfonamide

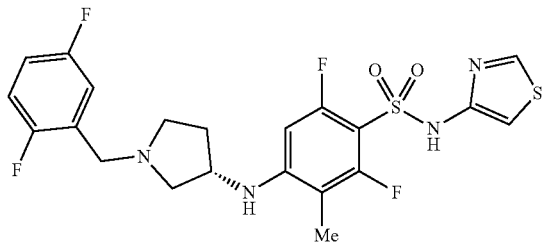 [SMILES: Cc1c(N[C@H]2CCN(Cc3cc(F)ccc3F)C2)cc(F)c(S(=O)(=O)Nc2cscn2)c1F]

To a solution (S)-2,6-difluoro-3-methyl-4-(pyrrolidin-3-ylamino)-N-(thiazol-4-yl)benzenesulfonamide 2,2,2-trifluoroacetate (0.40 g, 0.82 mmol) and 2,5-difluorobenzaldehyde (0.23 g, 1.64 mmol) in anhydrous N,N-dimethylformamide (2 mL) and anhydrous dichloromethane (8 mL) was added sodium triacetoxyborohydride (0.34 g, 1.62 mmol) and the reaction mixture was stirred at ambient temperature for 18 h. The reaction mixture was then quenched by addition of 2 M sodium hydroxide (10 mL) and brine (30 mL). The mixture was extracted with ethyl acetate (2×60 mL). The combined organic fractions were washed with saturated ammonium chloride (30 mL), brine (30 mL), dried over anhydrous sodium sulfate, and filtered. The filtrate was concentrated in vacuo and the residue purified by column chromatography, eluting with a gradient of 10 to 60% of ethyl acetate (containing 20% of ethanol and 0.1% of ammonium hydroxide) in hexanes, to afford the title compound as a colorless solid (0.27 g, 66% yield): MS (ES+) m/z 501.2 (M+H).

Step 2. (S)-4-((1-(2,5-difluorobenzyl)pyrrolidin-3-yl)(methyl)amino)-2,6-difluoro-3-methyl-N-(thiazol-4-yl)benzenesulfonamide 2,2,2-trifluoroacetate

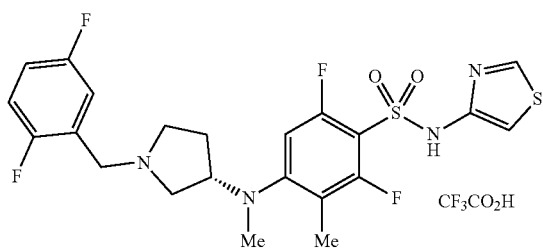 [SMILES: Cc1c(N(C)[C@H]2CCN(Cc3cc(F)ccc3F)C2)cc(F)c(S(=O)(=O)Nc2cscn2)c1F ; "CF3CO2H"]

Following the procedure as described for EXAMPLE 103, Step 4 and making non-critical variations as required to replace (S)-4-((1-benzylpyrrolidin-3-yl)amino)-2,6-difluoro-3-methyl-N-(thiazol-4-yl)benzenesulfonamide with (S)-4-((1-(2,5-difluorobenzyl)pyrrolidin-3-yl)amino)-2,6-difluoro-3-methyl-N-(thiazol-4-yl)benzenesulfonamide, and purification by preparative reverse-phase HPLC, eluting with a gradient of 7 to 50% of acetonitrile in water containing 0.1% of trifluoroacetic acid, afforded the title compound as a colorless solid (0.095 g, 38% yield): $^1$H NMR (300 MHz, DMSO-$d_6$) δ 11.48 (s, 1H), 10.90 (s, 1H), 8.91 (d, J=2.2 Hz, 1H), 7.53-7.47 (m, 1H), 7.40 (td, J=6.4, 1.5 Hz, 2H), 6.99 (d, J=2.2 Hz, 1H), 6.86 (d, J=13.0 Hz, 1H), 4.44-4.41 (m, 2H), 4.31-4.04 (m, 1H), 3.57-3.43 (m, 3H), 2.74-2.62 (m, 3H), 2.19-2.00 (m, 6H); MS (ES+) m/z 515.3 (M+H).

Example 241

Synthesis of 4-((1-benzyl-3-methylpyrrolidin-3-yl)(methyl)amino)-3-chloro-N-(thiazol-2-yl)benzenesulfonamide

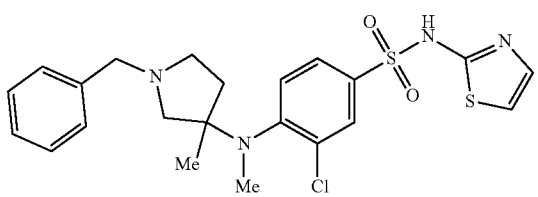 [SMILES: CN(c1ccc(S(=O)(=O)Nc2nccs2)cc1Cl)C1(C)CCN(Cc2ccccc2)C1]

To a mixture of 4-((1-benzyl-3-methylpyrrolidin-3-yl)amino)-3-chloro-N-(2,4-dimethoxybenzyl)-N-(thiazol-2-yl)benzenesulfonamide (0.180 g, 0.293 mmol) in formic acid (2 mL) was added paraformaldehyde (2.18 g, 26.86 mmol) and the reaction mixture was heated to 90° C. for 12 h. Concentration in vacuo and purification of the residue by reverse-phase preparative HPLC, eluting with a gradient of 20-80% of acetonitrile in water (containing 0.05% of ammonium hydroxide), afforded the title compound as a colorless solid (0.015 g, 15% yield): $^1$H NMR (400 MHz, CDCl$_3$) δ 7.90 (d, J=2.0 Hz, 1H), 7.67 (dd, J=2.0, 8.6 Hz, 1H), 7.33-7.29 (m, 5H), 7.26-7.22 (m, 1H), 7.14 (d, J=4.6 Hz, 1H), 6.54 (d, J=4.6 Hz, 1H), 3.69-3.55 (m, 2H), 2.79-2.70 (m, 5H), 2.68-2.61 (m, 1H), 2.59-2.56 (m, 1H), 2.21-2.10 (m, 1H), 1.82-1.71 (m, 1H), 1.44 (s, 3H), NH not observed; MS (ES+) m/z 477.0 (M+1)

Example 242

Synthesis of 5-chloro-2-fluoro-4-(methyl((S)-1-((S)-1-phenylpropyl)pyrrolidin-3-yl)amino)-N-(thiazol-4-yl)benzenesulfonamide

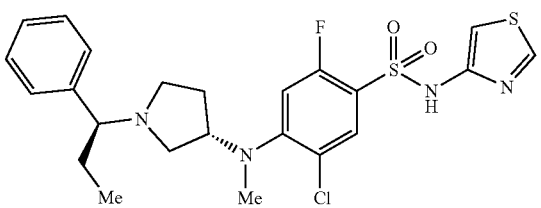 [SMILES: CC[C@@H](c1ccccc1)N1CC[C@H](N(C)c2cc(F)c(S(=O)(=O)Nc3cscn3)cc2Cl)C1]

Step 1. Preparation of tert-butyl ((S)-1-((S)-1-phenylpropyl)pyrrolidin-3-yl)carbamate

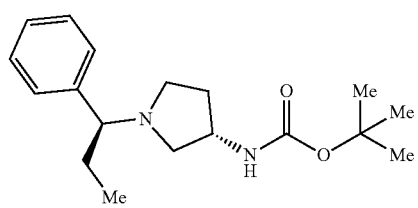 [SMILES: CC[C@@H](c1ccccc1)N1CC[C@H](NC(=O)OC(C)(C)C)C1]

Following the procedure as described in EXAMPLE 42, Step 2 and making non-critical variations as required to replace (S)-1-phenylethan-1-amine with (S)-1-phenylpropan-1-amine, the title compound was obtained as a yellow syrup (1.42 g, 58% yield): MS (ES+) m/z 305.2 (M+1).

Step 2. Preparation of (S)—N-methyl-1-((S)-1-phenylpropyl)pyrrolidin-3-amine

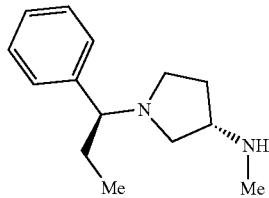 [SMILES: CC[C@@H](c1ccccc1)N1CC[C@H](NC)C1]

Following the procedure as described in EXAMPLE 42, Step 3 and making non-critical variations as required to replace tert-butyl ((S)-1-((S)-1-phenylethyl)pyrrolidin-3-yl)carbamate with tert-butyl ((S)-1-((S)-1-phenylpropyl)pyrrolidin-3-yl)carbamate, the title compound was obtained as a light yellow syrup (0.76 g, 74% yield): MS (ES+) m/z 219.3 (M+1).

Step 3. Preparation of 5-chloro-N-(2,4-dimethoxybenzyl)-2,4-difluoro-N-(thiazol-4-yl)benzenesulfonamide

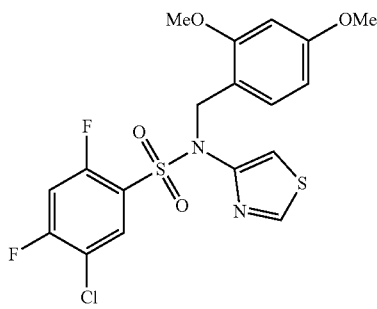 [SMILES: COc1ccc(CN(c2cscn2)S(=O)(=O)c2cc(Cl)c(F)cc2F)c(OC)c1]

To a solution of 5-chloro-2,4-difluoro-N-(thiazol-4-yl)benzenesulfonamide (29.0 g, 93.3 mmol), (2,4-dimethoxyphenyl)methanol (19.6 g, 117 mmol) and tri-n-butylphosphine (28.3 g, 140 mmol) in anhydrous tetrahydrofuran (300 mL) was added a solution of 1,1'-(azodicarbonyl)dipiperidine (35.3 g, 140 mmol) in tetrahydrofuran (100 mL). The reaction mixture was stirred at ambient temperature for 2 h and then heated to 60° C. for 10 h. After cooling to ambient temperature, the reaction mixture was diluted with water (500 mL) and extracted with dichloromethane (3×400 mL). The combined organic phase was washed with brine (100 mL), dried over anhydrous sodium sulfate, and filtered. Concentration in vacuo and purification of the residue by column chromatography, eluting with a gradient of 10-20% of ethyl acetate in petroleum ether, provided the title compound as a colorless solid (19.0 g, 44% yield): $^1$H NMR (400 MHz, CDCl$_3$) δ 8.58 (d, J=2.4 Hz, 1H), 7.88 (t, J=8.0 Hz, 1H), 7.22-7.17 (m, 2H), 7.04 (t, J=8.0 Hz, 1H), 6.43-6.35 (m, 2H), 5.04 (s, 2H), 3.79 (s, 3H), 3.71 (s, 3H); MS (ES+) m/z 461.0 (M+1), 463.0 (M+1).

Step 4. Preparation of 5-chloro-N-(2,4-dimethoxybenzyl)-2-fluoro-4-(methyl((S)-1-((S)-1-phenylpropyl)pyrrolidin-3-yl)amino)-N-(thiazol-4-yl)benzenesulfonamide

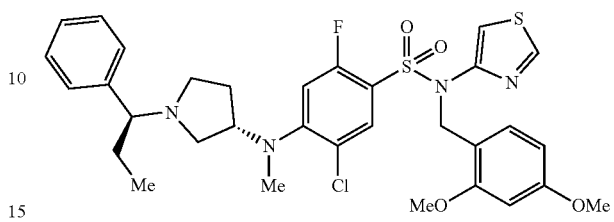

To a solution of (S)—N-methyl-1-((S)-1-phenylpropyl)pyrrolidin-3-amine (0.20 g, 0.92 mmol) and 5-chloro-N-(2,4-dimethoxybenzyl)-2,4-difluoro-N-(thiazol-4-yl)benzenesulfonamide (0.41 g, 0.88 mmol) in anhydrous dimethyl sulfoxide (5 mL) was added N,N-diisopropylethylamine (0.80 mL, 4.6 mmol). The solution was heated 25 to 80° C. for 22 h, then cooled to ambient temperature and diluted with ethyl acetate (150 mL). The mixture was washed with saturated aqueous ammonium chloride (100 mL), brine (100 mL), dried over anhydrous magnesium sulfate, filtered, and concentrated in vacuo. The residue was purified by column chromatography, eluting with a 0-30% gradient of ethyl acetate (containing 10% of triethylamine and 10% of isopropanol) in hexanes, to afford the title compound as a light yellow syrup (0.26 g, 44% yield): $^1$H NMR (300 MHz, CDCl$_3$) δ 8.54 (d, J=2.3 Hz, 1H), 7.66 (d, J=7.4 Hz, 1H), 7.38-7.26 (m, 5H), 7.22 (d, J=8.2 Hz, 1H), 7.19 (d, J=2.3 Hz, 1H), 6.63 (d, J=12.2 Hz, 1H), 6.40-6.34 (m, 2H), 5.02 (s, 2H), 4.24-4.14 (m, 1H), 3.77 (s, 3H), 3.69 (s, 3H), 3.01-2.95 (m, 2H), 2.85 (s, 3H), 3.60-2.46 (m, 2H), 2.29-2.10 (m, 2H), 1.98-1.85 (m, 2H), 1.75-1.65 (m, 1H), 0.70 (t, J=7.4 Hz, 3H); MS (ES+) m/z 659.3 (M+1), 661.3 (M+1).

Step 5. Preparation of 5-chloro-2-fluoro-4-(methyl((S)-1-((S)-1-phenylpropyl)pyrrolidin-3-yl)amino)-N-(thiazol-4-yl)benzenesulfonamide

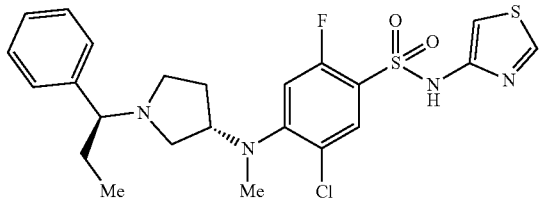 [SMILES: CC[C@@H](c1ccccc1)N1CC[C@H](N(C)c2cc(F)c(S(=O)(=O)Nc3cscn3)cc2Cl)C1]

To a solution of 5-chloro-N-(2,4-dimethoxybenzyl)-2-fluoro-4-(methyl((S)-1-((S)-1-phenylpropyl)pyrrolidin-3-yl)amino)-N-(thiazol-4-yl)benzenesulfonamide (0.26 g, 0.39 mmol) in dichloromethane (10 mL) was added trifluoroacetic acid (3 mL). The solution was stirred at ambient temperature for 15 h, then concentrated in vacuo. The residue was purified by column chromatography, eluting with a 0-10% gradient of methanol in dichloromethane, to afford the title compound as a colorless solid (0.052 g, 26% yield): $^1$H NMR (300 MHz, DMSO-d$_6$) δ 11.26 (br s, 1H), 8.88 (d, J=2.1 Hz, 1H), 7.65 (d, J=7.6 Hz, 1H), 7.35-7.23 (m, 5H), 7.04-7.00 (m, 2H), 4.18-4.09 (m, 1H), 3.07-3.01 (m, 1H), 2.91-2.83 (m, 1H), 2.77 (s, 3H), 2.47-2.42 (m, 2H), 2.21-2.13 (m, 1H), 2.10-1.99 (m, 1H), 1.93-1.73 (m, 2H), 1.66-1.55 (m, 1H), 0.61 (t, J=7.3 Hz, 3H); MS (ES+) m/z 509.1 (M+1), 511.1 (M+1).

Example 243

Synthesis of 5-chloro-2-fluoro-4-(methyl((S)-1-((R)-1-phenylpropyl)pyrrolidin-3-yl)amino)-N-(thiazol-4-yl)benzenesulfonamide

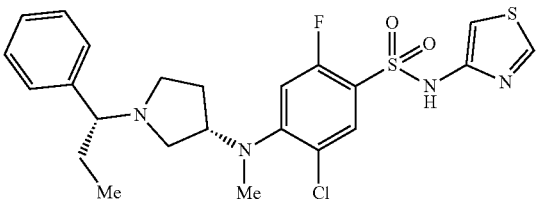 [SMILES: CC[C@H](c1ccccc1)N1CC[C@H](N(C)c2cc(F)c(S(=O)(=O)Nc3cscn3)cc2Cl)C1]

Step 1. Preparation of tert-butyl ((S)-1-((R)-1-phenylpropyl)pyrrolidin-3-yl)carbamate

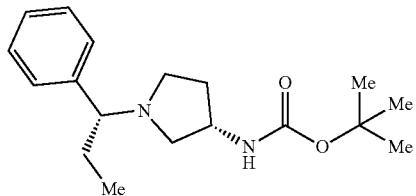 [SMILES: CC[C@H](c1ccccc1)N1CC[C@H](NC(=O)OC(C)(C)C)C1]

Following the procedure as described in EXAMPLE 42, Step 2 and making non-critical variations as required to replace (S)-1-phenylethan-1-amine with (R)-1-phenylpropan-1-amine, the title compound was obtained as a yellow solid (1.65 g, 68% yield): MS (ES+) m/z 305.3 (M+1).

Step 2. Preparation of (S)—N-methyl-1-((R)-1-phenylpropyl)pyrrolidin-3-amine

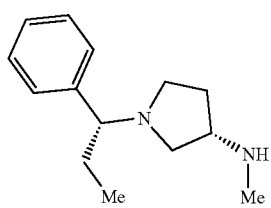 [SMILES: CC[C@H](c1ccccc1)N1CC[C@H](NC)C1]

Following the procedure as described in EXAMPLE 42, Step 3 and making non-critical variations as required to replace tert-butyl ((S)-1-((S)-1-phenylethyl)pyrrolidin-3-yl)carbamate with tert-butyl ((S)-1-((R)-1-phenylpropyl)pyrrolidin-3-yl)carbamate, the title compound was obtained as a light yellow oil (0.96 g, 81% yield): MS (ES+) m/z 219.3 (M+1).

Step 3. Preparation of 5-chloro-N-(2,4-dimethoxybenzyl)-2-fluoro-4-(methyl((S)-1-((R)-1-phenylpropyl)pyrrolidin-3-yl)amino)-N-(thiazol-4-yl)benzenesulfonamide

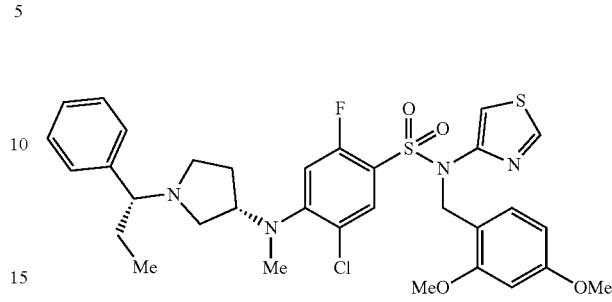

Following the procedure as described in EXAMPLE 242, Step 4 and making non-critical variations as required to replace (S)—N-methyl-1-((S)-1-phenylpropyl)pyrrolidin-3-amine with (S)—N-methyl-1-((R)-1-phenylpropyl)pyrrolidin-3-amine, the title compound was obtained as a yellow syrup (0.29 g, 48% yield): $^1$H NMR (300 MHz, CDCl$_3$) δ 8.56 (d, J=2.3 Hz, 1H), 7.69 (d, J=7.4 Hz, 1H), 7.38-7.26 (m, 5H), 7.23 (d, J=8.2 Hz, 1H), 7.20 (d, J=2.3 Hz, 1H), 6.72 (d, J=12.2 Hz, 1H), 6.40-6.35 (m, 2H), 5.04 (s, 2H), 4.26-4.16 (m, 1H), 3.77 (s, 3H), 3.70 (s, 3H), 3.01 (dd, J=3.9, 9.4 Hz, 1H), 2.89 (s, 3H), 2.84 (dd, J=4.4, 10.0 Hz, 1H), 2.66-2.50 (m, 2H), 2.35 (q, J=8.4 Hz, 1H), 1.96-1.65 (m, 4H), 0.70 (t, J=7.4 Hz, 3H); MS (ES+) m/z 659.2 (M+1), 661.2 (M+1).

Step 4. Preparation of 5-chloro-2-fluoro-4-(methyl ((S)-1-((R)-1-phenylpropyl)-pyrrolidin-3-yl)amino)-N-(thiazol-4-yl)benzenesulfonamide

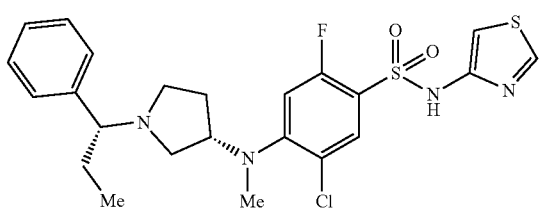 [SMILES: CC[C@H](c1ccccc1)N1CC[C@H](N(C)c2cc(F)c(S(=O)(=O)Nc3cscn3)cc2Cl)C1]

Following the procedure as described in EXAMPLE 242, Step 5 and making non-critical variations as required to replace 5-chloro-N-(2,4-dimethoxybenzyl)-2-fluoro-4-(methyl((S)-1-((S)-1-phenylpropyl)pyrrolidin-3-yl)amino)-N-(thiazol-4-yl)benzenesulfonamide with 5-chloro-N-(2,4-dimethoxybenzyl)-2-fluoro-4-(methyl((S)-1-((R)-1-phenylpropyl)pyrrolidin-3-yl)amino)-N-(thiazol-4-yl) benzenesulfonamide, the title compound was obtained as a colorless solid (0.10 g, 47% yield): $^1$H NMR (300 MHz, DMSO-d$_6$) δ 11.39 (br s, 1H), 8.92-8.89 (m, 1H), 7.78-7.71 (m, 1H), 7.50-7.43 (m, 5H), 7.23-7.14 (m, 1H), 7.09-7.06 (m, 1H), 4.48-4.10 (m, 2H), 3.79-3.60 (m, 2H), 3.08-2.98 (m, 1H), 2.91-2.83 (m, 1H), 2.80-2.70 (m, 3H), 2.22-1.88 (m, 4H), 0.62 (t, J=7.3 Hz, 3H); MS (ES+) m/z 509.1 (M+1), 511.1 (M+1).

Example 244

Synthesis of (S)-5-chloro-2-fluoro-4-((1-(1-(2-fluorophenyl)cyclobutyl)pyrrolidin-3-yl)(methyl)amino)-N-(thiazol-4-yl)benzenesulfonamide Formate

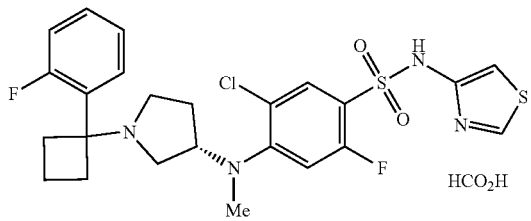 [SMILES: CN(c1cc(F)c(S(=O)(=O)Nc2cscn2)cc1Cl)[C@H]1CCN(C2(c3ccccc3F)CCC2)C1 ; "HCO2H"]

Step 1. Preparation of tert-butyl (S)-(1-(1-(2-fluorophenyl)cyclobutyl)pyrrolidin-3-yl)carbamate

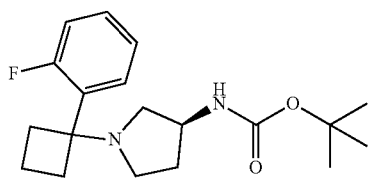 [SMILES: CC(C)(C)OC(=O)N[C@H]1CCN(C2(c3ccccc3F)CCC2)C1]

To a solution of (S)-2-((tert-butoxycarbonyl)amino)butane-1,4-diyl dimethanesulfonate (2.19 g, 6.05 mmol) in anhydrous dimethyl sulfoxide (12 mL) was added 1-(2-fluorophenyl)cyclobutan-1-amine (1.00 g, 6.05 mmol) and N,N-diisopropylethylamine (3.30 mL, 24.21 mmol) and the resulting solution was heated to 50° C. for 16 h. The reaction mixture was then cooled to ambient temperature and diluted with saturated ammonium chloride and extracted with ethyl acetate (2×50 mL).

The combined organic extracts were dried over anhydrous magnesium sulfate, filtered and concentrated in vacuo to provide the title compound as colorless oil (2.0 g, 99% yield), which and used without further purification: MS (ES+) m/z 335.3 (M+1).

Step 2. Preparation of (S)-1-(1-(2-fluorophenyl)cyclobutyl)-N-methylpyrrolidin-3-amine

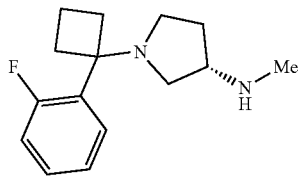 [SMILES: CN[C@H]1CCN(C2(c3ccccc3F)CCC2)C1]

To a solution of tert-butyl (S)-(1-(1-(2-fluorophenyl)cyclobutyl)pyrrolidin-3-yl)carbamate (2.00 g, 5.98 mmol) in anhydrous tetrahydrofuran (20 mL) was added a 1 M solution of lithium aluminum hydride in tetrahydrofuran (12.10 mL, 12.10 mmol), and the resulting solution was heated to reflux for 3 h and then stirred at ambient temperature for 16 h. The reaction mixture was cooled to 0° C., quenched by addition of 1 M sodium hydroxide (50 mL) and extracted with diethyl ether (3×50 mL). The combined organic extracts were washed with water (25 mL), dried over anhydrous magnesium sulfate, and filtered. Concentration of the filtrate in vacuo provided the title compound as a colorless oil (0.72 g, 48% yield): MS (ES+) m/z 249.1 (M+1).

Step 3. Preparation of (S)-5-chloro-N-(2,4-dimethoxybenzyl)-2-fluoro-4-((1-(1-(2-fluorophenyl)cyclobutyl)pyrrolidin-3-yl)(methyl)amino)-N-(thiazol-4-yl)benzenesulfonamide

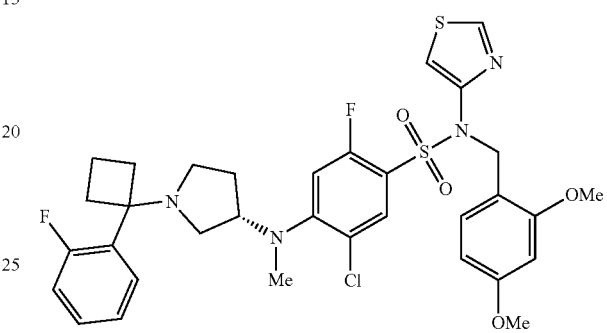

To a solution of (S)-1-(1-(2-fluorophenyl)cyclobutyl)-N-methylpyrrolidin-3-amine (0.72 g, 2.91 mmol) in anhydrous dimethyl sulfoxide (5 mL) was added N,N-diisopropylethylamine (1.70 mL, 9.72 mmol) and 5-chloro-N-(2,4-dimethoxybenzyl)-2,4-difluoro-N-(thiazol-4-yl)benzenesulfonamide (1.12 g, 2.43 mmol) and the resulting solution was heated to 70° C. for 16 h. The reaction mixture was purified by column chromatography, eluting with a gradient of 10 to 100% of ethyl acetate in heptane, to provide the title compound as a pale yellow oil (0.20 g, 10% yield): $^1$H NMR (300 MHz, CDCl$_3$) δ 8.56 (d, J=2.3 Hz, 1H), 7.67 (d, J=7.5 Hz, 1H), 7.21-7.02 (m, 6H), 6.70 (d, J=12.3 Hz, 1H), 6.37 (td, J=6.7, 2.3 Hz, 2H), 5.03 (s, 2H), 4.11-4.05 (m, 1H), 3.85-3.67 (m, 6H), 2.89-2.79 (m, 4H), 2.45-2.39 (m, 5H), 2.23-2.17 (m, 2H), 2.07-2.01 (m, 2H), 1.86-1.80 (m, 2H); MS (ES+) m/z 689.3 (M+1), 691.3 (M+1).

Step 4. (S)-5-chloro-2-fluoro-4-((1-(1-(2-fluorophenyl)cyclobutyl)pyrrolidin-3-yl)(methyl)amino)-N-(thiazol-4-yl)benzenesulfonamide Formate

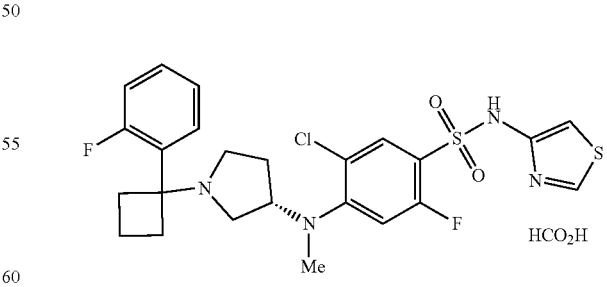

To a solution of (S)-5-chloro-N-(2,4-dimethoxybenzyl)-2-fluoro-4-((1-(1-(2-fluorophenyl)cyclobutyl)pyrrolidin-3-yl)(methyl)amino)-N-(thiazol-4-yl)benzenesulfonamide (0.20 g, 0.29 mmol) in anhydrous dichloromethane (5 mL) was added trifluoroacetic acid (0.22 mL, 2.90 mmol). The resulting solution was heated to reflux for 3 h, and then concentrated in vacuo. Purification of the residue by reverse-phase HPLC, eluting with a gradient of acetonitrile in water containing 0.1% formic acid, provided the title compound as a colorless solid (0.033 g, 19% yield): $^1$H NMR (300 MHz, DMSO-$d_6$), 8.89 (d, J=2.1 Hz, 1H), 8.15 (s, 1H), 7.66 (d, J=7.6 Hz, 1H), 7.31-7.27 (m, 1H), 7.17-7.02 (m, 5H), 4.05-4.02 (m, 1H), 2.76 (s, 3H), 2.70-2.60 (m, 2H), 2.43-2.26 (m, 5H), 2.13-1.97 (m, 3H), 1.77-1.69 (m, 2H), NH and COOH not observed; MS (ES+) m/z 537.2 (M+1), 539.2 (M+1).

Example 245

Synthesis of (S)-4-((1-((2,5-dimethyloxazol-4-yl)methyl)pyrrolidin-3-yl)(methyl)amino)-2-fluoro-5-methyl-N-(thiazol-4-yl)benzenesulfonamide 2,2,2-trifluoroacetate

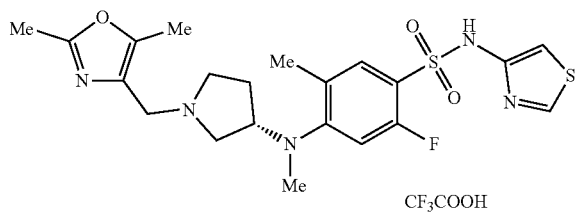 [SMILES: Cc1nc(CN2CC[C@H](N(C)c3cc(F)c(S(=O)(=O)Nc4cscn4)cc3C)C2)c(C)o1 ; "CF3COOH"]

Step 1. Preparation of (S)-4-((1-(2,5-dimethyloxazole-4-carbonyl)pyrrolidin-3-yl)(methyl)amino)-2-fluoro-N-(4-methoxybenzyl)-5-methyl-N-(thiazol-4-yl)benzenesulfonamide

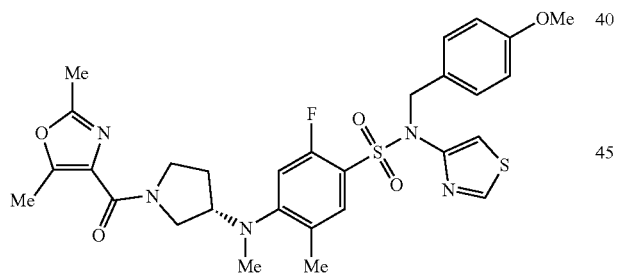

To a solution of (S)-2-fluoro-N-(4-methoxybenzyl)-5-methyl-4-(methyl(pyrrolidin-3-yl)amino)-N-(thiazol-4-yl)benzenesulfonamide (0.25 g, 0.50 mmol) in dichloromethane (5 mL) was added 2,5-dimethyloxazole-4-carboxylic acid (0.105 g, 0.75 mmol), N-(3-dimethylaminopropyl)-N'-ethylcarbodiimide hydrochloride (0.286 g, 1.50 mmol) and 4-(dimethylamino)pyridine (0.244 g, 2.0 mmol). The reaction mixture was stirred at ambient temperature for 1 h. The mixture was diluted with ethyl acetate (20 mL), washed with saturated ammonium chloride (2×20 mL), brine (10 mL), dried over anhydrous sodium sulfate, and filtered. Concentration of the filtrate in vacuo and purification of the residue by column chromatography, eluting with a gradient of 0 to 60% of ethyl acetate in hexanes, provided the title compound as a colorless solid (0.20 g, 65% yield): MS (ES+) m/z 614.4 (M+1).

Step 2. Preparation of (S)-4-((1-((2,5-dimethyloxazol-4-yl)methyl)pyrrolidin-3-yl)(methyl)amino)-2-fluoro-N-(4-methoxybenzyl)-5-methyl-N-(thiazol-4-yl)benzenesulfonamide

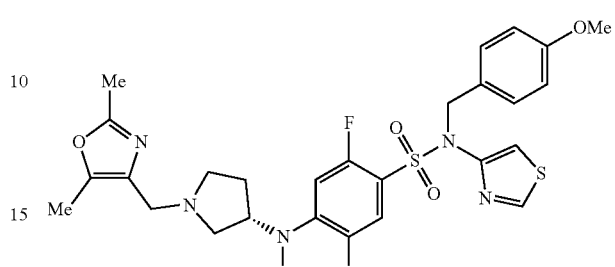

To a solution of (S)-4-((1-(2,5-dimethyloxazole-4-carbonyl)pyrrolidin-3-yl)(methyl)amino)-2-fluoro-N-(4-methoxybenzyl)-5-methyl-N-(thiazol-4-yl)benzenesulfonamide (0.15 g, 0.24 mmol) in anhydrous tetrahydrofuran (5 mL) was added a 1 M solution of lithium aluminum hydride in tetrahydrofuran (1.22 mL, 1.22 mmol) dropwise at 0° C. The reaction mixture was stirred at 0° C. for another 15 minutes and then quenched by slow addition of sodium sulfate decahydrate (1.22 g). The mixture was stirred at ambient temperature for 4 h, and filtered. Concentration of the filtrate in vacuo and purification of the residue by column chromatography, eluting with a gradient of 0-8% of methanol in dichloromethane, afforded the title compound as a colorless solid (0.055 g, 38% yield): MS (ES+) m/z 600.2 (M+1).

Step 3. Preparation of (S)-4-((1-((2,5-dimethyloxazol-4-yl)methyl)pyrrolidin-3-yl)(methyl)amino)-2-fluoro-5-methyl-N-(thiazol-4-yl)benzenesulfonamide 2,2,2-trifluoroacetate

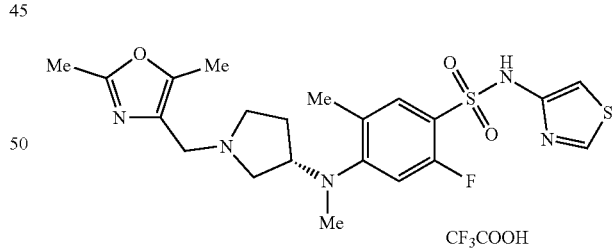

To a solution of (S)-4-((1-((2,5-dimethyloxazol-4-yl)methyl)pyrrolidin-3-yl)(methyl)amino)-2-fluoro-N-(4-methoxybenzyl)-5-methyl-N-(thiazol-4-yl)benzenesulfonamide (0.055 g, 0.091 mmol) in dichloromethane (4 mL) was added trifluoroacetic acid (2 mL). The reaction mixture was stirred at ambient temperature for 1 h and then concentrated in vacuo. Purification of the residue by column chromatography, eluting with a gradient of 0-10% of methanol in dichloromethane, afforded the title compound as a colorless solid (0.039 g, 89% yield): MS (ES+) m/z 480.2 (M+1).

Example 246

Synthesis of 5-chloro-4-(((S)-1-((R)-2,3-dihydro-1H-inden-1-yl)pyrrolidin-3-yl)(methyl)amino)-2-fluoro-N-(thiazol-4-yl)benzenesulfonamide 2,2,2-trifluoroacetate

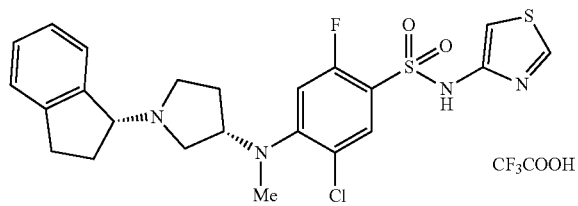 [SMILES: CN(c1cc(F)c(S(=O)(=O)Nc2cscn2)cc1Cl)[C@H]1CCN([C@@H]2CCc3ccccc32)C1 ; "CF3COOH"]

Step 1. Preparation of tert-butyl ((S)-1-((R)-2,3-dihydro-1H-inden-1-yl)pyrrolidin-3-yl)carbamate

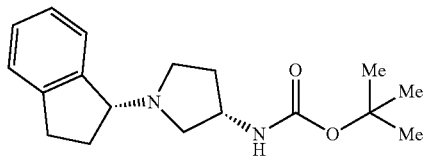 [SMILES: CC(C)(C)OC(=O)N[C@H]1CCN([C@@H]2CCc3ccccc32)C1]

Following the procedure as described in EXAMPLE 42, Step 2 and making non-critical variations as required to replace (S)-1-phenylethan-1-amine with (R)-2,3-dihydro-1H-inden-1-amine, the title compound was obtained as a brown syrup (1.44 g, 58% yield): MS (ES+) m/z 303.3 (M+1).

Step 2. Preparation of (S)-1-((R)-2,3-dihydro-1H-inden-1-yl)-N-methylpyrrolidin-3-amine

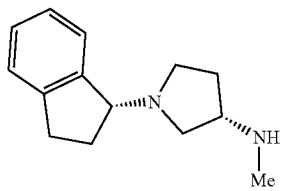 [SMILES: CN[C@H]1CCN([C@@H]2CCc3ccccc32)C1]

Following the procedure as described in EXAMPLE 42, Step 3 and making non-critical variations as required to replace tert-butyl ((S)-1-((S)-1-phenylethyl)pyrrolidin-3-yl)carbamate with tert-butyl ((S)-1-((R)-2,3-dihydro-1H-inden-1-yl)pyrrolidin-3-yl)carbamate, the title compound was obtained as a brown oil (0.86 g, 83% yield): MS (ES+) m/z 217.2 (M+1).

Step 3. Preparation of 5-chloro-4-(((S)-1-((R)-2,3-dihydro-1H-inden-1-yl)pyrrolidin-3-yl)(methyl)amino)-N-(2,4-dimethoxybenzyl)-2-fluoro-N-(thiazol-4-yl)benzenesulfonamide

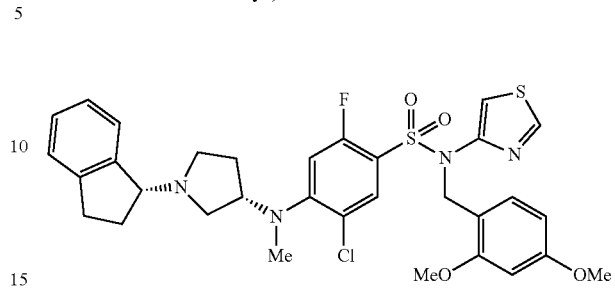

Following the procedure as described in EXAMPLE 242, Step 4 and making non-critical variations as required to replace (S)—N-methyl-1-((S)-1 phenylpropyl)pyrrolidin-3-amine with (S)-1-((R)-2,3-dihydro-1H-inden-1-yl)-N-methylpyrrolidin-3-amine, the title compound was obtained as a light brown syrup (0.28 g, 47% yield): $^1$H NMR (300 MHz, CDCl$_3$) δ 8.56 (d, J=2.3 Hz, 1H), 7.68 (d, J=7.4 Hz, 1H), 7.36-7.34 (m, 1H), 7.26-7.19 (m, 5H), 6.68 (d, J=12.2 Hz, 1H), 6.40-6.34 (m, 2H), 5.03 (s, 2H), 4.28-4.18 (m, 2H), 3.77 (s, 3H), 3.69 (s, 3H), 3.10-2.99 (m, 1H), 2.93-2.78 (m, 4H), 2.74-2.53 (m, 4H), 2.17-2.07 (m, 3H), 1.96-1.84 (m, 1H); MS (ES+) m/z 657.3 (M+1), 659.3 (M+1).

Step 4. Preparation of 5-chloro-4-(((S)-1-((R)-2,3-dihydro-1H-inden-1-yl)pyrrolidin-3-yl)(methyl)amino)-2-fluoro-N-(thiazol-4-yl)benzenesulfonamide 2,2,2-trifluoroacetate

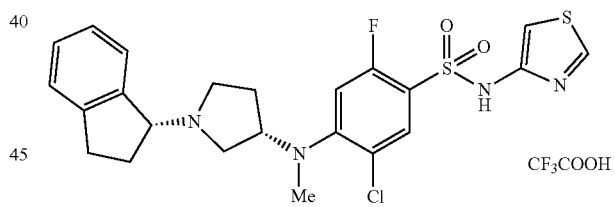

Following the procedure as described in EXAMPLE 242, Step 5 and making non-critical variations as required to replace 5-chloro-N-(2,4-dimethoxybenzyl)-2-fluoro-4-(methyl((S)-1-((S)-1-phenylpropyl)pyrrolidin-3-yl)amino)-N-(thiazol-4-yl)benzenesulfonamide with 5-chloro-4-(((S)-1-((R)-2,3-dihydro-1H-inden-1-yl)pyrrolidin-3-yl)(methyl)amino)-N-(2,4-dimethoxybenzyl)-2-fluoro-N-(thiazol-4-yl)benzenesulfonamide, the title compound was obtained as a colorless solid (0.21 g, 79% yield): $^1$H NMR (300 MHz, DMSO-d$_6$) δ 11.39 (br s, 1H), 10.39 (br s, 0.5H), 10.20 (br s, 0.5H), 8.91 (d, J=2.2 Hz, 1H), 7.75 (d, J=7.5 Hz, 1H), 7.65-7.58 (m, 1H), 7.42-7.38 (m, 2H), 7.34-7.28 (m, 1H), 7.24-7.18 (m, 1H), 7.08 (d, J=2.2 Hz, 1H), 4.98-4.85 (m, 1H), 4.53-4.42 (m, 0.5H), 4.33-4.22 (m, 0.5H), 3.62-3.46 (m, 3H), 3.38-3.08 (m, 2H), 2.94-2.84 (m, 1H), 2.76 (s, 3H), 2.43-2.35 (m, 2H), 2.21-1.99 (m, 2H); MS (ES+) m/z 507.1 (M+1), 509.1 (M+1).

Example 247

Synthesis of 3-chloro-4-(((S)-1-((S)-2,3-dihydro-1H-inden-1-yl)pyrrolidin-3-yl)(methyl)amino)-2-fluoro-N-(thiazol-4-yl)benzenesulfonamide 2,2,2-trifluoroacetate

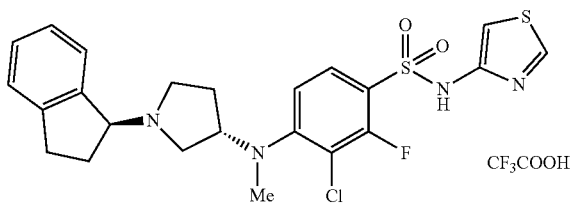 [SMILES: CN(c1ccc(S(=O)(=O)Nc2cscn2)c(F)c1Cl)[C@H]1CCN([C@H]2CCc3ccccc32)C1 ; "CF3COOH"]

Step 1. Preparation of tert-butyl ((3-chloro-2,4-difluorophenyl)sulfonyl)(thiazol-4-yl)carbamate

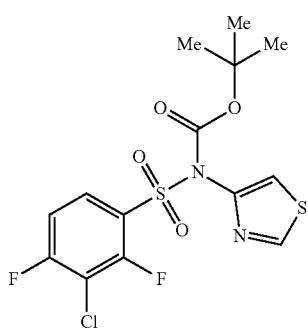 [SMILES: CC(C)(C)OC(=O)N(c1cscn1)S(=O)(=O)c1ccc(F)c(Cl)c1F]

To a solution of tert-butyl thiazol-4-ylcarbamate (110.00 g, 549.3 mmol) in anhydrous tetrahydrofuran (1000 mL) was added a 1 M solution of lithium bis(trimethylsilyl)amide in tetrahydrofuran (659 mL, 659 mmol) at −78° C. The reaction mixture was warmed to 5° C., stirred for 30 minutes, and cooled −78° C. To it was then added a solution of 3-chloro-2,4-difluoro-benzenesulfonyl chloride (162.8 g, 659 mmol) in anhydrous tetrahydrofuran (300 mL) at −78° C. The reaction mixture was allowed to warm to ambient temperature, stirred for 12 h, and then quenched by addition of saturated ammonium chloride (200 mL). The mixture was extracted with ethyl acetate (3×1000 mL), washed with brine (3×1000 mL), dried over anhydrous sodium sulfate, and filtered. Concentration of the filtrate in vacuo and trituration of the residue in methanol (300 mL) provided the title compound as colorless solid (75.0 g, 33% yield): $^1$H NMR (400 MHz, CDCl$_3$) δ 9.14 (s, 1H), 8.26-8.09 (m, 1H), 8.03 (s, 1H), 7.66 (br t, J=8.6 Hz, 1H), 1.27 (s, 9H); MS (ES+) m/z 432.8 (M+23), 434.8 (M+23).

Step 2. Preparation of 3-chloro-2,4-difluoro-N-(thiazol-4-yl)benzenesulfonamide

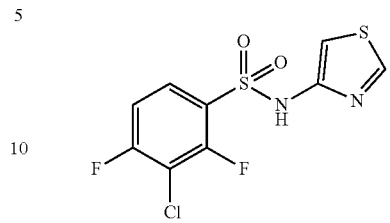

Following the procedure as described in EXAMPLE 107, Step 1 and making non-critical variations as required to replace of tert-butyl ((5-chloro-2,4-difluorophenyl)sulfonyl)(thiazol-4-yl)carbamate with tert-butyl ((3-chloro-2,4-difluorophenyl)sulfonyl)(thiazol-4-yl)carbamate, the title compound was obtained as a colorless solid (2.83 g, 87% yield): MS (ES+) m/z 311.0 (M+1), 313.0 (M+1).

Step 3. Preparation of 3-chloro-2,4-difluoro-N-(4-methoxybenzyl)-N-(thiazol-4-yl)benzenesulfonamide

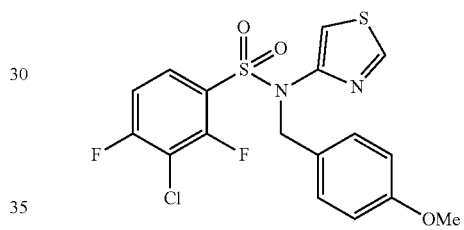

To a solution of 3-chloro-2,4-difluoro-N-(thiazol-4-yl)benzenesulfonamide (2.83 g, 9.11 mmol) in anhydrous dimethyl sulfoxide (10 mL) was added sodium bicarbonate (3.87 g, 46.1 mmol) and 1-(chloromethyl)-4-methoxybenzene (1.35 mL, 9.96 mmol). The mixture was stirred at 55° C. for 1 h, then cooled and filtered. The filtrate was purified by column chromatography, eluting with a 0-30% gradient of ethyl acetate in hexanes, to afford the title compound as a colorless solid (3.08 g, 78% yield): $^1$H NMR (300 MHz, CDCl$_3$) δ 8.56 (d, J=2.3 Hz, 1H), 7.70 (ddd, J=5.8, 7.4, 9.0 Hz, 1H), 7.25-7.20 (m, 2H), 7.18 (d, J=2.3 Hz, 1H), 7.04 (ddd, J=1.7, 7.6, 9.1 Hz, 1H), 6.82-6.77 (m, 2H), 5.03 (s, 2H), 3.77 (s, 3H); MS (ES+) m/z 431.1 (M+1), 433.1 (M+1).

Step 4. Preparation of 3-chloro-4-(((S)-1-((S)-2,3-dihydro-1H-inden-1-yl)pyrrolidin-3-yl)(methyl)amino)-2-fluoro-N-(4-methoxybenzyl)-N-(thiazol-4-yl)benzenesulfonamide

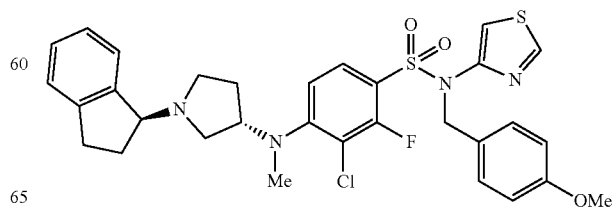

To a solution of 3-chloro-2,4-difluoro-N-(4-methoxybenzyl)-N-(thiazol-4-yl)benzenesulfonamide (0.48 g, 1.12 mmol) and (S)-1-((S)-2,3-dihydro-1H-inden-1-yl)-N-methylpyrrolidin-3-amine (0.25 g, 1.16 mmol) in anhydrous dimethyl sulfoxide (5 mL) was added N,N-diisopropylethylamine (0.80 mL, 4.6 mmol). The solution was heated to 80° C. for 21 h, then cooled to ambient temperature and diluted with ethyl acetate (150 mL). The mixture was washed with saturated aqueous ammonium chloride (100 mL), brine (100 mL), dried over anhydrous magnesium sulfate, filtered, and concentrated in vacuo. The residue was purified by column chromatography, eluting with a 0-50% gradient of ethyl acetate (containing 10% of triethylamine and 10% of isopropanol) in hexanes to afford the title compound as a light yellow syrup (0.23 g, 32% yield): $^1$H NMR (300 MHz, CDCl$_3$) δ 8.55 (d, J=2.3 Hz, 1H), 7.52 (dd, J=7.8, 8.8 Hz, 1H), 7.37-7.34 (m, 1H), 7.28-7.18 (m, 6H), 6.81-6.76 (m, 2H), 6.72 (dd, J=1.4, 8.9 Hz, 1H), 5.04 (s, 2H), 4.30-4.26 (m, 1H), 4.24-4.13 (m, 1H), 3.77 (s, 3H), 3.09-2.99 (m, 1H), 2.89-2.75 (m, 7H), 2.71-2.63 (m, 1H), 2.20-2.08 (m, 3H), 1.94-1.82 (m, 1H); MS (ES+) m/z 627.3 (M+1), 629.3 (M+1).

Step 5. Preparation of 3-chloro-4-(((S)-1-((S)-2,3-dihydro-1H-inden-1-yl)pyrrolidin-3-yl)(methyl)amino)-2-fluoro-N-(thiazol-4-yl)benzenesulfonamide 2,2,2-trifluoroacetate

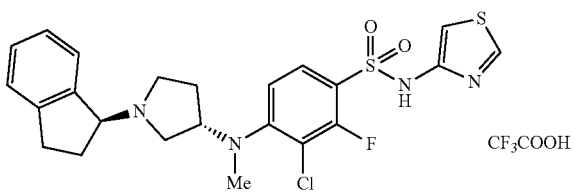 [SMILES: CN(c1ccc(S(=O)(=O)Nc2cscn2)c(F)c1Cl)[C@H]1CCN([C@H]2CCc3ccccc32)C1 ; "CF3COOH"]

To a solution of 3-chloro-4-(((S)-1-((S)-2,3-dihydro-1H-inden-1-yl)pyrrolidin-3-yl)(methyl)amino)-2-fluoro-N-(4-methoxybenzyl)-N-(thiazol-4-yl)benzenesulfonamide (0.11 g, 0.17 mmol) in dichloromethane (5 mL) was added trifluoroacetic acid (10 mL). The solution was heated to reflux for 6 h, then allowed to cool to ambient temperature and concentrated in vacuo. The residue was purified by column chromatography, eluting with a 0-10% gradient of methanol in dichloromethane, to afford the title compound as a colorless solid (0.091 g, 87% yield): H NMR (300 MHz, DMSO-d$_6$) δ 11.42 (br s, 1H), 10.55 (br s, 0.5H), 10.20 (br s, 0.5H), 8.90 (d, J=2.2 Hz, 1H), 7.72-7.60 (m, 2H), 7.44-7.38 (m, 2H), 7.34-7.28 (m, 1H), 7.13-7.09 (m, 1H), 7.06 (d, J=2.1 Hz, 1H), 4.97-4.92 (m, 1H), 4.51-4.24 (m, 1H), 3.87-3.42 (m, 3H), 3.30-3.05 (m, 2H), 2.93-2.76 (m, 4H), 2.46-2.36 (m, 2H), 2.21-1.98 (m, 2H); MS (ES+) m/z 507.1 (M+1), 509.1 (M+1).

Example 248

Synthesis of 5-chloro-4-(((S)-1-((S)-1-(2-chlorophenyl)propyl)pyrrolidin-3-yl)(methyl)amino)-2-fluoro-N-(thiazol-4-yl)benzenesulfonamide 2,2,2-trifluoroacetate

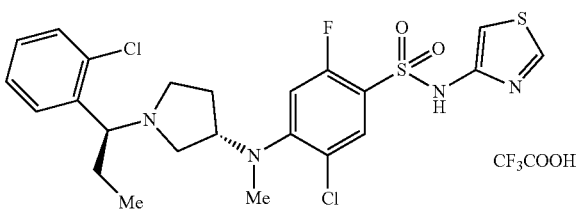 [SMILES: CC[C@@H](c1ccccc1Cl)N1CC[C@H](N(C)c2cc(F)c(S(=O)(=O)Nc3cscn3)cc2Cl)C1 ; "CF3COOH"]

Step 1. Preparation of tert-butyl ((S)-1-((S)-1-(2-chlorophenyl)propyl)pyrrolidin-3-yl)carbamate

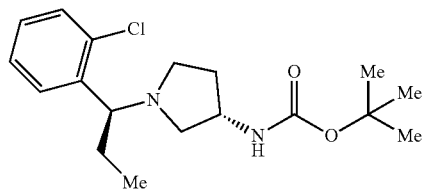 [SMILES: CC[C@@H](c1ccccc1Cl)N1CC[C@H](NC(=O)OC(C)(C)C)C1]

Following the procedure as described in EXAMPLE 42, Step 2 and making non-critical variations as required to replace (S)-1-phenylethan-1-amine with (S)-1-(2-chlorophenyl)propan-1-amine hydrochloride, the title compound was obtained as a yellow syrup (1.12 g, 68% yield): MS (ES+) m/z 339.3 (M+1), 341.3 (M+1).

Step 2. Preparation of (S)-1-((S)-1-(2-chlorophenyl)propyl)-N-methylpyrrolidin-3-amine

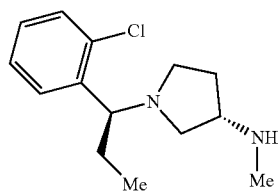 [SMILES: CC[C@@H](c1ccccc1Cl)N1CC[C@H](NC)C1]

Following the procedure as described in EXAMPLE 42, Step 3 and making non-critical variations as required to replace tert-butyl ((S)-1-((S)-1-phenylethyl)pyrrolidin-3-yl)carbamate with tert-butyl ((S)-1-((S)-1-(2-chlorophenyl)propyl)pyrrolidin-3-yl)carbamate, the title compound was obtained as a light yellow oil (0.63 g, 78% yield): MS (ES+) m/z 253.3 (M+1), 255.3 (M+1).

273

Step 3. Preparation of 5-chloro-4-(((S)-1-((S)-1-(2-chlorophenyl)propyl)-pyrrolidin-3-yl)(methyl)amino)-2-fluoro-N-(thiazol-4-yl)benzenesulfonamide 2,2,2-trifluoroacetate

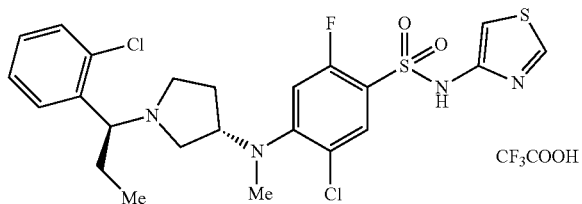 [SMILES: CC[C@@H](c1ccccc1Cl)N1CC[C@H](N(C)c2cc(F)c(S(=O)(=O)Nc3cscn3)cc2Cl)C1 ; "CF3COOH"]

To a solution of (S)-1-((S)-1-(2-chlorophenyl)propyl)-N-methylpyrrolidin-3-amine (0.56 g, 2.20 mmol) and 5-chloro-N-(2,4-dimethoxybenzyl)-2,4-difluoro-N-(thiazol-4-yl)benzenesulfonamide (0.98 g, 2.12 mmol) in anhydrous dimethyl sulfoxide (5 mL) was added N,N-diisopropylethylamine (1.4 mL, 7.7 mmol). The solution was heated to 80° C. for 22 h, then cooled to ambient temperature and diluted with ethyl acetate (150 mL). The mixture was washed with saturated aqueous ammonium chloride (100 mL), brine (100 mL), dried over anhydrous magnesium sulfate, filtered, and concentrated in vacuo. The residue was partially purified by column chromatography, eluting with a 0-30% gradient of ethyl acetate (containing 10% of triethylamine and 10% of isopropanol) in hexanes. The partially purified compound was dissolved in dichloromethane (10 mL) and trifluoroacetic acid (30 mL) and heated to reflux. After 5 minutes, the mixture was allowed to cool to ambient temperature and concentrated in vacuo. The residue was purified by reverse-phase preparative HPLC, eluting with a 20-80% gradient of acetonitrile in water (containing 0.1% trifluoroacetic acid) to afford the title compound as a colorless solid (0.047 g, 33% yield): $^1$H NMR (300 MHz, DMSO-$d_6$) δ 11.42-11.36 (m, 1H), 10.79 (br s, 0.5H), 10.53 (br s, 0.5H), 8.92-8.89 (m, 1H), 7.78-7.45 (m, 5H), 7.26-7.05 (m, 2H), 4.94-4.72 (m, 1H), 4.55-4.31 (m, 1H), 4.04-3.86 (m, 1H), 3.64-3.33 (m, 1H), 3.14-2.95 (m, 2H), 2.85-2.67 (m, 3H), 2.30-1.86 (m, 4H), 0.63 (t, J=7.3 Hz, 3H); MS (ES+) m/z 543.1 (M+1), 545.1 (M+1).

Example 249

Synthesis of 5-chloro-4-(((S)-1-((S)-2,3-dihydro-1H-inden-1-yl)pyrrolidin-3-yl)(methyl)amino)-2-fluoro-N-(thiazol-4-yl)benzenesulfonamide 2,2,2-trifluoroacetate

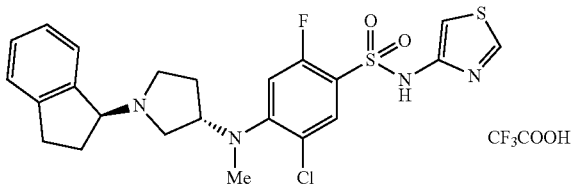 [SMILES: CN(c1cc(F)c(S(=O)(=O)Nc2cscn2)cc1Cl)[C@H]1CCN([C@H]2CCc3ccccc32)C1 ; "CF3COOH"]

274

Step 1. Preparation of tert-butyl ((S)-1-((S)-2,3-dihydro-1H-inden-1-yl)pyrrolidin-3-yl)carbamate

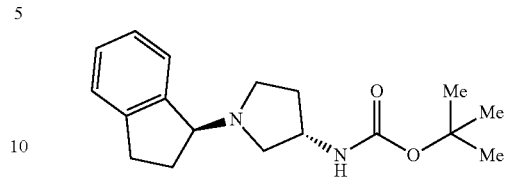

Following the procedure as described in EXAMPLE 42, Step 2 and making non-critical variations as required to replace (S)-1-phenylethan-1-amine with (S)-2,3-dihydro-1H-inden-1-amine, the title compound was obtained as a brown syrup (1.39 g, 58% yield): MS (ES+) m/z 303.3 (M+1).

Step 2. Preparation of (S)-1-((S)-2,3-dihydro-1H-inden-1-yl)-N-methylpyrrolidin-3-amine

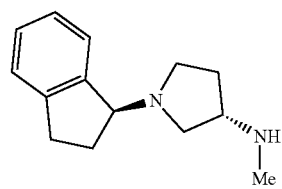 [SMILES: CN[C@H]1CCN([C@H]2CCc3ccccc32)C1]

Following the procedure as described in EXAMPLE 42, Step 3 and making non-critical variations as required to replace tert-butyl ((S)-1-((S)-1-phenylethyl)pyrrolidin-3-yl)carbamate with tert-butyl ((S)-1-((S)-2,3-dihydro-1H-inden-1-yl)pyrrolidin-3-yl)carbamate, the title compound was obtained as a brown oil (0.84 g, 85% yield): MS (ES+) m/z 217.3 (M+1).

Step 3. Preparation of 5-chloro-4-(((S)-1-((S)-2,3-dihydro-1H-inden-1-yl)pyrrolidin-3-yl)(methyl)amino)-N-(2,4-dimethoxybenzyl)-2-fluoro-N-(thiazol-4-yl)benzenesulfonamide

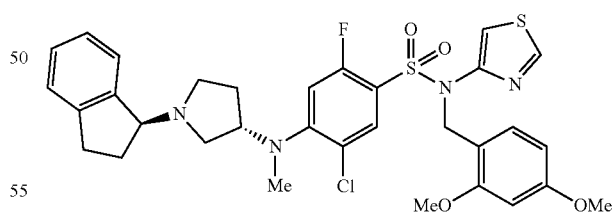

Following the procedure as described in EXAMPLE 242, Step 4 and making non-critical variations as required to replace (S)—N-methyl-1-((S)-1-phenylpropyl)pyrrolidin-3-amine with (S)-1-((S)-2,3-dihydro-1H-inden-1-yl)-N-methylpyrrolidin-3-amine, the title compound was obtained as a light brown syrup (0.33 g, 55% yield): $^1$H NMR (300 MHz, CDCl$_3$) δ 8.56 (d, J=2.3 Hz, 1H), 7.69 (d, J=7.4 Hz, 1H), 7.36-7.33 (m, 1H), 7.27-7.20 (m, 5H), 6.70 (d, J=12.2 Hz, 1H), 6.40-6.34 (m, 2H), 5.03 (s, 2H), 4.28-4.24 (m, 1H), 4.21-4.15 (m, 1H), 3.77 (s, 3H), 3.70 (s, 3H), 3.09-2.99 (m, 1H), 2.91-2.74 (m, 7H), 2.67-2.59 (m, 1H), 2.19-2.08 (m, 3H), 1.92-1.80 (m, 1H); MS (ES+) m/z 657.3 (M+1), 659.3 (M+1).

Step 4. Preparation of 5-chloro-4-(((S)-1-((S)-2,3-dihydro-1H-inden-1-yl)pyrrolidin-3-yl)(methyl)amino)-2-fluoro-N-(thiazol-4-yl)benzenesulfonamide 2,2,2-trifluoroacetate

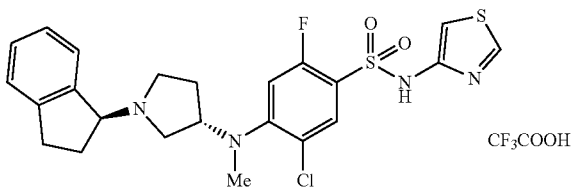 [SMILES: CN(c1cc(F)c(S(=O)(=O)Nc2cscn2)cc1Cl)[C@H]1CCN([C@H]2CCc3ccccc32)C1 ; "CF3COOH"]

Following the procedure as described in EXAMPLE 242, Step 5 and making non-critical variations as required to replace 5-chloro-N-(2,4-dimethoxybenzyl)-2-fluoro-4-(methyl((S)-1-((S)-1-phenylpropyl)pyrrolidin-3-yl)amino)-N-(thiazol-4-yl)benzenesulfonamide with 5-chloro-4-(((S)-1-((S)-2,3-dihydro-1H-inden-1-yl)pyrrolidin-3-yl)(methyl)amino)-N-(2,4-dimethoxybenzyl)-2-fluoro-N-(thiazol-4-yl)benzenesulfonamide, the title compound was obtained as a colorless solid (0.23 g, 74% yield): $^1$H NMR (300 MHz, DMSO-$d_6$) δ 11.40 (br s, 1H), 10.43 (br s, 0.5H), 10.10 (br s, 0.5H), 8.92 (d, J=2.1 Hz, 1H), 7.76 (d, J=7.4 Hz, 1H), 7.65-7.60 (m, 1H), 7.42-7.38 (m, 2H), 7.34-7.28 (m, 1H), 7.23 (d, J=12.2 Hz, 1H), 7.08 (d, J=2.2 Hz, 1H), 4.97-4.91 (m, 1H), 4.51-4.43 (m, 0.5H), 4.32-4.25 (m, 0.5H), 3.86-3.40 (m, 3H), 3.27-3.04 (m, 2H), 2.94-2.72 (m, 4H), 2.46-2.35 (m, 2H), 2.19-2.04 (m, 2H); MS (ES+) m/z 507.1 (M+1), 509.1 (M+1).

Example 250

Synthesis of 3-chloro-4-(methyl((S)-1-((S)-1-phenylethyl)pyrrolidin-3-yl)amino)-N-(thiazol-4-yl)benzenesulfonamide 2,2,2-trifluoroacetate

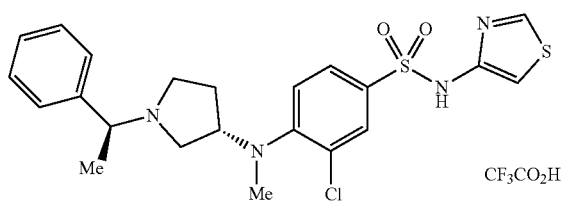 [SMILES: C[C@@H](c1ccccc1)N1CC[C@H](N(C)c2ccc(S(=O)(=O)Nc3cscn3)cc2Cl)C1 ; "CF3CO2H"]

Following the procedure as described for EXAMPLE 62, Step 5 and making non-critical variations as required to replace (S)—N-methyl-1-(2-phenylpropan-2-yl)pyrrolidin-3-amine with (S)—N-methyl-1-((S)-1-phenylethyl)pyrrolidin-3-amine and purification by preparative reverse-phase HPLC, eluting with a gradient of 10 to 60% of acetonitrile in water containing 0.1% of trifluoroacetic acid, the title compound was obtained as a colorless solid (0.045 g, 8% yield): $^1$H NMR (300 MHz, DMSO-$d_6$) δ 11.17-11.07 (br s, 1H), 10.56-10.24 (br s, 1H), 8.94-8.87 (m, 1H), 7.84-7.75 (m, 1H), 7.74-7.61 (m, 1H), 7.54-7.42 (m, 5H), 7.37-7.22 (m, 1H), 7.12-7.06 (m, 1H), 4.58-4.20 (m, 2H), 4.00-3.45 (m, 1H), 3.35-3.03 (m, 2H), 2.97-2.83 (m, 1H), 2.81-2.64 (m, 3H), 2.35-1.95 (m, 2H), 1.66-1.54 (m, 3H); MS (ES+) m/z 477.1 (M+1), 479.1 (M+1).

Example 251

Synthesis of 3-chloro-4-(methyl((S)-1-((R)-1-phenylethyl)pyrrolidin-3-yl)amino)-N-(thiazol-4-yl)benzenesulfonamide 2,2,2-trifluoroacetate

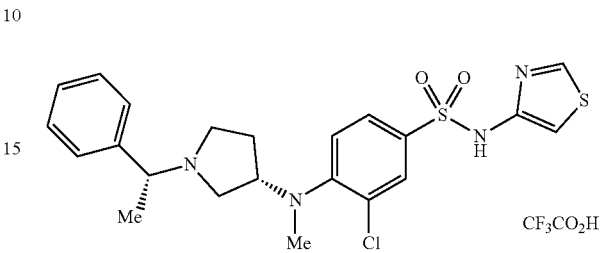

Following the procedure as described for EXAMPLE 62, Step 5 and making non-critical variations as required to replace (S)—N-methyl-1-(2-phenylpropan-2-yl)pyrrolidin-3-amine with (S)—N-methyl-1-((R)-1-phenylethyl)pyrrolidin-3-amine and purification by preparative reverse-phase HPLC, eluting with a gradient of 10 to 60% of acetonitrile in water containing 0.1% of trifluoroacetic acid, the title compound was obtained as a colorless solid (0.018 g, 3% yield): $^1$H NMR (300 MHz, DMSO-$d_6$) b 11.15-11.12 (m, 1H), 10.35-10.19 (m, 1H), 8.92-8.89 (m, 1H), 7.84-7.78 (m, 1H), 7.74-7.64 (m, 1H), 7.51-7.43 (m, 5H), 7.34-7.25 (m, 1H), 7.11-7.08 (m, 1H), 4.43-4.39 (m, 2H), 4.20-4.15 (m, 1H), 3.74-3.61 (m, 1H), 3.07-2.90 (m, 2H), 2.76-2.70 (m, 3H), 2.19-2.08 (m, 2H), 1.64-1.57 (m, 3H); MS (ES+) m/z 477.1 (M+1), 479.1 (M+1).

Example 252

Synthesis of (S)-3-chloro-4-((1-(2-chlorobenzyl)pyrrolidin-3-yl)(methyl)amino)-N-(1,2,4-thiadiazol-5-yl)benzenesulfonamide 2,2,2-trifluoroacetate

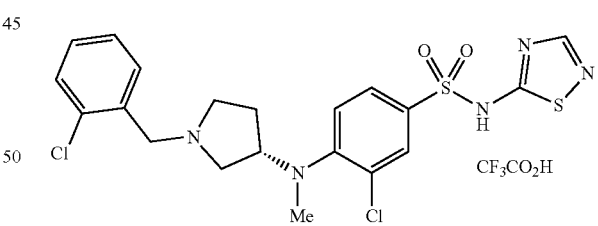

Following the procedure as described for EXAMPLE 29, Step 4 and making non-critical variations as required to replace benzaldehyde with 2-chlorobenzaldehyde and purification by preparative reverse-phase HPLC, eluting with a gradient of 10 to 60% of acetonitrile in water containing 0.1% of trifluoroacetic acid, the title compound was obtained as a colorless solid (0.060 g, 32% yield): $^1$H NMR (300 MHz, DMSO-$d_6$) δ 10.51 (br s, 2H), 8.53-8.47 (m, 1H), 7.75 (d, J=2.2 Hz, 1H), 7.72-7.68 (m, 2H), 7.61-7.58 (m, 1H), 7.53-7.43 (m, 2H), 7.35 (d, J=8.5 Hz, 1H), 4.57 (s, 2H), 4.37-4.34 (m, 1H), 3.67-3.59 (m, 1H), 3.45-3.38 (m, 3H), 2.77 (s, 3H), 2.15-2.12 (m, 2H); MS (ES+) m/z 498.0 (M+1), 500.0 (M+1).

Example 253

Synthesis of (S)-3-chloro-4-((1-(3-(difluoromethyl) benzyl)pyrrolidin-3-yl)(methyl)amino)-N-(thiazol-4-yl)benzenesulfonamide Formate

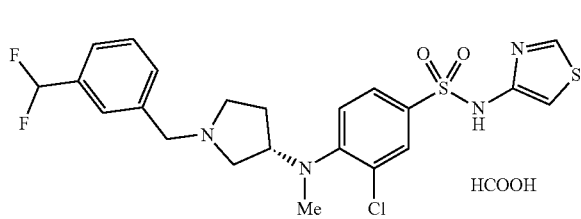 [SMILES: CN(c1ccc(S(=O)(=O)Nc2cscn2)cc1Cl)[C@H]1CCN(Cc2cccc(C(F)F)c2)C1 ; "HCOOH"]

Step 1. Preparation of tert-butyl (S)-3-((2-chloro-4-(N-(thiazol-4-yl)sulfamoyl)phenyl)(methyl)amino) pyrrolidine-1-carboxylate

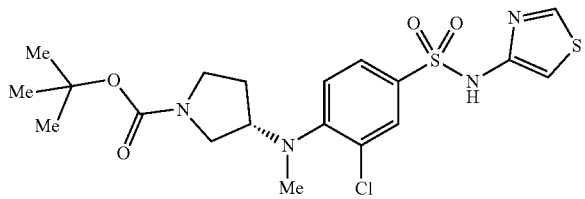 [SMILES: CN(c1ccc(S(=O)(=O)Nc2cscn2)cc1Cl)[C@H]1CCN(C(=O)OC(C)(C)C)C1]

Following the procedure as described for EXAMPLE 62, Step 5 and making non-critical variations as required to replace (S)—N-methyl-1-(2-phenylpropan-2-yl)pyrrolidin-3-amine with tert-butyl (S)-3-(methylamino)pyrrolidine-1-carboxylate and purification by column chromatography, eluting with a gradient of 0 to 60% of ethyl acetate in hexanes, the title compound was obtained as a beige solid (0.92 g, 49% yield): MS (ES+) m/z 473.0 (M+1), 475.0 (M+1).

Step 2. Preparation of (S)-3-chloro-4-(methyl(pyrrolidin-3-yl)amino)-N-(thiazol-4-yl)benzenesulfonamide 2,2,2-trifluoroacetate

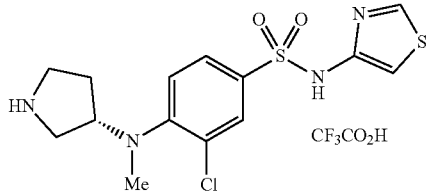 [SMILES: CN(c1ccc(S(=O)(=O)Nc2cscn2)cc1Cl)[C@H]1CCNC1 ; "CF3CO2H"]

To a solution of tert-butyl (S)-3-((2-chloro-4-(N-(thiazol-4-yl)sulfamoyl)phenyl)-(methyl)amino)pyrrolidine-1-carboxylate (0.92 g, 1.95 mmol) in dichloromethane (50 mL) was added trifluoroacetic acid (15 mL). The reaction mixture was stirred for 30 minutes. Concentration in vacuo afforded the title compound as beige foam (0.94 g, quantitative yield): 373.0 (M+1), 375.0 (M+1).

Step 3. Preparation of (S)-3-chloro-4-((1-(3-(difluoromethyl)benzyl)pyrrolidin-3-yl)(methyl)amino)-N-(thiazol-4-yl)benzenesulfonamide Formate

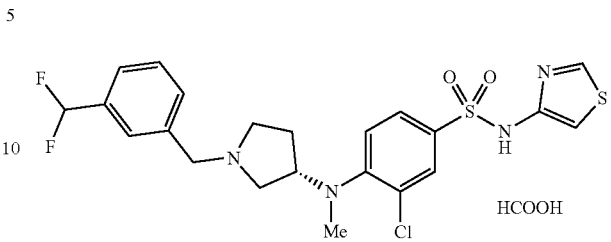

To a mixture of (S)-3-chloro-4-(methyl(pyrrolidin-3-yl)amino)-N-(thiazol-4-yl)benzenesulfonamide 2,2,2-trifluoroacetate (0.36 g, 0.75 mmol) and 3-(difluoromethyl)benzaldehyde (0.023 g, 1.50 mmol) in 1,2-dichloroethane (5 mL) and N,N-dimethylformamide (5 mL) was added sodium triacetoxyborohydride (0.32 g, 1.50 mmol). The reaction mixture was stirred for 5 h at ambient temperature and then diluted with ethyl acetate (60 mL). The mixture was washed with saturated ammonium chloride (2×30 mL), dried over anhydrous sodium sulfate, and filtered. The filtrate was concentrated in vacuo and the residue purified by column chromatography, eluting with a gradient of 0 to 20% of methanol (containing 0.2% of ammonium hydroxide) in dichloromethane. Additional purification by preparative reverse-phase HPLC, eluting with a gradient of 10 to 55% of acetonitrile in water containing 0.1% of formic acid, afforded the title compound as a colorless solid (0.050 g, 12% yield): $^{1}$H NMR (300 MHz, DMSO-$d_6$) δ 11.56 (s, 2H), 8.89 (d, J=2.2 Hz, 1H), 8.15 (s, 1H), 7.75 (d, J=2.2 Hz, 1H), 7.63 (dd, J=8.6, 2.3 Hz, 1H), 7.51-7.44 (m, 4H), 7.21 (d, J=8.6 Hz, 1H), 7.05 (d, J=2.1 Hz, 1H), 7.03 (t, J=55.9 Hz, 1H), 4.17-4.07 (m, 1H), 3.70 (d, J=13.4 Hz, 1H), 3.57 (d, J=13.3 Hz, 1H), 2.76 (s, 3H), 2.73-2.66 (m, 1H), 2.60 (d, J=6.4 Hz, 2H), 2.43-2.33 (m, 1H), 2.11-1.99 (m, 1H), 1.85-1.73 (m, 1H); MS (ES+) m/z 513.1 (M+1) δ 15.0 (M+1).

Example 254

Synthesis of (S)-3-chloro-4-((1-(5-chloro-2-fluorobenzyl)pyrrolidin-3-yl)(methyl)amino)-N-(thiazol-4-yl)benzenesulfonamide Formate

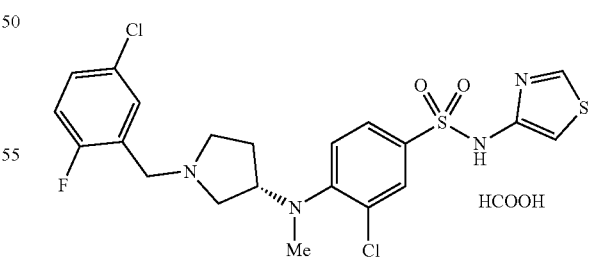

Following the procedure as described for EXAMPLE 253, Step 3 and making non-critical variations as required to replace 3-(difluoromethyl)benzaldehyde with 5-chloro-2-fluorobenzaldehyde, the title compound was obtained as a colorless solid (0.080 g, 19% yield): $^{1}$H NMR (300 MHz, DMSO-$d_6$) δ 11.62 (s, 1H), 8.89 (d, J=2.2 Hz, 1H), 8.15 (s, 1H), 7.75 (d, J=2.3 Hz, 1H), 7.64 (dd, J=8.6, 2.3 Hz, 1H), 7.46 (dd, J=6.3, 2.7 Hz, 1H), 7.37 (ddd, J=8.7, 4.5, 2.8 Hz, 1H), 7.23 (t, J=8.8 Hz, 2H), 7.06 (d, J=2.2 Hz, 1H), 4.15-4.06 (m, 1H), 3.67-3.55 (m, 2H), 2.74 (s, 3H), 2.70-2.58 (m, 3H), 2.43-2.35 (m, 1H), 2.10-1.98 (m, 1H), 1.83-1.71 (m, 1H), COOH not observed; MS (ES+) m/z 515.0 (M+1), 517.0 (M+1).

Example 255

Synthesis of 4-((1-benzyl-3-methylazetidin-3-yl)amino)-3-chloro-N-(thiazol-4-yl)benzenesulfonamide 2,2,2-trifluoroacetate

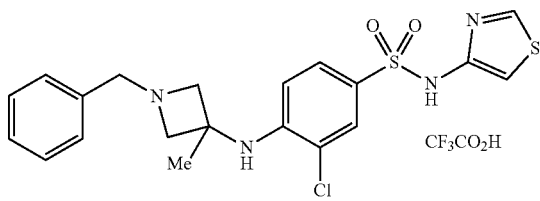 [SMILES: CC1(Nc2ccc(S(=O)(=O)Nc3cscn3)cc2Cl)CN(Cc2ccccc2)C1 ; "CF3CO2H"]

To a mixture of tert-butyl ((3-chloro-4-fluorophenyl)sulfonyl)(thiazol-4-yl)carbamate (0.56 g, 1.42 mmol) and 1-benzyl-3-methylazetidin-3-amine (0.25 g, 1.42 mmol) in anhydrous dimethyl sulfoxide (3 mL) was added potassium carbonate (0.39 g, 2.84 mmol). The reaction mixture was heated to 50° C. under nitrogen for 18 h and then diluted with ethyl acetate (150 mL). The mixture was washed with water (15 mL), brine (15 mL), dried over anhydrous sodium sulfate, and filtered. The filtrate was concentrated in vacuo. The residue was dissolved in dichloromethane (10 mL) and trifluoroacetic acid (2 mL) was added. The mixture was stirred for 18 h at ambient temperature and then concentrated in vacuo. The residue was purified by preparative reverse-phase HPLC, eluting with a gradient of 8 to 60% of acetonitrile in water containing 0.1% of trifluoroacetic acid, to afford the title compound as a colorless solid (0.035 g, 4% yield): $^1$H NMR (300 MHz, CD$_3$OD) b 8.72 (d, J=2.0 Hz, 1H), 7.78 (d, J=2.2 Hz, 1H), 7.62 (dd, J=8.7, 2.2 Hz, 1H), 7.49 (s, 5H), 7.04 (d, J=2.2 Hz, 1H), 6.47-6.39 (m, 1H), 4.45 (s, 2H), 4.38-4.28 (m, 4H), 1.67 (s, 3H), NH and COOH not observed; MS (ES+) m/z 449.1 (M+1), 451.0 (M+1).

Example 256

Synthesis of 3-chloro-4-(((1R,3s,5S)-8-(3-(difluoromethyl)benzyl)-8-azabicyclo[3.2.1]octan-3-yl)oxy)-N-(thiazol-4-yl)benzenesulfonamide

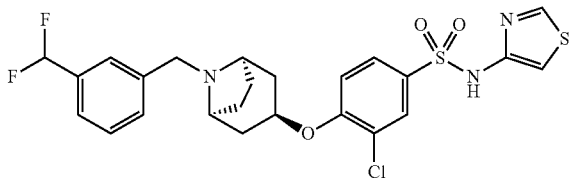 [SMILES: O=S(=O)(Nc1cscn1)c1ccc(O[C@@H]2C[C@H]3CC[C@@H](C2)N3Cc2cccc(C(F)F)c2)c(Cl)c1]

Step 1. Preparation of tert-butyl (1R,3s,5S)-3-(2-chloro-4-(N-(thiazol-4-yl)sulfamoyl)phenoxy)-8-azabicyclo[3.2.1]octane-8-carboxylate

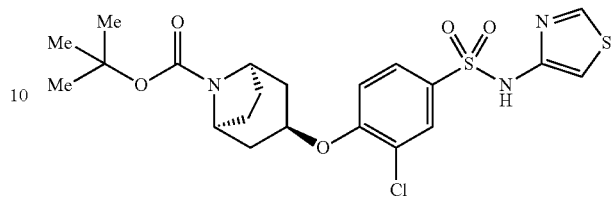

Following the procedure as described for EXAMPLE 57, Step 3 and making non-critical variations as required to replace (R)-1-(1-phenylethyl)piperidin-4-ol with tert-butyl (1R,3s,5S)-3-hydroxy-8-azabicyclo[3.2.1]octane-8-carboxylate and purification by trituration with diethyl ether (25 mL), the title compound was obtained as a colorless solid (2.01 g, 83% yield): MS (ES-) m/z 498.4 (M−1), 500.4 (M−1).

Step 2. Preparation of 4-(((1R,3s,5S)-8-azabicyclo[3.2.1]octan-3-yl)oxy)-3-chloro-N-(thiazol-4-yl)benzenesulfonamide 2,2,2-trifluoroacetate

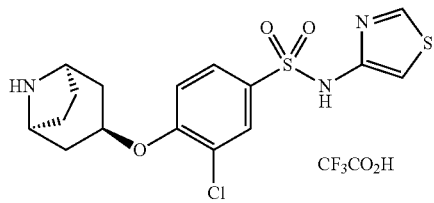 [SMILES: O=S(=O)(Nc1cscn1)c1ccc(O[C@@H]2C[C@H]3CC[C@@H](C2)N3)c(Cl)c1 ; "CF3CO2H"]

Following the procedure as described for EXAMPLE 253, Step 2 and making non-critical variations as required to replace tert-butyl (S)-3-((2-chloro-4-(N-(thiazol-4-yl)sulfamoyl)phenyl)(methyl)amino)pyrrolidine-1-carboxylate with tert-butyl (1R,3s,5S)-3-(2-chloro-4-(N-(thiazol-4-yl)sulfamoyl)phenoxy)-8-azabicyclo[3.2.1]octane-8-carboxylate, the title compound was obtained as a colorless foam (2.06 g, quantitative yield): MS (ES+) m/z 400.2 (M+1), 402.2 (M+1).

Step 3. Preparation of 3-chloro-4-(((1R,3s,5S)-8-(3-(difluoromethyl)benzyl)-8-azabicyclo[3.2.1]octan-3-yl)oxy)-N-(thiazol-4-yl)benzenesulfonamide

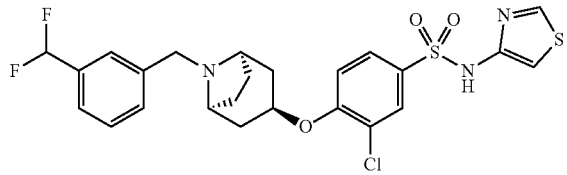 [SMILES: O=S(=O)(Nc1cscn1)c1ccc(O[C@@H]2C[C@H]3CC[C@@H](C2)N3Cc2cccc(C(F)F)c2)c(Cl)c1]

Following the procedure as described for 257, Step 3 and making non-critical variations as required to replace (S)-3-chloro-4-(methyl(pyrrolidin-3-yl)amino)-N-(thiazol-4-yl)benzenesulfonamide 2,2,2-trifluoroacetate with 4-(((1R,3s, 5S)-8-azabicyclo[3.2.1]octan-3-yl)oxy)-3-chloro-N-(thiazol-4-yl)benzenesulfonamide 2,2,2-trifluoroacetate, and purification by column chromatography, eluting with a gradient of 0 to 15% of methanol (containing 0.1% of ammonium hydroxide) in dichloromethane, the title compound was obtained as a colorless solid (0.12 g, 38% yield): $^1$H NMR (300 MHz, DMSO-$d_6$) δ 10.94 (s, 1H), 8.89 (d, J=2.2 Hz, 1H), 7.83 (d, J=2.3 Hz, 1H), 7.75-7.67 (m, 3H), 7.54 (t, J=5.1 Hz, 2H), 7.49 (d, J=9.0 Hz, 1H), 7.25-6.88 (m, 2H), 4.97-4.86 (m, 1H), 4.00-3.93 (m, 2H), 3.58-3.50 (m, 2H), 2.17-2.12 (m, 4H), 1.99-1.91 (m, 4H); MS (ES+) m/z 540.1 (M+1), 542.1 (M+1).

Example 257

Synthesis of (S)-5-chloro-2-fluoro-4-(methyl(1-(2-phenylpropan-2-yl)pyrrolidin-3-yl)amino)-N-(thiazol-4-yl)benzenesulfonamide Formate

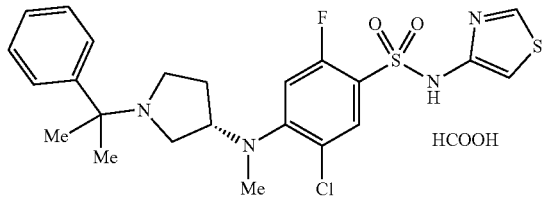 [SMILES: CN(c1cc(F)c(S(=O)(=O)Nc2cscn2)cc1Cl)[C@H]1CCN(C(C)(C)c2ccccc2)C1 ; "HCOOH"]

To a mixture of 5-chloro-N-(2,4-dimethoxybenzyl)-2,4-difluoro-N-(thiazol-4-yl)benzenesulfonamide (0.38 g, 0.82 mmol) and (S)—N-methyl-1-(2-phenylpropan-2-yl)pyrrolidin-3-amine (0.18 g, 0.82 mmol) in anhydrous dimethyl sulfoxide (6 mL) was added cesium carbonate (0.53 g, 1.64 mmol). The resulting mixture was stirred for 18 h at ambient temperature and then diluted with ethyl acetate (60 mL). The mixture was washed with water (50 mL), saturated ammonium chloride (50 mL), brine (30 mL), dried over anhydrous sodium sulfate, and filtered. Concentration of the filtrate in vacuo provided a residue which was dissolved in dichloromethane (10 mL) and trifluoroacetic acid (2 mL) was added to it. The reaction mixture was stirred for 20 minutes at ambient temperature and then concentrated in vacuo. The residue was triturated in methanol (20 mL). Filtration and concentration of the filtrate in vacuo provided a residue which was dissolved in ethyl acetate (25 mL). The organic phase was washed with saturated sodium bicarbonate (2×25 mL), brine (25 mL), dried over anhydrous sodium sulfate, and filtered. Concentration of the filtrate in vacuo and purification of the residue was purified by preparative reverse-phase HPLC, eluting with a gradient of 7 to 60% of acetonitrile in water containing 0.1% of formic acid, afforded the title compound as a colorless solid (0.020 g, 4% yield): $^1$H NMR (300 MHz, DMSO-$d_6$) δ 8.82 (d, J=2.2 Hz, 1H), 8.23-8.17 (m, 1H), 7.66 (d, J=7.6 Hz, 1H), 7.50-7.46 (m, 2H), 7.33-7.28 (m, 2H), 7.22-7.17 (m, 1H), 7.03 (d, J=12.3 Hz, 1H), 6.80 (d, J=2.0 Hz, 1H), 4.11-4.01 (m, 1H), 2.77 (s, 3H), 2.68-2.53 (m, 3H), 2.40-2.32 (m, 1H), 2.03-1.92 (m, 1H), 1.79-1.69 (m, 1H), 1.34 (s, 6H), NH and COOH not observed; MS (ES+) m/z 509.2 (M+1), 511.2 (M+1).

Example 258

Synthesis of (S)-4-((1-benzylpyrrolidin-3-yl)amino)-5-chloro-2-fluoro-N-(thiazol-4-yl)benzenesulfonamide Formate

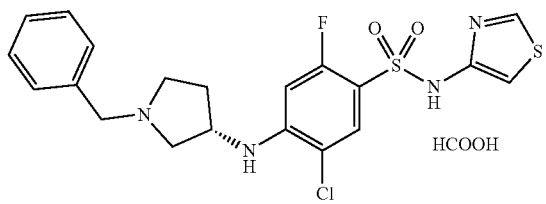 [SMILES: O=S(=O)(Nc1cscn1)c1cc(Cl)c(N[C@H]2CCN(Cc3ccccc3)C2)cc1F ; "HCOOH"]

Step 1. Preparation of (S)-5-chloro-2-fluoro-4-(pyrrolidin-3-ylamino)-N-(thiazol-4-yl)benzenesulfonamide 2,2,2-trifluoroacetate

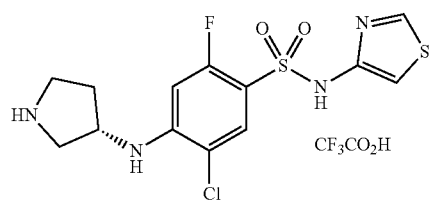 [SMILES: O=S(=O)(Nc1cscn1)c1cc(Cl)c(N[C@H]2CCNC2)cc1F ; "CF3CO2H"]

Following the procedure as described for EXAMPLE 253, Step 2 and making non-critical variations as required to replace tert-butyl (S)-3-((2-chloro-4-(N-(thiazol-4-yl)sulfamoyl)phenyl)(methyl)amino)pyrrolidine-1-carboxylate with tert-butyl (S)-3-((4-(N-(tert-butoxycarbonyl)-N-(thiazol-4-yl)sulfamoyl)-2-chloro-5-fluorophenyl)amino)pyrrolidine-1-carboxylate, the title compound was obtained as a colorless foam (2.53 g, quantitative yield): MS (ES+) m/z 377.2 (M+1), 379.2 (M+1).

Step 2. Preparation of (S)-4-((1-benzylpyrrolidin-3-yl)amino)-5-chloro-2-fluoro-N-(thiazol-4-yl)benzenesulfonamide Formate

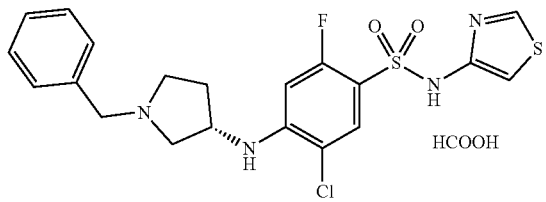 [SMILES: O=S(=O)(Nc1cscn1)c1cc(Cl)c(N[C@H]2CCN(Cc3ccccc3)C2)cc1F ; "HCOOH"]

Following the procedure as described for EXAMPLE 29, Step 4 and making non-critical variations as required to replace (S)-3-chloro-4-(methyl(pyrrolidin-3-yl)amino)-N-(1,2,4-thiadiazol-5-yl)benzenesulfonamide 2,2,2-trifluoroacetate with (S)-5-chloro-2-fluoro-4-(pyrrolidin-3-ylamino)-N-(thiazol-4-yl)benzenesulfonamide 2,2,2-trifluoroacetate and purification by preparative reverse-phase HPLC, eluting with a gradient of 10 to 60% of acetonitrile in water containing 0.1% of formic acid, the title compound was obtained as a colorless solid (0.140 g, 22% yield): $^1$H NMR (300 MHz, DMSO-$d_6$) δ 8.88 (d, J=2.2 Hz, 1H), 8.18 (s, 1H), 7.59 (d, J=7.4 Hz, 1H), 7.33-7.22 (m, 5H), 6.95 (d, J=2.2 Hz, 1H), 6.75 (d, J=13.3 Hz, 1H), 6.14 (dd, J=7.1, 1.4 Hz, 1H), 4.10-4.03 (m, 1H), 3.61 (s, 2H), 2.80 (dd, J=9.4, 6.9 Hz, 1H), 2.71-2.63 (m, 1H), 2.45-2.40 (m, 2H), 2.27-2.17 (m, 1H), 1.80-1.70 (m, 1H), NH and COOH not observed; MS (ES+) m/z 467.2 (M+1), 469.2 (M+1).

Example 259

Synthesis of (S)-5-chloro-2-fluoro-4-(methyl(1-(1-phenylcyclopropyl)pyrrolidin-3-yl)amino)-N-(thiazol-4-yl)benzenesulfonamide 2,2,2-trifluoroacetate

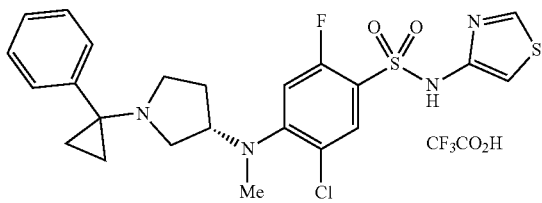 [SMILES: CN(c1cc(F)c(S(=O)(=O)Nc2cscn2)cc1Cl)[C@H]1CCN(C2(c3ccccc3)CC2)C1 ; "CF3CO2H"]

Step 1. Preparation of tert-butyl (S)-(1-(1-phenylcyclopropyl)pyrrolidin-3-yl)carbamate

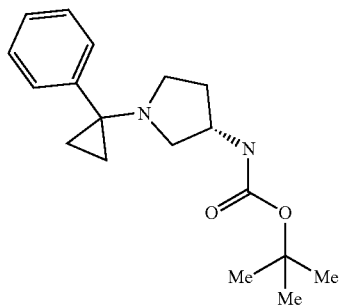 [SMILES: CC(C)(C)OC(=O)N[C@H]1CCN(C2(c3ccccc3)CC2)C1]

Following the procedure as described for EXAMPLE 42, Step 2 and making non-critical variations as required to replace (S)-1-phenylethan-1-amine with 1-phenylcyclopropan-1-amine and purification by trituration with ethyl acetate (35 mL), the title compound was obtained as a colorless oil (2.73 g, 65% yield): MS (ES+) m/z 303.2 (M+1).

Step 2. Preparation of (S)—N-methyl-1-(1-phenylcyclopropyl)pyrrolidin-3-amine

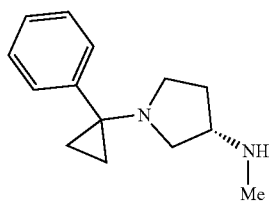 [SMILES: CN[C@H]1CCN(C2(c3ccccc3)CC2)C1]

Following the procedure as described for EXAMPLE 42, Step 3 and making non-critical variations as required to replace tert-butyl ((S)-1-((S)-1-phenylethyl)-pyrrolidin-3-yl)carbamate with tert-butyl (S)-(1-(1-phenylcyclopropyl) pyrrolidin-3-yl)carbamate, the title compound was obtained as a colorless oil (1.36 g, 70% yield): MS (ES+) m/z 217.3 (M+1).

Step 3. Preparation of (S)-5-chloro-2-fluoro-4-(methyl(1-(1-phenylcyclopropyl)pyrrolidin-3-yl)amino)-N-(thiazol-4-yl)benzenesulfonamide 2,2,2-trifluoroacetate

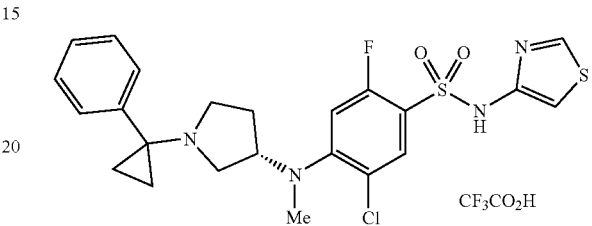

Following the procedure as described for EXAMPLE 257 and making non-critical variations as required to replace (S)—N-methyl-1-(2-phenylpropan-2-yl)pyrrolidin-3-amine with (S)—N-methyl-1-(1-phenylcyclopropyl)pyrrolidin-3-amine, and purification by preparative reverse-phase HPLC, eluting with a gradient of 10 to 60% of acetonitrile in water containing 0.1% of trifluoroacetic acid, the title compound was obtained as a colorless solid (0.045 g, 7% yield): $^1$H NMR (300 MHz, CD$_3$OD) δ 8.73 (d, J=2.2 Hz, 1H), 7.79 (d, J=7.4 Hz, 1H), 7.64 (dt, J=5.3, 2.1 Hz, 2H), 7.53-7.46 (m, 4H), 7.05 (d, J=2.2 Hz, 1H), 7.02 (d, J=11.7 Hz, 1H), 4.20-4.07 (m, 1H), 3.83-3.76 (m, 1H), 3.55-3.41 (m, 2H), 2.63-2.57 (m, 3H), 2.12-1.96 (m, 2H), 1.59-1.55 (m, 2H), 1.31-1.27 (m, 2H), NH and COOH not observed; MS (ES+) m/z 507.3 (M+1), 509.3 (M+1).

Example 260

Synthesis of (S)-5-chloro-2-fluoro-N-(6-fluoropyridin-2-yl)-4-(methyl(1-(2-phenylpropan-2-yl)pyrrolidin-3-yl)amino)benzenesulfonamide 2,2,2-trifluoroacetate

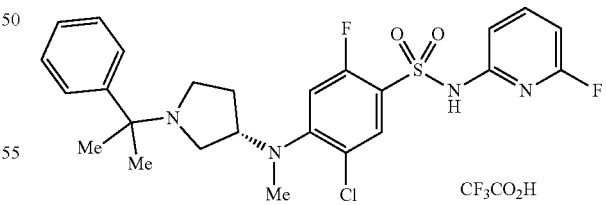

Following the procedure as described for EXAMPLE 257 and making non-critical variations as required to replace 5-chloro-N-(2,4-dimethoxybenzyl)-2,4-difluoro-N-(thiazol-4-yl)benzenesulfonamide with 5-chloro-N-(2,4-dimethoxybenzyl)-2,4-difluoro-N-(6-fluoropyridin-2-yl)benzenesulfonamide, and purification by preparative reverse-phase HPLC, eluting with a gradient of 10 to 60% of acetonitrile in water containing 0.1% of trifluoroacetic acid, the title compound was obtained as a colorless solid (0.34 g, 54% yield): ¹H NMR (300 MHz, CD₃OD) b 7.99 (d, J=7.1 Hz, 1H), 7.78 (q, J=8.1 Hz, 1H), 7.71-7.65 (m, 2H), 7.56-7.45 (m, 3H), 7.07 (d, J=11.8 Hz, 1H), 6.93 (dd, J=7.8, 1.9 Hz, 1H), 6.62 (dd, J=7.9, 2.4 Hz, 1H), 4.34-4.24 (m, 1H), 3.63-3.56 (m, 1H), 3.43-3.35 (m, 1H), 3.29-3.21 (m, 2H), 2.82-2.66 (m, 3H), 2.18-2.08 (m, 2H), 1.87 (s, 6H), NH and COOH not observed; MS (ES+) m/z 521.3 (M+1), 523.3 (M+1).

Example 261

Synthesis of (R)-4-((1-benzylpyrrolidin-3-yl) amino)-5-chloro-2-fluoro-N-(thiazol-4-yl)benzenesulfonamide

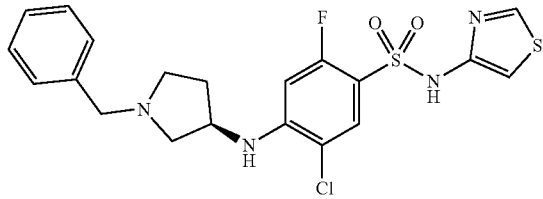 [SMILES: O=S(=O)(Nc1cscn1)c1cc(Cl)c(N[C@@H]2CCN(Cc3ccccc3)C2)cc1F]

Step 1. Preparation of tert-butyl (R)-3-((4-(N-(tert-butoxycarbonyl)-N-(thiazol-4-yl)sulfamoyl)-2-chloro-5-fluorophenyl)amino)pyrrolidine-1-carboxylate

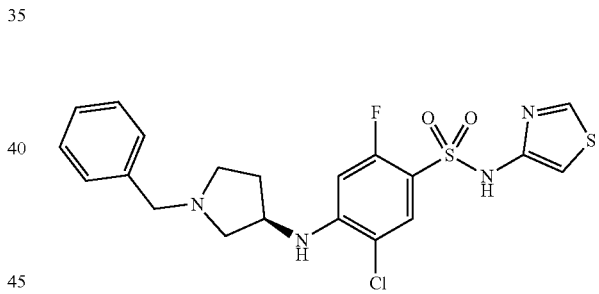

Following the procedure as described for EXAMPLE 101, Step 1 and making non-critical variations as required to replace tert-butyl (S)-3-aminopyrrolidine-1-carboxylate with tert-butyl (R)-3-aminopyrrolidine-1-carboxylate, the title compound was obtained as a colorless foam (2.04 g, 68% yield): ¹H NMR (300 MHz, CDCl₃) δ 8.81 (d, J=2.3 Hz, 1H), 7.99 (d, J=7.1 Hz, 1H), 7.52 (d, J=2.2 Hz, 1H), 6.42 (d, J=12.2 Hz, 1H), 5.05-5.01 (m, 1H), 4.08-4.06 (m, 1H), 3.81-3.76 (m, 1H), 3.57-3.52 (m, 2H), 3.39-3.30 (m, 1H), 2.36-2.25 (m, 1H), 2.02-1.98 (m, 1H), 1.50 (s, 9H), 1.40 (s, 9H); MS (ES-) m/z 575.4 (M−1), 577.4 (M−1).

Step 2. Preparation of (R)-5-chloro-2-fluoro-4-(pyrrolidin-3-ylamino)-N-(thiazol-4-yl)benzenesulfonamide 2,2,2-trifluoroacetate

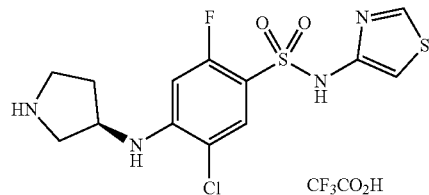

Following the procedure as described for EXAMPLE 253, Step 2 and making non-critical variations as required to replace tert-butyl (S)-3-((2-chloro-4-(N-(thiazol-4-yl)sulfamoyl)phenyl)(methyl)amino)pyrrolidine-1-carboxylate with tert-butyl (R)-3-((4-(N-(tert-butoxycarbonyl)-N-(thiazol-4-yl)sulfamoyl)-2-chloro-5-fluorophenyl)amino)pyrrolidine-1-carboxylate, the title compound was obtained as a colorless foam (0.51 g, quantitative yield): MS (ES+) m/z 377.2 (M+1), 379.2 (M+1).

Step 3. Preparation of (R)-4-((1-benzylpyrrolidin-3-yl)amino)-5-chloro-2-fluoro-N-(thiazol-4-yl)benzenesulfonamide

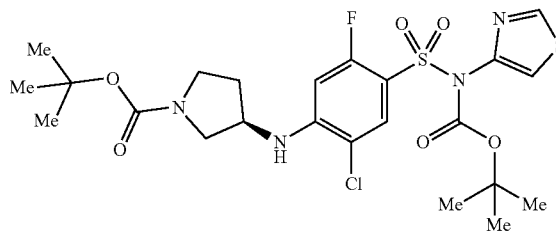

Following the procedure as described for EXAMPLE 29, Step 4 and making non-critical variations as required to replace (S)-3-chloro-4-(methyl(pyrrolidin-3-yl)amino)-N-(1,2,4-thiadiazol-5-yl)benzenesulfonamide 2,2,2-trifluoroacetate with (R)-5-chloro-2-fluoro-4-(pyrrolidin-3-ylamino)-N-(thiazol-4-yl)benzenesulfonamide 2,2,2-trifluoroacetate and purification by column chromatography, eluting with a gradient of 0 to 60% of ethyl acetate (containing 20% of ethanol and 0.1% of ammonium hydroxide) in hexanes, the title compound was obtained as a colorless solid (0.35 g, 75% yield): ¹H NMR (300 MHz, DMSO-d₆), 11.11 (s, 1H), 8.88 (d, J=2.2 Hz, 1H), 7.59 (d, J=7.4 Hz, 1H), 7.33-7.29 (m, 4H), 7.28-7.21 (m, 1H), 6.96 (d, J=2.2 Hz, 1H), 6.75 (d, J=13.3 Hz, 1H), 6.14-6.11 (m, 1H), 4.12-4.00 (m, 1H), 3.61 (s, 2H), 2.80 (dd, J=9.4, 6.9 Hz, 1H), 2.71-2.64 (m, 1H), 2.45-2.40 (m, 2H), 2.27-2.15 (m, 1H), 1.80-1.70 (m, 1H); MS (ES+) m/z 467.2 (M+1), 469.2 (M+1).

Example 262

Synthesis of (R)-4-((1-benzylpyrrolidin-3-yl)(methyl)amino)-5-chloro-2-fluoro-N-(thiazol-4-yl)benzenesulfonamide

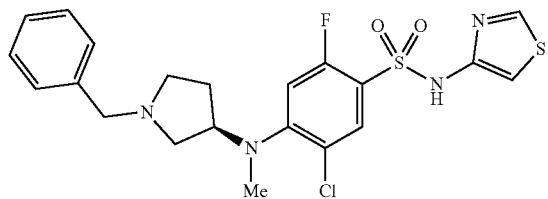 [SMILES: CN(c1cc(F)c(S(=O)(=O)Nc2cscn2)cc1Cl)[C@@H]1CCN(Cc2ccccc2)C1]

Step 1. Preparation of tert-butyl (R)-3-((4-(N-(tert-butoxycarbonyl)-N-(thiazol-4-yl)sulfamoyl)-2-chloro-5-fluorophenyl)(methyl)amino)pyrrolidine-1-carboxylate

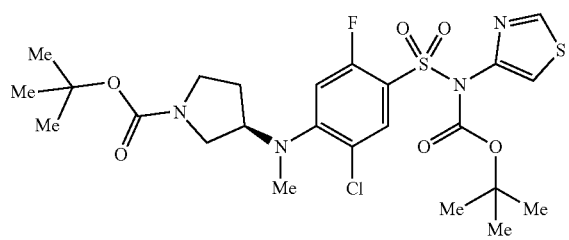 [SMILES: CN(c1cc(F)c(S(=O)(=O)N(C(=O)OC(C)(C)C)c2cscn2)cc1Cl)[C@@H]1CCN(C(=O)OC(C)(C)C)C1]

Following the procedure as described for EXAMPLE 101, Step 3 and making non-critical variations as required to replace tert-butyl (S)-3-((4-(N-(tert-butoxycarbonyl)-N-(thiazol-4-yl)sulfamoyl)-5-fluoro-2-methylphenyl)amino)pyrrolidine-1-carboxylate with tert-butyl (R)-3-((4-(N-(tert-butoxycarbonyl)-N-(thiazol-4-yl)sulfamoyl)-2-chloro-5-fluorophenyl)amino)pyrrolidine-1-carboxylate, the title compound was obtained as a colorless foam (0.47 g, 33% yield): $^1$H NMR (300 MHz, CDCl$_3$) δ 8.82 (d, J=2.3 Hz, 1H), 8.08 (d, J=7.5 Hz, 1H), 7.54 (d, J=2.2 Hz, 1H), 6.84 (d, J=11.8 Hz, 1H), 4.28-4.24 (m, 1H), 3.63-3.59 (m, 2H), 3.36-3.32 (m, 2H), 2.86 (s, 3H), 2.10 (dd, J=7.8, 5.1 Hz, 2H), 1.49 (s, 9H), 1.40 (s, 9H); MS (ES+) m/z 467.2 (M+23), 469.2 (M+23).

Step 2. Preparation of (R)-5-chloro-2-fluoro-4-(methyl(pyrrolidin-3-yl)amino)-N-(thiazol-4-yl)benzenesulfonamide 2,2,2-trifluoroacetate

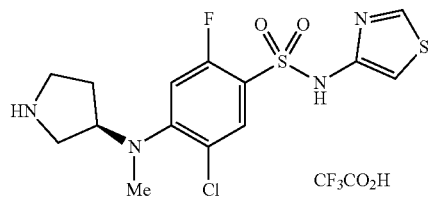 [SMILES: CN(c1cc(F)c(S(=O)(=O)Nc2cscn2)cc1Cl)[C@@H]1CCNC1 ; "CF3CO2H"]

Following the procedure as described for EXAMPLE 253, Step 2 and making non-critical variations as required to replace tert-butyl (S)-3-((2-chloro-4-(N-(thiazol-4-yl)sulfamoyl)phenyl)(methyl)amino)pyrrolidine-1-carboxylate with tert-butyl (R)-3-((4-(N-(tert-butoxycarbonyl)-N-(thiazol-4-yl)sulfamoyl)-2-chloro-5-fluorophenyl)(methyl)amino)pyrrolidine-1-carboxylate, the title compound was obtained as a colorless foam (0.32 g, quantitative yield): MS (ES+) m/z 391.2 (M+1), 393.2 (M+1).

Step 3. Preparation of (R)-4-((1-benzylpyrrolidin-3-yl)(methyl)amino)-5-chloro-2-fluoro-N-(thiazol-4-yl)benzenesulfonamide

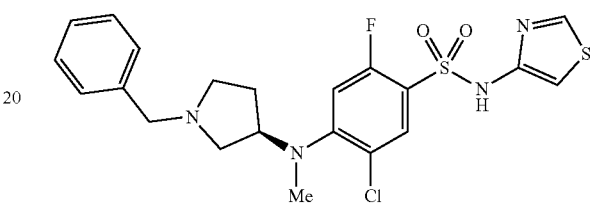

Following the procedure as described for EXAMPLE 29, Step 4 and making non-critical variations as required to replace (S)-3-chloro-4-(methyl(pyrrolidin-3-yl)amino)-N-(1,2,4-thiadiazol-5-yl)benzenesulfonamide 2,2,2-trifluoroacetate with (R)-5-chloro-2-fluoro-4-(methyl(pyrrolidin-3-yl)amino)-N-(thiazol-4-yl)benzenesulfonamide 2,2,2-trifluoroacetate and purification by column chromatography, eluting with a gradient of 0 to 60% of ethyl acetate (containing 20% of ethanol and 0.1% of ammonium hydroxide) in hexanes, the title compound was obtained as a colorless solid (0.14 g, 29% yield): $^1$H NMR (300 MHz, DMSO-d$_6$), 11.28 (s, 1H), 8.89 (d, J=2.2 Hz, 1H), 7.68 (d, J=7.6 Hz, 1H), 7.33-7.28 (m, 4H), 7.28-7.21 (m, 1H), 7.07 (d, J=12.5 Hz, 1H), 7.00 (d, J=2.2 Hz, 1H), 4.24-4.15 (m, 1H), 3.64 (d, J=13.1 Hz, 1H), 3.52 (d, J=13.0 Hz, 1H), 2.80 (s, 3H), 2.77-2.53 (m, 3H), 2.38-2.30 (m, 1H), 2.13-2.02 (m, 1H), 1.86-1.74 (m, 1H); MS (ES+) m/z 481.2 (M+1), 483.2 (M+1).

Example 263

Synthesis of (S)-4-((1-benzylpyrrolidin-3-yl)(ethyl)amino)-5-chloro-2-fluoro-N-(thiazol-4-yl)benzenesulfonamide

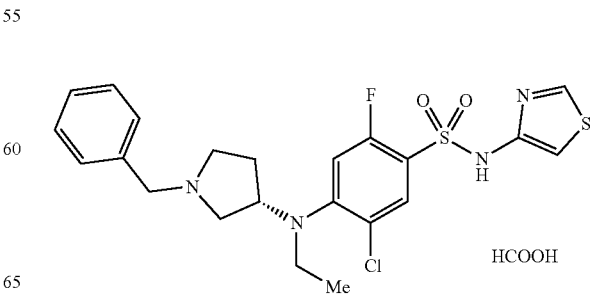

Step 1. Preparation of tert-butyl (S)-3-((4-(N-(tert-butoxycarbonyl)-N-(thiazol-4-yl)sulfamoyl)-2-chloro-5-fluorophenyl)(ethyl)amino)pyrrolidine-1-carboxylate

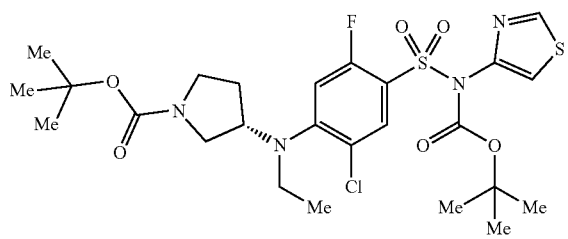 [SMILES: CCN(c1cc(F)c(S(=O)(=O)N(C(=O)OC(C)(C)C)c2cscn2)cc1Cl)[C@H]1CCN(C(=O)OC(C)(C)C)C1]

To a solution of tert-butyl (S)-3-((4-(N-(tert-butoxycarbonyl)-N-(thiazol-4-yl)sulfamoyl)-2-chloro-5-fluorophenyl)amino)pyrrolidine-1-carboxylate (1.67 g, 2.89 mmol) and iodoethane (0.70 mL, 8.67 mmol) in anhydrous N,N-dimethylformamide (12 mL) was added a 60% dispersion of sodium hydride in mineral oil (0.35 g, 8.67 mmol) at 0° C. The reaction mixture was allowed to warm to ambient temperature and stirred for 2 h. After quench with saturated ammonium chloride (50 mL), the mixture was extracted with ethyl acetate (80 mL). The organic layer was washed with saturated ammonium chloride (40 mL), brine (40 mL), dried over anhydrous sodium sulfate, and filtered. Concentration of the filtrate in vacuo and purification of the residue by column chromatography, eluting with a gradient of 25 to 50% of ethyl acetate in hexanes, afforded the title compound as a colorless foam (1.23 g, 70% yield): $^1$H NMR (300 MHz, CDCl$_3$) δ 8.83 (d, J=2.3 Hz, 1H), 8.11 (d, J=7.5 Hz, 1H), 7.55 (d, J=2.2 Hz, 1H), 6.93 (d, J=11.5 Hz, 1H), 4.09-4.06 (m, 1H), 3.65-3.60 (m, 2H), 3.37-3.18 (m, 4H), 2.11-2.09 (m, 1H), 2.00-1.90 (m, 1H), 1.47 (s, 9H), 1.39 (s, 9H), 1.03-0.98 (m, 3H); MS (ES+) m/z 627.4 (M+23), 629.4 (M+23).

Step 2. Preparation of (S)-5-chloro-4-(ethyl(pyrrolidin-3-yl)amino)-2-fluoro-N-(thiazol-4-yl)benzenesulfonamide 2,2,2-trifluoroacetate

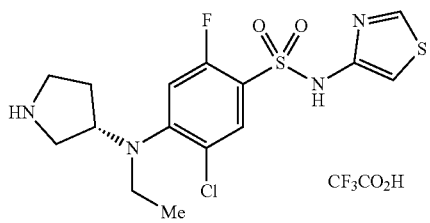 [SMILES: CCN(c1cc(F)c(S(=O)(=O)Nc2cscn2)cc1Cl)[C@H]1CCNC1 ; "CF3CO2H"]

Following the procedure as described for EXAMPLE 253, Step 2 and making non-critical variations as required to replace tert-butyl (S)-3-((2-chloro-4-(N-(thiazol-4-yl)sulfamoyl)phenyl)(methyl)amino)pyrrolidine-1-carboxylate with tert-butyl (S)-3-((4-(N-(tert-butoxycarbonyl)-N-(thiazol-4-yl)sulfamoyl)-2-chloro-5-fluorophenyl)(ethyl)amino)-pyrrolidine-1-carboxylate, the title compound was obtained as a colorless foam (1.05 g, quantitative yield): MS (ES+) m/z 405.2 (M+1), 407.2 (M+1).

Step 3. Preparation of (S)-4-((1-benzylpyrrolidin-3-yl)(ethyl)amino)-5-chloro-2-fluoro-N-(thiazol-4-yl)benzenesulfonamide

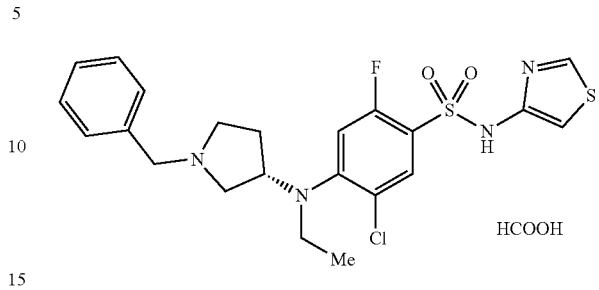

To a solution of (S)-5-chloro-4-(ethyl(pyrrolidin-3-yl)amino)-2-fluoro-N-(thiazol-4-yl)benzenesulfonamide 2,2,2-trifluoroacetate (0.55 g, 1.06 mmol) and benzaldehyde (0.22 mL, 2.12 mol) in anhydrous dichloromethane (20 mL) was added sodium triacetoxyborohydride (0.45 g, 2.12 mmol). The mixture was stirred at ambient temperature for 3 h, and then quenched by addition of 2 M sodium hydroxide (50 mL). The mixture was extracted with ethyl acetate (80 mL). The organic layer was washed with saturated ammonium chloride (50 mL), brine (30 mL), dried over anhydrous sodium sulfate, and filtered. Concentration of the filtrate in vacuo provided a residue which was purified by column chromatography, eluting with a gradient of 0 to 60% of ethyl acetate (containing 20% of ethanol and 0.1% of ammonium hydroxide) in hexanes. The purified compound was then dissolved in ethanol (10 mL) containing 0.1% formic acid, filtered, and concentrated in vacuo to afford the title compound as a colorless solid (0.23 g, 40% yield): $^1$H NMR (300 MHz, DMSO-d$_6$) δ 8.88 (d, J=2.2 Hz, 1H), 8.19 (s, 1H), 7.74 (d, J=7.6 Hz, 1H), 7.33-7.24 (m, 5H), 7.02 (d, J=2.2 Hz, 1H), 4.19-4.10 (m, 1H), 3.76 (d, J=13.0 Hz, 1H), 3.65 (d, J=13.0 Hz, 1H), 3.41-3.20 (m, 2H), 2.83-2.74 (m, 2H), 2.65 (dd, J=10.0, 5.6 Hz, 1H), 2.57-2.51 (m, 2H), 2.12-2.01 (m, 1H), 1.80-1.68 (m, 1H), 0.84 (t, J=7.0 Hz, 3H), NH and COOH not observed; MS (ES+) m/z 495.1 (M+1), 497.1 (M+1).

Example 264

Synthesis of (S)-4-((5-benzyl-5-azaspiro[2.4]heptan-7-yl)amino)-5-chloro-2-fluoro-N-(thiazol-4-yl)benzenesulfonamide 2,2,2-trifluoroacetate

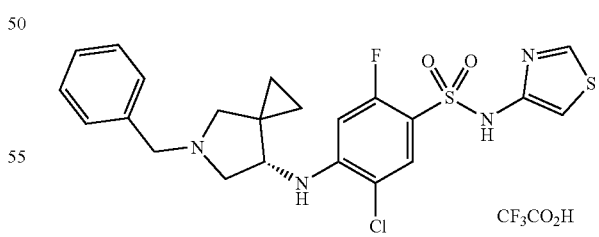

Following the procedure as described for EXAMPLE 257 and making non-critical variations as required to replace (S)—N-methyl-1-(2-phenylpropan-2-yl)pyrrolidin-3-amine with (S)-5-benzyl-5-azaspiro[2.4]heptan-7-amine hydrochloride, and purification by preparative reverse-phase HPLC, eluting with a gradient of 10 to 60% of acetonitrile in water containing 0.1% of trifluoroacetic acid, the title compound was obtained as a colorless solid (0.060 g, 22% yield): ¹H NMR (300 MHz, DMSO-d₆) δ 11.17 (s, 1H), 10.71 (s, 0.5H), 10.24 (s, 0.5H), 8.89 (d, J=2.2 Hz, 1H), 7.63 (d, J=7.4 Hz, 1H), 7.52-7.46 (m, 5H), 7.00 (d, J=2.2 Hz, 1H), 6.90-6.71 (m, 1H), 6.55-6.46 (m, 0.5H), 6.20-6.14 (m, 0.5H), 4.52-4.25 (m, 2H), 4.12-4.03 (m, 1H), 3.79-3.54 (m, 1H), 3.42-3.28 (m, 2H), 0.90-0.69 (m, 4H), NH not observed; MS (ES+) m/z 493.2 (M+1), 495.2 (M+1).

Example 265

Synthesis of (S)-4-((5-benzyl-5-azaspiro[2.4]heptan-7-yl)(methyl)amino)-5-chloro-2-fluoro-N-(thiazol-4-yl)benzenesulfonamide 2,2,2-trifluoroacetate

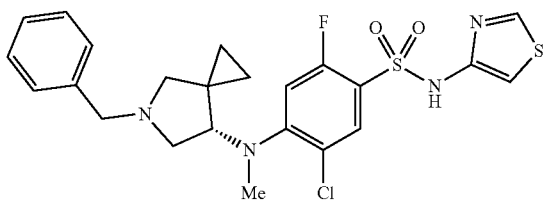 [SMILES: CN(c1cc(F)c(S(=O)(=O)Nc2cscn2)cc1Cl)[C@@H]1CN(Cc2ccccc2)CC12CC2]

Step 1. Preparation of tert-butyl (S)-(5-benzyl-5-azaspiro[2.4]heptan-7-yl)carbamate

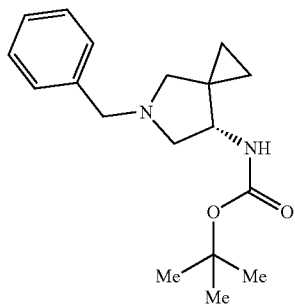 [SMILES: CC(C)(C)OC(=O)N[C@@H]1CN(Cc2ccccc2)CC12CC2]

To a mixture of (S)-5-benzyl-5-azaspiro[2.4]heptan-7-amine hydrochloride (0.70 g, 2.55 mmol) and 2 M sodium hydroxide (25.5 mmol, 12.75 mL) in tetrahydrofuran (30 mL) was added di-tert-butyl dicarbonate (1.11 g, 5.10 mmol) at 0° C. The mixture was allowed to warm to ambient temperature, stirred for 18 h, and then diluted with ethyl acetate (85 mL). The mixture was washed with water (50 mL), brine (2×50 mL), dried over anhydrous sodium sulfate, and filtered. Concentration of the filtrate in vacuo and purification of the residue by column chromatography, eluting with a gradient of 0 to 50% of ethyl acetate (containing 20% of ethanol and 0.1% of ammonium hydroxide) in hexanes, afforded the title compound as a colorless oil (0.74 g, 96% yield): ¹H NMR (300 MHz, CDCl₃) 7.35-7.31 (m, 5H), 4.98-4.92 (m, 1H), 3.83 (ddd, J=9.1, 6.0, 3.1 Hz, 1H), 3.69-3.55 (m, 2H), 2.92 (dd, J=9.6, 5.9 Hz, 1H), 2.71-2.65 (m, 2H), 2.35 (d, J=9.0 Hz, 1H), 1.44 (s, 9H), 0.82-0.73 (m, 2H), 0.60 (ddd, J=9.3, 5.6, 3.7 Hz, 1H), 0.46 (ddd, J=9.5, 5.7, 3.9 Hz, 1H); MS (ES+) m/z 303.4 (M+1).

Step 2. Preparation of (S)-5-benzyl-N-methyl-5-azaspiro[2.4]heptan-7-amine

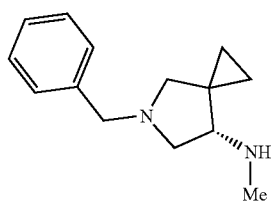 [SMILES: CN[C@@H]1CN(Cc2ccccc2)CC12CC2]

Following the procedure as described for EXAMPLE 42, Step 3 and making non-critical variations as required to replace tert-butyl ((S)-1-((S)-1-phenylethyl)-pyrrolidin-3-yl)carbamate with tert-butyl (S)-(5-benzyl-5-azaspiro[2.4]heptan-7-yl)carbamate, the title compound was obtained as a colorless oil (0.52 g, 98% yield): MS (ES+) m/z 217.3 (M+1).

Step 3. Preparation of (S)-4-((5-benzyl-5-azaspiro[2.4]heptan-7-yl)(methyl)amino)-5-chloro-2-fluoro-N-(thiazol-4-yl)benzenesulfonamide 2,2,2-trifluoroacetate

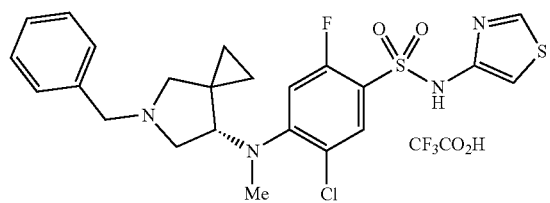

Following the procedure as described for EXAMPLE 257 and making non-critical variations as required to replace (S)—N-methyl-1-(2-phenylpropan-2-yl)pyrrolidin-3-amine with (S)-5-benzyl-N-methyl-5-azaspiro[2.4]heptan-7-amine, and purification by preparative reverse-phase HPLC, eluting with a gradient of 10 to 60% of acetonitrile in water containing 0.1% of trifluoroacetic acid, the title compound was obtained as a colorless solid (0.15 g, 3% yield): ¹H NMR (300 MHz, DMSO-d₆) δ 11.37 (s, 1H), 10.74 (s, 1H), 8.90 (d, J=2.2 Hz, 1H), 7.70 (d, J=7.4 Hz, 1H), 7.53-7.49 (m, 2H), 7.46-7.43 (m, 3H), 7.21 (d, J=12.2 Hz, 1H), 7.06 (d, J=2.2 Hz, 1H), 4.46-4.44 (m, 2H), 4.16-4.10 (m, 1H), 3.90-3.83 (m, 1H), 3.62-3.56 (m, 1H), 3.48-3.42 (m, 1H), 3.03-2.98 (m, 1H), 2.94 (s, 3H), 0.96-0.71 (m, 4H); MS (ES+) m/z 507.2 (M+1), 509.2 (M+1).

Example 266

Synthesis of (S)-3-chloro-4-((1-(2-fluoro-5-methyl-benzyl)-3-methylpyrrolidin-3-yl)amino)-N-(thiazol-4-yl)benzenesulfonamide Formate

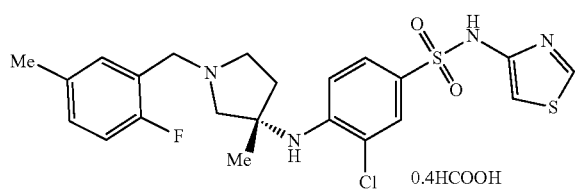 [SMILES: Cc1ccc(F)c(CN2CC[C@](C)(Nc3ccc(S(=O)(=O)Nc4cscn4)cc3Cl)C2)c1]

Step 1. Preparation of (S)—N-(3-methylpyrrolidin-3-yl)acetamide

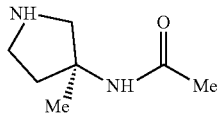

To (S)—N-(1-benzyl-3-methylpyrrolidin-3-yl)acetamide (1.0 g, 4.3 mmol) and 10% Pd/C (0.46 mg) was added methanol (10 mL) and the mixture was heated to 40° C. under an atmosphere of hydrogen (50 psi) for 24 h. After cooling the ambient temperature, the reaction mixture was filtered and the filtrate concentrated under reduced pressure to give the title compound as colorless oil (0.600 g, 98% yield): $^1$H NMR (400 MHz, CDCl$_3$) δ 5.67 (s, 1H), 3.22 (d, J=11.6 Hz, 1H), 3.11 (ddd, J=11.2, 8.0, 5.9 Hz, 1H), 2.94 (ddd, J=11.2, 8.2, 6.5 Hz, 1H), 2.76 (d, J=11.6 Hz, 1H), 2.21 (br s, 1H), 2.19-2.10 (m, 1H), 1.95 (s, 3H), 1.76 (ddd, J=13.1, 8.2, 5.9 Hz, 1H), 1.46 (s, 3H).

Step 2. Preparation of (S)—N-(1-(2-fluoro-5-methylbenzyl)-3-methylpyrrolidin-3-yl)acetamide

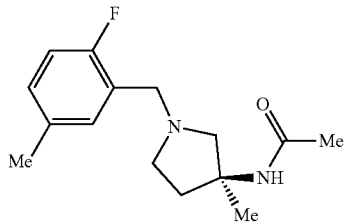 [SMILES: CC(=O)N[C@@]1(C)CCN(Cc2cc(C)ccc2F)C1]

To a solution of (S)—N-(3-methylpyrrolidin-3-yl)acetamide (0.240 g, 1.6 mmol) and 2-fluoro-5-methyl-benzaldehyde (0.233 g, 1.6 mmol) in dichloromethane (2 mL) was added acetic acid (0.101 g, 1.6 mmol), followed by the addition of sodium triacetoxy borohydride (0.358 g, 1.6 mmol). The reaction mixture was stirred at ambient temperature for 12 h. Water (10 mL) was added to it, and the mixture was extracted with ethyl acetate (3×20 mL). The combined organic phase was washed with brine (3×10 mL), dried over anhydrous sodium sulfate, and filtered. Concentration of the filtrate in vacuo and purification of the residue by reverse phase column chromatography, eluting with a gradient of acetonitrile in water containing 0.1% of ammonium hydroxide, afforded the title compound as a colorless oil (0.200 g, 0.757 mmol): $^1$H NMR (400 MHz, CDCl$_3$) δ 7.45 (d, J=6.8 Hz, 1H), 7.23-7.12 (m, 2H), 4.18-4.06 (m, 2H), 3.76 (d, J=11.2 Hz, 1H), 3.64-3.53 (m, 1H), 3.05 (dt, J=10.2, 4.4 Hz, 1H), 2.84-2.74 (m, 1H), 2.70 (d, J=11.2 Hz, 1H), 2.27 (s, 3H), 1.98 (td, J=13.6, 8.8 13.6 Hz, 1H), 1.91 (s, 3H), 1.59 (s, 3H), NH not observed; MS (ES+) m/z 265.1 (M+1)

Step 3. Preparation of (S)-1-(2-fluoro-5-methylbenzyl)-3-methylpyrrolidin-3-amine

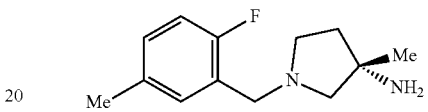

Following the procedure as described in EXAMPLE 226, Step 3 and making non-critical variations to replace (S)—N-(1-benzyl-3-methylpyrrolidin-3-yl)acetamide with (S)—N-(1-(2-fluoro-5-methylbenzyl)-3-methylpyrrolidin-3-yl) acetamide, the title compound was obtained as a yellow oil (0.135 g, 80% yield): $^1$H NMR (400 MHz, CDCl$_3$) δ 7.24-7.16 (m, 1H), 7.07-6.99 (m, 1H), 6.95-6.89 (m, 1H), 3.72-3.59 (m, 2H), 2.90 (dt, J=8.8, 5.2 Hz, 1H), 2.56 (d, J=9.0 Hz, 1H), 2.53-2.45 (m, 1H), 2.38 (d, J=9.2 Hz, 1H), 2.33 (s, 3H), 1.86 (ddd, J=13.2, 8.4, 5.0 Hz, 1H), 1.79-1.74 (m, 1H), 1.28 (s, 3H), NH not observed.

Step 4. Preparation of tert-butyl (S)-((3-chloro-4-((1-(2-fluoro-5-methylbenzyl)-3-methylpyrrolidin-3-yl)amino)phenyl)sulfonyl)(thiazol-4-yl)carbamate

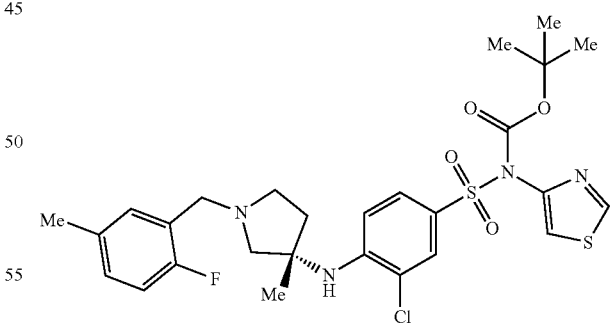

Following the procedure as described in EXAMPLE 225, Step 2 and making non-critical variations to replace (R)-1-benzyl-3-methylpyrrolidin-3-amine with (S)-1-(2-fluoro-5-methylbenzyl)-3-methylpyrrolidin-3-amine, the title compound was obtained as a yellow solid (0.150 g, 41% yield): MS (ES+) m/z 595.1 (M+1), 597.1 (M+1).

Step 5. Preparation of (S)-3-chloro-4-((1-(2-fluoro-5-methylbenzyl)-3-methylpyrrolidin-3-yl)amino)-N-(thiazol-4-yl)benzenesulfonamide Formate

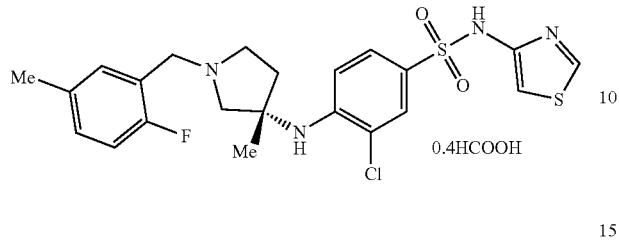

Following the procedure as described in EXAMPLE 225, Step 3 and making non-critical variations to replace tert-butyl (R)-((4-((1-benzyl-3-methylpyrrolidin-3-yl)amino)-3-chlorophenyl)sulfonyl)(thiazol-4-yl)carbamate with tert-butyl (S)-((3-chloro-4-((1-(2-fluoro-5-methylbenzyl)-3-methylpyrrolidin-3-yl)amino)phenyl)sulfonyl)(thiazol-4-yl)carbamate, the title compound was obtained as a colorless solid (0.052 g, 41% yield): $^1$H NMR (400 MHz, DMSO-$d_6$) δ 8.87 (d, J=2.0 Hz, 1H), 8.20 (s, 0.4H), 7.66 (d, J=2.4 Hz, 1H), 7.53 (dd, J=8.8, 2.2 Hz, 1H), 7.22-7.18 (m, 1H), 7.12 (d, J=8.8 Hz, 1H), 7.10-7.06 (m, 1H), 7.06-7.00 (m, 1H), 6.96 (d, J=2.0 Hz, 1H), 5.47 (s, 1H), 3.67-3.57 (m, 2H), 2.84 (d, J=9.8 Hz, 1H), 2.78-2.70 (m, 1H), 2.59-2.53 (m, 2H), 2.25 (s, 3H), 2.19-2.07 (m, 1H), 1.90-1.80 (m, 1H), 1.44 (s, 3H), NH and COOH not observed; MS (ES+) m/z 495.0 (M+1), 497.0 (M+1).

Example 267

Synthesis of (S)-3-chloro-2,6-difluoro-4-(methyl(1-((6-methylpyridin-2-yl)methyl)pyrrolidin-3-yl)amino)-N-(thiazol-4-yl)benzenesulfonamide

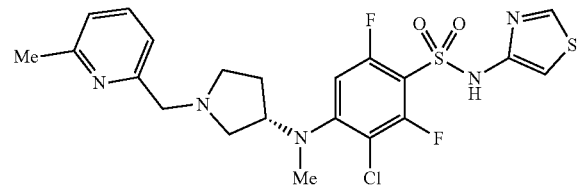 [SMILES: Cc1cccc(CN2CC[C@H](N(C)c3cc(F)c(S(=O)(=O)Nc4cscn4)c(F)c3Cl)C2)n1]

Following the procedure as described for EXAMPLE 102, Step 6 and making non-critical variations as required to replace benzaldehyde with 6-methylpicolinaldehyde, the title compound was obtained as a colorless solid (0.26 g, 67% yield): $^1$H NMR (300 MHz, DMSO-$d_6$), 8.88 (d, J=2.2 Hz, 1H), 7.64 (t, J=7.7 Hz, 1H), 7.21 (d, J=7.7 Hz, 1H), 7.10 (d, J=7.6 Hz, 1H), 6.96 (d, J=2.2 Hz, 1H), 6.88 (dd, J=13.3, 1.4 Hz, 1H), 4.32-4.23 (m, 1H), 3.76 (d, J=14.0 Hz, 1H), 3.64 (d, J=13.9 Hz, 1H), 2.90-2.75 (m, 5H), 2.66 (dd, J=9.9, 8.2 Hz, 1H), 2.46-2.34 (m, 4H), 2.18-2.06 (m, 1H), 1.92-1.77 (m, 1H), NH not observed; MS (ES+) m/z 514.2 (M+1), 516.2 (M+1).

Example 268

Synthesis of (S)-4-((1-benzylpyrrolidin-3-yl)oxy)-3-chloro-2,6-difluoro-N-(thiazol-4-yl)benzenesulfonamide hydrochloride

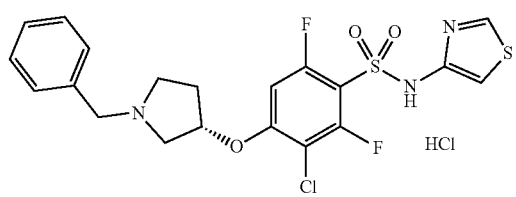 [SMILES: O=S(=O)(Nc1cscn1)c1c(F)cc(O[C@H]2CCN(Cc3ccccc3)C2)c(Cl)c1F ; Cl]

Step 1. Preparation of tert-butyl (S)-((4-((1-benzylpyrrolidin-3-yl)oxy)-3-chloro-2,6-difluorophenyl)sulfonyl)(thiazol-4-yl)carbamate

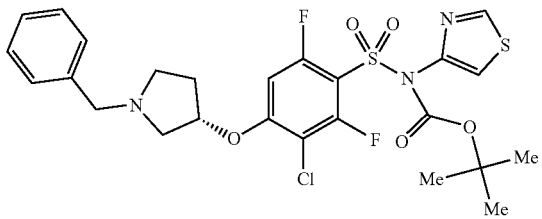 [SMILES: CC(C)(C)OC(=O)N(c1cscn1)S(=O)(=O)c1c(F)cc(O[C@H]2CCN(Cc3ccccc3)C2)c(Cl)c1F]

To a mixture of (S)-1-benzylpyrrolidin-3-ol (0.87 g, 4.66 mmol) and tert-butyl ((3-chloro-2,4,6-trifluorophenyl)sulfonyl)(thiazol-4-yl)carbamate (2.00 g, 4.66 mmol) in anhydrous N,N-dimethylformamide (25 mL) was added a 60% dispersion of sodium hydride in mineral oil (0.19 g, 4.66 mmol) at 0° C. The mixture was allowed to warm to ambient temperature and stirred for 2 h. The reaction mixture was then quenched by addition of water (20 mL) and extracted with ethyl acetate (80 mL). The organic layer was washed with saturated ammonium chloride (2×50 mL), brine (2×50 mL), dried over anhydrous sodium sulfate, and filtered. Concentration of the filtrate in vacuo and purification of the residue by column chromatography, eluting with a gradient of 10 to 60% of ethyl acetate (containing 20% of ethanol and 0.1% of ammonium hydroxide) in hexanes afforded the title compound as a colorless foam (0.97 g, 36% yield): $^1$H NMR (300 MHz, CDCl$_3$) δ 8.82 (d, J=2.3 Hz, 1H), 7.54 (d, J=2.2 Hz, 1H), 7.38-7.34 (m, 4H), 7.33-7.29 (m, 1H), 6.53 (dd, J=11.9, 1.9 Hz, 1H), 4.94-4.88 (m, 1H), 3.78-3.69 (m, 2H), 3.11 (dd, J=10.8, 6.1 Hz, 1H), 2.88-2.78 (m, 2H), 2.76-2.68 (m, 1H), 2.47-2.35 (m, 1H), 2.12-2.02 (m, 1H), 1.40 (s, 9H); MS (ES+) m/z 586.4 (M+1), 588.4 (M+1).

Step 2. Preparation of (S)-4-((1-benzylpyrrolidin-3-yl)oxy)-3-chloro-2,6-difluoro-N-(thiazol-4-yl)benzenesulfonamide hydrochloride

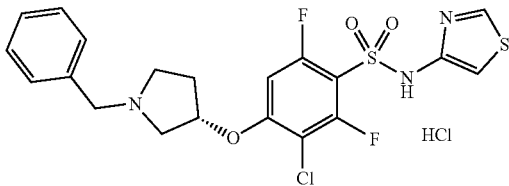 [SMILES: O=S(=O)(Nc1cscn1)c1c(F)cc(O[C@H]2CCN(Cc3ccccc3)C2)c(Cl)c1F ; Cl]

To tert-butyl(S)-((4-((1-benzylpyrrolidin-3-yl)oxy)-3-chloro-2,6-difluorophenyl)sulfonyl)(thiazol-4-yl)carbamate (0.19 g, 0.32 mmol) was added 4 M hydrochloric acid in dioxane (10 mL). The mixture was stirred at ambient temperature for 5 h at and then concentrated in vacuo. The residue was treated with ethanol (20 mL) and 3 M aqueous hydrochloric acid (0.3 mL). The mixture was filtered and the filtrate concentrated in vacuo to afford the title compound as colorless solid (0.15 g, 89% yield): $^1$H NMR (300 MHz, CD$_3$OD) δ 8.82-8.75 (m, 1H), 7.62-7.48 (m, 5H), 7.10-7.02 (m, 2H), 5.39-5.37 (m, 1H), 4.58-4.48 (m, 2H), 3.76-3.59 (m, 3H), 3.53-3.45 (m, 1H), 2.91-2.75 (m, 0.5H), 2.52-2.41 (m, 1H), 2.37-2.21 (m, 0.5H), HCl and NH not observed; MS (ES+) m/z 486.1 (M+1), 488.1 (M+1).

Example 269

Synthesis of (S)-4-((1-benzylpyrrolidin-3-yl)oxy)-2,6-difluoro-3-methyl-N-(thiazol-4-yl)benzenesulfonamide hydrochloride

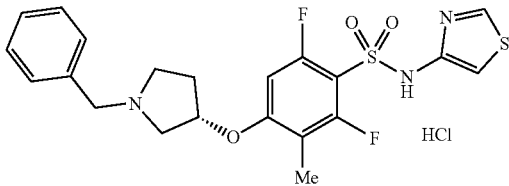 [SMILES: Cc1c(O[C@H]2CCN(Cc3ccccc3)C2)cc(F)c(S(=O)(=O)Nc2cscn2)c1F ; Cl]

To a mixture of tert-butyl (S)-((4-((1-benzylpyrrolidin-3-yl)oxy)-3-chloro-2,6-difluorophenyl)sulfonyl)(thiazol-4-yl) carbamate (0.97 g, 1.66 mmol), methylboronic acid (0.99 g, 16.60 mmol), and potassium phosphate (1.76 g, 8.30 mmol) in anhydrous dioxane (20 mL) was added palladium acetate (0.075 g, 0.33 mmol) and tricyclohexylphosphonium tetrafluoroborate (0.25 g, 0.66 mmol). The resulting mixture was degasses and heated to reflux for 6 h. After cooling to ambient temperature, the mixture was diluted with ethyl acetate (50 mL) and saturated ammonium chloride (50 mL), and filtered. The organic layer of the filtrate was washed with saturated ammonium chloride (30 mL), brine (2×20 mL), dried over anhydrous sodium sulfate, and filtered. Concentration of the filtrate in vacuo and purification of the residue by column chromatography, eluting with a gradient of 10 to 60% of ethyl acetate (containing 20% of ethanol and 0.1% of ammonium hydroxide) in hexanes provided a residue, which was treated with ethanol (10 mL) and 3 M aqueous hydrochloric acid (0.3 mL). Filtration and concentration of the filtrate in vacuo afforded the title compound as a colorless solid (0.30 g, 36% yield): $^1$H NMR (300 MHz, DMSO-d$_6$) δ 12.03 (s, 0.5H), 11.85 (s, 0.5H), 11.50 (s, 0.5H), 11.46 (s, 0.5H), 8.91 (dd, J=5.4, 2.2 Hz, 1H), 7.71-7.61 (m, 2H), 7.42 (ddd, J=7.8, 5.5, 2.4 Hz, 3H), 7.04-6.99 (m, 2H), 5.28-5.19 (m, 1H), 4.44-4.35 (m, 2H), 3.94-3.86 (m, 0.5H), 3.59-3.39 (m, 2H), 3.33-3.19 (m, 1.5H), 2.68-2.56 (m, 0.5H), 2.35-2.09 (m, 1.5H), 2.10-1.99 (m, 3H); MS (ES+) m/z 466.1 (M+1).

Example 270

Synthesis of (S)-4-((1-benzylpyrrolidin-3-yl)(methyl)amino)-5-(difluoromethyl)-2-fluoro-N-(thiazol-4-yl)benzenesulfonamide Formate

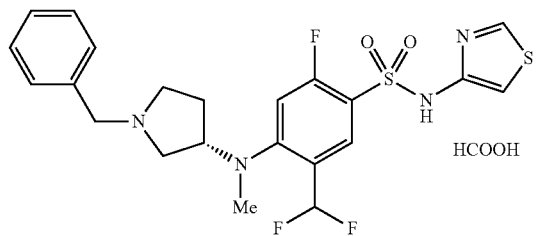 [SMILES: CN(c1cc(F)c(S(=O)(=O)Nc2cscn2)cc1C(F)F)[C@H]1CCN(Cc2ccccc2)C1 ; "HCOOH"]

Step 1. Preparation of 2,4-difluoro-5-formyl-N-(4-methoxybenzyl)-N-(thiazol-4-yl)benzenesulfonamide

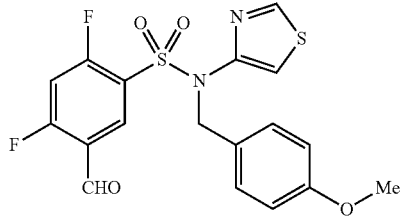 [SMILES: COc1ccc(CN(c2cscn2)S(=O)(=O)c2cc(C=O)c(F)cc2F)cc1]

To a solution of 5-bromo-2,4-difluoro-N-(4-methoxybenzyl)-N-(thiazol-4-yl)benzenesulfonamide (2.73 g, 5.74 mmol) in anhydrous tetrahydrofuran (45 mL) was added a 1.3 M solution of isopropylmagnesium chloride lithium chloride complex in tetrahydrofuran (5.74 mL, 7.47 mmol) at −42° C. The reaction mixture was stirred at −42° C. for 1 h and then N,N-dimethylformamide (1.11 mL, 14.35 mmol) was added to it. The reaction mixture was allowed to warm to ambient temperature and stirred for 3 h. After quench with saturated ammonium chloride (60 mL), the mixture was extracted with ethyl acetate (80 mL). The organic layer washed with saturated ammonium chloride (60 mL), brine (50 mL), dried over anhydrous sodium sulfate, and filtered. Concentration of the filtrate in vacuo and purification of the residue by column chromatography, eluting with a gradient of 10 to 50% of ethyl acetate in hexanes, afforded the title compound as a colorless solid (1.07 g, 44% yield): $^1$H NMR (300 MHz, CDCl$_3$) δ 10.23 (s, 1H), 8.56 (d, J=2.3 Hz, 1H), 8.30 (t, J=7.7 Hz, 1H), 7.25-7.19 (m, 3H), 7.05 (t, J=9.5 Hz, 1H), 6.81-6.75 (m, 2H), 5.01 (s, 2H), 3.77 (s, 3H); MS (ES+) m/z 425.2 (M+1).

Step 2. Preparation of tert-butyl (S)-3-((5-fluoro-2-formyl-4-(N-(4-methoxybenzyl)-N-(thiazol-4-yl)sulfamoyl)phenyl)(methyl)amino)pyrrolidine-1-carboxylate

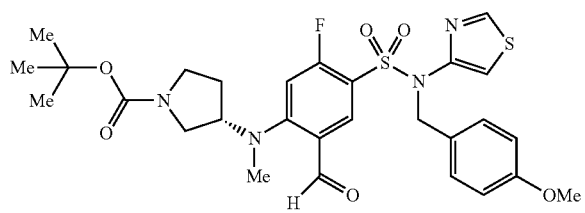 [SMILES: COc1ccc(CN(c2cscn2)S(=O)(=O)c2cc(C=O)c(N(C)[C@H]3CCN(C(=O)OC(C)(C)C)C3)cc2F)cc1]

To a solution of 2,4-difluoro-5-formyl-N-(4-methoxybenzyl)-N-(thiazol-4-yl)benzenesulfonamide (1.07 g, 2.52 mmol) in anhydrous dimethyl sulfoxide (20 mL) was added tert-butyl (S)-3-(methylamino)pyrrolidine-1-carboxylate (1.01 g, 5.04 mmol). The reaction mixture was heated to 80° C. for 30 minutes. After cooling to ambient temperature, the mixture was diluted with ethyl acetate (80 mL). The organic layer washed with saturated ammonium chloride (2×50 mL), brine (50 mL), dried over anhydrous sodium sulfate, and filtered. Concentration of the filtrate in vacuo afforded the title compound as a beige oil (1.45 g, 95% yield): $^1$H NMR (300 MHz, CDCl$_3$) δ 9.89 (s, 1H), 8.56 (d, J=2.3 Hz, 1H), 8.10 (d, J=8.3 Hz, 1H), 7.25-7.21 (m, 3H), 6.81-6.71 (m, 3H), 5.02 (s, 2H), 4.15-4.09 (m, 1H), 3.76 (s, 3H), 3.64-3.59 (m, 1H), 3.46-3.32 (m, 2H), 2.92 (s, 3H), 2.21-2.12 (m, 2H), 1.72-1.70 (m, 1H), 1.49 (s, 9H); MS (ES+) m/z 605.5 (M+1).

Step 3. Preparation of tert-butyl (S)-3-((2-(difluoromethyl)-5-fluoro-4-(N-(4-methoxybenzyl)-N-(thiazol-4-yl)sulfamoyl)phenyl)(methyl)amino)pyrrolidine-1-carboxylate

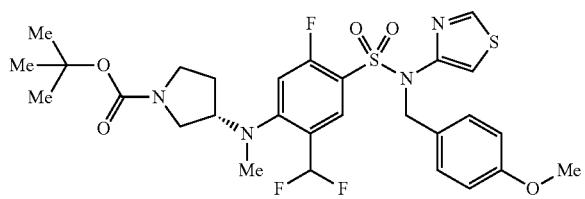 [SMILES: COc1ccc(CN(c2cscn2)S(=O)(=O)c2cc(C(F)F)c(N(C)[C@H]3CCN(C(=O)OC(C)(C)C)C3)cc2F)cc1]

To a solution of tert-butyl (S)-3-((5-fluoro-2-formyl-4-(N-(4-methoxybenzyl)-N-(thiazol-4-yl)sulfamoyl)phenyl)(methyl)amino)pyrrolidine-1-carboxylate (1.45 g, 2.40 mmol) in dichloromethane (25 mL) was added diethylaminosulfur trifluoride (0.63 mL, 4.80 mmol) at 0° C. The mixture was stirred at 0° C. for 2 h and then at ambient temperature for 18 h. The reaction mixture was poured into ice cold saturated sodium bicarbonate (300 mL) and extracted with ethyl acetate (110 mL). The organic layer was washed with saturated sodium bicarbonate (100 mL), saturated ammonium chloride (50 mL), brine (50 mL), dried over anhydrous sodium sulfate, and filtered. Concentration of the filtrate in vacuo and purification of the residue by column chromatography, eluting with a gradient of 10 to 45% of ethyl acetate in hexanes, afforded the title compound as a colorless solid (1.00 g, 66% yield): $^1$H NMR (300 MHz, CDCl$_3$) δ 8.57 (d, J=0.3 Hz, 1H), 8.00 (d, J=7.4 Hz, 1H), 7.26-7.22 (m, 3H), 6.97 (d, J=11.3 Hz, 1H), 6.84-6.66 (m, 3H), 5.03 (s, 2H), 3.76 (s, 3H), 3.73-3.69 (m, 1H), 3.62-3.52 (m, 2H), 3.36-3.21 (m, 2H), 2.72 (s, 3H), 2.04-2.00 (m, 1H), 1.89 (dq, J=12.6, 8.5 Hz, 1H), 1.47 (s, 9H); MS (ES+) m/z 627.3 (M+1).

Step 4. Preparation of (S)-4-((1-benzylpyrrolidin-3-yl)(methyl)amino)-5-(difluoromethyl)-2-fluoro-N-(thiazol-4-yl)benzenesulfonamide Formate

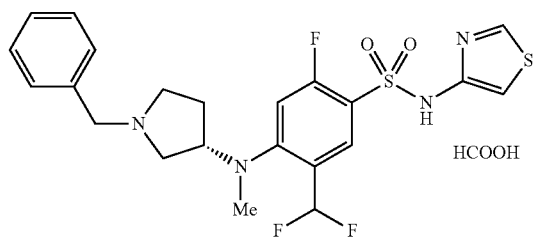 [SMILES: CN(c1cc(F)c(S(=O)(=O)Nc2cscn2)cc1C(F)F)[C@H]1CCN(Cc2ccccc2)C1 ; "HCOOH"]

To a solution of tert-butyl (S)-3-((2-(difluoromethyl)-5-fluoro-4-(N-(4-methoxybenzyl)-N-(thiazol-4-yl)sulfamoyl)phenyl)(methyl)amino)pyrrolidine-1-carboxylate (1.00 g, 1.60 mmol) in dichloromethane (10 mL) was added trifluoroacetic acid (10 mL) and the reaction mixture was heated to reflux for 5 h. After cooling to ambient temperature, the mixture was concentrated in vacuo. The residue was dissolved in dichloromethane (5 mL) and N,N-dimethylformamide (5 mL). To this mixture was then added benzaldehyde (0.33 mL, 3.2 mmol) and sodium triacetoxyborohydride (0.68 g, 3.2 mmol). The reaction mixture was stirred at ambient temperature for 18 h, and then quenched by addition of 2 M sodium hydroxide (30 mL). The mixture was extracted with ethyl acetate (100 mL). The organic layer was washed with saturated ammonium chloride (50 mL), brine (50 mL), dried over anhydrous sodium sulfate, and filtered. Concentration of the filtrate in vacuo provided a residue which was purified by column chromatography, eluting with a gradient of 10 to 60% of ethyl acetate (containing 20% of ethanol and 0.1% of ammonium hydroxide) in hexanes. Additional purification by preparative reverse-phase HPLC, eluting with a gradient of 7 to 50% of acetonitrile in water containing 0.5% of formic acid, afforded the title compound as a colorless solid (0.045 g, 5% yield): $^1$H NMR (300 MHz, DMSO-d$_6$) δ 8.86 (d, J=2.2 Hz, 1H), 8.16 (s, 1H), 7.88 (d, J=8.2 Hz, 1H), 7.35-7.22 (m, 5H), 7.16 (d, J=12.7 Hz, 1H), 7.09 (t, J=54.4 Hz, 1H), 6.99 (d, J=2.2 Hz, 1H), 3.99-3.90 (m, 1H), 3.64 (d, J=13.1 Hz, 1H), 3.52 (d, J=13.0 Hz, 1H), 2.77 (s, 3H), 2.74-2.66 (m, 1H), 2.60 (d, J=6.2 Hz, 2H), 2.42-2.34 (m, 1H), 2.13-2.02 (m, 1H), 1.81-1.69 (m, 1H), NH and COOH not observed; MS (ES+) m/z 497.2 (M+1).

Example 271

Synthesis of (R)-4-((1-benzylpyrrolidin-3-yl)amino)-2-fluoro-5-methyl-N-(thiazol-4-yl)benzenesulfonamide Formate

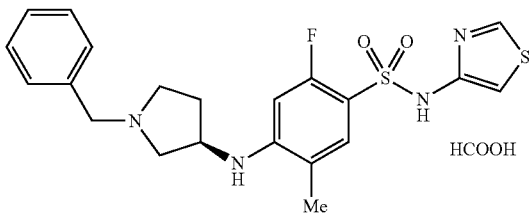 [SMILES: Cc1cc(S(=O)(=O)Nc2cscn2)c(F)cc1N[C@@H]1CCN(Cc2ccccc2)C1 ; "HCOOH"]

Step 1. Preparation of tert-butyl (R)-((4-((1-benzylpyrrolidin-3-yl)amino)-5-chloro-2-fluorophenyl)sulfonyl)(thiazol-4-yl)carbamate

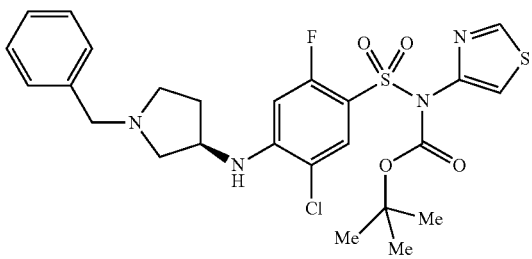 [SMILES: CC(C)(C)OC(=O)N(c1cscn1)S(=O)(=O)c1cc(Cl)c(N[C@@H]2CCN(Cc3ccccc3)C2)cc1F]

To a solution of tert-butyl ((5-chloro-2,4-difluorophenyl)sulfonyl)(thiazol-4-yl)carbamate (2.46 g, 6.00 mmol) in anhydrous N,N-dimethylformamide (10 mL) was added (R)-1-benzylpyrrolidin-3-amine (1.20 g, 6.81 mmol) at 0° C. The reaction mixture was allowed to warm to ambient temperature and was stirred for 18 h. The mixture was diluted with water (100 mL) and the resulting precipitate was filtered off and rinsed with water (50 mL) to afford the title compound as a grey solid (3.10 g, 91% yield): $^1$H NMR (300 MHz, CDCl$_3$) δ 8.80 (d, J=2.3 Hz, 1H), 7.95 (d, J=7.1 Hz, 1H), 7.52 (dd, J=2.3, 0.4 Hz, 1H), 7.38-7.33 (m, 5H), 6.36 (d, J=12.4 Hz, 1H), 5.31-5.28 (m, 1H), 4.04-3.99 (m, 1H), 3.70 (s, 2H), 2.95-2.87 (m, 1H), 2.85-2.80 (m, 1H), 2.70-2.65 (m, 1H), 2.55-2.46 (m, 1H), 2.44-2.35 (m, 1H), 1.81-1.73 (m, 1H), 1.40 (s, 9H); MS (ES+) m/z 567.4 (M+1), 569.4 (M+1).

Step 2. Preparation of (R)-4-((1-benzylpyrrolidin-3-yl)amino)-2-fluoro-5-methyl-N-(thiazol-4-yl)benzenesulfonamide Formate

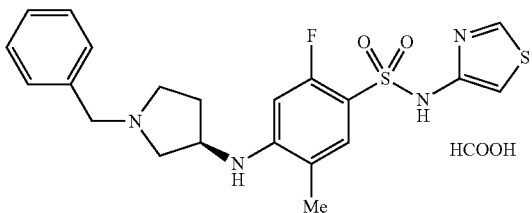 [SMILES: Cc1cc(S(=O)(=O)Nc2cscn2)c(F)cc1N[C@@H]1CCN(Cc2ccccc2)C1 ; "HCOOH"]

Following the procedure as described for EXAMPLE 269 and making non-critical variations as required to replace tert-butyl (S)-((4-((1-benzylpyrrolidin-3-yl)oxy)-3-chloro-2,6-difluorophenyl)sulfonyl)(thiazol-4-yl)carbamate with tert-butyl (R)-((4-((1-benzylpyrrolidin-3-yl)amino)-5-chloro-2-fluorophenyl)sulfonyl)(thiazol-4-yl)carbamate, afforded 0.68 g of 4:1 a mixture of tert-butyl (R)-((4-((1-benzylpyrrolidin-3-yl)amino)-2-fluoro-5-methylphenyl)sulfonyl)(thiazol-4-yl)carbamate (MS (ES+) m/z 547.4 (M+1)) and the title compound. An aliquot of the mixture (0.10 g) was stirred in formic acid (10 mL) for 30 minutes and then purified by preparative reverse-phase HPLC, eluting with a gradient of 7 to 50% of acetonitrile in water containing 0.5% of formic acid, to afford the title compound as a colorless solid (0.070 g): $^1$H NMR (300 MHz, DMSO-d$_6$) δ 88.85 (d, J=2.2 Hz, 1H), 8.19 (s, 1H), 7.36-7.29 (m, 5H), 7.25 (dtd, J=8.1, 5.2, 2.9 Hz, 1H), 6.86 (d, J=2.2 Hz, 1H), 6.40 (d, J=13.8 Hz, 1H), 5.78-5.74 (m, 1H), 4.04-3.93 (m, 1H), 3.62 (s, 2H), 2.87 (dd, J=9.4, 7.2 Hz, 1H), 2.69-2.61 (m, 1H), 2.54-2.44 (m, 2H), 2.27-2.16 (m, 1H), 2.05 (s, 3H), 1.79-1.68 (m, 1H), NH and COOH not observed; MS (ES+) m/z 447.1 (M+1).

Example 272

Synthesis of (R)-4-((1-benzylpyrrolidin-3-yl)(methyl)amino)-2-fluoro-5-methyl-N-(thiazol-4-yl)benzenesulfonamide

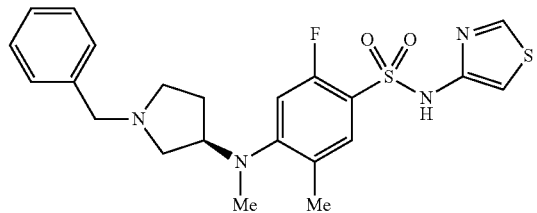 [SMILES: Cc1cc(S(=O)(=O)Nc2cscn2)c(F)cc1N(C)[C@@H]1CCN(Cc2ccccc2)C1]

Following the procedure as described for EXAMPLE 103, Step 4 and making non-critical variations as required to replace (S)-4-((1-benzylpyrrolidin-3-yl)amino)-2,6-difluoro-3-methyl-N-(thiazol-4-yl)benzenesulfonamide with tert-butyl (R)-((4-((1-benzylpyrrolidin-3-yl)amino)-2-fluoro-5-methylphenyl)sulfonyl)(thiazol-4-yl)carbamate, and purification by column chromatography, eluting with a gradient of 10 to 60% of ethyl acetate (containing 20% of ethanol and 0.1% of ammonium hydroxide) in hexanes, afforded the title compound as a colorless solid (0.37 g, 76% yield): $^1$H NMR (300 MHz, DMSO-d$_6$) δ 11.09 (s, 1H), 8.87 (d, J=2.2 Hz, 1H), 7.54 (d, J=8.5 Hz, 1H), 7.29 (d, J=1.8 Hz, 4H), 7.23 (ddd, J=8.5, 5.3, 3.3 Hz, 1H), 6.94 (d, J=2.2 Hz, 1H), 6.88 (d, J=12.8 Hz, 1H), 3.96-3.87 (m, 1H), 3.63 (d, J=13.1 Hz, 1H), 3.51 (d, J=13.0 Hz, 1H), 2.70-2.62 (m, 4H), 2.57 (d, J=6.2 Hz, 2H), 2.37 (q, J=8.1 Hz, 1H), 2.19 (s, 3H), 2.06-1.95 (m, 1H), 1.80-1.69 (m, 1H); MS (ES+) m/z 461.3 (M+1).

Example 273

Synthesis of (S)-4-((1-benzylpyrrolidin-3-yl)oxy)-2-fluoro-5-methyl-N-(thiazol-4-yl)benzenesulfonamide 2,2,2-trifluoroacetate

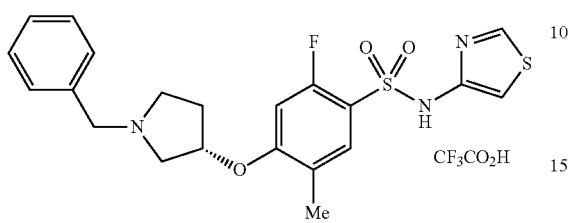

Step 1. Preparation of tert-butyl (S)-((4-((1-benzylpyrrolidin-3-yl)oxy)-5-chloro-2-fluorophenyl)sulfonyl)(thiazol-4-yl)carbamate

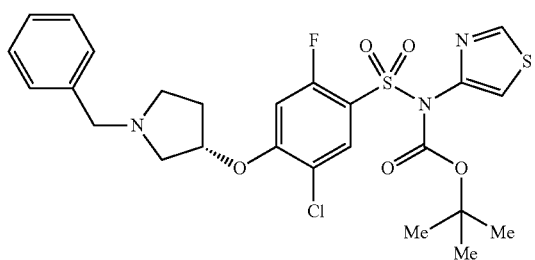 [SMILES: CC(C)(C)OC(=O)N(c1cscn1)S(=O)(=O)c1cc(Cl)c(O[C@H]2CCN(Cc3ccccc3)C2)cc1F]

Following the procedure as described for EXAMPLE 268, Step 1 and making non-critical variations as required to replace tert-butyl ((3-chloro-2,4,6-trifluorophenyl)sulfonyl)(thiazol-4-yl)carbamate with tert-butyl ((5-chloro-2,4-difluorophenyl)sulfonyl)(thiazol-4-yl)carbamate, afforded the title compound as a colorless solid (2.35 g, 63% yield): $^1$H NMR (300 MHz, CDCl$_3$) δ 8.81 (d, J=2.2 Hz, 1H), 8.12 (d, J=7.4 Hz, 1H), 7.53 (dd, J=2.3, 0.4 Hz, 1H), 7.38-7.32 (m, 5H), 6.66 (d, J=11.4 Hz, 1H), 4.92-4.86 (m, 1H), 3.75-3.71 (m, 2H), 3.15-3.10 (m, 1H), 2.87-2.71 (m, 3H), 2.40 (dq, J=14.0, 7.1 Hz, 1H), 2.12-2.07 (m, 1H), 1.39 (s, 9H).

Step 2. Preparation of tert-butyl (S)-((4-((1-benzylpyrrolidin-3-yl)oxy)-2-fluoro-5-methylphenyl)sulfonyl)(thiazol-4-yl)carbamate

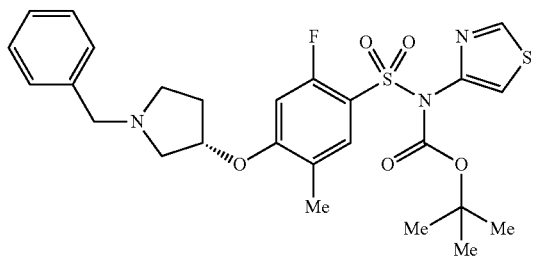 [SMILES: Cc1cc(S(=O)(=O)N(C(=O)OC(C)(C)C)c2cscn2)c(F)cc1O[C@H]1CCN(Cc2ccccc2)C1]

Following the procedure as described for EXAMPLE 101, Step 2 and making non-critical variations as required to replace tert-butyl (S)-3-((4-(N-(tert-butoxycarbonyl)-N-(thiazol-4-yl)sulfamoyl)-2-chloro-5-fluorophenyl)amino)pyrrolidine-1-carboxylate with tert-butyl (S)-((4-((1-benzylpyrrolidin-3-yl)oxy)-5-chloro-2-fluorophenyl)sulfonyl)(thiazol-4-yl)carbamate, the title compound was obtained as a colorless solid (1.16 g, 51% yield): MS (ES+) m/z 461.3 (M+1).

Step 3. Preparation of (S)-4-((1-benzylpyrrolidin-3-yl)oxy)-2-fluoro-5-methyl-N-(thiazol-4-yl)benzenesulfonamide 2,2,2-trifluoroacetate

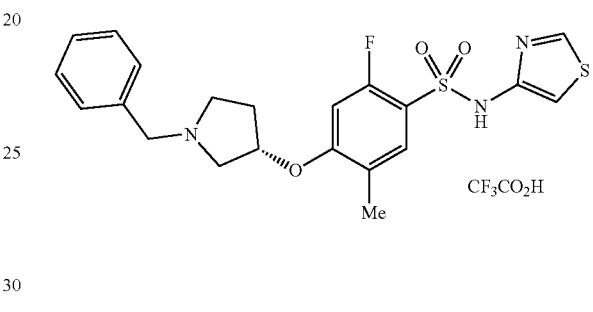

To a solution of tert-butyl (S)-((4-((1-benzylpyrrolidin-3-yl)oxy)-2-fluoro-5-methylphenyl)sulfonyl)(thiazol-4-yl)carbamate (1.30 g, 2.37 mmol) in dichloromethane (10 mL) was added trifluoroacetic acid (10 mL). The reaction mixture was stirred at ambient temperature for 1 h and then concentrated in vacuo. Purification of the residue by preparative reverse-phase HPLC, eluting with a gradient of 7 to 50% of acetonitrile in water containing 0.1% of trifluoroacetic acid, afforded the title compound as a colorless solid (0.22 g, 17% yield): $^1$H NMR (300 MHz, DMSO-d$_6$) δ 11.24 (s, 1H), 11.02-10.97 (m, 1H), 8.88 (d, J=1.8 Hz, 1H), 7.65-7.59 (m, 1H), 7.54-7.49 (m, 2H), 7.49-7.41 (m, 3H), 7.11 (d, J=12.3 Hz, 1H), 6.98 (s, 1H), 5.24-5.22 (m, 1H), 4.50-4.37 (m, 2H), 4.29-4.15 (m, 2H), 3.59-3.53 (m, 2H), 2.68-2.62 (m, 1H), 2.12-2.05 (m, 4H); MS (ES+) m/z 448.3 (M+1).

Example 274

Synthesis of (S)-4-((1-benzylpyrrolidin-3-yl)oxy)-3-bromo-2,6-difluoro-N-(thiazol-4-yl)benzenesulfonamide Formate

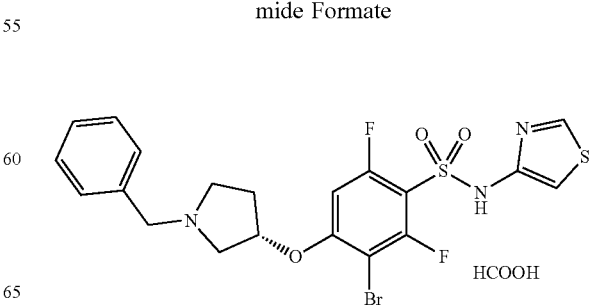

305

Step 1. Preparation of tert-butyl (S)-((4-((1-benzylpyrrolidin-3-yl)oxy)-3-bromo-2,6-difluorophenyl)sulfonyl)(thiazol-4-yl)carbamate

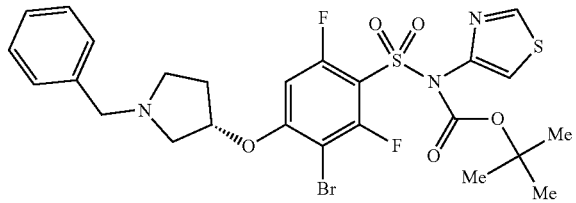 [SMILES: CC(C)(C)OC(=O)N(c1cscn1)S(=O)(=O)c1c(F)cc(O[C@H]2CCN(Cc3ccccc3)C2)c(Br)c1F]

Following the procedure as described for EXAMPLE 268, Step 1 and making non-critical variations as required to replace tert-butyl ((3-chloro-2,4,6-trifluorophenyl)sulfonyl)(thiazol-4-yl)carbamate with tert-butyl ((3-bromo-2,4,6-trifluorophenyl)sulfonyl)(thiazol-4-yl)carbamate, the title compound was obtained as a colorless solid (1.15 g, 53% yield): $^1$H NMR (300 MHz, CDCl$_3$) δ 8.82 (d, J=2.2 Hz, 1H), 7.54 (d, J=2.2 Hz, 1H), 7.37-7.35 (m, 4H), 7.32 (ddd, J=8.0, 3.5, 1.7 Hz, 1H), 6.52 (dd, J=11.9, 1.9 Hz, 1H), 4.95-4.89 (m, 1H), 3.80-3.71 (m, 2H), 3.18-3.12 (m, 1H), 2.87-2.75 (m, 3H), 2.47-2.35 (m, 1H), 2.13-2.08 (m, 1H), 1.40 (s, 9H); MS (ES+) m/z 630.4 (M+1), 632.4 (M+1).

Step 2. Preparation of (S)-4-((1-benzylpyrrolidin-3-yl)oxy)-3-bromo-2,6-difluoro-N-(thiazol-4-yl)benzenesulfonamide Formate

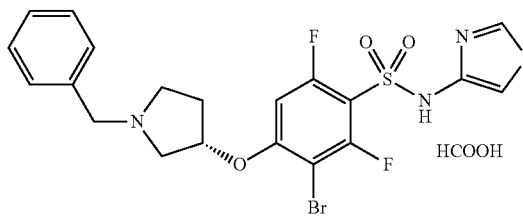

Following the procedure as described for EXAMPLE 273, Step 3 and making non-critical variations as required to replace tert-butyl (S)-((4-((1-benzylpyrrolidin-3-yl)oxy)-2-fluoro-5-methylphenyl)sulfonyl)(thiazol-4-yl)carbamate with tert-butyl (S)-((4-((1-benzylpyrrolidin-3-yl)oxy)-3-bromo-2,6-difluorophenyl)sulfonyl)(thiazol-4-yl)carbamate, and purification by preparative reverse-phase HPLC, eluting with a gradient of 7 to 50% of acetonitrile in water containing 0.5% of formic acid, afforded the title compound as a colorless solid (0.045 g, 49% yield): $^1$H NMR (300 MHz, DMSO-d$_6$) δ 8.89 (d, J=2.2 Hz, 1H), 8.15 (s, 1H), 7.35-7.30 (m, 4H), 7.28-7.21 (m, 1H), 7.09 (dd, J=12.7, 1.8 Hz, 1H), 6.99 (d, J=2.2 Hz, 1H), 5.09-5.03 (m, 1H), 3.65 (d, J=13.1 Hz, 1H), 3.62 (d, J=13.0 Hz, 1H), 2.91 (dd, J=11.0, 6.0 Hz, 1H), 2.75-2.66 (m, 2H), 2.47-2.29 (m, 2H), 1.85-1.75 (m, 1H); NH and COOH not observed; MS (ES+) m/z 530.1 (M+1), 532.1 (M+1).

306

Example 275

Synthesis of (S)-4-((1-benzylpyrrolidin-3-yl)oxy)-2,6-difluoro-N-(thiazol-4-yl)-3-vinylbenzenesulfonamide 2,2,2-trifluoroacetate

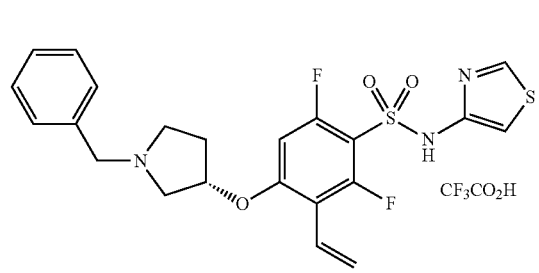 [SMILES: C=Cc1c(O[C@H]2CCN(Cc3ccccc3)C2)cc(F)c(S(=O)(=O)Nc2cscn2)c1F ; "CF3CO2H"]

To a mixture of tert-butyl (S)-((4-((1-benzylpyrrolidin-3-yl)oxy)-3-bromo-2,6-difluorophenyl)sulfonyl)(thiazol-4-yl)carbamate (1.00 g, 1.59 mmol), vinylboronic acid pinacol ester (0.81 mL, 4.77 mmol), and potassium phosphate (1.69 g, 7.95 mmol) in anhydrous dioxane (24 mL) was added palladium acetate (0.071 g, 0.32 mmol) and tricyclohexylphosphonium tetrafluoroborate (0.24 g, 0.64 mmol). The resulting mixture was degassed with nitrogen and then heated to reflux for 4 h. The mixture was allowed to cool to ambient temperature. To it was then added 2 M aqueous sodium carbonate (3 mL, 6.00 mmol), vinylboronic acid pinacol ester (0.81 mL, 4.77 mmol), and tetrakis(triphenylphosphine)palladium(0) (0.37 g, 0.32 mmol) and the reaction mixture was heated to reflux for 18 h. After cooling to ambient temperature, the reaction mixture was diluted with ethyl acetate (80 mL). The mixture was washed with saturated ammonium chloride (2×60 mL), brine (30 mL), dried over anhydrous sodium sulfate, and filtered. Concentration of the filtrate in vacuo provided a residue which was purified by column chromatography, eluting with a gradient of 10 to 65% of ethyl acetate (containing 20% of ethanol and 0.1% of ammonium hydroxide) in hexanes.

Additional purification by preparative reverse-phase HPLC, eluting with a gradient of 7 to 50% of acetonitrile in water containing 0.1% of trifluoroacetic acid, afforded the title compound as a colorless solid (0.75 g, 80% yield): $^1$H NMR (300 MHz, DMSO-d$_6$) δ 11.53 (s, 1H), 10.90 (s, 1H), 8.92 (d, J=2.1 Hz, 1H), 7.57-7.43 (m, 5H), 7.11 (s, 1H), 7.05 (d, J=2.2 Hz, 1H), 6.65 (dd, J=18.0, 11.8 Hz, 1H), 5.88 (d, J=18.0 Hz, 1H), 5.60-5.55 (m, 1H), 5.29-5.26 (m, 1H), 4.48-4.40 (m, 2H), 3.59-3.50 (m, 4H), 2.31-2.12 (m, 2H); MS (ES+) m/z 478.2 (M+1).

Example 276

Synthesis of (S)-4-((1-benzylpyrrolidin-3-yl)oxy)-3-ethyl-2,6-difluoro-N-(thiazol-4-yl)benzenesulfonamide 2,2,2-trifluoroacetate

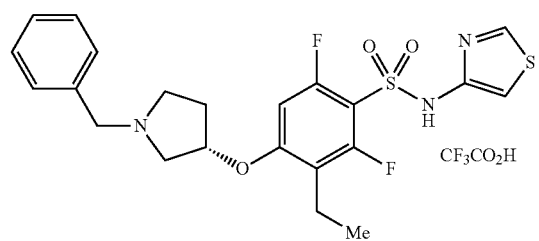 [SMILES: CCc1c(O[C@H]2CCN(Cc3ccccc3)C2)cc(F)c(S(=O)(=O)Nc2cscn2)c1F ; "CF3CO2H"]

To a mixture of (S)-4-((1-benzylpyrrolidin-3-yl)oxy)-2,6-difluoro-N-(thiazol-4-yl)-3-vinylbenzenesulfonamide (0.37 g, 0.77 mmol) in methanol (30 mL) and ethyl acetate (20 mL) was added 10% palladium on carbon (0.20 g) and the mixture was stirred under an atmosphere of hydrogen (1 bar) for 4 h. Filtration through a pad of Celite and concentration of the filtrate in vacuo provided a residue. Purification of the residue by preparative reverse-phase HPLC, eluting with a gradient of 7 to 50% of acetonitrile in water containing 0.1% of trifluoroacetic acid, afforded the title compound as a colorless solid (0.15 g, 32% yield): $^1$H NMR (300 MHz, DMSO-$d_6$) δ 11.47 (s, 1H), 11.25 (s, 1H), 8.91 (d, J=2.1 Hz, 1H), 7.55-7.43 (m, 5H), 7.05-7.00 (m, 2H), 5.28-5.21 (m, 1H), 4.50-4.38 (m, 2H), 3.62-3.51 (m, 4H), 2.56-2.51 (m, 2H), 2.35-2.13 (m, 2H), 1.08-0.90 (m, 3H); MS (ES+) m/z 480.3 (M+1).

Example 277

Synthesis of (S)-4-((1-benzylpyrrolidin-3-yl)(methyl)amino)-2-fluoro-N-(isothiazol-3-yl)-5-methylbenzenesulfonamide 2,2,2-trifluoroacetate

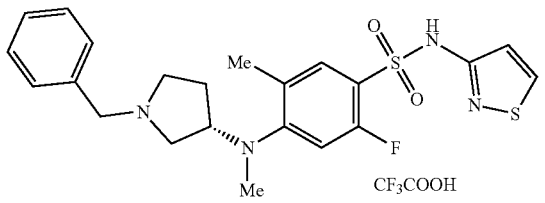

Step 1. Preparation of tert-butyl isothiazol-3-ylcarbamate

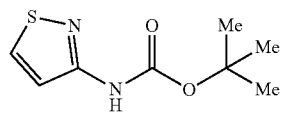 [SMILES: CC(C)(C)OC(=O)Nc1ccsn1]

To a slurry of isothiazole-3-carboxylic acid (5.0 g, 38.7 mmol) in tert-butanol (194 mL) was added triethylamine (4.3 g, 42.6 mmol) followed by diphenylphosphoryl azide (11.9 g, 43.3 mmol). The reaction mixture was heated to reflux for 9 hours. Concentration under reduced pressure provided a residue which was dissolved in ethyl acetate (300 mL). The organic layer was washed with water (100 mL), 1 N sodium hydroxide solution (50 mL), water (100 mL), and brine (50 mL). The organic layer was dried over anhydrous magnesium sulfate, filtered, and the filtrate concentrated in vacuo. Purification of the residue by column chromatography, eluting with a gradient of 0 to 10% of ethyl acetate in heptane, provided the title compound as a colorless solid (6.16 g, 79% yield): $^1$H NMR (300 MHz, CDCl$_3$) δ 9.03-8.98 (m, 1H), 8.58 (d, J=4.9 Hz, 1H), 7.70 (d, J=4.9 Hz, 1H), 1.53 (d, J=0.7 Hz, 9H).

Step 2. Preparation of tert-butyl ((5-chloro-2,4-difluorophenyl)sulfonyl)(isothiazol-3-yl)carbamate

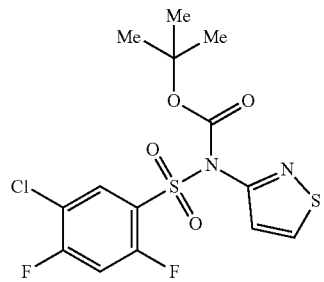 [SMILES: CC(C)(C)OC(=O)N(c1ccsn1)S(=O)(=O)c1cc(Cl)c(F)cc1F]

To a solution of tert-butyl isothiazol-3-ylcarbamate (1.0 g, 5.0 mmol) in anhydrous tetrahydrofuran (13 mL) was added a 1 M solution of lithium bis(trimethylsilyl)amide in tetrahydrofuran (5 mL, 5 mmol) at −78° C. The reaction mixture was stirred at −78° C. for 10 minutes, then allowed to warm to ambient temperature, and stirred for 1 h. The reaction mixture was then cooled −78° C., and a solution of 5-chloro-2,4-difluorobenzenesulfonyl chloride (1.23 g, 5 mmol) in anhydrous tetrahydrofuran (2.8 mL) was added to it. The reaction mixture was allowed to warm to ambient temperature and stirred for 12 h. The reaction mixture was quenched by addition of saturated ammonium chloride solution (50 mL), and the mixture was extracted with ethyl acetate (3×50 mL). The combined organic layers were washed with water (50 mL), brine (50 mL), dried over anhydrous magnesium sulfate, and filtered. Concentration of the filtrate in vacuo provided the title compound as a brown solid (2.0 g, 97% yield): MS (ES+) m/z 311.0 (M+1), 313.0 (M+1).

Step 3. Preparation of tert-butyl (S)-((4-((1-benzylpyrrolidin-3-yl)amino)-5-chloro-2-fluorophenyl)sulfonyl)(isothiazol-3-yl)carbamate

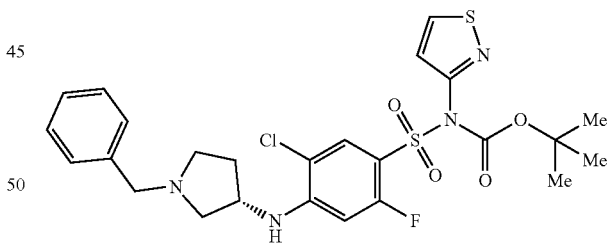

To a solution of tert-butyl ((5-chloro-2,4-difluorophenyl)sulfonyl)(isothiazol-3-yl)carbamate (2.0 g, 4.86 mmol) in anhydrous N,N-dimethylformamide (25 mL) was added (S)-1-benzylpyrrolidin-3-amine (1.06 g, 6.0 mmol) followed by N,N-diisopropylethylamine (3.23 g, 25 mmol). The reaction mixture was heated to 50° C. for 16 h. After cooling to ambient temperature, the reaction mixture was diluted with ethyl acetate (150 mL). The organic layer was washed with water (3×50 mL), brine (50 mL), and dried over anhydrous magnesium sulfate. The solution was filtered, and the filtrate concentrated in vacuo to afford the title compound as a beige solid (2.6 g, 94% yield): MS (ES+) m/z 567.0 (M+1), 569.0 (M+1).

Step 4. Preparation of tert-butyl (S)-((4-((1-benzylpyrrolidin-3-yl)amino)-2-fluoro-5-methylphenyl)sulfonyl)(isothiazol-3-yl)carbamate

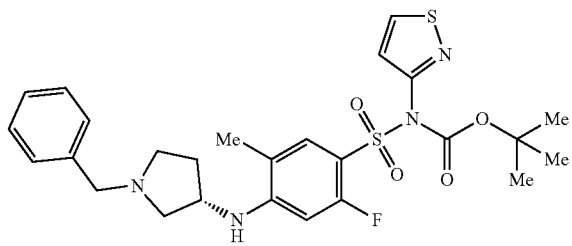 [SMILES: Cc1cc(S(=O)(=O)N(C(=O)OC(C)(C)C)c2ccsn2)c(F)cc1N[C@H]1CCN(Cc2ccccc2)C1]

A solution of tert-butyl (S)-((4-((1-benzylpyrrolidin-3-yl)amino)-5-chloro-2-fluorophenyl)sulfonyl)(isothiazol-3-yl)carbamate (2.6 g, 4.58 mmol) in anhydrous 1,4-dioxane (53 mL) was sparged with argon for 10 minutes. To the solution was then added methylboronic acid (1.8 g, 30 mmol), potassium phosphate tribasic (3.18 g, 15 mmol), palladium acetate (0.112 g, 0.5 mmol), and tricyclohexylphosphonium tetrafluoroborate (0.368 g, 1.06 mmol). The reaction mixture was sparged with argon for 5 minutes and then heated to reflux for 12 h. The reaction mixture was allowed to cool to ambient temperature and filtered through a pad of Celite. The filter pad was washed with ethyl acetate (3×30 mL) and the combined organic layer was concentrated in vacuo. Purification of the residue by column chromatography, eluting with a gradient of 10 to 100% of ethyl acetate in heptane, afforded the title compound as a brown solid (0.91 g, 36% yield): MS (ES+) m/z 547.4 (M+1).

Step 5. Preparation of (S)-4-((1-benzylpyrrolidin-3-yl)(methyl)amino)-2-fluoro-N-(isothiazol-3-yl)-5-methylbenzenesulfonamide 2,2,2-trifluoroacetate

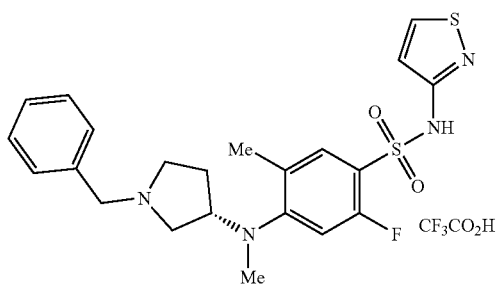 [SMILES: Cc1cc(S(=O)(=O)Nc2ccsn2)c(F)cc1N(C)[C@H]1CCN(Cc2ccccc2)C1 ; "CF3CO2H"]

To a solution of tert-butyl (S)-((4-((1-benzylpyrrolidin-3-yl)amino)-2-fluoro-5-methylphenyl)sulfonyl)(isothiazol-3-yl)carbamate (0.91 g, 1.66 mmol) in trifluoroacetic acid (3.5 mL) was added paraformaldehyde (0.150 g, 4.98 mmol). The reaction mixture was stirred for 10 minutes before sodium triacetoxyborohydride (1.4 g, 6.64 mmol) was added to it. The reaction mixture was stirred for 1 h at ambient temperature and then diluted with ethyl acetate (50 mL) and water (50 mL). Sodium bicarbonate was carefully added until evolution of gas ceased. The layers were separated and the aqueous layer was extracted with ethyl acetate (2×30 mL). The organic layers were washed with water (30 mL), brine (30 mL), and dried over anhydrous magnesium sulfate. Filtration and concentration of the filtrate in vacuo provided a residue which was purified by column chromatography, eluting with a gradient of 5 to 50% of ethyl acetate (containing 20% of ethanol and 1% of ammonium hydroxide) in heptane. Further purification by preparative The solid was further purified by reverse-phase preparative HPLC, using a gradient of 5 to 95% of acetonitrile in water with 0.1% of trifluoroacetic acid, provided the title compound as a colorless solid (0.159 g, 21% yield): $^1$H NMR (300 MHz, DMSO-$d_6$) δ 11.86-11.73 (m, 1H), 10.37-10.04 (m, 1H), 8.97-8.90 (m, 1H), 7.75-7.64 (m, 1H), 7.56-7.43 (m, 5H), 7.09-7.00 (m, 1H), 6.99-6.94 (m, 1H), 4.46-3.97 (m, 3H), 3.57-3.07 (m, 4H), 2.72-2.56 (m, 3H), 2.30-2.21 (m, 3H), 2.20-1.87 (m, 2H); $^{19}$F NMR (282 MHz, DMSO-$d_6$) δ −74.1 (s, 3F), −112.2 (s, 1F); MS (ES+) m/z 461.2 (M+1).

Example 278

Synthesis of (S)-2-fluoro-5-methyl-4-(methyl(1-(pyridin-2-ylmethyl)pyrrolidin-3-yl)amino)-N-(thiazol-4-yl)benzenesulfonamide 2,2,2-trifluoroacetate

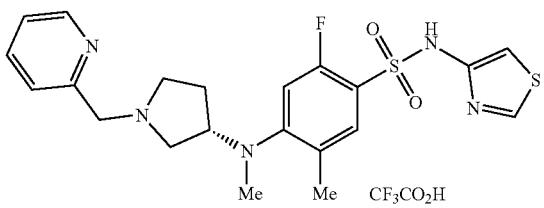

Step 1. Preparation of (S)-5-chloro-2-fluoro-4-((1-(pyridin-2-ylmethyl)pyrrolidin-3-yl)amino)-N-(thiazol-4-yl)benzenesulfonamide 2,2,2-trifluoroacetate

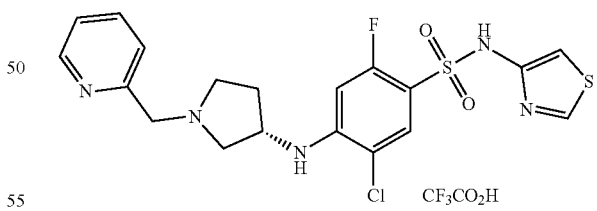

Following the procedure as described for EXAMPLE 258, Step 3 and making non-critical variations as required to replace benzaldehyde with picolinaldehyde, and purification by preparative reverse-phase HPLC, eluting with a gradient of 10 to 50% of acetonitrile in water containing 0.1% of trifluoroacetic acid, afforded the title compound as a colorless solid (0.125 g, 13% yield): MS (ES+) m/z 468.2 (M+1), 470.1 (M+1).

Step 2. Preparation of (S)-2-fluoro-5-methyl-4-((1-(pyridin-2-ylmethyl)pyrrolidin-3-yl)amino)-N-(thiazol-4-yl)benzenesulfonamide

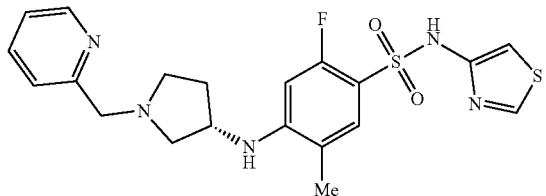 [SMILES: Cc1cc(S(=O)(=O)Nc2cscn2)c(F)cc1N[C@H]1CCN(Cc2ccccn2)C1]

To a mixture of (S)-5-chloro-2-fluoro-4-((1-(pyridin-2-ylmethyl)pyrrolidin-3-yl)amino)-N-(thiazol-4-yl)benzenesulfonamide 2,2,2-trifluoroacetate (0.125 g, 0.21 mmol), methylboronic acid (0.16 g, 2.7 mmol), and potassium phosphate (0.28 g, 1.30 mmol) in anhydrous dioxane (5 mL) was added palladium acetate (0.018 g, 0.08 mmol) and tricyclohexylphosphonium tetrafluoroborate (0.059 g, 0.16 mmol). The resulting mixture was degassed by sparging with nitrogen and then heated to reflux for 4 h.

After cooling to ambient temperature, the mixture was diluted with water (15 mL) and extracted with ethyl acetate (3×15 mL). The combined organic fractions were washed with brine (10 mL), dried over anhydrous magnesium sulfate, and filtered. The filtrate was concentrated in vacuo to afford the title compound as a grey solid (0.87 g, 98% yield): MS (ES+) m/z 448.3 (M+1).

Step 3. Preparation of (S)-2-fluoro-5-methyl-4-(methyl(1-(pyridin-2-ylmethyl)pyrrolidin-3-yl)amino)-N-(thiazol-4-yl)benzenesulfonamide 2,2,2-trifluoroacetate

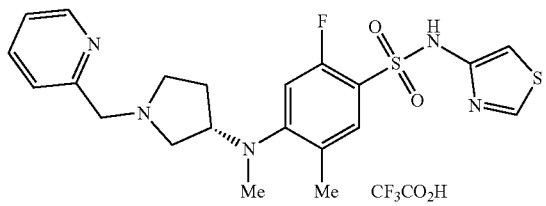

Following the procedure as described for EXAMPLE 155, Step 4 and making non-critical variations as required to replace (S)-2-fluoro-4-((1-(2-fluorobenzyl)pyrrolidin-3-yl)amino)-5-methyl-N-(thiazol-4-yl)benzenesulfonamide with (S)-2-fluoro-5-methyl-4-((1-(pyridin-2-ylmethyl)pyrrolidin-3-yl)amino)-N-(thiazol-4-yl)benzenesulfonamide, and purification by preparative reverse-phase HPLC, eluting with a gradient of 8 to 50% of acetonitrile in water containing 0.1% of trifluoroacetic acid, afforded the title compound as a colorless solid (0.009 g, 7% yield): $^1$H NMR (300 MHz, DMSO-$d_6$) δ 11.24 (s, 1H), 10.54-10.43 (m, 1H), 8.88 (d, J=2.2 Hz, 1H), 8.65 (ddd, J=0.9, 1.6, 4.8 Hz, 1H), 7.92 (td, J=1.8, 7.7 Hz, 1H), 7.62 (d, J=8.2 Hz, 1H), 7.51-7.44 (m, 2H), 7.04 (d, J=12.5 Hz, 1H), 6.99 (d, J=2.2 Hz, 1H), 4.60-4.55 (m, 2H), 4.17-4.12 (m, 1H), 3.57-3.50 (m, 2H), 3.38-3.31 (m, 2H), 2.63 (s, 3H), 2.23 (s, 3H), 2.18-2.04 (m, 2H); MS (ES+) m/z 462.2 (M+1).

Example 279

Synthesis of (S)-4-((1-benzylpyrrolidin-3-yl)(methyl)amino)-2,6-difluoro-N-(isothiazol-3-yl)-3-methylbenzenesulfonamide 2,2,2-trifluoroacetate

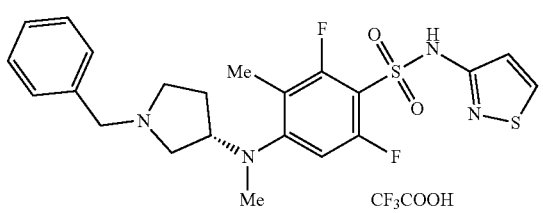

Step 1. Preparation of 3-bromo-2,4,6-trifluorobenzenesulfonyl chloride

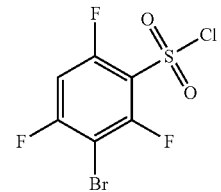 [SMILES: O=S(=O)(Cl)c1c(F)cc(F)c(Br)c1F]

To 4-bromo-1,3,5-trifluorobenzene (25 g, 0.118 mmol) was added chlorosulfonic acid (24 mL) and the reaction mixture was heated to 80° C. for 72 h. The reaction mixture was allowed to cool to ambient temperature and very slowly added onto ice. The resulting solid was filtered off and dissolved in dichloromethane (200 mL). The organic phase was washed with water (2×50 mL), brine (50 mL), and dried over anhydrous magnesium sulfate. Filtration and concentration of the filtrate in vacuo afforded the title compound as a colorless solid (28.6 g, 78% yield): $^1$H NMR (300 MHz, CDCl$_3$) δ 7.06 (ddd, J=9.9, 7.8, 2.2 Hz, 1H).

Step 2. Preparation of tert-butyl ((3-bromo-2,4,6-trifluorophenyl)sulfonyl)(isothiazol-3-yl)carbamate

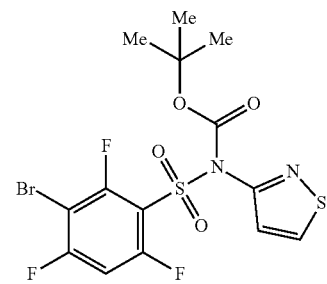 [SMILES: CC(C)(C)OC(=O)N(c1ccsn1)S(=O)(=O)c1c(F)cc(F)c(Br)c1F]

To a solution of tert-butyl isothiazol-3-ylcarbamate (0.9 g, 4.49 mmol) in anhydrous tetrahydrofuran (12 mL) was added a 1 M solution of lithium bis(trimethylsilyl)amide in tetrahydrofuran (4.94 mL, 4.94 mmol) at −78° C. The reaction mixture was stirred −78° C. for 10 minutes, allowed to warm to ambient temperature and stirred for 1 hour. The solution was then cooled to −78° C. and a solution of 5-bromo-2,4,6-trifluorobenzenesulfonyl chloride (1.39 g, 4.49 mmol) in anhydrous tetrahydrofuran (2.6 mL) was added to it. The reaction mixture was allowed to warm to ambient temperature, stirred for 12 h, and quenched by addition of saturated ammonium chloride solution (50 mL). The aqueous layer was extracted with ethyl acetate (3×50 mL). The combined organic layers were washed with water (50 mL), brine (50 mL), dried over anhydrous magnesium sulfate, and filtered. Concentration of the filtrate in vacuo and purification of the residue by column chromatography, eluting with a gradient of 0 to 5% of ethyl acetate in heptane, afforded the title compound as a beige solid (1.08 g, 97% yield): $^1$H NMR (300 MHz, CDCl$_3$) B 8.76 (d, J=4.7 Hz, 1H), 7.33 (d, J=4.7 Hz, 1H), 6.99 (ddd, J=9.9, 7.9, 2.1 Hz, 1H), 1.44-1.35 (m, 9H).

Step 3. Preparation of tert-butyl (S)-((4-((1-benzylpyrrolidin-3-yl)amino)-3-bromo-2,6-difluorophenyl)sulfonyl)(isothiazol-3-yl)carbamate

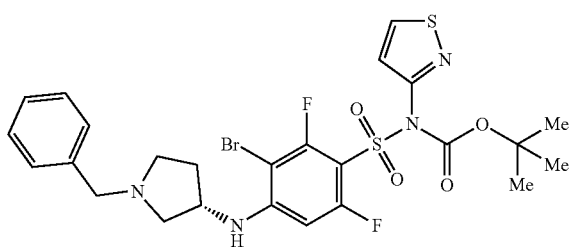 [SMILES: CC(C)(C)OC(=O)N(c1ccsn1)S(=O)(=O)c1c(F)cc(N[C@H]2CCN(Cc3ccccc3)C2)c(Br)c1F]

To a solution of tert-butyl ((3-bromo-2,4,6-trifluorophenyl)sulfonyl)(isothiazol-3-yl)carbamate (1.08 g, 2.28 mmol) in anhydrous N,N-dimethylformamide (12 mL) was added (S)-1-benzylpyrrolidin-3-amine (0.48 g, 2.74 mmol) followed by N,N-diisopropylethylamine (0.59 g, 4.56 mmol). The reaction mixture was heated to 50° C. for 3 h and then diluted with ethyl acetate (150 mL). The organic layer was washed with water (2×50 mL), brine (50 mL), and dried over anhydrous magnesium sulfate. Filtration and concentration of the filtrate in vacuo afforded a residue. Purification of the residue by column chromatography, using a gradient of 5 to 60% of ethyl acetate (containing 20% of ethanol and 1% of ammonium hydroxide) in heptane, provided the title compound as a colorless solid (1.02 g, 71% yield): $^1$H NMR (300 MHz, CDCl$_3$) δ 8.75-8.71 (m, 1H), 7.40-7.29 (m, 6H), 6.26-6.20 (m, 1H), 5.52-5.46 (m, 1H), 4.07-3.97 (m, 1H), 3.76-3.64 (m, 2H), 2.97-2.88 (m, 1H), 2.82-2.74 (m, 1H), 2.72-2.66 (m, 1H), 2.53-2.34 (m, 2H), 1.82-1.71 (m, 1H), 1.38-1.34 (s, 9H).

Step 4. Preparation of tert-butyl (S)-4-((1-benzylpyrrolidin-3-yl)amino)-2,6-difluoro-3-methylphenyl)sulfonyl)(isothiazol-3-yl)carbamate

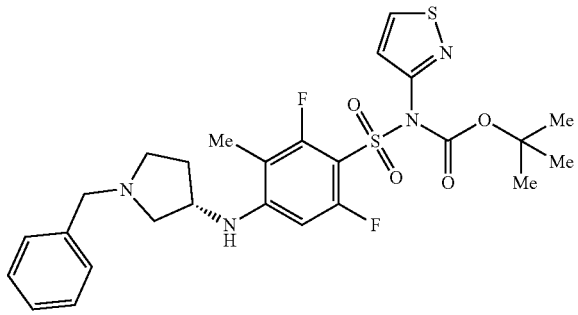 [SMILES: Cc1c(N[C@H]2CCN(Cc3ccccc3)C2)cc(F)c(S(=O)(=O)N(C(=O)OC(C)(C)C)c2ccsn2)c1F]

To a mixture of tert-butyl (S)-((4-((1-benzylpyrrolidin-3-yl)amino)-3-bromo-2,6-difluorophenyl)sulfonyl)(isothiazol-3-yl)carbamate (1.02 g, 1.62 mmol) in anhydrous 1,4-dioxane (16 mL) was added methylboronic acid (0.58 g, 9.7 mmol), potassium phosphate tribasic (1.03 g, 4.86 mmol), palladium acetate (0.036 g, 0.16 mmol), and tricyclohexylphosphonium tetrafluoroborate (0.119 g, 0.32 mmol). The slurry was degassed by sparging with argon and then heated reflux for 16 h. The reaction mixture was allowed to cool to ambient temperature and filtered through a pad of Celite. The filter pad was washed with ethyl acetate (3×30 mL), and the combined organic phase was concentrated in vacuo. Purification of the residue by column chromatography, eluting with a gradient of 0 to 10% of methanol in dichloromethane, provided the title compound as a brown solid (0.89 g, 97% yield): MS (ES+) m/z 565.4 (M+1).

Step 5. Preparation of (S)-4-((1-benzylpyrrolidin-3-yl)(methyl)amino)-2,6-difluoro-N-(isothiazol-3-yl)-3-methylbenzenesulfonamide 2,2,2-trifluoroacetate

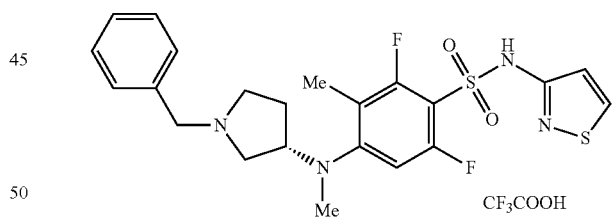

To a solution of tert-butyl (S)-4-((1-benzylpyrrolidin-3-yl)amino)-2,6-difluoro-3-methylphenyl)sulfonyl)(isothiazol-3-yl)carbamate (0.89 g, 1.63 mmol) in trifluoroacetic acid (3 mL) was added paraformaldehyde (0.120 g, 4.26 mmol). The reaction mixture was stirred for 10 minutes before sodium triacetoxyborohydride (0.92 g, 4.2 mmol) was added to it. The reaction mixture was stirred at ambient temperature for 1 h and subsequently diluted with ethyl acetate (50 mL) and water (50 mL). To the mixture was then added sodium bicarbonate until bubbling ceased. The layers were separated and the aqueous layer was extracted with ethyl acetate (2×30 mL). The combined organic layers were washed with water (30 mL), brine (30 mL), dried over anhydrous magnesium sulfate, and filtered. Concentration of the filtrate in vacuo provided a residue which was purified by column chromatography, eluting with a gradient of 0 to 10% of methanol in dichloromethane. Further purification by preparative reverse-phase HPLC, eluting with a gradient of 5 to 95% of acetonitrile in water containing 0.1% of trifluoroacetic acid, provided the title compound as a colorless solid (0.136 g, 14% yield): $^1$H NMR (300 MHz, DMSO-$d_6$) δ 12.09-11.96 (m, 1H), 10.36-9.94 (m, 1H), 8.93 (d, J=4.8 Hz, 1H), 7.61-7.43 (m, 5H), 6.95 (d, J=4.8 Hz, 1H), 6.93-6.85 (m, 1H), 4.47-4.30 (m, 2H), 4.30-3.92 (m, 2H), 3.62-3.08 (m, 2H), 2.77-2.59 (m, 3H), 2.07 (m, 5H); $^{19}$F NMR (282 MHz, DMSO-$d_6$) δ −73.5 (s, 3F), −108.1 (s, 1F), −111.5 (s, 1F); MS (ES+) m/z 479.1 (M+1).

Example 280

Synthesis of (R)-5-chloro-2-fluoro-4-(methyl(1-(1-phenylethyl)piperidin-4-yl)amino)-N-(thiazol-4-yl)benzenesulfonamide Formate

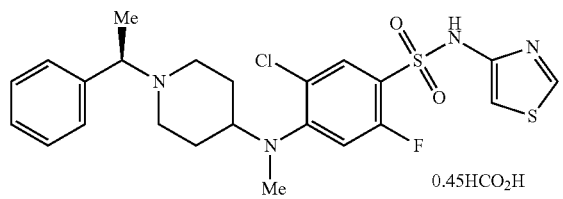

Step 1. Preparation of tert-butyl ((4-amino-5-chloro-2-fluorophenyl)sulfonyl)(thiazol-4-yl)carbamate

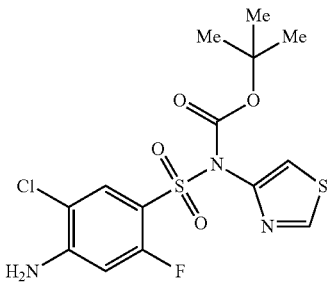

To a solution of tert-butyl ((5-chloro-2,4-difluorophenyl)sulfonyl)(thiazol-4-yl)carbamate (3.0 g, 7.3 mmol) in anhydrous N,N-dimethylformamide (37 mL) was added sodium azide (0.570 g, 8.8 mmol) and the reaction mixture was stirred at ambient temperature for 18 h. Water (50 mL) was added to the reaction mixture and the formed precipitate was collected by filtration. The obtained solid was dissolved in tetrahydrofuran (94 mL) and the mixture cooled to 0° C. Zinc dust (1.43 g, 21.8 mmol) and saturated ammonium chloride solution (31 mL) were then added to the mixture. The reaction mixture was allowed to warm to ambient temperature, stirred for 18 h, and then filtered through a pad of Celite. The filter pad was washed with tetrahydrofuran (2×30 mL). The combined organic phase was washed with brine (50 mL), dried over anhydrous magnesium sulfate, and filtered. Concentration of the filtrate in vacuo afforded the title compound as a colorless solid (2.67 g, 90% yield): MS (ES+) m/z 408.2 (M+1), 410.2 (M+1).

Step 2. Preparation of (R)-1-(1-phenylethyl)piperidin-4-one

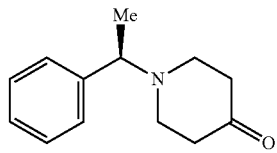 [SMILES: C[C@H](c1ccccc1)N1CCC(=O)CC1]

To a mixture of (R)-1-phenylethan-1-amine (9.7 g, 80.4 mmol) in a mixture of denatured ethanol (287 mL) and water (72 mL) was added potassium carbonate (24.4 g, 176.8 mmol) and the mixture was heated to reflux. A solution of 1,1-dimethyl-4-oxopiperidin-1-ium iodide in water (75 mL) was added dropwise to the hot mixture over the course of 1 h. After complete addition, heating of the reaction mixture to reflux was continued for 3 h. The solution was then allowed cooled to ambient temperature and concentrated under reduced pressure. The remaining aqueous mixture was extracted with diethyl ether (2×150 mL). The combined organic phase was dried over anhydrous magnesium sulfate and filtered. Concentration of the filtrate in vacuo and purification of the residue by column chromatography, eluting with diethyl ether as eluent, provided the title compound as a yellowish oil (10.5 g, 64% yield): $^1$H NMR (300 MHz, CDCl$_3$) 7.39-7.25 (m, 5H), 3.65 (q, J=6.7 Hz, 1H), 2.84-2.69 (m, 4H), 2.44 (t, J=6.1 Hz, 4H), 1.44 (d, J=6.7 Hz, 3H).

Step 3. Preparation of (R)-5-chloro-2-fluoro-4-(methyl(1-(1-phenylethyl)piperidin-4-yl)amino)-N-(thiazol-4-yl)benzenesulfonamide Formate

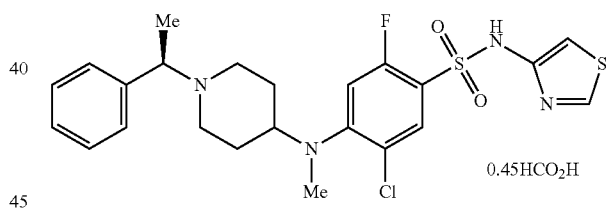

To a mixture of tert-butyl ((4-amino-5-chloro-2-fluorophenyl)sulfonyl)(thiazol-4-yl)carbamate (1.0 g, 2.5 mmol) and (R)-1-(1-phenylethyl)piperidin-4-one (0.55 g, 2.7 mmol) was added trifluoroacetic acid (4.2 mL). The mixture was stirred at ambient temperature for 10 minutes, and then sodium triacetoxyborohydride (0.74 g, 3.5 mmol) was added to it. The reaction mixture was stirred at ambient temperature for 10 minutes, and then paraformaldehyde (0.225 g, 7.5 mmol) was added to it, followed by trifluoroacetic acid (1 mL). The reaction mixture was stirred at ambient temperature for 10 minutes, and then sodium triacetoxyborohydride (1.06 g, 5 mmol) was added to it. After stirring for another 30 minutes, the reaction mixture was diluted with dichloromethane (125 mL). The mixture was washed with brine (50 mL), dried over anhydrous magnesium sulfate, and filtered. Concentration of the filtrate in vacuo provided a residue which was purified by column chromatography, eluting with a gradient of 10 to 60% of ethyl acetate (containing 20% of ethanol and 1% of ammonium hydroxide) in heptane. Further purification by preparative reverse-phase HPLC, eluting with a gradient of 5 to 95% of acetonitrile in water containing 0.5% of formic acid, provided the title compound as a colorless solid (0.195 g, 15% yield): $^1$H NMR (300 MHz, DMSO-$d_6$) δ 11.75-11.03 (m, 1H), 8.90 (d, J=2.2 Hz, 1H), 8.14 (s, 0.45H), 7.68 (d, J=7.6 Hz, 1H), 7.38-7.26 (m, 5H), 7.09 (d, J=12.6 Hz, 1H), 7.03 (d, J=2.2 Hz, 1H), 3.74-3.68 (m, 1H), 3.39-3.30 (m, 1H), 3.17-3.10 (m, 1H), 2.93-2.88 (m, 1H), 2.73-2.67 (m, 3H), 2.18-2.01 (m, 2H), 1.87-1.57 (m, 4H), 1.37-1.33 (m, 3H), COOH not observed; $^{19}$F NMR (282 MHz, DMSO-$d_6$) δ 3-110.1 (s, 1F); MS (ES+) m/z 509.1 (M+1), 511.0 (M+1).

Example 281

Synthesis of (R)-2-fluoro-5-methyl-4-(methyl(1-(1-phenylethyl)piperidin-4-yl)amino)-N-(thiazol-4-yl)benzenesulfonamide 2,2,2-trifluoroacetate

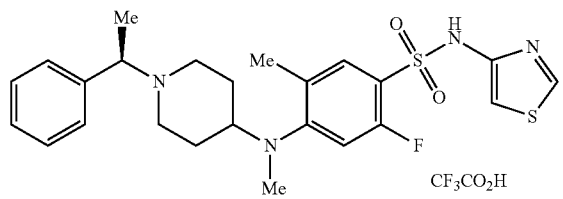 [SMILES: Cc1cc(S(=O)(=O)Nc2cscn2)c(F)cc1N(C)C1CCN([C@H](C)c2ccccc2)CC1 ; "CF3CO2H"]

Step 1. Preparation of tert-butyl ((4-amino-2-fluoro-5-methylphenyl)sulfonyl)(thiazol-4-yl)carbamate

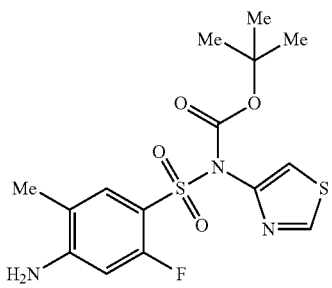 [SMILES: Cc1cc(S(=O)(=O)N(C(=O)OC(C)(C)C)c2cscn2)c(F)cc1N]

To a solution of tert-butyl ((4-amino-5-chloro-2-fluorophenyl)sulfonyl)(thiazol-4-yl)carbamate (1.0 g, 2.46 mmol) in anhydrous 1,4-dioxane (25 mL) was added methylboronic acid (0.88 g, 15 mmol), potassium phosphate tribasic (1.66 g, 7.8 mmol), palladium acetate (0.55 g, 0.25 mmol), and tricyclohexylphosphonium tetrafluoroborate (0.18 g, 0.49 mmol). The resulting slurry was degassed by sparging with argon and then heated to reflux for 18 h. The reaction mixture was allowed to cool to ambient temperature, diluted with ethyl acetate (25 mL), and filtered through a pad of Celite. The filter pad was washed with ethyl acetate (2×30 mL) and the combined organic phase was concentrated in vacuo. Purification of the residue by column chromatography, eluting with a gradient of 20 to 100% of ethyl acetate (containing 20% of ethanol and 1% of ammonium hydroxide) in heptane, provided the title compound as a brown solid (0.496 g, 70% yield): MS (ES+) m/z 388.2 (M+1).

Step 2. Preparation of (R)-2-fluoro-5-methyl-4-(methyl(1-(1-phenylethyl)piperidin-4-yl)amino)-N-(thiazol-4-yl)benzenesulfonamide 2,2,2-trifluoroacetate

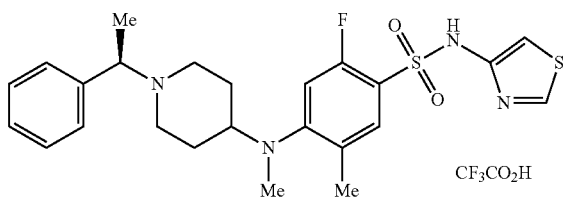 [SMILES: Cc1cc(S(=O)(=O)Nc2cscn2)c(F)cc1N(C)C1CCN([C@H](C)c2ccccc2)CC1 ; "CF3CO2H"]

Following the procedure as described for EXAMPLE 280, Step 3, and making non-critical variations as required to replace tert-butyl ((4-amino-5-chloro-2-fluorophenyl)sulfonyl)(thiazol-4-yl)carbamate with tert-butyl ((4-amino-2-fluoro-5-methylphenyl)sulfonyl)(thiazol-4-yl)carbamate, and purification by preparative reverse-phase HPLC, eluting with a gradient of 5 to 95% of acetonitrile in water containing 0.1% of trifluoroacetic acid, provided the title compound as a colorless solid (0.074 g, 7% yield): $^1$H NMR (300 MHz, DMSO-$d_6$) δ 11.23-11.19 (m, 1H), 9.61-9.51 (m, 1H), 8.90-8.85 (m, 1H), 7.66-7.36 (m, 6H), 7.03-6.93 (m, 2H), 4.55-4.43 (m, 1H), 3.67-3.55 (m, 1H), 3.33-3.19 (m, 1H), 2.93-2.71 (m, 2H), 2.63-2.57 (m, 3H), 2.20-2.14 (m, 3H), 2.13-1.89 (m, 3H), 1.84-1.70 (m, 2H), 1.68-1.55 (m, 3H); MS (ES+) 489.1 m/z (M+1).

Example 282

Synthesis of (R)-2,6-difluoro-3-methyl-4-((1-(1-phenylethyl)piperidin-4-yl)oxy)-N-(thiazol-4-yl)benzenesulfonamide 2,2,2-trifluoroacetate

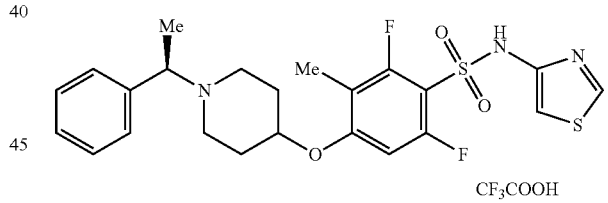

Step 1. Preparation of (R)-1-(1-phenylethyl)piperidin-4-ol

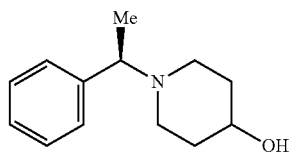 [SMILES: C[C@H](c1ccccc1)N1CCC(O)CC1]

To a solution of (R)-1-(1-phenylethyl)piperidin-4-one (5.5 g, 27.1 mmol) in methanol (68 mL) was added sodium borohydride (1.4 g, 37.9 mmol) and the reaction mixture was stirred at ambient temperature for 15 minutes. The reaction mixture was diluted with ethyl acetate (150 mL). The organic layer was washed with water (50 mL), saturated ammonium chloride (50 mL), water (2×50 mL), brine (50 mL), and dried over anhydrous magnesium sulfate. Filtration and concentration of the filtrate in vacuo afforded the title compound as a yellowish oil (5.5 g, quantitative yield): $^1$H NMR (300 MHz, CDCl$_3$) 7.36-7.23 (m, 5H), 3.65-3.62 (m, 1H), 3.44 (q, J=6.8 Hz, 1H), 2.91-2.85 (m, 1H), 2.74-2.68 (m, 1H), 2.16-2.04 (m, 2H), 1.94-1.82 (m, 2H), 1.66-1.49 (m, 2H), 1.41-1.36 (m, 3H), OH not observed.

Step 2. Preparation of tert-butyl (R)-((3-bromo-2,6-difluoro-4-((1-(1-phenylethyl)piperidin-4-yl)oxy)phenyl)sulfonyl)(thiazol-4-yl)carbamate

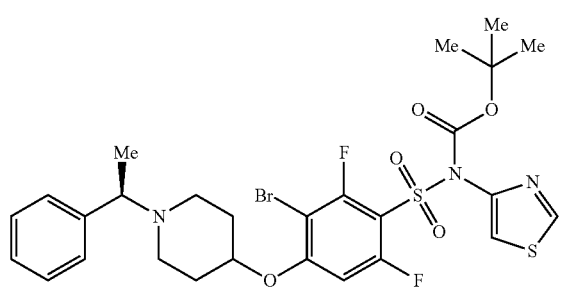

To a solution of tert-butyl ((3-bromo-2,4,6-trifluorophenyl)sulfonyl)(thiazol-4-yl)carbamate (3.1 g, 6.6 mmol) and (R)-1-(1-phenylethyl)piperidin-4-ol (4.04 g, 19.7 mmol) in anhydrous N,N-dimethylformamide (44 mL) was added sodium hydride (60% suspension in mineral oil) (1.31 g, 32.8 mmol) and the reaction mixture was stirred at ambient temperature for 2 h. The reaction mixture was then cooled to −78° C. and slowly added to a 1:10 mixture of 1 M hydrochloric acid and water at 0° C. After dilution with ethyl acetate (75 mL), the layers were separated and the aqueous layer was extracted with ethyl acetate (3×50 mL). The combined organic layers were washed with water (2×30 mL), brine (50 mL), and dried over anhydrous magnesium sulfate. Filtration and concentration of the filtrate in vacuo provided a residue which was purified by column chromatography, eluting with a gradient of 10 to 60% of ethyl acetate (containing 20% of ethanol and 1% of ammonium hydroxide) in heptane, to afford the title compound as an orange oil (2.2 g, 51% yield): MS (ES+) m/z 658.4 (M+1), 660.4 (M+1).

Step 3. Preparation of (R)-2,6-difluoro-3-methyl-4-((1-(1-phenylethyl)piperidin-4-yl)oxy)-N-(thiazol-4-yl)benzenesulfonamide 2,2,2-trifluoroacetate

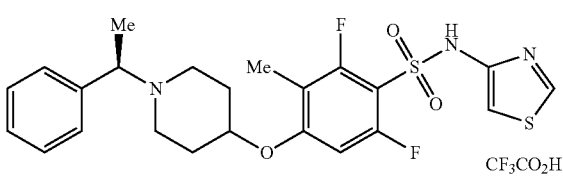 [SMILES: Cc1c(OC2CCN([C@H](C)c3ccccc3)CC2)cc(F)c(S(=O)(=O)Nc2cscn2)c1F ; "CF3CO2H"]

To a solution of tert-butyl (R)-((3-bromo-2,6-difluoro-4-((1-(1-phenylethyl)-piperidin-4-yl)oxy)phenyl)sulfonyl)(thiazol-4-yl)carbamate (2.2 g, 3.4 mmol) in anhydrous N,N-dimethylformamide (61 mL) was added lithium chloride (0.43 g, 10.0 mmol), bis(triphenylphosphine)palladium dichloride (0.47 g, 0.67 mmol) and tetraethyltin (1.80 g, 10.0 mmol). The mixture was degassed with argon and heated to 100° C. for 5 h. The reaction mixture was concentrated in vacuo and the residue diluted with ethyl acetate (130 mL). The organic layer was washed with water (2×30 mL), brine (30 mL), dried over anhydrous magnesium sulfate, and filtered. Concentration of the filtrate in vacuo and purification by column chromatography, eluting with a gradient of 10 to 100% of ethyl acetate (containing 20% of ethanol and 1% of ammonium hydroxide) in heptane, afforded an orange oil. The oil was dissolved in dichloromethane (15 mL) and trifluoroacetic acid (6 mL) was added to it. The reaction mixture was stirred at ambient temperature for 4 h and then concentrated in vacuo. Purification of the residue by column chromatography, eluting with a gradient of 10 to 100% of ethyl acetate (containing 20% of ethanol and 1% of ammonium hydroxide) in heptane, followed by purification by preparative reverse-phase HPLC, eluting with a gradient of 5 to 95% of acetonitrile in water containing 0.1% of trifluoroacetic acid, afforded the title compound as a colorless solid (0.403 g, 19% yield): $^1$H NMR (601 MHz, DMSO-d$_6$) δ 11.41-11.40 (m, 1H), 10.08-9.83 (m, 1H), 8.89 (d, J=2.1 Hz, 1H), 7.57-7.49 (m, 5H), 7.10-6.98 (m, 2H), 4.77 (m, 2H), 3.71-3.54 (m, 1H), 3.46-3.20 (m, 1H), 2.92-2.76 (m, 2H), 2.28-2.22 (m, 1H), 2.10-1.97 (m, 3H), 1.89-1.77 (m, 3H), 1.69 (d, J=7.0 Hz, 3H); $^1$F NMR (565 MHz, DMSO-d$_6$) δ −73.9 (s, 3F), −109.6 (s, 1F), −110.5 (s, 1F); MS (ES+) m/z 494.1 (M+1).

Example 283

Synthesis of (R)-2,6-difluoro-3-methyl-4-((1-(1-phenylethyl)piperidin-4-yl)oxy)-N-(thiazol-4-yl)benzenesulfonamide trifluoroacetic formate

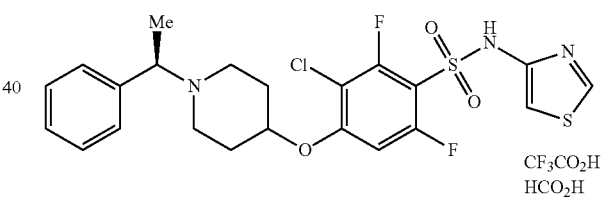

Step 1. Preparation of tert-butyl (R)-((3-chloro-2,6-difluoro-4-((1-(1-phenylethyl)piperidin-4-yl)oxy)phenyl)sulfonyl)(thiazol-4-yl)carbamate

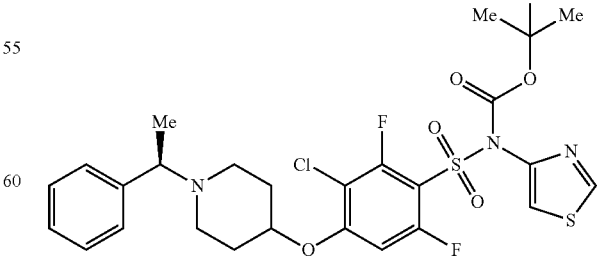

Following the procedure as described for EXAMPLE 282, Step 2, and making non-critical variations as required to replace tert-butyl ((3-bromo-2,4,6-trifluorophenyl)sulfonyl)(thiazol-4-yl)carbamate with tert-butyl ((3-chloro-2,4,6-trifluorophenyl)sulfonyl)(thiazol-4-yl)carbamate, the title compound was obtained as a colorless solid (1.3 g, 38% yield): MS (ES+) m/z 614.1 (M+1), 616.1 (M+1).

Step 2. Preparation of (R)-3-chloro-2,6-difluoro-4-((1-(1-phenylethyl)piperidin-4-yl)oxy)-N-(thiazol-4-yl)benzenesulfonamide 2,2,2-trifluoroacetate formate

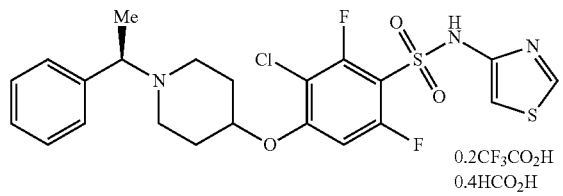

0.2CF$_3$CO$_2$H
0.4HCO$_2$H

To a mixture of tert-butyl (R)-((3-chloro-2,6-difluoro-4-((1-(1-phenylethyl)piperidin-4-yl)oxy)phenyl)sulfonyl)(thiazol-4-yl)carbamate (0.40 g, 0.65 mmol) in dichloromethane (2 mL) was added trifluoroacetic acid (3 mL) and the reaction mixture was stirred at ambient temperature for 4 h. Concentration in vacuo provided a residue which was purified by column chromatography, eluting with a gradient of 10 to 100% of ethyl acetate (containing 20% of ethanol and 1% of ammonium hydroxide) in heptane, and then by preparative reverse-phase HPLC, eluting with a gradient of 5 to 95% of acetonitrile in water containing 0.5% of formic acid, to give the title compound as a colorless solid (0.403 g, 19% yield): $^1$H NMR (300 MHz, DMSO-d$_6$) δ 11.83-10.99 (m, 2H), 8.90 (d, J=2.2 Hz, 1H), 8.14 (s, 0.4H), 7.39-7.28 (m, 6H), 7.03 (d, J=2.1 Hz, 1H), 4.71-4.65 (m, 1H), 3.79-3.74 (m, 1H), 2.80-2.69 (m, 2H), 2.47-2.34 (m, 2H), 2.00-1.91 (m, 2H), 1.77-1.66 (m, 2H), 1.40-1.36 (m, 3H), COOH not observed; $^{19}$F NMR (282 MHz, DMSO-d$_6$) δ−73.4 (s, 0.6F), −106.9 (s, 1F), −107.8 (s, 1F); MS (ES+) m/z 514.0 (M+1), 516.0 (M+1).

Example 284

Synthesis of (S)-4-((1-benzylpyrrolidin-3-yl)(methyl)amino)-3-methyl-N-(thiazol-4-yl)benzenesulfonamide 2,2,2-trifluoroacetate

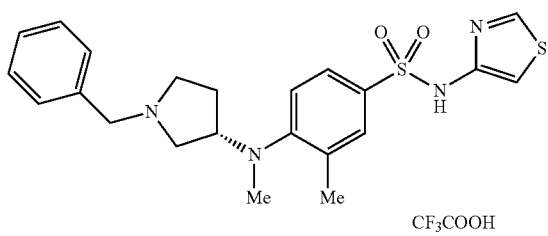 [SMILES: Cc1cc(S(=O)(=O)Nc2cscn2)ccc1N(C)[C@H]1CCN(Cc2ccccc2)C1 ; "CF3COOH"]

CF$_3$COOH

Step 1. Preparation of tert-butyl (S)-3-((2-chloro-4-(N-(4-methoxybenzyl)-N-(thiazol-4-yl)sulfamoyl)phenyl)amino)pyrrolidine-1-carboxylate

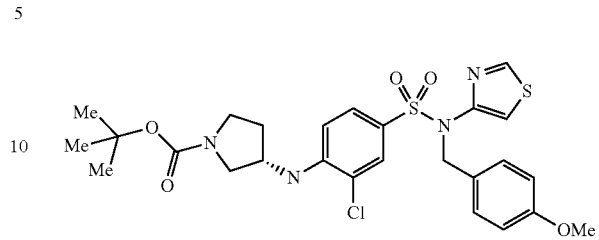

To a mixture of 3-chloro-4-fluoro-N-(4-methoxybenzyl)-N-(thiazol-4-yl)benzenesulfonamide (prepared analogous to EXAMPLE 107, Step 1 and 2, 0.70 g, 1.69 mmol) and tert-butyl (S)-3-aminopyrrolidine-1-carboxylate (0.35 g, 1.89 mmol) in anhydrous dimethyl sulfoxide (10 mL) was added potassium carbonate (0.70 g, 5.07 mmol) and the reaction mixture was heated to 60° C. for 16 h. After cooling to ambient temperature, the reaction mixture was diluted with ethyl acetate (50 mL), washed with saturated ammonium chloride (2×20 mL), brine (20 mL), dried over anhydrous sodium sulfate, and filtered. Concentration of the filtrate in vacuo and purification of the residue by column chromatography, eluting with a gradient of 0 to 40% of ethyl acetate in hexanes, provided the title compound as a colorless foam (0.90 g, 92% yield): MS (ES+) m/z 579.3 (M+1), 581.3 (M+1).

Step 2. Preparation of tert-butyl (S)-3-((4-(N-(4-methoxybenzyl)-N-(thiazol-4-yl)sulfamoyl)-2-methylphenyl)amino)pyrrolidine-1-carboxylate

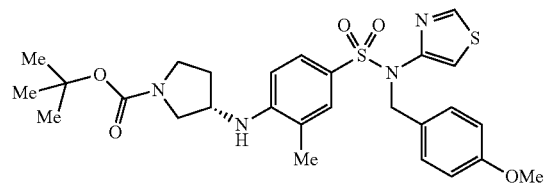 [SMILES: COc1ccc(CN(c2cscn2)S(=O)(=O)c2ccc(N[C@H]3CCN(C(=O)OC(C)(C)C)C3)c(C)c2)cc1]

To a mixture of tert-butyl (S)-3-((2-chloro-4-(N-(4-methoxybenzyl)-N-(thiazol-4-yl)sulfamoyl)phenyl)amino)pyrrolidine-1-carboxylate (0.90 g, 1.55 mmol) in 1,4-dioxane (10 mL) was added methylboronic acid (0.28 g, 4.67 mmol), palladium acetate (0.10 g, 0.31 mmol), potassium phosphate (1.30 g, 6.20 mmol), and tricyclohexylphosphonium tetrafluoroborate (0.23 g, 0.62 mmol). The resulting mixture was degassed by passing a stream of argon through it for 15 minutes, and then heated at 110° C. for 2 h. The reaction mixture was allowed to cool to ambient temperature and filtered through a pad of Celite. The filter pad was washed with ethyl acetate (20 mL) and the combined filtrate concentrated in vacuo. Purification of the residue by column chromatography, eluting with a gradient of 0 to 50% of ethyl acetate in hexanes, afforded the title compound as a colorless solid (0.60 g, 69% yield): MS (ES+) m/z 559.3 (M+1).

Step 3. Preparation of (S)—N-(4-methoxybenzyl)-3-methyl-4-(pyrrolidin-3-ylamino)-N-(thiazol-4-yl)benzenesulfonamide 2,2,2-trifluoroacetate

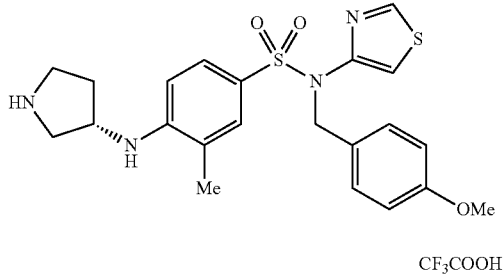 [SMILES: COc1ccc(CN(c2cscn2)S(=O)(=O)c2ccc(N[C@H]3CCNC3)c(C)c2)cc1 ; "CF3COOH"]

To a solution of tert-butyl (S)-3-((4-(N-(4-methoxybenzyl)-N-(thiazol-4-yl)sulfamoyl)-2-methylphenyl)amino)pyrrolidine-1-carboxylate (0.60 g, 1.08 mmol) in dichloromethane (4 mL) was added trifluoroacetic acid (2 mL) and the reaction mixture was stirred at ambient temperature for 2 h. The reaction mixture was concentrated in vacuo to afford the title compound as a beige solid (0.56 g, quantitative yield): MS (ES+) m/z 459.3 (M+1).

Step 4. Preparation of (S)-4-((1-benzylpyrrolidin-3-yl)amino)-N-(4-methoxybenzyl)-3-methyl-N-(thiazol-4-yl)benzenesulfonamide 2,2,2-trifluoroacetate

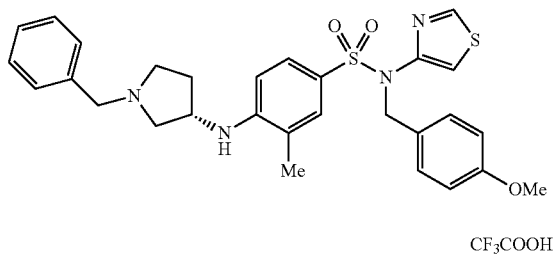 [SMILES: COc1ccc(CN(c2cscn2)S(=O)(=O)c2ccc(N[C@H]3CCN(Cc4ccccc4)C3)c(C)c2)cc1 ; "CF3COOH"]

To a mixture of benzaldehyde (0.07 g, 0.63 mmol) and (S)—N-(4-methoxybenzyl)-3-methyl-4-(pyrrolidin-3-ylamino)-N-(thiazol-4-yl)benzenesulfonamide 2,2,2-trifluoroacetate (0.30 g, 0.53 mmol) in anhydrous N,N-dimethylformamide (4 mL) was added sodium triacetoxyborohydride (0.17 g, 0.79 mmol) and the reaction mixture was stirred at ambient temperature for 2 h. The reaction mixture was diluted with ethyl acetate (30 mL), washed with saturated ammonium chloride (20 mL), and concentrated in vacuo. Purification of the residue by column chromatography, eluting with a gradient of 0 to 5% of methanol (containing 0.2% of trifluroacetic acid) in dichloromethane, provided the title compound as a colorless solid (0.20 g, 57% yield): MS (ES+) m/z 549.3 (M+1).

Step 5. Preparation of (S)-4-((1-benzylpyrrolidin-3-yl)(methyl)amino)-3-methyl-N-(thiazol-4-yl)benzenesulfonamide 2,2,2-trifluoroacetate

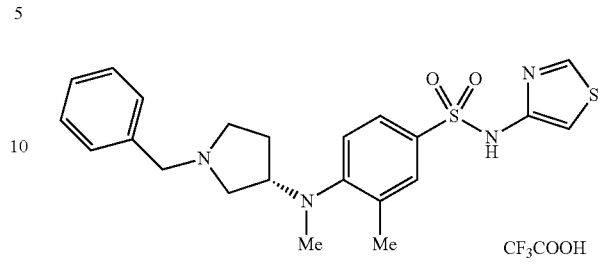

To a solution of (S)-4-((1-benzylpyrrolidin-3-yl)amino)-N-(4-methoxybenzyl)-3-methyl-N-(thiazol-4-yl)benzenesulfonamide 2,2,2-trifluoroacetate (0.20 g, 0.30 mmol) in trifluoroacetic acid (2.0 mL) was added sodium triacetoxyborohydride (0.19 g, 0.90 mmol) at 0° C. The resulting mixture was stirred at 0° C. for 10 minutes, and then paraformaldehyde was added (14 mg, 0.45 mmol) to it. The reaction mixture was stirred at 0° C. for 15 minutes and then concentrated in vacuo. To the residue was added 2 M sodium hydroxide (15 mL) and brine (15 mL), and the mixture was extracted with ethyl acetate (30 mL). The aqueous layer was diluted with saturated ammonium chloride (30 mL) and then extracted with ethyl acetate (50 mL). The combined organic layers were washed with saturated ammonium chloride (30 mL), brine (30 mL), dried over anhydrous sodium sulfate, and filtered. Concentration of the filtrate in vacuo and purification of the residue by column chromatography, eluting with a gradient of 0 to 10% of methanol (containing 0.2% of trifluoroacetic acid) in dichloromethane, provided the title compound as a colorless solid (0.067 g, 40% yield): $^1$H NMR (300 MHz, DMSO-$d_6$) δ 11.02 (s, 1H), 10.39 (br s, 0.5H), 10.24 (br s, 0.5H), 8.88 (d, J=2.2 Hz, 1H), 7.65-7.59 (m, 2H), 7.49-7.45 (m, 5H), 7.18 (d, J=8.4 Hz, 1H), 7.02 (d, J=2.2 Hz, 1H), 4.39-4.31 (m, 2H), 4.21-3.92 (m, 1H), 3.55-3.08 (m, 4H), 2.65-2.54 (m, 3H), 2.27 (s, 3H), 2.22-1.84 (m, 2H); MS (ES+) m/z 443.1 (M+1).

Example 285

Synthesis of (S)-4-((1-(2,5-difluorobenzyl)pyrrolidin-3-yl)(methyl)amino)-3-methyl-N-(thiazol-4-yl)benzenesulfonamide 2,2,2-trifluoroacetate

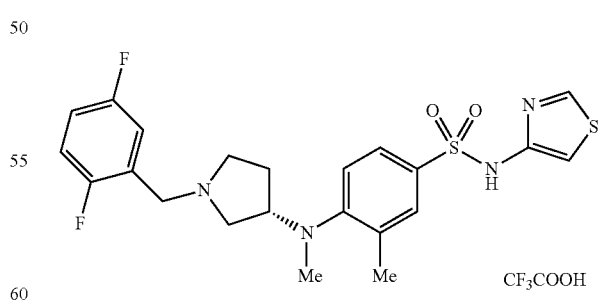

Following the procedure as described in EXAMPLE 284, Step 4 to 5, and making non-critical variations as required to replace benzaldehyde with 2,5-difluorobenzaldehyde, the title compound was obtained as a colorless solid (0.045 g, 17% yield): $^1$H NMR (300 MHz, DMSO-$d_6$) δ 11.02 (s, 1H), 8.88 (d, J=2.2 Hz, 1H), 7.65-7.59 (m, 2H), 7.52-7.47 (m, 1H), 7.39 (t, J=6.4 Hz, 2H), 7.18 (d, J=8.5 Hz, 1H), 7.02 (d, J=2.2 Hz, 1H), 4.41 (s, 2H), 4.23-3.94 (m, 1H), 3.54-3.09 (m, 4H), 2.60 (s, 3H), 2.27 (s, 3H), 2.20-1.86 (m, 2H), NH not observed; MS (ES+) m/z 479.2 (M+1).

Example 286

Synthesis of (S)-4-((1-benzylpyrrolidin-3-yl)(methyl)amino)-2,6-difluoro-N-(thiazol-4-yl)benzenesulfonamide Formate

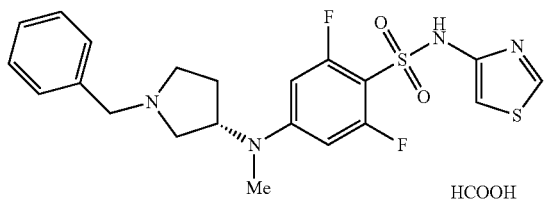 [SMILES: CN(c1cc(F)c(S(=O)(=O)Nc2cscn2)c(F)c1)[C@H]1CCN(Cc2ccccc2)C1 ; "HCOOH"]

Step 1. Preparation of tert-butyl thiazol-4-yl((2,4,6-trifluorophenyl)sulfonyl)carbamate

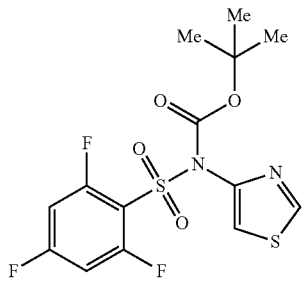 [SMILES: CC(C)(C)OC(=O)N(c1cscn1)S(=O)(=O)c1c(F)cc(F)cc1F]

To a solution of tert-butyl thiazol-4-ylcarbamate (0.96 g, 4.8 mmol) in anhydrous tetrahydrofuran (20 mL) was added a 1 M solution of lithium bis(trimethylsilyl)amide in tetrahydrofuran (5.76 mL, 5.76 mmol) at −78° C. The reaction mixture was allowed to warm to ambient temperature and stirred for 1 h. The reaction mixture was cooled to −78° C., and a solution of 2,4,6-trifluorobenzenesulfonyl chloride (1.32 g, 5.76 mmol) in anhydrous tetrahydrofuran (10 mL) was added to it. The reaction mixture was allowed to warm to ambient temperature and stirred for 3 h. The mixture was diluted with ethyl acetate (35 mL), washed with saturated ammonium chloride (2×30 mL), brine (2×30 mL), dried over anhydrous sodium sulfate, and filtered. Concentration of the filtrate in vacuo and purification of the residue by column chromatography, eluting with a gradient of 0 to 50% of ethyl acetate in hexanes, provided the title compound as a colorless solid (0.67 g, 47% yield): MS (ES+) m/z 395.0 (M+1).

Step 2. Preparation of tert-butyl (S)-3-((4-(N-(tert-butoxycarbonyl)-N-(thiazol-4-yl)sulfamoyl)-3,5-difluorophenyl)amino)pyrrolidine-1-carboxylate

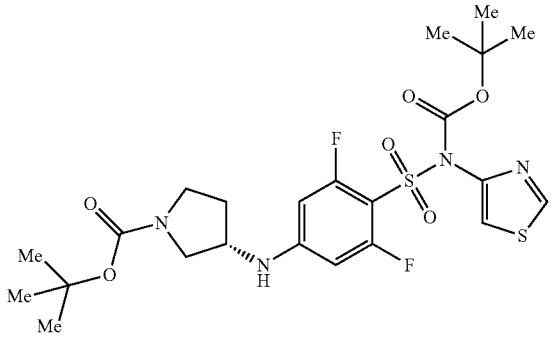 [SMILES: CC(C)(C)OC(=O)N1CC[C@H](Nc2cc(F)c(S(=O)(=O)N(C(=O)OC(C)(C)C)c3cscn3)c(F)c2)C1]

Following the procedure as described in EXAMPLE 284, Step 2 and making non-critical variations as required to replace 3-chloro-4-fluoro-N-(4-methoxybenzyl)-N-(thiazol-4-yl)benzenesulfonamide with tert-butyl thiazol-4-yl((2,4,6-trifluorophenyl)sulfonyl)carbamate, the title compound was obtained as a colorless solid (0.36 g, 40% yield): $^1$H NMR (300 MHz, CDCl$_3$) δ 8.77 (d, J=2.3 Hz, 1H), 7.48 (d, J=2.2 Hz, 1H), 6.15 (d, J=11.7 Hz, 2H), 4.00-3.92 (m, 1H), 3.67-3.62 (m, 1H), 3.49-3.42 (m, 2H), 2.25-2.12 (m, 1H), 1.97-1.87 (m, 2H), 1.45 (s, 9H), 1.37 (s, 9H), NH not observed; MS (ES-) m/z 559 (M−1).

Step 3. Preparation of tert-butyl (S)-3-((4-(N-(tert-butoxycarbonyl)-N-(thiazol-4-yl)sulfamoyl)-3,5-difluorophenyl)amino)pyrrolidine-1-carboxylate

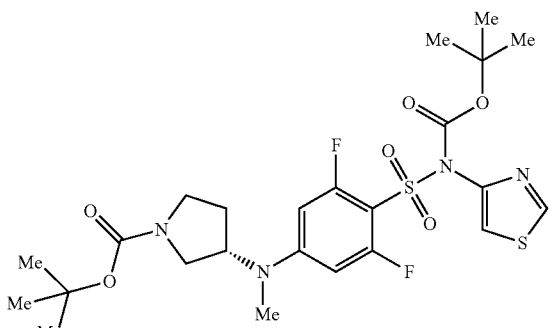

To a solution of tert-butyl (S)-3-((4-(N-(tert-butoxycarbonyl)-N-(thiazol-4-yl)sulfamoyl)-3,5-difluorophenyl)amino)pyrrolidine-1-carboxylate (0.20 g, 0.36 mmol) and dimethyl sulfate (0.10 mL, 1.07 mmol) in anhydrous N,N-dimethylformamide (20 mL) was added a 60% dispersion of sodium hydride in mineral oil (0.025 g, 1.07 mmol) at 0° C. The resulting mixture was stirred at 0° C. for 1 h and then quenched by slow addition of water (5 mL). The mixture was diluted with ethyl acetate (20 mL), washed with saturated ammonium chloride (2×20 mL), brine (15 mL), and dried over anhydrous sodium sulfate. Filtration and concentration of the filtrate in vacuo provided a residue which was purified by column chromatography, eluting with a gradient of 0 to 60% of ethyl acetate in hexanes, to provide the title compound as a colorless foam (0.13 g, 63% yield): $^1$H NMR (300 MHz, CDCl$_3$) δ 8.78 (d, J=2.3 Hz, 1H), 7.49 (d, J=2.3 Hz, 1H), 6.30 (d, J=12.7 Hz, 2H), 4.40-4.28 (m, 1H), 3.68-3.52 (m, 1H), 3.45-3.31 (m, 2H), 2.95-2.87 (m, 3H), 2.19-2.08 (m, 2H), 1.67 (s, 1H), 1.47 (s, 9H), 1.38 (s, 9H); MS (ES+) m/z 575.1 (M+1).

Step 4. Preparation of (S)-2,6-difluoro-4-(methyl(pyrrolidin-3-yl)amino)-N-(thiazol-4-yl)benzenesulfonamide 2,2,2-trifluoroacetate

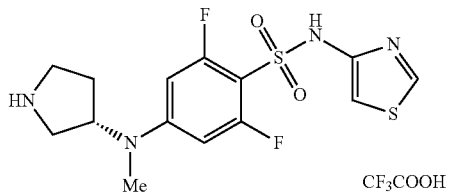 [SMILES: CN(c1cc(F)c(S(=O)(=O)Nc2cscn2)c(F)c1)[C@H]1CCNC1 ; "CF3COOH"]

To a solution of tert-butyl (S)-3-((4-(N-(tert-butoxycarbonyl)-N-(thiazol-4-yl)sulfamoyl)-3,5-difluorophenyl)amino)pyrrolidine-1-carboxylate (0.13 g, 0.22 mmol) in dichloromethane (4 mL) was added trifluoroacetic acid (2 mL). The resulting mixture was stirred for 2 h and then concentrated in vacuo to provide the title compound as a yellowish foam (0.14 g, quantitative yield): MS (ES+) m/z 375.1 (M+1).

Step 5. Preparation of (S)-4-((1-benzylpyrrolidin-3-yl)(methyl)amino)-2,6-difluoro-N-(thiazol-4-yl)benzenesulfonamide Formate

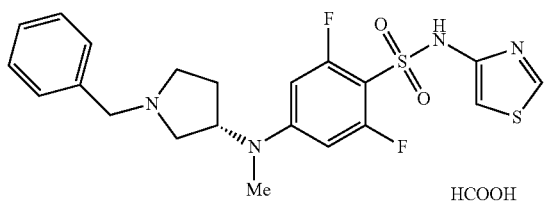 [SMILES: CN(c1cc(F)c(S(=O)(=O)Nc2cscn2)c(F)c1)[C@H]1CCN(Cc2ccccc2)C1 ; "HCOOH"]

To a mixture of benzaldehyde (0.056 g, 0.45 mmol) and (S)-2,6-difluoro-4-(methyl(pyrrolidin-3-yl)amino)-N-(thiazol-4-yl)benzenesulfonamide 2,2,2-trifluoroacetate (0.14 g, 0.37 mmol) in anhydrous N,N-dimethylformamide (4 mL) was added sodium triacetoxyborohydride (0.24 g, 1.11 mmol) and the reaction mixture was stirred at ambient temperature for 2 h. The reaction mixture was diluted with ethyl acetate (20 mL), washed with saturated ammonium chloride (20 mL), and concentrated in vacuo. The obtained residue was purified by preparative reverse-phase HPLC, eluting with a gradient of 10 to 60% of acetonitrile in water containing 0.5% of formic acid, to afford the title compound as a colorless solid (0.020 g, 11% yield): $^1$H NMR (300 MHz, DMSO-d$_6$) δ 8.83 (d, J=2.2 Hz, 1H), 8.22 (s, 1H), 7.36-7.31 (m, 4H), 7.31-7.23 (m, 1H), 7.12-7.04 (m, 2H), 6.79 (d, J=2.2 Hz, 1H), 3.83-3.76 (m, 1H), 3.68 (d, J=13.0 Hz, 1H), 3.59 (d, J=12.9 Hz, 1H), 2.74 (d, J=12.2 Hz, 1H), 2.65-2.54 (m, 5H), 2.31 (q, J=7.8 Hz, 1H), 1.95-1.83 (m, 1H), 1.74-1.60 (m, 1H), NH and COOH not observed; MS (ES+) m/z 465.2 (M+1).

Example 287

Synthesis of (S)-4-((1-(3-(difluoromethyl)benzyl)pyrrolidin-3-yl)(methyl)amino)-2,6-difluoro-N-(thiazol-4-yl)benzenesulfonamide 2,2,2-trifluoroacetate

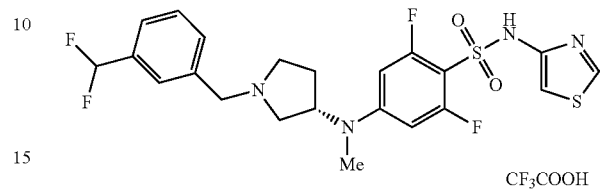

Following the procedure as described in EXAMPLE 286, Step 5 and making non-critical variations as required to replace benzaldehyde with 3-(difluoromethyl)benzaldehyde, the title compound was obtained as a colorless solid (0.035 g, 36% yield): $^1$H NMR (300 MHz, DMSO-d$_6$) δ 11.16 (s, 1H), 8.89-8.88 (m, 1H), 7.52-7.46 (m, 5H), 6.89-6.89 (m, 1H), 6.51 (d, J=13.6 Hz, 2H), 4.57-4.50 (m, 1H), 3.65 (q, J=16.0 Hz, 2H), 2.96-2.83 (m, 5H), 2.68-2.64 (m, 1H), 2.30-2.16 (m, 2H), 1.72-1.58 (m, 1H), NH not observed; MS (ES+) m/z 515.3 (M+1).

Example 288

Synthesis of (S)-4-((1-benzylpyrrolidin-3-yl)amino)-2-fluoro-5-methyl-N-(thiazol-4-yl)benzenesulfonamide 2,2,2-trifluoroacetate

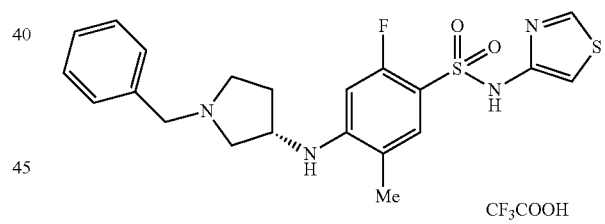

To a mixture of benzaldehyde (0.27 g, 2.58 mmol) and (S)-2-fluoro-5-methyl-4-(pyrrolidin-3-ylamino)-N-(thiazol-4-yl)benzenesulfonamide 2,2,2-trifluoroacetate (0.77 g, 2.15 mmol) in anhydrous N,N-dimethylformamide (8 mL) was added sodium triacetoxyborohydride (0.68 g, 3.22 mmol) and the reaction mixture was stirred at ambient temperature for 2 h. The reaction mixture was diluted with ethyl acetate (30 mL), washed with saturated ammonium chloride (20 mL), and concentrated in vacuo. Purification of the residue by column chromatography eluting with a gradient of 0 to 10% of methanol (containing 0.2% of trifluroacetic acid) in dichloromethane provided the title compound as a colorless solid (0.12 g, 12% yield): $^1$H NMR (300 MHz, DMSO-d$_6$) δ 11.01 (s, 1H), 10.54 (s, 1H), 8.86 (d, J=2.2 Hz, 1H), 7.54-7.38 (m, 5H), 6.89 (d, J=2.2 Hz, 1H), 6.57-6.45 (m, 1H), 6.12-5.68 (m, 1H), 4.41 (s, 2H), 4.22-3.75 (m, 2H), 3.60-3.31 (m, 3H), 3.26-3.14 (m, 1H), 2.59-2.25 (m, 1H), 2.10-1.91 (m, 4H); MS (ES+) m/z 447.2 (M+1).

Example 289

Synthesis of (S)-4-((1-benzylpyrrolidin-3-yl)(methyl)amino)-5-cyclopropyl-2-fluoro-N-(thiazol-4-yl)benzenesulfonamide 2,2,2-trifluoroacetate

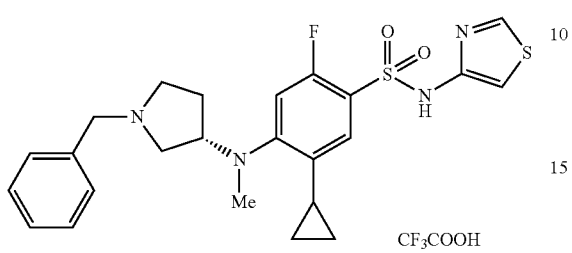

Step 1. Preparation of tert-butyl (S)-3-((4-(N-(tert-butoxycarbonyl)-N-(thiazol-4-yl)sulfamoyl)-2-cyclopropyl-5-fluorophenyl)(methyl)amino)pyrrolidine-1-carboxylate

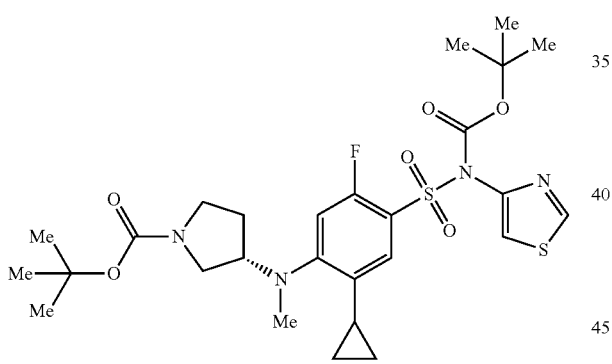

To a mixture of tert-butyl (S)-3-((4-(N-(tert-butoxycarbonyl)-N-(thiazol-4-yl)sulfamoyl)-2-chloro-5-fluorophenyl)(methyl)amino)pyrrolidine-1-carboxylate (0.35 g, 0.60 mmol) in 1,4-dioxane (5 mL) was added cyclopropylboronic acid (0.15 g, 1.8 mmol), palladium acetate (0.027 g, 0.12 mmol), potassium phosphate (0.50 g, 2.40 mmol), and tricyclohexylphosphonium tetrafluoroborate (0.088 g, 0.24 mmol). The resulting mixture was degassed by passing a stream of argon through it for 15 minutes, and then heated at 100° C. for 4 h. The reaction mixture was allowed to cool to ambient temperature and filtered through a pad of Celite. The filter pad was washed with ethyl acetate (30 mL) and the combined filtrate was concentrated in vacuo. Purification of the residue by column chromatography, eluting with a gradient of 0 to 70% of ethyl acetate in hexanes, afforded the title compound as a colorless solid (0.30 g, 85% yield): MS (ES+) m/z 483.2 (M+1).

Step 2. Preparation of (S)-5-cyclopropyl-2-fluoro-4-(pyrrolidin-3-ylamino)-N-(thiazol-4-yl)benzenesulfonamide 2,2,2-trifluoroacetate

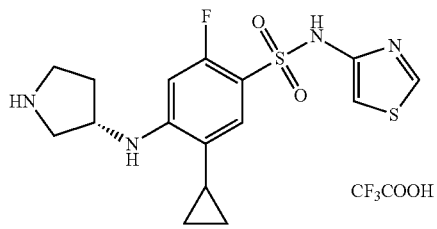 [SMILES: O=S(=O)(Nc1cscn1)c1cc(C2CC2)c(N[C@H]2CCNC2)cc1F ; "CF3COOH"]

To a solution of tert-butyl (S)-3-((4-(N-(tert-butoxycarbonyl)-N-(thiazol-4-yl)sulfamoyl)-2-cyclopropyl-5-fluorophenyl)(methyl)amino)pyrrolidine-1-carboxylate (0.30 g, 0.51 mmol) in dichloromethane (4 mL) was added trifluoroacetic acid (2 mL). The resulting mixture was stirred for 2 h and then concentrated in vacuo to provide the title compound as a yellowish foam (0.32 g, quantitative yield): MS (ES+) m/z 383.2 (M+1).

Step 3. Preparation of (S)-4-((1-benzylpyrrolidin-3-yl)amino)-5-cyclopropyl-2-fluoro-N-(thiazol-4-yl)benzenesulfonamide 2,2,2-trifluoroacetate

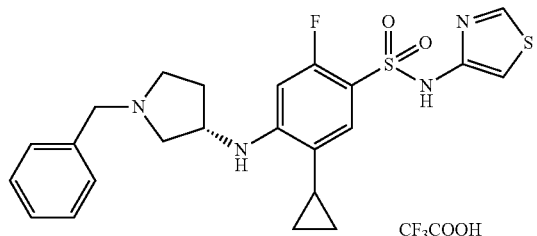

To a mixture of benzaldehyde (0.13 g, 1.27 mmol) and (S)-5-cyclopropyl-2-fluoro-4-(pyrrolidin-3-ylamino)-N-(thiazol-4-yl)benzenesulfonamide 2,2,2-trifluoroacetate (0.30 g, 1.06 mmol) in anhydrous N,N-dimethylformamide (4 mL) was added sodium triacetoxyborohydride (0.34 g, 1.59 mmol) and the reaction mixture was stirred at ambient temperature for 2 h. The reaction mixture was diluted with ethyl acetate (30 mL), washed with saturated ammonium chloride (20 mL), and concentrated in vacuo. Purification of the residue by column chromatography, eluting with a gradient of 0 to 5% of methanol (containing 0.2% of trifluoroacetic acid) in dichloromethane, provided the title compound as a colorless solid (0.10 g, 19% yield): MS (ES+) m/z 473.1 (M+1).

331

Step 4. Preparation of (S)-4-((1-benzylpyrrolidin-3-yl)(methyl)amino)-5-cyclopropyl-2-fluoro-N-(thiazol-4-yl)benzenesulfonamide 2,2,2-trifluoroacetate

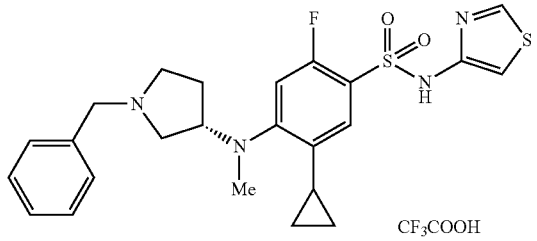 [SMILES: CN(c1cc(F)c(S(=O)(=O)Nc2cscn2)cc1C1CC1)[C@H]1CCN(Cc2ccccc2)C1 ; "CF3COOH"]

CF₃COOH

To a solution of (S)-4-((1-benzylpyrrolidin-3-yl)amino)-5-cyclopropyl-2-fluoro-N-(thiazol-4-yl)benzenesulfonamide 2,2,2-trifluoroacetate (0.10 g, 0.21 mmol) in trifluoroacetic acid (2.0 mL) was added sodium triacetoxyborohydride (0.13 g, 0.63 mmol) at 0° C. The resulting mixture was stirred at 0° C. for 10 minutes, and then paraformaldehyde was added (9 mg, 0.32 mmol) to it. The reaction mixture was stirred at 0° C. for 15 minutes and then concentrated in vacuo. To the residue was added 2 M sodium hydroxide (10 mL) and brine (10 mL), and the mixture was extracted with ethyl acetate (30 mL). The aqueous layer was diluted with saturated ammonium chloride (30 mL) and then extracted with ethyl acetate (20 mL). The combined organic layers were washed with saturated ammonium chloride (30 mL), brine (30 mL), dried over anhydrous sodium sulfate, and filtered. Concentration of the filtrate in vacuo and purification of the residue by preparative reverse-phase HPLC, eluting with a gradient of 10 to 50% of acetonitrile in water containing 0.1% of trifluoroacetic acid, afforded the title compound as a colorless solid (0.040 g, 39% yield): ¹H NMR (300 MHz, DMSO-d₆) δ 11.24 (s, 1H), 10.48 (br s, 0.5H), 10.29 (br s, 0.5H), 8.90 (d, J=2.1 Hz, 1H), 7.52-7.45 (m, 5H), 7.20 (dd, J=7.9, 3.2 Hz, 1H), 7.06-7.01 (m, 2H), 4.41 (s, 2H), 4.29-4.22 (m, 1H), 3.57-3.08 (m, 4H), 2.777-2.66 (m, 3H), 2.29-1.90 (m, 3H), 1.02-0.99 (m, 2H), 0.62-0.60 (m, 2H); MS (ES+) m/z 487.2 (M+1).

Example 290

Synthesis of (S)-4-((1-benzylpyrrolidin-3-yl)(methyl)amino)-5-ethyl-2-fluoro-N-(thiazol-4-yl)benzenesulfonamide 2,2,2-trifluoroacetate

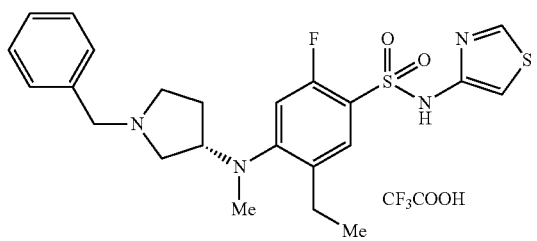

CF₃COOH

Following the procedure as described in EXAMPLE 289, Step 1 to 5, and making non-critical variations as required to replace cyclopropylboronic acid with ethylboronic acid, the title compound was obtained as a colorless solid (0.015 g,

332

5% yield): ¹H NMR (300 MHz, DMSO-d₆) δ 11.03 (s, 1H), 8.87 (d, J=2.2 Hz, 1H), 7.57 (d, J=8.3 Hz, 1H), 7.44-7.28 (m, 5H), 7.08-6.99 (m, 2H), 3.96-3.71 (m, 2H), 2.92-2.77 (m, 2H), 2.66-2.56 (m, 4H), 2.07-1.64 (m, 4H), 1.23 (s, 2H), 1.12 (t, J=7.5 Hz, 3H), NH not observed; MS (ES+) m/z 475.2 (M+1).

Example 291

Synthesis of (R)-2,6-difluoro-4-((1-(1-phenylethyl)piperidin-4-yl)oxy)-N-(thiazol-4-yl)benzenesulfonamide 2,2,2-trifluoroacetate

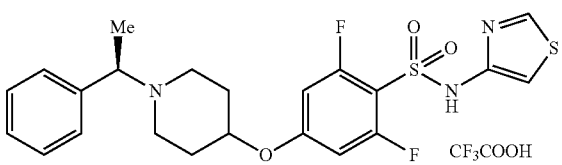 [SMILES: C[C@H](c1ccccc1)N1CCC(Oc2cc(F)c(S(=O)(=O)Nc3cscn3)c(F)c2)CC1 ; "CF3COOH"]

CF₃COOH

Step 1. Preparation of tert-butyl (R)-((2,6-difluoro-4-((1-(1-phenylethyl)piperidin-4-yl)oxy)phenyl)sulfonyl)(thiazol-4-yl)carbamate

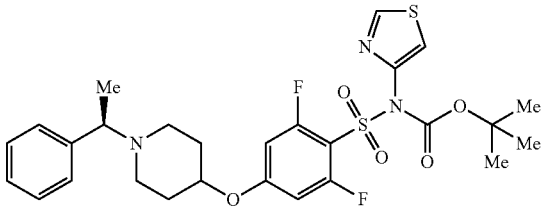 [SMILES: C[C@H](c1ccccc1)N1CCC(Oc2cc(F)c(S(=O)(=O)N(C(=O)OC(C)(C)C)c3cscn3)c(F)c2)CC1]

To a solution of (R)-1-(1-phenylethyl)piperidin-4-ol (0.70 g, 3.41 mmol) in anhydrous N,N-dimethylformamide (10 mL) was added a dispersion of 60% sodium hydride in mineral oil (0.40 g, 10.2 mmol) and the reaction mixture was stirred at ambient temperature for 45 minutes. To it was then added tert-butyl thiazol-4-yl((2,4,6-trifluorophenyl)sulfonyl)carbamate (1.60 g, 4.09 mmol) and the reaction mixture was stirred at ambient temperature for 4 h. The reaction mixture was quenched by careful addition of water (50 mL), and extracted with ethyl acetate (100 mL). The organic layer was washed with saturated ammonium chloride (2×50 mL), brine (50 mL), dried over anhydrous sodium sulfate, and filtered. Concentration of the filtrate in vacuo gave a residue which was purified by column chromatography, eluting with a gradient of 0 to 5% of methanol in dichloromethane, to provide the title compound as a colorless foam (0.52 g, 22% yield): MS (ES+) m/z 580.1 (M+1).

Step 2. Preparation of (R)-2,6-difluoro-4-((1-(1-phenylethyl)piperidin-4-yl)oxy)-N-(thiazol-4-yl)benzenesulfonamide 2,2,2-trifluoroacetate

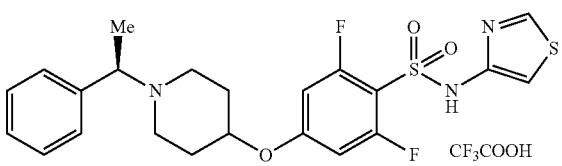 [SMILES: C[C@H](c1ccccc1)N1CCC(Oc2cc(F)c(S(=O)(=O)Nc3cscn3)c(F)c2)CC1 ; "CF3COOH"]

CF₃COOH

To a solution of tert-butyl (R)-((2,6-difluoro-4-((1-(1-phenylethyl)piperidin-4-yl)oxy)phenyl)sulfonyl)(thiazol-4-yl)carbamate (0.52 g, 0.89 mmol) in dichloromethane (6 mL) was added trifluoroacetic acid (3 mL). The resulting mixture was stirred for 2 h and then concentrated in vacuo. Purification of the residue by column chromatography, eluting with a gradient of 0 to 10% of methanol (containing 0.2% of trifluroacetic acid) in dichloromethane, provided the title compound as a colorless foam (0.41 g, 95% yield): $^1$H NMR (300 MHz, DMSO-$d_6$) δ 311.45 (s, 1H), 10.09 (s, 1H), 8.90 (s, 1H), 7.56-7.48 (m, 5H), 7.01-6.87 (m, 3H), 4.85 (s, 0.5H), 4.58 (s, 1.5H), 3.50-3.35 (m, 1H), 3.07-2.67 (m, 3H), 2.27-1.75 (m, 4H), 1.67 (d, J=7.2 Hz, 3H); MS (ES+) m/z 480.2 (M+1).

Example 292

Synthesis of (R)-3-chloro-4-((1-(1-(5-(difluoromethyl)-2-fluorophenyl)ethyl)piperidin-4-yl)oxy)-N-(thiazol-4-yl)benzenesulfonamide Formate

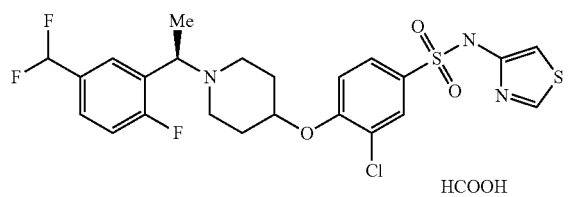 [SMILES: C[C@H](c1cc(C(F)F)ccc1F)N1CCC(Oc2ccc(S(=O)(=O)Nc3cscn3)cc2Cl)CC1 ; "HCOOH"]

HCOOH

Step 1. Preparation of 5-(difluoromethyl)-2-fluorobenzonitrile

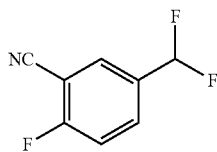

To a solution of 2-fluoro-5-formylbenzonitrile (5.15 g, 34.5 mmol) in anhydrous 1,2-dichloroethane (200 mL) was added diethylaminosulfur trifluoride (5.86 mL, 44.4 mmol). The reaction mixture was stirred at ambient temperature for 16 h, and then quenched by addition of saturated sodium bicarbonate solution (100 mL) at 0° C. The organic phase was washed with brine (100 mL), dried over anhydrous sodium sulfate, and filtered. Concentration of the filtrate in vacuo provided a residue which was purified by column chromatography, eluting with a gradient of 0 to 20% of ethyl acetate in hexanes, to provide the title compound as a colorless oil (5.10 g, 86% yield): $^1$H-NMR (300 MHz, CDCl$_3$) δ7.82-7.75 (m, 2H), 7.34 (t, J=8.5 Hz, 1H), 6.66 (t, J=55.9 Hz, 1H).

Step 2. Preparation of 1-(5-(difluoromethyl)-2-fluorophenyl)ethan-1-one

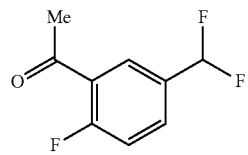 [SMILES: CC(=O)c1cc(C(F)F)ccc1F]

To a solution of 5-(difluoromethyl)-2-fluorobenzonitrile (1.80 g, 10.5 mmol) in anhydrous tetrahydrofuran (70 mL) was added a 3 M solution of methylmagnesium bromide in diethyl ether (7.0 mL, 21.0 mmol) dropwise at −78° C. The reaction mixture was allowed to warm to ambient temperature and stirred for 2 h. The mixture was diluted with 1 M hydrochloric acid (200 mL) and extracted with ethyl acetate (3×200 mL). The combined organic phase was washed with brine (50 mL), dried over anhydrous sodium sulfate, and filtered. Concentration of the filtrate in vacuo provided a residue which was purified by column chromatography, eluting with a gradient of 0 to 20% of ethyl acetate in hexanes, to provide the title compound as a colorless oil (0.70 g, 35% yield): $^1$H-NMR (300 MHz, CDCl$_3$) δ 8.03 (d, J=6.8 Hz, 1H), 7.73-7.68 (m, 1H), 7.25 (t, J=9.5 Hz, 1H), 6.65 (t, J=56.1 Hz, 1H), 2.67 (d, J=5.0 Hz, 3H).

Step 3. Preparation of (R)-1-(5-(difluoromethyl)-2-fluorophenyl)ethan-1-ol

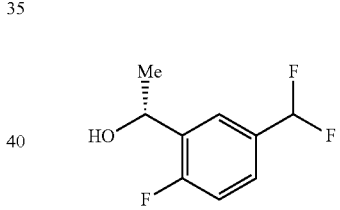

To a solution of 1-(5-(difluoromethyl)-2-fluorophenyl)ethan-1-one (0.70 g, 3.68 mmol) in anhydrous tetrahydrofuran (10 mL) was added a 1 M solution of (S)-(−)-2-methyl-CBS-oxazaborolidine in tetrahydrofuran (3.68 mL, 3.68 mmol) dropwise at −78° C. followed by slow addition of borane dimethyl sulfide complex (0.35 mL, 3.68 mmol). The reaction mixture was stirred at −78° C. for 20 minutes, allowed to warm to ambient temperature, and stirred for 20 minutes. After quench by slow addition of MeOH (20 mL), the reaction mixture was concentrated in vacuo. To the residue was added 1 M hydrochloric acid (20 mL), and the mixture was extracted with ethyl acetate (2×20 mL). The combined organic phase was washed with brine (50 mL), dried over anhydrous sodium sulfate, and filtered. Concentration of the filtrate in vacuo provided a residue which was purified by column chromatography, eluting with a gradient of 0 to 20% of ethyl acetate in hexanes, to provide the title compound as a colorless oil (0.60 g, 87% yield): $^1$H-NMR (300 MHz, CDCl$_3$) δ 7.68 (d, J=6.9 Hz, 1H), 7.44-7.39 (m, 1H), 7.11 (d, J=9.7 Hz, 1H), 6.63 (t, J=56.4 Hz, 1H), 5.22 (qd, J=6.4, 5.2 Hz, 1H), 1.52 (d, J=7.0 Hz, 3H), OH not observed.

Step 4. Preparation of (R)-1-(5-(difluoromethyl)-2-fluorophenyl)ethyl methanesulfonate

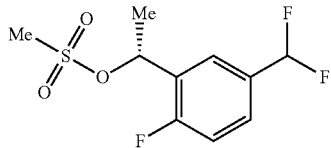 [SMILES: C[C@@H](OS(C)(=O)=O)c1cc(C(F)F)ccc1F]

To a solution of (R)-1-(5-(difluoromethyl)-2-fluorophenyl)ethan-1-ol (0.60 g, 3.12 mmol) in methyl isobutyl ketone (5 mL) was added a methanesulfonic anhydride (0.90 g, 5.31 mmol) at 0° C. followed by dropwise addition of triethylamine (0.87 mL, 6.24 mmol). After 20 minutes, the reaction was quenched by addition of saturated ammonium chloride (10 mL) and extracted with methyl isobutyl ketone (2×10 mL). The combined organic extracts were carried into the next step. MS (ES+) m/z 269.1 (M+1).

Step 5. Preparation of (R)-4-(benzyloxy)-1-(1-(5-(difluoromethyl)-2-fluorophenyl)ethyl)-piperidine

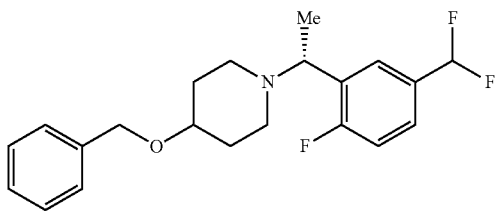 [SMILES: C[C@H](c1cc(C(F)F)ccc1F)N1CCC(OCc2ccccc2)CC1]

To a solution of (R)-1-(5-(difluoromethyl)-2-fluorophenyl)ethyl methanesulfonate (3.12 mmol) in methyl isobutyl ketone (25 mL) and water (3 mL) was added 4-(benzyloxy)piperidine (0.59 g, 3.12 mmol) and potassium carbonate (0.64 g, 4.68 mmol) and the reaction mixture was heated to 75° C. for 16 h. After cooling to ambient temperature, saturated ammonium chloride (15 mL) was added to the reaction mixture and the mixture was extracted with ethyl acetate (2×20 mL). The organic phase was washed with water (15 mL), brine (15 mL), dried over anhydrous sodium sulfate, and filtered. Concentration of the filtrate in vacuo and purification of the residue by column chromatography, eluting with a gradient of 0 to 15% of ethyl acetate in hexanes, provided the title compound as a yellow oil (0.61 g, 53% yield): MS (ES+) m/z 364.0 (M+1).

Step 6. Preparation of (R)-1-(1-(5-(difluoromethyl)-2-fluorophenyl)ethyl)piperidin-4-ol

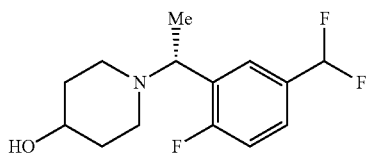 [SMILES: C[C@H](c1cc(C(F)F)ccc1F)N1CCC(O)CC1]

To a solution of (R)-4-(benzyloxy)-1-(1-(5-(difluoromethyl)-2-fluorophenyl)-ethyl)piperidine (0.12 g, 0.33 mmol) in tetrahydrofuran (3 mL) and 1 M hydrochloric acid (1 mL) was added palladium hydroxide on activated charcoal (0.03 g). The reaction mixture was then stirred under an atmosphere of hydrogen (1 atm) at ambient temperature for 2 h. After addition of saturated sodium bicarbonate solution (10 mL), the mixture was extracted with ethyl acetate (2×20 mL). The organic phase was washed with brine (15 mL), dried over anhydrous sodium sulfate, and filtered. Concentration of the filtrate in vacuo and purification of the residue by column chromatography, eluting with a gradient of 0 to 40% of ethyl acetate in hexanes, provided the title compound as a yellow oi (0.08 g, 88% yield): MS (ES+) m/z 274.0 (M+1).

Step 7. Preparation of (R)-3-chloro-4-((1-(1-(5-(difluoromethyl)-2-fluorophenyl)-ethyl)piperidin-4-yl)oxy)-N-(thiazol-4-yl)benzenesulfonamide Formate

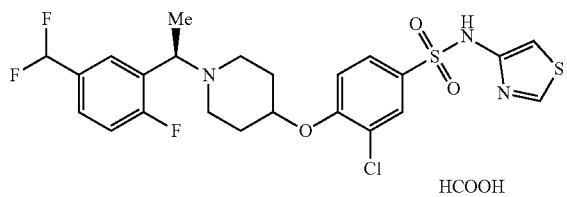 [SMILES: C[C@H](c1cc(C(F)F)ccc1F)N1CCC(Oc2ccc(S(=O)(=O)Nc3cscn3)cc2Cl)CC1 ; "HCOOH"]

To a mixture of (R)-1-(1-(5-(difluoromethyl)-2-fluorophenyl)ethyl)piperidin-4-ol (0.08 g, 0.29 mmol) and 3-chloro-4-fluoro-N-(thiazol-4-yl)benzenesulfonamide (0.085 g, 0.29 mmol) in anhydrous dimethyl sulfoxide (4 mL) was added potassium carbonate (0.10 g, 0.73 mmol) and the reaction mixture was heated to 60° C. for 16 h. After cooling to ambient temperature, the reaction mixture was diluted with ethyl acetate (20 mL), washed with saturated ammonium chloride (2×15 mL), brine (15 mL), dried over anhydrous sodium sulfate, and filtered. Concentration of the filtrate in vacuo and purification of the residue by preparative reverse-phase HPLC, eluting with a gradient of 20 to 60% of acetonitrile in water containing 0.1% of formic acid, afforded the title compound as a colorless solid (0.078 g, 48% yield): $^1$H NMR (300 MHz, DMSO-$d_6$) δ 8.88 (d, J=2.2 Hz, 1H), 8.15 (s, 1H), 7.79 (d, J=2.3 Hz, 1H), 7.69-7.65 (m, 2H), 7.55-7.50 (m, 1H), 7.30 (d, J=13.9 Hz, 2H), 7.05 (d, J=2.7 Hz, 2H), 4.62-4.55 (m, 1H), 3.93 (q, J=6.9 Hz, 1H), 2.71-2.57 (m, 2H), 2.30-2.21 (m, 2H), 1.95-1.86 (m, 2H), 1.70-1.60 (m, 2H), 1.34 (d, J=6.9 Hz, 3H), NH and COOH not observed; MS (ES+) m/z 546.0 (M+1), 548.0 (M+1).

Example 293

Synthesis of (S)-4-((1-benzylpyrrolidin-3-yl)(methyl)amino)-2,5-difluoro-N-(thiazol-4-yl)benzenesulfonamide 2,2,2-trifluoroacetate

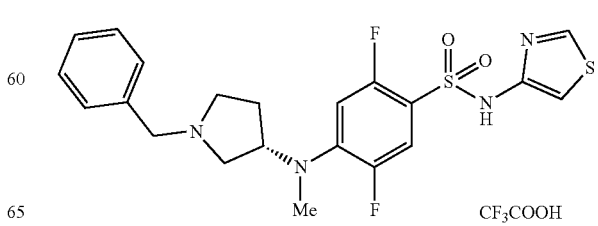

Step 1. Preparation of tert-butyl thiazol-4-yl((2,4,5-trifluorophenyl)sulfonyl)carbamate

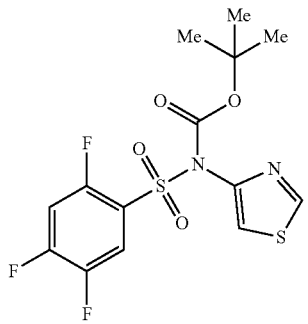 [SMILES: CC(C)(C)OC(=O)N(c1cscn1)S(=O)(=O)c1cc(F)c(F)cc1F]

To a solution of tert-butyl thiazol-4-ylcarbamate (1.47 g, 7.35 mmol) in anhydrous tetrahydrofuran (10 mL) was added a 1 M solution of lithium bis(trimethylsilyl)amide in tetrahydrofuran (10.3 mL, 10.3 mmol) at −78° C. The reaction mixture was allowed to warm to ambient temperature and stirred for 1 h. The reaction mixture was then cooled to −78° C., and a solution of 2,4,5-trifluorobenzenesulfonyl chloride (1.22 mL, 8.82 mmol) in anhydrous tetrahydrofuran (10 mL) was added to it. The reaction mixture was allowed to warm to ambient temperature and stirred for 3 h. The mixture was diluted with ethyl acetate (50 mL), washed with saturated ammonium chloride (2×30 mL), brine (2×30 mL), dried over anhydrous sodium sulfate, and filtered. Concentration of the filtrate in vacuo and purification of the residue by column chromatography, eluting with a gradient of 0 to 50% of ethyl acetate in hexanes, provided the title compound as a colorless solid (2.0 g, 68% yield): MS (ES+) m/z 395.0 (M+1).

Step 2. Preparation of tert-butyl (S)-((4-((1-benzylpyrrolidin-3-yl)amino)-2,5-difluorophenyl)sulfonyl)(thiazol-4-yl)carbamate

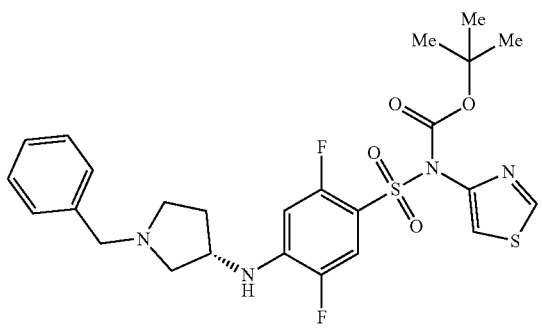 [SMILES: CC(C)(C)OC(=O)N(c1cscn1)S(=O)(=O)c1cc(F)c(N[C@H]2CCN(Cc3ccccc3)C2)cc1F]

To a mixture of tert-butyl thiazol-4-yl((2,4,5-trifluorophenyl)sulfonyl)carbamate (0.18 g, 0.46 mmol) and (S)-1-benzylpyrrolidin-3-amine (0.08 g, 0.46 mmol) in anhydrous dimethyl sulfoxide (10 mL) was added potassium carbonate (0.19 g, 1.38 mmol) and the reaction mixture was stirred at ambient temperature for 2 h. The reaction mixture was diluted with ethyl acetate (30 mL), washed with saturated ammonium chloride (2×20 mL), brine (20 mL), dried over anhydrous sodium sulfate, and filtered. Concentration of the filtrate in vacuo and purification of the residue by column chromatography, eluting with a gradient of 0 to 8% of methanol in dichloromethane, provided the title compound as a colorless foam (0.22 g, 86% yield): MS (ES+) m/z 551.0 (M+1).

Step 3. Preparation of (S)-4-((1-benzylpyrrolidin-3-yl)(methyl)amino)-2,5-difluoro-N-(thiazol-4-yl)benzenesulfonamide 2,2,2-trifluoroacetate

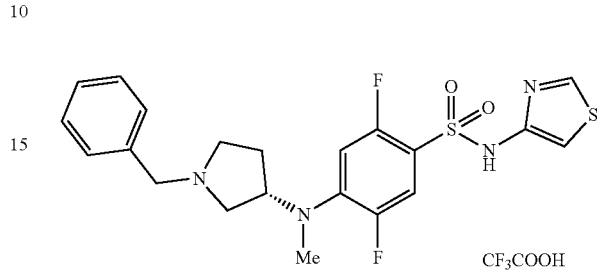

To a solution of tert-butyl (S)-((4-((1-benzylpyrrolidin-3-yl)amino)-2,5-difluorophenyl)sulfonyl)(thiazol-4-yl)carbamate (0.22 g, 0.40 mmol) in trifluoroacetic acid (2.0 mL) was added sodium triacetoxyborohydride (0.20 g, 0.97 mmol) at 0° C. The resulting mixture was stirred at 0° C. for 10 minutes, and then paraformaldehyde was added (29 mg, 0.97 mmol) to it. The reaction mixture was stirred at 0° C. for 15 minutes and then concentrated in vacuo. To the residue was added 2 M sodium hydroxide (10 mL) and brine (10 mL), and the mixture was extracted with ethyl acetate (30 mL). The aqueous layer was diluted with saturated ammonium chloride (30 mL) and then extracted with ethyl acetate (20 mL). The combined organic layers were washed with saturated ammonium chloride (30 mL), brine (30 mL), dried over anhydrous sodium sulfate, and filtered. Concentration of the filtrate in vacuo and purification of the residue by column chromatography, eluting with a gradient of 0 to 10% of methanol in dichloromethane, afforded the title compound as a colorless solid (0.098 g, 42% yield): $^1$H NMR (300 MHz, DMSO-$d_6$) δ 11.29 (s, 1H), 10.37-10.31 (m, 1H), 8.89 (d, J=2.2 Hz, 1H), 7.53-7.45 (m, 6H), 7.02-6.92 (m, 2H), 4.64 (s, 1H), 4.41 (s, 2H), 3.56-3.12 (m, 4H), 2.84 (s, 3H), 2.18 (s, 2H); MS (ES+) m/z 465.2 (M+1).

Example 294

Synthesis of (S)-4-((1-benzylpyrrolidin-3-yl)(methyl)amino)-N-(thiazol-4-yl)-3-(trifluoromethyl)benzenesulfonamide Formate

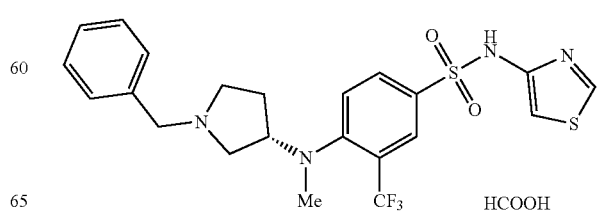

339

Step 1. Preparation of tert-butyl (4-fluoro-3-(trifluoromethyl)phenyl)sulfonyl(thiazol-4-yl)carbamate

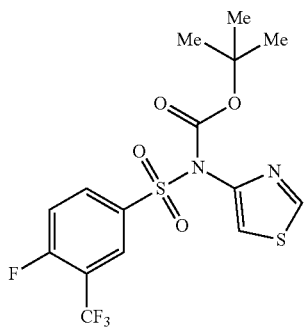 [SMILES: CC(C)(C)OC(=O)N(c1cscn1)S(=O)(=O)c1ccc(F)c(C(F)(F)F)c1]

To a mixture of tert-butyl thiazol-4-ylcarbamate (0.500 g, 2.50 mmol) in tetrahydrofuran (8 mL) was added a 1.0 M solution of lithium bis(trimethylsilyl)amide in tetrahydrofuran (3.25 mL, 3.25 mmol) at −78° C. The reaction mixture was allowed to warm to ambient temperature and stirred for 30 minutes. The reaction mixture was then cooled to −78° C. and a solution of 4-fluoro-3-(trifluoromethyl) benzene-1-sulfonyl chloride (0.985 g, 3.75 mmol) in anhydrous tetrahydrofuran (1 mL) was added slowly. The reaction mixture was stirred at −78° C. for 30 minutes, allowed to warm to ambient temperature, and stirred for 11 h. The mixture was then poured into ice-water (20 mL) and the aqueous phase was extracted with ethyl acetate (3×30 mL). The combined organic phase was washed with brine (30 mL), dried over anhydrous sodium sulfate, and filtered. Concentration of the filtrate in vacuo and purification of the residue by column chromatography, eluting with a gradient of 10-12.5% of ethyl acetate in petroleum ether, afforded the title compound as a yellow solid (0.400 g, 38% yield): $^1$H NMR (400 MHz, CDCl$_3$) δ 8.80 (d, J=2.4 Hz, 1H), 8.49-8.44 (m, 1H), 8.44-8.37 (m, 1H), 7.57 (d, J=2.4 Hz, 1H), 7.42 (t, J=9.2 Hz, 1H), 1.36 (s, 9H); MS (ES+) m/z 326.6 (M−99).

Step 2. Preparation of (S)-tert-butyl 3-((4-(N-(tert-butoxycarbonyl)-N-(thiazol-4-yl)sulfamoyl)-2-(trifluoromethyl)phenyl)amino)pyrrolidine-1-carboxylate

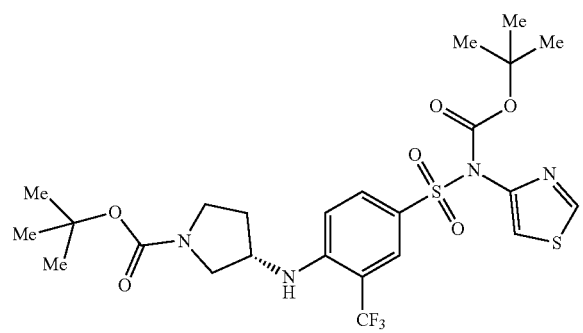 [SMILES: CC(C)(C)OC(=O)N1CC[C@H](Nc2ccc(S(=O)(=O)N(C(=O)OC(C)(C)C)c3cscn3)cc2C(F)(F)F)C1]

340

To a mixture of tert-butyl (4-fluoro-3-(trifluoromethyl)phenyl)sulfonyl(thiazol-4-yl)carbamate (0.200 g, 0.469 mmol) and (S)-tert-butyl 3-aminopyrrolidine-1-carboxylate (0.105 g, 0.563 mmol) in anhydrous dimethyl sulfoxide (1 mL) was added N,N-diisopropylethylamine (0.073 g, 0.563 mmol) and the reaction mixture was heated to 36° C. for 12 h. The residue was poured into ice-water (20 mL) and the aqueous phase was extracted with ethyl acetate (3×30 mL). The combined organic phase was washed with brine (30 mL), dried over anhydrous sodium sulfate, and filtered. Concentration of the filtrate in vacuo and purification of the residue by preparative thin layer chromatography, eluting with a 3:1 mixture of petroleum ether and ethyl acetate, afforded the title compound as a colorless oil (0.140 g, 49% yield); $^1$H NMR (400 MHz, CDCl$_3$) δ 8.80 (d, J=2.4 Hz, 1H), 8.22 (s, 1H), 8.12 (br s, 1H), 7.53 (s, 1H), 6.85 (d, J=9.0 Hz, 1H), 4.92 (br s, 1H), 4.25-4.17 (m, 1H), 3.81 (br s, 1H), 3.56 (br s, 2H), 3.42-3.22 (m, 1H), 2.33 (s, 1H), 1.99 (br s, 1H), 1.50 (s, 9H), 1.40 (s, 9H); MS (ES+) m/z 615.4 (M+23).

Step 3. Preparation of (S)-tert-butyl 3-((4-(N-(tert-butoxycarbonyl)-N-(thiazol-4-yl)sulfamoyl)-2-(trifluoromethyl)phenyl)(methyl)amino)pyrrolidine-1-carboxylate

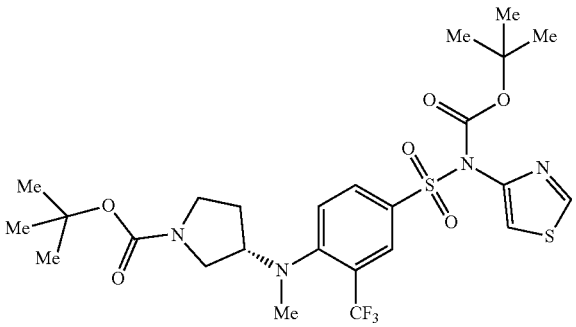 [SMILES: CN(c1ccc(S(=O)(=O)N(C(=O)OC(C)(C)C)c2cscn2)cc1C(F)(F)F)[C@H]1CCN(C(=O)OC(C)(C)C)C1]

To a mixture of (S)-tert-butyl 3-((4-(N-(tert-butoxycarbonyl)-N-(thiazol-4-yl)sulfamoyl)-2-(trifluoromethyl)phenyl)amino)pyrrolidine-1-carboxylate (0.300 g, 0.506 mmol) and iodomethane (0.144 g, 1.01 mmol) in N,N-dimethylformamide (8 mL) was added sodium hydride (60% dispersion in mineral oil, 0.020 g, 0.506 mmol) at 0° C. The mixture was stirred at 0° C. for 30 minutes and ambient temperature for 1 h. The residue was poured into ice-water (30 mL) and the aqueous phase was extracted with ethyl acetate (3×40 mL). The combined organic phase was washed with brine (50 mL), dried over anhydrous sodium sulfate, and filtered. Concentration of the filtrate in vacuo and purification of the residue by column chromatography, eluting with a gradient of 9-25% of ethyl acetate in petroleum ether, afforded the title compound as a yellow oil (0.250 g, 81% yield): $^1$H NMR (400 MHz, CDCl$_3$) δ 8.81 (d, J=2.4 Hz, 1H), 8.42 (br s, 1H), 8.31 (br s, 1H), 7.56 (s, 1H), 7.51 (d, J=8.6 Hz, 1H), 3.82 (br s, 1H), 3.67-3.48 (m, 2H), 3.32-3.11 (m, 2H), 2.74 (s, 3H), 2.02-1.84 (m, 2H), 1.45 (s, 9H), 1.36 (s, 9H); MS (ES+) m/z 629.0 (M+23).

Step 4. Preparation of (S)-4-(methyl(pyrrolidin-3-yl)amino)-N-(thiazol-4-yl)-3-(trifluoromethyl)benzenesulfonamide

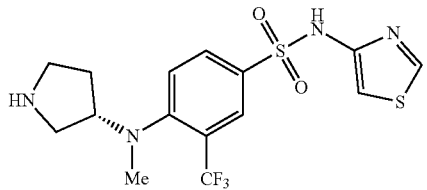 [SMILES: CN(c1ccc(S(=O)(=O)Nc2cscn2)cc1C(F)(F)F)[C@H]1CCNC1]

To a (S)-tert-butyl 3-((4-(N-(tert-butoxycarbonyl)-N-(thiazol-4-yl)sulfamoyl)-2-(trifluoromethyl)phenyl)(methyl)amino)pyrrolidine-1-carboxylate (0.250 g, 0.412 mmol) was added a solution of hydrogen chloride in methanol (25 mL) and the reaction mixture was stirred at ambient temperature for 12 h. Concentration of the mixture in vacuo and purification of the residue by preparative reverse phase HPLC, using acetonitrile in water containing 0.225% of formic acid as eluent, afforded the title compound as a yellow solid (0.120 g, 66% yield): $^1$H NMR (400 MHz, CD$_3$OD) δ 8.76 (d, J=2.4 Hz, 1H), 8.16 (d, J=1.8 Hz, 1H), 8.14-8.09 (m, 1H), 7.75 (d, J=8.4 Hz, 1H), 7.16 (d, J=2.2 Hz, 1H), 4.13-4.02 (m, 1H), 3.50-3.38 (m, 2H), 3.32-3.25 (m, 1H), 3.17 (dd, J=6.4, 12.4 Hz, 1H), 2.71 (s, 3H), 2.15 (qd, J=6.6, 13.4 Hz, 1H), 1.95 (qd, J=7.0, 13.8 Hz, 1H), NH not observed; MS (ES+) m/z 406.9 (M+1).

Step 5. Preparation of (S)-4-((1-benzylpyrrolidin-3-yl)(methyl)amino)-N-(thiazol-4-yl)-3-(trifluoromethyl)benzenesulfonamide Formate

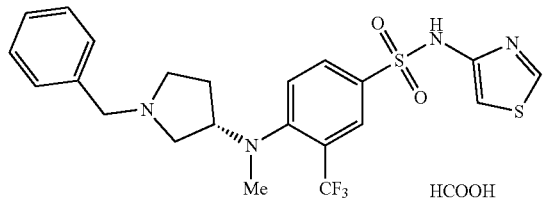 [SMILES: CN(c1ccc(S(=O)(=O)Nc2cscn2)cc1C(F)(F)F)[C@H]1CCN(Cc2ccccc2)C1 ; "HCOOH"]

To a solution of (S)-4-(methyl(pyrrolidin-3-yl)amino)-N-(thiazol-4-yl)-3-(trifluoromethyl) benzenesulfonamide (0.070 g, 0.172 mmol) and benzaldehyde (0.037 g, 0.344 mmol) in tetrahydrofuran (2 mL) was added trifluoroacetic acid (0.001 g, 0.009 mmol) and sodium triacetoxyborohydride (0.109 g, 0.517 mmol) and the mixture was stirred at ambient temperature for 1.5 h. Concentration in vacuo and purification of the residue by preparative reverse phase HPLC, using acetonitrile in water containing 0.225% of formic acid as eluent, afforded the title compound as a colorless solid (0.026 g, 30% yield): $^1$H NMR (400 MHz, CD$_3$OD) δ 8.72 (d, J=2.0 Hz, 1H), 8.45 (br s, 1H), 8.13 (d, J=2.0 Hz, 1H), 8.06 (dd, J=2.2, 8.4 Hz, 1H), 7.63 (d, J=8.4 Hz, 1H), 7.44 (s, 5H), 7.11 (d, J=2.2 Hz, 1H), 4.20-4.10 (m, 2H), 4.09-4.00 (m, 1H), 3.39-3.35 (m, 1H), 3.17 (dt, J=2.8, 7.0 Hz, 2H), 3.00 (dd, J=6.8, 11.2 Hz, 1H), 2.69 (s, 3H), 2.16 (qd, J=7.2, 13.7 Hz, 1H), 1.93 (qd, J=6.8, 13.8 Hz, 1H), NH and COOH not observed; MS (ES+) m/z 497.1 (M+1), 499.1 (M+1).

Example 295

Synthesis of (S)-4-((1-benzylpyrrolidin-3-yl)(methyl)amino)-2,6-difluoro-3-methyl-N-(1,2,4-thiadiazol-5-yl)benzenesulfonamide

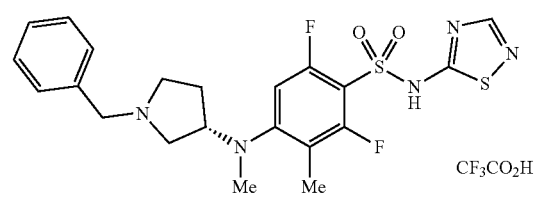 [SMILES: Cc1c(N(C)[C@H]2CCN(Cc3ccccc3)C2)cc(F)c(S(=O)(=O)Nc2ncns2)c1F ; "CF3CO2H"]

Step 1. Preparation of (S)-4-((1-benzylpyrrolidin-3-yl)(methyl)amino)-3-bromo-N-(2,4-dimethoxybenzyl)-2,6-difluoro-N-(1,2,4-thiadiazol-5-yl)benzenesulfonamide

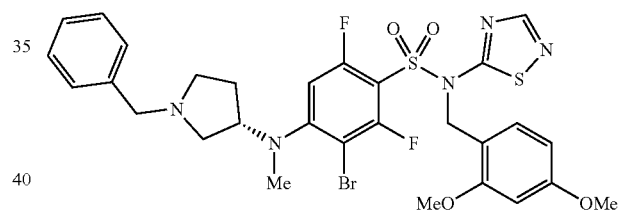

To a mixture of 3-bromo-N-(2,4-dimethoxybenzyl)-2,4,6-trifluoro-N-(1,2,4-thiadiazol-5-yl)benzenesulfonamide (1.00 g, 1.91 mmol) and (S)-1-benzyl-N-methylpyrrolidin-3-amine (0.363 g, 1.91 mmol) in N,N-dimethylformamide (5 mL) was added cesium carbonate (1.24 g, 3.82 mmol) and the reaction mixture was stirred at ambient temperature for 2 h. Water (20 mL) and ethyl acetate (20 mL) were added to the mixture, the layers were separated, and the aqueous phase was extracted with ethyl acetate (3×20 mL). The combined organic phase was washed with brine (20 mL), dried over anhydrous sodium sulfate, filtered, and concentrated in vacuo. The crude residue was purified by column chromatography, eluting with a gradient of 5-25% of ethyl acetate in petroleum ether, to provide the title compound as a light brown gum (0.450 g, 34% yield): $^1$H NMR (400 MHz, CDCl$_3$) δ 88.20-8.11 (m, 1H), 7.27-7.18 (m, 5H), 7.14 (d, J=8.4 Hz, 1H), 6.28-6.20 (m, 2H), 6.06 (d, J=2.4 Hz, 1H), 5.32 (s, 2H), 4.18-4.09 (m, 1H), 3.70-3.60 (m, 7H), 2.81 (s, 2H), 2.80 (s, 3H), 2.65 (dd, J=3.8, 10.4 Hz, 1H), 2.47 (dd, J=8.2, 10.2 Hz, 1H), 2.30 (q, J=8.2 Hz, 1H), 2.16-2.05 (m, 1H), 1.88-1.77 (m, 1H).

Step 2. Preparation of (S)-4-((1-benzylpyrrolidin-3-yl)(methyl)amino)-N-(2,4-dimethoxybenzyl)-2,6-difluoro-3-methyl-N-(1,2,4-thiadiazol-5-yl)benzenesulfonamide

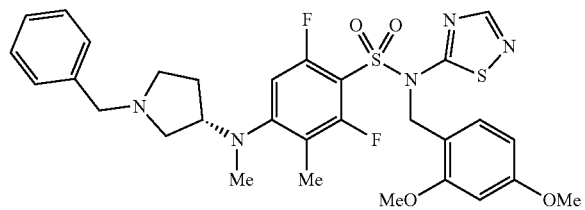 [SMILES: COc1ccc(CN(c2ncns2)S(=O)(=O)c2c(F)cc(N(C)[C@H]3CCN(Cc4ccccc4)C3)c(C)c2F)c(OC)c1]

To a mixture of (S)-4-((1-benzylpyrrolidin-3-yl)(methyl)amino)-3-bromo-N-(2,4-dimethoxybenzyl)-2,6-difluoro-N-(1,2,4-thiadiazol-5-yl)benzenesulfonamide (0.240 g, 0.346 mmol), methylboronic acid (0.041 g, 0.691 mmol), and potassium phosphate (0.220 g, 1.04 mmol) in anhydrous toluene (5 mL) was added palladium(II) acetate (0.016 g, 0.069 mmol) and 2-dicyclohexylphosphino-2',6'-dimethoxybiphenyl (0.029 g, 0.069 mmol) and the reaction mixture was heated to 110° C. for 12 h. Concentration of the mixture in vacuo and purification of the residue by column chromatography, eluting with a gradient of 5-25% of ethyl acetate in petroleum ether, afforded the title compound as a light brown solid (0.060 g, 40% yield).

Step 3. Preparation of (S)-4-((1-benzylpyrrolidin-3-yl)(methyl)amino)-2,6-difluoro-3-methyl-N-(1,2,4-thiadiazol-5-yl)benzenesulfonamide 2,2,2-trifluoroacetate

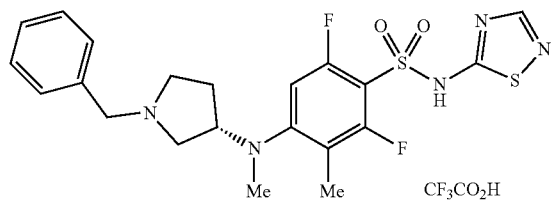 [SMILES: Cc1c(N(C)[C@H]2CCN(Cc3ccccc3)C2)cc(F)c(S(=O)(=O)Nc2ncns2)c1F ; "CF3CO2H"]

To a mixture of (S)-4-((1-benzylpyrrolidin-3-yl)(methyl)amino)-N-(2,4-dimethoxybenzyl)-2,6-difluoro-3-methyl-N-(1,2,4-thiadiazol-5-yl)benzenesulfonamide (0.070 g, 0.114 mmol) in dichloromethane (1 mL) was added trifluoroacetic acid (0.046 g, 0.405 mmol). The resulting mixture was stirred at ambient temperature for 2 h and then concentrated in vacuo. The residue was purified by preparative reverse phase HPLC, eluting with a gradient of 15-45% of acetonitrile in water containing 0.1% trifluoroacetic acid, to afford the title compound as a light brown solid (0.017 g, 30% yield): $^1$H NMR (400 MHz, CD$_3$OD) δ 8.27 (s, 1H), 7.51 (s, 5H), 6.87 (d, J=12.4 Hz, 1H), 4.42 (br s, 2H), 4.30-4.01 (m, 1H), 3.80-3.35 (m, 4H), 2.71 (br s, 3H), 2.19 (d, J=2.8 Hz, 5H); NH and COOH not observed; MS (ES+) m/z 480.4 (M+1).

Example 296

Synthesis of (S)-4-((1-benzylpyrrolidin-3-yl)(methyl)amino)-2,6-difluoro-3-methyl-N-(1,2,4-thiadiazol-5-yl)benzenesulfonamide 2,2,2-trifluoroacetate

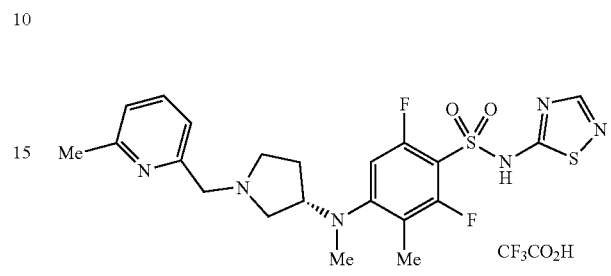

Step 1. Preparation of 3-bromo-N-(2,4-dimethoxybenzyl)-2,4,6-trifluoro-N-(1,2,4-thiadiazol-5-yl)benzenesulfonamide

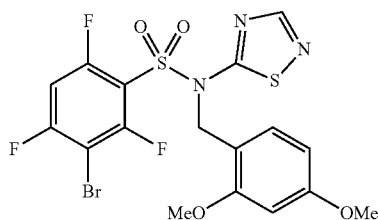 [SMILES: COc1ccc(CN(c2ncns2)S(=O)(=O)c2c(F)cc(F)c(Br)c2F)c(OC)c1]

To a solution of N-(2,4-dimethoxybenzyl)-1,2,4-thiadiazol-5-amine (0.665 g, 2.65 mmol) in anhydrous tetrahydrofuran (10 mL) was added a 1 M solution of lithium bis(trimethylsilyl)amide in tetrahydrofuran (2.91 mL, 2.91 mmol) at −78° C. The reaction mixture was allowed to warm to ambient temperature and stirred for 30 minutes. To it was then added a solution of 3-bromo-2,4,6-trifluorobenzene-1-sulfonyl chloride (1.00 g, 3.23 mmol) in anhydrous tetrahydrofuran (10 mL) at −78° C. The reaction mixture was allowed to warm to ambient temperature and stirred for 2 h. Water (20 mL) was added to the mixture, which was then extracted with ethyl acetate (3×40 mL). The combined organic phase was washed with brine (3×20 mL), dried over anhydrous sodium sulfate, and filtered. Concentration of the filtrate in vacuo and purification of the residue by column chromatography, eluting with a gradient of 5-10% of ethyl acetate in petroleum ether, afforded the title compound as a colorless solid (1.00 g, 72% yield): $^1$H NMR (400 MHz, CDCl$_3$) δ 8.27 (s, 1H), 7.37-7.18 (m, 1H), 6.74 (ddd, J=9.8, 7.8, 2.2 Hz, 1H), 6.36 (dd, J=8.6, 2.4 Hz, 1H), 6.19 (d, J=2.4 Hz, 1H), 5.46 (s, 2H), 3.77 (s, 3H), 3.71 (s, 3H).

Step 2. Preparation of (S)-tert-butyl 3-((2-bromo-4-(N-(2,4-dimethoxybenzyl)-N-(1,2,4-thiadiazol-5-yl)sulfamoyl)-3,5-difluorophenyl)amino)pyrrolidine-1-carboxylate

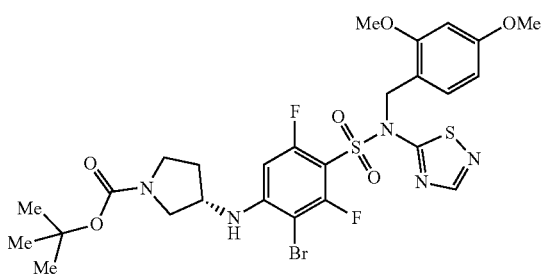 [SMILES: COc1ccc(CN(c2ncns2)S(=O)(=O)c2c(F)cc(N[C@H]3CCN(C(=O)OC(C)(C)C)C3)c(Br)c2F)c(OC)c1]

To a mixture of 3-bromo-N-(2,4-dimethoxybenzyl)-2,4,6-trifluoro-N-(1,2,4-thiadiazol-5-yl)benzenesulfonamide (1.00 g, 1.91 mmol) and tert-butyl (3S)-3-aminopyrrolidine-1-carboxylate (0.284 g, 1.53 mmol) in N,N-dimethyl formamide (5 mL) was added cesium carbonate (1.24 g, 3.81 mmol) and the reaction mixture was stirred at ambient temperature for 12 h. Water (20 mL) was added and the mixture was extracted with ethyl acetate (3×50 mL). The combined organic phase was washed with brine (3×20 mL), dried over anhydrous sodium sulfate, and filtered. Concentration of the filtrate in vacuo and purification of the residue by column chromatography, eluting with a gradient of 5-50% of ethyl acetate in petroleum ether, afforded the title compound as a colorless solid (0.600 g, 45% yield): $^1$H NMR (400 MHz, CDCl$_3$) δ 8.14 (s, 1H), 7.13 (d, J=8.6 Hz, 1H), 6.25 (dd, J=8.4, 2.4 Hz, 1H), 6.16 (d, J=2.4 Hz, 1H), 5.98 (dd, J=12.8, 1.2 Hz, 1H), 5.31 (d, J=2.8 Hz, 2H), 5.02 (br d, J=6.2 Hz, 1H), 3.90 (br s, 1H), 3.66 (d, J=1.2 Hz, 6H), 3.46 (br s, 2H), 3.33-3.13 (m, 1H), 2.25-2.12 (m, 1H), 1.86 (br s, 1H), 1.41 (s, 9H), NH not observed.

Step 3. Preparation of (S)-tert-butyl 3-((4-(N-(2,4-dimethoxybenzyl)-N-(1,2,4-thiadiazol-5-yl)sulfamoyl)-3,5-difluoro-2-methylphenyl)amino)pyrrolidine-1-carboxylate

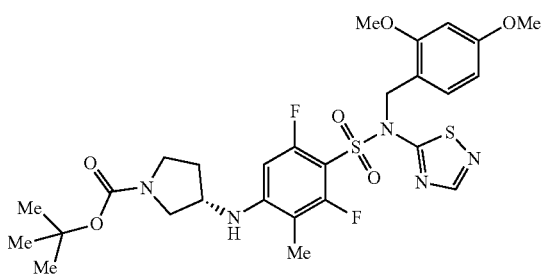 [SMILES: COc1ccc(CN(c2ncns2)S(=O)(=O)c2c(F)cc(N[C@H]3CCN(C(=O)OC(C)(C)C)C3)c(C)c2F)c(OC)c1]

To a solution of (S)-tert-butyl 3-((2-bromo-4-(N-(2,4-dimethoxybenzyl)-N-(1,2,4-thiadiazol-5-yl)sulfamoyl)-3,5-difluorophenyl)amino)pyrrolidine-1-carboxylate (0.600 g, 0.869 mmol), methylboronic acid (0.104 g, 1.74 mmol), palladium(II) acetate (0.0975 g, 0.434 mmol), 2-dicyclohexylphosphino-2',6'-dimethoxybiphenyl (0.178 g, 0.434 mmol) in anhydrous toluene (10 mL) and anhydrous tetrahydrofuran (10 mL) was added potassium phosphate (0.369 g, 1.74 mmol). The reaction mixture was heated to 110° C. for 1 h using a microwave. After cooling to ambient temperature, the mixture was concentrated in vacuo. Water (15 mL) was added to the residue, which was then extracted with ethyl acetate (3×20 mL). The combined organic extracts were washed with brine (3×10 mL), dried over anhydrous sodium sulfate, and filtered. Concentration of the filtrate in vacuo and purification of the residue by column chromatography, eluting with a gradient of 9-20% of ethyl acetate in petroleum ether, afforded the title compound as a colorless solid (0.300 g, 30% yield): $^1$H NMR (400 MHz, CDCl$_3$) 98.19 (d, J=2.0 Hz, 1H), 7.20 (d, J=8.4 Hz, 1H), 6.39-6.35 (m, 1H), 6.31 (d, J=2.3 Hz, 1H), 6.11-6.01 (m, 1H), 5.37-5.31 (m, 2H), 4.02 (br s, 1H), 3.78-3.73 (m, 6H), 3.72-3.71 (m, 1H), 3.60-3.46 (m, 3H), 3.38-3.16 (m, 1H), 2.34-2.17 (m, 1H), 1.89 (s, 3H), 1.50 (s, 9H), NH not observed.

Step 4. Preparation of (S)-tert-butyl 3-((4-(N-(2,4-dimethoxybenzyl)-N-(1,2,4-thiadiazol-5-yl)sulfamoyl)-3,5-difluoro-2-methylphenyl)(methyl)amino)pyrrolidine-1-carboxylate

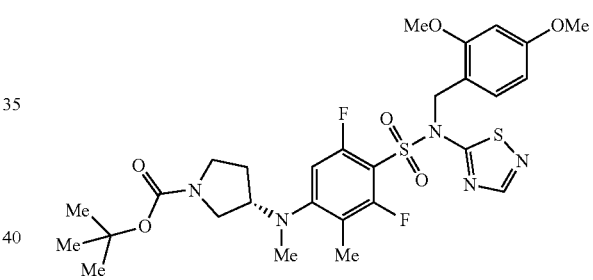

To a solution of (S)-tert-butyl 3-((4-(N-(2,4-dimethoxybenzyl)-N-(1,2,4-thiadiazol-5-yl)sulfamoyl)-3,5-difluoro-2-methylphenyl)amino)pyrrolidine-1-carboxylate (0.270 g, 0.432 mmol), iodomethane (32 μL, 0.518 mmol) in anhydrous N,N-dimethylformamide (3 mL) was added sodium hydride (60% dispersion in mineral oil 0.035 g, 0.863 mmol) at 0° C. The resulting mixture was allowed to warm to ambient temperature and stirred for 2 h. Water (15 mL) was added and the aqueous phase was extracted with ethyl acetate (3×20 mL). The combined organic extracts were washed with brine (3×10 mL), dried over anhydrous sodium sulfate, and filtered. Concentration of the filtrate in vacuo and purification of the residue by column chromatography, eluting with a gradient of 5-33% of ethyl acetate in petroleum ether, afforded the title compound as a light yellow solid (0.070 g, 23% yield): $^1$H NMR (400 MHz, CDCl$_3$) δ 8.22 (s, 1H), 7.24 (d, J=8.6 Hz, 1H), 6.53-6.44 (m, 1H), 6.35 (dd, J=8.4, 2.2 Hz, 1H), 6.25 (d, J=2.2 Hz, 1H), 5.39 (s, 2H), 3.85-3.79 (m, 1H), 3.75 (d, J=3.4 Hz, 6H), 3.70-3.47 (m, 3H), 3.41-3.17 (m, 3H), 2.69 (s, 3H), 2.05 (br d, J=2.4 Hz, 3H), 1.49 (s, 9H).

347

Step 5. Preparation of (S)-3-chloro-2,6-difluoro-4-(methyl(pyrrolidin-3-yl)amino)-N-(1,2,4-thiadiazol-5-yl)benzenesulfonamide hydrochloride

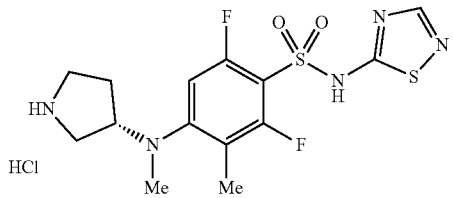

To a solution of (S)-tert-butyl 3-((4-(N-(2,4-dimethoxybenzyl)-N-(1,2,4-thiadiazol-5-yl)sulfamoyl)-3,5-difluoro-2-methylphenyl)(methyl)amino)pyrrolidine-1-carboxylate (0.040 g, 0.0625 mmol) in dichloromethane (1 mL) was added a 4 M solution of hydrogen chloride in dioxane (0.100 mL, 0.40 mmol) at 0° C. The resulting mixture was stirred for 2 h at ambient temperature and was then concentrated in vacuo to afford the title compound as a light brown solid (0.025 g, 94% yield), which was used without further purification.

Step 6. Preparation of (S)-4-((1-benzylpyrrolidin-3-yl)(methyl)amino)-2,6-difluoro-3-methyl-N-(1,2,4-thiadiazol-5-yl)benzenesulfonamide 2,2,2-trifluoroacetate

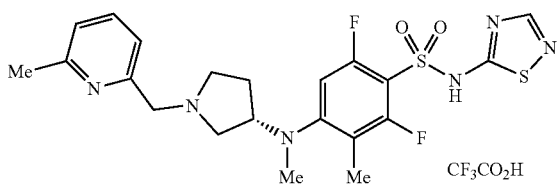 [SMILES: Cc1cccc(CN2CC[C@H](N(C)c3cc(F)c(S(=O)(=O)Nc4ncns4)c(F)c3C)C2)n1 ; "CF3CO2H"]

To a solution of (S)-3-chloro-2,6-difluoro-4-(methyl(pyrrolidin-3-yl)amino)-N-(1,2,4-thiadiazol-5-yl)benzenesulfonamide hydrochloride salt (0.0240 g, 0.0616 mmol) and 6-methylpicolinaldehyde (0.00896 g, 0.0739 mmol) in methanol (2 mL) was added sodium cyanoborohydride (0.00775 g, 0.123 mmol) and acetic acid (0.07 mL) at 0° C. The resulting mixture was allowed to warm to ambient temperature and stirred for 2 h. Concentration in vacuo and purification of the residue by preparative reverse phase HPLC, eluting with a gradient of 10-40% of acetonitrile in water containing 0.1% of trifluoroacetic acid, afforded the title compound as a light brown solid (0.011 g, 34% yield): $^1$H NMR (400 MHz, CD$_3$OD) δ 8.27 (s, 1H), 7.77 (t, J=7.8 Hz, 1H), 7.30 (dd, J=16.2, 7.6 Hz, 2H), 6.88 (br d, J=11.8 Hz, 1H), 4.62-4.47 (m, 2H), 4.22 (quin, J=6.8 Hz, 1H), 3.72-3.58 (m, 2H), 3.58-3.46 (m, 2H), 2.74 (s, 3H), 2.57 (s, 3H), 2.37 (qd, J=13.4, 6.8 Hz, 1H), 2.28-2.17 (m, 4H), NH and COOH not observed; MS (ES+) m/z 495.4 (M+1).

348

Example 297

Synthesis of (S)-3-chloro-2,6-difluoro-4-(methyl(1-((6-methylpyridin-2-yl)methyl)pyrrolidin-3-yl)amino)-N-(1,2,4-thiadiazol-5-yl)benzenesulfonamide 2,2,2-trifluoroacetate

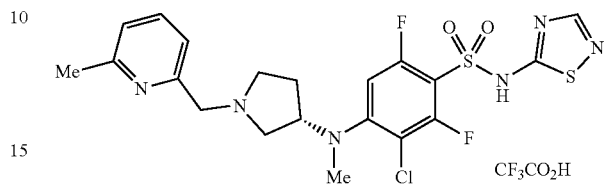

Step 1. Preparation of 3-chloro-N-(2,4-dimethoxybenzyl)-2,4,6-trifluoro-N-(1,2,4-thiadiazol-5-yl)benzenesulfonamide

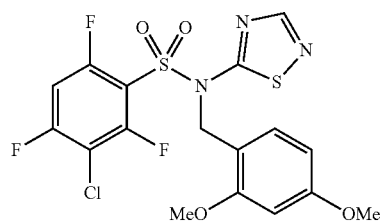 [SMILES: COc1ccc(CN(c2ncns2)S(=O)(=O)c2c(F)cc(F)c(Cl)c2F)c(OC)c1]

Following the procedure as described for EXAMPLE 102, Step 2 and making non-critical variations as required to replace tert-butyl thiazol-4-ylcarbamate with N-(2,4-dimethoxybenzyl)-1,2,4-thiadiazol-5-amine, the title compound was obtained as a colorless solid (0.538 g, 56% yield): $^1$H NMR (400 MHz, CDCl$_3$) δ 88.26 (s, 1H), 7.27 (d, J=8.8 Hz, 1H), 6.83-6.69 (m, 1H), 6.36 (dd, J=2.3, 8.6 Hz, 1H), 6.19 (d, J=2.4 Hz, 1H), 5.45 (s, 2H), 3.76 (s, 3H), 3.70 (s, 3H).

Step 2. Preparation of (S)-tert-butyl 3-((2-chloro-4-(N-(2,4-dimethoxybenzyl)-N-(1,2,4-thiadiazol-5-yl)sulfamoyl)-3,5-difluorophenyl)amino)pyrrolidine-1-carboxylate

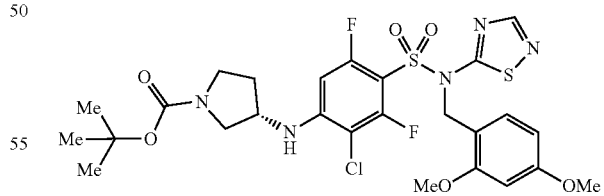

Following the procedure as described for EXAMPLE 296, Step 2 and making non-critical variations as required to replace 3-bromo-N-(2,4-dimethoxybenzyl)-2,4,6-trifluoro-N-(1,2,4-thiadiazol-5-yl)benzenesulfonamide with 3-chloro-N-(2,4-dimethoxybenzyl)-2,4,6-trifluoro-N-(1,2,4-thiadiazol-5-yl)benzenesulfonamide, the title compound was obtained as a colorless solid (0.130 g, 22% yield): $^1$H NMR (400 MHz, CDCl$_3$) δ 8.23 (s, 1H), 7.23 (d, J=8.4 Hz, 1H), 6.35 (dd, J=8.4, 2.4 Hz, 1H), 6.26 (d, J=2.4 Hz, 1H), 6.08 (d, J=11.8 Hz, 1H), 5.40 (d, J=2.6 Hz, 2H), 5.06 (br d, J=5.8 Hz, 1H), 4.00 (br s, 1H), 3.75 (d, J=1.6 Hz, 6H), 3.55 (br s, 2H), 3.42-3.18 (m, 1H), 2.34-2.20 (m, 1H), 1.96 (br s, 1H), 1.50 (s, 9H), NH not observed.

Step 3. Preparation of (S)-tert-butyl 3-((4-(N-(2,4-dimethoxybenzyl)-N-(1,2,4-thiadiazol-5-yl)sulfamoyl)-3,5-difluoro-2-methylphenyl)amino)pyrrolidine-1-carboxylate

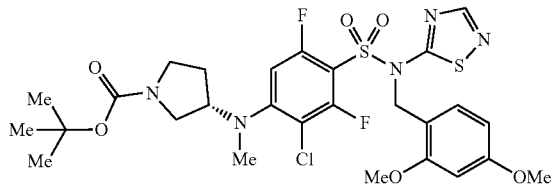 [SMILES: COc1ccc(CN(c2ncns2)S(=O)(=O)c2c(F)cc(N(C)[C@H]3CCN(C(=O)OC(C)(C)C)C3)c(Cl)c2F)c(OC)c1]

Following the procedure as described for EXAMPLE 296, Step 4 and making non-critical variations as required to replace (S)-tert-butyl 3-((4-(N-(2,4-dimethoxy-benzyl)-N-(1,2,4-thiadiazol-5-yl)sulfamoyl)-3,5-difluoro-2-methylphenyl)amino)-pyrrolidine-1-carboxylate with (S)-tert-butyl 3-((2-chloro-4-(N-(2,4-dimethoxybenzyl)-N-(1,2,4-thiadiazol-5-yl)sulfamoyl)-3,5-difluorophenyl)amino) pyrrolidine-1-carboxylate, the title compound was obtained as a light yellow solid (0.070 g, 64% yield): $^1$H NMR (400 MHz, CDCl$_3$) δ 8.16 (s, 1H), 7.17 (d, J=8.4 Hz, 1H), 6.31 (br d, J=11.8 Hz, 1H), 6.25 (dd, J=8.4, 2.2 Hz, 1H), 6.08 (d, J=2.2 Hz, 1H), 5.34 (d, J=6.2 Hz, 2H), 4.07 (s, 1H), 3.66 (s, 3H), 3.62 (s, 3H), 3.56-3.43 (m, 2H), 3.25 (br s, 2H), 2.73 (s, 3H), 1.85 (br s, 2H), 1.40 (s, 9H).

Step 4. Preparation of (S)-tert-butyl 3-((2-chloro-4-(N-(2,4-dimethoxybenzyl)-N-(1,2,4-thiadiazol-5-yl)sulfamoyl)-3,5-difluorophenyl)(methyl)amino)pyrrolidine-1-carboxylate Hydrochloride Salt

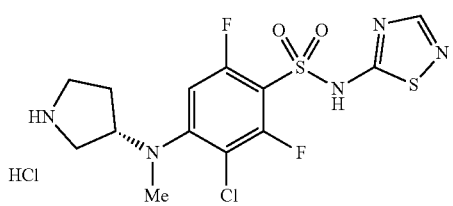 [SMILES: Cl ; CN(c1cc(F)c(S(=O)(=O)Nc2ncns2)c(F)c1Cl)[C@H]1CCNC1]

Following the procedure as described for EXAMPLE 296, Step 5 and making non-critical variations as required to replace (S)-tert-butyl 3-((4-(N-(2,4-dimethoxybenzyl)-N-(1,2,4-thiadiazol-5-yl)sulfamoyl)-3,5-difluoro-2-methylphenyl)-(methyl)amino)pyrrolidine-1-carboxylate with (S)-tert-butyl 3-((2-chloro-4-(N-(2,4-dimethoxybenzyl)-N-(1,2,4-thiadiazol-5-yl)sulfamoyl)-3,5-difluorophenyl)-amino)pyrrolidine-1-carboxylate, the title compound was obtained as a light brown solid (0.095 g, 94% yield), which was used with no further purification.

Step 5. Preparation of (S)-3-chloro-2,6-difluoro-4-(methyl (1-((6-methylpyridin-2-yl)methyl)pyrrolidin-3-yl)amino)-N-(1,2,4-thiadiazol-5-yl)benzenesulfonamide 2,2,2-trifluoroacetate

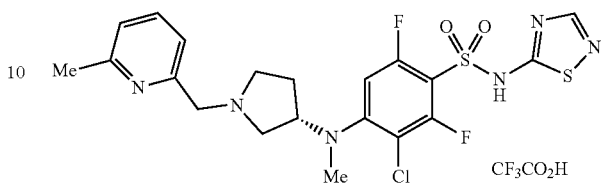

Following the procedure as described for EXAMPLE 296, Step 6 and making non-critical variations as required to replace (S)-3-chloro-2,6-difluoro-4-(methyl(pyrrolidin-3-yl)amino)-N-(1,2,4-thiadiazol-5-yl)benzenesulfonamide hydrochloride salt with (S)-tert-butyl 3-((2-chloro-4-(N-(2,4-dimethoxybenzyl)-N-(1,2,4-thiadiazol-5-yl)sulfamoyl)-3,5-difluorophenyl)(methyl)amino)pyrrolidine-1-carboxylate hydrochloride salt, the title compound was obtained as a colorless solid (0.0340 g, 23% yield): $^1$H NMR (400 MHz, CD$_3$OD) δ 8.29 (s, 1H), 7.78 (t, J=7.8 Hz, 1H), 7.31 (dd, J=17.8, 7.8 Hz, 2H), 6.98 (br d, J=11.2 Hz, 1H), 4.64-4.50 (m, 3H), 3.79-3.68 (m, 1H), 3.64-3.44 (m, 3H), 2.90 (s, 3H), 2.59 (s, 3H), 2.42-2.27 (m, 2H), NH and COOH not observed; MS (ES+) m/z 515.3 (M+1).

Example 298

Synthesis of (S)-4-((1-benzylpyrrolidin-3-yl)(methyl)amino)-2,6-difluoro-N-(6-fluoropyridin-2-yl)-3-methylbenzenesulfonamide Formate

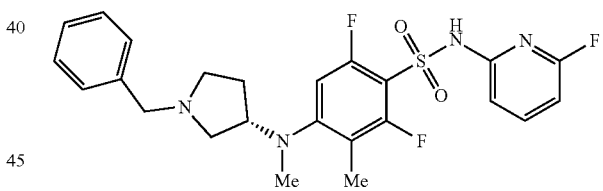

Step 1. Preparation of 3-bromo-N-(2,4-dimethoxybenzyl)-2,4,6-trifluoro-N-(6-fluoropyridin-2-yl)benzenesulfonamide

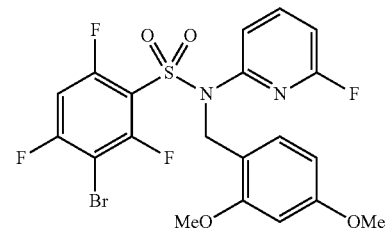 [SMILES: COc1ccc(CN(c2cccc(F)n2)S(=O)(=O)c2c(F)cc(F)c(Br)c2F)c(OC)c1]

To a solution of N-(2,4-dimethoxybenzyl)-6-fluoropyridin-2-amine (2.50 g, 9.53 mmol) in anhydrous tetrahydrofuran (10 mL) was added methyllithium (1.6 M, 7.15 mL, 11.44) at −78° C. The mixture was warmed to 0° C. and stirred for 30 minutes. The reaction mixture was then cooled to −78° C., and a solution of 3-bromo-2,4,6-trifluorobenzene-1-sulfonyl chloride (3.54 g, 11.4 mmol) in anhydrous tetrahydrofuran (2 mL) was added to it dropwise. The reaction mixture was allowed to warm to ambient temperature and stirred for 12 h. The mixture was diluted with saturated aqueous ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 10-25% of ethyl acetate in petroleum ether, afforded the title compound as a yellow oil (2.30 g, 45% yield): $^1$H NMR (400 MHz, CDCl3) δ 7.69 (q, J=8.0 Hz, 1H), 7.26-7.22 (m, 1H), 7.09 (dd, J=1.6, 7.8 Hz, 1H), 6.94-6.83 (m, 1H), 6.70 (dd, J=2.8, 8.0 Hz, 1H), 6.43-6.40 (m, 1H), 6.40 (s, 1H), 5.11 (s, 2H), 3.76 (d, J=9.6 Hz, 6H).

Step 2. Preparation of tert-butyl (S)-3-((2-bromo-4-(N-(2,4-dimethoxybenzyl)-N-(6-fluoropyridin-2-yl)sulfamoyl)-3,5-difluorophenyl)amino)pyrrolidine-1-carboxylate

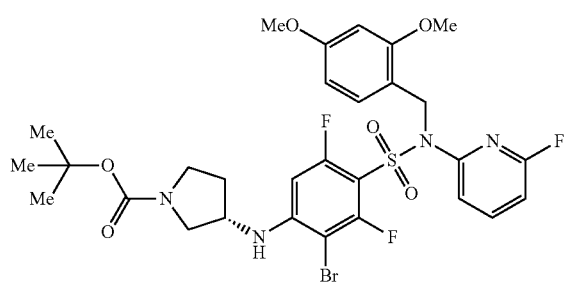 [SMILES: COc1ccc(CN(c2cccc(F)n2)S(=O)(=O)c2c(F)cc(N[C@H]3CCN(C(=O)OC(C)(C)C)C3)c(Br)c2F)c(OC)c1]

Following the procedure as described for EXAMPLE 296, Step 2 and making non-critical variations as required to replace 3-bromo-N-(2,4-dimethoxybenzyl)-2,4,6-trifluoro-N-(1,2,4-thiadiazol-5-yl)benzenesulfonamide with 3-bromo-N-(2,4-dimethoxybenzyl)-2,4,6-trifluoro-N-(6-fluoropyridin-2-yl)benzenesulfonamide, the title compound was obtained as a colorless solid (2.00 g, 66% yield): $^1$H NMR (400 MHz, CDCl3) 97.73-7.61 (m, 1H), 7.30-7.25 (m, 2H), 7.23 (br d, J=8.0 Hz, 1H), 6.66 (dd, J=2.4, 7.8 Hz, 1H), 6.42-6.36 (m, 2H), 6.20 (br d, J=12.4 Hz, 1H), 5.11 (s, 2H), 5.06 (br d, J=6.2 Hz, 1H), 4.03 (br s, 1H), 3.75 (d, J=6.8 Hz, 6H), 3.52 (br d, J=17.2 Hz, 2H), 3.42-3.21 (m, 1H), 2.34-2.20 (m, 1H), 2.05-1.88 (m, 1H), 1.49 (s, 9H); MS (ES+) m/z 701.1 (M+1), 703.1 (M+1).

Step 3. Preparation of tert-butyl (S)-3-((4-(N-(2,4-dimethoxybenzyl)-N-(6-fluoropyridin-2-yl)sulfamoyl)-3,5-difluoro-2-methylphenyl)amino)pyrrolidine-1-carboxylate

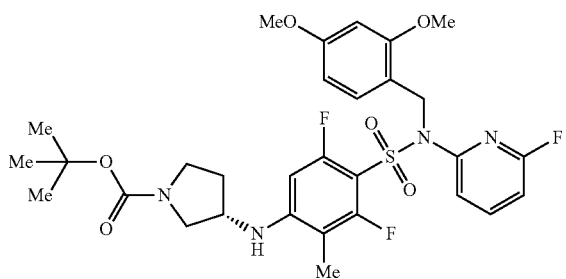 [SMILES: COc1ccc(CN(c2cccc(F)n2)S(=O)(=O)c2c(F)cc(N[C@H]3CCN(C(=O)OC(C)(C)C)C3)c(C)c2F)c(OC)c1]

To a solution of (S)-tert-butyl 3-((2-bromo-4-(N-(2,4-dimethoxybenzyl)-N-(6-fluoropyridin-2-yl)sulfamoyl)-3,5-difluorophenyl)amino)pyrrolidine-1-carboxylate (1.70 g, 2.42 mmol) in N,N-dimethylformamide (5 mL) was added tetramethyltin (1.30 g, 7.27 mmol), lithium chloride (0.30 g, 7.27 mmol) and bis(triphenylphosphine)palladium(II) chloride (0.34 g, 0.484 mmol). The resulting mixture was heated to 80° C. for 12 h. After cooling to ambient temperature, the mixture was diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 10-50% of ethyl acetate in petroleum ether, afforded the title compound as a yellow oil (1.30 g, 84% yield): $^1$H NMR (400 MHz, CDCl$_3$) δ 7.67 (q, J=8.1 Hz, 1H), 7.33-7.27 (m, 2H), 6.62 (dd, J=2.8, 8.0 Hz, 1H), 6.44-6.31 (m, 2H), 6.17-6.07 (m, 1H), 5.19-5.09 (m, 2H), 4.20 (br d, J=5.8 Hz, 1H), 4.03 (br s, 1H), 3.78-3.76 (m, 1H), 3.78 (s, 3H), 3.75 (s, 3H), 3.60-3.44 (m, 2H), 3.37-3.16 (m, 1H), 2.31-2.18 (m, 1H), 1.94 (s, 3H), 1.48 (s, 9H), NH not observed; MS (ES+) m/z 637.3 (M+1).

Step 4. Preparation of tert-butyl (S)-3-((4-(N-(2,4-dimethoxybenzyl)-N-(6-fluoropyridin-2-yl)sulfamoyl)-3,5-difluoro-2-methylphenyl)(methyl)amino) pyrrolidine-1-carboxylate

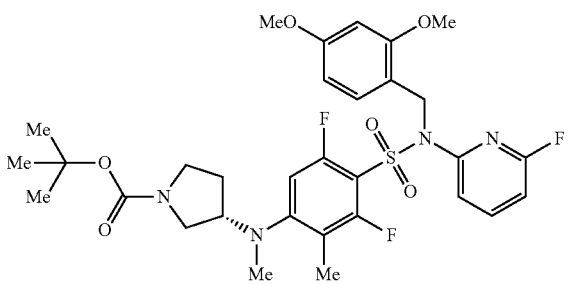 [SMILES: COc1ccc(CN(c2cccc(F)n2)S(=O)(=O)c2c(F)cc(N(C)[C@H]3CCN(C(=O)OC(C)(C)C)C3)c(C)c2F)c(OC)c1]

Following the procedure as described for EXAMPLE 296, Step 4 and making non-critical variations as required to replace (S)-tert-butyl 3-((4-(N-(2,4-dimethoxybenzyl)-N-(1,2,4-thiadiazol-5-yl)sulfamoyl)-3,5-difluoro-2-methylphenyl)amino)pyrrolidine-1-carboxylate with tert-butyl (S)-3-((4-(N-(2,4-dimethoxybenzyl)-N-(6-fluoropyridin-2-yl)

sulfamoyl)-3,5-difluoro-2-methylphenyl)amino)pyrrolidine-1-carboxylate, the title compound was obtained as a yellow oil (0.80 g, 71% yield): $^1$H NMR (400 MHz, CDCl$_3$) 7.69 (q, J=8.2 Hz, 1H), 7.31 (s, 2H), 6.66 (dd, J=2.9, 8.0 Hz, 1H), 6.60 (d, J=12.4 Hz, 1H), 6.44-6.37 (m, 2H), 5.15 (s, 2H), 3.86-3.79 (m, 1H), 3.78 (s, 3H), 3.76 (s, 3H), 3.70-3.47 (m, 2H), 3.40-3.17 (m, 2H), 2.70 (s, 3H), 2.14 (d, J=2.8 Hz, 3H), 2.06-1.90 (m, 2H), 1.49 (s, 9H); MS (ES+) m/z 673.3 (M+23).

Step 5. Preparation of (S)—N-(2,4-dimethoxybenzyl)-2,6-difluoro-N-(6-fluoropyridin-2-yl)-3-methyl-4-(methyl(pyrrolidin-3-yl)amino)benzenesulfonamide

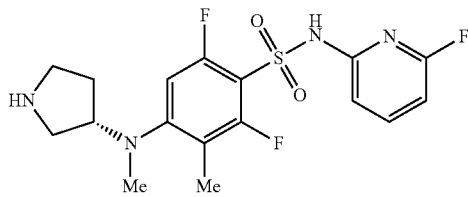 [SMILES: Cc1c(N(C)[C@H]2CCNC2)cc(F)c(S(=O)(=O)Nc2cccc(F)n2)c1F]

To (S)-tert-butyl 3-((4-(N-(2,4-dimethoxybenzyl)-N-(6-fluoropyridin-2-yl)sulfamoyl)-3,5-difluoro-2-methylphenyl)(methyl)amino)pyrrolidine-1-carboxylate (0.30 g, 0.46 mmol) was added a 4 M solution in hydrogen chloride in dioxane (20 mL, 80 mmol) and the resulting mixture was heated to 45° C. for 4 h. The mixture was concentrated in vacuo and the residue was purified by preparative reverse phase HPLC, eluting with a gradient of 5-60% of acetonitrile in water containing 0.1% ammonium hydroxide, to afford the title compound as a colorless solid (0.10 g, 56% yield): $^1$H NMR (400 MHz, CD$_3$OD) δ 7.46-7.38 (m, 1H), 6.73-6.64 (m, 2H), 6.17 (dd, J=2.4, 7.8 Hz, 1H), 4.51 (br s, 1H), 3.94 (quin, J=6.5 Hz, 1H), 3.36-3.26 (m, 3H), 3.09-3.01 (m, 1H), 2.56-2.54 (m, 3H), 2.14-2.03 (m, 1H), 1.99 (d, J=2.7 Hz, 3H), 1.97-1.90 (m, 1H), NH not observed; MS (ES+) m/z 401.2 (M+1).

Step 6. Preparation of (S)-4-((1-benzylpyrrolidin-3-yl)(methyl)amino)-2,6-difluoro-N-(6-fluoropyridin-2-yl)-3-methylbenzenesulfonamide Formate

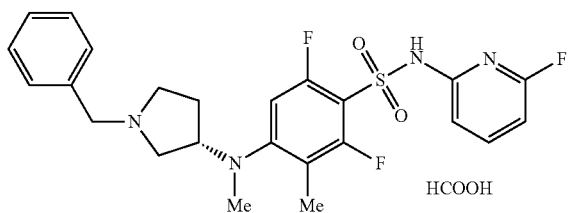 [SMILES: Cc1c(N(C)[C@H]2CCN(Cc3ccccc3)C2)cc(F)c(S(=O)(=O)Nc2cccc(F)n2)c1F ; "HCOOH"]

To a solution of (S)-2,6-difluoro-N-(6-fluoropyridin-2-yl)-3-methyl-4-(methyl(pyrrolidin-3-yl) amino)benzenesulfonamide (0.09 g, 0.2 mmol) in anhydrous tetrahydrofuran (2 mL) was added benzaldehyde (0.047 g, 0.45 mmol) and sodium triacetoxyhydroborate (0.095 g, 0.45 mmol). The resulting mixture was stirred at ambient temperature for 10 minutes. The mixture was concentrated in vacuum, and the residue purified by preparative reverse phase HPLC, using acetonitrile in water containing 0.225% formic acid as eluent, to afford the title compound as a colorless solid (0.363 g, 32% yield): $^1$H-NMR (400 MHz, DMSO-d$_6$) δ 8.17 (s, 0.4H), 7.75 (q, J=8.3 Hz, 1H), 7.32-7.30 (m, 4H), 7.28-7.22 (m, 1H), 6.82 (dd, J=8.0, 2.1 Hz, 1H), 6.71 (d, J=12.9 Hz, 1H), 6.57 (dd, J=7.9, 2.4 Hz, 1H), 3.97-3.92 (m, 1H), 3.66 (d, J=13.1 Hz, 1H), 3.56 (d, J=13.0 Hz, 1H), 2.76-2.70 (m, 1H), 2.68 (s, 3H), 2.66-2.60 (m, 2H), 2.42-2.36 (m, 1H), 2.05-2.01 (m, 4H), 1.83-1.75 (m, 1H), NH and COOH not observed; 19F NMR (376.5 MHz, DMSO-d$_6$) δ −68.9 (s, 1F), −108.2 (s, 1F), −111.8 (s, 1F); MS (ES+) m/z 491.1 (M+1).

Example 299

Synthesis of 4-((1-benzylpiperidin-4-yl)oxy)-2-fluoro-3-methyl-N-(thiazol-4-yl)benzenesulfonamide hydrochloride

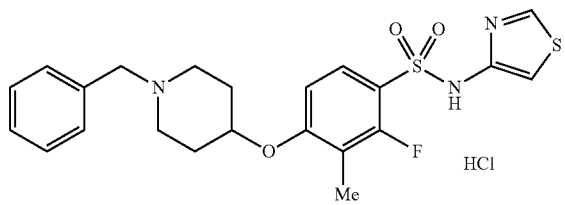 [SMILES: Cc1c(OC2CCN(Cc3ccccc3)CC2)ccc(S(=O)(=O)Nc2cscn2)c1F ; Cl]

Step 1. Preparation of tert-butyl (3-chloro-2,4-difluorophenyl)sulfonyl(thiazol-4-yl)carbamate

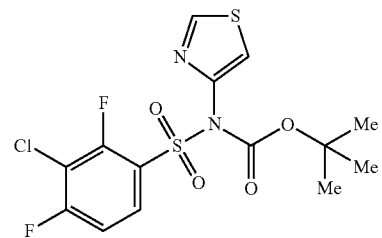 [SMILES: CC(C)(C)OC(=O)N(c1cscn1)S(=O)(=O)c1ccc(F)c(Cl)c1F]

To a solution of tert-butyl N-thiazol-4-ylcarbamate (110.0 g, 549.3 mmol) in anhydrous tetrahydrofuran (1000 mL) was added lithium bis(trimethylsilyl)amide (1.0 M in tetrahydrofuran, 659.1 mL, 659.1 mmol) at −78° C. The was mixture was warmed to 5° C., stirred for 30 minutes, and then cooled to −78° C. To it was then added a solution of 3-chloro-2,4-difluorobenzenesulfonyl chloride (162.8 g, 659.2 mmol) in anhydrous tetrahydrofuran (300 mL) at −78° C. The mixture was allowed to warm to ambient temperature and stirred for 12 h. The mixture was diluted with saturated ammonium chloride (200 mL) and extracted with ethyl acetate (3×1000 mL). The combined organic phase was washed with brine (3×1000 mL), dried over anhydrous sodium sulfate, and filtered. Concentration of the filtrate in vacuo and trituration of the residue with methanol (300 mL) provided the title compound as a colorless solid (75.00 g, 33% yield): $^1$H NMR (400 MHz, CDCl$_3$) δ 9.14 (s, 1H), 8.26-8.09 (m, 1H), 8.03 (s, 1H), 7.66 (t, J=8.6 Hz, 1H), 1.27 (s, 9H); MS (ES+) m/z 432.8 (M+23), 434.8 (M+23).

Step 2. Preparation of tert-butyl ((4-((1-benzylpip-eridin-4-yl)oxy)-3-chloro-2-fluorophenyl)sulfonyl)(thiazol-4-yl)carbamate

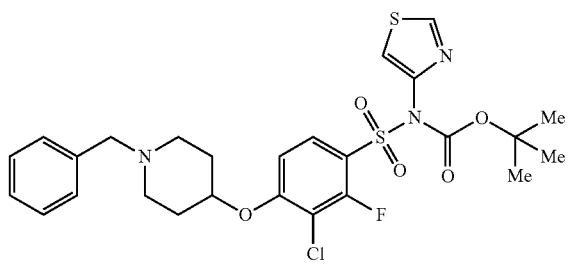 [SMILES: CC(C)(C)OC(=O)N(c1cscn1)S(=O)(=O)c1ccc(OC2CCN(Cc3ccccc3)CC2)c(Cl)c1F]

To a mixture of tert-butyl (3-chloro-2,4-difluorophenyl)sulfonyl(thiazol-4-yl)carbamate (2.70 g, 6.57 mmol) and 1-benzylpiperidin-4-ol (1.01 g, 5.26 mmol) in anhydrous dimethyl sulfoxide (4 mL) was added cesium carbonate (4.28 g, 13.14 mmol) and the reaction mixture was stirred at ambient temperature for 12 h. Water (20 mL) was added to the mixture and the aqueous phase was extracted with ethyl acetate (4×30 mL). The combined organic extracts were washed with brine (3×20 mL), dried over anhydrous sodium sulfate, and filtered. Concentration of the filtrate in vacuo and purification of the residue by column chromatography, eluting with a gradient of 10-66% of ethyl acetate in petroleum ether, afforded the title compound as a yellow oil (1.00 g, 26% yield): $^1$H NMR (400 MHz, CDCl$_3$) δ 8.71 (d, J=2.2 Hz, 1H), 8.10 (dd, J=9.1, 6.1 Hz, 1H), 7.47 (d, J=2.3 Hz, 1H), 7.26-7.15 (m, 5H), 6.98 (dd, J=7.7, 9.0 Hz, 1H), 4.62-4.48 (m, 1H), 3.39 (s, 2H), 2.73 (br d, J=12.0 Hz, 2H), 1.95-1.85 (m, 2H), 1.79-1.65 (m, 4H), 1.26 (s, 9H).

Step 3. Preparation of tert-butyl ((4-((1-benzylpip-eridin-4-yl)oxy)-2-fluoro-3-methylphenyl)sulfonyl)(thiazol-4-yl)carbamate

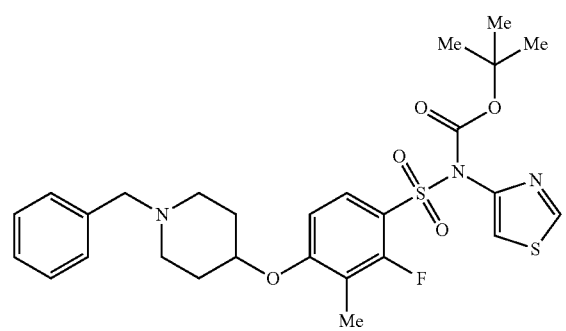 [SMILES: Cc1c(OC2CCN(Cc3ccccc3)CC2)ccc(S(=O)(=O)N(C(=O)OC(C)(C)C)c2cscn2)c1F]

To a mixture of tert-butyl (4-((1-benzylpiperidin-4-yl)oxy)-3-chloro-2-fluorophenyl)sulfonyl(thiazol-4-yl)car-bamate (0.200 g, 0.344 mmol) and methylboronic acid (0.031 g, 0.52 mmol) in anhydrous tetrahydrofuran (5 mL) and toluene (5 mL) was added potassium phosphate (0.146 mg, 0.687 mmol), palladium(II) acetate (0.015 g, 0.069 mmol) and 2-dicyclohexylphosphino-2',6'-dimethoxybiphenyl (0.028 g, 0.069 mmol). The resulting mixture was heated to 110° C. for 1 h using a microwave reactor. Concentration in vacuo and purification of the residue by column chromatography, eluting with a gradient of 10-25% of ethyl acetate in petroleum ether, afforded the title compound as light brown gum (0.150 g, 78% yield): MS (ES+) m/z 562.2 (M+1).

Step 4. Preparation of 4-((1-benzylpiperidin-4-yl)oxy)-2-fluoro-3-methyl-N-(thiazol-4-yl)benzene-sulfonamide Hydrochloride

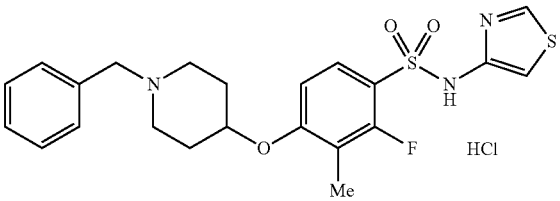 [SMILES: Cc1c(OC2CCN(Cc3ccccc3)CC2)ccc(S(=O)(=O)Nc2cscn2)c1F ; Cl]

To a mixture of tert-butyl (4-((1-benzylpiperidin-4-yl)oxy)-2-fluoro-3-methylphenyl)sulfonyl(thiazol-4-yl)car-bamate (0.130 g, 0.231 mmol) in tert-butanol (10 mL) was added potassium tert-butoxide (0.0779 g, 0.694 mmol) and the reaction was stirred at ambient temperature for 1 h. Concentration in vacuo and purification of the residue by preparative reverse phase HPLC, eluting with a gradient of 20-40% of acetonitrile in water containing 0.05% hydrochloric acid, afforded the title compound as a colorless solid (0.040 g, 37% yield): $^1$H NMR (400 MHz, CD$_3$OD) δ 8.75-8.69 (m, 1H), 7.76-7.66 (m, 1H), 7.62-7.50 (m, 5H), 6.98 (d, J=2.1 Hz, 1H), 6.97-6.87 (m, 1H), 4.93 (br s, 1H), 4.45-4.37 (m, 2H), 3.66-3.38 (m, 2H), 3.31-3.17 (m, 2H), 2.46-2.15 (m, 3H), 2.15-2.08 (m, 3H), 2.03-1.86 (m, 1H), NH and HCl not observed; MS (ES+) m/z 462.1 (M+1).

Example 300

Synthesis of (R)-3-chloro-4-((1-(1-phenylethyl)pip-eridin-4-yl)oxy)-N-(pyrimidin-4-yl)benzenesulfona-mide

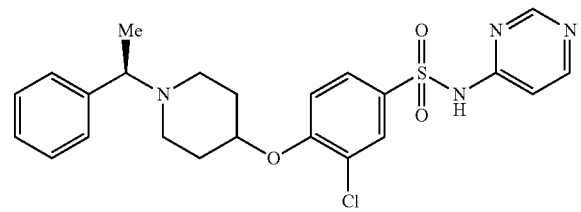 [SMILES: C[C@H](c1ccccc1)N1CCC(Oc2ccc(S(=O)(=O)Nc3ccncn3)cc2Cl)CC1]

Step 1. Preparation of 3-chloro-N-(2,4-dimethoxybenzyl)-4-fluoro-N-(pyrimidin-4-yl)benzenesulfonamide

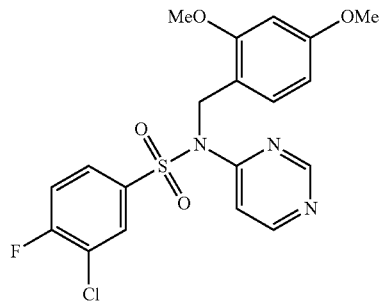 [SMILES: COc1ccc(CN(c2ccncn2)S(=O)(=O)c2ccc(F)c(Cl)c2)c(OC)c1]

To a solution of N-(2,4-dimethoxybenzyl)pyrimidin-4-amine (prepared according to WO2013064983, 15.0 g, 61.2 mmol) and 1,4-diazabicyclo[2.2.2]octane (13.7 g, 122.0 mmol) in anhydrous acetonitrile (150 mL) was added a solution of 3-chloro-4-fluorobenzene-1-sulfonyl chloride (21.0 g, 91.7 mmol) in anhydrous acetonitrile (100 mL) at 0° C. The reaction mixture was allowed to warm to ambient temperature and stirred for 12 h. The mixture was then diluted with water (200 mL) and extracted with ethyl acetate (2×300 mL). The combined organic phase was washed with brine (50 mL), dried over sodium sulfate, and filtered. Concentration in vacuo and trituration of the with methanol (2×200 mL) provided the title compound as a light yellow solid (20.0 g, 75% yield): $^1$H NMR (400 MHz, CDCl$_3$) δ 8.88 (d, J=0.8 Hz, 1H), 8.53 (d, J=5.6 Hz, 1H), 7.89 (dd, J=6.8, 2.0 Hz, 1H), 7.86-7.81 (m, 1H), 7.24 (t, J=8.4 Hz, 1H), 7.20 (dd, J=5.6, 1.2 Hz, 1H), 7.17 (d, J=8.0 Hz, 1H), 6.46-6.39 (m, 2H), 5.20 (s, 2H), 3.80 (s, 3H), 3.71 (s, 3H); MS (ES+) m/z 460.1 (M+23), 462.1 (M+1).

Step 2. Preparation of (R)-3-chloro-N-(2,4-dimethoxybenzyl)-4-((1-(1-phenylethyl)piperidin-4-yl)oxy)-N-(pyrimidin-4-yl)benzenesulfonamide

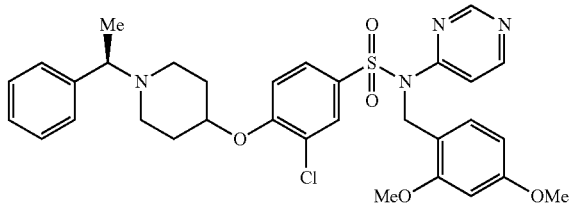 [SMILES: COc1ccc(CN(c2ccncn2)S(=O)(=O)c2ccc(OC3CCN([C@@H](C)c4ccccc4)CC3)c(Cl)c2)c(OC)c1]

To a solution of 3-chloro-N-(2,4-dimethoxybenzyl)-4-fluoro-N-(pyrimidin-4-yl)benzenesulfonamide (0.100 g, 0.228 mmol) in anhydrous dimethyl sulfoxide (5 mL) was added cesium carbonate (0.149 g, 0.457 mmol) and (R)-1-(1-phenylethyl)piperidin-4-ol (0.056 g, 0.274 mmol) and the reaction mixture was stirred at ambient temperature for 12 h. The reaction mixture was diluted with water (10 mL) and extracted with ethyl acetate (2×10 mL). The combined organic extracts were washed with brine (10 mL), dried over anhydrous sodium sulfate, and filtered. Concentration of the filtrate in vacuo afforded the title compound as a yellow oil (0.120 g, 84% yield): MS (ES+) m/z 623.2 (M+1).

Step 3. Preparation of (R)-3-chloro-4-((1-(1-phenylethyl)piperidin-4-yl)oxy)-N-(pyrimidin-4-yl)benzenesulfonamide

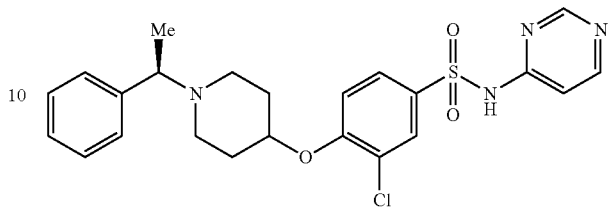

To a solution of (R)-3-chloro-N-(2,4-dimethoxybenzyl)-4-((1-(1-phenylethyl)piperidin-4-yl)oxy)-N-(pyrimidin-4-yl)benzenesulfonamide (0.100 mg, 0.160 mmol) in dichloromethane (10 mL) was added trifluoroacetic acid (1 mL). The mixture was stirred at ambient temperature for 30 minutes and then concentrated in vacuo. The residue was purified by preparative reverse phase HPLC, eluting with acetonitrile in water containing 0.05% of ammonium hydroxide, to afford the title compound as a colorless solid (0.030 g, 40% yield): $^1$H NMR (400 MHz, CDCl$_3$) δ 88.79 (s, 1H), 8.42 (d, J=6.0 Hz, 1H), 7.93 (d, J=2.4 Hz, 1H), 7.78 (dd, J=8.8, 2.4 Hz, 1H), 7.34-7.38 (m, 4H), 7.29-7.33 (m, 1H), 7.17 (d, J=6.0 Hz, 1H), 6.95 (d, J=8.8 Hz, 1H), 4.52 (br s, 1H), 3.75 (d, J=7.2 Hz, 1H), 2.75-2.90 (m, 2H), 2.49-2.75 (m, 2H), 2.12 (d, J=9.2 Hz, 2H), 1.95 (br s, 2H), 1.51 (d, J=6.8 Hz, 3H), NH not observed; MS (ES+) m/z 473.1 (M+1).

Example 301

Synthesis of (S)-3-chloro-4-((1-(1-phenylethyl)piperidin-4-yl)oxy)-N-(pyrimidin-4-yl)benzenesulfonamide

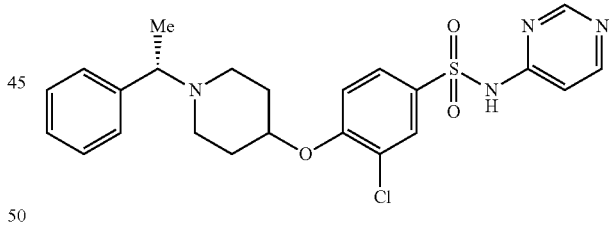

Step 1. Preparation of (S)-3-chloro-N-(2,4-dimethoxybenzyl)-4-((1-(1-phenylethyl)piperidin-4-yl)oxy)-N-(pyrimidin-4-yl)benzenesulfonamide

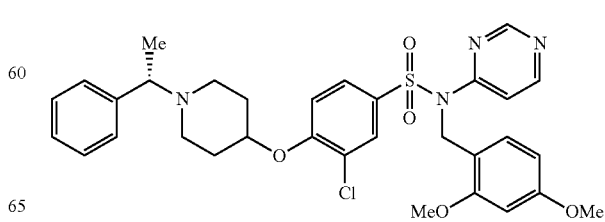

Following the procedure as described for EXAMPLE 300, Step 2 and making non-critical variations as required to replace (R)-1-(1-phenylethyl)piperidin-4-ol with (S)-1-(1-phenylethyl)piperidin-4-ol the title compound was obtained as a brown oil (0.320 g, 8% yield) that was used without purification: MS (ES+) m/z 623.1 (M+1).

Step 2. Preparation of (S)-3-chloro-4-((1-(1-phenylethyl)piperidin-4-yl)oxy)-N-(pyrimidin-4-yl)benzenesulfonamide

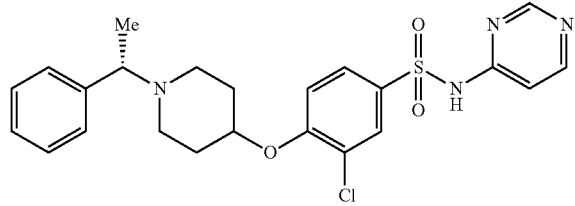 [SMILES: C[C@@H](c1ccccc1)N1CCC(Oc2ccc(S(=O)(=O)Nc3ccncn3)cc2Cl)CC1]

Following the procedure as described for EXAMPLE 300, Step 3 and making non-critical variations as required to replace (R)-3-chloro-N-(2,4-dimethoxybenzyl)-4-((1-(1-phenylethyl)piperidin-4-yl)oxy)-N-(pyrimidin-4-yl)benzenesulfonamide with (S)-3-chloro-N-(2,4-dimethoxybenzyl)-4-((1-(1-phenylethyl)piperidin-4-yl)oxy)-N-(pyrimidin-4-yl)benzenesulfonamide the title compound was obtained as a colorless solid (0.073 g, 30% yield): ¹H NMR (400 MHz, CDCl₃) δ 8.76 (s, 1H), 8.36 (d, J=5.6 Hz, 1H), 7.91 (d, J=2.0 Hz, 1H), 7.76 (d, J=8.4 Hz, 1H), 7.30-7.45 (m, 5H), 7.12 (d, J=5.2 Hz, 1H), 6.92 (d, J=8.8 Hz, 1H), 4.53 (br s, 1H), 3.89 (br s, 1H), 2.64-3.02 (m, 4H), 2.07-2.28 (m, 2H), 1.97 (d, J=3.6 Hz, 2H), 1.56 (d, J=6.8 Hz, 3H), NH not observed; MS (ES+) m/z 473.1 (M+1).

Example 302

Synthesis of (S)-4-((1-benzylpyrrolidin-3-yl)(methyl)amino)-2,6-difluoro-N-(5-fluoropyridin-2-yl)-3-methylbenzenesulfonamide Formate

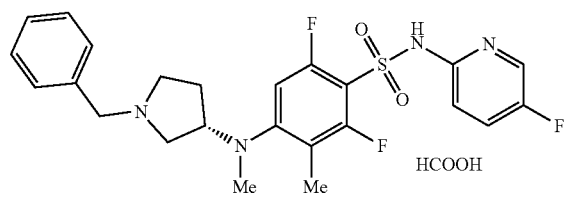 [SMILES: Cc1c(N(C)[C@H]2CCN(Cc3ccccc3)C2)cc(F)c(S(=O)(=O)Nc2ccc(F)cn2)c1F ; "HCOOH"]

Step 1. Preparation of 3-bromo-N-(2,4-dimethoxybenzyl)-2,4,6-trifluoro-N-(5-fluoropyridin-2-yl)benzenesulfonamide

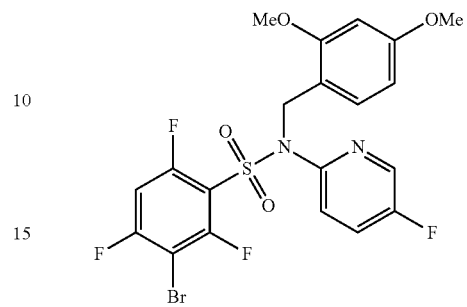

Following the procedure as described for EXAMPLE 298, Step 1 and making non-critical variations as required to replace N-(2,4-dimethoxybenzyl)-6-fluoropyridin-2-amine with N-(2,4-dimethoxybenzyl)-5-fluoropyridin-2-amine (prepared according to WO 2012004743) the title compound was obtained as an yellow solid (0.500 g, 38% yield): ¹H NMR (400 MHz, CDCl₃) 388.14 (d, J=2.9 Hz, 1H), 7.38-7.31 (m, 1H), 7.27-7.23 (m, 1H), 7.16 (d, J=8.9 Hz, 1H), 6.85 (ddd, J=9.9, 8.1, 2.1 Hz, 1H), 6.38-6.33 (m, 2H), 5.03 (s, 2H), 3.75 (s, 3H), 3.69 (s, 3H); MS (ES+) m/z 559.2 (M+23).

Step 2. Preparation of (S)-4-((1-benzylpyrrolidin-3-yl)amino)-3-bromo-N-(2,4-dimethoxybenzyl)-2,6-difluoro-N-(5-fluoropyridin-2-yl)benzenesulfonamide

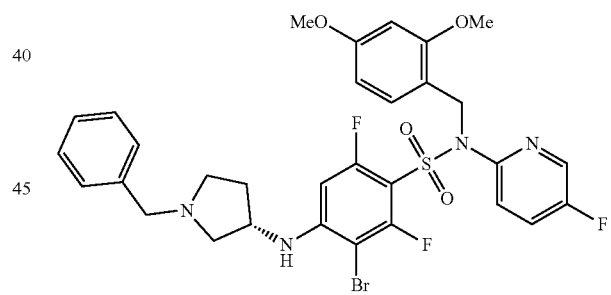

To a solution of 3-bromo-N-(2,4-dimethoxybenzyl)-2,4,6-trifluoro-N-(5-fluoropyridin-2-yl)benzenesulfonamide (0.40, 0.75 mmol) and (S)-1-benzylpyrrolidin-3-amine (0.16 g, 0.90 mmol) in N,N-dimethylformamide (5 mL) was added N,N-diisopropylethylamine (0.19 g, 1.5 mmol), and the mixture was heated to 35° C. for 12 h. After dilution with saturated ammonium chloride (20 mL) the mixture was extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 10-50% of ethyl acetate in petroleum ether, afforded the title compound as an yellow oil (0.50 g, 96% yield): ¹H NMR (400 MHz, CDCl₃) δ 8.16 (d, J=2.8 Hz, 1H), 7.43-7.30 (m, 7H), 7.22 (d, J=8.9 Hz, 1H), 6.40-6.31 (m, 2H), 6.13 (dd, J=13.1, 1.4 Hz, 1H), 5.35 (br d, J=7.0 Hz, 1H), 5.05 (s, 2H), 4.03-3.92 (m, 1H), 3.76 (s, 3H), 3.70 (s, 3H), 3.70-3.66 (m, 2H), 2.96-2.85 (m, 1H), 2.85-2.75 (m, 1H), 2.67 (br d, J=7.3 Hz, 1H), 2.55-2.45 (m, 1H), 2.45-2.29 (m, 1H), 1.83-1.69 (m, 1H).

Step 3. Preparation of (S)-4-((1-benzylpyrrolidin-3-yl)amino)-N-(2,4-dimethoxybenzyl)-2,6-difluoro-N-(5-fluoropyridin-2-yl)-3-methylbenzenesulfonamide

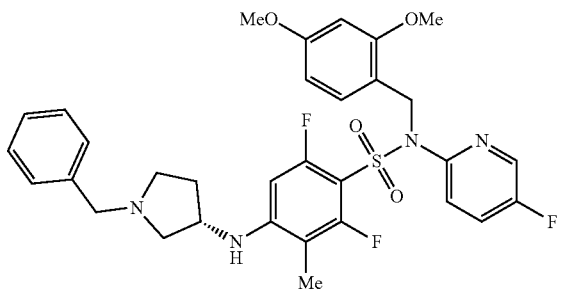 [SMILES: COc1ccc(CN(c2ccc(F)cn2)S(=O)(=O)c2c(F)cc(N[C@H]3CCN(Cc4ccccc4)C3)c(Br)c2F)c(OC)c1]

To a solution of (S)-4-((1-benzylpyrrolidin-3-yl)amino)-3-bromo-N-(2,4-dimethoxybenzyl)-2,6-difluoro-N-(5-fluoropyridin-2-yl)benzenesulfonamide (0.40 g, 0.58 mmol) in anhydrous toluene (5 mL) was added methylboronic acid (0.35 g, 5.8 mmol), potassium phosphate (0.37 g, 1.7 mmol), palladium(II) acetate (0.013 g, 0.58 mmol), 2-dicyclohexylphosphino-2',6'-dimethoxybiphenyl (0.048 g, 0.12 mmol) and the mixture was degassed by purging with nitrogen for 3 minutes. The resulting mixture was heated at 120° C. for 1 h in a microwave reactor. After cooling to ambient temperature, the mixture was diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 10-50% of ethyl acetate in petroleum ether, afforded the title compound as an yellow oil (0.3 g, 82% yield): $^1$H NMR (400 MHz, CDCl$_3$) δ 8.15-8.11 (m, 1H), 7.47-7.42 (m, 1H), 7.36-7.31 (m, 5H), 7.23 (d, J=8.8 Hz, 1H), 6.61 (d, J=8.4 Hz, 1H), 6.39-6.32 (m, 2H), 6.01 (d, J=13.0 Hz, 1H), 5.07 (s, 2H), 4.67 (br s, 1H), 3.75 (s, 3H), 3.69 (s, 3H), 2.94 (br d, J=3.6 Hz, 1H), 2.77-2.70 (m, 2H), 2.50-2.31 (m, 2H), 2.07 (s, 1H), 1.93 (d, J=1.3 Hz, 3H), 1.77-1.70 (m, 2H), 1.62-1.51 (m, 1H); MS (ES+) m/z 627.3 (M+1).

Step 4. Preparation of (S)-4-((1-benzylpyrrolidin-3-yl)(methyl)amino)-N-(2,4-dimethoxybenzyl)-2,6-difluoro-N-(5-fluoropyridin-2-yl)-3-methylbenzenesulfonamide

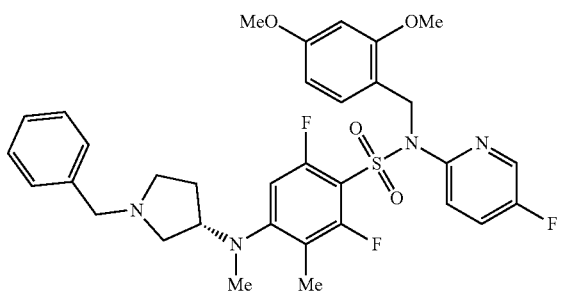 [SMILES: COc1ccc(CN(c2ccc(F)cn2)S(=O)(=O)c2c(F)cc(N(C)[C@H]3CCN(Cc4ccccc4)C3)c(C)c2F)c(OC)c1]

To a solution of (S)-4-((1-benzylpyrrolidin-3-yl)amino)-N-(2,4-dimethoxybenzyl)-2,6-difluoro-N-(5-fluoropyridin-2-yl)-3-methylbenzenesulfonamide (0.1 g, 0.2 mmol) in N,N-dimethylformamide (1 mL) was added sodium hydride (60% dispersion in mineral oil, 0.006 g, 0.2 mmol) at −5° C. Iodomethane (0.020 g, 143 umol) was then added and the mixture was stirred at ambient temperature for 1 h. The mixture was diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by preparative reverse phase HPLC, eluting with acetonitrile in water containing 0.05% of ammonium hydroxide, afforded the title compound as a colorless solid (0.029 g, 28% yield): $^1$H NMR (400 MHz, CDCl$_3$) δ 8.13 (d, J=2.8 Hz, 1H), 7.46-7.40 (m, 1H), 7.37-7.27 (m, 6H), 7.23 (d, J=8.4 Hz, 1H), 6.43 (dd, J=12.9, 1.4 Hz, 1H), 6.38-6.33 (m, 2H), 5.07 (s, 2H), 3.96-3.86 (m, 1H), 3.75 (s, 3H), 3.73-3.65 (m, 4H), 3.53 (d, J=12.9 Hz, 1H), 2.82-2.75 (m, 1H), 2.74 (s, 3H), 2.69-2.57 (m, 2H), 2.51-2.42 (m, 1H), 2.16-2.09 (m, 1H), 2.08 (d, J=3.0 Hz, 3H), 1.94-1.83 (m, 1H); MS (ES+) m/z 641.5 (M+1).

Step 5. Preparation of (S)-4-((1-benzylpyrrolidin-3-yl)(methyl)amino)-2,6-difluoro-N-(5-fluoropyridin-2-yl)-3-methylbenzenesulfonamide Formate

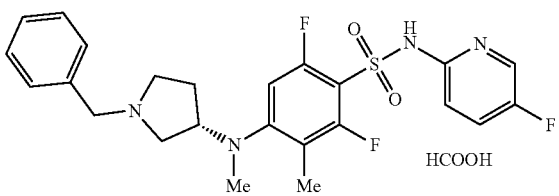 [SMILES: Cc1c(N(C)[C@H]2CCN(Cc3ccccc3)C2)cc(F)c(S(=O)(=O)Nc2ccc(F)cn2)c1F ; "HCOOH"]

To a solution of (S)-4-((1-benzylpyrrolidin-3-yl)(methyl)amino)-N-(2,4-dimethoxybenzyl)-2,6-difluoro-N-(5-fluoropyridin-2-yl)-3-methylbenzenesulfonamide (0.060 g, 0.093 mmol) in dichloromethane (5 mL) was added trifluoroacetic acid (1 mL) and the resulting mixture was stirred at ambient temperature for 30 minutes. The mixture was concentrated in vacuo and the residue was purified by preparative reverse phase HPLC, using acetonitrile in water containing 0.225% of formic acid as eluent, to afford the title compound as a colorless solid (0.042 g, 83% yield): $^1$H NMR (400 MHz, CD$_3$OH) δ 8.22 (br s, 1H), 8.03 (d, J=2.8 Hz, 1H), 7.56-7.50 (m, 1H), 7.47 (s, 5H), 7.16 (dd, J=9.2, 3.7 Hz, 1H), 6.81 (dd, J=12.4, 1.3 Hz, 1H), 4.34 (s, 2H), 4.14 (quin, J=7.2 Hz, 1H), 3.56-3.48 (m, 1H), 3.46-3.38 (m, 1H), 3.36-3.32 (m, 1H), 3.30-3.26 (m, 1H), 2.68 (s, 3H), 2.33-2.23 (m, 1H), 2.15 (d, J=2.8 Hz, 3H), 2.15-2.07 (m, 1H), NH and COOH not observed; MS (ES+) m/z 491.3 (M+1).

Example 303

Synthesis of 3-chloro-4-((1-(1-phenylcyclopropyl)piperidin-4-yl)oxy)-N-(thiazol-4-yl)benzenesulfonamide

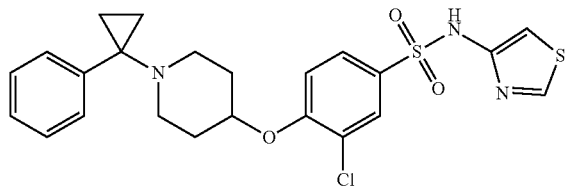 [SMILES: O=S(=O)(Nc1cscn1)c1ccc(OC2CCN(C3(c4ccccc4)CC3)CC2)c(Cl)c1]

Step 1. Preparation of 1-(1-phenylcyclopropyl)piperidin-4-one

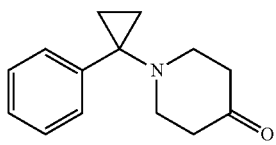 [SMILES: O=C1CCN(C2(c3ccccc3)CC2)CC1]

To a solution of 1-phenylcyclopropanamine hydrochloride (0.300 mg, 1.77 mmol) in ethanol (10 mL) was added potassium carbonate (0.0367 g, 0.265 mmol) and a mixture of 1-dimethyl-4-oxopiperidin-1-ium iodide (0.451 g, 1.77 mmol) in water (5 mL). The reaction mixture was heated to 80° C. for 3 h and was then concentrated in vacuo, quenched with water (20 mL) and extracted with dichloromethane (2×50 mL). The combined organic extracts were dried over anhydrous sodium sulfate, filtered and concentrated in vacuo. The residue was purified by column chromatography, eluting with a gradient of 0-10% of ethyl acetate in petroleum ether, to afford the title compound as an yellow solid (0.200 g, 53% yield): $^1$H NMR (400 MHz, CDCl$_3$) 357.26-7.36 (m, 5H), 2.82 (t, J=6.0 Hz, 4H), 2.39 (t, J=6.0 Hz, 4H), 1.01-1.06 (m, 2H), 0.88-0.94 (m, 2H).

Step 2. Preparation of 1-(1-phenylcyclopropyl)piperidin-4-ol

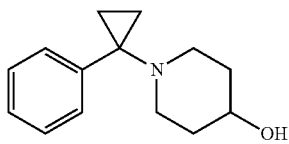 [SMILES: OC1CCN(C2(c3ccccc3)CC2)CC1]

To a solution of 1-(1-phenylcyclopropyl)piperidin-4-one (0.200 mg, 0.929 mmol) in methanol (5 mL) was added sodium borohydride (0.070 g, 1.86 mmol). The reaction mixture was stirred at ambient temperature for 3 h and was then concentrated in vacuo, diluted with water (10 mL) and extracted with dichloromethane (2×30 mL). The combined organic extracts were dried over anhydrous sodium sulfate, filtered and concentrated in vacuo to afford the title compound as a colorless solid (0.180 g, 89% yield): $^1$H NMR (400 MHz, CDCl$_3$) 37.27-7.34 (m, 4H), 7.23-7.27 (m, 1H), 3.40-3.53 (m, 1H), 2.78-2.95 (m, 2H), 2.12-2.26 (m, 2H), 1.79-1.93 (m, 2H,) 1.42-1.53 (m, 2H), 1.26 (d, J=5.2 Hz, 1H), 0.90-0.96 (m, 2H), 0.76-0.86 (m, 2H).

Step 3. Preparation of 3-chloro-4-((1-(1-phenylcyclopropyl)piperidin-4-yl)oxy)-N-(thiazol-4-yl)benzenesulfonamide

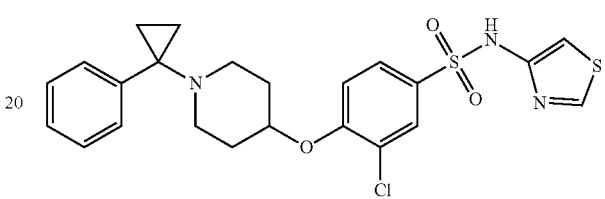

To a solution of 1-(1-phenylcyclopropyl)piperidin-4-ol (0.150 g, 0.690 mmol) in anhydrous N,N-dimethylformamide (5 mL) was added sodium hydride (60% dispersion in mineral oil, 0.055 g, 1.38 mmol). The reaction mixture was stirred at ambient temperature for 30 minutes and then tert-butyl (3-chloro-4-fluorophenyl)sulfonyl(thiazol-4-yl)carbamate (0.298 g, 0.759 mmol) was added to it. The reaction mixture was stirred at ambient temperature for 18 h and then quenched with water (20 mL) and extracted with ethyl acetate (2×50 mL). The combined organic extracts were washed with brine (3×20 mL), dried over anhydrous sodium sulfate, and filtered. Concentration of the filtrate in vacuo and purification of the residue by preparative reverse phase HPLC, using acetonitrile in water containing 0.225% of formic acid as eluent, afforded the title compound as a colorless solid (0.021 g, 6% yield): $^1$H NMR (400 MHz, CDCl$_3$) δ 8.61 (d, J=2.0 Hz, 1H), 7.74 (d, J=2.4 Hz, 1H), 7.57 (dd, J=8.8, 2.4 Hz, 1H), 7.27-7.39 (m, 5H), 7.05 (d, J=2.2 Hz, 1H), 6.80 (d, J=9.2 Hz, 1H), 4.18-4.41 (m, 1H), 2.82-3.03 (m, 2H), 2.33-2.66 (m, 2H), 1.89-2.20 (m, 4H), 0.99-1.35 (m, 2H), 0.79-0.95 (m, 2H), NH not observed; MS (ES+) m/z 490.1 (M+1

Example 304

Synthesis of (R)-3-chloro-N-(5-fluoropyrimidin-2-yl)-4-((1-(1-phenylethyl)piperidin-4-yl)oxy)benzenesulfonamide

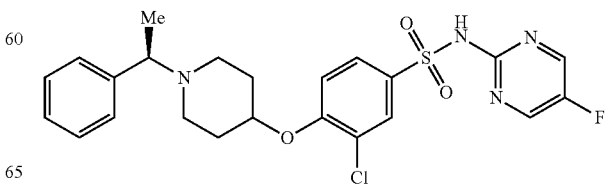

Step 1. Preparation of N-(2,4-dimethoxybenzyl)-5-fluoropyrimidin-2-amine

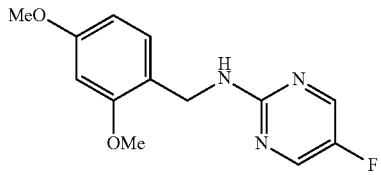 [SMILES: COc1ccc(CNc2ncc(F)cn2)c(OC)c1]

To a solution of 5-fluoropyrimidin-2-amine (1.20 g, 10.6 mmol) in dichloromethane (30 mL) was added 2,4-dimethoxybenzaldehyde (1.94 g, 11.7 mmol). The reaction was stirred at ambient temperature for 2 h, and then chloro(triisopropoxy)titanium (4.15 g, 15.9 mmol, 5.32 mL) was added dropwise at 0° C. The resulting mixture was stirred at ambient temperature for 12 h and then diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 10-25% of ethyl acetate in petroleum ether, afforded the title compound as a yellow oil (1.30 g, 47% yield): $^1$H NMR (400 MHz, CDCl$_3$) δ 8.15 (s, 2H), 7.22 (d, J=8.3 Hz, 1H), 6.46 (d, J=2.0 Hz, 1H), 6.41 (dd, J=8.2, 2.1 Hz, 1H), 5.59 (br s, 1H), 4.49 (d, J=6.0 Hz, 2H), 3.82 (s, 3H), 3.79 (s, 3H).

Step 2. Preparation of 3-chloro-N-(2,4-dimethoxybenzyl)-4-fluoro-N-(5-fluoropyrimidin-2-yl)benzenesulfonamide

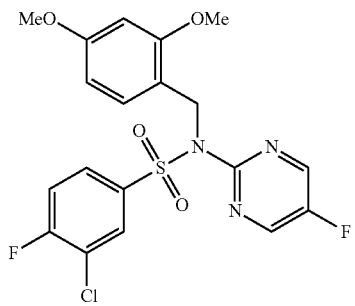 [SMILES: COc1ccc(CN(c2ncc(F)cn2)S(=O)(=O)c2ccc(F)c(Cl)c2)c(OC)c1]

Following the procedure as described for EXAMPLE 41, Step 1 and making non-critical variations as required to replace tert-butyl thiazol-4-ylcarbamate with N-(2,4-dimethoxybenzyl)-5-fluoropyrimidin-2-amine the title compound was obtained as a colorless solid (0.800 g, 92% yield): $^1$H NMR (400 MHz, CDCl$_3$) δ 8.40 (s, 2H), 7.86-7.79 (m, 1H), 7.75-7.68 (m, 1H), 7.18-7.06 (m, 2H), 6.42 (d, J=8.4 Hz, 1H), 6.28 (s, 1H), 5.39 (s, 2H), 3.79 (s, 3H), 3.43 (s, 3H).

Step 3. Preparation of (R)-3-chloro-N-(2,4-dimethoxybenzyl)-N-(5-fluoropyrimidin-2-yl)-4-((1-(1-phenylethyl)piperidin-4-yl)oxy)benzenesulfonamide

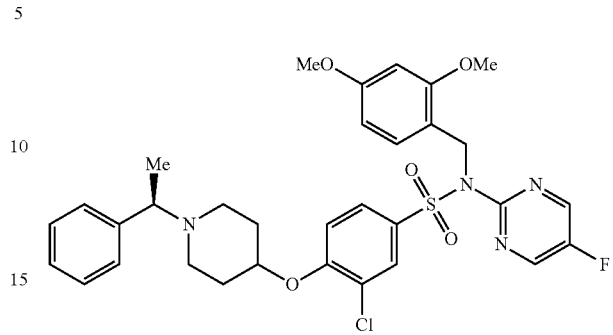

To a solution of (R)-1-(1-phenylethyl)piperidin-4-ol (0.100 g, 0.487 mmol) in anhydrous dimethyl sulfoxide (5 mL) was added 3-chloro-N-(2,4-dimethoxybenzyl)-4-fluoro-N-(5-fluoropyrimidin-2-yl) benzenesulfonamide (0.222 g, 0.487 mmol) and cesium carbonate (0.317 g, 0.974 mmol). The reaction mixture was heated to 80° C. for 12 h and then diluted with saturated ammonium chloride (20 mL) and extracted with ethyl acetate (3×10 mL). The combined organic extracts were washed with brine (3×10 mL), dried over anhydrous sodium sulfate, and filtered. Concentration of the filtrate in vacuo and purification of the residue by preparative reverse phase HPLC, using acetonitrile in water containing 0.1% of formic acid as eluent, afforded the title compound as a yellow oil (0.030 g, 10% yield): $^1$H NMR (400 MHz, CDCl$_3$) δ 8.36 (s, 2H), 7.78-7.72 (m, 2H), 7.42-7.35 (m, 5H), 7.10 (d, J=8.4 Hz, 1H), 6.80 (d, J=8.8 Hz, 1H), 6.41-6.35 (m, 1H), 6.28 (d, J=2.0 Hz, 1H), 5.35 (s, 2H), 4.61 (br s, 1H), 4.03 (d, J=6.8 Hz, 1H), 3.76 (s, 3H), 3.50 (s, 3H), 3.05 (br s, 1H), 2.96-2.78 (m, 3H), 2.27 (d, J=12.0 Hz, 2H), 1.97 (d, J=11.3 Hz, 2H), 1.64 (d, J=6.8 Hz, 3H).

Step 4. Preparation of (R)-3-chloro-N-(5-fluoropyrimidin-2-yl)-4-((1-(1-phenylethyl)piperidin-4-yl)oxy)benzenesulfonamide

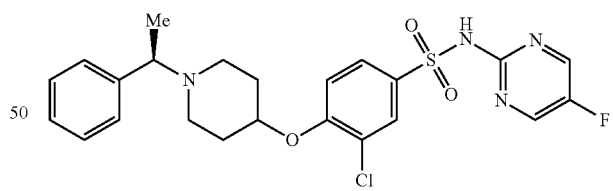

Following the procedure as described for EXAMPLE 41, Step 2 and making non-critical variations as required to replace (R)-5-chloro-N-(2,4-dimethoxybenzyl)-2-fluoro-4-((1-(1-phenylethyl)piperidin-4-yl)oxy)-N-(thiazol-2-yl)benzenesulfonamide with (R)-3-chloro-N-(2,4-dimethoxybenzyl)-N-(5-fluoropyrimidin-2-yl)-4-((1-(1-phenylethyl)piperidin-4-yl)oxy)benzenesulfonamide the title compound was obtained as a colorless solid (0.012 g, 48% yield): $^1$H NMR (400 MHz, CDCl$_3$) δ 8.44 (s, 2H), 8.10 (d, J=2.3 Hz, 1H), 7.98-7.89 (m, 1H), 7.39-7.27 (m, 5H), 6.94 (d, J=9.2 Hz, 1H), 4.54 (br s, 1H), 3.71 (d, J=5.6 Hz, 1H), 2.86-2.55 (m, 4H), 2.13 (br s, 2H), 1.93 (br s, 1H), 1.51 (d, J=6.4 Hz, 3H), NH not observed; MS (ES+) m/z 491.1 (M+1).

Example 305

Synthesis of (R)-3-chloro-N-(isoxazol-3-yl)-4-((1-(1-phenylethyl)piperidin-4-yl)oxy)benzenesulfonamide Formate

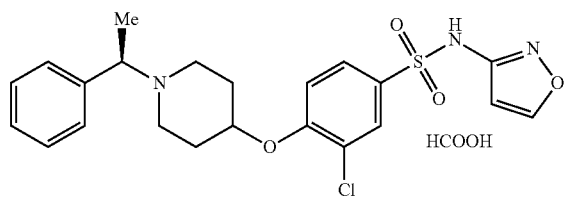 [SMILES: C[C@H](c1ccccc1)N1CCC(Oc2ccc(S(=O)(=O)Nc3ccon3)cc2Cl)CC1 ; "HCOOH"]

Step 1. Preparation of 3-chloro-4-fluoro-N-(isoxazol-3-yl)benzenesulfonamide

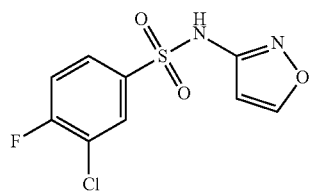

To a mixture of isoxazol-3-amine (0.500 g, 5.95 mmol), 4-dimethylaminopyridine (0.0727 g, 0.595 mmol) and pyridine (0.941 g, 11.9 mmol) in dichloromethane (2 mL) was added a solution of 3-chloro-4-fluoro-benzene-1-sulfonyl chloride (1.64 g, 7.14 mmol) in dichloromethane (1 mL) at 0° C. The mixture was stirred at ambient temperature for 12 h and was then diluted with water (20 mL) and extracted with dichloromethane (2×30 mL). The combined organic extracts were washed with water (20 mL), dried over anhydrous sodium sulfate, and filtered. Concentration of the filtrate in vacuo and purification of the residue by preparative reverse phase HPLC, using acetonitrile in water containing 0.1% of formic acid as eluent, afforded the title compound as a colorless solid (0.250 g, 15% yield): $^1$H NMR (400 MHz, CDCl$_3$) δ 8.31 (d, J=1.8 Hz, 1H), 7.92-7.90 (m, 1H), 7.76-7.74 (m, 1H), 7.22 (t, J=8.5 Hz, 1H), 6.62 (s, 1H), NH not observed; MS (ES+) m/z 276.9 (M+1).

Step 2. Preparation of (R)-3-chloro-N-(isoxazol-3-yl)-4-((1-(1-phenylethyl)piperidin-4-yl)oxy)benzenesulfonamide Formate

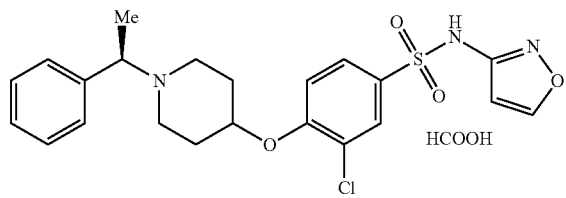 [SMILES: C[C@H](c1ccccc1)N1CCC(Oc2ccc(S(=O)(=O)Nc3ccon3)cc2Cl)CC1 ; "HCOOH"]

To a solution of (R)-1-(1-phenylethyl)piperidin-4-ol (0.089 g, 0.433 mmol) in N,N-dimethylformamide (1.50 mL) was added sodium hydride (60% dispersion in mineral oil, 0.029 g, 0.723 mmol) and the mixture was stirred at ambient temperature for 30 minutes. To it was then added 3-chloro-4-fluoro-N-(isoxazol-3-yl)benzenesulfonamide (0.100 g, 0.361 mmo) and the reaction mixture was stirred at ambient temperature for 12 h. The reaction mixture was then quenched with water (20 mL) and extracted with ethyl acetate (2×30 mL). The combined organic extracts were washed with brine (20 mL), dried over anhydrous sodium sulfate, and filtered. Concentration of the filtrate in vacuo and purification of the residue by preparative reverse phase HPLC, using acetonitrile in water containing 0.1% of formic acid as eluent, afforded the title compound as a colorless solid (0.072 g, 43% yield): $^1$H NMR (400 MHz, CDCl$_3$) δ 8.58 (s, 1H), 8.19 (s, 1H), 7.83 (d, J=1.7 Hz, 1H), 7.70 (d, J=8.1 Hz, 1H), 7.42 (s, 5H), 6.89 (d, J=8.6 Hz, 1H), 6.52 (s, 1H), 4.67 (br s, 1H), 4.32 (br s, 1H), 3.27 (br s, 1H), 3.14 (br s, 1H), 3.04-2.93 (m, 2H), 2.43-2.40 (m, 2H), 2.02 (br s, 2H), 1.76-1.74 (d, J=6.5 Hz, 3H), NH and COOH not observed.

Example 306

Synthesis of (S)-4-((1-benzylpyrrolidin-3-yl)(methyl)amino)-2-fluoro-N-(5-fluoropyridin-2-yl)-5-methylbenzenesulfonamide

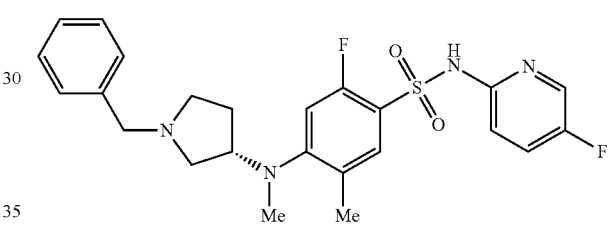

Step 1. Preparation of 4-bromo-2-fluoro-5-methylbenzenesulfonyl chloride

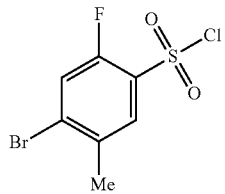 [SMILES: Cc1cc(S(=O)(=O)Cl)c(F)cc1Br]

To 4-bromo-2-fluoro-5-methylaniline (5.00 g, 24.5 mmol) was added concentrated hydrochloric acid (20 mL) at 0° C. The mixture was stirred at 0° C. for 30 minutes, and then a solution of sodium nitrite (2.54 g, 36.7 mmol) in water (8 mL) was added dropwise at 0° C. In a separate flask, sulfur dioxide (15 psi) was bubbled through acetic acid (25 mL) at 0° C. for 30 minutes. To this solution was then added cuprous chloride (0.72 g, 7.35 mmol) at 0° C. followed by dropwise addition of the mixture prepared from 4-bromo-2-fluoro-5-methylaniline and sodium nitrite in hydrochloric acid. The reaction mixture was allowed to warm to ambient temperature and stirred for 1 h. The mixture was diluted with brine (20 mL) and extracted with ethyl acetate (3×20 mL). The combined organic fractions were washed with brine (3×20 mL), dried over anhydrous sodium sulfate, and filtered. Concentration of the filtrate in vacuo and purification of the residue by column chromatography, eluting with a gradient of 2-17% of ethyl acetate in petroleum ether, afforded the title compound as a yellow solid (5.00 g, 70% yield): $^1$H NMR (400 MHz, CDCl$_3$) δ 7.82 (d, J=7.2 Hz, 1H), 7.57 (d, J=9.0 Hz, 1H), 2.48 (s, 3H).

Step 2. Preparation of 4-bromo-N-(2,4-dimethoxybenzyl)-2-fluoro-N-(5-fluoropyridin-2-yl)-5-methylbenzenesulfonamide

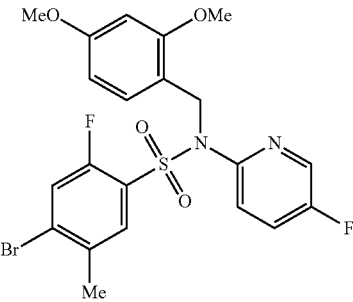 [SMILES: COc1ccc(CN(c2ccc(F)cn2)S(=O)(=O)c2cc(C)c(Br)cc2F)c(OC)c1]

To a solution of N-(2,4-dimethoxybenzyl)-5-fluoropyridin-2-amine (1.00 g, 3.81 mmol) in anhydrous tetrahydrofuran (30 mL) was added methyllithium (1.6 M, 3.10 mL, 4.96 mmol) at −78° C. The reaction mixture was stirred at 0° C. for 30 minutes. After cooling to −78° C., a solution of 4-bromo-2-fluoro-5-methylbenzene-1-sulfonyl Chloride (1.42 g, 4.95 mmol) in anhydrous tetrahydrofuran (10 mL) was added dropwise at −78° C. The reaction mixture was allowed to warm to ambient temperature and stirred for 12 h. The reaction mixture was then diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 9-25% of ethyl acetate in petroleum ether, afforded the title compound as a yellow solid (1.00 g, 51% yield): $^1$H NMR (400 MHz, CDCl$_3$) δ 8.15 (d, J=2.6 Hz, 1H), 7.66 (d, J=7.2 Hz, 1H), 7.40-7.31 (m, 3H), 7.18 (d, J=8.2 Hz, 1H), 6.38-6.32 (m, 2H), 4.99 (s, 2H), 3.76 (s, 3H), 3.67 (s, 3H), 2.39 (s, 3H); MS (ES+) m/z 536.8 (M+23).

Step 3. Preparation of (S)-4-((1-benzylpyrrolidin-3-yl)amino)-N-(2,4-dimethoxybenzyl)-2-fluoro-N-(5-fluoropyridin-2-yl)-5-methylbenzenesulfonamide

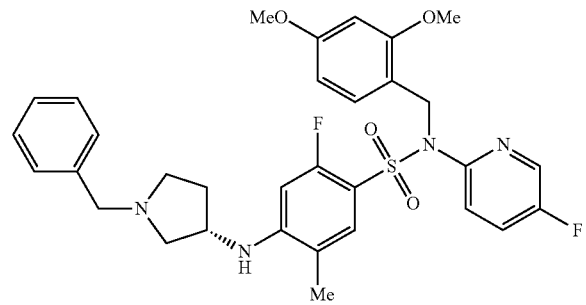 [SMILES: COc1ccc(CN(c2ccc(F)cn2)S(=O)(=O)c2cc(C)c(N[C@H]3CCN(Cc4ccccc4)C3)cc2F)c(OC)c1]

To a solution of (S)-1-benzylpyrrolidin-3-amine (0.31 g, 1.8 mmol) and 4-bromo-N-(2,4-dimethoxybenzyl)-2-fluoro-N-(5-fluoropyridin-2-yl)-5-methylbenzenesulfonamide (0.60 g, 1.2 mmol) in 2-methyl-2-butanol (5 mL) was added chloro(2-dicyclohexylphosphino-2',6'-diisopropoxy-1,1'-biphenyl)[2-(2'-amino-1,1'-biphenyl)]palladium(II) (0.091 g, 0.12 mmol) and cesium carbonate (1.14 g, 3.64 mmol). The mixture was heated to 90° C. for 12 h and then diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 9-50% of ethyl acetate in petroleum ether, afforded the title compound as a yellow solid (0.650 g, 91% yield): $^1$H NMR (400 MHz, CDCl$_3$) δ 8.13 (d, J=2.9 Hz, 1H), 7.46 (dd, J=8.8, 4.1 Hz, 1H), 7.40 (d, J=7.9 Hz, 1H), 7.36-7.26 (m, 7H), 7.22 (d, J=8.0 Hz, 1H), 6.38-6.31 (m, 2H), 6.18 (d, J=12.9 Hz, 1H), 4.99 (s, 2H), 4.36 (br d, J=7.0 Hz, 1H), 4.01-3.91 (m, 1H), 3.74 (s, 3H), 3.68 (s, 3H), 3.66 (s, 2H), 2.87 (dt, J=8.6, 4.5 Hz, 1H), 2.77 (dd, J=9.7, 6.3 Hz, 1H), 2.63 (dd, J=9.7, 2.9 Hz, 1H), 2.50-2.42 (m, 1H), 2.40-2.29 (m, 2H), 1.77-1.64 (m, 2H); MS (ES+) m/z 609.4 (M+1).

Step 4. Preparation of (S)-4-((1-benzylpyrrolidin-3-yl)(methyl)amino)-N-(2,4-dimethoxybenzyl)-2-fluoro-N-(5-fluoropyridin-2-yl)-5-methylbenzenesulfonamide

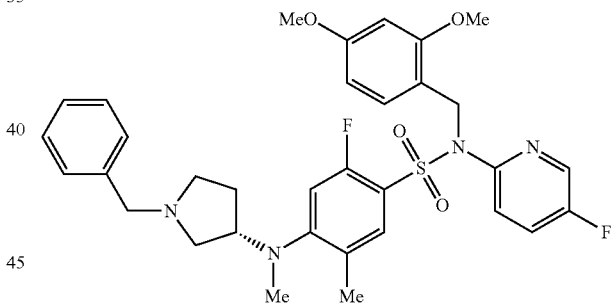

Following the procedure as described for EXAMPLE 296, Step 4 and making non-critical variations as required to replace (S)-tert-butyl 3-((4-(N-(2,4-dimethoxybenzyl)-N-(1,2,4-thiadiazol-5-yl)sulfamoyl)-3,5-difluoro-2-methylphenyl)amino)pyrrolidine-1-carboxylate with (S)-4-((1-benzylpyrrolidin-3-yl)amino)-N-(2,4-dimethoxybenzyl)-2-fluoro-N-(5-fluoropyridin-2-yl)-5-methylbenzenesulfonamide the title compound was obtained as a yellow solid (0.12 g, 58% yield): $^1$H NMR (400 MHz, CDCl$_3$) δ 8.14 (d, J=3.0 Hz, 1H), 7.52 (d, J=8.2 Hz, 1H), 7.44 (dd, J=8.8, 4.0 Hz, 1H), 7.38-7.27 (m, 6H), 7.21 (d, J=8.2 Hz, 1H), 6.62 (d, J=12.4 Hz, 1H), 6.38-6.30 (m, 2H), 5.00 (s, 2H), 3.95-3.84 (m, 1H), 3.79-3.69 (m, 5H), 3.67 (s, 3H), 2.71 (s, 3H), 2.63 (br s, 1H), 2.53 (br s, 1H), 2.22 (s, 3H), 2.14-2.04 (m, 1H), 1.86 (td, J=6.6, 3.2 Hz, 2H), 1.62 (br s, 1H); MS (ES+) m/z 623.5 (M+1).

Step 5. Preparation of (S)-4-((1-benzylpyrrolidin-3-yl)(methyl)amino)-2-fluoro-N-(5-fluoropyridin-2-yl)-5-methylbenzenesulfonamide

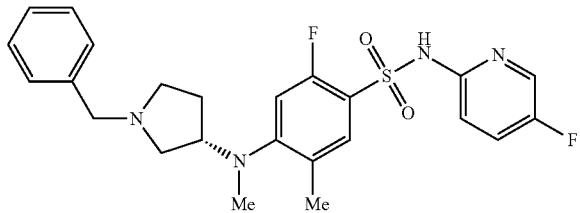 [SMILES: Cc1cc(S(=O)(=O)Nc2ccc(F)cn2)c(F)cc1N(C)[C@H]1CCN(Cc2ccccc2)C1]

Following the procedure as described for EXAMPLE 295, Step 3 and making non-critical variations as required to replace (S)-4-((1-benzylpyrrolidin-3-yl)(methyl)amino)-N-(2,4-dimethoxybenzyl)-2,6-difluoro-3-methyl-N-(1,2,4-thiadiazol-5-yl)benzenesulfonamide with (S)-4-((1-benzylpyrrolidin-3-yl)(methyl)amino)-N-(2,4-dimethoxybenzyl)-2-fluoro-N-(5-fluoropyridin-2-yl)-5-methylbenzenesulfonamide the title compound was obtained as a colorless solid (0.0498 g, 49% yield): $^1$H NMR (400 MHz, CD$_3$OD) δ 8.02 (d, J=3.0 Hz, 1H), 7.75 (d, J=8.2 Hz, 1H), 7.49 (dt, J=8.6, 3.0 Hz, 1H), 7.44 (s, 5H), 7.18 (dd, J=9.0, 3.6 Hz, 1H), 6.94 (d, J=12.2 Hz, 1H), 4.23 (br s, 2H), 4.08 (br s, 1H), 3.39 (br s, 1H), 3.30-3.12 (m, 3H), 2.65 (s, 3H), 2.30 (s, 3H), 2.27-2.18 (m, 1H), 2.12-1.99 (m, 1H), NH not observed; MS (ES+) m/z 473.1 (M+1).

Example 307

Synthesis of (S)-4-((1-benzylpyrrolidin-3-yl)(methyl)amino)-2-fluoro-N-(isothiazol-4-yl)-5-methylbenzenesulfonamide Formate

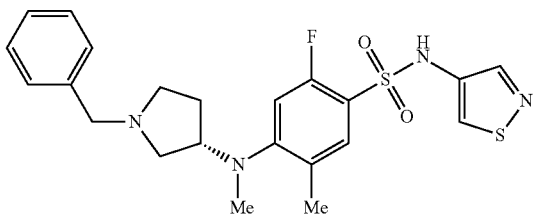 [SMILES: Cc1cc(S(=O)(=O)Nc2cnsc2)c(F)cc1N(C)[C@H]1CCN(Cc2ccccc2)C1]

Step 1. Preparation of 4-bromo-2-fluoro-N-(isothiazol-4-yl)-5-methylbenzene-sulfonamide

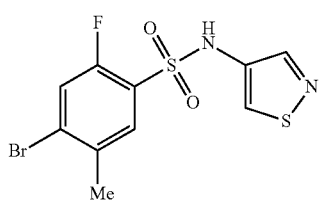 [SMILES: Cc1cc(S(=O)(=O)Nc2cnsc2)c(F)cc1Br]

To a solution of isothiazol-4-amine (0.45 g, 4.5 mmol) in dichloromethane (2 mL) was added 4-(dimethylamino)pyridine (0.05 g, 0.45 mmol), pyridine (0.71 mg, 9.0 mmol), and then 4-bromo-2-fluoro-5-methylbenzene-1-sulfonyl chloride (1.55 g, 5.39 mmol). The mixture was stirred at ambient temperature for 12 h and then concentrated in vacuo. The mixture was diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 9-50% of ethyl acetate in petroleum ether, afforded the title compound as a colorless solid (1.3 g, 82% yield): $^1$H NMR (400 MHz, CDCl$_3$) δ 8.34 (s, 1H), 8.30 (s, 1H), 7.65 (d, J=7.5 Hz, 1H), 7.44 (d, J=9.4 Hz, 1H), 7.00 (s, 1H), 2.38 (s, 3H).

Step 2. Preparation of 4-bromo-2-fluoro-N-(isothiazol-4-yl)-5-methyl-N-((2-(trimethylsilyl)ethoxy)methyl)benzenesulfonamide

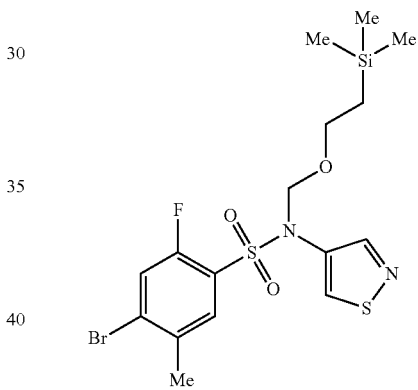

To a mixture of 4-bromo-2-fluoro-N-(isothiazol-4-yl)-5-methylbenzenesulfonamide (0.40 g, 1.1 mmol) in anhydrous N,N-dimethylformamide (5 mL) was added potassium carbonate (0.47 g, 3.4 mmol) and the reaction mixture was heated to 40° C. for 30 minutes. The reaction mixture was cooled to 0° C. and 2-(chloromethoxy)ethyltrimethylsilane (0.19 g, 1.14 mmol) was added to it. The reaction mixture was allowed to warm to ambient temperature, stirred for 12 h, and was then diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 9-50% of ethyl acetate in petroleum ether, afforded the title compound as a yellow oil (0.5 g, 91% yield): $^1$H NMR (400 MHz, CDCl$_3$) δ 8.50 (s, 1H), 8.38 (s, 1H), 7.59 (d, J=7.5 Hz, 1H), 7.41 (d, J=9.4 Hz, 1H), 5.13 (s, 2H), 3.74-3.63 (m, 2H), 2.37 (s, 3H), 0.96-0.85 (m, 2H), 0.01 (s, 9H); MS (ES+) m/z 483.2 (M+1).

Step 3. Preparation of tert-butyl (S)-3-((5-fluoro-4-(N-(isothiazol-4-yl)-N-((2-(trimethylsilyl)ethoxy)methyl)sulfamoyl)-2-methylphenyl)amino)pyrrolidine-1-carboxylate Step 4. Preparation of tert-butyl (S)-3-((5-fluoro-4-(N-(isothiazol-4-yl)-N-((2-(trimethylsilyl)ethoxy)methyl)sulfamoyl)-2-methylphenyl)(methyl)amino)pyrrolidine-1-carboxylate

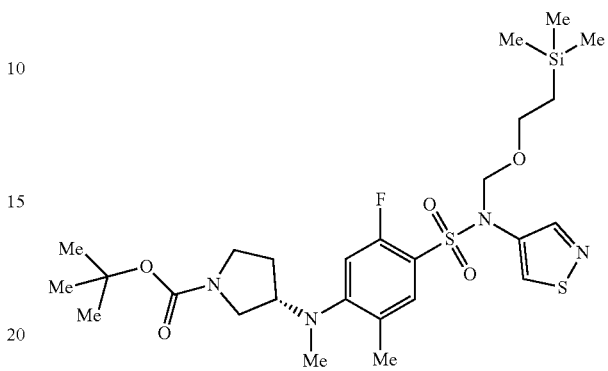

Following the procedure as described for EXAMPLE 296, Step 4 and making non-critical variations as required to replace (S)-tert-butyl 3-((4-(N-(2,4-dimethoxybenzyl)-N-(1,2,4-thiadiazol-5-yl)sulfamoyl)-3,5-difluoro-2-methylphenyl)amino)pyrrolidine-1-carboxylate with tert-butyl (S)-3-((5-fluoro-4-(N-(isothiazol-4-yl)-N-((2-(trimethylsilyl)ethoxy)methyl)sulfamoyl)-2-methyl phenyl)amino)pyrrolidine-1-carboxylate the title compound was obtained as a yellow oil (0.2 g, 48% yield): $^1$H NMR (400 MHz, CDCl$_3$) δ 8.48 (br s, 1H), 8.38 (s, 1H), 7.52 (br d, J=8.2 Hz, 1H), 6.78 (d, J=12.2 Hz, 1H), 5.16 (s, 2H), 3.77 (br d, J=6.1 Hz, 1H), 3.74-3.68 (m, 2H), 3.66-3.45 (m, 2H), 3.38-3.16 (m, 2H), 2.67 (s, 3H), 2.23 (s, 3H), 2.04-1.88 (m, 2H), 1.47 (s, 9H), 0.97-0.89 (m, 2H), 0.03-0.01 (m, 9H).

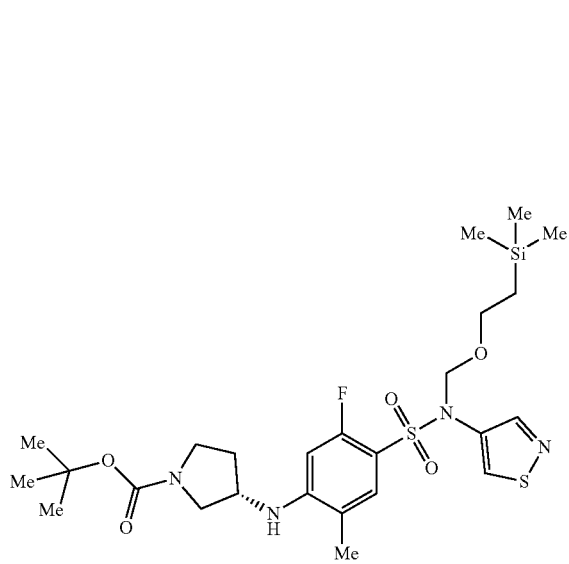 [SMILES: Cc1cc(S(=O)(=O)N(COCC[Si](C)(C)C)c2cnsc2)c(F)cc1N[C@H]1CCN(C(=O)OC(C)(C)C)C1]

To a solution of 4-bromo-2-fluoro-N-(isothiazol-4-yl)-5-methyl-N-((2-(trimethylsilyl)ethoxy)methyl)benzenesulfonamide (1.13 g, 2.34 mmol) in anhydrous toluene (1 mL) was added (S)-tert-butyl 3-aminopyrrolidine-1-carboxylate (0.48 g, 2.6 mmol), bis(dibenzylideneacetone)palladium (0.27 g, 0.47 mmol), cesium carbonate (2.29 g, 7.03 mmol), and 4,5-bis(diphenylphosphino)-9,9-dimethylxanthene (0.27 g, 0.47 mmol). The mixture was degassed by sparging with nitrogen and then heated to 80° C. for 12 h. After cooling to ambient temperature, the mixture was diluted with saturated ammonium chloride (20 mL) and extracted with ethyl acetate (3×20 mL). The combined organic extracts were washed with brine (3×20 mL), dried over anhydrous sodium sulfate, and filtered. Concentration of the filtrate in vacuo and purification of the residue by column chromatography, eluting with a gradient of 9-33% of ethyl acetate in petroleum ether, afforded the title compound as a yellow oil (1.0 g, 72% yield): $^1$H NMR (400 MHz, CDCl$_3$) δ 8.47 (s, 1H), 8.38 (s, 1H), 7.36 (br d, J=8.1 Hz, 1H), 6.28 (d, J=13.0 Hz, 1H), 5.16 (br s, 2H), 4.17-4.11 (m, 2H), 4.03 (br s, 1H), 3.82-3.63 (m, 3H), 3.51 (br s, 2H), 3.40-3.18 (m, 1H), 2.30-2.21 (m, 1H), 1.49 (s, 9H), 1.28 (dd, J=7.2 Hz, 2H), 0.97-0.88 (m, 2H), 0.02 (s, 9H), NH not observed; MS (ES+) m/z 610.9 (M+23).

Step 5. Preparation of (S)-2-fluoro-N-(isothiazol-4-yl)-5-methyl-4-(methyl(pyrrolidin-3-yl)amino)benzenesulfonamide

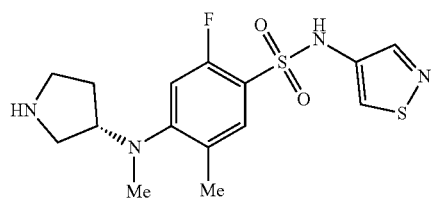 [SMILES: Cc1cc(S(=O)(=O)Nc2cnsc2)c(F)cc1N(C)[C@H]1CCNC1]

Following the procedure as described for EXAMPLE 295, Step 3 and making non-critical variations as required to replace (S)-4-((1-benzylpyrrolidin-3-yl)(methyl)amino)-N-(2,4-dimethoxybenzyl)-2,6-difluoro-3-methyl-N-(1,2,4-thiadiazol-5-yl)benzenesulfonamide with tert-butyl (S)-3-((5-fluoro-4-(N-(isothiazol-4-yl)-N-((2-(trimethylsilyl)ethoxy)methyl)sulfamoyl)-2-methylphenyl)(methyl)amino)pyrrolidine-1-carboxylate the title compound was obtained as an yellow oil (0.1 g, 58% yield): MS (ES+) m/z 371.1 (M+1).

Step 6. Preparation of (S)-4-((1-benzylpyrrolidin-3-yl)(methyl)amino)-2-fluoro-N-(isothiazol-4-yl)-5-methylbenzenesulfonamide Formate

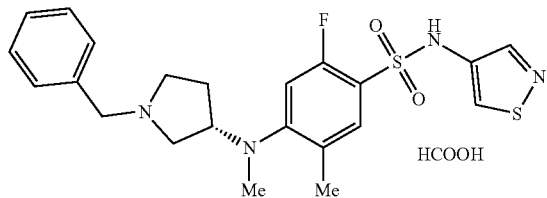 [SMILES: Cc1cc(S(=O)(=O)Nc2cnsc2)c(F)cc1N(C)[C@H]1CCN(Cc2ccccc2)C1 ; "HCOOH"]

To a solution of (S)-2-fluoro-N-(isothiazol-4-yl)-5-methyl-4-(methyl(pyrrolidin-3-yl)amino)benzenesulfonamide (0.08 g, 0.22 mmol) in anhydrous tetrahydrofuran (3 mL) was added benzaldehyde (0.023 g, 0.22 mmol) and acetic acid (0.039 g, 0.65 mmol), and the mixture was stirred at ambient temperature for 30 minutes. Sodium triacetoxyborohydride (0.091 g, 0.43 mmol) was then added and the mixture was stirred at ambient temperature for 12 h. Concentration in vacuo and purification of the residue by preparative reverse phase HPLC, using acetonitrile in water containing 0.225% of formic acid as eluent, afforded the title compound as a colorless solid (0.053 g, 46% yield): $^1$H NMR (400 MHz, CDCl$_3$) δ 8.43 (s, 1H), 8.33 (s, 1H), 8.29 (s, 1H), 7.56 (d, J=8.3 Hz, 1H), 7.39 (s, 5H), 6.77 (d, J=12.0 Hz, 1H), 4.15-3.98 (m, 3H), 3.37 (br dd, J=10.8, 7.7 Hz, 1H), 3.18-3.00 (m, 2H), 2.94 (br dd, J=10.6, 6.6 Hz, 1H), 2.63 (s, 3H), 2.29-2.21 (m, 1H), 2.20 (s, 3H), 1.98 (qd, J=13.8, 6.9 Hz, 1H), NH and COOH not observed; MS (ES+) m/z 461.3 (M+1).

Example 308

Synthesis of (S)-4-((1-benzylpyrrolidin-3-yl)(methyl)amino)-2-fluoro-N-(6-fluoropyridin-2-yl)-5-methylbenzenesulfonamide

Step 1. Preparation of 4-bromo-N-(2,4-dimethoxybenzyl)-2-fluoro-N-(6-fluoropyridin-2-yl)-5-methylbenzenesulfonamide

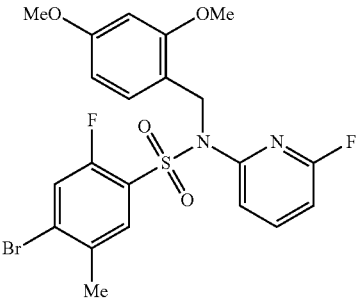 [SMILES: COc1ccc(CN(c2cccc(F)n2)S(=O)(=O)c2cc(C)c(Br)cc2F)c(OC)c1]

Following the procedure as described for EXAMPLE 306, Step 2 and making non-critical variations as required to N-(2,4-dimethoxybenzyl)-5-fluoropyridin-2-amine with N-(2,4-dimethoxybenzyl)-6-fluoropyridin-2-amine the title compound was obtained as a yellow solid (0.550 g, 94% yield): $^1$H NMR (400 MHz, CDCl$_3$) 97.78 (d, J=7.2 Hz, 1H), 7.70 (q, J=8.0 Hz, 1H), 7.38 (d, J=9.6 Hz, 1H), 7.27-7.21 (m, 2H), 6.69 (dd, J=7.6, 3.2 Hz, 1H), 6.42-6.37 (m, 2H), 5.06 (s, 2H), 3.78 (s, 3H), 3.73 (s, 3H), 2.42 (s, 3H).

Step 2. Preparation of tert-butyl (S)-3-((4-(N-(2,4-dimethoxybenzyl)-N-(6-fluoropyridin-2-yl)sulfamoyl)-5-fluoro-2-methylphenyl)amino)pyrrolidine-1-carboxylate Following the procedure as described for EXAMPLE 307, Step 3 and making non-critical variations as required to replace 4-bromo-2-fluoro-N-(isothiazol-4-yl)-5-methyl-N-((2-(trimethylsilyl)ethoxy)methyl)benzenesulfonamide with 4-bromo-N-(2,4-dimethoxybenzyl)-2-fluoro-N-(6-fluoropyridin-2-yl)-5-methylbenzenesulfonamide the title compound was obtained as a yellow oil (0.514 g, 94% yield): $^1$H NMR (400 MHz, CDCl$_3$) δ 7.68 (q, J=8.0 Hz, 1H), 7.54 (d, J=8.0 Hz, 1H), 7.33 (br d, J=8.0 Hz, 1H), 7.29 (br s, 1H), 6.63 (dd, J=7.6, 3.2 Hz, 1H), 6.43-6.34 (m, 2H), 6.27 (d, J=12.8 Hz, 1H), 5.08 (s, 2H), 4.16-4.01 (m, 2H), 3.77 (s, 3H), 3.75 (s, 3H), 3.60-3.40 (m, 2H), 3.39-3.14 (m, 1H), 2.34-2.19 (m, 1H), 2.09 (s, 3H), 1.96 (br s, 1H), 1.62 (s, 9H), NH not observed; MS (ES+) m/z 519.0 (M−99).

Step 3. Preparation of tert-butyl (S)-3-((4-(N-(2,4-dimethoxybenzyl)-N-(6-fluoropyridin-2-yl)sulfamoyl)-5-fluoro-2-methylphenyl)(methyl)amino)pyrrolidine-1-carboxylate

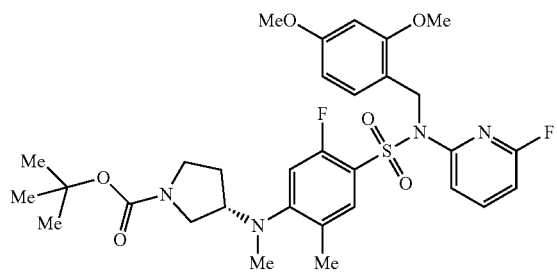 [SMILES: COc1ccc(CN(c2cccc(F)n2)S(=O)(=O)c2cc(C)c(N(C)[C@H]3CCN(C(=O)OC(C)(C)C)C3)cc2F)c(OC)c1]

Following the procedure as described for EXAMPLE 296, Step 4 and making non-critical variations as required to replace (S)-tert-butyl 3-((4-(N-(2,4-dimethoxybenzyl)-N-(1,2,4-thiadiazol-5-yl)sulfamoyl)-3,5-difluoro-2-methylphenyl)amino)pyrrolidine-1-carboxylate tert-butyl (S)-3-((4-(N-(2,4-dimethoxybenzyl)-N-(6-fluoropyridin-2-yl)sulfamoyl)-5-fluoro-2-methylphenyl)amino)pyrrolidine-1-carboxylate the title compound was obtained as a yellow oil (0.520 g, 91% yield): $^1$H NMR (400 MHz, CDCl$_3$) δ 7.68 (dd, J=8.4, 5.6 Hz, 2H), 7.34-7.29 (m, 2H), 6.77 (d, J=11.6 Hz, 1H), 6.66 (dd, J=8.0, 2.8 Hz, 1H), 6.42-6.36 (m, 2H), 5.08 (s, 2H), 3.77 (s, 3H), 3.73 (s, 3H), 3.49-3.61 (m, 2H), 3.31 (br d, J=8.4 Hz, 2H), 2.67 (s, 3H), 2.27 (s, 3H), 2.04-1.88 (m, 3H), 1.48 (s, 9H). MS (ES+) m/z 655.0 (M+23).

Step 4. Preparation of (S)-2-fluoro-N-(6-fluoropyridin-2-yl)-5-methyl-4-(methyl(pyrrolidin-3-yl)amino)benzenesulfonamide

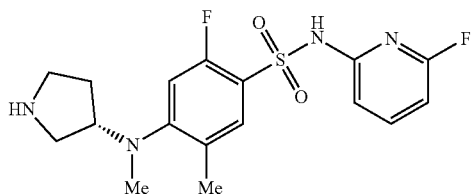 [SMILES: Cc1cc(S(=O)(=O)Nc2cccc(F)n2)c(F)cc1N(C)[C@H]1CCNC1]

To tert-butyl (S)-3-((4-(N-(2,4-dimethoxybenzyl)-N-(6-fluoropyridin-2-yl)sulfamoyl)-5-fluoro-2-methylphenyl)(methyl)amino)pyrrolidine-1-carboxylate (0.320 g, 0.506 mmol) was added a 4 M solution of hydrogen chloride in dioxane (4.0 mL, 16.0 mmol) and the mixture was stirred at ambient temperature for 2 h. Water (30 mL) was added and the mixture was extracted with ethyl acetate (3×30 mL). The combined organic extracts were washed with brine (3×30 mL), dried over anhydrous sodium sulfate, and filtered. Concentration of the filtrate in vacuo and purification of the residue by preparative reverse phase HPLC, using acetonitrile in water containing 0.225% of formic acid as eluent, afforded the title compound as a colorless solid (0.140 g, 72% yield): $^1$H NMR (400 MHz, CDCl$_3$) δ 8.44 (s, 1H), 7.74 (d, J=8.0 Hz, 1H), 7.63 (q, J=8.0 Hz, 1H), 7.09-7.05 (m, 1H), 6.76 (d, J=12.0 Hz, 1H), 6.51 (dd, J=8.0, 2.4 Hz, 1H), 4.04-3.94 (m, 1H), 3.47-3.33 (m, 3H), 3.09 (br dd, J=12.0, 6.4 Hz, 1H), 2.63 (s, 3H), 2.26 (s, 3H), 2.23-2.15 (m, 2H), one NH not observed.

Step 5. Preparation of (S)-4-((1-benzylpyrrolidin-3-yl)(methyl)amino)-2-fluoro-N-(6-fluoropyridin-2-yl)-5-methylbenzenesulfonamide

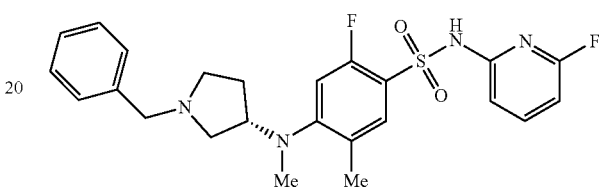

To a solution of (S)-2-fluoro-N-(6-fluoropyridin-2-yl)-5-methyl-4(methyl(pyrrolidin-3-yl) amino)benzenesulfonamide (0.070 g, 0.18 mmol), benzaldehyde (0.023 g, 0.22 mmol) and acetic acid (0.0003 g, 0.005 mmol) in methanol (3 mL) was added sodium cyanoborohydride (0.0230 g, 0.366 mmol) and the reaction mixture was stirred at ambient temperature for 12 h. The mixture was concentrated under reduced pressure to give a residue. Purification of the residue by preparative reverse phase HPLC, eluting with a gradient of 5-60% of acetonitrile in water containing 0.05% of ammonium hydroxide, afforded the title compound as a colorless solid (0.251 g, 29% yield): $^1$H NMR (400 MHz, CDCl$_3$) δ 7.71-7.62 (m, 2H), 7.36-7.30 (m, 4H), 7.28-7.25 (m, 1H), 7.16 (dd, J=8.0, 1.6 Hz, 1H), 6.65 (d, J=12.8 Hz, 1H), 6.56 (dd, J=8.0, 2.4 Hz, 1H), 3.98-3.85 (m, 1H), 3.76-3.66 (m, 1H), 3.56 (d, J=12.8 Hz, 1H), 2.79-2.72 (m, 1H), 2.70 (s, 3H), 2.69-2.59 (m, 2H), 2.58-2.51 (m, 1H), 2.25 (s, 3H), 2.13-2.02 (m, 1H), 1.90-1.80 (m, 1H), NH not observed; MS (ES+) m/z 473.2 (M+1).

Example 309

Synthesis of rac-4-(((2R,3R)-1-benzyl-2-methylpyrrolidin-3-yl)(methyl)amino)-5-chloro-2-fluoro-N-(thiazol-4-yl)benzenesulfonamide

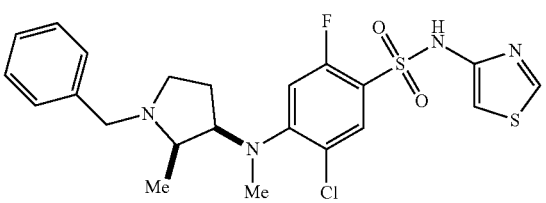 [SMILES: C[C@@H]1[C@H](N(C)c2cc(F)c(S(=O)(=O)Nc3cscn3)cc2Cl)CCN1Cc1ccccc1]

Step 1. Preparation of rac-tert-butyl (2R,3R)-3-((2-chloro-4-(N-(2,4-dimethoxybenzyl)-N-(thiazol-4-yl)sulfamoyl)-5-fluorophenyl)amino)-2-methylpyrrolidine-1-carboxylate

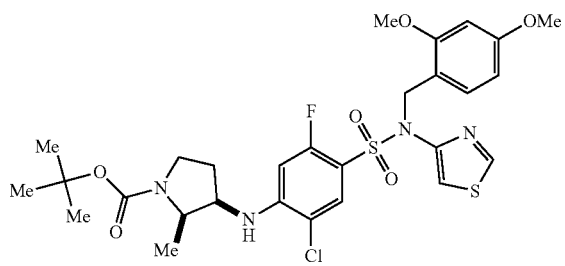 [SMILES: COc1ccc(CN(c2cscn2)S(=O)(=O)c2cc(Cl)c(N[C@@H]3CCN(C(=O)OC(C)(C)C)[C@@H]3C)cc2F)c(OC)c1]

To a suspension of 5-chloro-N-(2,4-dimethoxybenzyl)-2,4-difluoro-N-(thiazol-4-yl)benzenesulfonamide (1.04 g, 2.35 mmol) and cis-3-amino-1-Boc-2-methylpyrrolidine (0.470 g, 2.35 mmol) in anhydrous dimethylsulfoxide (10 mL) was added potassium carbonate (0.974 g, 7.05 mmol). The reaction mixture was stirred at ambient temperature for 18 hours, and then heated to 50° C. for 2 hours. The reaction mixture was cooled to ambient temperature, diluted with ethyl acetate (50 mL) and water (20 mL) and the layers were separated. The aqueous phase was extracted with ethyl acetate (2×50 mL). The combined organic phase was washed with brine (3×20 mL), dried over anhydrous sodium sulfate, and filtered. Concentration of the filtrate in vacuo and purification of the residue by column chromatography, eluting with a gradient of 0-50% of ethyl acetate in hexanes, provided the title compound as a yellowish foam (0.556 g, 37% yield): MS (ES+) m/z 641.2 (M+1), 643.5 (M+1).

Step 2. Preparation rac-tert-butyl (2R,3R)-3-((2-chloro-4-(N-(2,4-dimethoxybenzyl)-N-(thiazol-4-yl)sulfamoyl)-5-fluorophenyl)(methyl)amino)-2-methylpyrrolidine-1-carboxylate

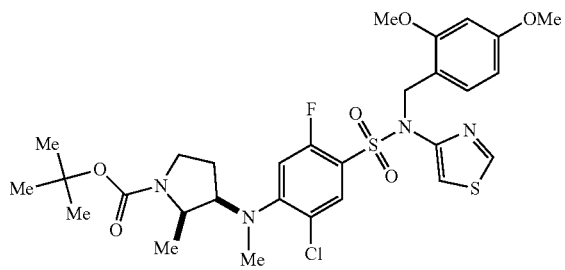 [SMILES: COc1ccc(CN(c2cscn2)S(=O)(=O)c2cc(Cl)c(N(C)[C@@H]3CCN(C(=O)OC(C)(C)C)[C@@H]3C)cc2F)c(OC)c1]

To a solution of rac-tert-butyl (2R,3R)-3-((2-chloro-4-(N-(2,4-dimethoxybenzyl)-N-(thiazol-4-yl)sulfamoyl)-5-fluorophenyl)amino)-2-methylpyrrolidine-1-carboxylate (0.377 g, 0.588 mmol) and methyl iodide (0.040 mL, 0.70 mmol) in anhydrous N,N-dimethylformamide (6 mL) was added a 60% dispersion of sodium hydride in mineral oil (0.035 g, 0.88 mmol) at 0° C. The resulting mixture was warmed to ambient temperature, stirred for 2 hours and then quenched by slow addition to water (100 mL). Filtration of the resulting suspension provided the title compound as a yellowish solid (0.458 g) which was dried in vacuo and used without further purification: MS (ES+) m/z 655.3 (M+1), 667.3 (M+1).

Step 3. Preparation of rac-5-chloro-2-fluoro-4-(((2R,3R)-2-methylpyrrolidin-3-yl)amino)-N-(thiazol-4-yl)benzenesulfonamide 2,2,2-trifluoroacetate To a cooled (0° C.) solution of rac-tert-butyl (2R,3R)-3-((2-chloro-4-(N-(2,4-dimethoxybenzyl)-N-(thiazol-4-yl)sulfamoyl)-5-fluorophenyl)(methyl)amino)-2-methylpyrrolidine-1-carboxylate (0.458 g, 0.588 mmol) in dichloromethane (7 mL) was added trifluoroacetic acid (1.4 mL, 18.3 mmol). The reaction was allowed to warm to ambient temperature and stirred for 16 h. The reaction mixture was concentrated and the residue triturated with methanol (30 mL). The precipitate was removed by filtration and the filter residue rinsed with methanol (2×25 mL). The combined filtrate was concentrated in vacuo to yield the title compound as a yellow oil (0.340 g) which was used without further purification: MS (ES+) m/z 405.1 (M+1), 407.1 (M+1).

Step 4. Preparation of rac-4-(((2R,3R)-1-benzyl-2-methylpyrrolidin-3-yl)(methyl)amino)-5-chloro-2-fluoro-N-(thiazol-4-yl)benzenesulfonamide To a solution of rac-5-chloro-2-fluoro-4-(((2R,3R)-2-methylpyrrolidin-3-yl)amino)-N-(thiazol-4-yl)benzenesulfonamide 2,2,2-trifluoroacetate (0.340 g, 0.588 mmol) in anhydrous 1,2-dichloroethane (3 mL) and anhydrous N,N-dimethylformamide (3 mL) was added benzaldehyde (0.178 mL, 1.76 mmol). After 15 minutes, sodium triacetoxyborohydride (0.373 g, 1.76 mmol) was added and the reaction was stirred at ambient temperature for 16 hours. The reaction mixture was diluted with ethyl acetate (50 mL) and washed with brine (2×25 mL). The combined aqueous layers were extracted with ethyl acetate (3×75 mL). The combined organic layers were dried over anhydrous sodium sulfate and filtered. Concentration of the filtrate in vacuo and purification of the residue by column chromatography, eluting with a gradient of 0-5% of methanol (containing 2% of ammonium hydroxide) in dichloromethane, provided the title compound as a colourless solid (0.119 g, 41% yield) $^1$H NMR (300 MHz, DMSO-$d_6$) $\delta$ 11.13-11.06 (m, 1H), 8.91 (d, J=2.2 Hz, 1H), 7.69 (d, J=7.7 Hz, 1H), 7.37-7.28 (m, 5H), 7.16 (s, 1H), 7.06 (d, J=2.2 Hz, 1H), 4.32-4.25 (m, 1H), 4.13-4.07 (m, 1H), 3.37-3.24 (m, 2H), 2.98-2.82 (m, 4H), 2.04-1.83 (m, 3H), 1.19-1.17 (m, 3H); MS (ES+) m/z 495.1 (M+1), 497.1 (M+1).

Example 310

Synthesis of rac-4-((1-benzyl-3-methylpyrrolidin-3-yl)oxy)-5-chloro-2-fluoro-N-(thiazol-4-yl)benzenesulfonamide

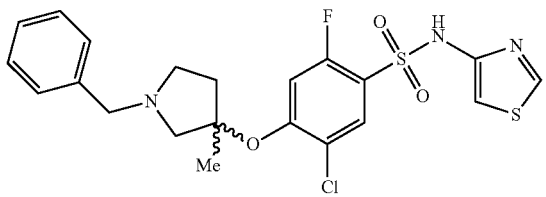

Step 1. Preparation of rac-tert-butyl 3-hydroxy-3-methylpyrrolidine-1-carboxylate

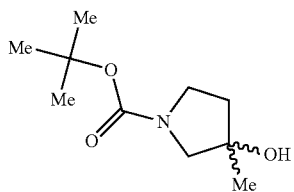

To a cooled (0° C.) solution of tert-butyl 3-oxopyrrolidine-1-carboxylate (0.975 g, 5.26 mmol) in anhydrous diethyl ether (20 mL)) was added a 3 M solution of methylmagnesium bromide in diethyl ether (3.50 mL, 10.53 mmol). The reaction was allowed to warm to ambient temperature, stirred for 1 hour, and then cooled to 0° C. and quenched by addition of saturated aqueous ammonium chloride (15 mL). The aqueous layer was separated and extracted with ethyl acetate (3×100 mL). The combined organic phases were washed with brine (50 mL), dried with magnesium sulfate, and filtered. Concentration of the filtrate in vacuo and purification of the residue by column chromatography, eluting with a gradient of 0-40% of ethyl acetate in hexanes, provided the title compound as a yellowish oil (0.735 g, 69% yield) $^1$H NMR (300 MHz, CDCl$_3$) δ 3.54-3.44 (m, 2H), 3.42-3.33 (m, 1H), 3.28-3.20 (m, 1H), 1.93-1.79 (m, 2H), 1.60-1.56 (m, 1H), 1.46 (s, 9H), 1.42 (s, 3H); MS (ES+) m/z 202.3 (M+1).

Step 2. Preparation of rac-tert-butyl 3-(2-chloro-4-(N-(2,4-dimethoxybenzyl)-N-(thiazol-4-yl)sulfamoyl)-5-fluorophenoxy)-3-methylpyrrolidine-1-carboxylate

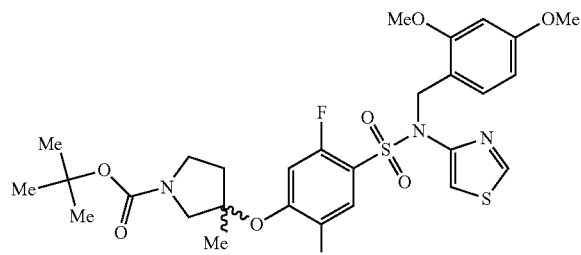

To a solution of 5-chloro-N-(2,4-dimethoxybenzyl)-2,4-difluoro-N-(thiazol-4-yl)benzenesulfonamide (0.500 g, 1.13 mmol) and tert-butyl 3-hydroxy-3-methylpyrrolidine-1-carboxylate (0.250 g, 1.24 mmol) in anhydrous N,N-dimethylformamide (8 mL) was added a dispersion of 60% of sodium hydride in mineral oil (0.185 g, 4.62 mmol) and the reaction mixture was stirred at ambient temperature for 2 hours. The reaction mixture was then added slowly to rapidly stirred saturated aqueous ammonium chloride (150 mL). The resulting slurry was filtered and the obtained precipitate was purified by column chromatography, eluting with a gradient of 0-60% of ethyl acetate in hexanes, to give the title compound as a pale yellow solid (0.323 g, 45% yield): MS (ES+) m/z 664.3 (M+23), 666.3 (M+23).

Step 3. Preparation of Rac-5-chloro-2-fluoro-4-((3-methylpyrrolidin-3-yl)oxy)-N-(thiazol-4-yl)benzenesulfonamide 2,2,2-trifluoroacetate

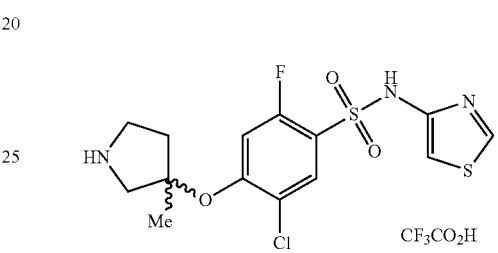

To a solution of rac-tert-butyl 3-(2-chloro-4-(N-(2,4-dimethoxybenzyl)-N-(thiazol-4-yl)sulfamoyl)-5-fluorophenoxy)-3-methylpyrrolidine-1-carboxylate (0.323 g, 0.503 mmol) in dichloromethane (6 mL) was added trifluoroacetic acid (0.554 mL, 7.23 mmol). The reaction mixture was stirred at ambient temperature for 3 h. The reaction mixture was concentrated and the residue was triturated with methanol (10 mL). The precipitate was removed by filtration and rinsed with methanol (2×15 mL). The combined filtrate was concentrated in vacuo to yield the title compound as yellow foam (0.364 g, quantitative yield) which was used without further purification.

Step 4. Preparation of rac-4-((1-benzyl-3-methylpyrrolidin-3-yl)oxy)-5-chloro-2-fluoro-N-(thiazol-4-yl)benzenesulfonamide

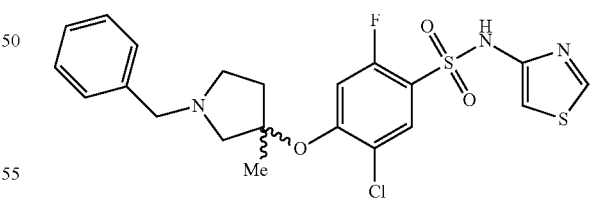

To a solution of rac-5-chloro-2-fluoro-4-((3-methylpyrrolidin-3-yl)oxy)-N-(thiazol-4-yl)benzenesulfonamide 2,2,2-trifluoroacetate (0.364 g) in anhydrous 1,2-dichloroethane (4 mL) and N,N-dimethylformamide (4 mL) was added benzaldehyde (0.218 mL, 2.16 mmol). After 15 minutes, sodium triacetoxyborohydride (0.457 g, 2.16 mmol) was added to it and the reaction was stirred at ambient temperature for 16 h. The reaction mixture was diluted with ethyl acetate (75 mL) and washed with brine (2×50 mL). The combined aqueous layers were extracted with ethyl acetate (3×100 mL). The combined organic phase were dried over sodium sulfate, filtered and the filtrate concentrated in vacuo. Purification of the residue by column chromatography, eluting with a gradient of 0-5% methanol (containing 2% of ammonium hydroxide) in dichloromethane, provided the title compound as a pale yellow solid (0.100 g, 41% yield): $^1$H NMR (300 MHz, DMSO-d$_6$) δ 11.39-11.34 (m, 1H), 8.91 (d, J=2.2 Hz, 1H), 7.79 (d, J=7.6 Hz, 1H), 7.59 (d, J=12.3 Hz, 1H), 7.33-7.23 (m, 5H), 7.05 (d, J=2.2 Hz, 1H), 3.67-3.54 (m, 2H), 3.00-2.96 (m, 1H), 2.81-2.75 (m, 1H), 2.64-2.61 (m, 1H), 2.56-2.52 (m, 1H), 2.31-2.21 (m, 1H), 2.09-2.02 (m, 1H), 1.56 (s, 3H); MS (ES+) m/z 482.1 (M+1), 484.1 (M+1).

Example 311A and 311B

Synthesis of (S)-4-((1-benzyl-3-methylpyrrolidin-3-yl)oxy)-5-chloro-2-fluoro-N-(thiazol-4-yl)benzenesulfonamide and (R)-4-((1-benzyl-3-methylpyrrolidin-3-yl)oxy)-5-chloro-2-fluoro-N-(thiazol-4-yl)benzenesulfonamide

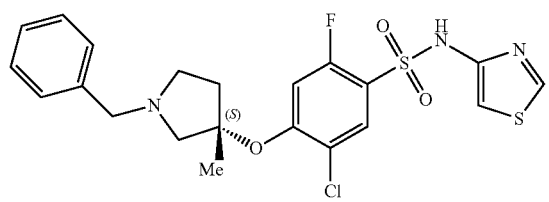

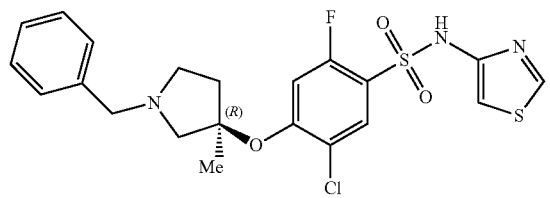

Resolution of rac-4-((1-benzyl-3-methylpyrrolidin-3-yl)oxy)-5-chloro-2-fluoro-N-(thiazol-4-yl)benzenesulfonamide (0.090 g) by supercritical fluid chromatography, using 30% of ethanol (containing 0.1% of ammonium hydroxide) in supercritical carbon dioxide as eluent and a Chiralcel AS-H column (250×25 mm, 10 μm), provided (S)-4-((1-benzyl-3-methylpyrrolidin-3-yl)oxy)-5-chloro-2-fluoro-N-(thiazol-4-yl)benzenesulfonamide (0.030 g, 97% ee) as the first eluting enantiomer and (R)-4-((1-benzyl-3-methylpyrrolidin-3-yl)oxy)-5-chloro-2-fluoro-N-(thiazol-4-yl)benzenesulfonamide (0.036 g, 96% ee) and as the second enantiomer. The absolute configuration was arbitrarily assigned. Data for (R)-4-((1-benzyl-3-methylpyrrolidin-3-yl)oxy)-5-chloro-2-fluoro-N-(thiazol-4-yl)benzenesulfonamide:
$^1$H-NMR (400 MHz, CDCl$_3$) δ 8.65 (d, J=2.2 Hz, 1H), 7.86 (d, J=7.6 Hz, 1H), 7.46 (d, J=12.0 Hz, 1H), 7.35-7.31 (m, 4H), 7.30-7.24 (m, 1H), 7.03 (d, J=2.3 Hz, 1H), 3.70 (d, J=12.9 Hz, 1H), 3.60 (d, J=13.8 Hz, 1H), 3.09 (d, J=10.5 Hz, 1H), 2.98-2.90 (m, 1H), 2.64-2.54 (m, 2H), 2.47-2.37 (m, 1H), 2.01-1.92 (m, 1H), 1.62 (s, 3H), NH not observed; MS (ES+) m/z 481.9 (M+1), 483.9 (M+1).

Example 312

Synthesis of (S)-4-((1-benzylpyrrolidin-3-yl)(ethyl)amino)-2-fluoro-5-methyl-N-(thiazol-4-yl)benzenesulfonamide 2,2,2-trifluoroacetate

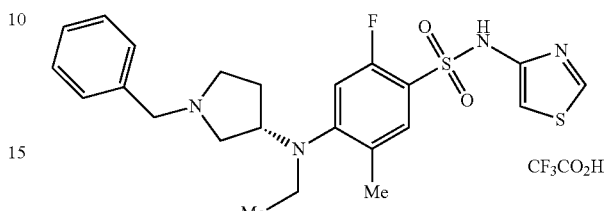

Step 1. Preparation of tert-butyl (S)-3-((4-(N-(tert-butoxycarbonyl)-N-(thiazol-4-yl)sulfamoyl)-5-fluoro-2-methylphenyl)(ethyl)amino)pyrrolidine-1-carboxylate

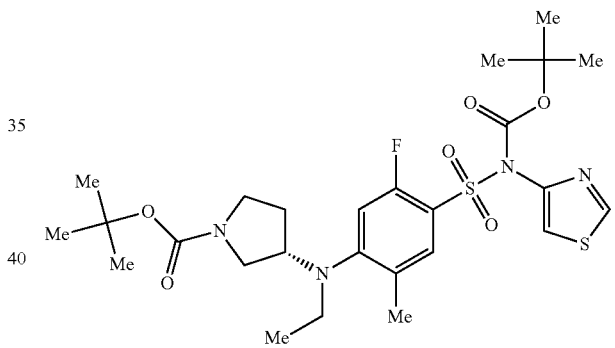

To a cooled (0° C.) solution of tert-butyl (S)-3-((4-(N-(tert-butoxycarbonyl)-N-(thiazol-4-yl)sulfamoyl)-5-fluoro-2-methylphenyl)amino)pyrrolidine-1-carboxylate (0.300 g, 0.539 mmol) in anhydrous N,N-dimethylformamide (6 mL) was added a 60% dispersion of sodium hydride in mineral oil (0.032 g, 0.808 mmol). The resulting suspension was stirred at 0° C. for 15 minutes before iodoethane (0.052 mL, 0.647 mmol) was added to it. The reaction mixture was allowed to warm to ambient temperature and stirred for 16 h. The reaction mixture was diluted with ethyl acetate (100 mL) and saturated aqueous ammonium chloride (50 mL) and the layers were separated. The aqueous phase was extracted with ethyl acetate (3×50 mL). The combined organic phase was washed with brine (3×20 mL), dried over anhydrous sodium sulfate, and filtered. Concentration of the filtrate in vacuo and purification of the residue by column chromatography, eluting with a gradient of 0-50% of ethyl acetate in hexanes, provided the title compound as a yellow oil (0.085 g, 27% yield): MS (ES+) m/z 585.3 (M+1).

Step 2. Preparation of (S)-4-(ethyl(pyrrolidin-3-yl) amino)-2-fluoro-5-methyl-N-(thiazol-4-yl)benzenesulfonamide 2,2,2-trifluoroacetate

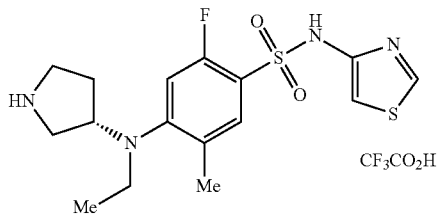 [SMILES: CCN(c1cc(F)c(S(=O)(=O)Nc2cscn2)cc1C)[C@H]1CCNC1 ; "CF3CO2H"]

To a solution of tert-butyl (S)-3-((4-(N-(tert-butoxycarbonyl)-N-(thiazol-4-yl)sulfamoyl)-5-fluoro-2-methylphenyl)(ethyl)amino)pyrrolidine-1-carboxylate (0.085 g, 0.145 mmol) in dichloromethane (2 mL) was added trifluoroacetic acid (1 mL) and the reaction mixture was stirred at ambient temperature for 16 h. Concentration in vacuo provided the title compound as a yellow oil (0.190 g, quantitative yield) which was used without further purification: MS (ES+) m/z 385.2 (M+1).

Step 3. (S)-4-((1-benzylpyrrolidin-3-yl)(ethyl) amino)-2-fluoro-5-methyl-N-(thiazol-4-yl)benzenesulfonamide 2,2,2-trifluoroacetate

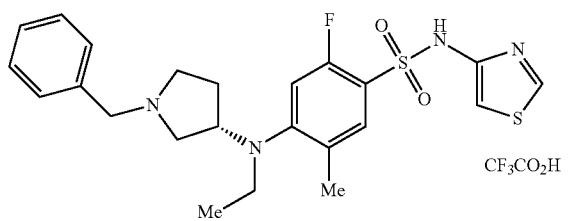 [SMILES: CCN(c1cc(F)c(S(=O)(=O)Nc2cscn2)cc1C)[C@H]1CCN(Cc2ccccc2)C1 ; "CF3CO2H"]

To a solution of (S)-4-(ethyl(pyrrolidin-3-yl)amino)-2-fluoro-5-methyl-N-(thiazol-4-yl)benzenesulfonamide 2,2,2-trifluoroacetate (0.190 g) in anhydrous 1,2-dichloroethane (3 mL) and anhydrous N,N-dimethylformamide (3 mL) was added benzaldehyde (0.115 mL, 1.14 mmol). After 15 minutes, sodium triacetoxyborohydride (0.242 g, 1.14 mmol) was added and the reaction mixture was stirred at ambient temperature for 16 h. The reaction mixture was diluted with ethyl acetate (50 mL) and washed with brine (2×25 mL). The combined aqueous layers were extracted with ethyl acetate (3×100 mL). The combined organic phase was dried over anhydrous sodium sulfate and filtered. Concentration of the filtrate in vacuo and purification of the residue by reverse-phase HPLC, eluting with a gradient of acetonitrile in water (containing 0.1% of trifluoroacetic acid) afforded the title compound as a pale yellow solid (0.037 g, 53% yield) $^1$H NMR (300 MHz, DMSO-$d_6$) δ 10.39-10.17 (m, 1H), 8.89 (d, J=2.2 Hz, 1H), 7.65 (d, J=8.6 Hz, 1H), 7.49-7.45 (m, 5H), 7.20 (d, J=12.2 Hz, 1H), 7.01 (d, J=2.2 Hz, 1H), 4.39-4.31 (m, 2H), 4.18 (td, J=1.4, 0.8 Hz, 1H), 3.95-3.94 (m, 1H), 3.60-3.03 (m, 5H), 2.25-2.15 (m, 3H), 2.08-1.81 (m, 2H), 0.79-0.77 (m, 3H), NH not observed; MS (ES+) m/z 475.1 (M+1), 476.1 (M+1).

Example 313

Synthesis of (R)-2,3-difluoro-4-((1-(1-phenylethyl) piperidin-4-yl)oxy)-N-(thiazol-4-yl)benzenesulfonamide Formate

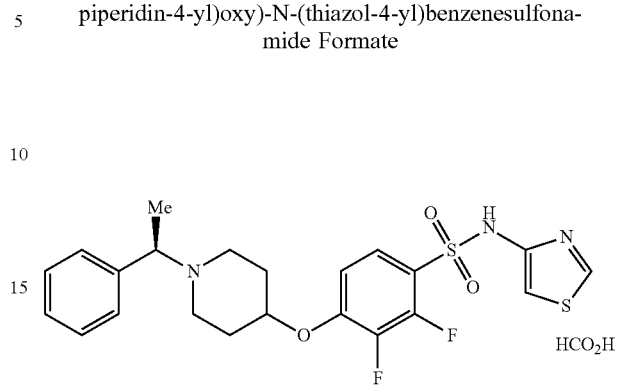

Step 1. Preparation of tert-butyl thiazol-4-yl((2,3,4-trifluorophenyl)sulfonyl)carbamate

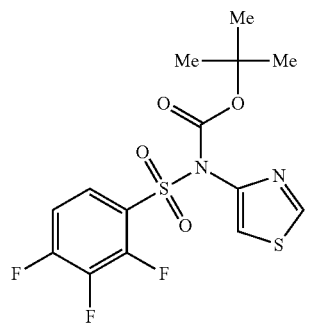 [SMILES: CC(C)(C)OC(=O)N(c1cscn1)S(=O)(=O)c1ccc(F)c(F)c1F]

To a cooled (−50° C.) solution of tert-butyl N-thiazol-4-ylcarbamate (2.87 g, 14.3 mmol) in tetrahydrofuran (50 mL) was added lithium bis(trimethylsilyl)amide (1 M in tetrahydrofuran, 14.3 mL, 14.3 mmol). The reaction mixture was allowed to warm to ambient temperature and stirred for 30 minutes. The resulting suspension was cooled to 0° C. and then added dropwise to a cooled (−78° C.) solution of 2,3,4-trifluorobenzenesulfonyl chloride (1.82 mL, 13.0 mmol) in tetrahydrofuran (60 mL). The reaction mixture was allowed to warm to ambient temperature and stirred for 16 h. The reaction mixture was then diluted with saturated aqueous ammonium chloride (50 mL) and extracted with ethyl acetate (3×100 mL). The combined organic layers were washed with brine (2×50 mL), dried over anhydrous sodium sulfate, and filtered. Concentration of the filtrate in vacuo and purification of the residue by column chromatography, eluting with a gradient of 0-30% of ethyl acetate in hexanes, provided the title compound as a colorless solid (4.34 g, 85% yield): MS (ES+) m/z 395.1 (M+1).

Step 2. Preparation of 2,3,4-trifluoro-N-(thiazol-4-yl)benzenesulfonamide

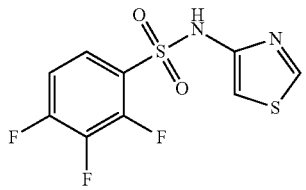 [SMILES: O=S(=O)(Nc1cscn1)c1ccc(F)c(F)c1F]

To a solution of tert-butyl thiazol-4-yl((2,3,4-trifluorophenyl)sulfonyl)carbamate (2.50 g, 6.34 mmol) in dichloromethane (13 mL) was added trifluoroacetic acid (3.88 mL, 50.7 mmol) and the reaction mixture was stirred at ambient temperature for 5 h. Concentration in vacuo and trituration of the residue in diethyl ether (25 mL) afforded the title compound as a pale yellow solid (1.68 g, 90% yield) which was used without further purification: MS (ES+) m/z 295.1 (M+1).

Step 3. Preparation of (R)-2,3-difluoro-4-((1-(1-phenylethyl)piperidin-4-yl)oxy)-N-(thiazol-4-yl)benzenesulfonamide Formate

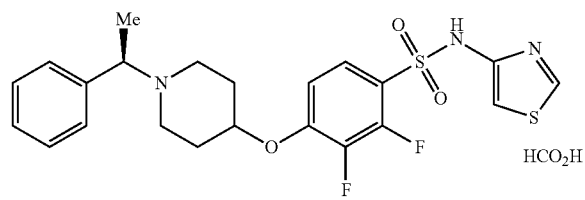 [SMILES: C[C@H](c1ccccc1)N1CCC(Oc2ccc(S(=O)(=O)Nc3cscn3)c(F)c2F)CC1 ; "HCO2H"]

To a solution of 2,3,4-trifluoro-N-(thiazol-4-yl)benzenesulfonamide (0.265 g, 0.901 mmol) and (R)-1-(1-phenylethyl)piperidin-4-ol (0.185 g, 0.901 mmol) in anhydrous N,N-dimethylformamide (4 mL) was added a dispersion of 60% of sodium hydride in mineral oil (0.108 g, 2.70 mmol) and the reaction mixture was stirred at ambient temperature for 16 h. The reaction mixture was then added slowly to rapidly stirred saturated aqueous ammonium chloride (150 mL). The resulting slurry was filtered and the obtained solid purified by reverse-phase HPLC, using a gradient of acetonitrile in water (containing 0.5% of formic acid) to yield the title compound as a colorless solid (0.023 g, % yield) $^1$H NMR (300 MHz, DMSO-d$_6$) δ 8.83 (d, J=2.2 Hz, 1H), 8.19 (s, 1H), 7.50 (td, J=8.5, 1.9 Hz, 1H), 7.35-7.13 (m, 6H), 6.88 (d, J=2.1 Hz, 1H), 4.55-4.47 (m, 1H), 3.55-3.48 (m, 1H), 2.75-2.61 (m, 2H), 2.23-2.17 (m, 2H), 1.95-1.89 (m, 2H), 1.70-1.55 (m, 2H), 1.30 (d, J=6.8 Hz, 3H), NH and COOH not observed; MS (ES+) m/z 480.3 (M+1).

Example 314

Synthesis of (S)-5-chloro-2-fluoro-4-((1-((3-fluoro-6-methylpyridin-2-yl)methyl)pyrrolidin-3-yl)(methyl)amino)-N-(thiazol-4-yl)benzenesulfonamide

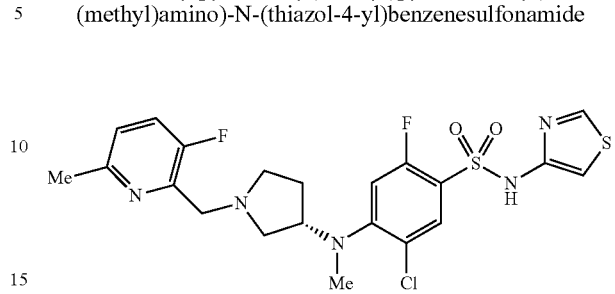

Step 1. Preparation of 3-fluoro-6-methylpicolinaldehyde

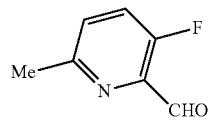

To a solution of 2-bromo-3-fluoro-6-methylpyridine (2.00 g, 10.53 mmol) in anhydrous tetrahydrofuran (35 mL) was added a 1.3 M solution of isopropylmagnesium chloride lithium chloride complex in tetrahydrofuran (16.20 mL, 21.06 mmol) at 0° C. The mixture was stirred at 0° C. for 5 h, then cooled to −42° C., and anhydrous N,N-dimethylformamide (3 mL) was added to it. The reaction mixture was stirred at −42° C. for 2 h and then diluted with ethyl acetate. The mixture was washed with saturated ammonium chloride (2×60 mL), brine (50 mL), dried over anhydrous sodium sulfate, and filtered. The filtrate was concentrated in vacuo to afford the title compound as a orange oil (1.47 g, quantitative yield): $^1$H NMR (300 MHz, CDCl$_3$) δ 10.18 (s, 1H), 7.50-7.38 (m, 2H), 2.63 (s, 3H); MS (ES+) m/z: 140.1 (M+1).

Step 2. Preparation of (S)-5-chloro-2-fluoro-4-((1-((3-fluoro-6-methylpyridin-2-yl)methyl)pyrrolidin-3-yl)(methyl)amino)-N-(thiazol-4-yl)benzenesulfonamide

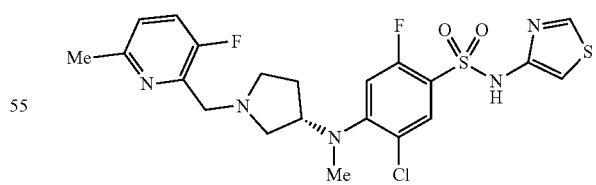

Following the procedure as described for EXAMPLE 160, Step 5 and making non-critical variations as required to replace 6-(difluoromethyl)picolinaldehyde with 3-fluoro-6-methylpicolinaldehyde, the title compound was obtained as a colorless solid (0.22 g, 43% yield): $^1$H NMR (300 MHz, DMSO-d$_6$) δ 10.97 (s, 1H), 8.89 (d, J=2.2 Hz, 1H), 7.68 (d, J=7.6 Hz, 1H), 7.53 (dd, J=9.7, 8.6 Hz, 1H), 7.21 (dd, J=8.4, 3.7 Hz, 1H), 7.07 (s, 1H), 7.00 (d, J=2.2 Hz, 1H), 4.20-4.11

(m, 1H), 3.76-3.64 (m, 2H), 2.77-2.67 (m, 6H), 2.47-2.39 (m, 4H), 2.08-1.99 (m, 1H), 1.80-1.68 (m, 1H); MS (ES+) m/z: 514.2 (M+1) 516.2 (M+1).

Example 315

Synthesis of (R)-3-chloro-4-((1-(1-(5-chloro-2-fluorophenyl)ethyl)piperidin-4-yl)oxy)-N-(thiazol-4-yl)benzenesulfonamide

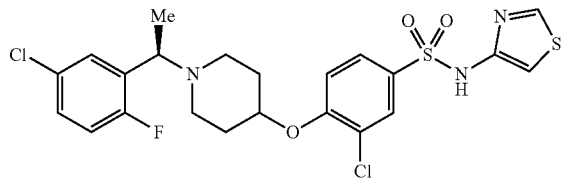 [SMILES: C[C@H](c1cc(Cl)ccc1F)N1CCC(Oc2ccc(S(=O)(=O)Nc3cscn3)cc2Cl)CC1]

Step 1. Preparation of (S,E)-N-(5-chloro-2-fluorobenzylidene)-2-methylpropane-2-sulfinamide

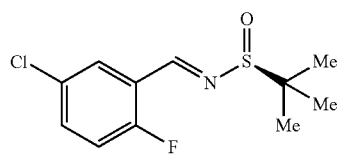 [SMILES: CC(C)(C)[S@](=O)/N=C/c1cc(Cl)ccc1F]

To a solution of (S)-2-methylpropane-2-sulfinamide (3.87 g, 31.91 mmol) and 5-chloro-2-fluorobenzaldehyde (4.60 g, 29.01 mmol) in anhydrous dichloromethane (100 mL) was added titanium(IV) isopropoxide (17.10 mL, 58.02 mmol). The mixture was stirred at ambient temperature for 18 h and then quended by slow addition of 2 M sodium hydroxide (80 mL). The resulting slurry was filtered and the filter cake was rinsed with dichloromethane (200 mL). The combined filtrate was concentrated in vacuo to afford the title compound as an orange solid (7.52 g, 99% yield): $^1$H NMR (300 MHz, CDCl$_3$) δ 8.83 (s, 1H), 7.97-7.94 (m, 1H), 7.48-7.42 (m, 1H), 7.15-7.09 (m, 1H), 1.28 (s, 9H).

Step 2. Preparation of (S)—N—((R)-1-(5-chloro-2-fluorophenyl)ethyl)-2-methylpropane-2-sulfinamide

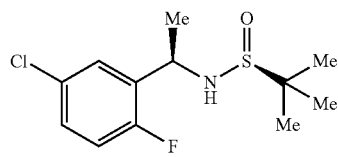 [SMILES: C[C@@H](N[S@@](=O)C(C)(C)C)c1cc(Cl)ccc1F]

To a solution of (S,E)-N-(5-chloro-2-fluorobenzylidene)-2-methylpropane-2-sulfinamide (3.14 g, 12.00 mmol) in anhydrous dichloromethane (45 mL) was added a 3.0 M solution of methylmagnesiumbromide in diethyl ether (5.20 mL, 15.60 mmol) at −78° C. The reaction mixture was stirred at −78° C. for 1 h and was then warmed to ambient temperature for 1 h. The reaction mixture was quenched with water (5 mL) and diluted with ethyl acetate (100 mL). The mixture was washed with saturated ammonium chloride (2×75 mL), brine (50 mL), dried over anhydrous sodium sulfate, and filtered. The filtrate was concentrated in vacuo and the residue purified by column chromatography, eluting with a gradient of 10 to 80% of ethyl acetate in hexanes, to afford the title compound as a colorless solid (2.38 g, 71% yield): $^1$H NMR (300 MHz, CDCl$_3$) δ 7.34 (dd, J=6.3, 2.7 Hz, 1H), 7.21 (ddd, J=8.7, 4.4, 2.7 Hz, 1H), 6.99 (dd, J=9.7, 8.8 Hz, 1H), 4.88-4.80 (m, 1H), 3.37 (d, J=4.4 Hz, 1H), 1.57 (d, J=6.8 Hz, 3H), 1.22 (s, 9H); MS (ES+) m/z: 287.2 (M+1), 280.2 (M+1).

Step 3. Preparation of (R)-1-(5-chloro-2-fluorophenyl)ethan-1-amine hydrochloride

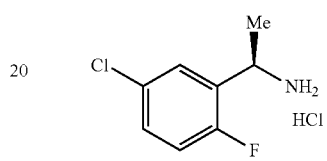

To a 4 M solution of hydrogen chloride in dioxane (10 mL) was added (S)—N—((R)-1-(5-chloro-2-fluorophenyl)ethyl)-2-methylpropane-2-sulfinamide (2.38 g, 8.57 mmol). The mixture was stirred at ambient temperature for 2 h and then concentrated in vacuo to afford the title compound as a colorless solid (1.80 g, quantitative yield): MS (ES+) m/z 174.2 (M+1), 176.2 (M+1).

Step 4. Preparation of (R)-1-(1-(5-chloro-2-fluorophenyl)ethyl)piperidin-4-one

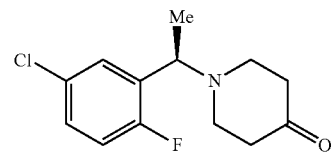 [SMILES: C[C@H](c1cc(Cl)ccc1F)N1CCC(=O)CC1]

To a mixture of (R)-1-(5-chloro-2-fluorophenyl)ethan-1-amine hydrochloride (2.54 g, 12.09 mmol) and 1-ethyl-1-methyl-4-oxopiperidin-1-ium iodide (3.25 g, 12.09 mmol) in ethanol (19 mL) and water (6 mL) was added potassium carbonate (1.84 g, 13.30 mmol) and the reaction mixture was heated to reflux for 3h. After cooling to ambient temperature, the reaction mixture was diluted with water (80 mL) and extracted with ethyl acetate (3×60 mL). The combined organic fractions were washed with brine (3×30 mL), dried over anhydrous sodium sulfate, and filtered. The filtrate was concentrated in vacuo to provide a residue, which was purified by column chromatography, eluting with a gradient of 0 to 5% of methanol (containing 0.1% ammonium hydroxide) in dichloromethane, to afford the title compound as a colorless solid (2.41 g, 78% yield): $^1$H NMR (300 MHz, CDCl$_3$) δ 7.43 (dd, J=6.2, 2.7 Hz, 1H), 7.19 (ddd, J=8.7, 4.5, 2.7 Hz, 1H), 6.98 (dd, J=9.5, 8.8 Hz, 1H), 4.01 (q, J=6.8 Hz, 1H), 2.74 (qd, J=11.4, 6.0 Hz, 4H), 2.44 (dd, J=7.0, 5.3 Hz, 4H), 1.41 (d, J=6.8 Hz, 3H); MS (ES+) m/z 256.1 (M+1), 258.1 (M+1).

Step 5. Preparation of (R)-1-(1-(5-chloro-2-fluoro-phenyl)ethyl)piperidin-4-ol

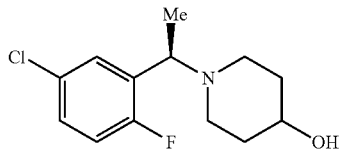 [SMILES: C[C@H](c1cc(Cl)ccc1F)N1CCC(O)CC1]

To a solution of (R)-1-(1-(5-chloro-2-fluorophenyl)ethyl)piperidin-4-one (2.41 g, 9.42 mmol) in anhydrous methanol (75 mL) was added sodium borohydride (0.36 g, 9.42 mmol) at 0° C. The mixture was stirred at 0° C. for 2 h, and then quenched with saturated ammonium hydroxide (50 mL). The mixture was concentrated in vacuo. The residue was diluted with 2 M sodium hydroxide (110 mL) and extracted with dichloromethane (3×80 mL). The combined organic layers were, washed with brine (80 mL), dried over anhydrous sodium sulfate, and filtered. The filtrate was concentrated in vacuo to afford the title compound as a colorless oil (2.32 g, 96% yield): $^1$H NMR (300 MHz, CDCl$_3$) δ 7.39 (dd, J=6.1, 2.7 Hz, 1H), 7.16 (ddd, J=8.7, 4.4, 2.7 Hz, 1H), 6.96 (dd, J=9.4, 8.8 Hz, 1H), 3.84 (q, J=6.8 Hz, 1H), 3.64 (tt, J=8.9, 4.4 Hz, 1H), 2.91-2.87 (m, 1H), 2.74-2.67 (m, 1H), 2.18-2.05 (m, 2H), 1.94-1.81 (m, 2H), 1.66-1.51 (m, 2H), 1.35 (d, J=6.8 Hz, 3H), OH not observed; MS (ES+) m/z 258.2 (M+1), 260.2 (M+1).

Step 6. Preparation of (R)-3-chloro-4-((1-(1-(5-chloro-2-fluorophenyl)ethyl)piperidin-4-yl)oxy)-N-(thiazol-4-yl)benzenesulfonamide

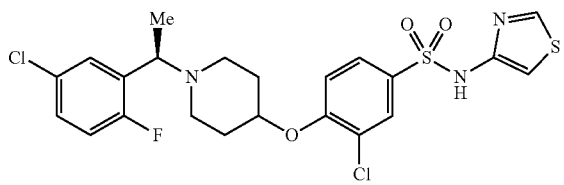 [SMILES: C[C@H](c1cc(Cl)ccc1F)N1CCC(Oc2ccc(S(=O)(=O)Nc3cscn3)cc2Cl)CC1]

To a solution of (R)-1-(1-(5-chloro-2-fluorophenyl)ethyl)piperidin-4-ol (0.39 g, 1.51 mmol) and 3-chloro-4-fluoro-N-(thiazol-4-yl)benzenesulfonamide (0.44 g, 1.51 mmol) in anhydrous N,N-dimethylformamide (10 mL) was added a 60% dispersion of sodium hydride in mineral oil (0.18 g, 4.53 mmol) mmol) at 0° C. The mixture was allowed to warm to ambient temperature, stirred for 2 h, and then heated to 75° C. for 3 h. The mixture was cooled to 0° C., quenched by addition of water (5 mL), and diluted with saturated ammonium chloride (80 mL). The mixture was extracted with ethyl acetate (2×60 mL). The combined organic phase was washed with saturated ammonium chloride (30 mL), brine (30 mL), dried over anhydrous sodium sulfate, and filtered. The filtrate was concentrated in vacuo to provide a residue which was purified by preparative reverse-phase HPLC, eluting with a gradient of 10 to 60% of acetonitrile in water containing 0.1% of formic acid, to afford the title compound as a colorless solid (0.20 g, 25% yield): $^1$H NMR (300 MHz, DMSO-d$_6$) δ 11.04 (br s, 1H), 8.89 (d, J=2.2 Hz, 1H), 7.80 (d, J=2.3 Hz, 1H), 7.67 (dd, J=8.8, 2.3 Hz, 1H), 7.46 (dd, J=6.1, 2.7 Hz, 1H), 7.39-7.32 (m, 2H), 7.23 (dd, J=9.7, 8.8 Hz, 1H), 7.07 (d, J=2.1 Hz, 1H), 4.60-4.54 (m, 1H), 3.89 (q, J=6.8 Hz, 1H), 2.66-2.60 (m, 2H), 2.30-2.22 (m, 2H), 1.94-1.88 (m, 2H), 1.67-1.60 (m, 2H), 1.33 (d, J=6.9 Hz, 3H); MS (ES+) m/z 530.1 (M+1), 532.1 (M+1).

Example 316

Synthesis of 3-chloro-4-(((1R,3s,5S)-8-(5-chloro-2-fluorobenzyl)-8-azabicyclo[3.2.1]octan-3-yl)oxy)-N-(thiazol-4-yl)benzenesulfonamide Formate

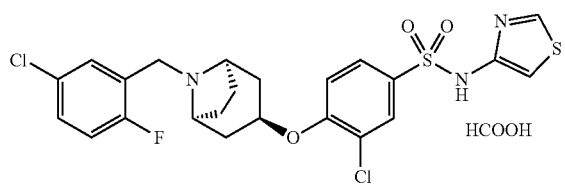 [SMILES: O=S(=O)(Nc1cscn1)c1ccc(O[C@@H]2C[C@H]3CC[C@@H](C2)N3Cc2cc(Cl)ccc2F)c(Cl)c1 ; "HCOOH"]

To a solution of 4-(((1R,3s,5S)-8-azabicyclo[3.2.1]octan-3-yl)oxy)-3-chloro-N-(thiazol-4-yl)benzenesulfonamide 2,2,2-trifluoroacetate (0.30 g, 0.58 mmol) and 5-chloro-2-fluorobenzaldehyde (0.18 g, 1.16 mol) in anhydrous N,N-dimethylformamide (5 mL) and anhydrous dichloromethane (5 mL) was added sodium triacetoxyborohydride (0.25 g, 1.16 mmol) and the reaction mixture was stirred at ambient temperature for 18 h. The mixture was then diluted with saturated ammonium chloride (50 mL) and extracted with ethyl acetate (2×40 mL). The combined organic phase was washed with brine (30 mL), dried over anhydrous sodium sulfate, and filtered. The filtrate was concentrated in vacuo and the residue purified by column chromatography, eluting with a gradient of 0 to 15% of methanol (containing 0.1% of ammonium hydroxide) in dichloromethane. Additional purification by preparative reverse-phase HPLC, eluting with a gradient of 10 to 55% of acetonitrile in water containing 0.1% of formic acid, afforded the title compound as a colorless solid (0.10 g, 29% yield): $^1$H NMR (300 MHz, DMSO-d$_6$) δ 8.89 (d, J=2.2 Hz, 1H), 8.15 (s, 1H), 7.82 (d, J=2.3 Hz, 1H), 7.69 (dd, J=8.8, 2.3 Hz, 1H), 7.57 (dd, J=6.3, 2.7 Hz, 1H), 7.43 (d, J=9.0 Hz, 1H), 7.35 (ddd, J=8.7, 4.5, 2.8 Hz, 1H), 7.22 (dd, J=9.6, 8.8 Hz, 1H), 7.07 (d, J=2.2 Hz, 1H), 4.85-4.74 (m, 1H), 3.59 (s, 2H), 3.28-3.20 (m, 2H), 2.05-1.96 (m, 4H), 1.80-1.64 (m, 4H), NH and COOH not observed; MS (ES+) m/z 542.1 (M+1), 544.1 (M+1).

Example 317

Synthesis of (S)-4-((1-((6-(azetidin-1-yl)pyridin-2-yl)methyl)pyrrolidin-3-yl)(methyl)amino)-5-chloro-2-fluoro-N-(thiazol-4-yl)benzenesulfonamide 2,2,2-trifluoroacetate

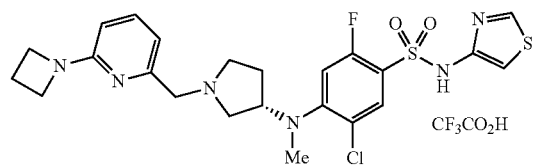 [SMILES: CN(c1cc(F)c(S(=O)(=O)Nc2cscn2)cc1Cl)[C@H]1CCN(Cc2cccc(N3CCC3)n2)C1 ; "CF3CO2H"]

Step 1. Preparation of 6-(azetidin-1-yl)picolinaldehyde

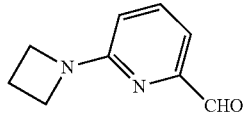 [SMILES: O=Cc1cccc(N2CCC2)n1]

To a solution of 6-chloropicolinaldehyde (1.00 g, 7.06 mmol) in anhydrous dimethyl sulfoxide (12 mL) was added azetidine (1.05 mL, 15.54 mmol) and the mixture was heated to 120° C. for 1 h. The mixture was diluted with ethyl acetate (80 mL), washed with brine (2×60 mL), dried over anhydrous sodium sulfate, and filtered. The filtrate was concentrated in vacuo to afford the title compound as dark red oil (1.14 g, quantitative yield): MS (ES+) m/z 163.3 (M+1).

Step 2. Preparation of (S)-4-((1-((6-(azetidin-1-yl) pyridin-2-yl)methyl)pyrrolidin-3-yl)(methyl)amino)- 5-chloro-2-fluoro-N-(thiazol-4-yl)benzenesulfonamide 2,2,2-trifluoroacetate

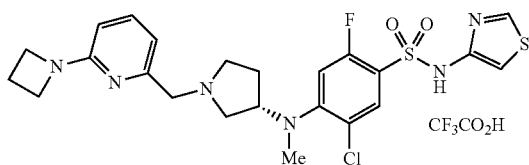 [SMILES: CN(c1cc(F)c(S(=O)(=O)Nc2cscn2)cc1Cl)[C@H]1CCN(Cc2cccc(N3CCC3)n2)C1 ; "CF3CO2H"]

Following the procedure as described for EXAMPLE 160, Step 5 and making non-critical variations as required to replace 6-(difluoromethyl)picolinaldehyde with 6-(azetidin-1-yl)picolinaldehyde, and purification by preparative reverse-phase HPLC, eluting with a gradient of 7 to 50% of acetonitrile in water containing 0.5% of formic acid, afforded the title compound as a colorless solid (0.020 g, 10% yield): $^1$H NMR (300 MHz, DMSO-$d_6$) δ 11.40 (s, 1H), 10.19 (s, 1H), 8.91 (d, J=2.2 Hz, 1H), 7.76 (d, J=7.5 Hz, 1H), 7.57 (dd, J=8.3, 7.2 Hz, 1H), 7.23 (d, J=12.1 Hz, 1H), 7.08 (d, J=2.2 Hz, 1H), 6.68 (d, J=7.1 Hz, 1H), 6.38 (d, J=8.4 Hz, 1H), 4.45-4.35 (m, 3H), 3.95 (t, J=7.4 Hz, 4H), 3.69-3.61 (m, 1H), 3.53-3.35 (m, 3H), 2.79 (s, 3H), 2.38-2.27 (m, 2H), 2.20-2.10 (m, 2H); MS (ES+) m/z 537.3 (M+1), 539.3 (M+1).

Example 318

Synthesis of 4-(((1R,3s,5S)-8-benzyl-8-azabicyclo [3.2.1]octan-3-yl)oxy)-3-chloro-N-(thiazol-4-yl) benzenesulfonamide

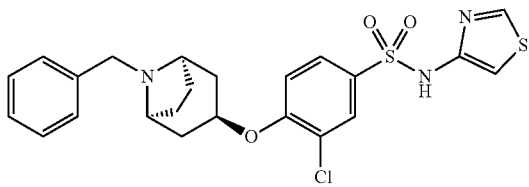 [SMILES: O=S(=O)(Nc1cscn1)c1ccc(O[C@@H]2C[C@H]3CC[C@@H](C2)N3Cc2ccccc2)c(Cl)c1]

Following the procedure as described for EXAMPLE 316 and making non-critical variations as required to replace 5-chloro-2-fluorobenzaldehyde with benzaldehyde, and purification by column chromatography, eluting with a gradient of 0 to 15% of methanol (containing 0.1% ammonium hydroxide) in dichloromethane, afforded the title compound as a colorless solid (0.21 g, 74% yield): $^1$H NMR (300 MHz, DMSO-$d_6$) δ 11.07 (s, 1H), 8.88 (d, J=2.2 Hz, 1H), 7.81 (d, J=2.3 Hz, 1H), 7.68 (dd, J=8.8, 2.3 Hz, 1H), 7.42 (d, J=9.0 Hz, 1H), 7.39-7.29 (m, 4H), 7.25-7.20 (m, 1H), 7.04 (d, J=2.2 Hz, 1H), 4.85-4.74 (m, 1H), 3.58 (s, 2H), 3.24-3.21 (m, 2H), 2.01-1.96 (m, 4H), 1.78-1.65 (m, 4H); MS (ES+) m/z 490.1 (M+1), 492.1 (M+1).

Example 319

Synthesis of 3-chloro-4-(((1R,3s,5S)-8-(3-chloro-4-fluorobenzyl)-8-azabicyclo[3.2.1]octan-3-yl)oxy)-N-(thiazol-4-yl)benzenesulfonamide Formate

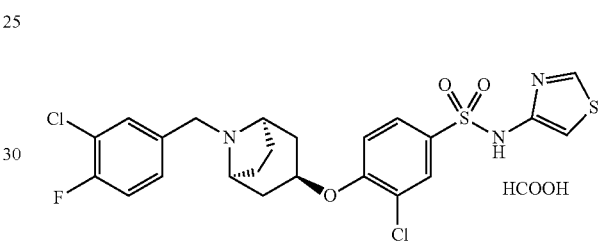

Following the procedure as described for EXAMPLE 316 and making non-critical variations as required to replace 5-chloro-2-fluorobenzaldehyde with 3-chloro-4-fluorobenzaldehyde, afforded the title compound as a colorless solid (0.11 g, 32% yield): $^1$H NMR (300 MHz, DMSO-$d_6$) δ 8.89 (d, J=2.1 Hz, 1H), 8.16 (s, 1H), 7.81 (d, J=2.3 Hz, 1H), 7.69 (dd, J=8.8, 2.3 Hz, 1H), 7.56 (dd, J=7.4, 1.9 Hz, 1H), 7.44-7.31 (m, 3H), 7.06 (d, J=2.1 Hz, 1H), 4.85-4.73 (m, 1H), 3.56 (s, 2H), 3.21-3.17 (m, 2H), 2.03-1.93 (m, 4H), 1.79-1.64 (m, 4H), NH and COOH not observed; MS (ES+) m/z 542.1 (M+1), 544.1 (M+1).

Example 320

Synthesis of (R)-3-chloro-4-((1-(1-(5-cyclopropyl-2-fluorophenyl)ethyl)piperidin-4-yl)oxy)-N-(thiazol-4-yl)benzenesulfonamide

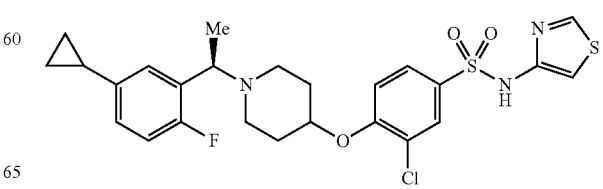

Step 1. Preparation of (R)-1-(1-(5-cyclopropyl-2-fluorophenyl)ethyl)piperidin-4-ol

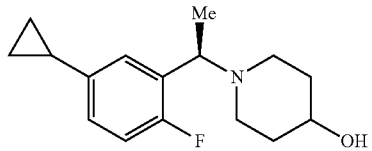 [SMILES: C[C@H](c1cc(C2CC2)ccc1F)N1CCC(O)CC1]

To a mixture of (R)-1-(1-(5-chloro-2-fluorophenyl)ethyl)piperidin-4-ol (1.93 g, 5.04 mmol), cyclopropylboronic acid (0.87 g, 10.01 mmol), and potassium phosphate (4.28 g, 20.16 mmol) in toluene (60 mL) and water (6 mL) was added palladium acetate (0.11 g, 0.50 mmol) and tricyclohexylphosphonium tetrafluoroborate (0.37 g, 1.00 mmol). The resulting mixture was degassed by sparging with nitrogen and then heated to reflux for 18 h. After cooling to ambient temperature, the reaction mixture was diluted with ethyl acetate (50 mL) and filtered. The filtrate was washed with saturated ammonium chloride (50 mL), brine (50 mL), dried over anhydrous sodium sulfate, and filtered. The filtrate was concentrated in vacuo and the residue purified by column chromatography, eluting with a gradient of 0 to 10% of methanol (containing 0.2% of ammonium hydroxide) in dichloromethane, to afford the title compound as a colorless oil (0.71 g, 53% yield): $^1$H NMR (300 MHz, CDCl$_3$) δ 7.13 (dd, J=6.9, 2.0 Hz, 1H), 6.92-6.87 (m, 2H), 3.87 (q, J=6.8 Hz, 1H), 3.69-3.60 (m, 1H), 2.95-2.89 (m, 1H), 2.79-2.72 (m, 1H), 2.19-2.05 (m, 2H), 1.96-1.84 (m, 3H), 1.69-1.52 (m, 3H), 1.39 (d, J=6.8 Hz, 3H), 0.99-0.93 (m, 2H), 0.68-0.63 (m, 2H); MS (ES+) m/z 264.2 (M+1).

Step 2. Preparation of R)-3-chloro-4-((1-(1-(5-cyclopropyl-2-fluorophenyl)ethyl)piperidin-4-yl)oxy)-N-(thiazol-4-yl)benzenesulfonamide

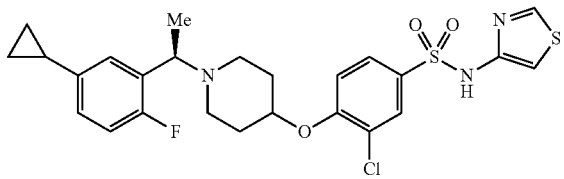 [SMILES: C[C@H](c1cc(C2CC2)ccc1F)N1CCC(Oc2ccc(S(=O)(=O)Nc3cscn3)cc2Cl)CC1]

Following the procedure as described for EXAMPLE 315, Step 6 and making non-critical variations as required to replace (R)-1-(1-(5-chloro-2-fluorophenyl)ethyl)-piperidin-4-ol with (R)-1-(1-(5-cyclopropyl-2-fluorophenyl)ethyl)piperidin-4-ol, and purification by column chromatography, eluting with a gradient of 0 to 10% of methanol (containing 0.2% of ammonium hydroxide) in dichloromethane, afforded the title compound as a colorless solid (0.35 g 49% yield): $^1$H NMR (300 MHz, DMSO-d$_6$) δ 11.03 (br s, 1H), 8.89 (d, J=2.2 Hz, 1H), 7.81 (d, J=2.3 Hz, 1H), 7.68 (dd, J=8.8, 2.3 Hz, 1H), 7.34 (d, J=9.1 Hz, 1H), 7.14 (dd, J=6.9, 2.3 Hz, 1H), 7.07 (d, J=2.2 Hz, 1H), 7.01 (dd, J=10.1, 8.5 Hz, 1H), 6.92 (ddd, J=8.2, 5.3, 2.6 Hz, 1H), 4.59-4.53 (m, 1H), 3.86 (q, J=6.8 Hz, 1H), 2.73-2.62 (m, 2H), 2.29-2.20 (m, 2H), 1.96-1.87 (m, 3H), 1.70-1.59 (m, 2H), 1.33 (d, J=6.9 Hz, 3H), 0.95-0.88 (m, 2H), 0.68-0.56 (m, 2H), MS (ES+) m/z 536.3 (M+1), 538.3 (M+1).

Example 321

Synthesis of (S)-4-((1-benzylpyrrolidin-3-yl)(methyl)amino)-2-fluoro-3-methyl-N-(thiazol-4-)benzenesulfonamide 2,2,2-trifluoroacetate

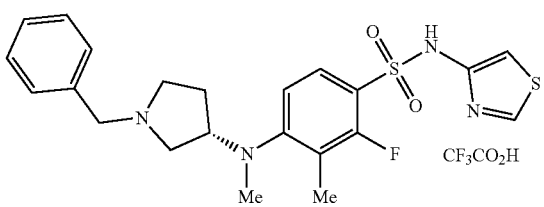 [SMILES: Cc1c(N(C)[C@H]2CCN(Cc3ccccc3)C2)ccc(S(=O)(=O)Nc2cscn2)c1F ; "CF3CO2H"]

Step 1. Preparation of tert-butyl (S)-3-((4-(N-(tert-butoxycarbonyl)-N-(thiazol-4-yl)sulfamoyl)-2-chloro-3-fluorophenyl)amino)pyrrolidine-1-carboxylate

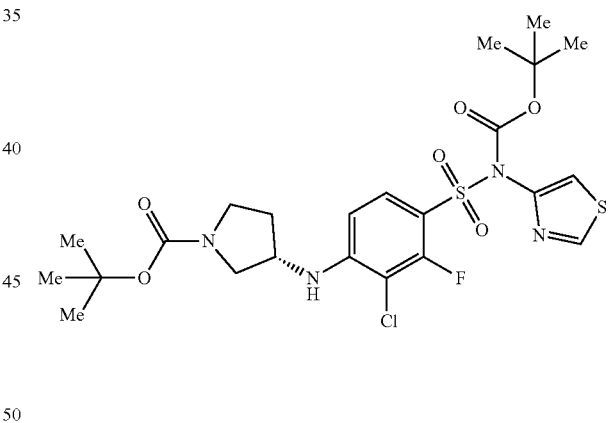

To a solution of tert-butyl ((3-chloro-2,4-difluorophenyl)sulfonyl)(thiazol-4-yl)carbamate (7.50 g, 18.27 mmol) in anhydrous dimethyl sulfoxide (44 mL) was added triethylamine (3.10 mL, 21.92 mmol) and tert-butyl (S)-3-amino-pyrrolidine-1-carboxylate (4.10 g, 21.92 mmol) and the reaction mixture was stirred at ambient temperature for 2 h. Concentration in vacuo and purification of the residue by column chromatography, eluting with a gradient of 5 to 50% of ethyl acetate in hexanes, afforded the title compound as a colorless solid (6.67 g, 64% yield): $^1$H NMR (300 MHz, CDCl$_3$) δ 8.79 (d, J=2.3 Hz, 1H), 7.86 (t, J=7.9 Hz, 1H), 7.51 (d, J=2.2 Hz, 1H), 6.53 (d, J=9.2 Hz, 1H), 5.01 (d, J=6.5 Hz, 1H), 4.17-4.11 (m, 1H), 3.78-3.75 (m, 1H), 3.53-3.50 (m, 2H), 3.35-3.23 (m, 1H), 2.33-2.22 (m, 1H), 1.97-1.93 (m, 1H), 1.46 (s, 9H), 1.34 (s, 9H); MS (ES+) m/z 577.3 (M+1), 579.3 (M+1).

Step 2. Preparation of tert-butyl (S)-3-((4-(N-(tert-butoxycarbonyl)-N-(thiazol-4-yl)sulfamoyl)-3-fluoro-2-methylphenyl)amino)pyrrolidine-1-carboxylate

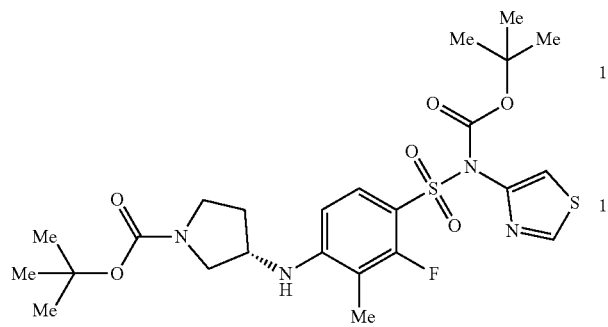

To a solution of tert-butyl (S)-3-((4-(N-(tert-butoxycarbonyl)-N-(thiazol-4-yl)sulfamoyl)-2-chloro-3-fluorophenyl)amino)pyrrolidine-1-carboxylate (6.80 g, 11.71 mmol), methylboronic acid (7.05 g, 117.10 mmol), palladium acetate (0.40 g, 1.76 mmol), and tricyclohexyl phosphonium tetrafluoroborate (1.30 g, 3.51 mmol) in anhydrous 1,4-dioxane (117 mL) was added potassium phosphate (12.49 g, 59.00 mmol). The reaction mixture was degassed by sparging with nitrogen for 5 minutes, and then heated to 90° C. for 4 h. After cooling to ambient temperature, the reaction mixture was filtered through a pad of Celite. The filter pad was washed with ethyl acetate (150 mL), and the combined filtrate concentrated in vacuo. The residue was purified by column chromatography, eluting with a gradient of 10 to 50% of ethyl acetate in hexanes, to yield the title compound as a colorless solid (6.23 g, 96% yield): MS (ES+) m/z 557.3 (M+1).

Step 3. Preparation of tert-butyl (S)-3-((4-(N-(tert-butoxycarbonyl)-N-(thiazol-4-yl)sulfamoyl)-3-fluoro-2-methylphenyl)(methyl)amino)pyrrolidine-1-carboxylate

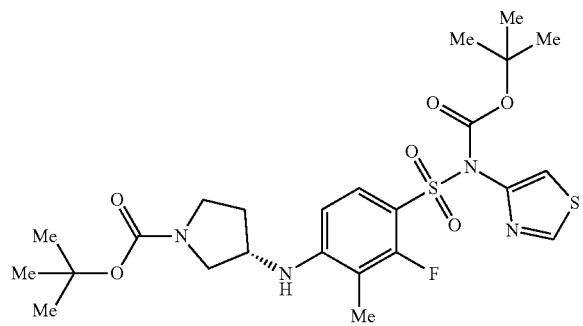 [SMILES: Cc1c(N[C@H]2CCN(C(=O)OC(C)(C)C)C2)ccc(S(=O)(=O)N(C(=O)OC(C)(C)C)c2cscn2)c1F]

To a solution of tert-butyl (S)-3-((4-(N-(tert-butoxycarbonyl)-N-(thiazol-4-yl)sulfamoyl)-3-fluoro-2-methylphenyl)amino)pyrrolidine-1-carboxylate (6.23 g, 11.20 mmol) in anhydrous N,N-dimethylformamide (22 mL) was added iodomethane (1.40 mL, 22.41 mmol), followed by sodium hydride (0.67 g, 16.80 mmol). The reaction mixture was stirred at ambient temperature for 16 h, and then quenched by addition of methanol (5 mL). Concentration in vacuo and purification of the residue by column chromatography, eluting with a gradient of 10 to 50% of ethyl acetate in hexanes, afforded the title compound as a light brown foam (5.84 g, 91% yield): MS (ES+) m/z 571.2 (M+1).

Step 4. Preparation of (S)-4-((1-benzylpyrrolidin-3-yl)(methyl)amino)-2-fluoro-3-methyl-N-(thiazol-4-yl)benzenesulfonamide 2,2,2-trifluoroacetate

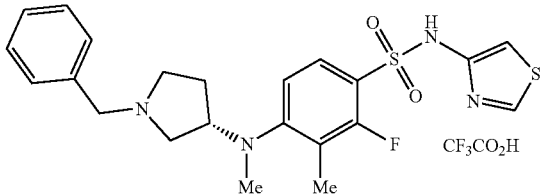 [SMILES: Cc1c(N(C)[C@H]2CCN(Cc3ccccc3)C2)ccc(S(=O)(=O)Nc2cscn2)c1F ; "CF3CO2H"]

To a solution of tert-butyl (S)-3-((4-(N-(tert-butoxycarbonyl)-N-(thiazol-4-yl)sulfamoyl)-3-fluoro-2-methylphenyl)(methyl)amino)pyrrolidine-1-carboxylate (5.30 g, 9.36 mmol) in dichloromethane (10 mL) was added trifluoroacetic acid (5 mL) and the reaction mixture was stirred at ambient temperature for 16 h. Concentration in vacuo provided a residue, which was used without further purification. The residue was dissolved in anhydrous N,N-dimethylformamide (18 mL), and benzaldehyde (1.99 g, 18.73 mmol) and sodium triacetoxyborohydride (5.96 g, 28.10 mmol) were added to it. The reaction mixture was stirred at ambient temperature for 16 h, and then quenched by addition of 5% aqueous lithium chloride (25 mL). The mixture was extracted with ethyl acetate (7×25 mL), and the combined organic extracts were dried over anhydrous magnesium sulfate and filtered. The filtrate was concentrated in vacuo and a portion of the residue purified by reverse-phase HPLC, eluting with water in acetonitrile to obtain the title compound as a colorless solid (0.31 g, 6% yield): $^1$H NMR (300 MHz, DMSO-$d_6$) δ 11.27 (t, J=0.7 Hz, 1H), 8.89 (d, J=2.2 Hz, 1H), 7.60 (t, J=8.0 Hz, 3H), 7.43-7.43 (m, 3H), 6.97 (q, J=2.7 Hz, 2H), 4.38-4.31 (m, 2H), 4.23-4.07 (m, 1H), 3.38 (s, 4H), 2.66 (s, 3H), 2.14-2.06 (m, 5H); MS (ES+) m/z 461.2 (M+1). Note: acidic protons not observed.

Examples 322-324

In a similar manner as described in the EXAMPLE 321, Step 4, utilizing the appropriately substituted starting materials and intermediates, the following compounds were prepared:

| Example No. | Name | MS (ES+) m/z | $^1$H NMR |
|---|---|---|---|
| 322 | (S)-4-((1-(2,5-difluorobenzyl)-pyrrolidin-3-yl)(methyl)amino)-2-fluoro-3-methyl-N-(thiazol-4-yl)benzenesulfonamide 2,2,2-trifluoroacetate | 497.1 (M + 1) | (300 MHz, DMSO-$d_6$) δ 11.30 (s, 1H), 8.89 (d, J = 2.2 Hz, 1H), 7.61 (t, J = 8.5 Hz, 1H), 7.52-7.48 (m, 1H), 7.39 (td, J = 6.4, 1.6 Hz, 2H), 7.00-6.97 (m, 2H), 4.46-4.44 (m, 2H), 4.25-4.02 (m, 1H), 3.71-3.16 (m, 4H), 2.65 (s, 3H), 2.24-2.10 (m, 5H), NH not observed. |
| 323 | (S)-4-((1-(3-(difluoromethyl) | 511.5 (M + 1) | (300 MHz, DMSO-$d_6$) δ 11.30 (s, 1H), 8.89 (d, J = 2.1 Hz, |

| Example No. | Name | MS (ES+) m/z | ¹H NMR |
|---|---|---|---|
|  | benzyl)-pyrrolidin-3-yl)(methyl)amino)-2-fluoro-3-methyl-N-(thiazol-4-yl)benzenesulfonamide |  | 1H), 7.74 (d, J = 0.6 Hz, 1H), 7.67-7.59 (m, 4H), 7.27-6.90 (m, 3H), 4.56-4.42 (m, 2H), 4.24-4.01 (m, 1H), 3.65-3.55 (m, 3H), 3.44-3.40 (m, 1H), 2.69-2.59 (m, 3H), 2.25-1.96 (m, 5H). |
| 324 | (S)-2-fluoro-4-((1-((3-fluoro-6-methylpyridin-2-yl)methyl)pyrrolidin-3-yl)(methyl)amino)-3-methyl-N-(thiazol-4-yl)benzenesulfonamide 2,2,2-trifluoroacetate | 494.1 (M + 1) | (300 MHz, DMSO-d₆) δ 11.31 (s, 1H), 10.73 (br s, 1H), 8.88 (d, J = 2.1 Hz, 1H), 7.76-7.65 (m, 2H), 7.39 (dd, J = 8.6, 3.8 Hz, 1H), 7.01 (d, J = 8.6 Hz, 1H), 6.97 (d, J = 2.1 Hz, 1H), 4.64 (s, 2H), 4.21-4.15 (m, 1H), 3.65-3.31 (m, 4H), 2.67 (s, 3H), 2.48 (s, 3H), 2.26-2.10 (m, 5H). |

Examples 325-327

In a similar manner as described in the EXAMPLE 29, Step 4, utilizing the appropriately substituted starting materials and intermediates, the following compounds were prepared:

| Example No. | Name | MS (ES+) m/z | ¹H NMR |
|---|---|---|---|
| 325 | (S)-3-chloro-4-((1-(2,5-difluorobenzyl)pyrrolidin-3-yl)(methyl)amino)-N-(1,2,4-thiadiazol-5-yl)benzenesulfonamide | 500.0 (M + 1), 502.0 (M + 1) | (300 MHz, DMSO-d₆) δ 7.99 (s, 1H), 7.68 (d, J = 2.1 Hz, 1H), 7.63 (dd, J = 8.4, 2.1 Hz, 1H), 7.47-7.42 (m, 1H), 7.39-7.34 (m, 2H), 7.27 (d, J = 8.5 Hz, 1H), 4.27 (s, 2H), 4.23-4.16 (m, 1H), 3.42-3.36 (m, 1H), 3.24-3.16 (m, 3H), 2.70 (s, 3H), 2.04-1.92 (m, 2H), NH not observed. |
| 326 | (S)-3-chloro-4-((1-(2,6-difluorobenzyl)pyrrolidin-3-yl)(methyl)amino)-N-(1,2,4-thiadiazol-5-yl)benzenesulfonamide | 500.0 (M + 1), 502.0 (M + 1) | (300 MHz, DMSO-d₆) δ 8.01 (s, 1H), 7.68-7.54 (m, 3H), 7.23 (q, J = 7.9 Hz, 3H), 4.28-4.24 (m, 2H), 4.23-4.16 (m, 1H), 3.37 (t, J = 9.3 Hz, 1H), 3.21-3.11 (m, 3H), 2.69 (s, 3H), 2.11-1.92 (m, 2H), NH not observed |
| 327 | (S)-3-chloro-4-((1-(3,5-difluorobenzyl)pyrrolidin-3-yl)(methyl)amino)-N-(1,2,4-thiadiazol-5-yl)benzenesulfonamide formate | 500.0 (M + 1), 501.9 (M + 1) | (300 MHz, DMSO-d₆) δ 8.14 (s, 1H), 7.96 (s, 1H), 7.68 (d, J = 2.0 Hz, 1H), 7.65-7.61 (m, 1H), 7.33-7.23 (m, 4H), 4.26 (s, 2H), 4.25-4.12 (m, 1H), 3.35 (t, J = 9.1 Hz, 1H), 3.20-3.12 (m, 3H), 2.70 (s, 3H), 2.18-2.08 (m, 1H), 2.05-1.92 (m, 1H), NH and COOH not observed. |

Example 328

Synthesis of (S)-4-((1-benzylpyrrolidin-3-yl)(methyl)amino)-3-chloro-2-fluoro-N-(thiazol-4-yl)benzenesulfonamide 2,2,2-trifluoroacetate

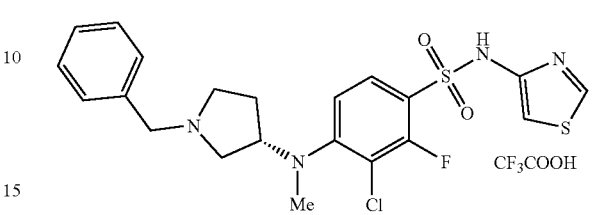

Step 1. Preparation of tert-butyl (S)-3-((4-(N-(tert-butoxycarbonyl)-N-(thiazol-4-yl)sulfamoyl)-2-chloro-3-fluorophenyl)(methyl)amino)pyrrolidine-1-carboxylate

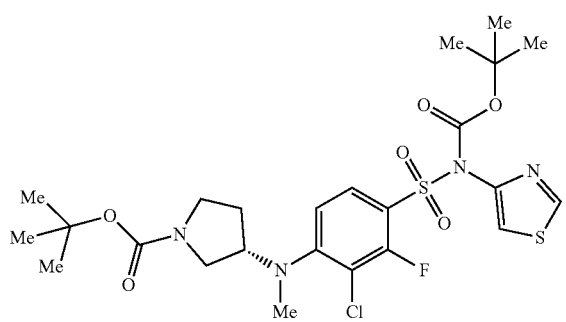 [SMILES: CN(c1ccc(S(=O)(=O)N(C(=O)OC(C)(C)C)c2cscn2)c(F)c1Cl)[C@H]1CCN(C(=O)OC(C)(C)C)C1]

Following the procedure as described in EXAMPLE 321, Step 3 and making variations as required to replace tert-butyl (S)-3-((4-(N-(tert-butoxycarbonyl)-N-(thiazol-4-yl)sulfamoyl)-3-fluoro-2-methylphenyl)amino)pyrrolidine-1-carboxylate with tert-butyl (S)-3-((4-(N-(tert-butoxycarbonyl)-N-(thiazol-4-yl)sulfamoyl)-2-chloro-3-fluorophenyl)amino)pyrrolidine-1-carboxylate, the title compound was obtained as a colorless solid (0.70 g, 86% yield): ¹H NMR (300 MHz, CDCl₃) δ 8.81-8.80 (m, 1H), 7.96-7.91 (m, 1H), 7.55 (d, J=2.3 Hz, 1H), 6.98-6.94 (m, 1H), 4.24-4.19 (m, 1H), 3.68-3.54 (m, 2H), 3.38-3.28 (m, 2H), 2.87 (s, 3H), 2.11-2.03 (m, 2H), 1.47 (s, 9H), 1.35 (s, 9H).

Step 2. Preparation of (S)-4-((1-benzylpyrrolidin-3-yl)(methyl)amino)-3-chloro-2-fluoro-N-(thiazol-4-yl)benzenesulfonamide 2,2,2-trifluoroacetate

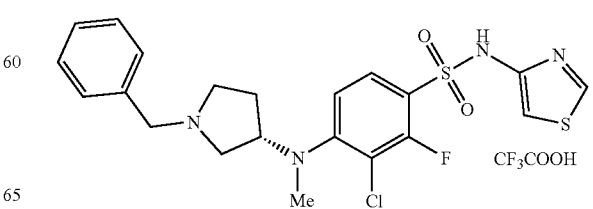

Following the procedure as described in EXAMPLE 321, Step 4 and making variations as required to replace tert-butyl (S)-3-((4-(N-(tert-butoxycarbonyl)-N-(thiazol-4-yl)sulfamoyl)-3-fluoro-2-methylphenyl)(methyl)amino)pyrrolidine-1-carboxylate with tert-butyl (S)-3-((4-(N-(tert-butoxycarbonyl)-N-(thiazol-4-yl)sulfamoyl)-2-chloro-3-fluorophenyl)(methyl)amino)pyrrolidine-1-carboxylate, the title compound was obtained as a colourless solid (0.12 g, 45% yield): $^1$H-NMR (300 MHz, DMSO-$d_6$) δ 8.87 (d, J=2.2 Hz, 1H), 7.61 (t, J=8.5 Hz, 1H), 7.32-7.22 (m, 5H), 6.98-6.96 (m, 2H), 5.76 (s, 1H), 4.22-4.12 (m, 1H), 3.68-3.49 (m, 2H), 2.81 (s, 3H), 2.77-2.54 (m, 3H), 2.39-2.30 (m, 1H), 2.12-2.04 (m, 1H), 1.88-1.76 (m, 1H), NH not observed; MS (ES+) m/z 481.0 (M+1), 483.0 (M+1).

BIOLOGICAL ASSAYS

Various techniques are known in the art for testing the activity of the compound of the invention or determining their solubility in known pharmaceutically acceptable excipients. In order that the invention described herein may be more fully understood, the following biological assays are set forth. It should be understood that these examples are for illustrative purposes only and are not to be construed as limiting this invention in any manner.

Biological Example 1

Electrophysiological Assay (In Vitro Assay)

Patch voltage clamp electrophysiology allows for the direct measurement and quantification of block of voltage-gated sodium channels ($Na_V$'s), and allows the determination of the time- and voltage-dependence of block which has been interpreted as differential binding to the resting, open, and inactivated states of the sodium channel (Hille, B., *Journal of General Physiology* (1977), 69: 497-515).

The following patch voltage clamp electrophysiology studies were performed on representative compounds of the invention using human embryonic kidney cells (HEK), permanently transfected with an expression vector containing the full-length cDNA coding for the desired human sodium channel a-subunit, grown in culture media containing 10% FBS, 1% PSG, and 0.5 mg/mL G418 at 37° C. with 5% $CO_2$. HEK cells used for the electrophysiology (EP) recordings had a passage number of less than 40 for all studies and were used within three days from the time of plating. $Na_V1.1$, $Na_V1.5$ and $Na_V1.6$ cDNAs (NM_001165964 (SCN1A), NM_000335 (SCN5A) and NM_014191 (SCN8A), respectively) were stably expressed in HEK-293 cells.

Sodium currents were measured using the patch clamp technique in the whole-cell configuration using either a PatchXpress automated voltage clamp or manually using an Axopatch 200B (Axon Instruments) or Model 2400 (A-M systems) amplifier. The manual voltage clamp protocol was as follows: Borosilicate glass micropipettes were fire-polished to a tip diameter yielding a resistance of 2-4 Mohms in the working solutions. The pipette was filled with a solution comprised of: 5 mM NaCl, 10 mM CsCl, 120 mM CsF, 0.1 mM $CaCl_2$, 2 mM $MgCl_2$, 10 mM HEPES, 10 mM EGTA; and adjusted to pH 7.2 with CsOH. The external solution had the following composition: 140 mM NaCl, 5 mM KCl, 2 mM $CaCl_2$, 1 mM $MgCl_2$, 10 mM HEPES; and adjusted to pH 7.4 with NaOH. In some studies, the external sodium was reduced by equimolar replacement with choline. Osmolarity in the CsF internal and NaCl external solutions was adjusted to 300 mOsm/kg and 310 mOsm/kg with glucose, respectively. All recordings were performed at ambient temperature in a bath chamber with a volume of 150 μL. Control sodium currents were measured in 0.5% DMSO. Controls and representative compounds of the invention were applied to the recording chamber through a 4-pinch or 8-pinch valve bath perfusion system manufactured by ALA Scientific Instruments.

Currents were recorded at 40 kHz sampling frequency, filtered at 5 Hz, and stored using a Digidata-1322A analogue/digital interface with the pClamp software (Axon Instruments). Series resistance compensation was applied (60-80%). Cells were rejected if currents showed inadequate voltage control (as judged by the IV relationship during stepwise activation). All statistics in this study are given as mean±SD.

The membrane potential was maintained at a voltage where inactivation of the channel is complete. The voltage is then stepped back to a very negative (Vhold=−150 mV) voltage for 20 ms and then a test pulse is applied to quantify the compound block. The 20 ms brief repolarization was long enough for compound-free channels to completely recover from fast inactivation, but the compound-bound channels recovered more slowly such that negligible recovery could occur during this interval. The percent decrease in sodium current following wash-on of compound was taken as the percent block of sodium channels.

Representative compounds of the invention, when tested in this assay, demonstrated the $IC_{50}$'s as set forth below in Table 9.

Biological Example 2

Sodium Influx Assay (In Vitro Assay)

This sodium influx assay employs the use of the cell permeable, sodium sensitive dye ANG2 to quantify sodium ion influx through sodium channels which are maintained in an open state by use of sodium channel modulators. This high throughput sodium influx assay allows for rapid profiling and characterization of sodium channel blockers.

In general, Trex HEK293 cells were stably transfected with an inducible expression vector containing the full-length cDNA coding for the desired human sodium channel α-subunit and with an expression vector containing full length cDNA coding for the β1-subunit. Sodium channel expressing cell lines were induced with tetracycline (1 μg/mL) and plated on 384-well PDL-coated plates at a density of 25K-30K cells/well in culture media (DMEM, containing 10% FBS and 1% L-glutamine). After overnight incubation (37° C., 5% $CO_2$), culture media was removed and cells were loaded with 5 uM ANG2 dye for 1-1.5h in Buffer 1 (155 mM NMDG, 5 mM KCl, 2 mM $CaCl_2$, 1 mM $MgCl_2$, 10 mM HEPES, 10 mM glucose, adjusted with Tris to pH 7.4). Access dye was removed and cells were incubated with test compounds for 1 hr in buffer 1 containing sodium channel modulator(s) at room temperature.

Hamamatsu FDSS μCell was used to perform a 1:1 addition of Na/K challenge buffer (140 mM NaCl, 20 mM HEPES, 1 mM $CaCl_2$, 15 mM KCl, 1 mM $MgCl_2$, 10 mM glucose, adjusted with Tris to pH 7.4) and simultaneously read plates at excitation wavelength of 530 nm and emission wavelength set at 558 nm. Percent inhibition of sodium ion influx was calculated for each test compound at each test concentration to determine the $IC_{50}$ values.

Representative compounds of the invention, when tested in this model, demonstrated affinities for the inactivated state of $Na_V1.6$, $Na_V1.5$ and $Na_V1.1$ as set forth below in Table 9.

The Example numbers provided in Table 1 below correspond to the Examples herein, "Flux" refers to the Sodium Influx Assay and "EP" refers to the Electrophysiological Assay. $IC_{50}$ values listed are arithmetic mean values.

TABLE 1

Inhibition of Nav1.6, Nav1.5 and Nav1.1

| Ex. No. | Flux $Na_V1.6$ $IC_{50}$ (μM) | Flux $Na_V1.5$ $IC_{50}$ (μM) | Flux $Na_V1.1$ $IC_{50}$ (μM) | EP $Na_V1.6$ $IC_{50}$ (μM) | EP $Na_V1.5$ $IC_{50}$ (μM) | EP $Na_V1.1$ $IC_{50}$ (μM) |
|---|---|---|---|---|---|---|
| 1 | 10.296 | >30 | >30 | | | |
| 2 | 1.358 | 6.325 | 22.501 | 0.381 | | |
| 3 | 6.595 | 6.169 | 20.767 | | | |
| 4 | >30 | 10.962 | >30 | | | |
| 5 | 1.362 | 4.372 | 6.304 | | | |
| 6 | 7.523 | >30 | 12.152 | | | |
| 7 | 27.307 | >30 | >30 | | | |
| 8A | 1.090 | 4.806 | 5.009 | | | |
| 8B | 0.632 | 14.673 | 4.313 | | | |
| 9A | 1.748 | 5.919 | 6.244 | | | |
| 9B | 0.874 | 8.745 | 5.100 | | | |
| 10A | 1.268 | 5.155 | 4.661 | | | |
| 10B | 1.161 | 8.557 | 5.077 | | | |
| 11 | 0.253 | 7.583 | 8.123 | 0.082 | | 7.211 |
| 12 | 13.328 | 6.347 | 13.287 | | | |
| 13 | 1.703 | 5.086 | 6.830 | | | |
| 14 | 0.878 | 10.688 | >30 | | | |
| 15 | 2.570 | 23.905 | 9.232 | | | |
| 16 | 0.429 | >30 | 22.836 | 0.030 | | >10 |
| 17 | 0.392 | >30 | >30 | 0.155 | | >10 |
| 18 | 1.057 | >30 | >30 | | | |
| 19 | 3.167 | 4.680 | 4.956 | | | |
| 20 | 5.622 | 6.098 | 5.926 | | | |
| 21 | 3.178 | 4.685 | 3.154 | | | |
| 22 | 3.636 | 16.142 | 14.812 | | | |
| 23 | >30 | 29.578 | >30 | | | |
| 24 | 2.539 | 13.530 | 12.630 | | | |
| 25 | 0.569 | 24.682 | 5.764 | 0.138 | | >10 |
| 26 | 0.235 | >30 | 15.014 | 0.164 | | |
| 27 | 0.437 | 6.901 | 3.732 | 0.070 | | 3.413 |
| 28 | 0.221 | 5.730 | 3.229 | 0.036 | | 4.206 |
| 29 | 0.244 | 29.511 | >30 | 0.060 | >10 | >10 |
| 30 | 0.021 | 18.695 | 7.969 | | | |
| 31 | 0.013 | >30 | 27.674 | 0.029 | | |
| 32 | 0.047 | 7.410 | 6.549 | | | |
| 33 | 0.041 | 7.791 | 5.109 | 0.070 | | >10 |
| 34 | 0.039 | >30 | 19.920 | | | |
| 35 | 0.021 | >30 | 15.867 | | | |
| 36 | 0.615 | >30 | >30 | 0.685 | | >10 |
| 37 | 0.195 | >30 | >30 | | | |
| 38 | 1.942 | 26.308 | 17.922 | 0.803 | >30 | >10 |
| 39 | 0.732 | 13.070 | 4.964 | | | |
| 40 | 3.253 | 15.801 | 6.793 | 3.880 | | >10 |
| 41 | 1.043 | 9.013 | 6.644 | 0.748 | | >10 |
| 42 | 0.155 | 9.107 | 4.380 | | | |
| 43 | 1.890 | 17.102 | 7.866 | | | |
| 44 | 0.100 | >30 | 10.714 | 0.089 | | >10 |
| 45 | 1.980 | >30 | 11.215 | | | |
| 46 | 0.731 | >30 | 4.128 | 0.278 | | |
| 47 | 0.943 | 15.902 | 12.294 | 0.479 | | |
| 48 | 3.665 | 7.821 | 10.547 | | | |
| 49 | 0.491 | 5.395 | 5.586 | | | |
| 50 | 1.078 | 5.713 | 4.150 | | | |
| 51 | 6.580 | 3.476 | 17.585 | | | |
| 52 | 0.305 | 14.422 | 8.370 | | | |
| 53 | 0.601 | 24.525 | 7.407 | | | |
| 54 | 0.156 | 16.652 | 9.927 | | | |
| 55 | 0.187 | 9.834 | 11.752 | 0.032 | | >10 |
| 56 | 0.392 | 10.064 | 12.475 | | | |
| 57 | 0.970 | 5.246 | 13.656 | 0.268 | | >10 |
| 58 | 0.402 | 5.578 | 5.137 | 0.093 | | 9.145 |
| 59 | 0.255 | 7.444 | 7.437 | 0.092 | | 9.914 |

TABLE 1-continued

Inhibition of Nav1.6, Nav1.5 and Nav1.1

| Ex. No. | Flux $Na_v1.6$ $IC_{50}$ (μM) | Flux $Na_v1.5$ $IC_{50}$ (μM) | Flux $Na_v1.1$ $IC_{50}$ (μM) | EP $Na_v1.6$ $IC_{50}$ (μM) | EP $Na_v1.5$ $IC_{50}$ (μM) | EP $Na_v1.1$ $IC_{50}$ (μM) |
|---|---|---|---|---|---|---|
| 60 | 0.452 | 15.905 | 13.302 | | | |
| 61 | 0.176 | 6.957 | 6.367 | 0.137 | | >10 |
| 62 | 0.536 | 4.527 | 4.242 | 0.150 | | 6.547 |
| 63 | 27.721 | >30 | >30 | | | |
| 64 | 5.628 | >30 | >30 | | | |
| 65 | 0.552 | 29.737 | >30 | 0.839 | | >10 |
| 66 | 0.148 | >30 | 5.508 | 0.144 | | |
| 67 | 0.310 | >30 | >30 | 0.453 | | |
| 68 | 1.411 | >30 | >30 | 2.920 | | >10 |
| 69 | 0.697 | 6.154 | 1.764 | | | |
| 70 | 0.664 | 4.201 | 3.178 | | | |
| 71 | 1.257 | 9.273 | 3.351 | | 0.863 | |
| 72 | 6.074 | 13.492 | 6.806 | | | |
| 73 | 1.877 | 13.112 | 5.848 | | | |
| 74 | 0.167 | 8.668 | 1.540 | 0.025 | | 1.030 |
| 75 | 0.661 | 8.991 | 4.194 | | | |
| 76 | 4.699 | 16.766 | 11.366 | | | |
| 77 | 7.614 | 26.567 | 19.036 | 5.567 | | |
| 78 | 6.597 | 2.858 | 8.171 | | | |
| 79 | 0.570 | >30 | 6.336 | 0.138 | | >10 |
| 80 | 0.378 | 29.098 | 12.169 | 0.124 | | >10 |
| 81 | 0.572 | 7.217 | 7.482 | | | |
| 82 | 0.423 | >30 | >30 | 0.056 | | >10 |
| 83 | 0.029 | >30 | >30 | 0.036 | | >10 |
| 84 | 0.525 | 3.536 | 6.000 | | | |
| 85 | 0.353 | 5.712 | 8.701 | | | |
| 86 | 0.588 | 12.453 | 5.374 | | | |
| 87 | 0.744 | 14.288 | 5.959 | 0.393 | | 7.276 |
| 88 | 0.381 | 5.913 | 1.588 | 0.039 | | 1.245 |
| 89 | 0.501 | 12.012 | 2.130 | 0.091 | | 2.874 |
| 90 | 0.464 | 8.160 | 12.412 | | | |
| 91 | 1.197 | 6.944 | 7.198 | | | |
| 92 | 0.203 | 3.641 | 6.398 | 0.081 | | 7.534 |
| 93 | 3.625 | 12.485 | 12.573 | | | |
| 94 | 3.441 | 7.615 | 11.384 | | | |
| 95 | 0.416 | 20.852 | 14.689 | 0.177 | | |
| 96 | 11.914 | >30 | 25.698 | | | |
| 97 | 1.450 | >30 | >30 | 2.937 | | |
| 98 | 7.531 | >30 | 21.869 | | | |
| 99 | 1.408 | >30 | >30 | 4.440 | | |
| 100 | 0.190 | >30 | 29.992 | 0.164 | | >10 |
| 101 | 0.272 | 24.339 | 15.599 | 0.054 | >30 | 31.664 |
| 102 | 0.703 | >30 | >30 | 0.152 | | >10 |
| 103 | 0.061 | 28.245 | 28.506 | 0.017 | >30 | 40.945 |
| 104 | 0.026 | >30 | >30 | 0.011 | | >10 |
| 105 | 0.268 | 17.562 | 27.643 | 0.151 | | >10 |
| 106 | 0.099 | 20.582 | 23.200 | 0.034 | | >10 |
| 107 | 0.049 | 9.603 | 4.096 | | | |
| 108 | 5.486 | >30 | 12.484 | | | |
| 109 | 1.114 | 2.803 | 1.988 | | | |
| 110 | 0.262 | >30 | >30 | | | |
| 111 | 0.763 | >30 | >30 | | | |
| 112 | 0.773 | 8.192 | 4.596 | | | |
| 113 | 0.258 | 13.019 | 17.928 | | | |
| 114 | 2.254 | >30 | 25.882 | | | |
| 115 | 1.603 | 19.301 | 6.749 | | | |
| 116 | 0.529 | >30 | 29.293 | | | |
| 117 | 1.445 | 3.089 | 2.263 | | | |
| 118 | 0.058 | >30 | 12.860 | | | |
| 119 | 0.368 | 20.160 | 28.797 | | | |
| 120 | 0.390 | 22.878 | >30 | | | |
| 121 | 1.466 | >30 | >30 | | | |
| 122 | 1.715 | 24.164 | 26.873 | | | |
| 123 | 4.005 | >30 | 7.481 | | | |
| 124 | 9.918 | >30 | >30 | | | |
| 125 | 2.323 | >30 | 14.708 | | | |
| 126 | 4.520 | >30 | >30 | | | |
| 127 | 0.520 | 10.146 | 10.725 | | | |
| 128 | 0.185 | 22.531 | >30 | | | |
| 129 | 0.828 | >30 | >30 | | | |
| 130 | 0.285 | 24.220 | >30 | | | |
| 131 | 2.859 | >30 | >30 | | | |
| 132 | 0.146 | >30 | 20.900 | | | |
| 133 | 0.245 | >30 | 10.948 | | | |

TABLE 1-continued

Inhibition of Nav1.6, Nav1.5 and Nav1.1

| Ex. No. | Flux $Na_v1.6$ $IC_{50}$ (µM) | Flux $Na_v1.5$ $IC_{50}$ (µM) | Flux $Na_v1.1$ $IC_{50}$ (µM) | EP $Na_v1.6$ $IC_{50}$ (µM) | EP $Na_v1.5$ $IC_{50}$ (µM) | EP $Na_v1.1$ $IC_{50}$ (µM) |
|---|---|---|---|---|---|---|
| 134 | 0.412 | >30 | 12.058 | | | |
| 135 | 0.640 | 1.665 | 0.564 | | | |
| 136 | 6.795 | >30 | >30 | | | |
| 137 | 0.217 | 16.537 | 5.066 | | | |
| 138 | 0.050 | 10.374 | 9.481 | | | |
| 139 | 7.727 | >30 | >30 | | | |
| 140 | 2.082 | >30 | >30 | | | |
| 141 | 0.582 | >30 | >30 | | | |
| 142 | 0.531 | 6.763 | 3.701 | | | |
| 143 | 10.181 | >30 | >30 | | | |
| 144 | 4.802 | 8.474 | 6.717 | | | |
| 145 | 0.515 | 17.097 | 9.630 | | | |
| 146 | 4.402 | 12.134 | 9.321 | | | |
| 147 | 0.482 | >30 | >30 | | | |
| 148 | 0.129 | 12.432 | 7.576 | | | |
| 149 | 0.613 | 9.180 | 6.023 | | | |
| 150 | 0.954 | >30 | >30 | | | |
| 151 | 0.410 | >30 | >30 | | | |
| 152 | 1.699 | 8.911 | 7.211 | | | |
| 153 | 0.185 | >30 | >30 | | | |
| 154 | 5.572 | 21.740 | 16.556 | | | |
| 155 | 0.220 | 14.389 | 12.583 | | | |
| 156 | 0.298 | 10.348 | 7.798 | | | |
| 157 | 0.211 | 18.628 | 8.062 | | | |
| 158 | 0.009 | >30 | 24.171 | 0.008 | | |
| 159 | 0.178 | >30 | >30 | | | |
| 160 | 1.686 | >30 | 26.678 | | | |
| 161 | 4.848 | >30 | 26.045 | | | |
| 162 | 6.134 | 5.779 | 6.880 | | | |
| 163 | 2.801 | >30 | >30 | | | |
| 164 | 4.449 | 12.943 | 6.028 | | | |
| 165 | 3.343 | 6.967 | 4.608 | | | |
| 166 | 3.672 | 10.130 | 7.792 | | | |
| 167 | 1.689 | 8.848 | 6.440 | | | |
| 168 | 2.020 | 5.892 | 4.170 | | | |
| 169 | 0.821 | 5.273 | 4.618 | | | |
| 170 | 1.615 | 21.207 | 11.259 | | | |
| 171 | 1.863 | 4.961 | 2.348 | | | |
| 172 | 0.432 | 4.968 | 5.454 | | | |
| 173 | 3.337 | 9.860 | 8.754 | | | |
| 174 | 9.156 | 16.222 | 10.200 | | | |
| 175 | 2.548 | >30 | 13.150 | | | |
| 176 | 0.740 | >30 | >30 | | | |
| 177 | 3.150 | 7.522 | 3.909 | | | |
| 178 | 1.088 | 15.985 | 12.866 | | | |
| 179 | 4.892 | 20.413 | 6.905 | | | |
| 180 | 5.289 | 25.358 | 16.841 | | | |
| 181 | 3.152 | >30 | >30 | | | |
| 182 | 0.877 | 9.858 | 9.410 | | | |
| 183 | 6.928 | >30 | >30 | | | |
| 184 | 5.385 | >30 | >30 | | | |
| 185 | 7.019 | 22.397 | 8.807 | | | |
| 186 | 3.274 | 20.119 | 19.205 | | | |
| 187 | 1.011 | 25.371 | 17.283 | | | |
| 188 | 4.145 | 8.241 | 3.247 | | | |
| 189 | 1.868 | 16.551 | 7.378 | | | |
| 190 | 2.333 | 8.252 | 5.169 | | | |
| 191 | 0.587 | 8.215 | 8.899 | | | |
| 192 | 0.857 | >30 | >30 | 0.370 | >10 | |
| 193 | 0.774 | 9.021 | 3.567 | 0.330 | >10 | |
| 194 | 3.197 | 23.538 | 29.205 | | | |
| 195 | 1.492 | 3.782 | 5.102 | | | |
| 196 | 1.262 | 8.196 | 1.871 | | | |
| 197 | 3.329 | 3.172 | 5.204 | | | |
| 198 | 1.462 | 4.699 | 5.363 | | | |
| 199 | 8.421 | >30 | 7.882 | | | |
| 200 | 4.624 | 7.215 | 4.967 | | | |
| 201 | 3.322 | 15.047 | 5.738 | | | |
| 202 | 4.324 | >30 | 25.069 | | | |
| 203 | 4.146 | 6.702 | 5.741 | | | |
| 204 | 1.775 | >30 | >30 | | | |
| 205 | 1.160 | 8.001 | 10.303 | | | |
| 206 | 0.532 | >30 | 22.461 | 0.462 | >10 | |
| 207 | 1.384 | 7.478 | 7.309 | | | |

TABLE 1-continued

Inhibition of Nav1.6, Nav1.5 and Nav1.1

| Ex. No. | Flux $Na_v1.6$ $IC_{50}$ (μM) | Flux $Na_v1.5$ $IC_{50}$ (μM) | Flux $Na_v1.1$ $IC_{50}$ (μM) | EP $Na_v1.6$ $IC_{50}$ (μM) | EP $Na_v1.5$ $IC_{50}$ (μM) | EP $Na_v1.1$ $IC_{50}$ (μM) |
|---|---|---|---|---|---|---|
| 208 | 1.087 | 5.689 | 4.413 | | | |
| 209 | 2.146 | 20.224 | 20.037 | | | |
| 210 | 1.267 | 8.363 | 7.133 | | | |
| 211 | 2.915 | 7.850 | 4.979 | | | |
| 212 | 2.144 | 18.950 | 10.519 | | | |
| 213 | 3.456 | 12.843 | 16.111 | | | |
| 214 | 1.792 | 5.536 | 2.942 | | | |
| 215 | 5.202 | >30 | 27.541 | | | |
| 216 | 3.710 | >30 | >30 | | | |
| 217 | 5.642 | 6.695 | 4.571 | | | |
| 218 | 1.996 | 14.174 | 13.652 | | | |
| 219 | 3.202 | 13.037 | 7.532 | | | |
| 220 | 3.688 | 8.187 | 5.838 | | | |
| 221 | 0.127 | >30 | 10.782 | 0.098 | | >10 |
| 222 | 0.959 | 19.352 | 27.908 | 0.278 | | >10 |
| 223 | 0.009 | 23.193 | 2.578 | | | |
| 224 | 0.024 | >30 | 8.892 | | | |
| 225 | 3.895 | 5.551 | 5.451 | 5.310 | | >10 |
| 226 | 2.428 | 9.041 | 11.490 | 3.085 | | >10 |
| 227 | 0.855 | >30 | >30 | | | |
| 228 | 0.031 | 23.110 | 5.275 | | | |
| 229 | 1.558 | >30 | >30 | | | |
| 230 | 0.967 | 23.041 | 13.100 | | | |
| 231 | 5.515 | 15.079 | 25.464 | | | |
| 232 | 0.858 | 3.764 | 4.600 | | | |
| 233 | 0.375 | 27.286 | 6.021 | | | |
| 234 | 1.423 | 20.730 | 6.874 | | | |
| 235 | 0.047 | 15.411 | 10.205 | | | |
| 236 | 0.067 | >30 | 24.258 | | | |
| 237 | 0.064 | 14.717 | 8.521 | | | |
| 238 | 2.100 | 12.969 | 27.775 | | | |
| 239 | 0.708 | 16.473 | 27.033 | | | |
| 240 | 0.093 | 7.456 | 8.062 | | | |
| 241 | 0.274 | 15.058 | 9.928 | | | |
| 242 | 0.650 | 9.963 | 5.375 | 0.668 | | >10 |
| 243 | 1.056 | 25.660 | 13.105 | | | |
| 244 | 1.234 | 5.080 | 6.935 | | | |
| 245 | 2.124 | >30 | >30 | | | |
| 246 | 0.629 | 18.726 | 8.507 | 1.033 | | >10 |
| 247 | 0.469 | 13.951 | 6.869 | | | |
| 248 | 3.310 | 7.056 | 5.526 | | | |
| 249 | 0.285 | 17.442 | 11.182 | 0.110 | | >10 |
| 250 | 1.420 | 6.482 | 5.502 | | | |
| 251 | 1.505 | 7.324 | 7.447 | 0.412 | | >10 |
| 252 | 0.304 | 8.081 | 17.146 | | | |
| 253 | 0.756 | 2.523 | 2.674 | 0.491 | | 4.761 |
| 254 | 1.158 | 0.962 | 2.320 | | 16.987 | |
| 255 | 3.701 | 12.700 | 9.144 | | | |
| 256 | 3.312 | 6.719 | 4.413 | | | |
| 257 | 0.701 | 10.588 | 10.313 | 0.170 | | >10 |
| 258 | 7.982 | 15.368 | 12.904 | | | |
| 259 | 1.577 | 5.811 | 3.769 | 0.440 | | 3.518 |
| 260 | 1.681 | 10.086 | 7.352 | 0.842 | | 9.643 |
| 261 | 6.037 | 24.613 | 8.294 | | | |
| 262 | 13.321 | 28.784 | 25.152 | | | |
| 263 | 3.097 | 19.078 | 4.444 | 3.810 | | >10 |
| 264 | 4.785 | 13.077 | 6.007 | | | |
| 265 | 4.786 | 6.800 | 6.351 | | | |
| 266 | 1.771 | 2.065 | 2.670 | | | |
| 267 | 0.182 | >30 | >30 | 0.066 | | |
| 268 | 4.921 | 28.159 | >30 | | | |
| 269 | 0.647 | >30 | >30 | 0.329 | | >10 |
| 270 | 4.740 | 28.668 | 21.862 | | | |
| 271 | 4.091 | 8.175 | 8.702 | | | |
| 272 | 3.765 | 18.226 | 11.740 | | | |
| 273 | 1.993 | 7.100 | 22.537 | | | |
| 274 | 1.855 | 10.036 | >30 | | | |
| 275 | 0.738 | 17.562 | 29.737 | | | |
| 276 | 0.566 | 17.867 | 18.684 | | | |
| 277 | 0.153 | >30 | 24.910 | 0.027 | | |
| 278 | 0.893 | >30 | >30 | | | |
| 279 | 0.064 | >30 | 21.203 | 0.011 | | >10 |
| 280 | 0.228 | 27.124 | 17.423 | | | |
| 281 | 0.021 | 13.129 | 14.584 | | | |

TABLE 1-continued

Inhibition of Nav1.6, Nav1.5 and Nav1.1

| Ex. No. | Flux Na$_v$1.6 IC$_{50}$ (µM) | Flux Na$_v$1.5 IC$_{50}$ (µM) | Flux Na$_v$1.1 IC$_{50}$ (µM) | EP Na$_v$1.6 IC$_{50}$ (µM) | EP Na$_v$1.5 IC$_{50}$ (µM) | EP Na$_v$1.1 IC$_{50}$ (µM) |
|---|---|---|---|---|---|---|
| 282 | 0.005 | 23.949 | 17.278 | 0.005 | | |
| 283 | 0.067 | >30 | >30 | 0.037 | | >10 |
| 284 | 0.718 | 13.044 | 10.482 | | | |
| 285 | 0.389 | 2.710 | 4.374 | | | |
| 286 | 2.223 | 1.987 | 2.268 | | | |
| 287 | 6.672 | 8.260 | 7.812 | | | |
| 288 | 4.316 | 27.401 | 15.898 | | | |
| 289 | 1.274 | 19.408 | 7.021 | | | |
| 290 | 1.787 | 5.305 | 6.240 | | | |
| 291 | 0.578 | >30 | >30 | 0.447 | | |
| 292 | 2.782 | 1.881 | 3.795 | | | |
| 293 | 10.912 | >30 | >30 | | | |
| 294 | 2.350 | 16.442 | 15.662 | | | |
| 295 | 0.009 | 25.943 | 17.083 | 0.001 | | |
| 296 | 0.010 | >30 | >30 | 0.002 | | |
| 297 | 0.062 | >30 | >30 | 0.012 | | |
| 298 | 0.079 | >30 | 26.039 | 0.043 | >10 | >10 |
| 299 | 0.324 | 26.630 | >30 | | | |
| 300 | 1.066 | >30 | >30 | 0.972 | | >10 |
| 301 | 2.139 | >30 | >30 | | | |
| 302 | 1.157 | 28.880 | 9.549 | | | |
| 303 | 2.440 | 4.617 | 7.064 | | | |
| 304 | 2.478 | >30 | >30 | | | |
| 305 | 4.595 | >30 | >30 | 5.569 | | >10 |
| 306 | 4.564 | 11.912 | 6.725 | | | |
| 307 | 5.312 | 9.790 | 4.112 | | | |
| 308 | 1.470 | >30 | 24.651 | | | |
| 309 | 6.859 | 7.350 | 8.437 | | | |
| 310 | 2.384 | 18.180 | 27.729 | | | |
| 311A | 18.341 | 10.536 | >30 | | | |
| 311B | 1.298 | 26.057 | 18.144 | | | |
| 312 | 2.768 | 6.452 | 10.200 | | | |
| 313 | 0.936 | >30 | 29.567 | | | |
| 314 | 0.730 | >30 | >30 | | | |
| 315 | 1.071 | 6.383 | 5.624 | 0.377 | | 4.248 |
| 316 | 3.902 | 5.087 | 2.796 | | | |
| 317 | 1.030 | 8.121 | 9.892 | | | |
| 318 | 5.465 | 17.373 | 13.768 | 1.147 | | >10 |
| 319 | 3.317 | 2.484 | 3.685 | | | |
| 320 | 3.236 | 4.737 | 4.251 | | | |
| 321 | 0.354 | 21.356 | 12.276 | 0.137 | | >10 |
| 322 | 0.237 | 7.346 | 6.019 | | | |
| 323 | 0.209 | 13.645 | 12.306 | | | |
| 324 | 0.403 | >30 | >30 | | | |
| 325 | 0.260 | 27.026 | 23.226 | | | |
| 326 | 0.303 | 24.466 | >30 | | | |
| 327 | 1.040 | >30 | 17.337 | | | |
| 328 | 0.786 | 18.264 | 16.255 | | | |

Biological Example 3

Electrical Stimulation Seizure Assays

Many electric stimulation seizure tests have been used to identify compounds with anti-convulsion activity, i.e., which raise seizure threshold. Two examples of electrical stimulation seizure assays frequently used in the field are the 6 Hz psychomotor seizure assay (6 Hz) and the Maximal Electroshock Seizure (MES). The 6 Hz assay is considered a model of partial seizures observed in humans (Löscher, W. and Schmidt, D., *Epilepsy Res*. (1988), Vol. 2, pp 145-81; Barton, M. E. et al., *Epilepsy Res*. (2001), Vol. 47, pp. 217-27). The MES assay is a model for generalized tonic-clonic seizures in humans and provides an indication of a compound's ability to prevent seizure spread when all neuronal circuits in the brain are maximally active. These seizures are highly reproducible and are electrophysiologically consistent with human seizures (Toman et al., 1946; Piredda et al., 1984; White et al., 1995). Experiments can be performed with healthy animals, or with seizure prone animals that have been genetically modified to model genetic epilepsy syndromes (Piredda, S. G. et al., *J. Pharmacol. Exp. Ther*. (1985), Vol. 232, pp. 741-5; Toman, J. E. et al., *J. Neurophysiol*. (1946), Vol. 9, pp. 231-9; and White, H. S. et al., *Ital. J. Neurol. Sci*. (1995), Vol. 16 (1-2), pp. 73-7).

To facilitate testing mice can be pretreated with the test compound or with the appropriate vehicle prior to the application of the electroshock. Each treatment group (n=4-8 mice/group) is examined for anticonvulsive effects at different time points after administration of the compound and the vehicle. The eyes of mice are first anesthetized with a topical application of Alcaine (proparacaine hydrochloride) 0.5%, one drop in each eye 30 minutes prior to the stimulation. Seizures are then induced by placing electrodes on the eyes which deliver a transcorneal current.

The 6 Hz Psychomotor Seizure Test:

Following pretreatment, each mouse is challenged with the low-frequency (6 Hz, 0.3 ms pulse width) stimulation for 3 sec. delivered through corneal electrodes at several intensities (12-44 mA). Animals are manually restrained and released immediately following the stimulation and observed for the presence or absence of seizure activity. Typically, the 6 Hz stimulation results in a seizure characterized by a minimal clonic phase that is followed by stereotyped, automatist behaviors, including twitching of the vibrissae, and Straub-tail or by a generalized tonic clonic seizure. The presence, type and latency to seizure (in seconds) after the application of the current are monitored. Animals not displaying a clonic or generalized tonic clonic seizure are considered "protected". All animals are euthanized at the end of assay. Plasma and brain samples are collected.

Maximal Electroshock Test (MES):

Following pretreatment, each mouse is challenged with an alternating current (60 Hz, 0.4-0.6 ms pulse width) for 0.2-0.5 sec. delivered through corneal electrodes at intensities (44-55 mA).

Typically, the MES stimulation results in a generalized tonic seizure that can be followed by a clonic seizure, automatist behaviors and Straub-tail. The presence, type and latency to seizure (in seconds) after the application of the current are monitored. An animal is considered "protected" from MES-induced seizures upon abolition of the hindlimb tonic extensor component of the seizure. After the seizure, mice are expected to resume normal exploratory behaviour within 1 to 4 minutes. Latency to seizure is recorded with a cut-off of 1 minute after which all animals are euthanized.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method of treating a disease or a condition associated with aberrant Nav1.6 activity in a patient, wherein the disease or condition is epilepsy or epileptic seizure disorder, comprising administering to the patient a therapeutically effective amount of a compound of the following formula:

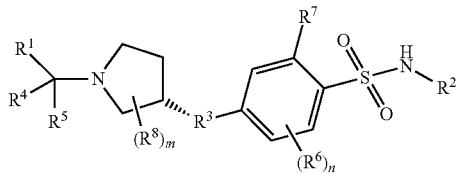

wherein:
$R^1$ is an optionally substituted phenyl or optionally substituted pyridyl;
$R^2$ is an optionally substituted thiazolyl, an optionally substituted thiadiazolyl, an optionally substituted isothiazolyl, or an optionally substituted pyridinyl;
$R^3$ is —O— or —N($R^{13}$)—;
$R^4$, $R^5$, and $R^{13}$ are each independently selected from hydrogen, alkyl, and haloalkyl;
each $R^6$ is independently selected from hydrogen, halo, alkyl, and haloalkyl;
$R^7$ is halo;
each $R^8$ is independently selected from hydrogen, alkyl, and haloalkyl;
m is 1 or 2; and
n is 1 or 2;
as an individual stereoisomer, enantiomer or tautomer thereof or a mixture thereof;
or a pharmaceutically acceptable salt or solvate thereof.

2. The method of claim 1, wherein the disease or condition is epilepsy.

3. The method of claim 1, wherein the disease or condition is epileptic seizure disorder.

4. The method of claim 1, wherein the disease or condition is SCN8A developmental and epileptic encephalopathy (SCN8A-DEE).

5. The method of claim 1, wherein the patient has a SCN8A mutation.

6. The method of claim 1, wherein:
$R^1$ is phenyl or pyridyl, each optionally substituted with halo or alkyl;
$R^2$ is thiazolyl, thiadiazolyl, isothiazolyl, or pyridinyl, each optionally substituted with halo or alkyl;
$R^3$ is —O— or —N($R^{13}$)—;
$R^4$ and $R^5$ are each hydrogen;
$R^{13}$ is hydrogen, alkyl, or haloalkyl;
each $R^6$ is independently selected from hydrogen, halo, alkyl, and haloalkyl;
$R^7$ is halo;
$R^8$ is hydrogen;
m is 1; and
n is 1 or 2;
as an individual stereoisomer, enantiomer or tautomer thereof or a mixture thereof;
or a pharmaceutically acceptable salt or solvate thereof.

7. The method of claim 1, wherein the compound is (S)-4-((1-benzylpyrrolidin-3-yl)(methyl)amino)-2-fluoro-5-methyl-N-(thiazol-4-yl)benzenesulfonamide, represented by the formula:

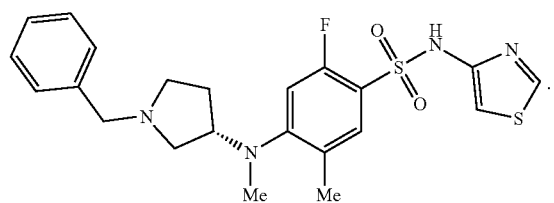 [SMILES: Cc1cc(S(=O)(=O)Nc2cscn2)c(F)cc1N(C)[C@H]1CCN(Cc2ccccc2)C1]

8. The method of claim 1, wherein the compound is (S)-4-((1-benzylpyrrolidin-3-yl)(methyl)amino)-2-fluoro-5-methyl-N-(thiazol-4-yl)benzenesulfonamide, represented by the formula:

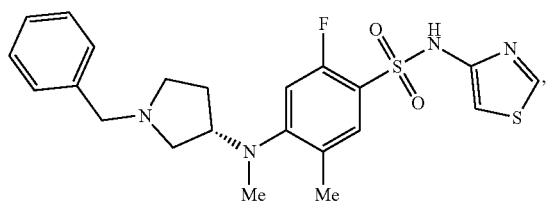 [SMILES: Cc1cc(S(=O)(=O)Nc2cscn2)c(F)cc1N(C)[C@H]1CCN(Cc2ccccc2)C1]

or a pharmaceutically acceptable salt or solvate thereof.

9. The method of claim 1, wherein the compound is (S)-4-((1-benzylpyrrolidin-3-yl)(methyl)amino)-2,6-difluoro-3-methyl-N-(thiazol-4-yl)benzenesulfonamide, represented by the formula:

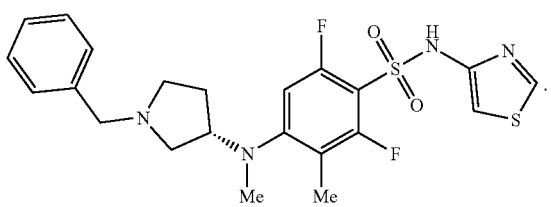 [SMILES: Cc1c(N(C)[C@H]2CCN(Cc3ccccc3)C2)cc(F)c(S(=O)(=O)Nc2cscn2)c1F]

10. The method of claim 1, wherein the compound is (S)-4-((1-benzylpyrrolidin-3-yl)(methyl)amino)-2,6-difluoro-3-methyl-N-(thiazol-4-yl)benzenesulfonamide, represented by the formula:

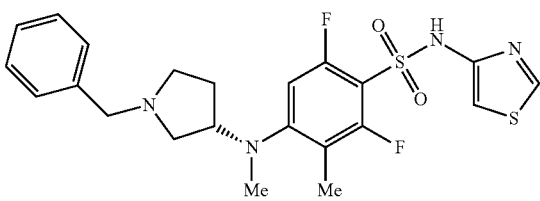

or a pharmaceutically acceptable salt or solvate thereof.

11. The method of claim 1, wherein the compound is (S)-2,6-difluoro-3-methyl-4-(methyl(1-((6-methylpyridin-2-yl)methyl)pyrrolidin-3-yl)amino)-N-(thiazol-4-yl)benzenesulfonamide, represented by the formula:

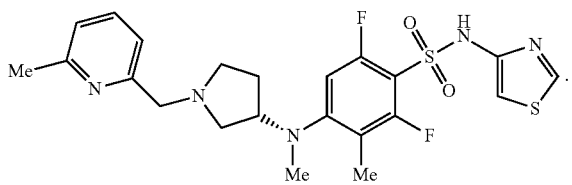

12. The method of claim 1, wherein the compound is (S)-2,6-difluoro-3-methyl-4-(methyl(1-((6-methylpyridin-2-yl)methyl)pyrrolidin-3-yl)amino)-N-(thiazol-4-yl)benzenesulfonamide, represented by the formula:

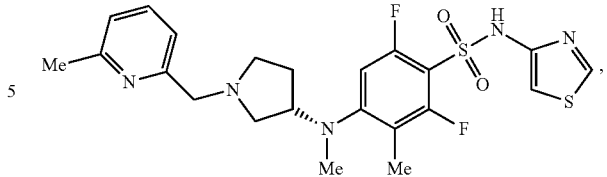

or a pharmaceutically acceptable salt or solvate thereof.

13. The method of claim 1, wherein the compound is (S)-4-((1-benzyl-3-methylpyrrolidin-3-yl)oxy)-2,6-difluoro-3-methyl-N-(thiazol-4-yl)benzenesulfonamide, represented by the formula:

14. The method of claim 1, wherein the compound is (S)-4-((1-benzyl-3-methylpyrrolidin-3-yl)oxy)-2,6-difluoro-3-methyl-N-(thiazol-4-yl)benzenesulfonamide, represented by the formula:

or a pharmaceutically acceptable salt or solvate thereof.

15. The method of claim 1, wherein the compound is (S)-3-chloro-2,6-difluoro-4-(methyl(1-((6-methylpyridin-2-yl)methyl)pyrrolidin-3-yl)amino)-N-(thiazol-4-yl)benzenesulfonamide, represented by the formula:

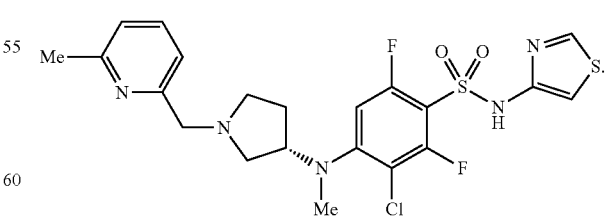

16. The method of claim 1, wherein the compound is (S)-3-chloro-2,6-difluoro-4-(methyl(1-((6-methylpyridin-2-yl)methyl)pyrrolidin-3-yl)amino)-N-(thiazol-4-yl)benzenesulfonamide, represented by the formula:

417

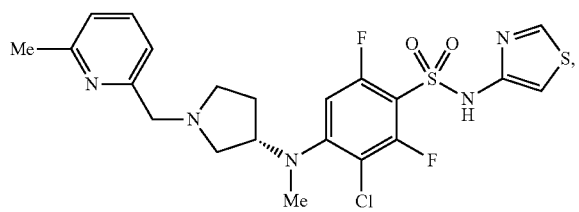 [SMILES: Cc1cccc(CN2CC[C@H](N(C)c3cc(F)c(S(=O)(=O)Nc4cscn4)c(F)c3Cl)C2)n1]

or a pharmaceutically acceptable salt or solvate thereof.

17. The method of claim 1, wherein the compound is (S)-4-((1-benzylpyrrolidin-3-yl)(methyl)amino)-2-fluoro-N-(isothiazol-3-yl)-5-methylbenzenesulfonamide, represented by the formula:

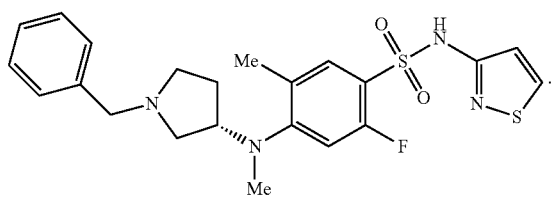 [SMILES: Cc1cc(S(=O)(=O)Nc2ccsn2)c(F)cc1N(C)[C@H]1CCN(Cc2ccccc2)C1]

18. The compound of claim 1, wherein the compound is (S)-4-((1-benzylpyrrolidin-3-yl)(methyl)amino)-2-fluoro-N-(isothiazol-3-yl)-5-methylbenzenesulfonamide, represented by the formula:

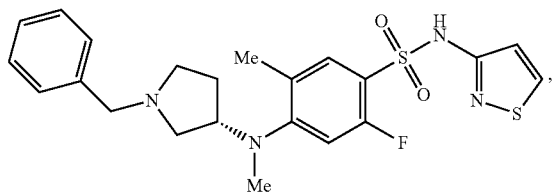 [SMILES: Cc1cc(S(=O)(=O)Nc2ccsn2)c(F)cc1N(C)[C@H]1CCN(Cc2ccccc2)C1]

or a pharmaceutically acceptable salt or solvate thereof.

19. The method of claim 1, wherein the compound is (S)-4-((1-benzylpyrrolidin-3-yl)(methyl)amino)-2,6-difluoro-N-(isothiazol-3-yl)-3-methylbenzenesulfonamide, represented by the formula:

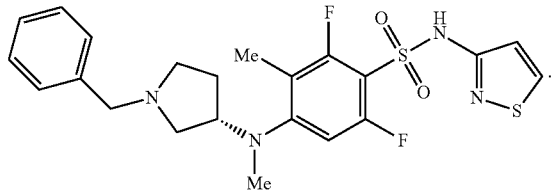 [SMILES: Cc1c(N(C)[C@H]2CCN(Cc3ccccc3)C2)cc(F)c(S(=O)(=O)Nc2ccsn2)c1F]

20. The method of claim 1, wherein the compound is (S)-4-((1-benzylpyrrolidin-3-yl)(methyl)amino)-2,6-difluoro-N-(isothiazol-3-yl)-3-methylbenzenesulfonamide, represented by the formula:

418

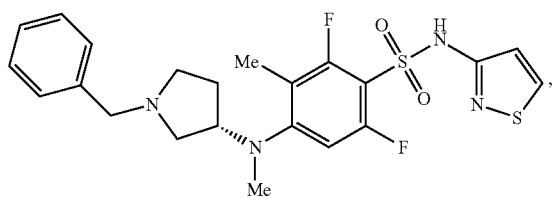 [SMILES: Cc1c(N(C)[C@H]2CCN(Cc3ccccc3)C2)cc(F)c(S(=O)(=O)Nc2ccsn2)c1F]

or a pharmaceutically acceptable salt or solvate thereof.

21. The method of claim 1, wherein the compound is (S)-4-((1-benzylpyrrolidin-3-yl)(methyl)amino)-2,6-difluoro-N-(6-fluoropyridin-2-yl)-3-methylbenzenesulfonamide, represented by the formula:

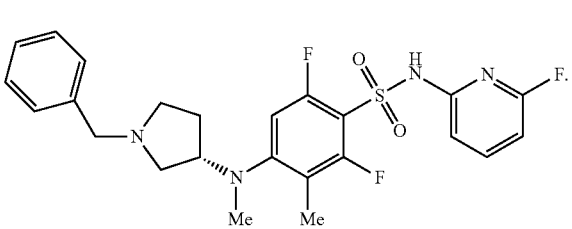 [SMILES: Cc1c(N(C)[C@H]2CCN(Cc3ccccc3)C2)cc(F)c(S(=O)(=O)Nc2cccc(F)n2)c1F]

22. The method of claim 1, wherein the compound is (S)-4-((1-benzylpyrrolidin-3-yl)(methyl)amino)-2,6-difluoro-N-(6-fluoropyridin-2-yl)-3-methylbenzenesulfonamide, represented by the formula:

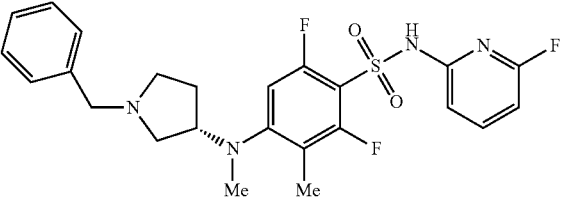 [SMILES: Cc1c(N(C)[C@H]2CCN(Cc3ccccc3)C2)cc(F)c(S(=O)(=O)Nc2cccc(F)n2)c1F]

or a pharmaceutically acceptable salt or solvate thereof.

23. The method of claim 1, wherein the compound is (S)-4-((1-benzylpyrrolidin-3-yl)(methyl)amino)-2-fluoro-3-methyl-N-(thiazol-4-yl)benzenesulfonamide, represented by the formula:

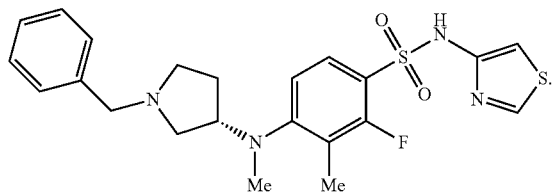 [SMILES: Cc1c(N(C)[C@H]2CCN(Cc3ccccc3)C2)ccc(S(=O)(=O)Nc2cscn2)c1F]

24. The method of claim 1, wherein the compound is (S)-4-((1-benzylpyrrolidin-3-yl)(methyl)amino)-2-fluoro-3-methyl-N-(thiazol-4-yl)benzenesulfonamide, represented by the formula:

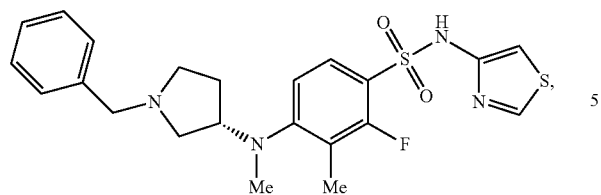
or a pharmaceutically acceptable salt or solvate thereof.
* * * * *